US010513711B2

(12) United States Patent
Frisch et al.

(10) Patent No.: US 10,513,711 B2
(45) Date of Patent: Dec. 24, 2019

(54) GENETIC TARGETING IN NON-CONVENTIONAL YEAST USING AN RNA-GUIDED ENDONUCLEASE

(71) Applicant: DUPONT US HOLDING, LLC, Wilmington, DE (US)

(72) Inventors: Ryan Frisch, Newark, DE (US); Xiaochun Fan, West Chester, PA (US); Seung-Pyo Hong, Hockessin, DE (US)

(73) Assignee: DUPONT US HOLDING, LLC, Wilmington, DE (US)

( * ) Notice: Subject to any disclaimer, the term of this patent is extended or adjusted under 35 U.S.C. 154(b) by 93 days.

(21) Appl. No.: 15/503,383

(22) PCT Filed: Jul. 5, 2015

(86) PCT No.: PCT/US2015/041256

§ 371 (c)(1),
(2) Date: Feb. 10, 2017

(87) PCT Pub. No.: WO2016/025131

PCT Pub. Date: Feb. 18, 2016

(65) Prior Publication Data

US 2017/0226533 A1 Aug. 10, 2017

Related U.S. Application Data

(60) Provisional application No. 62/036,652, filed on Aug. 13, 2014.

(51) Int. Cl.
*C12N 15/90* (2006.01)

(52) U.S. Cl.
CPC .................................. *C12N 15/905* (2013.01)

(58) Field of Classification Search
None
See application file for complete search history.

(56) References Cited

U.S. PATENT DOCUMENTS

| | | | |
|---|---|---|---|
| 5,580,967 | A | 12/1996 | Joyce |
| 5,616,459 | A | 4/1997 | Kramer et al. |
| 5,688,670 | A | 11/1997 | Szostak et al. |
| 6,063,566 | A | 5/2000 | Joyce |
| 6,660,830 | B1 | 12/2003 | Radulescu |
| 7,309,576 | B2 | 12/2007 | O'Dowd |
| 2014/0068797 | A1 | 3/2014 | Doudna et al. |
| 2014/0189896 | A1 | 7/2014 | Zhang et al. |
| 2015/0059010 | A1 | 2/2015 | Cigan et al. |
| 2015/0082478 | A1 | 3/2015 | Cigan et al. |

FOREIGN PATENT DOCUMENTS

| | | | |
|---|---|---|---|
| EP | 0707638 | | 4/1996 |
| WO | 94/13791 | | 6/1994 |
| WO | 2015/026883 | A1 | 2/2015 |
| WO | 2015/138855 | A1 | 9/2015 |

OTHER PUBLICATIONS

Gao et al., J. Integrative Plant Biol., 56, 4, 343-349 (Year: 2014).*
Sanders et al. , Nat. Biotech., 32, 347-355 (Year: 2014).*
Cereghino et al., FEMS Microbiol. Rev., 24, 45-66, (Year: 2000).*
Xue et al., Nature Biotech., 31, 8, 734-740, 2013 (Year: 2013).*
"Ciis-Acting Ribozymes for the Production of RNA In Vitro Transcripts with Defined 5' and 3' Ends", Avis et al., in Recombinant and In Vitro RNA Synthesis: Methods and PRotocols, Methods in Molecular Biology, vol. 941, ed. G. L. Conn, pp. 83-98 (Year: 2012).*
Austin, Christopher P. et al., The Knockout Mouse Project, Nat Genet, Sep. 2004, pp. 921-924, 36(9).
Bibikova, Marina et al., Stimulation of Homologous Recombination through Targeted Cleavage by Chimeric Nucleases, Molecular and Cellular Biology, Jan. 2011, pp. 289-297, vol. 21, No. 1.
Bibikova, Marina et al., Enhancing Gene Targeting with Designed Zinc Finger Nucleases, Science, May 2, 2003, p. 764, vol. 300.
Chen, Zao et al., Enhancement of the Gene Targeting Efficiency of Non-Conventional Yeasts by Increasing Genetic Redundancy, PLOS One, Mar. 2013, e57952, 9 pages, vol. 8, Issue 3.
Chylinski, Krzysztof et al., The tracrRNA and Cas9 families of type II CRISPR-Cas immunity systems, RNA Biology, May 2103, pp. 726-737, vol. 10:5.
Corrigan, Mary W et al., The Fate of Linear DNA in *Saccharomyces cerevisiae* and Candida glabrate: The Role of Homologous and Non-Homologous End Joining, PLOS One, Jul. 2013, e69628—8 pages, vol. 8, Issue 7.
Deltcheva, Elitza et al., CRISPR RNA maturation by trans-encoded small RNA and host factor RNase III, Nature, Mar. 31, 2011, pp. 602-607, vol. 471 (7340).
Dicarlo, James E. et al., Genome engineering in *Saccharomyces cerevisiae*, Nucleic Acids Research, 2013, pp. 4336-4343—vol. 41, No. 7.
Epinat, Jean-Charles et al., A novel engineered meganuclease induces homologous recombination in yeast and mammalian cells, Nucleic Acids Research, 2003, pp. 2952-2962, vol. 31, No. 11.
Ferrreira, Miguel Godinho et al., Two modes of DNA double-strand break repair are reciprocally regulated through the fission yeast cell cycle, Genes & Development, 2004, pp. 2249-2254, vol. 18.
Gao, Yangbin et al., Self-processing of ribozyme-flanked RNAs into guide RNAs in vitro and in vivo for CRISPR-mediated genome editing, Apr. 2014, pp. 343-349, vol. 56, Issue 4.

(Continued)

*Primary Examiner* — Nancy A Treptow

(57) ABSTRACT

Non-conventional yeasts are disclosed herein comprising at least one RNA-guided endonuclease (RGEN) comprising at least one RNA component that does not have a 5'-cap. This uncapped RNA component comprises a sequence complementary to a target site sequence in a chromosome or episome in the yeast. The RGEN can bind to, and optionally cleave, one or both DNA strands at the target site sequence. An example of an RGEN herein is a complex of a Cas9 protein with a guide RNA. A ribozyme is used in certain embodiments to provide an RNA component lacking a 5'-cap. Further disclosed are methods of genetic targeting in non-conventional yeast.

11 Claims, 20 Drawing Sheets

Figure 1:
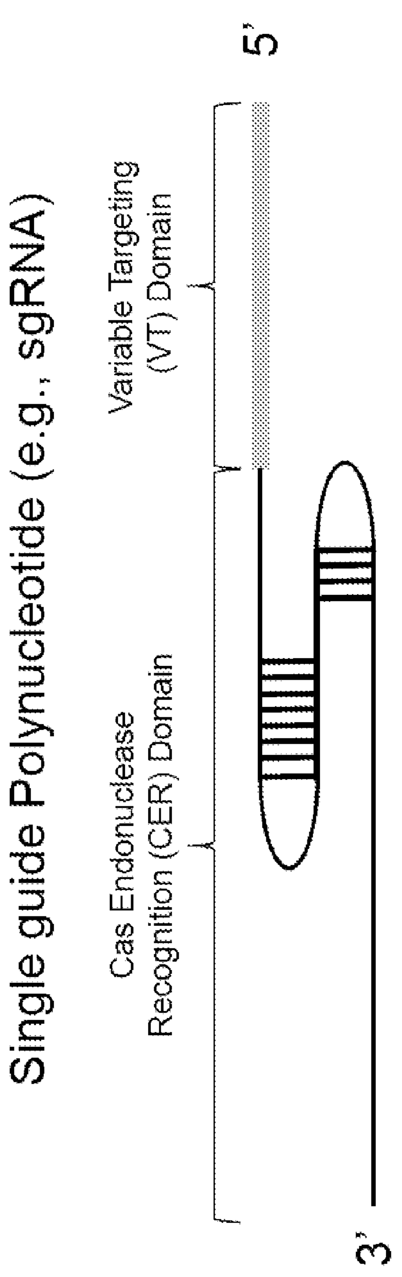

Specification includes a Sequence Listing.

(56) References Cited

OTHER PUBLICATIONS

Gasiunas, Giedrius et al., Cas9-crRNA ribonucleoprotein complex mediates specific DNA cleavage for adaptive immunity in bacteria, PNAS, Sep. 4, 2012, E2579-E2586, 109.
Guilinger, John P., Fusion of catalytically inactive Cas9 to Fokl nuclease improves the specificity of genome modification, Nat. Biotechnol, Jun. 2014, pp. 577-582, vol. 32(6).
Hammann, Christian et al., The ubiquitous hammerhead ribozyme, RNA, 2012, pp. 1-16, vol. 18, No. 5.
Haurwitz, Rachel E. et al., Sequence- and Structure-Specific RNA Processing by a CRISPR Endonuclease, Science, Sep. 10, 2010, pp. 1355-1358, vol. 329.
Horton, Robert M., Gene Splicing by Overlap Extension: Tailor-Made Genes Using the Polymerase Chain Reaction, BioTechniques, 2013, pp. 129-133, vol. 54, No. 3.
Horvath, Philippe et al., CRISPR/Cas, the Immune System of Bacteria and Archaea, Science, Jan. 8, 2010, pp. 167-170, vol. 327.
Hsu, Patrick D. et al., Development and Applications of CRISPR-Cas9 for Genome Engineering, Cell, Jun. 5, 2014, pp. 1262-1278, vol. 157.
Jacobs, Jake Z. et al., Implementation of the CRISPR-Cas9 system in fission yeast, Nature Communications, 2014, Article No. 5344, vol. 5.
Jinek, Martin et al., A Programmable Dual-RNA-Guided DNA Endonuclease in Adaptive Bacterial Immunity, Science, Aug. 17, 2012, pp. 816-821, vol. 337.
Karginov, Fedor V. et al., The CRISPR System: Small RNA-Guided Defense in Bacteria and Archaea, Molecular Cell, Jan. 15, 2010, pp. 7-19, vol. 37.
Kenney, Jill B et al., Efficient Targeted Integration at leu1-32 and ura4-294 in Schizosaccharomyces pombe, Genetics, Mar. 1994, pp. 849-856, vol. 136.
Lilley, David M.J., Catalysis by the nucleolytic ribozymes, Biochem Soc Trans, 2011, pp. 641-646, vol. 39.
Ma, Hongming et al., Pol III Promoters to Express Small RNAs: Delineation of Transcription Initiation, Molecular Therapy—Nucleic Acids, 2014, e161, 3.
Miller, Jeffrey C. et al., A TALE nuclease architecture for efficient genome editing, Nature Biotechnology, Feb. 2011, pp. 143-148, vol. 29, No. 2.
Nissim, Lir et al., Multiplexed and Programmable Regulation of Gene Networks with an Integrated RNA and CRISPR/Cas Toolkit in Human Cells, Molecular Cell, May 22, 2014, pp. 698-710, vol. 54.
Orr-Weaver, Terry L., Yeast transformation: A model system for the study of recombination, Genetics, Oct. 1981, pp. 6354-6358, vol. 78, No. 10.
Pley, Heinz W. et al., Three-dimensional structure of a hammerhead ribozyme, Nature, Nov. 3, 1994, pp. 68-74, vol. 372.
Richard, Mathias et al., Tagging Morphogenetic Genes by Insertional Mutagenesis in the Yeast Yarrowia lipolytica, Journal of Bacteriology, May 2001, pp. 3098-3107, vol. 183, No. 10.
Rudin, Norah et al., Genetic and Physical Analysis of Double-Strand Break Repair and Recombination in *Saccharomyces cerevisiae*, Genetics, Jul. 1989, pp. 519-534, vol. 122.
Ryan, Owen W. et al., Multiplex Engineering of Industrial Yeast Genomes Using CRISPRm, Methods in Enzymology, 2014, pp. 473-489, vol. 546.
Sapranauskas, Rimantas et al., The *Streptococcus thermophilus* CRISPR/Cas system provides immunity in *Escherichia coli*, Nucleic Acids Research, Aug. 3, 2011, pp. 9275-9282, vol. 39, No. 21.
Scott, William G. et al., The Crystal Structure of an All-RNA Hammerhead Ribozyme: A Proposed Mechanism for RNA Catalytic Cleavage, Cell, Jun. 30, 1995, pp. 991-1002, vol. 81.
Sibirny, Andrei A. et al., Thematic section 'Biochemistry, Genetics, Biotechnology and Ecology of Non-conventional Yeasts', FEMS Yeast Research, 2002, Vo. 2, p. 293.
Smih, Fatima et al., Nucleic Acids Research, 1995, pp. 5012-5019, vol. 23, No. 24.
Sternberg, Samuel H. et al., Mechanism of substrate selection by a highly specific CRISPR endoribonuclease, RNA, 2012, pp. 661-672, vol. 18.
Sternberg, Samuel H. et al., DNA interrogation by the CRISPR RNA-guided endonuclease Cas9, Nature, Mar. 6, 2014, pp. 62067, vol. 507 (7490).
International Search Report and Written Opinion—PCT/US2015/041256—dated Oct. 22, 2015.

* cited by examiner

Figure 5

| Name | Sequence | Number | Frequency | SEQ ID NO |
|---|---|---|---|---|
| WT | CAATGGAAAAGACATTT**TCAAACGATTACCCACC-CTC**CGGGACTGAGGCCCAC | 0 | 0 | 71 |
| 1 | CAATGGAAAAGACATTTTCAAACGATTACCCACC--TCCGGGACTGAGGCCCAC | 141 | 0.73 | 72 |
| 2 | CAATGGAAAAGACATTTTCAAACGATTACCCAC---TCCGGGACTGAGGCCCAC | 11 | 0.057 | 73 |
| 3 | CAATGGAAAAGACATTTTCAAACGATTACCCACC-----GGGACTGAGGCCCAC | 3 | 0.015 | 74 |
| 4 | CAATGGAAAAGACATTTTCAAACGATTACCC--------GGGACTGAGGCCCAC | 2 | 0.010 | 75 |
| 5 | C-----------------------------------------ACTGAGGCCCAC | 2 | 0.010 | 76 |
| 6 | CAATGGAAAAGACATTTTCAAACGATTACCCACCACTCCGGGACTGAGGCCCAC | 2 | 0.010 | 77 |
| 7 | CAATGGAAAAGACATTTTCAAACGATTACC------TCCGGGACTGAGGCCCAC | 1 | 0.005 | 78 |
| 8 | CAATGGAAAAGACATTTTCAAACGATTACCC--------GGGACTGAGGCCCAC | 1 | 0.005 | 79 |
| 9 | CAATGGAAAAGACATTTTCAAACGATTACCCACC----------TGAGGCCCAC | 1 | 0.005 | 80 |
| 10 | CAATGGAAAAGACATTTTCAAACGATTACCCA------CGGGACTGAGGCCCAC | 1 | 0.005 | 81 |
| 11 | CAATGGAAAAGACATTTTCAAACGATTACACAC--------------GGCCCAC | 1 | 0.005 | 82 |
| 12 | CAATGGAAAAGACATTTTC-----------------TCCGGGACTGAGGCCCAC | 1 | 0.005 | 83 |
| 13 | CAATGGAAAAGACATTTTCAAACG-----------CTCCGGGACTGAGGCCCAC | 1 | 0.005 | 84 |
| 14 | CAATGGAAAAGACATTTTCAAACGAT-----------CCGGGACTGAGGCCCAC | 1 | 0.005 | 85 |
| 15 | CAATGGAAAAGACATTTTCAAACGATAC---------------------CCCAC | 1 | 0.005 | 86 |
| 16 | CAATGGAAAAGACATTTTCAAACGATTACCCACCCCTCCGGGACTGAGGCCCAC | 1 | 0.005 | 87 |
| 17 | CAATGGAAAAGACATTTTCAAACGATTACCC-----TCCGGGACTGAGGCCCAC | 1 | 0.005 | 88 |
| 18 | CAATGGAAAAGACATTTTCAAACGATTACCCACCCCTCCGGGACTGAGGCCCAC | 1 | 0.005 | 89 |

Figure 12- A
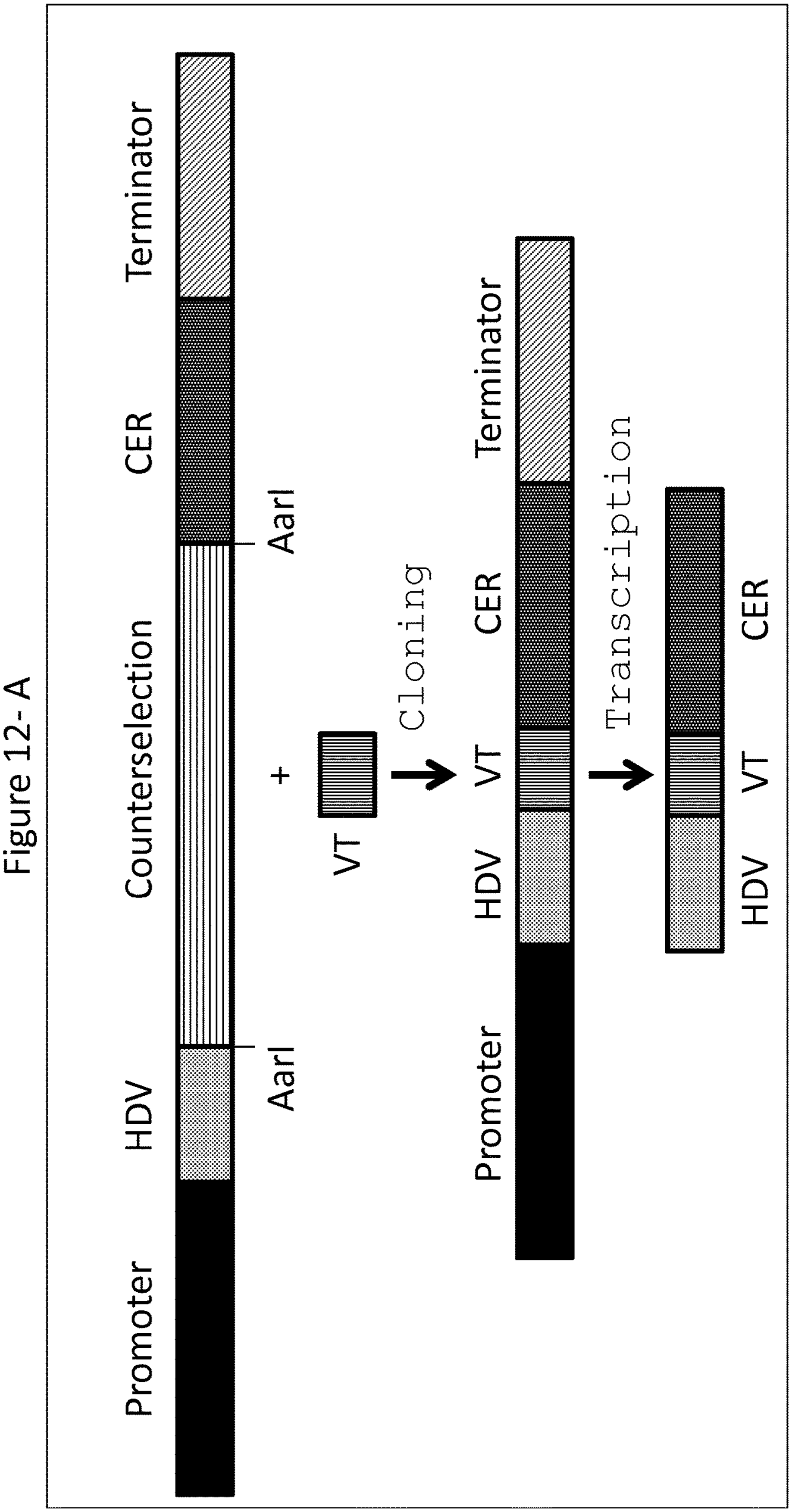
Figure 12- B
AATGGACTcaaacgattacccacctcGTTT SEQ ID NO: 99
CCTGagtttgctaatgggtgggagCAAAATCT SEQ ID NO: 100

Figure 13-A
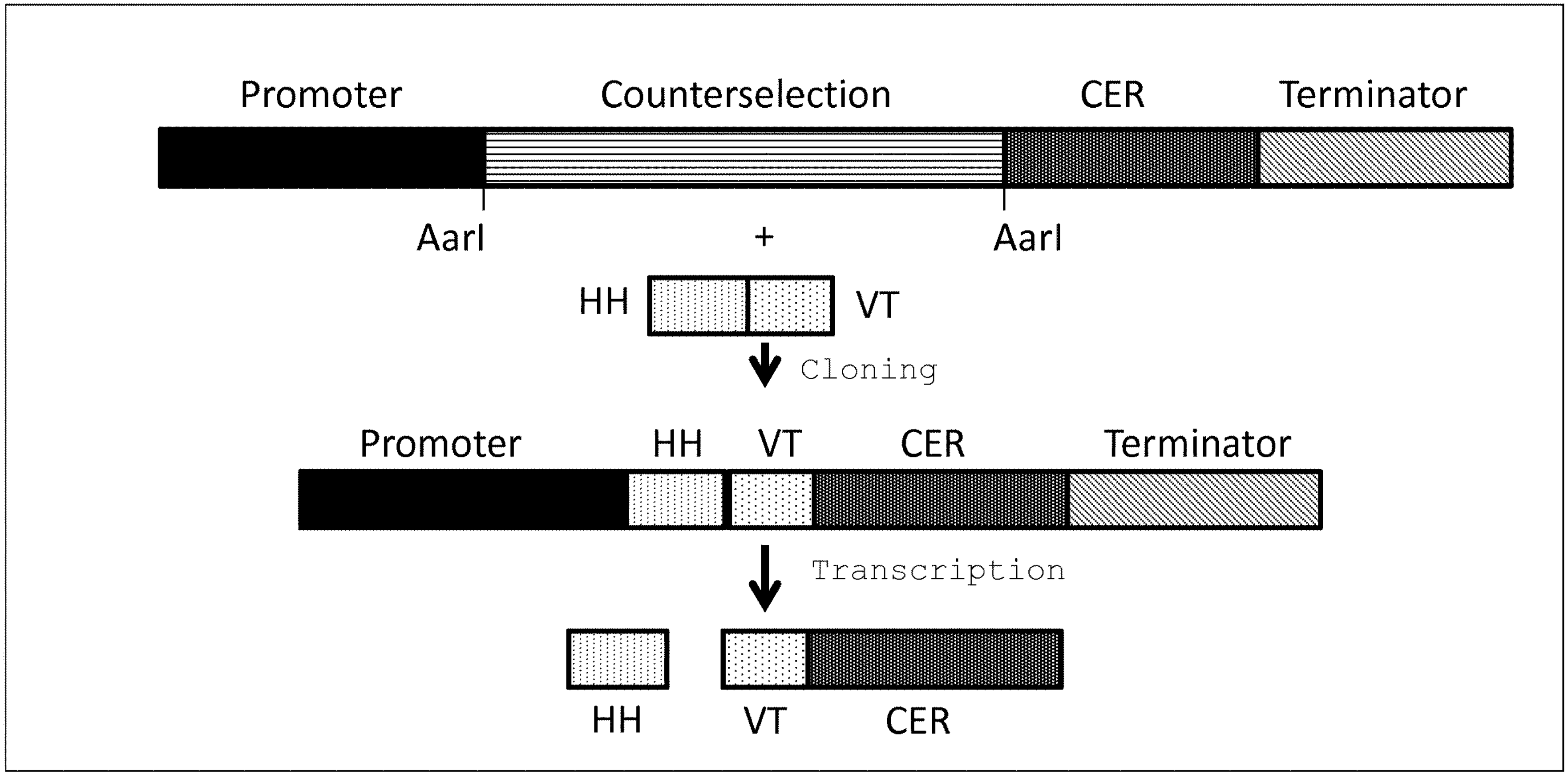
Figure 13-B
CATGCGTAAACTGACTGATGAGTCCGTGAGGACGAAACGAGTAAGCTCGTC TCAGTTTCAGTACGGTTCTAGTTT SEQIDNO:162
GCATTTGACTGACTACTCAGGCACTCCTGCTTTGCTCATTCGAGCAG AGTCAAAGTCATGCCAAGATCAAAATCT SEQIDNO:163
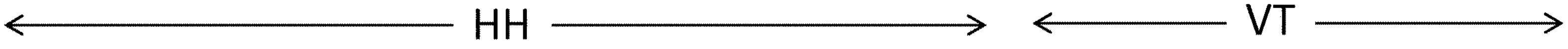

Figure 15

Plasmid URA3

| | | |
|---|---|---|
| URA3.1 | CGTCCTCCTTCTTCTGTTCAGAGACAGTTTCCTCGGCACCAGCTCGCAGGCCA | SEQ ID NO: 175 |
| Colony 1 | CGTCCTCCTTCTTCTGTTCAGAGACAGTT-CCTCGGCACCAGCTCGCAGGCCA | SEQ ID NO: 176 |
| Colony 2 | CGTCCTCCTTCTTCTGTTCAGAGACAGT-—CCTCGGCACCAGCTCGCAGGCCA | SEQ ID NO: 177 |
| Colony 3 | CGTCCTCCTTCTTCTGTTCAGAGACAGTT-CCTCGGCACCAGCTCGCAGGCCA | SEQ ID NO: 178 |
| Colony 5 | CGTCCTCCTTCTTCTGTTCAGAGACAGTT-CCTCGGCACCAGCTCGCAGGCCA | SEQ ID NO: 179 |
| Colony 6 | CGTCCTCCTTCTTCTGTTCAGAGACAGTT-CCTCGGCACCAGCTCGCAGGCCA | SEQ ID NO: 180 |

Genomic URA3

| | | |
|---|---|---|
| URA3.1 | CGTCCTCCTTCTTCTGTTCAGAGACAGTTTCCTCGGCACCAGCTCGCAGGCCA | SEQ ID NO: 175 |
| Colony 1 | CGTCCTCCTTCTTCTGTTCAGAGACAGTN-CCNCGGCCCC | SEQ ID NO: 181 |
| Colony 2 | CGTCCTCCTTCTTCTGTTCAGAGACAGTTT**A**CCTCGGCACCAGCTCGCAGGCCA | SEQ ID NO: 182 |
| Colony 3 | CGTCCTCCTTCTTCTGTTCAGAGACAGTTT---------CAGCTCGCAGGCCA | SEQ ID NO: 183 |
| Colony 5 | CGTCCTCCTTCTTCTGTTCAGANACAGTTT----GGCACCANCTCGCAGGCCA | SEQ ID NO: 184 |
| Colony 6 | CGTCCTCCTTCTTCTGTTCAGAGACAGTTT**C**CCTCGGCACCAGCTCGCAGGCCA | SEQ ID NO: 185 |

Figure 16-A

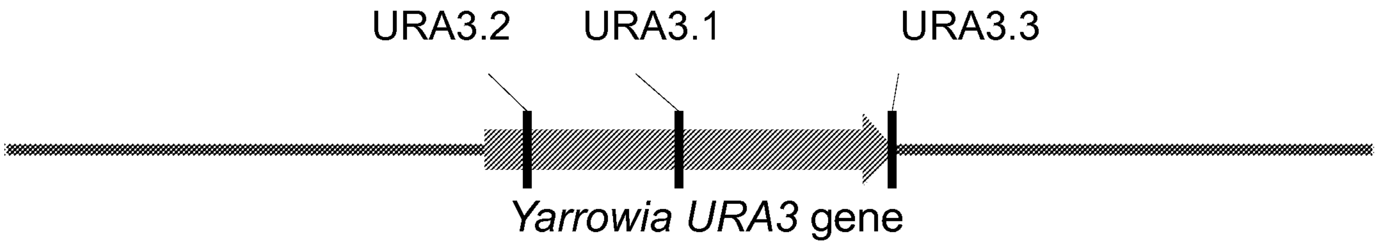

Figure 16-B

| pYRH222 | URA3.2 | |
|---|---|---|
| WT | AAACCAACCTGTGTGCTTCTCTGGATGTTACCACCACCA | SEQ ID NO: 195 |
| Colony3 | AAACCAACCTGTGT**T**GNTNNNNNG | SEQ ID NO: 196 |
| Colony4 | AAACCAACCTGTGTG**T**TTCTNGGNNTNNNCCCCCCCC | SEQ ID NO: 197 |
| Colony5 | AAACCAACCTGTGTG**TG**TCTCTGGATGTTACCACCACNN | SEQ ID NO: 198 |
| Colony6 | AAACCAACCTGTGTG**T**TTTCNNGGNNNT | SEQ ID NO: 199 |
| Colony9 | AAACCAACCTGTGT**T**GCTTCTCTGGATGT | SEQ ID NO: 200 |
| Colony10 | AAACCAACCTGTGNNTTCNNNNGNNNNTNCCNCCCCCNA | SEQ ID NO: 201 |

Figure 16-C

```
pYRH282   URA3.2                                  URA3.1                      SEQ ID NO
WT   AAACCAACCTGTGTGCTTCTCTGGATGTT       GCTGGTGCCGAGGAAACTGTCTCTGAACAGAAGA       202
23   AAACCAACCTGTG-----------------Deletion---------------AAACTGTCTCTGAACAGAAGA  203
24   AAACCAACCTGTG-----------------Deletion---------------AAACTGTCTCTGANCNNAANA  204
```

Figure 16-D

```
pYRH283   URA3.2                                            URA3.3            SEQ ID NO
WT   AAACCAACCTGTGTGCTTCTCTGGATGTT       ATTAACTGTTAGAGGTTAGACTATGGATATGTA        205
27   AAACCAACCTGTGT-----------------Deletion---------------------CTATGGATATGTA    206
36   AAACCAACCTGTG------------------Deletion--------------------------GATATGTA    207
```

Figure 18

| | | |
|---|---|---|
| CAN1-WT | GAAAAGACATTTTCAAACGATTACCCACCCTC**CGG**GACTGAGGCC | SEQ ID NO: 215 |
| Colony 14 | GAAAAGACATTTTCAAACGATTACCCACC-TC**CGG**GACTGAGGCC | SEQ ID NO: 216 |
| Colony 16 | GAAAAGACATTTTCAAACGATTACCCACCCTC**CGG**GACTGAGGCC | SEQ ID NO: 217 |
| Colony 18 | GAAAAGACATTTTCAAACGATTACCCACC-TC**CGG**GACTGAGGCC | SEQ ID NO: 218 |
| Colony 19 | GAAAANACNTTTTCAAACGATTACCCACC-TC**CGG**GACTGAGGCC | SEQ ID NO: 219 |
| Colony 24 | GAAAAGACATTTTCAAACGATTACCCACC-TC**CGG**GACTGAGGCC | SEQ ID NO: 220 |
| Colony 25 | GAAAAGACATTTTCAAACGATTACCCACC-TC**CGG**GACTGAGGCC | SEQ ID NO: 221 |

SEQUENCE LISTING

<160> NUMBER OF SEQ ID NOS: 224

<210> SEQ ID NO 1
<211> LENGTH: 80
<212> TYPE: RNA
<213> ORGANISM: artificial sequence
<220> FEATURE:
<223> OTHER INFORMATION: Cas9 endonuclease recognition (CER) domain

<400> SEQUENCE: 1
guuuuagagc uagaaauagc aaguuaaaau aaggcuaguc cguuaucaac uugaaaaagu 60
ggcaccgagu cggugcuuuu 80

<210> SEQ ID NO 2
<211> LENGTH: 20
<212> TYPE: DNA
<213> ORGANISM: Yarrowia lipolytica

<400> SEQUENCE: 2
tccaagaaga ttgttcttct 20

<210> SEQ ID NO 3
<211> LENGTH: 20
<212> TYPE: DNA
<213> ORGANISM: Yarrowia lipolytica

<400> SEQUENCE: 3
ctccgtcatc cccggttctc 20

<210> SEQ ID NO 4
<211> LENGTH: 20
<212> TYPE: DNA
<213> ORGANISM: Yarrowia lipolytica

<400> SEQUENCE: 4
cggcgacttc tgtggccccg 20

<210> SEQ ID NO 5
<211> LENGTH: 300
<212> TYPE: DNA
<213> ORGANISM: Saccharomyces cerevisiae

<400> SEQUENCE: 5
aacaattatc tcaaaattca cccactcttc atctttgaaa agataatgta tgattatgct 60
ttcactcata tttatacaga aacttgatgt tttctttcga gtatatacaa ggtgattaca 120
tgtacgtttg aagtacaact ctagattttg tagtgccctc ttgggctagc ggtaaaggtg 180
cgcatttttt cacaccctac aatgttctgt tcaaaagatt ttggtcaaac gctgtagaag 240
tgaaagttgg tgcgcatgtt tcggcgttcg aaacttctcc gcagtgaaag ataaatgatc 300

<210> SEQ ID NO 6
<211> LENGTH: 300
<212> TYPE: DNA
<213> ORGANISM: Saccharomyces cerevisiae

<400> SEQUENCE: 6
taaaaatcaa tcaatcatcg tgtgttttat atgtctctta tctaagtata agaatatcca 60
tagttaatat tcacttacgc taccttttaa cctgtaatca ttgtcaacag gatatgttaa 120
cgacccacat tgataaacgc tagtatttct ttttcctctt cttattggcc ggctgtctct 180
atactcccct atagtctgtt tcttttcgtt tcgattgttt tacgtttgag gcctcgtggc 240
gcacatggta cgctgtggtg ctcgcggctg ggaacgaaac tctgggagct gcgattggca 300

<210> SEQ ID NO 7
<211> LENGTH: 300
<212> TYPE: DNA
<213> ORGANISM: Yarrowia lipolytica

<400> SEQUENCE: 7
attttttttg attttctttt ttgaccccgt cttcaattac acttcccaac tgggaacacc 60
cctctttatc gacccatttt aggtaattta ccctagccca ttgtctccat aaggaatatt 120
accctaaccc acagtccagg gtgcccaggt ccttctttgg ccaaatttta acttcggtcc 180
tatggcacag cggtagcgcg tgagattgca aatcttaagg tcccgagttc gaatctcggt 240
gggacctagt tatttttgat agataatttc gtgatgatta gaaacttaac gcaaaataat 300

<210> SEQ ID NO 8
<211> LENGTH: 20
<212> TYPE: DNA
<213> ORGANISM: Saccharomyces cerevisiae

<400> SEQUENCE: 8
tttttttgtt ttttatgtct 20

<210> SEQ ID NO 9
<211> LENGTH: 4107
<212> TYPE: DNA
<213> ORGANISM: artificial sequence
<220> FEATURE:
<223> OTHER INFORMATION: S. pyogenes Cas9

<400> SEQUENCE: 9
atggacaaga aatactccat cggcctggac attggaacca actctgtcgg ctgggctgtc 60
atcaccgacg agtacaaggt gccctccaag aaattcaagg tcctcggaaa caccgatcga 120
cactccatca agaaaaacct cattggtgcc ctgttgttcg attctggcga gactgccgaa 180
gctaccagac tcaagcgaac tgctcggcga cgttacaccc gacggaagaa ccgaatctgc 240
tacctgcagg agatcttttc caacgagatg gccaaggtgg acgattcgtt ctttcatcga 300
ctggaggaat ccttcctcgt cgaggaagac aagaaacacg agcgtcatcc catctttggc 360
aacattgtgg acgaggttgc ttaccacgag aagtatccta ccatctacca cctgcgaaag 420
aaactcgtcg attccaccga caaggcggat ctcagactta tctacctcgc tctggcacac 480
atgatcaagt ttcgaggtca tttcctcatc gagggcgatc tcaatcccga caacagcgat 540
gtggacaagc tgttcattca gctcgttcag acctacaacc agctgttcga ggaaaacccc 600
atcaatgcct ccggagtcga tgcaaaggcc atcttgtctg ctcgactctc gaagagcaga 660
cgactggaga acctcattgc ccaacttcct ggcgagaaaa agaacggact gtttggcaac 720
ctcattgccc tttctcttgg tctcacaccc aacttcaagt ccaacttcga tctggcggag 780
gacgccaagc tccagctgtc caaggacacc tacgacgatg acctcgacaa cctgcttgca 840
cagattggcg atcagtacgc cgacctgttt ctcgctgcca agaacctttc ggatgctatt 900
ctcttgtctg acattctgcg agtcaacacc gagatcacaa aggctcccct ttctgcctcc 960
atgatcaagc gatacgacga gcaccatcag gatctcacac tgctcaaggc tcttgtccga 1020
cagcaactgc ccgagaagta caaggagatc tttttcgatc agtcgaagaa cggctacgct 1080
ggatacatcg acggcggagc ctctcaggaa gagttctaca agttcatcaa gccaattctc 1140

-continued

```
gagaagatgg acggaaccga ggaactgctt gtcaagctca atcgagagga tctgcttcgg   1200
aagcaacgaa ccttcgacaa cggcagcatt cctcatcaga tccacctcgg tgagctgcac   1260
gccattcttc gacgtcagga agacttctac ccctttctca aggacaaccg agagaagatc   1320
gagaagattc ttacctttcg aatcccctac tatgttggtc ctcttgccag aggaaactct   1380
cgatttgctt ggatgactcg aaagtccgag gaaaccatca ctccctggaa cttcgaggaa   1440
gtcgtggaca agggtgcctc tgcacagtcc ttcatcgagc gaatgaccaa cttcgacaag   1500
aatctgccca acgagaaggt tcttcccaag cattcgctgc tctacgagta ctttacagtc   1560
tacaacgaac tcaccaaagt caagtacgtt accgagggaa tgcgaaagcc tgccttcttg   1620
tctggcgaac agaagaaagc cattgtcgat ctcctgttca agaccaaccg aaaggtcact   1680
gttaagcagc tcaaggagga ctacttcaag aaaatcgagt gtttcgacag cgtcgagatt   1740
tccggagttg aggaccgatt caacgcctct ttgggcacct atcacgatct gctcaagatt   1800
atcaaggaca aggattttct cgacaacgag gaaaacgagg acattctgga ggacatcgtg   1860
ctcactctta ccctgttcga agatcgggag atgatcgagg aacgactcaa gacatacgct   1920
cacctgttcg acgacaaggt catgaaacaa ctcaagcgac gtagatacac cggctgggga   1980
agactttcgc gaaagctcat caacggcatc agagacaagc agtccggaaa gaccattctg   2040
gactttctca agtccgatgg ctttgccaac cgaaacttca tgcagctcat tcacgacgat   2100
tctcttacct tcaaggagga catccagaag gcacaagtgt ccggtcaggg cgacagcttg   2160
cacgaacata ttgccaacct ggctggttcg ccagccatca agaaaggcat tctccagact   2220
gtcaaggttg tcgacgagct ggtgaaggtc atgggacgtc acaagcccga gaacattgtg   2280
atcgagatgg ccagagagaa ccagacaact caaaagggtc agaaaaactc gcgagagcgg   2340
atgaagcgaa tcgaggaagg catcaaggag ctgggatccc agattctcaa ggagcatccc   2400
gtcgagaaca ctcaactgca gaacgagaag ctgtatctct actatctgca gaatggtcga   2460
gacatgtacg tggatcagga actggacatc aatcgtctca gcgactacga tgtggaccac   2520
attgtccctc aatcctttct caaggacgat tctatcgaca acaaggtcct tacacgatcc   2580
gacaagaaca gaggcaagtc ggacaacgtt cccagcgaag aggtggtcaa aaagatgaag   2640
aactactggc gacagctgct caacgccaag ctcattaccc agcgaaagtt cgacaatctt   2700
accaaggccg agcgaggcgg tctgtccgag ctcgacaagg ctggcttcat caagcgtcaa   2760
ctcgtcgaga ccagacagat cacaaagcac gtcgcacaga ttctcgattc tcggatgaac   2820
accaagtacg acgagaacga caagctcatc cgagaggtca aggtgattac tctcaagtcc   2880
aaactggtct ccgatttccg aaaggacttt cagttctaca aggtgcgaga gatcaacaat   2940
taccaccatg cccacgatgc ttacctcaac gccgtcgttg gcactgcgct catcaagaaa   3000
taccccaagc tcgaaagcga gttcgtttac ggcgattaca aggtctacga cgttcgaaag   3060
atgattgcca agtccgaaca ggagattggc aaggctactg ccaagtactt cttttactcc   3120
aacatcatga actttttcaa gaccgagatc accttggcca acggagagat tcgaaagaga   3180
ccacttatcg agaccaacgg cgaaactgga gagatcgtgt gggacaaggg tcgagacttt   3240
gcaaccgtgc gaaaggttct gtcgatgcct caggtcaaca tcgtcaagaa aaccgaggtt   3300
cagactggcg gattctccaa ggagtcgatt ctgcccaagc gaaactccga caagctcatc   3360
gctcgaaaga aagactggga tcccaagaaa tacggtggct tcgattctcc taccgtcgcc   3420
tattccgtgc ttgtcgttgc gaaggtcgag aagggcaagt ccaaaaagct caagtccgtc   3480
aaggagctgc tcggaattac catcatggag cgatcgagct tcgagaagaa tcccatcgac   3540
```

```
ttcttggaag ccaagggtta caaggaggtc aagaaagacc tcattatcaa gctgcccaag   3600

tactctctgt tcgaactgga gaacggtcga aagcgtatgc tcgcctccgc tggcgagctg   3660

cagaagggaa acgagcttgc cttgccttcg aagtacgtca actttctcta tctggcttct   3720

cactacgaga agctcaaggg ttctcccgag gacaacgaac agaagcaact cttcgttgag   3780

cagcacaaac attacctcga cgagattatc gagcagattt ccgagttttc gaagcgagtc   3840

atcctggctg atgccaactt ggacaaggtg ctctctgcct acaacaagca tcgggacaaa   3900

cccattcgag aacaggcgga gaacatcatt cacctgttta ctcttaccaa cctgggtgct   3960

cctgcagctt tcaagtactt cgataccact atcgaccgaa agcggtacac atccaccaag   4020

gaggttctcg atgccaccct gattcaccag tccatcactg gcctgtacga gacccgaatc   4080

gacctgtctc agcttggtgg cgactaa                                       4107
```

<210> SEQ ID NO 10
<211> LENGTH: 4140
<212> TYPE: DNA
<213> ORGANISM: artificial sequence
<220> FEATURE:
<223> OTHER INFORMATION: S. pyogenes Cas9 with NLS

<400> SEQUENCE: 10

```
atggacaaga aatactccat cggcctggac attggaacca actctgtcgg ctgggctgtc     60

atcaccgacg agtacaaggt gccctccaag aaattcaagg tcctcggaaa caccgatcga    120

cactccatca agaaaaacct cattggtgcc ctgttgttcg attctggcga gactgccgaa    180

gctaccagac tcaagcgaac tgctcggcga cgttacaccc gacggaagaa ccgaatctgc    240

tacctgcagg agatcttttc caacgagatg gccaaggtgg acgattcgtt ctttcatcga    300

ctggaggaat ccttcctcgt cgaggaagac aagaaacacg agcgtcatcc catctttggc    360

aacattgtgg acgaggttgc ttaccacgag aagtatccta ccatctacca cctgcgaaag    420

aaactcgtcg attccaccga caaggcggat ctcagactta tctacctcgc tctggcacac    480

atgatcaagt ttcgaggtca tttcctcatc gagggcgatc tcaatcccga caacagcgat    540

gtggacaagc tgttcattca gctcgttcag acctacaacc agctgttcga ggaaaacccc    600

atcaatgcct ccggagtcga tgcaaaggcc atcttgtctg ctcgactctc gaagagcaga    660

cgactggaga acctcattgc ccaacttcct ggcgagaaaa agaacggact gtttggcaac    720

ctcattgccc tttctcttgg tctcacaccc aacttcaagt ccaacttcga tctggcggag    780

gacgccaagc tccagctgtc caaggacacc tacgacgatg acctcgacaa cctgcttgca    840

cagattggcg atcagtacgc cgacctgttt ctcgctgcca agaacctttc ggatgctatt    900

ctcttgtctg acattctgcg agtcaacacc gagatcacaa aggctcccct ttctgcctcc    960

atgatcaagc gatacgacga gcaccatcag gatctcacac tgctcaaggc tcttgtccga   1020

cagcaactgc ccgagaagta caaggagatc tttttcgatc agtcgaagaa cggctacgct   1080

ggatacatcg acggcggagc ctctcaggaa gagttctaca agttcatcaa gccaattctc   1140

gagaagatgg acggaaccga ggaactgctt gtcaagctca atcgagagga tctgcttcgg   1200

aagcaacgaa ccttcgacaa cggcagcatt cctcatcaga tccacctcgg tgagctgcac   1260

gccattcttc gacgtcagga agacttctac ccctttctca aggacaaccg agagaagatc   1320

gagaagattc ttacctttcg aatcccctac tatgttggtc ctcttgccag aggaaactct   1380

cgatttgctt ggatgactcg aaagtccgag gaaaccatca ctccctggaa cttcgaggaa   1440
```

-continued

```
gtcgtggaca agggtgcctc tgcacagtcc ttcatcgagc gaatgaccaa cttcgacaag   1500
aatctgccca acgagaaggt tcttcccaag cattcgctgc tctacgagta ctttacagtc   1560
tacaacgaac tcaccaaagt caagtacgtt accgagggaa tgcgaaagcc tgccttcttg   1620
tctggcgaac agaagaaagc cattgtcgat ctcctgttca agaccaaccg aaaggtcact   1680
gttaagcagc tcaaggagga ctacttcaag aaaatcgagt gtttcgacag cgtcgagatt   1740
tccggagttg aggaccgatt caacgcctct ttgggcacct atcacgatct gctcaagatt   1800
atcaaggaca aggattttct cgacaacgag gaaaacgagg acattctgga ggacatcgtg   1860
ctcactctta ccctgttcga agatcgggag atgatcgagg aacgactcaa gacatacgct   1920
cacctgttcg acgacaaggt catgaaacaa ctcaagcgac gtagatacac cggctgggga   1980
agactttcgc gaaagctcat caacggcatc agagacaagc agtccggaaa gaccattctg   2040
gactttctca agtccgatgg ctttgccaac cgaaacttca tgcagctcat tcacgacgat   2100
tctcttacct tcaaggagga catccagaag gcacaagtgt ccggtcaggg cgacagcttg   2160
cacgaacata ttgccaacct ggctggttcg ccagccatca agaaaggcat tctccagact   2220
gtcaaggttg tcgacgagct ggtgaaggtc atgggacgtc acaagcccga gaacattgtg   2280
atcgagatgg ccagagagaa ccagacaact caaaagggtc agaaaaactc gcgagagcgg   2340
atgaagcgaa tcgaggaagg catcaaggag ctgggatccc agattctcaa ggagcatccc   2400
gtcgagaaca ctcaactgca gaacgagaag ctgtatctct actatctgca gaatggtcga   2460
gacatgtacg tggatcagga actggacatc aatcgtctca gcgactacga tgtggaccac   2520
attgtccctc aatcctttct caaggacgat tctatcgaca acaaggtcct tacacgatcc   2580
gacaagaaca gaggcaagtc ggacaacgtt cccagcgaag aggtggtcaa aaagatgaag   2640
aactactggc gacagctgct caacgccaag ctcattaccc agcgaaagtt cgacaatctt   2700
accaaggccg agcgaggcgg tctgtccgag ctcgacaagg ctggcttcat caagcgtcaa   2760
ctcgtcgaga ccagacagat cacaaagcac gtcgcacaga ttctcgattc tcggatgaac   2820
accaagtacg acgagaacga caagctcatc cgagaggtca aggtgattac tctcaagtcc   2880
aaactggtct ccgatttccg aaaggacttt cagttctaca aggtgcgaga gatcaacaat   2940
taccaccatg cccacgatgc ttacctcaac gccgtcgttg gcactgcgct catcaagaaa   3000
taccccaagc tcgaaagcga gttcgtttac ggcgattaca aggtctacga cgttcgaaag   3060
atgattgcca agtccgaaca ggagattggc aaggctactg ccaagtactt cttttactcc   3120
aacatcatga actttttcaa gaccgagatc accttggcca acggagagat tcgaaagaga   3180
ccacttatcg agaccaacgg cgaaactgga gagatcgtgt gggacaaggg tcgagacttt   3240
gcaaccgtgc gaaaggttct gtcgatgcct caggtcaaca tcgtcaagaa aaccgaggtt   3300
cagactggcg gattctccaa ggagtcgatt ctgcccaagc gaaactccga caagctcatc   3360
gctcgaaaga aagactggga tcccaagaaa tacggtggct tcgattctcc taccgtcgcc   3420
tattccgtgc ttgtcgttgc gaaggtcgag aagggcaagt ccaaaaagct caagtccgtc   3480
aaggagctgc tcggaattac catcatggag cgatcgagct tcgagaagaa tcccatcgac   3540
ttcttggaag ccaagggtta caaggaggtc aagaaagacc tcattatcaa gctgcccaag   3600
tactctctgt tcgaactgga gaacggtcga aagcgtatgc tcgcctccgc tggcgagctg   3660
cagaagggaa acgagcttgc cttgccttcg aagtacgtca actttctcta tctggcttct   3720
cactacgaga agctcaaggg ttctcccgag gacaacgaac agaagcaact cttcgttgag   3780
cagcacaaac attacctcga cgagattatc gagcagattt ccgagttttc gaagcgagtc   3840
```

```
atcctggctg atgccaactt ggacaaggtg ctctctgcct acaacaagca tcgggacaaa   3900

cccattcgag aacaggcgga gaacatcatt cacctgttta ctcttaccaa cctgggtgct   3960

cctgcagctt tcaagtactt cgataccact atcgaccgaa agcggtacac atccaccaag   4020

gaggttctcg atgccaccct gattcaccag tccatcactg gcctgtacga gacccgaatc   4080

gacctgtctc agcttggtgg cgactccaga gccgatccca agaaaaagcg aaaggtctaa   4140


<210> SEQ ID NO 11
<211> LENGTH: 1379
<212> TYPE: PRT
<213> ORGANISM: artificial sequence
<220> FEATURE:
<223> OTHER INFORMATION: S. pyogenes Cas9 with NLS

<400> SEQUENCE: 11

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
```

-continued

```
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735
```

-continued

```
Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140
```

```
Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

Ser Arg Ala Asp Pro Lys Lys Lys Arg Lys Val
    1370                1375
```

<210> SEQ ID NO 12
<211> LENGTH: 543
<212> TYPE: DNA
<213> ORGANISM: Yarrowia lipolytica

<400> SEQUENCE: 12

```
tcgacgttta aaccatcatc taagggcctc aaaactacct cggaactgct gcgctgatct     60

ggacaccaca gaggttccga gcactttagg ttgcaccaaa tgtcccacca ggtgcaggca    120

gaaaacgctg gaacagcgtg tacagtttgt cttaacaaaa agtgagggcg ctgaggtcga    180

gcagggtggt gtgacttgtt atagccttta gagctgcgaa agcgcgtatg gatttggctc    240

atcaggccag attgagggtc tgtggacaca tgtcatgtta gtgtacttca atcgcccccct    300

ggatatagcc ccgacaatag gccgtggcct catttttttg ccttccgcac atttccattg    360

ctcggtaccc acaccttgct tctcctgcac ttgccaacct taatactggt ttacattgac    420

caacatctta caagcggggg gcttgtctag ggtatatata aacagtggct ctcccaatcg    480

gttgccagtc tctttttcc tttctttccc cacagattcg aaatctaaac tacacatcac    540

acc                                                                   543
```

<210> SEQ ID NO 13
<211> LENGTH: 4683

<212> TYPE: DNA
<213> ORGANISM: artificial sequence
<220> FEATURE:
<223> OTHER INFORMATION: Cas9-NLS expression cassette

<400> SEQUENCE: 13
tcgacgttta aaccatcatc taagggcctc aaaactacct cggaactgct gcgctgatct 60
ggacaccaca gaggttccga gcactttagg ttgcaccaaa tgtcccacca ggtgcaggca 120
gaaaacgctg gaacagcgtg tacagtttgt cttaacaaaa agtgagggcg ctgaggtcga 180
gcagggtggt gtgacttgtt atagccttta gagctgcgaa agcgcgtatg gatttggctc 240
atcaggccag attgagggtc tgtggacaca tgtcatgtta gtgtacttca atcgcccct 300 ggatatagcc ccgacaatag gccgtggcct catttttttg ccttccgcac atttccattg 360
ctcggtaccc acaccttgct tctcctgcac ttgccaacct taatactggt ttacattgac 420
caacatctta caagcggggg gcttgtctag ggtatatata aacagtggct ctcccaatcg 480
gttgccagtc tcttttttcc tttctttccc cacagattcg aaatctaaac tacacatcac 540
accatggaca agaaatactc catcggcctg gacattggaa ccaactctgt cggctgggct 600
gtcatcaccg acgagtacaa ggtgccctcc aagaaattca aggtcctcgg aaacaccgat 660
cgacactcca tcaagaaaaa cctcattggt gccctgttgt tcgattctgg cgagactgcc 720
gaagctacca gactcaagcg aactgctcgg cgacgttaca cccgacggaa gaaccgaatc 780
tgctacctgc aggagatctt ttccaacgag atggccaagg tggacgattc gttctttcat 840
cgactggagg aatccttcct cgtcgaggaa gacaagaaac acgagcgtca tcccatcttt 900
ggcaacattg tggacgaggt tgcttaccac gagaagtatc ctaccatcta ccacctgcga 960
aagaaactcg tcgattccac cgacaaggcg gatctcagac ttatctacct cgctctggca 1020
cacatgatca agtttcgagg tcatttcctc atcgagggcg atctcaatcc cgacaacagc 1080
gatgtggaca agctgttcat tcagctcgtt cagacctaca accagctgtt cgaggaaaac 1140
cccatcaatg cctccggagt cgatgcaaag gccatcttgt ctgctcgact ctcgaagagc 1200
agacgactgg agaacctcat tgcccaactt cctggcgaga aaaagaacgg actgtttggc 1260
aacctcattg ccctttctct tggtctcaca cccaacttca agtccaactt cgatctggcg 1320
gaggacgcca agctccagct gtccaaggac acctacgacg atgacctcga caacctgctt 1380
gcacagattg gcgatcagta cgccgacctg tttctcgctg ccaagaacct ttcggatgct 1440
attctcttgt ctgacattct gcgagtcaac accgagatca caaaggctcc cctttctgcc 1500
tccatgatca agcgatacga cgagcaccat caggatctca cactgctcaa ggctcttgtc 1560
cgacagcaac tgcccgagaa gtacaaggag atctttttcg atcagtcgaa gaacggctac 1620
gctggataca tcgacggcgg agcctctcag gaagagttct acaagttcat caagccaatt 1680
ctcgagaaga tggacggaac cgaggaactg cttgtcaagc tcaatcgaga ggatctgctt 1740
cggaagcaac gaaccttcga caacggcagc attcctcatc agatccacct cggtgagctg 1800
cacgccattc ttcgacgtca ggaagacttc taccccttc tcaaggacaa ccgagagaag 1860
atcgagaaga ttcttacctt tcgaatcccc tactatgttg gtcctcttgc cagaggaaac 1920
tctcgatttg cttggatgac tcgaaagtcc gaggaaacca tcactccctg gaacttcgag 1980
gaagtcgtgg acaagggtgc ctctgcacag tccttcatcg agcgaatgac caacttcgac 2040
aagaatctgc ccaacgagaa ggttcttccc aagcattcgc tgctctacga gtactttaca 2100
gtctacaacg aactcaccaa agtcaagtac gttaccgagg gaatgcgaaa gcctgccttc 2160

-continued

```
ttgtctggcg aacagaagaa agccattgtc gatctcctgt tcaagaccaa ccgaaaggtc   2220
actgttaagc agctcaagga ggactacttc aagaaaatcg agtgtttcga cagcgtcgag   2280
atttccggag ttgaggaccg attcaacgcc tctttgggca cctatcacga tctgctcaag   2340
attatcaagg acaaggattt tctcgacaac gaggaaaacg aggacattct ggaggacatc   2400
gtgctcactc ttaccctgtt cgaagatcgg gagatgatcg aggaacgact caagacatac   2460
gctcacctgt tcgacgacaa ggtcatgaaa caactcaagc gacgtagata caccggctgg   2520
ggaagacttt cgcgaaagct catcaacggc atcagagaca agcagtccgg aaagaccatt   2580
ctggactttc tcaagtccga tggctttgcc aaccgaaact tcatgcagct cattcacgac   2640
gattctctta ccttcaagga ggacatccag aaggcacaag tgtccggtca gggcgacagc   2700
ttgcacgaac atattgccaa cctggctggt tcgccagcca tcaagaaagg cattctccag   2760
actgtcaagg ttgtcgacga gctggtgaag gtcatgggac gtcacaagcc cgagaacatt   2820
gtgatcgaga tggccagaga gaaccagaca actcaaaagg gtcagaaaaa ctcgcgagag   2880
cggatgaagc gaatcgagga aggcatcaag gagctgggat cccagattct caaggagcat   2940
cccgtcgaga acactcaact gcagaacgag aagctgtatc tctactatct gcagaatggt   3000
cgagacatgt acgtggatca ggaactggac atcaatcgtc tcagcgacta cgatgtggac   3060
cacattgtcc ctcaatcctt tctcaaggac gattctatcg acaacaaggt ccttacacga   3120
tccgacaaga acagaggcaa gtcggacaac gttcccagcg aagaggtggt caaaaagatg   3180
aagaactact ggcgacagct gctcaacgcc aagctcatta cccagcgaaa gttcgacaat   3240
cttaccaagg ccgagcgagg cggtctgtcc gagctcgaca aggctggctt catcaagcgt   3300
caactcgtcg agaccagaca gatcacaaag cacgtcgcac agattctcga ttctcggatg   3360
aacaccaagt acgacgagaa cgacaagctc atccgagagg tcaaggtgat tactctcaag   3420
tccaaactgg tctccgattt ccgaaaggac tttcagttct acaaggtgcg agagatcaac   3480
aattaccacc atgcccacga tgcttacctc aacgccgtcg ttggcactgc gctcatcaag   3540
aaatacccca agctcgaaag cgagttcgtt tacggcgatt acaaggtcta cgacgttcga   3600
aagatgattg ccaagtccga acaggagatt ggcaaggcta ctgccaagta cttcttttac   3660
tccaacatca tgaacttttt caagaccgag atcaccttgg ccaacggaga gattcgaaag   3720
agaccactta tcgagaccaa cggcgaaact ggagagatcg tgtgggacaa gggtcgagac   3780
tttgcaaccg tgcgaaaggt tctgtcgatg cctcaggtca acatcgtcaa gaaaaccgag   3840
gttcagactg gcggattctc caaggagtcg attctgccca agcgaaactc cgacaagctc   3900
atcgctcgaa agaaagactg ggatcccaag aaatacggtg gcttcgattc tcctaccgtc   3960
gcctattccg tgcttgtcgt tgcgaaggtc gagaagggca agtccaaaaa gctcaagtcc   4020
gtcaaggagc tgctcggaat taccatcatg gagcgatcga gcttcgagaa gaatcccatc   4080
gacttcttgg aagccaaggg ttacaaggag gtcaagaaag acctcattat caagctgccc   4140
aagtactctc tgttcgaact ggagaacggt cgaaagcgta tgctcgcctc cgctggcgag   4200
ctgcagaagg gaaacgagct tgccttgcct tcgaagtacg tcaactttct ctatctggct   4260
tctcactacg agaagctcaa gggttctccc gaggacaacg aacagaagca actcttcgtt   4320
gagcagcaca aacattacct cgacgagatt atcgagcaga tttccgagtt ttcgaagcga   4380
gtcatcctgg ctgatgccaa cttggacaag gtgctctctg cctacaacaa gcatcgggac   4440
aaacccattc gagaacaggc ggagaacatc attcacctgt ttactcttac caacctgggt   4500
gctcctgcag ctttcaagta cttcgatacc actatcgacc gaaagcggta cacatccacc   4560
```

-continued aaggaggttc tcgatgccac cctgattcac cagtccatca ctggcctgta cgagacccga 4620
atcgacctgt ctcagcttgg tggcgactcc agagccgatc ccaagaaaaa gcgaaaggtc 4680
taa 4683

<210> SEQ ID NO 14
<211> LENGTH: 10706
<212> TYPE: DNA
<213> ORGANISM: artificial sequence
<220> FEATURE:
<223> OTHER INFORMATION: pZUFCas9 plasmid

<400> SEQUENCE: 14
catggacaag aaatactcca tcggcctgga cattggaacc aactctgtcg gctgggctgt 60
catcaccgac gagtacaagg tgccctccaa gaaattcaag gtcctcggaa acaccgatcg 120
acactccatc aagaaaaacc tcattggtgc cctgttgttc gattctggcg agactgccga 180
agctaccaga ctcaagcgaa ctgctcggcg acgttacacc cgacggaaga accgaatctg 240
ctacctgcag gagatctttt ccaacgagat ggccaaggtg gacgattcgt tctttcatcg 300
actggaggaa tccttcctcg tcgaggaaga caagaaacac gagcgtcatc ccatctttgg 360
caacattgtg gacgaggttg cttaccacga gaagtatcct accatctacc acctgcgaaa 420
gaaactcgtc gattccaccg acaaggcgga tctcagactt atctacctcg ctctggcaca 480
catgatcaag tttcgaggtc atttcctcat cgagggcgat ctcaatcccg acaacagcga 540
tgtggacaag ctgttcattc agctcgttca gacctacaac cagctgttcg aggaaaaccc 600
catcaatgcc tccggagtcg atgcaaaggc catcttgtct gctcgactct cgaagagcag 660
acgactggag aacctcattg cccaacttcc tggcgagaaa aagaacggac tgtttggcaa 720
cctcattgcc ctttctcttg gtctcacacc caacttcaag tccaacttcg atctggcgga 780
ggacgccaag ctccagctgt ccaaggacac ctacgacgat gacctcgaca acctgcttgc 840
acagattggc gatcagtacg ccgacctgtt tctcgctgcc aagaaccttt cggatgctat 900
tctcttgtct gacattctgc gagtcaacac cgagatcaca aaggctcccc tttctgcctc 960
catgatcaag cgatacgacg agcaccatca ggatctcaca ctgctcaagg ctcttgtccg 1020
acagcaactg cccgagaagt acaaggagat ctttttcgat cagtcgaaga acggctacgc 1080
tggatacatc gacggcggag cctctcagga agagttctac aagttcatca agccaattct 1140
cgagaagatg gacggaaccg aggaactgct tgtcaagctc aatcgagagg atctgcttcg 1200
gaagcaacga accttcgaca acggcagcat tcctcatcag atccacctcg gtgagctgca 1260
cgccattctt cgacgtcagg aagacttcta cccctttctc aaggacaacc gagagaagat 1320
cgagaagatt cttacctttc gaatccccta ctatgttggt cctcttgcca gaggaaactc 1380
tcgatttgct tggatgactc gaaagtccga ggaaaccatc actccctgga acttcgagga 1440
agtcgtggac aagggtgcct ctgcacagtc cttcatcgag cgaatgacca acttcgacaa 1500
gaatctgccc aacgagaagg ttcttcccaa gcattcgctg ctctacgagt actttacagt 1560
ctacaacgaa ctcaccaaag tcaagtacgt taccgaggga atgcgaaagc ctgccttctt 1620
gtctggcgaa cagaagaaag ccattgtcga tctcctgttc aagaccaacc gaaaggtcac 1680
tgttaagcag ctcaaggagg actacttcaa gaaaatcgag tgtttcgaca gcgtcgagat 1740
ttccggagtt gaggaccgat tcaacgcctc tttgggcacc tatcacgatc tgctcaagat 1800
tatcaaggac aaggattttc tcgacaacga ggaaaacgag gacattctgg aggacatcgt 1860

-continued

```
gctcactctt accctgttcg aagatcggga gatgatcgag gaacgactca agacatacgc   1920
tcacctgttc gacgacaagg tcatgaaaca actcaagcga cgtagataca ccggctgggg   1980
aagactttcg cgaaagctca tcaacggcat cagagacaag cagtccggaa agaccattct   2040
ggactttctc aagtccgatg gctttgccaa ccgaaacttc atgcagctca ttcacgacga   2100
ttctcttacc ttcaaggagg acatccagaa ggcacaagtg tccggtcagg gcgacagctt   2160
gcacgaacat attgccaacc tggctggttc gccagccatc aagaaaggca ttctccagac   2220
tgtcaaggtt gtcgacgagc tggtgaaggt catgggacgt cacaagcccg agaacattgt   2280
gatcgagatg gccagagaga accagacaac tcaaaagggt cagaaaaact cgcgagagcg   2340
gatgaagcga atcgaggaag gcatcaagga gctgggatcc cagattctca aggagcatcc   2400
cgtcgagaac actcaactgc agaacgagaa gctgtatctc tactatctgc agaatggtcg   2460
agacatgtac gtggatcagg aactggacat caatcgtctc agcgactacg atgtggacca   2520
cattgtccct caatcctttc tcaaggacga ttctatcgac aacaaggtcc ttacacgatc   2580
cgacaagaac agaggcaagt cggacaacgt tcccagcgaa gaggtggtca aaaagatgaa   2640
gaactactgg cgacagctgc tcaacgccaa gctcattacc cagcgaaagt tcgacaatct   2700
taccaaggcc gagcgaggcg gtctgtccga gctcgacaag gctggcttca tcaagcgtca   2760
actcgtcgag accagacaga tcacaaagca cgtcgcacag attctcgatt ctcggatgaa   2820
caccaagtac gacgagaacg acaagctcat ccgagaggtc aaggtgatta ctctcaagtc   2880
caaactggtc tccgatttcc gaaaggactt tcagttctac aaggtgcgag agatcaacaa   2940
ttaccaccat gcccacgatg cttacctcaa cgccgtcgtt ggcactgcgc tcatcaagaa   3000
ataccccaag ctcgaaagcg agttcgttta cggcgattac aaggtctacg acgttcgaaa   3060
gatgattgcc aagtccgaac aggagattgg caaggctact gccaagtact tcttttactc   3120
caacatcatg aactttttca agaccgagat caccttggcc aacggagaga ttcgaaagag   3180
accacttatc gagaccaacg gcgaaactgg agagatcgtg tgggacaagg gtcgagactt   3240
tgcaaccgtg cgaaaggttc tgtcgatgcc tcaggtcaac atcgtcaaga aaaccgaggt   3300
tcagactggc ggattctcca aggagtcgat tctgcccaag cgaaactccg acaagctcat   3360
cgctcgaaag aaagactggg atcccaagaa atacggtggc ttcgattctc ctaccgtcgc   3420
ctattccgtg cttgtcgttg cgaaggtcga gaagggcaag tccaaaaagc tcaagtccgt   3480
caaggagctg ctcggaatta ccatcatgga gcgatcgagc ttcgagaaga atcccatcga   3540
cttcttggaa gccaagggtt acaaggaggt caagaaagac ctcattatca agctgcccaa   3600
gtactctctg ttcgaactgg agaacggtcg aaagcgtatg ctcgcctccg ctggcgagct   3660
gcagaaggga aacgagcttg ccttgccttc gaagtacgtc aactttctct atctggcttc   3720
tcactacgag aagctcaagg gttctcccga ggacaacgaa cagaagcaac tcttcgttga   3780
gcagcacaaa cattacctcg acgagattat cgagcagatt tccgagtttt cgaagcgagt   3840
catcctggct gatgccaact tggacaaggt gctctctgcc tacaacaagc atcgggacaa   3900
acccattcga gaacaggcgg agaacatcat tcacctgttt actcttacca acctgggtgc   3960
tcctgcagct ttcaagtact tcgataccac tatcgaccga aagcggtaca catccaccaa   4020
ggaggttctc gatgccaccc tgattcacca gtccatcact ggcctgtacg agacccgaat   4080
cgacctgtct cagcttggtg gcgactccag agccgatccc aagaaaaagc gaaaggtcta   4140
agcggccgca agtgtggatg gggaagtgag tgcccggttc tgtgtgcaca attggcaatc   4200
caagatggat ggattcaaca cagggatata gcgagctacg tggtggtgcg aggatatagc   4260
```

-continued

```
aacggatatt tatgtttgac acttgagaat gtacgataca agcactgtcc aagtacaata   4320
ctaaacatac tgtacatact catactcgta cccgggcaac ggtttcactt gagtgcagtg   4380
gctagtgctc ttactcgtac agtgtgcaat actgcgtatc atagtctttg atgtatatcg   4440
tattcattca tgttagttgc gtacgagccg gaagcataaa gtgtaaagcc tggggtgcct   4500
aatgagtgag ctaactcaca ttaattgcgt tgcgctcact gcccgctttc cagtcgggaa   4560
acctgtcgtg ccagctgcat taatgaatcg gccaacgcgc ggggagaggc ggtttgcgta   4620
ttgggcgctc ttccgcttcc tcgctcactg actcgctgcg ctcggtcgtt cggctgcggc   4680
gagcggtatc agctcactca aaggcggtaa tacggttatc cacagaatca ggggataacg   4740
caggaaagaa catgtgagca aaaggccagc aaaaggccag gaaccgtaaa aaggccgcgt   4800
tgctggcgtt tttccatagg ctccgccccc ctgacgagca tcacaaaaat cgacgctcaa   4860
gtcagaggtg gcgaaacccg acaggactat aaagatacca ggcgtttccc cctggaagct   4920
ccctcgtgcg ctctcctgtt ccgaccctgc cgcttaccgg atacctgtcc gcctttctcc   4980
cttcgggaag cgtggcgctt tctcatagct cacgctgtag gtatctcagt tcggtgtagg   5040
tcgttcgctc caagctgggc tgtgtgcacg aaccccccgt tcagcccgac cgctgcgcct   5100
tatccggtaa ctatcgtctt gagtccaacc cggtaagaca cgacttatcg ccactggcag   5160
cagccactgg taacaggatt agcagagcga ggtatgtagg cggtgctaca gagttcttga   5220
agtggtggcc taactacggc tacactagaa ggacagtatt tggtatctgc gctctgctga   5280
agccagttac cttcggaaaa agagttggta gctcttgatc cggcaaacaa accaccgctg   5340
gtagcggtgg tttttttgtt tgcaagcagc agattacgcg cagaaaaaaa ggatctcaag   5400
aagatccttt gatcttttct acggggtctg acgctcagtg gaacgaaaac tcacgttaag   5460
ggattttggt catgagatta tcaaaaagga tcttcaccta gatcctttta aattaaaaat   5520
gaagttttaa atcaatctaa agtatatatg agtaaacttg gtctgacagt taccaatgct   5580
taatcagtga ggcacctatc tcagcgatct gtctatttcg ttcatccata gttgcctgac   5640
tccccgtcgt gtagataact acgatacggg agggcttacc atctggcccc agtgctgcaa   5700
tgataccgcg agacccacgc tcaccggctc cagatttatc agcaataaac cagccagccg   5760
gaagggccga gcgcagaagt ggtcctgcaa ctttatccgc ctccatccag tctattaatt   5820
gttgccggga agctagagta agtagttcgc cagttaatag tttgcgcaac gttgttgcca   5880
ttgctacagg catcgtggtg tcacgctcgt cgtttggtat ggcttcattc agctccggtt   5940
cccaacgatc aaggcgagtt acatgatccc ccatgttgtg caaaaaagcg gttagctcct   6000
tcggtcctcc gatcgttgtc agaagtaagt tggccgcagt gttatcactc atggttatgg   6060
cagcactgca taattctctt actgtcatgc catccgtaag atgcttttct gtgactggtg   6120
agtactcaac caagtcattc tgagaatagt gtatgcggcg accgagttgc tcttgcccgg   6180
cgtcaatacg ggataatacc gcgccacata gcagaacttt aaaagtgctc atcattggaa   6240
aacgttcttc ggggcgaaaa ctctcaagga tcttaccgct gttgagatcc agttcgatgt   6300
aacccactcg tgcacccaac tgatcttcag catcttttac tttcaccagc gtttctgggt   6360
gagcaaaaac aggaaggcaa aatgccgcaa aaaagggaat aagggcgaca cggaaatgtt   6420
gaatactcat actcttcctt tttcaatatt attgaagcat ttatcagggt tattgtctca   6480
tgagcggata catatttgaa tgtatttaga aaaataaaca aataggggtt ccgcgcacat   6540
ttccccgaaa agtgccacct gacgcgccct gtagcggcgc attaagcgcg gcgggtgtgg   6600
```

-continued

```
tggttacgcg cagcgtgacc gctacacttg ccagcgccct agcgcccgct cctttcgctt   6660
tcttcccttc ctttctcgcc acgttcgccg gctttccccg tcaagctcta aatcgggggc   6720
tccctttagg gttccgattt agtgctttac ggcacctcga ccccaaaaaa cttgattagg   6780
gtgatggttc acgtagtggg ccatcgccct gatagacggt ttttcgccct ttgacgttgg   6840
agtccacgtt ctttaatagt ggactcttgt tccaaactgg aacaacactc aaccctatct   6900
cggtctattc ttttgattta taagggattt tgccgatttc ggcctattgg ttaaaaaatg   6960
agctgattta acaaaaattt aacgcgaatt ttaacaaaat attaacgctt acaatttcca   7020
ttcgccattc aggctgcgca actgttggga agggcgatcg gtgcgggcct cttcgctatt   7080
acgccagctg gcgaaagggg gatgtgctgc aaggcgatta agttgggtaa cgccagggtt   7140
ttcccagtca cgacgttgta aaacgacggc cagtgaattg taatacgact cactataggg   7200
cgaattgggt accgggcccc ccctcgaggt cgatggtgtc gataagcttg atatcgaatt   7260
catgtcacac aaaccgatct tcgcctcaag gaaacctaat tctacatccg agagactgcc   7320
gagatccagt ctacactgat taattttcgg gccaataatt taaaaaaatc gtgttatata   7380
atattatatg tattatatat atacatcatg atgatactga cagtcatgtc ccattgctaa   7440
atagacagac tccatctgcc gcctccaact gatgttctca atatttaagg ggtcatctcg   7500
cattgtttaa taataaacag actccatcta ccgcctccaa atgatgttct caaaatatat   7560
tgtatgaact tatttttatt acttagtatt attagacaac ttacttgctt tatgaaaaac   7620
acttcctatt taggaaacaa tttataatgg cagttcgttc atttaacaat ttatgtagaa   7680
taaatgttat aaatgcgtat gggaaatctt aaatatggat agcataaatg atatctgcat   7740
tgcctaattc gaaatcaaca gcaacgaaaa aaatcccttg tacaacataa atagtcatcg   7800
agaaatatca actatcaaag aacagctatt cacacgttac tattgagatt attattggac   7860
gagaatcaca cactcaactg tctttctctc ttctagaaat acaggtacaa gtatgtacta   7920
ttctcattgt tcatacttct agtcatttca tcccacatat tccttggatt tctctccaat   7980
gaatgacatt ctatcttgca aattcaacaa ttataataag atataccaaa gtagcggtat   8040
agtggcaatc aaaaagcttc tctggtgtgc ttctcgtatt tattttttatt ctaatgatcc   8100
attaaaggta tatatttatt tcttgttata taatcctttt gtttattaca tgggctggat   8160
acataaaggt attttgattt aattttttgc ttaaattcaa tccccccctcg ttcagtgtca   8220
actgtaatgg taggaaatta ccatactttt gaagaagcaa aaaaaatgaa agaaaaaaaa   8280
aatcgtattt ccaggttaga cgttccgcag aatctagaat gcggtatgcg gtacattgtt   8340
cttcgaacgt aaaagttgcg ctccctgaga tattgtacat ttttgctttt acaagtacaa   8400
gtacatcgta caactatgta ctactgttga tgcatccaca acagtttgtt ttgttttttt   8460
ttgttttttt tttttctaat gattcattac cgctatgtat acctacttgt acttgtagta   8520
agccgggtta ttggcgttca attaatcata gacttatgaa tctgcacggt gtgcgctgcg   8580
agttactttt agcttatgca tgctacttgg gtgtaatatt gggatctgtt cggaaatcaa   8640
cggatgctca atcgatttcg acagtaatta attaagtcat acacaagtca gctttcttcg   8700
agcctcatat aagtataagt agttcaacgt attagcactg tacccagcat ctccgtatcg   8760
agaaacacaa caacatgccc cattggacag atcatgcgga tacacaggtt gtgcagtatc   8820
atacatactc gatcagacag gtcgtctgac catcatacaa gctgaacaag cgctccatac   8880
ttgcacgctc tctatataca cagttaaatt acatatccat agtctaacct ctaacagtta   8940
atcttctggt aagcctccca gccagccttc tggtatcgct tggcctcctc aataggatct   9000
```

cggttctggc cgtacagacc tcggccgaca attatgatat ccgttccggt agacatgaca 9060
tcctcaacag ttcggtactg ctgtccgaga gcgtctccct tgtcgtcaag acccaccccg 9120
ggggtcagaa taagccagtc ctcagagtcg cccttaggtc ggttctgggc aatgaagcca 9180
accacaaact cggggtcgga tcgggcaagc tcaatggtct gcttggagta ctcgccagtg 9240
gccagagagc ccttgcaaga cagctcggcc agcatgagca gacctctggc cagcttctcg 9300
ttgggagagg ggactaggaa ctccttgtac tgggagttct cgtagtcaga gacgtcctcc 9360
ttcttctgtt cagagacagt ttcctcggca ccagctcgca ggccagcaat gattccggtt 9420
ccgggtacac cgtgggcgtt ggtgatatcg gaccactcgg cgattcggtg acaccggtac 9480
tggtgcttga cagtgttgcc aatatctgcg aactttctgt cctcgaacag gaagaaaccg 9540
tgcttaagag caagttcctt gagggggagc acagtgccgg cgtaggtgaa gtcgtcaatg 9600
atgtcgatat gggttttgat catgcacaca taaggtccga ccttatcggc aagctcaatg 9660
agctccttgg tggtggtaac atccagagaa gcacacaggt tggttttctt ggctgccacg 9720
agcttgagca ctcgagcggc aaaggcggac ttgtggacgt tagctcgagc ttcgtaggag 9780
ggcattttgg tggtgaagag gagactgaaa taaatttagt ctgcagaact ttttatcgga 9840
accttatctg gggcagtgaa gtatatgtta tggtaatagt tacgagttag ttgaacttat 9900
agatagactg gactatacgg ctatcggtcc aaattagaaa gaacgtcaat ggctctctgg 9960
gcgtcgcctt tgccgacaaa aatgtgatca tgatgaaagc cagcaatgac gttgcagctg 10020
atattgttgt cggccaaccg cgccgaaaac gcagctgtca gacccacagc ctccaacgaa 10080
gaatgtatcg tcaaagtgat ccaagcacac tcatagttgg agtcgtactc caaaggcggc 10140
aatgacgagt cagacagata ctcgtcgacg tttaaaccat catctaaggg cctcaaaact 10200
acctcggaac tgctgcgctg atctggacac cacagaggtt ccgagcactt taggttgcac 10260
caaatgtccc accaggtgca ggcagaaaac gctggaacag cgtgtacagt ttgtcttaac 10320
aaaaagtgag ggcgctgagg tcgagcaggg tggtgtgact tgttatagcc tttagagctg 10380
cgaaagcgcg tatggatttg gctcatcagg ccagattgag ggtctgtgga cacatgtcat 10440
gttagtgtac ttcaatcgcc ccctggatat agccccgaca ataggccgtg gcctcatttt 10500
tttgccttcc gcacatttcc attgctcggt acccacacct tgcttctcct gcacttgcca 10560
accttaatac tggtttacat tgaccaacat cttacaagcg gggggcttgt ctagggtata 10620
tataaacagt ggctctccca atcggttgcc agtctctttt ttcctttctt tccccacaga 10680
ttcgaaatct aaactacaca tcacac 10706

<210> SEQ ID NO 15
<211> LENGTH: 43
<212> TYPE: RNA
<213> ORGANISM: artificial sequence
<220> FEATURE:
<223> OTHER INFORMATION: Hammerhead (HH) ribozyme
<220> FEATURE:
<221> NAME/KEY: misc_feature
<222> LOCATION: (1)..(6)
<223> OTHER INFORMATION: n = A, C, U, or G

<400> SEQUENCE: 15
nnnnnncuga ugaguccgug aggacgaaac gaguaagcuc guc 43

<210> SEQ ID NO 16
<211> LENGTH: 68
<212> TYPE: RNA

```
<213> ORGANISM: hepatitis delta virus

<400> SEQUENCE: 16

ggccggcaug gucccagccu ccucgcuggc gccggcuggg caacaugcuu cggcauggcg     60

aaugggac                                                              68


<210> SEQ ID NO 17
<211> LENGTH: 20
<212> TYPE: DNA
<213> ORGANISM: Yarrowia lipolytica

<400> SEQUENCE: 17

tcaaacgatt acccaccctc                                                 20


<210> SEQ ID NO 18
<211> LENGTH: 760
<212> TYPE: DNA
<213> ORGANISM: artificial sequence
<220> FEATURE:
<223> OTHER INFORMATION: RGR expression cassette

<400> SEQUENCE: 18

tcgacgttta aaccatcatc taagggcctc aaaactacct cggaactgct gcgctgatct     60

ggacaccaca gaggttccga gcactttagg ttgcaccaaa tgtcccacca ggtgcaggca    120

gaaaacgctg gaacagcgtg tacagtttgt cttaacaaaa agtgagggcg ctgaggtcga    180

gcagggtggt gtgacttgtt atagccttta gagctgcgaa agcgcgtatg gatttggctc    240

atcaggccag attgagggtc tgtggacaca tgtcatgtta gtgtacttca atcgcccct     300

ggatatagcc ccgacaatag gccgtggcct cattttttg ccttccgcac atttccattg     360

ctcggtaccc acaccttgct tctcctgcac ttgccaacct taatactggt ttacattgac    420

caacatctta caagcggggg gcttgtctag ggtatatata aacagtggct ctcccaatcg    480

gttgccagtc tcttttttcc tttctttccc cacagattcg aaatctaaac tacacatcac    540

accatggttt gactgatgag tccgtgagga cgaaacgagt aagctcgtct caaacgatta    600

cccaccctcg ttttagagct agaaatagca agttaaaata aggctagtcc gttatcaact    660

tgaaaaagtg gcaccgagtc ggtggtgctt ttggccggca tggtcccagc ctcctcgctg    720

gcgccggctg ggcaacatgc ttcggcatgg cgaatgggac                          760


<210> SEQ ID NO 19
<211> LENGTH: 6793
<212> TYPE: DNA
<213> ORGANISM: artificial sequence
<220> FEATURE:
<223> OTHER INFORMATION: pRF38 plasmid

<400> SEQUENCE: 19

catggtttga ctgatgagtc cgtgaggacg aaacgagtaa gctcgtctca aacgattacc     60

caccctcgtt ttagagctag aaatagcaag ttaaaataag gctagtccgt tatcaacttg    120

aaaaagtggc accgagtcgg tggtgctttt ggccggcatg gtcccagcct cctcgctggc    180

gccggctggg caacatgctt cggcatggcg aatgggacaa gcttgggggc ggccgcaagt    240

gtggatgggg aagtgagtgc ccggttctgt gtgcacaatt ggcaatccaa gatggatgga    300

ttcaacacag ggatatagcg agctacgtgg tggtgcgagg atatagcaac ggatatttat    360

gtttgacact tgagaatgta cgatacaagc actgtccaag tacaatacta aacatactgt    420

acatactcat actcgtaccc gggcaacggt ttcacttgag tgcagtggct agtgctctta    480
```

ctcgtacagt gtgcaatact gcgtatcata gtctttgatg tatatcgtat tcattcatgt 540
tagttgcgta cgagccggaa gcataaagtg taaagcctgg ggtgcctaat gagtgagcta 600
actcacatta attgcgttgc gctcactgcc cgctttccag tcgggaaacc tgtcgtgcca 660
gctgcattaa tgaatcggcc aacgcgcggg gagaggcggt ttgcgtattg ggcgctcttc 720
cgcttcctcg ctcactgact cgctgcgctc ggtcgttcgg ctgcggcgag cggtatcagc 780
tcactcaaag gcggtaatac ggttatccac agaatcaggg gataacgcag gaaagaacat 840
gtgagcaaaa ggccagcaaa aggccaggaa ccgtaaaaag gccgcgttgc tggcgttttt 900
ccataggctc cgcccccctg acgagcatca caaaaatcga cgctcaagtc agaggtggcg 960
aaacccgaca ggactataaa gataccaggc gtttccccct ggaagctccc tcgtgcgctc 1020
tcctgttccg accctgccgc ttaccggata cctgtccgcc tttctccctt cgggaagcgt 1080
ggcgctttct catagctcac gctgtaggta tctcagttcg gtgtaggtcg ttcgctccaa 1140
gctgggctgt gtgcacgaac cccccgttca gcccgaccgc tgcgccttat ccggtaacta 1200
tcgtcttgag tccaacccgg taagacacga cttatcgcca ctggcagcag ccactggtaa 1260
caggattagc agagcgaggt atgtaggcgg tgctacagag ttcttgaagt ggtggcctaa 1320
ctacggctac actagaagga cagtatttgg tatctgcgct ctgctgaagc cagttacctt 1380
cggaaaaaga gttggtagct cttgatccgg caaacaaacc accgctggta gcggtggttt 1440
ttttgtttgc aagcagcaga ttacgcgcag aaaaaaagga tctcaagaag atcctttgat 1500
cttttctacg gggtctgacg ctcagtggaa cgaaaactca cgttaaggga ttttggtcat 1560
gagattatca aaaaggatct tcacctagat ccttttaaat taaaaatgaa gttttaaatc 1620
aatctaaagt atatatgagt aaacttggtc tgacagttac caatgcttaa tcagtgaggc 1680
acctatctca gcgatctgtc tatttcgttc atccatagtt gcctgactcc ccgtcgtgta 1740
gataactacg atacgggagg gcttaccatc tggccccagt gctgcaatga taccgcgaga 1800
cccacgctca ccggctccag atttatcagc aataaaccag ccagccggaa gggccgagcg 1860
cagaagtggt cctgcaactt tatccgcctc catccagtct attaattgtt gccgggaagc 1920
tagagtaagt agttcgccag ttaatagttt gcgcaacgtt gttgccattg ctacaggcat 1980
cgtggtgtca cgctcgtcgt ttggtatggc ttcattcagc tccggttccc aacgatcaag 2040
gcgagttaca tgatccccca tgttgtgcaa aaaagcggtt agctccttcg gtcctccgat 2100
cgttgtcaga agtaagttgg ccgcagtgtt atcactcatg gttatggcag cactgcataa 2160
ttctcttact gtcatgccat ccgtaagatg cttttctgtg actggtgagt actcaaccaa 2220
gtcattctga gaatagtgta tgcggcgacc gagttgctct tgcccggcgt caatacggga 2280
taataccgcg ccacatagca gaactttaaa agtgctcatc attggaaaac gttcttcggg 2340
gcgaaaactc tcaaggatct taccgctgtt gagatccagt tcgatgtaac ccactcgtgc 2400
acccaactga tcttcagcat cttttacttt caccagcgtt tctgggtgag caaaaacagg 2460
aaggcaaaat gccgcaaaaa agggaataag ggcgacacgg aaatgttgaa tactcatact 2520
cttccttttt caatattatt gaagcattta tcagggttat tgtctcatga gcggatacat 2580
atttgaatgt atttagaaaa ataaacaaat aggggttccg cgcacatttc cccgaaaagt 2640
gccacctgac gcgccctgta gcggcgcatt aagcgcggcg ggtgtggtgg ttacgcgcag 2700
cgtgaccgct acacttgcca gcgccctagc gcccgctcct ttcgctttct tcccttcctt 2760
tctcgccacg ttcgccggct ttccccgtca agctctaaat cgggggctcc ctttagggtt 2820

```
ccgatttagt gctttacggc acctcgaccc caaaaaactt gattagggtg atggttcacg   2880
tagtgggcca tcgccctgat agacggtttt tcgccctttg acgttggagt ccacgttctt   2940
taatagtgga ctcttgttcc aaactggaac aacactcaac cctatctcgg tctattcttt   3000
tgatttataa gggattttgc cgatttcggc ctattggtta aaaaatgagc tgatttaaca   3060
aaaatttaac gcgaatttta acaaaatatt aacgcttaca atttccattc gccattcagg   3120
ctgcgcaact gttgggaagg gcgatcggtg cgggcctctt cgctattacg ccagctggcg   3180
aaagggggat gtgctgcaag gcgattaagt tgggtaacgc cagggttttc ccagtcacga   3240
cgttgtaaaa cgacggccag tgaattgtaa tacgactcac tatagggcga attgggtacc   3300
gggccccccc tcgaggtcga tggtgtcgat aagcttgata tcgaattcat gtcacacaaa   3360
ccgatcttcg cctcaaggaa acctaattct acatccgaga gactgccgag atccagtcta   3420
cactgattaa ttttcgggcc aataatttaa aaaaatcgtg ttatataata ttatatgtat   3480
tatatatata catcatgatg atactgacag tcatgtccca ttgctaaata gacagactcc   3540
atctgccgcc tccaactgat gttctcaata tttaaggggt catctcgcat tgtttaataa   3600
taaacagact ccatctaccg cctccaaatg atgttctcaa aatatattgt atgaacttat   3660
ttttattact tagtattatt agacaactta cttgctttat gaaaaacact tcctatttag   3720
gaaacaattt ataatggcag ttcgttcatt taacaattta tgtagaataa atgttataaa   3780
tgcgtatggg aaatcttaaa tatggatagc ataaatgata tctgcattgc ctaattcgaa   3840
atcaacagca acgaaaaaaa tcccttgtac aacataaata gtcatcgaga aatatcaact   3900
atcaaagaac agctattcac acgttactat tgagattatt attggacgag aatcacacac   3960
tcaactgtct ttctctcttc tagaaataca ggtacaagta tgtactattc tcattgttca   4020
tacttctagt catttcatcc cacatattcc ttggatttct ctccaatgaa tgacattcta   4080
tcttgcaaat tcaacaatta taataagata taccaaagta gcggtatagt ggcaatcaaa   4140
aagcttctct ggtgtgcttc tcgtatttat ttttattcta atgatccatt aaaggtatat   4200
atttatttct tgttatataa tccttttgtt tattacatgg gctggataca taaaggtatt   4260
ttgatttaat tttttgctta aattcaatcc cccctcgttc agtgtcaact gtaatggtag   4320
gaaattacca tacttttgaa gaagcaaaaa aaatgaaaga aaaaaaaaat cgtatttcca   4380
ggttagacgt tccgcagaat ctagaatgcg gtatgcggta cattgttctt cgaacgtaaa   4440
agttgcgctc cctgagatat tgtacatttt tgcttttaca agtacaagta catcgtacaa   4500
ctatgtacta ctgttgatgc atccacaaca gtttgttttg tttttttttg tttttttttt   4560
ttctaatgat tcattaccgc tatgtatacc tacttgtact tgtagtaagc cgggttattg   4620
gcgttcaatt aatcatagac ttatgaatct gcacggtgtg cgctgcgagt tacttttagc   4680
ttatgcatgc tacttgggtg taatattggg atctgttcgg aaatcaacgg atgctcaatc   4740
gatttcgaca gtaattaatt aagtcataca caagtcagct ttcttcgagc ctcatataag   4800
tataagtagt tcaacgtatt agcactgtac ccagcatctc cgtatcgaga aacacaacaa   4860
catgccccat tggacagatc atgcggatac acaggttgtg cagtatcata catactcgat   4920
cagacaggtc gtctgaccat catacaagct gaacaagcgc tccatacttg cacgctctct   4980
atatacacag ttaaattaca tatccatagt ctaacctcta acagttaatc ttctggtaag   5040
cctcccagcc agccttctgg tatcgcttgg cctcctcaat aggatctcgg ttctggccgt   5100
acagacctcg gccgacaatt atgatatccg ttccggtaga catgacatcc tcaacagttc   5160
ggtactgctg tccgagagcg tctcccttgt cgtcaagacc caccccgggg gtcagaataa   5220
```

-continued

```
gccagtcctc agagtcgccc ttaggtcggt tctgggcaat gaagccaacc acaaactcgg   5280

ggtcggatcg ggcaagctca atggtctgct tggagtactc gccagtggcc agagagccct   5340

tgcaagacag ctcggccagc atgagcagac ctctggccag cttctcgttg ggagagggga   5400

ctaggaactc cttgtactgg gagttctcgt agtcagagac gtcctccttc ttctgttcag   5460

agacagtttc ctcggcacca gctcgcaggc cagcaatgat tccggttccg ggtacaccgt   5520

gggcgttggt gatatcggac cactcggcga ttcggtgaca ccggtactgg tgcttgacag   5580

tgttgccaat atctgcgaac tttctgtcct cgaacaggaa gaaaccgtgc ttaagagcaa   5640

gttccttgag gggagcacaa gtgccggcgt aggtgaagtc gtcaatgatg tcgatatggg   5700

ttttgatcat gcacacataa ggtccgacct tatcggcaag ctcaatgagc tccttggtgg   5760

tggtaacatc cagagaagca cacaggttgg ttttcttggc tgccacgagc ttgagcactc   5820

gagcggcaaa ggcggacttg tggacgttag ctcgagcttc gtaggagggc attttggtgg   5880

tgaagaggag actgaaataa atttagtctg cagaactttt tatcggaacc ttatctgggg   5940

cagtgaagta tatgttatgg taatagttac gagttagttg aacttataga tagactggac   6000

tatacggcta tcggtccaaa ttagaaagaa cgtcaatggc tctctgggcg tcgcctttgc   6060

cgacaaaaat gtgatcatga tgaaagccag caatgacgtt gcagctgata ttgttgtcgg   6120

ccaaccgcgc cgaaaacgca gctgtcagac ccacagcctc caacgaagaa tgtatcgtca   6180

aagtgatcca agcacactca tagttggagt cgtactccaa aggcggcaat gacgagtcag   6240

acagatactc gtcgacgttt aaaccatcat ctaagggcct caaaactacc tcggaactgc   6300

tgcgctgatc tggacaccac agaggttccg agcactttag gttgcaccaa atgtcccacc   6360

aggtgcaggc agaaaacgct ggaacagcgt gtacagtttg tcttaacaaa aagtgagggc   6420

gctgaggtcg agcagggtgg tgtgacttgt tatagccttt agagctgcga aagcgcgtat   6480

ggatttggct catcaggcca gattgagggt ctgtggacac atgtcatgtt agtgtacttc   6540

aatcgccccc tggatatagc cccgacaata ggccgtggcc tcattttttt gccttccgca   6600

catttccatt gctcggtacc cacaccttgc ttctcctgca cttgccaacc ttaatactgg   6660

tttacattga ccaacatctt acaagcgggg ggcttgtcta gggtatatat aaacagtggc   6720

tctcccaatc ggttgccagt ctcttttttc ctttctttcc ccacagattc gaaatctaaa   6780

ctacacatca cac                                                       6793
```

<210> SEQ ID NO 20
<211> LENGTH: 19
<212> TYPE: DNA
<213> ORGANISM: artificial sequence
<220> FEATURE:
<223> OTHER INFORMATION: RGR forward PCR primer

<400> SEQUENCE: 20

```
cgagtcagac agatactcg                                                  19
```

<210> SEQ ID NO 21
<211> LENGTH: 19
<212> TYPE: DNA
<213> ORGANISM: artificial sequence
<220> FEATURE:
<223> OTHER INFORMATION: RGR reverse PCR primer

<400> SEQUENCE: 21

```
ccctgtgttg aatccatcc                                                  19
```

<210> SEQ ID NO 22
<211> LENGTH: 20
<212> TYPE: DNA
<213> ORGANISM: Yarrowia lipolytica

<400> SEQUENCE: 22
ggaaggcaca tatggcaagg 20

<210> SEQ ID NO 23
<211> LENGTH: 21
<212> TYPE: DNA
<213> ORGANISM: Yarrowia lipolytica

<400> SEQUENCE: 23
gtaagagtgg tttgctccag g 21

<210> SEQ ID NO 24
<211> LENGTH: 21
<212> TYPE: DNA
<213> ORGANISM: Yarrowia lipolytica

<400> SEQUENCE: 24
gcacaggtat ttctgccctt c 21

<210> SEQ ID NO 25
<211> LENGTH: 709
<212> TYPE: DNA
<213> ORGANISM: artificial sequence
<220> FEATURE:
<223> OTHER INFORMATION: RG expression cassette

<400> SEQUENCE: 25
tcgacgttta aaccatcatc taagggcctc aaaactacct cggaactgct gcgctgatct 60
ggacaccaca gaggttccga gcactttagg ttgcaccaaa tgtcccacca ggtgcaggca 120
gaaaacgctg gaacagcgtg tacagtttgt cttaacaaaa agtgagggcg ctgaggtcga 180
gcagggtggt gtgacttgtt atagccttta gagctgcgaa agcgcgtatg gatttggctc 240
atcaggccag attgagggtc tgtggacaca tgtcatgtta gtgtacttca atcgcccct 300 ggatatagcc ccgacaatag gccgtggcct catttttttg ccttccgcac atttccattg 360
ctcggtaccc acaccttgct tctcctgcac ttgccaacct taatactggt ttacattgac 420
caacatctta caagcggggg gcttgtctag ggtatatata aacagtggct ctcccaatcg 480
gttgccagtc tcttttttcc tttctttccc cacagattcg aaatctaaac tacacatcac 540
accatggttt gactgatgag tccgtgagga cgaaacgagt aagctcgtct caaacgatta 600
cccaccctcg ttttagagct agaaatagca agttaaaata aggctagtcc gttatcaact 660
tgaaaaagtg gcaccgagtc ggtgcttttt ttttttgttt tttatgtct 709

<210> SEQ ID NO 26
<211> LENGTH: 10
<212> TYPE: DNA
<213> ORGANISM: unknown
<220> FEATURE:
<223> OTHER INFORMATION: poly-A

<400> SEQUENCE: 26
aaaaaaaaaa 10

<210> SEQ ID NO 27
<211> LENGTH: 10

<212> TYPE: DNA
<213> ORGANISM: unknown
<220> FEATURE:
<223> OTHER INFORMATION: poly-T

<400> SEQUENCE: 27
tttttttttt 10

<210> SEQ ID NO 28
<211> LENGTH: 100
<212> TYPE: DNA
<213> ORGANISM: artificial sequence
<220> FEATURE:
<223> OTHER INFORMATION: CAN1 frameshift donor

<400> SEQUENCE: 28
ccttaacgac cctgccgtct ccatccatcc gaccacaatg gaaaagacat gactgaggcc 60
cacatccaca tcaaccacac ggcccactcg gatgactcag 100

<210> SEQ ID NO 29
<211> LENGTH: 100
<212> TYPE: DNA
<213> ORGANISM: artificial sequence
<220> FEATURE:
<223> OTHER INFORMATION: CAN1 frameshift donor complement

<400> SEQUENCE: 29
ctgagtcatc cgagtgggcc gtgtggttga tgtggatgtg ggcctcagtc atgtcttttc 60
cattgtggtc ggatggatgg agacggcagg gtcgttaagg 100

<210> SEQ ID NO 30
<211> LENGTH: 106
<212> TYPE: DNA
<213> ORGANISM: artificial sequence
<220> FEATURE:
<223> OTHER INFORMATION: CAN1 point mutation donor

<400> SEQUENCE: 30
ccatccatcc gaccacaatg gaaaagacat tttcaaacga ttacccaccc tgatgaactg 60
aggcccacat ccacatcaac cacacggccc actcggatga ctcaga 106

<210> SEQ ID NO 31
<211> LENGTH: 106
<212> TYPE: DNA
<213> ORGANISM: artificial sequence
<220> FEATURE:
<223> OTHER INFORMATION: CAN1 point mutation donor complement

<400> SEQUENCE: 31
tctgagtcat ccgagtgggc cgtgtggttg atgtggatgt gggcctcagt tcatcagggt 60
gggtaatcgt ttgaaaatgt cttttccatt gtggtcggat ggatgg 106

<210> SEQ ID NO 32
<211> LENGTH: 655
<212> TYPE: DNA
<213> ORGANISM: artificial sequence
<220> FEATURE:
<223> OTHER INFORMATION: CAN1 upstream donor arm

<400> SEQUENCE: 32
gggaagcctt gctacgttag gagaagacgc acggcgatga tacgggtacc cctcatgaca 60
tcaatatccg ctgcccctct tgccagcaag gcgtcagcag gtgctttttt cgctattttc 120

```
accagaccac agcctttttc cttgtgtctc atcttggatt ccttcaaagg caactcaccg    180

cacctccgag tcgtgtgaac aatgtaataa taggctattg acttttttcc cacctgttta    240

gcgccaaacc caaagcgctt ttcgccccca ctgcagcccg atggaaggca catatggcaa    300

gggaaaagtc ttcaggtaat acatgcctgc tgcaactata tgtactctga ctcattccct    360

cagacgtggg tcatagacag ctgttttaaa ccgggcaaat caatctctgt cgcacaggta    420

tttctgccct tcaaaaccag gttgccacat cagattccat caaagttttt cagactaact    480

tcaatcttaa acggcatctc acaacaagcg aattggacgg aaaaaaagcg tctatcatta    540

ccggcaccta tccacactaa gacagtacta aaggacgacg ctccccacga aacgacgttt    600

cgaccttaac gaccctgccg tctccatcca tccgaccact cccgacgctc tctcc         655
```

<210> SEQ ID NO 33
<211> LENGTH: 29
<212> TYPE: DNA
<213> ORGANISM: artificial sequence
<220> FEATURE:
<223> OTHER INFORMATION: Forward PCR primer for amplifying CAN1 upstream donor arm

<400> SEQUENCE: 33

```
gggaagcttg ctacgttagg agaagacgc                                       29
```

<210> SEQ ID NO 34
<211> LENGTH: 37
<212> TYPE: DNA
<213> ORGANISM: artificial sequence
<220> FEATURE:
<223> OTHER INFORMATION: Reverse PCR primer for amplifying CAN1 upstream donor arm

<400> SEQUENCE: 34

```
ggagagagcg tcgggagtgg tcggatggat ggagacg                              37
```

<210> SEQ ID NO 35
<211> LENGTH: 658
<212> TYPE: DNA
<213> ORGANISM: artificial sequence
<220> FEATURE:
<223> OTHER INFORMATION: CAN1 downstream donor arm

<400> SEQUENCE: 35

```
cgtctccatc catccgacca ctcccgacgc tctctcctgg agcaaaccac tcttaccaag     60

catatagcat atataataac gtattgaatt tattaactga ttgaattgag agtaaagcca    120

gtagcgttgt acggctgtag ctttttagaa aagtggcaga tgagcgatgg tggatatgaa    180

agtaccttta cggcatgtag cgacacaaga tcgcttccaa gaactcgaca ttcaagccca    240

gctcgtacaa gaaaatgaac tagccaatca tatgaactag cacattgaag tcaccgcatc    300

atctctgttg gaaacgacgc gcatgtactc gtgcgtagta aatccgtatc tgtacactcg    360

aaagattaca gtatgtagta gtagcatgac taacgatgta acgtccaaat aacgctctgt    420

gcctactcct gtagatgcat tagaccacct gctaacgtct acacgttatg tccgttagct    480

ccaagattgc acttttccct caaagactct gctgggttac gtcatggtct ctttcgggtc    540

tctggtccgt tctctgcccg cccatatccg cccaggctgc tacgatacag gataagctca    600

taagcttaga ttatttttcc ggaatgacat cacgatgcag tggtggaagg atgtatgg      658
```

<210> SEQ ID NO 36
<211> LENGTH: 37

<212> TYPE: DNA
<213> ORGANISM: artificial sequence
<220> FEATURE:
<223> OTHER INFORMATION: Forward PCR primer for amplifying CAN1 downstream donor arm

<400> SEQUENCE: 36
cgtctccatc catccgacca ctcccgacgc tctctcc 37

<210> SEQ ID NO 37
<211> LENGTH: 22
<212> TYPE: DNA
<213> ORGANISM: artificial sequence
<220> FEATURE:
<223> OTHER INFORMATION: Reverse PCR primer for amplifying CAN1 downstream donor arm

<400> SEQUENCE: 37
ccatacatcc ttccaccact gc 22

<210> SEQ ID NO 38
<211> LENGTH: 1276
<212> TYPE: DNA
<213> ORGANISM: artificial sequence
<220> FEATURE:
<223> OTHER INFORMATION: CAN1 large deletion donor

<400> SEQUENCE: 38
gggaagcctt gctacgttag gagaagacgc acggcgatga tacgggtacc cctcatgaca 60
tcaatatccg ctgcccctct tgccagcaag gcgtcagcag gtgctttttt cgctattttc 120
accagaccac agcctttttc cttgtgtctc atcttggatt ccttcaaagg caactcaccg 180
cacctccgag tcgtgtgaac aatgtaataa taggctattg actttttttcc cacctgttta 240 gcgccaaacc caaagcgctt ttcgccccca ctgcagcccg atggaaggca catatggcaa 300
gggaaaagtc ttcaggtaat acatgcctgc tgcaactata tgtactctga ctcattccct 360
cagacgtggg tcatagacag ctgttttaaa ccgggcaaat caatctctgt cgcacaggta 420
tttctgccct tcaaaaccag gttgccacat cagattccat caaagttttt cagactaact 480
tcaatcttaa acggcatctc acaacaagcg aattggacgg aaaaaaagcg tctatcatta 540
ccggcaccta tccacactaa gacagtacta aaggacgacg ctccccacga aacgacgttt 600
cgaccttaac gaccctgccg tctccatcca tccgaccact cccgacgctc tctcctggag 660
caaaccactc ttaccaagca tatagcatat ataataacgt attgaattta ttaactgatt 720
gaattgagag taaagccagt agcgttgtac ggctgtagct ttttagaaaa gtggcagatg 780
agcgatggtg gatatgaaag tacctttacg gcatgtagcg acacaagatc gcttccaaga 840
actcgacatt caagcccagc tcgtacaaga aaatgaacta gccaatcata tgaactagca 900
cattgaagtc accgcatcat ctctgttgga aacgacgcgc atgtactcgt gcgtagtaaa 960
tccgtatctg tacactcgaa agattacagt atgtagtagt agcatgacta acgatgtaac 1020
gtccaaataa cgctctgtgc ctactcctgt agatgcatta gaccacctgc taacgtctac 1080
acgttatgtc cgttagctcc aagattgcac ttttccctca aagactctgc tgggttacgt 1140
catggtctct ttcgggtctc tggtccgttc tctgcccgcc catatccgcc caggctgcta 1200
cgatacagga taagctcata agcttagatt atttttccgg aatgacatca cgatgcagtg 1260
gtggaaggat gtatgg 1276

<210> SEQ ID NO 39

<211> LENGTH: 31
<212> TYPE: DNA
<213> ORGANISM: artificial sequence
<220> FEATURE:
<223> OTHER INFORMATION: RG/RGR forward PCR primer

<400> SEQUENCE: 39
ggggttaatt aacgagtcag acagatactc g 31

<210> SEQ ID NO 40
<211> LENGTH: 29
<212> TYPE: DNA
<213> ORGANISM: artificial sequence
<220> FEATURE:
<223> OTHER INFORMATION: RG/RGR reverse PCR primer

<400> SEQUENCE: 40
ggggatcgat ccctgtgttg aatccatcc 29

<210> SEQ ID NO 41
<211> LENGTH: 11568
<212> TYPE: DNA
<213> ORGANISM: artificial sequence
<220> FEATURE:
<223> OTHER INFORMATION: pRF84 plasmid

<400> SEQUENCE: 41
cgatccctgt gttgaatcca tccatcttgg attgccaatt gtgcacacag aaccgggcac 60
tcacttcccc atccacactt gcggccgccc ccaagcttgt cccattcgcc atgccgaagc 120
atgttgccca gccggcgcca gcgaggaggc tgggaccatg ccggccaaaa gcaccaccga 180
ctcggtgcca ctttttcaag ttgataacgg actagcctta ttttaacttg ctatttctag 240
ctctaaaacg agggtgggta atcgtttgag acgagcttac tcgtttcgtc ctcacggact 300
catcagtcaa accatggtgt gatgtgtagt ttagatttcg aatctgtggg gaaagaaagg 360
aaaaaagaga ctggcaaccg attgggagag ccactgttta tatataccct agacaagccc 420
cccgcttgta agatgttggt caatgtaaac cagtattaag gttggcaagt gcaggagaag 480
caaggtgtgg gtaccgagca atggaaatgt gcggaaggca aaaaaatgag gccacggcct 540
attgtcgggg ctatatccag gggcgattg aagtacacta acatgacatg tgtccacaga 600
ccctcaatct ggcctgatga gccaaatcca tacgcgcttt cgcagctcta aaggctataa 660
caagtcacac caccctgctc gacctcagcg ccctcacttt ttgttaagac aaactgtaca 720
cgctgttcca gcgttttctg cctgcacctg gtgggacatt tggtgcaacc taaagtgctc 780
ggaacctctg tggtgtccag atcagcgcag cagttccgag gtagttttga ggcccttaga 840
tgatggttta aacgtcgacg agtatctgtc tgactcgtta attaagtcat acacaagtca 900
gctttcttcg agcctcatat aagtataagt agttcaacgt attagcactg tacccagcat 960
ctccgtatcg agaaacacaa caacatgccc cattggacag atcatgcgga tacacaggtt 1020
gtgcagtatc atacatactc gatcagacag gtcgtctgac catcatacaa gctgaacaag 1080
cgctccatac ttgcacgctc tctatataca cagttaaatt acatatccat agtctaacct 1140
ctaacagtta atcttctggt aagcctccca gccagccttc tggtatcgct tggcctcctc 1200
aataggatct cggttctggc cgtacagacc tcggccgaca attatgatat ccgttccggt 1260
agacatgaca tcctcaacag ttcggtactg ctgtccgaga gcgtctccct tgtcgtcaag 1320
acccaccccg gggtcagaa taagccagtc ctcagagtcg cccttaggtc ggttctgggc 1380
aatgaagcca accacaaact cggggtcgga tcgggcaagc tcaatggtct gcttggagta 1440

```
ctcgccagtg gccagagagc ccttgcaaga cagctcggcc agcatgagca gacctctggc   1500
cagcttctcg ttgggagagg ggactaggaa ctccttgtac tgggagttct cgtagtcaga   1560
gacgtcctcc ttcttctgtt cagagacagt ttcctcggca ccagctcgca ggccagcaat   1620
gattccggtt ccgggtacac cgtgggcgtt ggtgatatcg gaccactcgg cgattcggtg   1680
acaccggtac tggtgcttga cagtgttgcc aatatctgcg aactttctgt cctcgaacag   1740
gaagaaaccg tgcttaagag caagttcctt gagggggagc acagtgccgg cgtaggtgaa   1800
gtcgtcaatg atgtcgatat gggttttgat catgcacaca taaggtccga ccttatcggc   1860
aagctcaatg agctccttgg tggtggtaac atccagagaa gcacacaggt tggttttctt   1920
ggctgccacg agcttgagca ctcgagcggc aaaggcggac ttgtggacgt tagctcgagc   1980
ttcgtaggag ggcattttgg tggtgaagag gagactgaaa taaatttagt ctgcagaact   2040
ttttatcgga accttatctg gggcagtgaa gtatatgtta tggtaatagt tacgagttag   2100
ttgaacttat agatagactg gactatacgg ctatcggtcc aaattagaaa gaacgtcaat   2160
ggctctctgg gcgtcgcctt tgccgacaaa aatgtgatca tgatgaaagc cagcaatgac   2220
gttgcagctg atattgttgt cggccaaccg cgccgaaaac gcagctgtca gacccacagc   2280
ctccaacgaa gaatgtatcg tcaaagtgat ccaagcacac tcatagttgg agtcgtactc   2340
caaaggcggc aatgacgagt cagacagata ctcgtcgacg tttaaaccat catctaaggg   2400
cctcaaaact acctcggaac tgctgcgctg atctggacac cacagaggtt ccgagcactt   2460
taggttgcac caaatgtccc accaggtgca ggcagaaaac gctggaacag cgtgtacagt   2520
ttgtcttaac aaaaagtgag ggcgctgagg tcgagcaggg tggtgtgact tgttatagcc   2580
tttagagctg cgaaagcgcg tatggatttg gctcatcagg ccagattgag ggtctgtgga   2640
cacatgtcat gttagtgtac ttcaatcgcc ccctggatat agccccgaca ataggccgtg   2700
gcctcatttt tttgccttcc gcacatttcc attgctcggt acccacacct tgcttctcct   2760
gcacttgcca accttaatac tggtttacat tgaccaacat cttacaagcg gggggcttgt   2820
ctagggtata tataaacagt ggctctccca atcggttgcc agtctctttt ttcctttctt   2880
tccccacaga ttcgaaatct aaactacaca tcacaccatg gacaagaaat actccatcgg   2940
cctggacatt ggaaccaact ctgtcggctg ggctgtcatc accgacgagt acaaggtgcc   3000
ctccaagaaa ttcaaggtcc tcggaaacac cgatcgacac tccatcaaga aaaacctcat   3060
tggtgccctg ttgttcgatt ctggcgagac tgccgaagct accagactca agcgaactgc   3120
tcggcgacgt tacacccgac ggaagaaccg aatctgctac ctgcaggaga tcttttccaa   3180
cgagatggcc aaggtggacg attcgttctt tcatcgactg gaggaatcct tcctcgtcga   3240
ggaagacaag aaacacgagc gtcatcccat ctttggcaac attgtggacg aggttgctta   3300
ccacgagaag tatcctacca tctaccacct gcgaaagaaa ctcgtcgatt ccaccgacaa   3360
ggcggatctc agacttatct acctcgctct ggcacacatg atcaagtttc gaggtcattt   3420
cctcatcgag ggcgatctca atcccgacaa cagcgatgtg gacaagctgt tcattcagct   3480
cgttcagacc tacaaccagc tgttcgagga aaaccccatc aatgcctccg gagtcgatgc   3540
aaaggccatc ttgtctgctc gactctcgaa gagcagacga ctggagaacc tcattgccca   3600
acttcctggc gagaaaaaga acggactgtt tggcaacctc attgcccttt ctcttggtct   3660
cacacccaac ttcaagtcca acttcgatct ggcggaggac gccaagctcc agctgtccaa   3720
ggacacctac gacgatgacc tcgacaacct gcttgcacag attggcgatc agtacgccga   3780
```

-continued

```
cctgtttctc gctgccaaga acctttcgga tgctattctc ttgtctgaca ttctgcgagt   3840
caacaccgag atcacaaagg ctcccctttc tgcctccatg atcaagcgat acgacgagca   3900
ccatcaggat ctcacactgc tcaaggctct tgtccgacag caactgcccg agaagtacaa   3960
ggagatcttt ttcgatcagt cgaagaacgg ctacgctgga tacatcgacg gcggagcctc   4020
tcaggaagag ttctacaagt tcatcaagcc aattctcgag aagatggacg gaaccgagga   4080
actgcttgtc aagctcaatc gagaggatct gcttcggaag caacgaacct tcgacaacgg   4140
cagcattcct catcagatcc acctcggtga gctgcacgcc attcttcgac gtcaggaaga   4200
cttctacccc tttctcaagg acaaccgaga gaagatcgag aagattctta cctttcgaat   4260
cccctactat gttggtcctc ttgccagagg aaactctcga tttgcttgga tgactcgaaa   4320
gtccgaggaa accatcactc cctggaactt cgaggaagtc gtggacaagg gtgcctctgc   4380
acagtccttc atcgagcgaa tgaccaactt cgacaagaat ctgcccaacg agaaggttct   4440
tcccaagcat tcgctgctct acgagtactt tacagtctac aacgaactca ccaaagtcaa   4500
gtacgttacc gagggaatgc gaaagcctgc cttcttgtct ggcgaacaga agaaagccat   4560
tgtcgatctc ctgttcaaga ccaaccgaaa ggtcactgtt aagcagctca aggaggacta   4620
cttcaagaaa atcgagtgtt tcgacagcgt cgagatttcc ggagttgagg accgattcaa   4680
cgcctctttg ggcacctatc acgatctgct caagattatc aaggacaagg attttctcga   4740
caacgaggaa aacgaggaca ttctggagga catcgtgctc actcttaccc tgttcgaaga   4800
tcgggagatg atcgaggaac gactcaagac atacgctcac ctgttcgacg acaaggtcat   4860
gaaacaactc aagcgacgta gatacaccgg ctggggaaga ctttcgcgaa agctcatcaa   4920
cggcatcaga gacaagcagt ccggaaagac cattctggac tttctcaagt ccgatggctt   4980
tgccaaccga aacttcatgc agctcattca cgacgattct cttaccttca aggaggacat   5040
ccagaaggca caagtgtccg gtcagggcga cagcttgcac gaacatattg ccaacctggc   5100
tggttcgcca gccatcaaga aaggcattct ccagactgtc aaggttgtcg acgagctggt   5160
gaaggtcatg ggacgtcaca agcccgagaa cattgtgatc gagatggcca gagagaacca   5220
gacaactcaa aagggtcaga aaaactcgcg agagcggatg aagcgaatcg aggaaggcat   5280
caaggagctg ggatcccaga ttctcaagga gcatcccgtc gagaacactc aactgcagaa   5340
cgagaagctg tatctctact atctgcagaa tggtcgagac atgtacgtgg atcaggaact   5400
ggacatcaat cgtctcagcg actacgatgt ggaccacatt gtccctcaat cctttctcaa   5460
ggacgattct atcgacaaca aggtccttac acgatccgac aagaacagag gcaagtcgga   5520
caacgttccc agcgaagagg tggtcaaaaa gatgaagaac tactggcgac agctgctcaa   5580
cgccaagctc attacccagc gaaagttcga caatcttacc aaggccgagc gaggcggtct   5640
gtccgagctc gacaaggctg gcttcatcaa gcgtcaactc gtcgagacca gacagatcac   5700
aaagcacgtc gcacagattc tcgattctcg gatgaacacc aagtacgacg agaacgacaa   5760
gctcatccga gaggtcaagg tgattactct caagtccaaa ctggtctccg atttccgaaa   5820
ggactttcag ttctacaagg tgcgagagat caacaattac caccatgccc acgatgctta   5880
cctcaacgcc gtcgttggca ctgcgctcat caagaaatac cccaagctcg aaagcgagtt   5940
cgtttacggc gattacaagg tctacgacgt tcgaaagatg attgccaagt ccgaacagga   6000
gattggcaag gctactgcca agtacttctt ttactccaac atcatgaact tttcaagac   6060
cgagatcacc ttggccaacg gagagattcg aaagagacca cttatcgaga ccaacggcga   6120
aactggagag atcgtgtggg acaagggtcg agactttgca accgtgcgaa aggttctgtc   6180
```

```
gatgcctcag gtcaacatcg tcaagaaaac cgaggttcag actggcggat tctccaagga   6240
gtcgattctg cccaagcgaa actccgacaa gctcatcgct cgaaagaaag actgggatcc   6300
caagaaatac ggtggcttcg attctcctac cgtcgcctat tccgtgcttg tcgttgcgaa   6360
ggtcgagaag ggcaagtcca aaaagctcaa gtccgtcaag gagctgctcg gaattaccat   6420
catggagcga tcgagcttcg agaagaatcc catcgacttc ttggaagcca agggttacaa   6480
ggaggtcaag aaagacctca ttatcaagct gcccaagtac tctctgttcg aactggagaa   6540
cggtcgaaag cgtatgctcg cctccgctgg cgagctgcag aagggaaacg agcttgcctt   6600
gccttcgaag tacgtcaact ttctctatct ggcttctcac tacgagaagc tcaagggttc   6660
tcccgaggac aacgaacaga agcaactctt cgttgagcag cacaaacatt acctcgacga   6720
gattatcgag cagatttccg agttttcgaa gcgagtcatc ctggctgatg ccaacttgga   6780
caaggtgctc tctgcctaca acaagcatcg ggacaaaccc attcgagaac aggcggagaa   6840
catcattcac ctgtttactc ttaccaacct gggtgctcct gcagctttca agtacttcga   6900
taccactatc gaccgaaagc ggtacacatc caccaaggag gttctcgatg ccaccctgat   6960
tcaccagtcc atcactggcc tgtacgagac ccgaatcgac ctgtctcagc ttggtggcga   7020
ctccagagcc gatcccaaga aaaagcgaaa ggtctaagcg gccgcaagtg tggatgggga   7080
agtgagtgcc cggttctgtg tgcacaattg gcaatccaag atggatggat tcaacacagg   7140
gatatagcga gctacgtggt ggtgcgagga tatagcaacg gatatttatg tttgacactt   7200
gagaatgtac gatacaagca ctgtccaagt acaatactaa acatactgta catactcata   7260
ctcgtacccg ggcaacggtt tcacttgagt gcagtggcta gtgctcttac tcgtacagtg   7320
tgcaatactg cgtatcatag tctttgatgt atatcgtatt cattcatgtt agttgcgtac   7380
gagccggaag cataaagtgt aaagcctggg gtgcctaatg agtgagctaa ctcacattaa   7440
ttgcgttgcg ctcactgccc gctttccagt cgggaaacct gtcgtgccag ctgcattaat   7500
gaatcggcca acgcgcgggg agaggcggtt tgcgtattgg gcgctcttcc gcttcctcgc   7560
tcactgactc gctgcgctcg gtcgttcggc tgcggcgagc ggtatcagct cactcaaagg   7620
cggtaatacg gttatccaca gaatcagggg ataacgcagg aaagaacatg tgagcaaaag   7680
gccagcaaaa ggccaggaac cgtaaaaagg ccgcgttgct ggcgtttttc cataggctcc   7740
gcccccctga cgagcatcac aaaaatcgac gctcaagtca gaggtggcga aacccgacag   7800
gactataaag ataccaggcg tttccccctg gaagctccct cgtgcgctct cctgttccga   7860
ccctgccgct taccggatac ctgtccgcct ttctcccttc gggaagcgtg gcgctttctc   7920
atagctcacg ctgtaggtat ctcagttcgg tgtaggtcgt tcgctccaag ctgggctgtg   7980
tgcacgaacc ccccgttcag cccgaccgct gcgccttatc cggtaactat cgtcttgagt   8040
ccaacccggt aagacacgac ttatcgccac tggcagcagc cactggtaac aggattagca   8100
gagcgaggta tgtaggcggt gctacagagt tcttgaagtg gtggcctaac tacggctaca   8160
ctagaaggac agtatttggt atctgcgctc tgctgaagcc agttaccttc ggaaaaagag   8220
ttggtagctc ttgatccggc aaacaaacca ccgctggtag cggtggtttt tttgtttgca   8280
agcagcagat tacgcgcaga aaaaaaggat ctcaagaaga tcctttgatc ttttctacgg   8340
ggtctgacgc tcagtggaac gaaaactcac gttaagggat tttggtcatg agattatcaa   8400
aaaggatctt cacctagatc cttttaaatt aaaaatgaag ttttaaatca atctaaagta   8460
tatatgagta aacttggtct gacagttacc aatgcttaat cagtgaggca cctatctcag   8520
```

-continued

```
cgatctgtct atttcgttca tccatagttg cctgactccc cgtcgtgtag ataactacga   8580
tacgggaggg cttaccatct ggccccagtg ctgcaatgat accgcgagac ccacgctcac   8640
cggctccaga tttatcagca ataaaccagc cagccggaag ggccgagcgc agaagtggtc   8700
ctgcaacttt atccgcctcc atccagtcta ttaattgttg ccgggaagct agagtaagta   8760
gttcgccagt taatagtttg cgcaacgttg ttgccattgc tacaggcatc gtggtgtcac   8820
gctcgtcgtt tggtatggct tcattcagct ccggttccca acgatcaagg cgagttacat   8880
gatcccccat gttgtgcaaa aaagcggtta gctccttcgg tcctccgatc gttgtcagaa   8940
gtaagttggc cgcagtgtta tcactcatgg ttatggcagc actgcataat tctcttactg   9000
tcatgccatc cgtaagatgc ttttctgtga ctggtgagta ctcaaccaag tcattctgag   9060
aatagtgtat gcggcgaccg agttgctctt gcccggcgtc aatacgggat aataccgcgc   9120
cacatagcag aactttaaaa gtgctcatca ttggaaaacg ttcttcgggg cgaaaactct   9180
caaggatctt accgctgttg agatccagtt cgatgtaacc cactcgtgca cccaactgat   9240
cttcagcatc ttttactttc accagcgttt ctgggtgagc aaaaacagga aggcaaaatg   9300
ccgcaaaaaa gggaataagg gcgacacgga aatgttgaat actcatactc ttcctttttc   9360
aatattattg aagcatttat cagggttatt gtctcatgag cggatacata tttgaatgta   9420
tttagaaaaa taaacaaata ggggttccgc gcacatttcc ccgaaaagtg ccacctgacg   9480
cgccctgtag cggcgcatta agcgcggcgg gtgtggtggt tacgcgcagc gtgaccgcta   9540
cacttgccag cgccctagcg cccgctcctt tcgctttctt cccttccttt ctcgccacgt   9600
tcgccggctt tccccgtcaa gctctaaatc gggggctccc tttagggttc cgatttagtg   9660
ctttacggca cctcgacccc aaaaaacttg attagggtga tggttcacgt agtgggccat   9720
cgccctgata gacggttttt cgccctttga cgttggagtc cacgttcttt aatagtggac   9780
tcttgttcca aactggaaca acactcaacc ctatctcggt ctattctttt gatttataag   9840
ggattttgcc gatttcggcc tattggttaa aaaatgagct gatttaacaa aaatttaacg   9900
cgaattttaa caaaatatta acgcttacaa tttccattcg ccattcaggc tgcgcaactg   9960
ttgggaaggg cgatcggtgc gggcctcttc gctattacgc cagctggcga aagggggatg  10020
tgctgcaagg cgattaagtt gggtaacgcc agggttttcc cagtcacgac gttgtaaaac  10080
gacggccagt gaattgtaat acgactcact atagggcgaa ttgggtaccg ggcccccccct  10140
cgaggtcgat ggtgtcgata agcttgatat cgaattcatg tcacacaaac cgatcttcgc  10200
ctcaaggaaa cctaattcta catccgagag actgccgaga tccagtctac actgattaat  10260
tttcgggcca ataatttaaa aaaatcgtgt tatataatat tatatgtatt atatatatac  10320
atcatgatga tactgacagt catgtcccat tgctaaatag acagactcca tctgccgcct  10380
ccaactgatg ttctcaatat ttaaggggtc atctcgcatt gtttaataat aaacagactc  10440
catctaccgc ctccaaatga tgttctcaaa atatattgta tgaacttatt tttattactt  10500
agtattatta gacaacttac ttgctttatg aaaaacactt cctatttagg aaacaattta  10560
taatggcagt tcgttcattt aacaatttat gtagaataaa tgttataaat gcgtatggga  10620
aatcttaaat atggatagca taaatgatat ctgcattgcc taattcgaaa tcaacagcaa  10680
cgaaaaaaat cccttgtaca acataaatag tcatcgagaa atatcaacta tcaaagaaca  10740
gctattcaca cgttactatt gagattatta ttggacgaga atcacacact caactgtctt  10800
tctctcttct agaaatacag gtacaagtat gtactattct cattgttcat acttctagtc  10860
atttcatccc acatattcct tggatttctc tccaatgaat gacattctat cttgcaaatt  10920
```

caacaattat aataagatat accaaagtag cggtatagtg gcaatcaaaa agcttctctg 10980
gtgtgcttct cgtatttatt tttattctaa tgatccatta aaggtatata tttatttctt 11040
gttatataat ccttttgttt attacatggg ctggatacat aaaggtattt tgatttaatt 11100
ttttgcttaa attcaatccc ccctcgttca gtgtcaactg taatggtagg aaattaccat 11160
acttttgaag aagcaaaaaa aatgaaagaa aaaaaaaatc gtatttccag gttagacgtt 11220
ccgcagaatc tagaatgcgg tatgcggtac attgttcttc gaacgtaaaa gttgcgctcc 11280
ctgagatatt gtacattttt gcttttacaa gtacaagtac atcgtacaac tatgtactac 11340
tgttgatgca tccacaacag tttgttttgt tttttttgt ttttttttt tctaatgatt 11400 cattaccgct atgtatacct acttgtactt gtagtaagcc gggttattgg cgttcaatta 11460
atcatagact tatgaatctg cacggtgtgc gctgcgagtt acttttagct tatgcatgct 11520
acttgggtgt aatattggga tctgttcgga aatcaacgga tgctcaat 11568

<210> SEQ ID NO 42
<211> LENGTH: 11507
<212> TYPE: DNA
<213> ORGANISM: artificial sequence
<220> FEATURE:
<223> OTHER INFORMATION: pRF85 plasmid

<400> SEQUENCE: 42
cgatccctgt gttgaatcca tccatcttgg attgccaatt gtgcacacag aaccgggcac 60
tcacttcccc atccacactt gcggccgcag acataaaaaa caaaaaaaaa aagcaccgac 120
tcggtgccac tttttcaagt tgataacgga ctagccttat tttaacttgc tatttctagc 180
tctaaaacga gggtgggtaa tcgtttgaga cgagcttact cgtttcgtcc tcacggactc 240
atcagtcaaa ccatggtgtg atgtgtagtt tagatttcga atctgtgggg aaagaaagga 300
aaaaagagac tggcaaccga ttgggagagc cactgtttat atatacccta gacaagcccc 360
ccgcttgtaa gatgttggtc aatgtaaacc agtattaagg ttggcaagtg caggagaagc 420
aaggtgtggg taccgagcaa tggaaatgtg cggaaggcaa aaaaatgagg ccacggccta 480
ttgtcggggc tatatccagg gggcgattga agtacactaa catgacatgt gtccacagac 540
cctcaatctg gcctgatgag ccaaatccat acgcgctttc gcagctctaa aggctataac 600
aagtcacacc accctgctcg acctcagcgc cctcactttt tgttaagaca aactgtacac 660
gctgttccag cgttttctgc ctgcacctgg tgggacattt ggtgcaacct aaagtgctcg 720
gaacctctgt ggtgtccaga tcagcgcagc agttccgagg tagttttgag gcccttagat 780
gatggtttaa acgtcgacga gtatctgtct gactcgttaa ttaagtcata cacaagtcag 840
ctttcttcga gcctcatata agtataagta gttcaacgta ttagcactgt acccagcatc 900
tccgtatcga gaaacacaac aacatgcccc attggacaga tcatgcggat acacaggttg 960
tgcagtatca tacatactcg atcagacagg tcgtctgacc atcatacaag ctgaacaagc 1020
gctccatact tgcacgctct ctatatacac agttaaatta catatccata gtctaacctc 1080
taacagttaa tcttctggta agcctcccag ccagccttct ggtatcgctt ggcctcctca 1140
ataggatctc ggttctggcc gtacagacct cggccgacaa ttatgatatc cgttccggta 1200
gacatgacat cctcaacagt tcggtactgc tgtccgagag cgtctccctt gtcgtcaaga 1260
cccaccccgg gggtcagaat aagccagtcc tcagagtcgc ccttaggtcg gttctgggca 1320
atgaagccaa ccacaaactc ggggtcggat cgggcaagct caatggtctg cttggagtac 1380

-continued

```
tcgccagtgg ccagagagcc cttgcaagac agctcggcca gcatgagcag acctctggcc   1440
agcttctcgt tgggagaggg gactaggaac tccttgtact gggagttctc gtagtcagag   1500
acgtcctcct tcttctgttc agagacagtt tcctcggcac cagctcgcag gccagcaatg   1560
attccggttc cgggtacacc gtgggcgttg gtgatatcgg accactcggc gattcggtga   1620
caccggtact ggtgcttgac agtgttgcca atatctgcga actttctgtc ctcgaacagg   1680
aagaaaccgt gcttaagagc aagttccttg agggggagca cagtgccggc gtaggtgaag   1740
tcgtcaatga tgtcgatatg ggttttgatc atgcacacat aaggtccgac cttatcggca   1800
agctcaatga gctccttggt ggtggtaaca tccagagaag cacacaggtt ggttttcttg   1860
gctgccacga gcttgagcac tcgagcggca aaggcggact tgtggacgtt agctcgagct   1920
tcgtaggagg gcattttggt ggtgaagagg agactgaaat aaatttagtc tgcagaactt   1980
tttatcggaa ccttatctgg ggcagtgaag tatatgttat ggtaatagtt acgagttagt   2040
tgaacttata gatagactgg actatacggc tatcggtcca aattagaaag aacgtcaatg   2100
gctctctggg cgtcgccttt gccgacaaaa atgtgatcat gatgaaagcc agcaatgacg   2160
ttgcagctga tattgttgtc ggccaaccgc gccgaaaacg cagctgtcag acccacagcc   2220
tccaacgaag aatgtatcgt caaagtgatc caagcacact catagttgga gtcgtactcc   2280
aaaggcggca atgacgagtc agacagatac tcgtcgacgt ttaaaccatc atctaagggc   2340
ctcaaaacta cctcggaact gctgcgctga tctggacacc acagaggttc cgagcacttt   2400
aggttgcacc aaatgtccca ccaggtgcag gcagaaaacg ctggaacagc gtgtacagtt   2460
tgtcttaaca aaaagtgagg gcgctgaggt cgagcagggt ggtgtgactt gttatagcct   2520
ttagagctgc gaaagcgcgt atggatttgg ctcatcaggc cagattgagg gtctgtggac   2580
acatgtcatg ttagtgtact tcaatcgccc cctggatata gccccgacaa taggccgtgg   2640
cctcattttt ttgccttccg cacatttcca ttgctcggta cccacacctt gcttctcctg   2700
cacttgccaa ccttaatact ggtttacatt gaccaacatc ttacaagcgg ggggcttgtc   2760
tagggtatat ataaacagtg gctctcccaa tcggttgcca gtctcttttt tcctttcttt   2820
ccccacagat tcgaaatcta aactacacat cacaccatgg acaagaaata ctccatcggc   2880
ctggacattg gaaccaactc tgtcggctgg gctgtcatca ccgacgagta caaggtgccc   2940
tccaagaaat tcaaggtcct cggaaacacc gatcgacact ccatcaagaa aaacctcatt   3000
ggtgccctgt tgttcgattc tggcgagact gccgaagcta ccagactcaa gcgaactgct   3060
cggcgacgtt acacccgacg gaagaaccga atctgctacc tgcaggagat cttttccaac   3120
gagatggcca aggtggacga ttcgttcttt catcgactgg aggaatcctt cctcgtcgag   3180
gaagacaaga aacacgagcg tcatcccatc tttggcaaca ttgtggacga ggttgcttac   3240
cacgagaagt atcctaccat ctaccacctg cgaaagaaac tcgtcgattc caccgacaag   3300
gcggatctca gacttatcta cctcgctctg gcacacatga tcaagtttcg aggtcatttc   3360
ctcatcgagg gcgatctcaa tcccgacaac agcgatgtgg acaagctgtt cattcagctc   3420
gttcagacct acaaccagct gttcgaggaa aaccccatca atgcctccgg agtcgatgca   3480
aaggccatct tgtctgctcg actctcgaag agcagacgac tggagaacct cattgcccaa   3540
cttcctggcg agaaaaagaa cggactgttt ggcaacctca ttgccctttc tcttggtctc   3600
acacccaact tcaagtccaa cttcgatctg gcggaggacg ccaagctcca gctgtccaag   3660
gacacctacg acgatgacct cgacaacctg cttgcacaga ttggcgatca gtacgccgac   3720
ctgtttctcg ctgccaagaa cctttcggat gctattctct tgtctgacat tctgcgagtc   3780
```

-continued

```
aacaccgaga tcacaaaggc tccccttct gcctccatga tcaagcgata cgacgagcac   3840
catcaggatc tcacactgct caaggctctt gtccgacagc aactgcccga gaagtacaag   3900
gagatctttt tcgatcagtc gaagaacggc tacgctggat acatcgacgg cggagcctct   3960
caggaagagt tctacaagtt catcaagcca attctcgaga agatggacgg aaccgaggaa   4020
ctgcttgtca agctcaatcg agaggatctg cttcggaagc aacgaacctt cgacaacggc   4080
agcattcctc atcagatcca cctcggtgag ctgcacgcca ttcttcgacg tcaggaagac   4140
ttctacccct ttctcaagga caaccgagag aagatcgaga agattcttac ctttcgaatc   4200
ccctactatg ttggtcctct tgccagagga aactctcgat ttgcttggat gactcgaaag   4260
tccgaggaaa ccatcactcc ctggaacttc gaggaagtcg tggacaaggg tgcctctgca   4320
cagtccttca tcgagcgaat gaccaacttc gacaagaatc tgcccaacga gaaggttctt   4380
cccaagcatt cgctgctcta cgagtacttt acagtctaca acgaactcac caaagtcaag   4440
tacgttaccg agggaatgcg aaagcctgcc ttcttgtctg gcgaacagaa gaaagccatt   4500
gtcgatctcc tgttcaagac caaccgaaag gtcactgtta agcagctcaa ggaggactac   4560
ttcaagaaaa tcgagtgttt cgacagcgtc gagatttccg gagttgagga ccgattcaac   4620
gcctctttgg gcacctatca cgatctgctc aagattatca aggacaagga ttttctcgac   4680
aacgaggaaa acgaggacat tctggaggac atcgtgctca ctcttaccct gttcgaagat   4740
cgggagatga tcgaggaacg actcaagaca tacgctcacc tgttcgacga caaggtcatg   4800
aaacaactca agcgacgtag atacaccggc tggggaagac tttcgcgaaa gctcatcaac   4860
ggcatcagag acaagcagtc cggaaagacc attctggact ttctcaagtc cgatggcttt   4920
gccaaccgaa acttcatgca gctcattcac gacgattctc ttaccttcaa ggaggacatc   4980
cagaaggcac aagtgtccgg tcagggcgac agcttgcacg aacatattgc caacctggct   5040
ggttcgccag ccatcaagaa aggcattctc cagactgtca aggttgtcga cgagctggtg   5100
aaggtcatgg gacgtcacaa gcccgagaac attgtgatcg agatggccag agagaaccag   5160
acaactcaaa agggtcagaa aaactcgcga gagcggatga agcgaatcga ggaaggcatc   5220
aaggagctgg gatcccagat tctcaaggag catcccgtcg agaacactca actgcagaac   5280
gagaagctgt atctctacta tctgcagaat ggtcgagaca tgtacgtgga tcaggaactg   5340
gacatcaatc gtctcagcga ctacgatgtg gaccacattg tccctcaatc ctttctcaag   5400
gacgattcta tcgacaacaa ggtccttaca cgatccgaca agaacagagg caagtcggac   5460
aacgttccca gcgaagaggt ggtcaaaaag atgaagaact actggcgaca gctgctcaac   5520
gccaagctca ttacccagcg aaagttcgac aatcttacca aggccgagcg aggcggtctg   5580
tccgagctcg acaaggctgg cttcatcaag cgtcaactcg tcgagaccag acagatcaca   5640
aagcacgtcg cacagattct cgattctcgg atgaacacca agtacgacga gaacgacaag   5700
ctcatccgag aggtcaaggt gattactctc aagtccaaac tggtctccga tttccgaaag   5760
gactttcagt tctacaaggt gcgagagatc aacaattacc accatgccca cgatgcttac   5820
ctcaacgccg tcgttggcac tgcgctcatc aagaaatacc ccaagctcga aagcgagttc   5880
gtttacggcg attacaaggt ctacgacgtt cgaaagatga ttgccaagtc cgaacaggag   5940
attggcaagg ctactgccaa gtacttcttt tactccaaca tcatgaactt tttcaagacc   6000
gagatcacct tggccaacgg agagattcga aagagaccac ttatcgagac caacggcgaa   6060
actggagaga tcgtgtggga caagggtcga gactttgcaa ccgtgcgaaa ggttctgtcg   6120
```

-continued

```
atgcctcagg tcaacatcgt caagaaaacc gaggttcaga ctggcggatt ctccaaggag   6180
tcgattctgc ccaagcgaaa ctccgacaag ctcatcgctc gaaagaaaga ctgggatccc   6240
aagaaatacg gtggcttcga ttctcctacc gtcgcctatt ccgtgcttgt cgttgcgaag   6300
gtcgagaagg gcaagtccaa aaagctcaag tccgtcaagg agctgctcgg aattaccatc   6360
atggagcgat cgagcttcga gaagaatccc atcgacttct tggaagccaa gggttacaag   6420
gaggtcaaga aagacctcat tatcaagctg cccaagtact ctctgttcga actggagaac   6480
ggtcgaaagc gtatgctcgc ctccgctggc gagctgcaga agggaaacga gcttgccttg   6540
ccttcgaagt acgtcaactt tctctatctg gcttctcact acgagaagct caagggttct   6600
cccgaggaca acgaacagaa gcaactcttc gttgagcagc acaaacatta cctcgacgag   6660
attatcgagc agatttccga gttttcgaag cgagtcatcc tggctgatgc caacttggac   6720
aaggtgctct ctgcctacaa caagcatcgg gacaaaccca ttcgagaaca ggcggagaac   6780
atcattcacc tgtttactct taccaacctg ggtgctcctg cagctttcaa gtacttcgat   6840
accactatcg accgaaagcg gtacacatcc accaaggagg ttctcgatgc caccctgatt   6900
caccagtcca tcactggcct gtacgagacc cgaatcgacc tgtctcagct tggtggcgac   6960
tccagagccg atcccaagaa aaagcgaaag gtctaagcgg ccgcaagtgt ggatggggaa   7020
gtgagtgccc ggttctgtgt gcacaattgg caatccaaga tggatggatt caacacaggg   7080
atatagcgag ctacgtggtg gtgcgaggat atagcaacgg atatttatgt ttgacacttg   7140
agaatgtacg atacaagcac tgtccaagta caatactaaa catactgtac atactcatac   7200
tcgtacccgg gcaacggttt cacttgagtg cagtggctag tgctcttact cgtacagtgt   7260
gcaatactgc gtatcatagt ctttgatgta tatcgtattc attcatgtta gttgcgtacg   7320
agccggaagc ataaagtgta aagcctgggg tgcctaatga gtgagctaac tcacattaat   7380
tgcgttgcgc tcactgcccg ctttccagtc gggaaacctg tcgtgccagc tgcattaatg   7440
aatcggccaa cgcgcgggga gaggcggttt gcgtattggg cgctcttccg cttcctcgct   7500
cactgactcg ctgcgctcgg tcgttcggct gcggcgagcg gtatcagctc actcaaaggc   7560
ggtaatacgg ttatccacag aatcagggga taacgcagga aagaacatgt gagcaaaagg   7620
ccagcaaaag gccaggaacc gtaaaaaggc cgcgttgctg gcgtttttcc ataggctccg   7680
cccccctgac gagcatcaca aaaatcgacg ctcaagtcag aggtggcgaa acccgacagg   7740
actataaaga taccaggcgt ttccccctgg aagctccctc gtgcgctctc ctgttccgac   7800
cctgccgctt accggatacc tgtccgcctt tctcccttcg ggaagcgtgg cgctttctca   7860
tagctcacgc tgtaggtatc tcagttcggt gtaggtcgtt cgctccaagc tgggctgtgt   7920
gcacgaaccc cccgttcagc ccgaccgctg cgccttatcc ggtaactatc gtcttgagtc   7980
caacccggta agacacgact tatcgccact ggcagcagcc actggtaaca ggattagcag   8040
agcgaggtat gtaggcggtg ctacagagtt cttgaagtgg tggcctaact acggctacac   8100
tagaaggaca gtatttggta tctgcgctct gctgaagcca gttaccttcg gaaaaagagt   8160
tggtagctct tgatccggca aacaaaccac cgctggtagc ggtggttttt ttgtttgcaa   8220
gcagcagatt acgcgcagaa aaaaaggatc tcaagaagat cctttgatct tttctacggg   8280
gtctgacgct cagtggaacg aaaactcacg ttaagggatt ttggtcatga gattatcaaa   8340
aaggatcttc acctagatcc ttttaaatta aaaatgaagt tttaaatcaa tctaaagtat   8400
atatgagtaa acttggtctg acagttacca atgcttaatc agtgaggcac ctatctcagc   8460
gatctgtcta tttcgttcat ccatagttgc ctgactcccc gtcgtgtaga taactacgat   8520
```

acgggagggc ttaccatctg gccccagtgc tgcaatgata ccgcgagacc cacgctcacc 8580
ggctccagat ttatcagcaa taaaccagcc agccggaagg gccgagcgca gaagtggtcc 8640
tgcaacttta tccgcctcca tccagtctat taattgttgc cgggaagcta gagtaagtag 8700
ttcgccagtt aatagtttgc gcaacgttgt tgccattgct acaggcatcg tggtgtcacg 8760
ctcgtcgttt ggtatggctt cattcagctc cggttcccaa cgatcaaggc gagttacatg 8820
atcccccatg ttgtgcaaaa aagcggttag ctccttcggt cctccgatcg ttgtcagaag 8880
taagttggcc gcagtgttat cactcatggt tatggcagca ctgcataatt ctcttactgt 8940
catgccatcc gtaagatgct tttctgtgac tggtgagtac tcaaccaagt cattctgaga 9000
atagtgtatg cggcgaccga gttgctcttg cccggcgtca atacgggata ataccgcgcc 9060
acatagcaga actttaaaag tgctcatcat tggaaaacgt tcttcggggc gaaaactctc 9120
aaggatctta ccgctgttga gatccagttc gatgtaaccc actcgtgcac ccaactgatc 9180
ttcagcatct tttactttca ccagcgtttc tgggtgagca aaaacaggaa ggcaaaatgc 9240
cgcaaaaaag ggaataaggg cgacacggaa atgttgaata ctcatactct tcctttttca 9300
atattattga agcatttatc agggttattg tctcatgagc ggatacatat ttgaatgtat 9360
ttagaaaaat aaacaaatag gggttccgcg cacatttccc cgaaaagtgc cacctgacgc 9420
gccctgtagc ggcgcattaa gcgcggcggg tgtggtggtt acgcgcagcg tgaccgctac 9480
acttgccagc gccctagcgc ccgctccttt cgctttcttc ccttcctttc tcgccacgtt 9540
cgccggcttt ccccgtcaag ctctaaatcg ggggctccct ttagggttcc gatttagtgc 9600
tttacggcac ctcgacccca aaaaacttga ttagggtgat ggttcacgta gtgggccatc 9660
gccctgatag acggtttttc gccctttgac gttggagtcc acgttcttta atagtggact 9720
cttgttccaa actggaacaa cactcaaccc tatctcggtc tattcttttg atttataagg 9780
gattttgccg atttcggcct attggttaaa aaatgagctg atttaacaaa aatttaacgc 9840
gaattttaac aaaatattaa cgcttacaat ttccattcgc cattcaggct gcgcaactgt 9900
tgggaagggc gatcggtgcg ggcctcttcg ctattacgcc agctggcgaa agggggatgt 9960
gctgcaaggc gattaagttg ggtaacgcca gggttttccc agtcacgacg ttgtaaaacg 10020
acggccagtg aattgtaata cgactcacta tagggcgaat tgggtaccgg gccccccctc 10080
gaggtcgatg gtgtcgataa gcttgatatc gaattcatgt cacacaaacc gatcttcgcc 10140
tcaaggaaac ctaattctac atccgagaga ctgccgagat ccagtctaca ctgattaatt 10200
ttcgggccaa taatttaaaa aaatcgtgtt atataatatt atatgtatta tatatataca 10260
tcatgatgat actgacagtc atgtcccatt gctaaataga cagactccat ctgccgcctc 10320
caactgatgt tctcaatatt taaggggtca tctcgcattg tttaataata aacagactcc 10380
atctaccgcc tccaaatgat gttctcaaaa tatattgtat gaacttattt ttattactta 10440
gtattattag acaacttact tgctttatga aaaacacttc ctatttagga aacaatttat 10500
aatggcagtt cgttcattta acaatttatg tagaataaat gttataaatg cgtatgggaa 10560
atcttaaata tggatagcat aaatgatatc tgcattgcct aattcgaaat caacagcaac 10620
gaaaaaaatc ccttgtacaa cataaatagt catcgagaaa tatcaactat caaagaacag 10680
ctattcacac gttactattg agattattat tggacgagaa tcacacactc aactgtcttt 10740
ctctcttcta gaaatacagg tacaagtatg tactattctc attgttcata cttctagtca 10800
tttcatccca catattcctt ggatttctct ccaatgaatg acattctatc ttgcaaattc 10860

```
aacaattata ataagatata ccaaagtagc ggtatagtgg caatcaaaaa gcttctctgg   10920

tgtgcttctc gtatttattt ttattctaat gatccattaa aggtatatat ttatttcttg   10980

ttatataatc cttttgttta ttacatgggc tggatacata aaggtatttt gatttaattt   11040

tttgcttaaa ttcaatcccc cctcgttcag tgtcaactgt aatggtagga aattaccata   11100

cttttgaaga agcaaaaaaa atgaaagaaa aaaaaaatcg tatttccagg ttagacgttc   11160

cgcagaatct agaatgcggt atgcggtaca ttgttcttcg aacgtaaaag ttgcgctccc   11220

tgagatattg tacatttttg cttttacaag tacaagtaca tcgtacaact atgtactact   11280

gttgatgcat ccacaacagt ttgttttgtt tttttttgtt tttttttttt ctaatgattc   11340

attaccgcta tgtataccta cttgtacttg tagtaagccg ggttattggc gttcaattaa   11400

tcatagactt atgaatctgc acggtgtgcg ctgcgagtta cttttagctt atgcatgcta   11460

cttgggtgta atattgggat ctgttcggaa atcaacggat gctcaat                11507
```

<210> SEQ ID NO 43
<211> LENGTH: 4
<212> TYPE: RNA
<213> ORGANISM: unknown
<220> FEATURE:
<223> OTHER INFORMATION: RNA loop-forming sequence (GAAA)

<400> SEQUENCE: 43 gaaa                                                                     4

<210> SEQ ID NO 44
<211> LENGTH: 4
<212> TYPE: RNA
<213> ORGANISM: unknown
<220> FEATURE:
<223> OTHER INFORMATION: RNA loop-forming sequence (CAAA)

<400> SEQUENCE: 44 caaa                                                                     4

<210> SEQ ID NO 45
<211> LENGTH: 4
<212> TYPE: RNA
<213> ORGANISM: unknown
<220> FEATURE:
<223> OTHER INFORMATION: RNA loop-forming sequence (AAAG)

<400> SEQUENCE: 45 aaag                                                                     4

<210> SEQ ID NO 46
<211> LENGTH: 23
<212> TYPE: DNA
<213> ORGANISM: unknown
<220> FEATURE:
<223> OTHER INFORMATION: Example of a Cas9 target site:PAM sequence
<220> FEATURE:
<221> NAME/KEY: misc_feature
<222> LOCATION: (1)..(20)
<223> OTHER INFORMATION: n = A, C, T, or G
<220> FEATURE:
<221> NAME/KEY: misc_feature
<222> LOCATION: (21)..(21)
<223> OTHER INFORMATION: n = A, C, T, or G (indicated as an "X" in
      Specification)

<400> SEQUENCE: 46
nnnnnnnnnn nnnnnnnnnn ngg                                               23

<210> SEQ ID NO 47
<211> LENGTH: 3
<212> TYPE: DNA
<213> ORGANISM: unknown
<220> FEATURE:
<223> OTHER INFORMATION: PAM sequence NGG
<220> FEATURE:
<221> NAME/KEY: misc_feature
<222> LOCATION: (1)..(1)
<223> OTHER INFORMATION: n = A, C, T, or G

<400> SEQUENCE: 47 ngg 3

<210> SEQ ID NO 48
<211> LENGTH: 6
<212> TYPE: DNA
<213> ORGANISM: unknown
<220> FEATURE:
<223> OTHER INFORMATION: PAM sequence NNAGAA
<220> FEATURE:
<221> NAME/KEY: misc_feature
<222> LOCATION: (1)..(2)
<223> OTHER INFORMATION: n = A, C, T, or G

<400> SEQUENCE: 48 nnagaa 6

<210> SEQ ID NO 49
<211> LENGTH: 7
<212> TYPE: DNA
<213> ORGANISM: unknown
<220> FEATURE:
<223> OTHER INFORMATION: PAM sequence NNAGAAW
<220> FEATURE:
<221> NAME/KEY: misc_feature
<222> LOCATION: (1)..(2)
<223> OTHER INFORMATION: n = A, C, T, or G
<220> FEATURE:
<221> NAME/KEY: misc_feature
<222> LOCATION: (7)..(7)
<223> OTHER INFORMATION: w = A or T

<400> SEQUENCE: 49 nnagaaw 7

<210> SEQ ID NO 50
<211> LENGTH: 5
<212> TYPE: DNA
<213> ORGANISM: unknown
<220> FEATURE:
<223> OTHER INFORMATION: PAM sequence NGGNG
<220> FEATURE:
<221> NAME/KEY: misc_feature
<222> LOCATION: (1)..(1)
<223> OTHER INFORMATION: n = A, C, T, or G
<220> FEATURE:
<221> NAME/KEY: misc_feature
<222> LOCATION: (4)..(4)
<223> OTHER INFORMATION: n = A, C, T, or G

<400> SEQUENCE: 50 nggng 5

<210> SEQ ID NO 51
<211> LENGTH: 8
<212> TYPE: DNA
<213> ORGANISM: unknown
<220> FEATURE:
<223> OTHER INFORMATION: PAM sequence NNNNGATT
<220> FEATURE:
<221> NAME/KEY: misc_feature
<222> LOCATION: (1)..(4)
<223> OTHER INFORMATION: n = A, C, T, or G

<400> SEQUENCE: 51 nnnngatt 8

<210> SEQ ID NO 52
<211> LENGTH: 6
<212> TYPE: DNA
<213> ORGANISM: unknown
<220> FEATURE:
<223> OTHER INFORMATION: PAM sequence NAAAAC
<220> FEATURE:
<221> NAME/KEY: misc_feature
<222> LOCATION: (1)..(1)
<223> OTHER INFORMATION: n = A, C, T, or G

<400> SEQUENCE: 52 naaaac 6

<210> SEQ ID NO 53
<211> LENGTH: 2
<212> TYPE: DNA
<213> ORGANISM: unknown
<220> FEATURE:
<223> OTHER INFORMATION: PAM sequence NG
<220> FEATURE:
<221> NAME/KEY: misc_feature
<222> LOCATION: (1)..(1)
<223> OTHER INFORMATION: n = A, C, T, or G

<400> SEQUENCE: 53 ng 2

<210> SEQ ID NO 54
<211> LENGTH: 22
<212> TYPE: RNA
<213> ORGANISM: unknown
<220> FEATURE:
<223> OTHER INFORMATION: TracrRNA mate sequence example 1

<400> SEQUENCE: 54
guuuuuguac ucucaagauu ua 22

<210> SEQ ID NO 55
<211> LENGTH: 15
<212> TYPE: RNA
<213> ORGANISM: unknown
<220> FEATURE:
<223> OTHER INFORMATION: TracrRNA mate sequence example 2

<400> SEQUENCE: 55
guuuuuguac ucuca 15

<210> SEQ ID NO 56
<211> LENGTH: 12
<212> TYPE: RNA
<213> ORGANISM: unknown
<220> FEATURE:
<223> OTHER INFORMATION: TracrRNA mate sequence example 3

<400> SEQUENCE: 56
guuuuagagc ua 12

<210> SEQ ID NO 57

<211> LENGTH: 13
<212> TYPE: RNA
<213> ORGANISM: unknown
<220> FEATURE:
<223> OTHER INFORMATION: TracrRNA mate sequence example 4

<400> SEQUENCE: 57
guuuuagagc uag 13

<210> SEQ ID NO 58
<211> LENGTH: 60
<212> TYPE: RNA
<213> ORGANISM: Streptococcus pyogenes

<400> SEQUENCE: 58
uagcaaguua aaauaaggcu aguccguuau caacuugaaa aaguggcacc gagucggugc 60

<210> SEQ ID NO 59
<211> LENGTH: 45
<212> TYPE: RNA
<213> ORGANISM: Streptococcus pyogenes

<400> SEQUENCE: 59
uagcaaguua aaauaaggcu aguccguuau caacuugaaa aagug 45

<210> SEQ ID NO 60
<211> LENGTH: 32
<212> TYPE: RNA
<213> ORGANISM: Streptococcus pyogenes

<400> SEQUENCE: 60
uagcaaguua aaauaaggcu aguccguuau ca 32

<210> SEQ ID NO 61
<211> LENGTH: 85
<212> TYPE: RNA
<213> ORGANISM: Streptococcus thermophilus

<400> SEQUENCE: 61
uaaaucuugc agaagcuaca aagauaaggc uucaugccga aaucaacacc cugucauuuu 60
auggcagggu guuuucguua uuuaa 85

<210> SEQ ID NO 62
<211> LENGTH: 77
<212> TYPE: RNA
<213> ORGANISM: Streptococcus thermophilus

<400> SEQUENCE: 62
ugcagaagcu acaaagauaa ggcuucaugc cgaaaucaac acccugucau uuuauggcag 60
gguguuuucg uuauuua 77

<210> SEQ ID NO 63
<211> LENGTH: 65
<212> TYPE: RNA
<213> ORGANISM: Streptococcus thermophilus

<400> SEQUENCE: 63
ugcagaagcu acaaagauaa ggcuucaugc cgaaaucaac acccugucau uuuauggcag 60
ggugu 65

<210> SEQ ID NO 64
<211> LENGTH: 131

<212> TYPE: RNA
<213> ORGANISM: artificial sequence
<220> FEATURE:
<223> OTHER INFORMATION: gRNA example 1
<220> FEATURE:
<221> NAME/KEY: misc_feature
<222> LOCATION: (1)..(20)
<223> OTHER INFORMATION: n = A, C, U, or G

<400> SEQUENCE: 64
nnnnnnnnnn nnnnnnnnnn guuuuuguac ucucaagauu uagaaauaaa ucuugcagaa 60
gcuacaaaga uaaggcuuca ugccgaaauc aacacccugu cauuuuaugg cagggguguuu 120 ucguuauuua a 131

<210> SEQ ID NO 65
<211> LENGTH: 117
<212> TYPE: RNA
<213> ORGANISM: artificial sequence
<220> FEATURE:
<223> OTHER INFORMATION: gRNA example 2
<220> FEATURE:
<221> NAME/KEY: misc_feature
<222> LOCATION: (1)..(20)
<223> OTHER INFORMATION: n = A, C, U, or G

<400> SEQUENCE: 65
nnnnnnnnnn nnnnnnnnnn guuuuuguac ucucagaaau gcagaagcua caaagauaag 60
gcuucaugcc gaaaucaaca cccugucauu uuauggcagg guguuuucgu uauuuaa 117

<210> SEQ ID NO 66
<211> LENGTH: 104
<212> TYPE: RNA
<213> ORGANISM: artificial sequence
<220> FEATURE:
<223> OTHER INFORMATION: gRNA example 3
<220> FEATURE:
<221> NAME/KEY: misc_feature
<222> LOCATION: (1)..(20)
<223> OTHER INFORMATION: n = A, C, U, or G

<400> SEQUENCE: 66
nnnnnnnnnn nnnnnnnnnn guuuuuguac ucucagaaau gcagaagcua caaagauaag 60
gcuucaugcc gaaaucaaca cccugucauu uuauggcagg gugu 104

<210> SEQ ID NO 67
<211> LENGTH: 99
<212> TYPE: RNA
<213> ORGANISM: artificial sequence
<220> FEATURE:
<223> OTHER INFORMATION: gRNA example 4
<220> FEATURE:
<221> NAME/KEY: misc_feature
<222> LOCATION: (1)..(20)
<223> OTHER INFORMATION: n = A, C, U, or G

<400> SEQUENCE: 67
nnnnnnnnnn nnnnnnnnnn guuuuuguac ucucagaaau agcaaguuaa aauaaggcua 60
guccguuauc aacuugaaaa aguggcaccg agucggugc 99

<210> SEQ ID NO 68
<211> LENGTH: 81
<212> TYPE: RNA
<213> ORGANISM: artificial sequence
<220> FEATURE:
<223> OTHER INFORMATION: gRNA example 5
<220> FEATURE:

-continued

<221> NAME/KEY: misc_feature
<222> LOCATION: (1)..(20)
<223> OTHER INFORMATION: n = A, C, U, or G

<400> SEQUENCE: 68
nnnnnnnnnn nnnnnnnnnn guuuuagagc uagaaauagc aaguuaaaau aaggcuaguc 60
cguuaucaac uugaaaaagu g 81

<210> SEQ ID NO 69
<211> LENGTH: 68
<212> TYPE: RNA
<213> ORGANISM: artificial sequence
<220> FEATURE:
<223> OTHER INFORMATION: gRNA example 6
<220> FEATURE:
<221> NAME/KEY: misc_feature
<222> LOCATION: (1)..(20)
<223> OTHER INFORMATION: n = A, C, U, or G

<400> SEQUENCE: 69
nnnnnnnnnn nnnnnnnnnn guuuuagagc uagaaauagc aaguuaaaau aaggcuaguc 60
cguuauca 68

<210> SEQ ID NO 70
<211> LENGTH: 100
<212> TYPE: RNA
<213> ORGANISM: artificial sequence
<220> FEATURE:
<223> OTHER INFORMATION: gRNA example 7
<220> FEATURE:
<221> NAME/KEY: misc_feature
<222> LOCATION: (1)..(20)
<223> OTHER INFORMATION: n = A, C, U, or G

<400> SEQUENCE: 70
nnnnnnnnnn nnnnnnnnnn guuuuagagc uagaaauagc aaguuaaaau aaggcuaguc 60
cguuaucaac uugaaaaagu ggcaccgagu cggugcuuuu 100

<210> SEQ ID NO 71
<211> LENGTH: 53
<212> TYPE: DNA
<213> ORGANISM: Yarrowia lipolytica

<400> SEQUENCE: 71
caatggaaaa gacattttca aacgattacc caccctccgg gactgaggcc cac 53

<210> SEQ ID NO 72
<211> LENGTH: 52
<212> TYPE: DNA
<213> ORGANISM: artificial sequence
<220> FEATURE:
<223> OTHER INFORMATION: Sequence 1 shown in Figure 5

<400> SEQUENCE: 72
caatggaaaa gacattttca aacgattacc cacctccggg actgaggccc ac 52

<210> SEQ ID NO 73
<211> LENGTH: 51
<212> TYPE: DNA
<213> ORGANISM: artificial sequence
<220> FEATURE:
<223> OTHER INFORMATION: Sequence 2 shown in Figure 5

<400> SEQUENCE: 73
caatggaaaa gacattttca aacgattacc cactccggga ctgaggccca c 51

<210> SEQ ID NO 74
<211> LENGTH: 49
<212> TYPE: DNA
<213> ORGANISM: artificial sequence
<220> FEATURE:
<223> OTHER INFORMATION: Sequence 3 shown in Figure 5

<400> SEQUENCE: 74
caatggaaaa gacattttca aacgattacc caccgggact gaggcccac 49

<210> SEQ ID NO 75
<211> LENGTH: 46
<212> TYPE: DNA
<213> ORGANISM: artificial sequence
<220> FEATURE:
<223> OTHER INFORMATION: Sequence 4 shown in Figure 5

<400> SEQUENCE: 75
caatggaaaa gacattttca aacgattacc cgggactgag gcccac 46

<210> SEQ ID NO 76
<211> LENGTH: 13
<212> TYPE: DNA
<213> ORGANISM: artificial sequence
<220> FEATURE:
<223> OTHER INFORMATION: Sequence 5 shown in Figure 5

<400> SEQUENCE: 76
cactgaggcc cac 13

<210> SEQ ID NO 77
<211> LENGTH: 54
<212> TYPE: DNA
<213> ORGANISM: artificial sequence
<220> FEATURE:
<223> OTHER INFORMATION: Sequence 6 shown in Figure 5

<400> SEQUENCE: 77
caatggaaaa gacattttca aacgattacc caccactccg ggactgaggc ccac 54

<210> SEQ ID NO 78
<211> LENGTH: 48
<212> TYPE: DNA
<213> ORGANISM: artificial sequence
<220> FEATURE:
<223> OTHER INFORMATION: Sequence 7 shown in Figure 5

<400> SEQUENCE: 78
caatggaaaa gacattttca aacgattacc tccgggactg aggcccac 48

<210> SEQ ID NO 79
<211> LENGTH: 46
<212> TYPE: DNA
<213> ORGANISM: artificial sequence
<220> FEATURE:
<223> OTHER INFORMATION: Sequence 8 shown in Figure 5

<400> SEQUENCE: 79
caatggaaaa gacattttca aacgattacc cgggactgag gcccac 46

<210> SEQ ID NO 80
<211> LENGTH: 44
<212> TYPE: DNA
<213> ORGANISM: artificial sequence
<220> FEATURE:

<223> OTHER INFORMATION: Sequence 9 shown in Figure 5

<400> SEQUENCE: 80
caatggaaaa gacattttca aacgattacc cacctgaggc ccac 44

<210> SEQ ID NO 81
<211> LENGTH: 48
<212> TYPE: DNA
<213> ORGANISM: artificial sequence
<220> FEATURE:
<223> OTHER INFORMATION: Sequence 10 shown in Figure 5

<400> SEQUENCE: 81
caatggaaaa gacattttca aacgattacc cacgggactg aggcccac 48

<210> SEQ ID NO 82
<211> LENGTH: 40
<212> TYPE: DNA
<213> ORGANISM: artificial sequence
<220> FEATURE:
<223> OTHER INFORMATION: Sequence 11 shown in Figure 5

<400> SEQUENCE: 82
caatggaaaa gacattttca aacgattaca cacggcccac 40

<210> SEQ ID NO 83
<211> LENGTH: 37
<212> TYPE: DNA
<213> ORGANISM: artificial sequence
<220> FEATURE:
<223> OTHER INFORMATION: Sequence 12 shown in Figure 5

<400> SEQUENCE: 83
caatggaaaa gacattttct ccgggactga ggcccac 37

<210> SEQ ID NO 84
<211> LENGTH: 43
<212> TYPE: DNA
<213> ORGANISM: artificial sequence
<220> FEATURE:
<223> OTHER INFORMATION: Sequence 13 shown in Figure 5

<400> SEQUENCE: 84
caatggaaaa gacattttca aacgctccgg gactgaggcc cac 43

<210> SEQ ID NO 85
<211> LENGTH: 43
<212> TYPE: DNA
<213> ORGANISM: artificial sequence
<220> FEATURE:
<223> OTHER INFORMATION: Sequence 14 shown in Figure 5

<400> SEQUENCE: 85
caatggaaaa gacattttca aacgatccgg gactgaggcc cac 43

<210> SEQ ID NO 86
<211> LENGTH: 33
<212> TYPE: DNA
<213> ORGANISM: artificial sequence
<220> FEATURE:
<223> OTHER INFORMATION: Sequence 15 shown in Figure 5

<400> SEQUENCE: 86
caatggaaaa gacattttca aacgataccc cac 33

<210> SEQ ID NO 87
<211> LENGTH: 54
<212> TYPE: DNA
<213> ORGANISM: artificial sequence
<220> FEATURE:
<223> OTHER INFORMATION: Sequence 16 shown in Figure 5

<400> SEQUENCE: 87
caatggaaaa gacattttca aacgattacc cacccctccg ggactgaggc ccac 54

<210> SEQ ID NO 88
<211> LENGTH: 49
<212> TYPE: DNA
<213> ORGANISM: artificial sequence
<220> FEATURE:
<223> OTHER INFORMATION: Sequence 17 shown in Figure 5

<400> SEQUENCE: 88
caatggaaaa gacattttca aacgattacc ctccgggact gaggcccac 49

<210> SEQ ID NO 89
<211> LENGTH: 54
<212> TYPE: DNA
<213> ORGANISM: artificial sequence
<220> FEATURE:
<223> OTHER INFORMATION: Sequence 18 shown in Figure 5

<400> SEQUENCE: 89
caatggaaaa gacattttca aacgattacc cacccctccg ggactgaggc ccac 54

<210> SEQ ID NO 90
<211> LENGTH: 47
<212> TYPE: DNA
<213> ORGANISM: Artificial sequence
<220> FEATURE:
<223> OTHER INFORMATION: AarI-removal-1

<400> SEQUENCE: 90
agaagtatcc taccatctac catctccgaa agaaactcgt cgattcc 47

<210> SEQ ID NO 91
<211> LENGTH: 47
<212> TYPE: DNA
<213> ORGANISM: Artificial sequence
<220> FEATURE:
<223> OTHER INFORMATION: AarI-removal-2

<400> SEQUENCE: 91
ggaatcgacg agtttctttc ggagatggta gatggtagga tacttct 47

<210> SEQ ID NO 92
<211> LENGTH: 10706
<212> TYPE: DNA
<213> ORGANISM: Artificial sequence
<220> FEATURE:
<223> OTHER INFORMATION: pRF109

<400> SEQUENCE: 92
catggacaag aaatactcca tcggcctgga cattggaacc aactctgtcg gctgggctgt 60
catcaccgac gagtacaagg tgccctccaa gaaattcaag gtcctcggaa acaccgatcg 120
acactccatc aagaaaaacc tcattggtgc cctgttgttc gattctggcg agactgccga 180
agctaccaga ctcaagcgaa ctgctcggcg acgttacacc cgacggaaga accgaatctg 240
ctacctgcag gagatctttt ccaacgagat ggccaaggtg gacgattcgt tctttcatcg 300

-continued

```
actggaggaa tccttcctcg tcgaggaaga caagaaacac gagcgtcatc ccatctttgg    360
caacattgtg gacgaggttg cttaccacga gaagtatcct accatctacc atctccgaaa    420
gaaactcgtc gattccaccg acaaggcgga tctcagactt atctacctcg ctctggcaca    480
catgatcaag tttcgaggtc atttcctcat cgagggcgat ctcaatcccg acaacagcga    540
tgtggacaag ctgttcattc agctcgttca gacctacaac cagctgttcg aggaaaaccc    600
catcaatgcc tccggagtcg atgcaaaggc catcttgtct gctcgactct cgaagagcag    660
acgactggag aacctcattg cccaacttcc tggcgagaaa aagaacggac tgtttggcaa    720
cctcattgcc ctttctcttg gtctcacacc caacttcaag tccaacttcg atctggcgga    780
ggacgccaag ctccagctgt ccaaggacac ctacgacgat gacctcgaca acctgcttgc    840
acagattggc gatcagtacg ccgacctgtt tctcgctgcc aagaaccttt cggatgctat    900
tctcttgtct gacattctgc gagtcaacac cgagatcaca aaggctcccc tttctgcctc    960
catgatcaag cgatacgacg agcaccatca ggatctcaca ctgctcaagg ctcttgtccg   1020
acagcaactg cccgagaagt acaaggagat ctttttcgat cagtcgaaga acggctacgc   1080
tggatacatc gacggcggag cctctcagga agagttctac aagttcatca agccaattct   1140
cgagaagatg gacggaaccg aggaactgct tgtcaagctc aatcgagagg atctgcttcg   1200
gaagcaacga accttcgaca acggcagcat tcctcatcag atccacctcg gtgagctgca   1260
cgccattctt cgacgtcagg aagacttcta ccccttttctc aaggacaacc gagagaagat  1320
cgagaagatt cttacctttc gaatccccta ctatgttggt cctcttgcca gaggaaactc   1380
tcgatttgct tggatgactc gaaagtccga ggaaaccatc actccctgga acttcgagga   1440
agtcgtggac aagggtgcct ctgcacagtc cttcatcgag cgaatgacca acttcgacaa   1500
gaatctgccc aacgagaagg ttcttcccaa gcattcgctg ctctacgagt actttacagt   1560
ctacaacgaa ctcaccaaag tcaagtacgt taccgaggga atgcgaaagc ctgccttctt   1620
gtctggcgaa cagaagaaag ccattgtcga tctcctgttc aagaccaacc gaaaggtcac   1680
tgttaagcag ctcaaggagg actacttcaa gaaaatcgag tgtttcgaca gcgtcgagat   1740
ttccggagtt gaggaccgat tcaacgcctc tttgggcacc tatcacgatc tgctcaagat   1800
tatcaaggac aaggattttc tcgacaacga ggaaaacgag gacattctgg aggacatcgt   1860
gctcactctt accctgttcg aagatcggga gatgatcgag gaacgactca agacatacgc   1920
tcacctgttc gacgacaagg tcatgaaaca actcaagcga cgtagataca ccggctgggg   1980
aagactttcg cgaaagctca tcaacggcat cagagacaag cagtccggaa agaccattct   2040
ggactttctc aagtccgatg gctttgccaa ccgaaacttc atgcagctca ttcacgacga   2100
ttctcttacc ttcaaggagg acatccagaa ggcacaagtg tccggtcagg gcgacagctt   2160
gcacgaacat attgccaacc tggctggttc gccagccatc aagaaaggca ttctccagac   2220
tgtcaaggtt gtcgacgagc tggtgaaggt catgggacgt cacaagcccg agaacattgt   2280
gatcgagatg gccagagaga accagacaac tcaaaagggt cagaaaaact cgcgagagcg   2340
gatgaagcga atcgaggaag gcatcaagga gctgggatcc cagattctca aggagcatcc   2400
cgtcgagaac actcaactgc agaacgagaa gctgtatctc tactatctgc agaatggtcg   2460
agacatgtac gtggatcagg aactggacat caatcgtctc agcgactacg atgtggacca   2520
cattgtccct caatcctttc tcaaggacga ttctatcgac aacaaggtcc ttacacgatc   2580
cgacaagaac agaggcaagt cggacaacgt tcccagcgaa gaggtggtca aaaagatgaa   2640
gaactactgg cgacagctgc tcaacgccaa gctcattacc cagcgaaagt tcgacaatct   2700
```

```
taccaaggcc gagcgaggcg gtctgtccga gctcgacaag gctggcttca tcaagcgtca   2760
actcgtcgag accagacaga tcacaaagca cgtcgcacag attctcgatt ctcggatgaa   2820
caccaagtac gacgagaacg acaagctcat ccgagaggtc aaggtgatta ctctcaagtc   2880
caaactggtc tccgatttcc gaaaggactt tcagttctac aaggtgcgag agatcaacaa   2940
ttaccaccat gcccacgatg cttacctcaa cgccgtcgtt ggcactgcgc tcatcaagaa   3000
ataccccaag ctcgaaagcg agttcgttta cggcgattac aaggtctacg acgttcgaaa   3060
gatgattgcc aagtccgaac aggagattgg caaggctact gccaagtact tcttttactc   3120
caacatcatg aactttttca agaccgagat caccttggcc aacggagaga ttcgaaagag   3180
accacttatc gagaccaacg gcgaaactgg agagatcgtg tgggacaagg gtcgagactt   3240
tgcaaccgtg cgaaaggttc tgtcgatgcc tcaggtcaac atcgtcaaga aaaccgaggt   3300
tcagactggc ggattctcca aggagtcgat tctgcccaag cgaaactccg acaagctcat   3360
cgctcgaaag aaagactggg atcccaagaa atacggtggc ttcgattctc ctaccgtcgc   3420
ctattccgtg cttgtcgttg cgaaggtcga gaagggcaag tccaaaaagc tcaagtccgt   3480
caaggagctg ctcggaatta ccatcatgga gcgatcgagc ttcgagaaga atcccatcga   3540
cttcttggaa gccaagggtt acaaggaggt caagaaagac ctcattatca agctgcccaa   3600
gtactctctg ttcgaactgg agaacggtcg aaagcgtatg ctcgcctccg ctggcgagct   3660
gcagaaggga aacgagcttg ccttgccttc gaagtacgtc aactttctct atctggcttc   3720
tcactacgag aagctcaagg gttctcccga ggacaacgaa cagaagcaac tcttcgttga   3780
gcagcacaaa cattacctcg acgagattat cgagcagatt tccgagtttt cgaagcgagt   3840
catcctggct gatgccaact tggacaaggt gctctctgcc tacaacaagc atcgggacaa   3900
acccattcga gaacaggcgg agaacatcat tcacctgttt actcttacca acctgggtgc   3960
tcctgcagct ttcaagtact tcgataccac tatcgaccga aagcggtaca catccaccaa   4020
ggaggttctc gatgccaccc tgattcacca gtccatcact ggcctgtacg agacccgaat   4080
cgacctgtct cagcttggtg gcgactccag agccgatccc aagaaaaagc gaaaggtcta   4140
agcggccgca agtgtggatg gggaagtgag tgcccggttc tgtgtgcaca attggcaatc   4200
caagatggat ggattcaaca cagggatata gcgagctacg tggtggtgcg aggatatagc   4260
aacggatatt tatgtttgac acttgagaat gtacgataca agcactgtcc aagtacaata   4320
ctaaacatac tgtacatact catactcgta cccgggcaac ggtttcactt gagtgcagtg   4380
gctagtgctc ttactcgtac agtgtgcaat actgcgtatc atagtctttg atgtatatcg   4440
tattcattca tgttagttgc gtacgagccg gaagcataaa gtgtaaagcc tggggtgcct   4500
aatgagtgag ctaactcaca ttaattgcgt tgcgctcact gcccgctttc cagtcgggaa   4560
acctgtcgtg ccagctgcat taatgaatcg gccaacgcgc ggggagaggc ggtttgcgta   4620
ttgggcgctc ttccgcttcc tcgctcactg actcgctgcg ctcggtcgtt cggctgcggc   4680
gagcggtatc agctcactca aaggcggtaa tacggttatc cacagaatca ggggataacg   4740
caggaaagaa catgtgagca aaaggccagc aaaaggccag gaaccgtaaa aaggccgcgt   4800
tgctggcgtt tttccatagg ctccgccccc ctgacgagca tcacaaaaat cgacgctcaa   4860
gtcagaggtg gcgaaacccg acaggactat aaagatacca ggcgtttccc cctggaagct   4920
ccctcgtgcg ctctcctgtt ccgaccctgc cgcttaccgg atacctgtcc gcctttctcc   4980
cttcgggaag cgtggcgctt tctcatagct cacgctgtag gtatctcagt tcggtgtagg   5040
```

-continued

```
tcgttcgctc caagctgggc tgtgtgcacg aaccccccgt tcagcccgac cgctgcgcct   5100
tatccggtaa ctatcgtctt gagtccaacc cggtaagaca cgacttatcg ccactggcag   5160
cagccactgg taacaggatt agcagagcga ggtatgtagg cggtgctaca gagttcttga   5220
agtggtggcc taactacggc tacactagaa ggacagtatt tggtatctgc gctctgctga   5280
agccagttac cttcggaaaa agagttggta gctcttgatc cggcaaacaa accaccgctg   5340
gtagcggtgg tttttttgtt tgcaagcagc agattacgcg cagaaaaaaa ggatctcaag   5400
aagatccttt gatcttttct acggggtctg acgctcagtg gaacgaaaac tcacgttaag   5460
ggattttggt catgagatta tcaaaaagga tcttcaccta gatcctttta aattaaaaat   5520
gaagttttaa atcaatctaa agtatatatg agtaaacttg gtctgacagt taccaatgct   5580
taatcagtga ggcacctatc tcagcgatct gtctatttcg ttcatccata gttgcctgac   5640
tccccgtcgt gtagataact acgatacggg agggcttacc atctggcccc agtgctgcaa   5700
tgataccgcg agacccacgc tcaccggctc cagatttatc agcaataaac cagccagccg   5760
gaagggccga gcgcagaagt ggtcctgcaa ctttatccgc ctccatccag tctattaatt   5820
gttgccggga agctagagta agtagttcgc cagttaatag tttgcgcaac gttgttgcca   5880
ttgctacagg catcgtggtg tcacgctcgt cgtttggtat ggcttcattc agctccggtt   5940
cccaacgatc aaggcgagtt acatgatccc ccatgttgtg caaaaaagcg gttagctcct   6000
tcggtcctcc gatcgttgtc agaagtaagt tggccgcagt gttatcactc atggttatgg   6060
cagcactgca taattctctt actgtcatgc catccgtaag atgcttttct gtgactggtg   6120
agtactcaac caagtcattc tgagaatagt gtatgcggcg accgagttgc tcttgcccgg   6180
cgtcaatacg ggataatacc gcgccacata gcagaacttt aaaagtgctc atcattggaa   6240
aacgttcttc ggggcgaaaa ctctcaagga tcttaccgct gttgagatcc agttcgatgt   6300
aacccactcg tgcacccaac tgatcttcag catcttttac tttcaccagc gtttctgggt   6360
gagcaaaaac aggaaggcaa aatgccgcaa aaaagggaat aagggcgaca cggaaatgtt   6420
gaatactcat actcttcctt tttcaatatt attgaagcat ttatcagggt tattgtctca   6480
tgagcggata catatttgaa tgtatttaga aaaataaaca aataggggtt ccgcgcacat   6540
ttccccgaaa agtgccacct gacgcgccct gtagcggcgc attaagcgcg gcgggtgtgg   6600
tggttacgcg cagcgtgacc gctacacttg ccagcgccct agcgcccgct cctttcgctt   6660
tcttcccttc ctttctcgcc acgttcgccg gctttccccg tcaagctcta aatcgggggc   6720
tccctttagg gttccgattt agtgctttac ggcacctcga ccccaaaaaa cttgattagg   6780
gtgatggttc acgtagtggg ccatcgccct gatagacggt ttttcgccct ttgacgttgg   6840
agtccacgtt ctttaatagt ggactcttgt tccaaactgg aacaacactc aaccctatct   6900
cggtctattc ttttgattta taagggattt tgccgatttc ggcctattgg ttaaaaaatg   6960
agctgattta acaaaaattt aacgcgaatt ttaacaaaat attaacgctt acaatttcca   7020
ttcgccattc aggctgcgca actgttggga agggcgatcg gtgcgggcct cttcgctatt   7080
acgccagctg gcgaaagggg gatgtgctgc aaggcgatta agttgggtaa cgccagggtt   7140
ttcccagtca cgacgttgta aaacgacggc cagtgaattg taatacgact cactataggg   7200
cgaattgggt accgggcccc ccctcgaggt cgatggtgtc gataagcttg atatcgaatt   7260
catgtcacac aaaccgatct tcgcctcaag gaaacctaat tctacatccg agagactgcc   7320
gagatccagt ctacactgat taattttcgg gccaataatt taaaaaaatc gtgttatata   7380
atattatatg tattatatat atacatcatg atgatactga cagtcatgtc ccattgctaa   7440
```

```
atagacagac tccatctgcc gcctccaact gatgttctca atatttaagg ggtcatctcg   7500
cattgtttaa taataaacag actccatcta ccgcctccaa atgatgttct caaaatatat   7560
tgtatgaact tatttttatt acttagtatt attagacaac ttacttgctt tatgaaaaac   7620
acttcctatt taggaaacaa tttataatgg cagttcgttc atttaacaat ttatgtagaa   7680
taaatgttat aaatgcgtat gggaaatctt aaatatggat agcataaatg atatctgcat   7740
tgcctaattc gaaatcaaca gcaacgaaaa aaatcccttg tacaacataa atagtcatcg   7800
agaaatatca actatcaaag aacagctatt cacacgttac tattgagatt attattggac   7860
gagaatcaca cactcaactg tctttctctc ttctagaaat acaggtacaa gtatgtacta   7920
ttctcattgt tcatacttct agtcatttca tcccacatat tccttggatt tctctccaat   7980
gaatgacatt ctatcttgca aattcaacaa ttataataag atataccaaa gtagcggtat   8040
agtggcaatc aaaaagcttc tctggtgtgc ttctcgtatt tatttttatt ctaatgatcc   8100
attaaaggta tatatttatt tcttgttata taatcctttt gtttattaca tgggctggat   8160
acataaaggt attttgattt aattttttgc ttaaattcaa tccccccctcg ttcagtgtca   8220
actgtaatgg taggaaatta ccatactttt gaagaagcaa aaaaaatgaa agaaaaaaaa   8280
aatcgtattt ccaggttaga cgttccgcag aatctagaat gcggtatgcg gtacattgtt   8340
cttcgaacgt aaaagttgcg ctccctgaga tattgtacat ttttgctttt acaagtacaa   8400
gtacatcgta caactatgta ctactgttga tgcatccaca acagtttgtt ttgttttttt   8460
ttgttttttt tttttctaat gattcattac cgctatgtat acctacttgt acttgtagta   8520
agccgggtta ttggcgttca attaatcata gacttatgaa tctgcacggt gtgcgctgcg   8580
agttactttt agcttatgca tgctacttgg gtgtaatatt gggatctgtt cggaaatcaa   8640
cggatgctca atcgatttcg acagtaatta attaagtcat acacaagtca gctttcttcg   8700
agcctcatat aagtataagt agttcaacgt attagcactg tacccagcat ctccgtatcg   8760
agaaacacaa caacatgccc cattggacag atcatgcgga tacacaggtt gtgcagtatc   8820
atacatactc gatcagacag gtcgtctgac catcatacaa gctgaacaag cgctccatac   8880
ttgcacgctc tctatataca cagttaaatt acatatccat agtctaacct ctaacagtta   8940
atcttctggt aagcctccca gccagccttc tggtatcgct tggcctcctc aataggatct   9000
cggttctggc cgtacagacc tcggccgaca attatgatat ccgttccggt agacatgaca   9060
tcctcaacag ttcggtactg ctgtccgaga gcgtctccct tgtcgtcaag acccaccccg   9120
ggggtcagaa taagccagtc ctcagagtcg cccttaggtc ggttctgggc aatgaagcca   9180
accacaaact cggggtcgga tcgggcaagc tcaatggtct gcttggagta ctcgccagtg   9240
gccagagagc ccttgcaaga cagctcggcc agcatgagca gacctctggc cagcttctcg   9300
ttgggagagg ggactaggaa ctccttgtac tgggagttct cgtagtcaga gacgtcctcc   9360
ttcttctgtt cagagacagt ttcctcggca ccagctcgca ggccagcaat gattccggtt   9420
ccgggtacac cgtgggcgtt ggtgatatcg gaccactcgg cgattcggtg acaccggtac   9480
tggtgcttga cagtgttgcc aatatctgcg aactttctgt cctcgaacag gaagaaaccg   9540
tgcttaagag caagttcctt gagggggagc acagtgccgg cgtaggtgaa gtcgtcaatg   9600
atgtcgatat gggttttgat catgcacaca taaggtccga ccttatcggc aagctcaatg   9660
agctccttgg tggtggtaac atccagagaa gcacacaggt tggttttctt ggctgccacg   9720
agcttgagca ctcgagcggc aaaggcggac ttgtggacgt tagctcgagc ttcgtaggag   9780
```

```
ggcattttgg tggtgaagag gagactgaaa taaatttagt ctgcagaact ttttatcgga   9840

accttatctg gggcagtgaa gtatatgtta tggtaatagt tacgagttag ttgaacttat   9900

agatagactg gactatacgg ctatcggtcc aaattagaaa gaacgtcaat ggctctctgg   9960

gcgtcgcctt tgccgacaaa aatgtgatca tgatgaaagc cagcaatgac gttgcagctg  10020

atattgttgt cggccaaccg cgccgaaaac gcagctgtca gacccacagc ctccaacgaa  10080

gaatgtatcg tcaaagtgat ccaagcacac tcatagttgg agtcgtactc caaaggcggc  10140

aatgacgagt cagacagata ctcgtcgacg tttaaaccat catctaaggg cctcaaaact  10200

acctcggaac tgctgcgctg atctggacac cacagaggtt ccgagcactt taggttgcac  10260

caaatgtccc accaggtgca ggcagaaaac gctggaacag cgtgtacagt ttgtcttaac  10320

aaaaagtgag ggcgctgagg tcgagcaggg tggtgtgact tgttatagcc tttagagctg  10380

cgaaagcgcg tatggatttg gctcatcagg ccagattgag ggtctgtgga cacatgtcat  10440

gttagtgtac ttcaatcgcc ccctggatat agccccgaca ataggccgtg gcctcatttt  10500

tttgccttcc gcacatttcc attgctcggt acccacacct tgcttctcct gcacttgcca  10560

accttaatac tggtttacat tgaccaacat cttacaagcg gggggcttgt ctagggtata  10620

tataaacagt ggctctccca atcggttgcc agtctctttt ttcctttctt tccccacaga  10680

ttcgaaatct aaactacaca tcacac                                        10706
```

<210> SEQ ID NO 93
<211> LENGTH: 4140
<212> TYPE: DNA
<213> ORGANISM: Artificial sequence
<220> FEATURE:
<223> OTHER INFORMATION: Aar1- Cas9 gene

<400> SEQUENCE: 93

```
atggacaaga aatactccat cggcctggac attggaacca actctgtcgg ctgggctgtc     60

atcaccgacg agtacaaggt gccctccaag aaattcaagg tcctcggaaa caccgatcga    120

cactccatca agaaaaacct cattggtgcc ctgttgttcg attctggcga gactgccgaa    180

gctaccagac tcaagcgaac tgctcggcga cgttacaccc gacggaagaa ccgaatctgc    240

tacctgcagg agatcttttc caacgagatg gccaaggtgg acgattcgtt ctttcatcga    300

ctggaggaat ccttcctcgt cgaggaagac aagaaacacg agcgtcatcc catctttggc    360

aacattgtgg acgaggttgc ttaccacgag aagtatccta ccatctacca tctccgaaag    420

aaactcgtcg attccaccga caaggcggat ctcagactta tctacctcgc tctggcacac    480

atgatcaagt ttcgaggtca tttcctcatc gagggcgatc tcaatcccga caacagcgat    540

gtggacaagc tgttcattca gctcgttcag acctacaacc agctgttcga ggaaaacccc    600

atcaatgcct ccggagtcga tgcaaaggcc atcttgtctg ctcgactctc gaagagcaga    660

cgactggaga acctcattgc ccaacttcct ggcgagaaaa agaacggact gtttggcaac    720

ctcattgccc tttctcttgg tctcacaccc aacttcaagt ccaacttcga tctggcggag    780

gacgccaagc tccagctgtc caaggacacc tacgacgatg acctcgacaa cctgcttgca    840

cagattggcg atcagtacgc cgacctgttt ctcgctgcca agaacctttc ggatgctatt    900

ctcttgtctg acattctgcg agtcaacacc gagatcacaa aggctcccct ttctgcctcc    960

atgatcaagc gatacgacga gcaccatcag gatctcacac tgctcaaggc tcttgtccga   1020

cagcaactgc ccgagaagta caaggagatc tttttcgatc agtcgaagaa cggctacgct   1080

ggatacatcg acggcggagc ctctcaggaa gagttctaca agttcatcaa gccaattctc   1140
```

gagaagatgg acggaaccga ggaactgctt gtcaagctca atcgagagga tctgcttcgg 1200
aagcaacgaa ccttcgacaa cggcagcatt cctcatcaga tccacctcgg tgagctgcac 1260
gccattcttc gacgtcagga agacttctac ccctttctca aggacaaccg agagaagatc 1320
gagaagattc ttacctttcg aatcccctac tatgttggtc ctcttgccag aggaaactct 1380
cgatttgctt ggatgactcg aaagtccgag gaaaccatca ctccctggaa cttcgaggaa 1440
gtcgtggaca agggtgcctc tgcacagtcc ttcatcgagc gaatgaccaa cttcgacaag 1500
aatctgccca acgagaaggt tcttcccaag cattcgctgc tctacgagta ctttacagtc 1560
tacaacgaac tcaccaaagt caagtacgtt accgagggaa tgcgaaagcc tgccttcttg 1620
tctggcgaac agaagaaagc cattgtcgat ctcctgttca agaccaaccg aaaggtcact 1680
gttaagcagc tcaaggagga ctacttcaag aaaatcgagt gtttcgacag cgtcgagatt 1740
tccggagttg aggaccgatt caacgcctct ttgggcacct atcacgatct gctcaagatt 1800
atcaaggaca aggattttct cgacaacgag gaaaacgagg acattctgga ggacatcgtg 1860
ctcactctta ccctgttcga agatcgggag atgatcgagg aacgactcaa gacatacgct 1920
cacctgttcg acgacaaggt catgaaacaa ctcaagcgac gtagatacac cggctgggga 1980
agactttcgc gaaagctcat caacggcatc agagacaagc agtccggaaa gaccattctg 2040
gactttctca agtccgatgg ctttgccaac cgaaacttca tgcagctcat tcacgacgat 2100
tctcttacct tcaaggagga catccagaag gcacaagtgt ccggtcaggg cgacagcttg 2160
cacgaacata ttgccaacct ggctggttcg ccagccatca agaaaggcat tctccagact 2220
gtcaaggttg tcgacgagct ggtgaaggtc atgggacgtc acaagcccga gaacattgtg 2280
atcgagatgg ccagagagaa ccagacaact caaaagggtc agaaaaactc gcgagagcgg 2340
atgaagcgaa tcgaggaagg catcaaggag ctgggatccc agattctcaa ggagcatccc 2400
gtcgagaaca ctcaactgca gaacgagaag ctgtatctct actatctgca gaatggtcga 2460
gacatgtacg tggatcagga actggacatc aatcgtctca gcgactacga tgtggaccac 2520
attgtccctc aatcctttct caaggacgat tctatcgaca acaaggtcct tacacgatcc 2580
gacaagaaca gaggcaagtc ggacaacgtt cccagcgaag aggtggtcaa aaagatgaag 2640
aactactggc gacagctgct caacgccaag ctcattaccc agcgaaagtt cgacaatctt 2700
accaaggccg agcgaggcgg tctgtccgag ctcgacaagg ctggcttcat caagcgtcaa 2760
ctcgtcgaga ccagacagat cacaaagcac gtcgcacaga ttctcgattc tcggatgaac 2820
accaagtacg acgagaacga caagctcatc cgagaggtca aggtgattac tctcaagtcc 2880
aaactggtct ccgatttccg aaaggacttt cagttctaca aggtgcgaga gatcaacaat 2940
taccaccatg cccacgatgc ttacctcaac gccgtcgttg gcactgcgct catcaagaaa 3000
taccccaagc tcgaaagcga gttcgtttac ggcgattaca aggtctacga cgttcgaaag 3060
atgattgcca agtccgaaca ggagattggc aaggctactg ccaagtactt cttttactcc 3120
aacatcatga actttttcaa gaccgagatc accttggcca acggagagat tcgaaagaga 3180
ccacttatcg agaccaacgg cgaaactgga gagatcgtgt gggacaaggg tcgagacttt 3240
gcaaccgtgc gaaaggttct gtcgatgcct caggtcaaca tcgtcaagaa aaccgaggtt 3300
cagactggcg gattctccaa ggagtcgatt ctgcccaagc gaaactccga caagctcatc 3360
gctcgaaaga aagactggga tcccaagaaa tacggtggct tcgattctcc taccgtcgcc 3420
tattccgtgc ttgtcgttgc gaaggtcgag aagggcaagt ccaaaaagct caagtccgtc 3480
aaggagctgc tcggaattac catcatggag cgatcgagct tcgagaagaa tcccatcgac 3540
ttcttggaag ccaagggtta caaggaggtc aagaaagacc tcattatcaa gctgcccaag 3600
tactctctgt tcgaactgga gaacggtcga aagcgtatgc tcgcctccgc tggcgagctg 3660
cagaagggaa acgagcttgc cttgccttcg aagtacgtca actttctcta tctggcttct 3720
cactacgaga agctcaaggg ttctcccgag gacaacgaac agaagcaact cttcgttgag 3780
cagcacaaac attacctcga cgagattatc gagcagattt ccgagttttc gaagcgagtc 3840
atcctggctg atgccaactt ggacaaggtg ctctctgcct acaacaagca tcgggacaaa 3900
cccattcgag aacaggcgga gaacatcatt cacctgttta ctcttaccaa cctgggtgct 3960
cctgcagctt tcaagtactt cgataccact atcgaccgaa agcggtacac atccaccaag 4020
gaggttctcg atgccaccct gattcaccag tccatcactg gcctgtacga gacccgaatc 4080
gacctgtctc agcttggtgg cgactccaga gccgatccca agaaaaagcg aaaggtctaa 4140

<210> SEQ ID NO 94
<211> LENGTH: 10706
<212> TYPE: DNA
<213> ORGANISM: ARtificial sequence
<220> FEATURE:
<223> OTHER INFORMATION: pRF141

<400> SEQUENCE: 94
catggacaag aaatactcca tcggcctgga cattggaacc aactctgtcg gctgggctgt 60
catcaccgac gagtacaagg tgccctccaa gaaattcaag gtcctcggaa acaccgatcg 120
acactccatc aagaaaaacc tcattggtgc cctgttgttc gattctggcg agactgccga 180
agctaccaga ctcaagcgaa ctgctcggcg acgttacacc cgacggaaga accgaatctg 240
ctacctgcag gagatctttt ccaacgagat ggccaaggtg gacgattcgt tctttcatcg 300
actggaggaa tccttcctcg tcgaggaaga caagaaacac gagcgtcatc ccatctttgg 360
caacattgtg gacgaggttg cttaccacga gaagtatcct accatctacc atctccgaaa 420
gaaactcgtc gattccaccg acaaggcgga tctcagactt atctacctcg ctctggcaca 480
catgatcaag tttcgaggtc atttcctcat cgagggcgat ctcaatcccg acaacagcga 540
tgtggacaag ctgttcattc agctcgttca gacctacaac cagctgttcg aggaaaaccc 600
catcaatgcc tccggagtcg atgcaaaggc catcttgtct gctcgactct cgaagagcag 660
acgactggag aacctcattg cccaacttcc tggcgagaaa aagaacggac tgtttggcaa 720
cctcattgcc ctttctcttg gtctcacacc caacttcaag tccaacttcg atctggcgga 780
ggacgccaag ctccagctgt ccaaggacac ctacgacgat gacctcgaca acctgcttgc 840
acagattggc gatcagtacg ccgacctgtt tctcgctgcc aagaaccttt cggatgctat 900
tctcttgtct gacattctgc gagtcaacac cgagatcaca aaggctcccc tttctgcctc 960
catgatcaag cgatacgacg agcaccatca ggatctcaca ctgctcaagg ctcttgtccg 1020
acagcaactg cccgagaagt acaaggagat ctttttcgat cagtcgaaga acggctacgc 1080
tggatacatc gacggcggag cctctcagga agagttctac aagttcatca agccaattct 1140
cgagaagatg gacggaaccg aggaactgct tgtcaagctc aatcgagagg atctgcttcg 1200
gaagcaacga accttcgaca acggcagcat tcctcatcag atccacctcg gtgagctgca 1260
cgccattctt cgacgtcagg aagacttcta ccccttttctc aaggacaacc gagagaagat 1320
cgagaagatt cttacctttc gaatccccta ctatgttggt cctcttgcca gaggaaactc 1380
tcgatttgct tggatgactc gaaagtccga ggaaaccatc actccctgga acttcgagga 1440
agtcgtggac aagggtgcct ctgcacagtc cttcatcgag cgaatgacca acttcgacaa 1500
gaatctgccc aacgagaagg ttcttcccaa gcattcgctg ctctacgagt actttacagt 1560
ctacaacgaa ctcaccaaag tcaagtacgt taccgaggga atgcgaaagc ctgccttctt 1620
gtctggcgaa cagaagaaag ccattgtcga tctcctgttc aagaccaacc gaaaggtcac 1680
tgttaagcag ctcaaggagg actacttcaa gaaaatcgag tgtttcgaca gcgtcgagat 1740
ttccggagtt gaggaccgat tcaacgcctc tttgggcacc tatcacgatc tgctcaagat 1800
tatcaaggac aaggattttc tcgacaacga ggaaaacgag gacattctgg aggacatcgt 1860
gctcactctt accctgttcg aagatcggga gatgatcgag gaacgactca agacatacgc 1920
tcacctgttc gacgacaagg tcatgaaaca actcaagcga cgtagataca ccggctgggg 1980
aagactttcg cgaaagctca tcaacggcat cagagacaag cagtccggaa agaccattct 2040
ggactttctc aagtccgatg gctttgccaa ccgaaacttc atgcagctca ttcacgacga 2100
ttctcttacc ttcaaggagg acatccagaa ggcacaagtg tccggtcagg gcgacagctt 2160
gcacgaacat attgccaacc tggctggttc gccagccatc aagaaaggca ttctccagac 2220
tgtcaaggtt gtcgacgagc tggtgaaggt catgggacgt cacaagcccg agaacattgt 2280
gatcgagatg gccagagaga accagacaac tcaaaagggt cagaaaaact cgcgagagcg 2340
gatgaagcga atcgaggaag gcatcaagga gctgggatcc cagattctca aggagcatcc 2400
cgtcgagaac actcaactgc agaacgagaa gctgtatctc tactatctgc agaatggtcg 2460
agacatgtac gtggatcagg aactggacat caatcgtctc agcgactacg atgtggacca 2520
cattgtccct caatcctttc tcaaggacga ttctatcgac aacaaggtcc ttacacgatc 2580
cgacaagaac agaggcaagt cggacaacgt tcccagcgaa gaggtggtca aaaagatgaa 2640
gaactactgg cgacagctgc tcaacgccaa gctcattacc cagcgaaagt tcgacaatct 2700
taccaaggcc gagcgaggcg gtctgtccga gctcgacaag gctggcttca tcaagcgtca 2760
actcgtcgag accagacaga tcacaaagca cgtcgcacag attctcgatt ctcggatgaa 2820
caccaagtac gacgagaacg acaagctcat ccgagaggtc aaggtgatta ctctcaagtc 2880
caaactggtc tccgatttcc gaaaggactt tcagttctac aaggtgcgag agatcaacaa 2940
ttaccaccat gcccacgatg cttacctcaa cgccgtcgtt ggcactgcgc tcatcaagaa 3000
ataccccaag ctcgaaagcg agttcgttta cggcgattac aaggtctacg acgttcgaaa 3060
gatgattgcc aagtccgaac aggagattgg caaggctact gccaagtact tcttttactc 3120
caacatcatg aactttttca agaccgagat caccttggcc aacggagaga ttcgaaagag 3180
accacttatc gagaccaacg gcgaaactgg agagatcgtg tgggacaagg gtcgagactt 3240
tgcaaccgtg cgaaaggttc tgtcgatgcc tcaggtcaac atcgtcaaga aaaccgaggt 3300
tcagactggc ggattctcca aggagtcgat tctgcccaag cgaaactccg acaagctcat 3360
cgctcgaaag aaagactggg atcccaagaa atacggtggc ttcgattctc ctaccgtcgc 3420
ctattccgtg cttgtcgttg cgaaggtcga gaagggcaag tccaaaaagc tcaagtccgt 3480
caaggagctg ctcggaatta ccatcatgga gcgatcgagc ttcgagaaga atcccatcga 3540
cttcttggaa gccaagggtt acaaggaggt caagaaagac ctcattatca agctgcccaa 3600
gtactctctg ttcgaactgg agaacggtcg aaagcgtatg ctcgcctccg ctggcgagct 3660
gcagaaggga aacgagcttg ccttgccttc gaagtacgtc aactttctct atctggcttc 3720
tcactacgag aagctcaagg gttctcccga ggacaacgaa cagaagcaac tcttcgttga 3780
gcagcacaaa cattacctcg acgagattat cgagcagatt tccgagtttt cgaagcgagt 3840
catcctggct gatgccaact tggacaaggt gctctctgcc tacaacaagc atcgggacaa 3900
acccattcga gaacaggcgg agaacatcat tcacctgttt actcttacca acctgggtgc 3960
tcctgcagct ttcaagtact tcgataccac tatcgaccga aagcggtaca catccaccaa 4020
ggaggttctc gatgccaccc tgattcacca gtccatcact ggcctgtacg agacccgaat 4080
cgacctgtct cagcttggtg gcgactccag agccgatccc aagaaaaagc gaaaggtcta 4140
agcggccgca agtgtggatg gggaagtgag tgcccggttc tgtgtgcaca attggcaatc 4200
caagatggat ggattcaaca cagggatata gcgagctacg tggtggtgcg aggatatagc 4260
aacggatatt tatgtttgac acttgagaat gtacgataca agcactgtcc aagtacaata 4320
ctaaacatac tgtacatact catactcgta cccgggcaac ggtttcactt gagtgcagtg 4380
gctagtgctc ttactcgtac agtgtgcaat actgcgtatc atagtctttg atgtatatcg 4440
tattcattca tgttagttgc gtacgagccg gaagcataaa gtgtaaagcc tggggtgcct 4500
aatgagtgag ctaactcaca ttaattgcgt tgcgctcact gcccgctttc cagtcgggaa 4560
acctgtcgtg ccagctgcat taatgaatcg gccaacgcgc ggggagaggc ggtttgcgta 4620
ttgggcgctc ttccgcttcc tcgctcactg actcgctgcg ctcggtcgtt cggctgcggc 4680
gagcggtatc agctcactca aaggcggtaa tacggttatc cacagaatca ggggataacg 4740
caggaaagaa catgtgagca aaaggccagc aaaaggccag gaaccgtaaa aaggccgcgt 4800
tgctggcgtt tttccatagg ctccgccccc ctgacgagca tcacaaaaat cgacgctcaa 4860
gtcagaggtg gcgaaacccg acaggactat aaagatacca ggcgtttccc cctggaagct 4920
ccctcgtgcg ctctcctgtt ccgaccctgc cgcttaccgg atacctgtcc gcctttctcc 4980
cttcgggaag cgtggcgctt tctcatagct cacgctgtag gtatctcagt tcggtgtagg 5040
tcgttcgctc caagctgggc tgtgtgcacg aaccccccgt tcagcccgac cgctgcgcct 5100
tatccggtaa ctatcgtctt gagtccaacc cggtaagaca cgacttatcg ccactggcag 5160
cagccactgg taacaggatt agcagagcga ggtatgtagg cggtgctaca gagttcttga 5220
agtggtggcc taactacggc tacactagaa ggacagtatt tggtatctgc gctctgctga 5280
agccagttac cttcggaaaa agagttggta gctcttgatc cggcaaacaa accaccgctg 5340
gtagcggtgg tttttttgtt tgcaagcagc agattacgcg cagaaaaaaa ggatctcaag 5400
aagatccttt gatcttttct acggggtctg acgctcagtg gaacgaaaac tcacgttaag 5460
ggattttggt catgagatta tcaaaaagga tcttcaccta gatcctttta aattaaaaat 5520
gaagttttaa atcaatctaa agtatatatg agtaaacttg gtctgacagt taccaatgct 5580
taatcagtga ggcacctatc tcagcgatct gtctatttcg ttcatccata gttgcctgac 5640
tccccgtcgt gtagataact acgatacggg agggcttacc atctggcccc agtgctgcaa 5700
tgataccgcg agacccacgc tcaccggctc cagatttatc agcaataaac cagccagccg 5760
gaagggccga gcgcagaagt ggtcctgcaa ctttatccgc ctccatccag tctattaatt 5820
gttgccggga agctagagta agtagttcgc cagttaatag tttgcgcaac gttgttgcca 5880
ttgctacagg catcgtggtg tcacgctcgt cgtttggtat ggcttcattc agctccggtt 5940
cccaacgatc aaggcgagtt acatgatccc ccatgttgtg caaaaaagcg gttagctcct 6000
tcggtcctcc gatcgttgtc agaagtaagt tggccgcagt gttatcactc atggttatgg 6060
cagcactgca taattctctt actgtcatgc catccgtaag atgcttttct gtgactggtg 6120
agtactcaac caagtcattc tgagaatagt gtatgcggcg accgagttgc tcttgcccgg 6180
cgtcaatacg ggataatacc gcgccacata gcagaacttt aaaagtgctc atcattggaa 6240
aacgttcttc ggggcgaaaa ctctcaagga tcttaccgct gttgagatcc agttcgatgt 6300
aacccactcg tgcacccaac tgatcttcag catcttttac tttcaccagc gtttctgggt 6360
gagcaaaaac aggaaggcaa aatgccgcaa aaaagggaat aagggcgaca cggaaatgtt 6420
gaatactcat actcttcctt tttcaatatt attgaagcat ttatcagggt tattgtctca 6480
tgagcggata catatttgaa tgtatttaga aaaataaaca aataggggtt ccgcgcacat 6540
ttccccgaaa agtgccacct gacgcgccct gtagcggcgc attaagcgcg gcgggtgtgg 6600
tggttacgcg cagcgtgacc gctacacttg ccagcgccct agcgcccgct cctttcgctt 6660
tcttcccttc ctttctcgcc acgttcgccg gctttccccg tcaagctcta aatcgggggc 6720
tccctttagg gttccgattt agtgctttac ggcacctcga ccccaaaaaa cttgattagg 6780
gtgatggttc acgtagtggg ccatcgccct gatagacggt ttttcgccct ttgacgttgg 6840
agtccacgtt ctttaatagt ggactcttgt tccaaactgg aacaacactc aaccctatct 6900
cggtctattc ttttgattta taagggattt tgccgatttc ggcctattgg ttaaaaaatg 6960
agctgattta acaaaaattt aacgcgaatt ttaacaaaat attaacgctt acaatttcca 7020
ttcgccattc aggctgcgca actgttggga agggcgatcg gtgcgggcct cttcgctatt 7080
acgccagctg gcgaaagggg gatgtgctgc aaggcgatta agttgggtaa cgccagggtt 7140
ttcccagtca cgacgttgta aaacgacggc cagtgaattg taatacgact cactataggg 7200
cgaattgggt accgggcccc ccctcgaggt cgatggtgtc gataagcttg atatcgaatt 7260
catgtcacac aaaccgatct tcgcctcaag gaaacctaat tctacatccg agagactgcc 7320
gagatccagt ctacactgat taattttcgg gccaataatt taaaaaaatc gtgttatata 7380
atattatatg tattatatat atacatcatg atgatactga cagtcatgtc ccattgctaa 7440
atagacagac tccatctgcc gcctccaact gatgttctca atatttaagg ggtcatctcg 7500
cattgtttaa taataaacag actccatcta ccgcctccaa atgatgttct caaaatatat 7560
tgtatgaact tatttttatt acttagtatt attagacaac ttacttgctt tatgaaaaac 7620
acttcctatt taggaaacaa tttataatgg cagttcgttc atttaacaat ttatgtagaa 7680
taaatgttat aaatgcgtat gggaaatctt aaatatggat agcataaatg atatctgcat 7740
tgcctaattc gaaatcaaca gcaacgaaaa aaatcccttg tacaacataa atagtcatcg 7800
agaaatatca actatcaaag aacagctatt cacacgttac tattgagatt attattggac 7860
gagaatcaca cactcaactg tctttctctc ttctagaaat acaggtacaa gtatgtacta 7920
ttctcattgt tcatacttct agtcatttca tcccacatat tccttggatt tctctccaat 7980
gaatgacatt ctatcttgca aattcaacaa ttataataag atataccaaa gtagcggtat 8040
agtggcaatc aaaaagcttc tctggtgtgc ttctcgtatt tatttttatt ctaatgatcc 8100
attaaaggta tatatttatt tcttgttata taatcctttt gtttattaca tgggctggat 8160
acataaaggt attttgattt aattttttgc ttaaattcaa tccccccctcg ttcagtgtca 8220 actgtaatgg taggaaatta ccatactttt gaagaagcaa aaaaaatgaa agaaaaaaaa 8280
aatcgtattt ccaggttaga cgttccgcag aatctagaat gcggtatgcg gtacattgtt 8340
cttcgaacgt aaaagttgcg ctccctgaga tattgtacat ttttgctttt acaagtacaa 8400
gtacatcgta caactatgta ctactgttga tgcatccaca acagtttgtt ttgttttttt 8460
ttgttttttt tttttctaat gattcattac cgctatgtat acctacttgt acttgtagta 8520

-continued agccgggtta ttggcgttca attaatcata gacttatgaa tctgcacggt gtgcgctgcg 8580
agttactttt agcttatgca tgctacttgg gtgtaatatt gggatctgtt cggaaatcaa 8640
cggatgctca atcgatttcg acagtaatta attaagtcat acacaagtca gctttcttcg 8700
agcctcatat aagtataagt agttcaacgt attagcactg tacccagcat ctccgtatcg 8760
agaaacacaa caacatgccc cattggacag atcatgcgga tacacaggtt gtgcagtatc 8820
atacatactc gatcagacag gtcgtctgac catcatacaa gctgaacaag cgctccatac 8880
ttgcacgctc tctatataca cagttaaatt acatatccat agtctaacct ctaacagtta 8940
atcttctggt aagcctccca gccagccttc tggtatcgct tggcctcctc aataggatct 9000
cggttctggc cgtacagacc tcggccgaca attatgatat ccgttccggt agacatgaca 9060
tcctcaacag ttcggtactg ctgtccgaga gcgtctccct tgtcgtcaag acccaccccg 9120
ggggtcagaa taagccagtc ctcagagtcg ccccttaggtc ggttctgggc aatgaagcca 9180
accacaaact cggggtcgga tcgggcaagc tcaatggtct gcttggagta ctcgccagtg 9240
gccagagagc ccttgcaaga cagctcggcc agcatgagca gacctctggc cagcttctcg 9300
ttgggagagg ggactaggaa ctccttgtac tgggagttct cgtagtcaga gacgtcctcc 9360
ttcttctgtt cagagacagt ttcctcggca ccagctcgca ggccagcaat gattccggtt 9420
ccgggtacac cgtgggcgtt ggtgatatcg gaccactcgg cgattcggtg acaccggtac 9480
tggtgcttga cagtgttgcc aatatctgcg aactttctgt cctcgaacag gaagaaaccg 9540
tgcttaagag caagttcctt gagggggagc acagtgccgg cgtaggtgaa gtcgtcaatg 9600
atgtcgatat gggttttgat catgcacaca taaggtccga ccttatcggc aagctcaatg 9660
agctccttgg tggtggtaac atccagagaa gcacacaggt tggtttttctt ggctgccacg 9720 agcttgagca ctcgagcggc aaaggcggac ttgtggacgt tagctcgagc ttcgtaggag 9780
ggcattttgg tggtgaagag gagactgaaa taaatttagt ctgcagaact ttttatcgga 9840
accttatctg gggcagtgaa gtatatgtta tggtaatagt tacgagttag ttgaacttat 9900
agatagactg gactatacgg ctatcggtcc aaattagaaa gaacgtcaat ggctctctgg 9960
gcgtcgcctt tgccgacaaa aatgtgatca tgatgaaagc cagcaatgac gttgcagctg 10020
atattgttgt cggccaaccg cgccgaaaac gcagctgtca gacccacagc ctccaacgaa 10080
gaatgtatcg tcaaagtgat ccaagcacac tcatagttgg agtcgtactc caaaggcggc 10140
aatgacgagt cagacagata ctcgtcgacg tttaaaccat catctaaggg cctcaaaact 10200
acctcggaac tgctgcgctg atctggacac cacagaggtt ccgagcactt taggttgcac 10260
caaatgtccc accaggtgca ggcagaaaac gctggaacag cgtgtacagt ttgtcttaac 10320
aaaaagtgag ggcgctgagg tcgagcaggg tggtgtgact tgttatagcc tttagagctg 10380
cgaaagcgcg tatggatttg gctcatcagg ccagattgag ggtctgtgga cacatgtcat 10440
gttagtgtac ttcaatcgcc ccctggatat agccccgaca ataggccgtg gcctcatttt 10500
tttgccttcc gcacatttcc attgctcggt acccacacct tgcttctcct gcacttgcca 10560
accttaatac tggtttacat tgaccaacat cttacaagcg gggggcttgt ctagggtata 10620
tataaacagt ggctctccca atcggttgcc agtctctttt ttcctttctt tccccacaga 10680
ttcgaaatct aaactacaca tcacac 10706

<210> SEQ ID NO 95
<211> LENGTH: 1048
<212> TYPE: DNA
<213> ORGANISM: Artificial sequence
<220> FEATURE:
<223> OTHER INFORMATION: High-throughput cloning cassette

<400> SEQUENCE: 95
gcgcacgtta attaaatttt ttttgatttt cttttttgac cccgtcttca attacacttc 60
ccaactggga acacccctct ttatcgaccc attttaggta atttacccta gcccattgtc 120
tccataagga atattaccct aacccacagt ccagggtgcc caggtccttc tttggccaaa 180
ttttaacttc ggtcctatgg cacagcggta gcgcgtgaga ttgcaaatct taaggtcccg 240
agttcgaatc tcggtgggac ctagttattt ttgatagata atttcgtgat gattagaaac 300
ttaacgcaaa ataatggccg gcatggtccc agcctcctcg ctggcgccgg ctgggcaaca 360
tgcttcggca tggcgaatgg gacgcaggtg atggcgggat cgttgtatat ttcttgacac 420
cttttcggca tcgccctaaa ttcggcgtcc tcatattgtg tgaggacgtt ttattacgtg 480
tttacgaagc aaaagctaaa accaggagct atttaatggc aacagttaac cagctggtac 540
gcaaaccacg tgctcgcaaa gttgcgaaaa gcaacgtgcc tgcgctggaa gcatgcccgc 600
aaaaacgtgg cgtatgtact cgtgtatata ctaccactcc taaaaaaccg aactccgcgc 660
tgcgtaaagt atgccgtgtt cgtctgacta acggtttcga agtgacttcc tacatcggtg 720
gtgaaggtca caacctgcag gagcactccg tgatcctgat ccgtggcggt cgtgttaaag 780
acctcccggg tgttcgttac cacaccgtac gtggtgcgct tgactgctcc ggcgttaaag 840
accgtaagca ggctcgttcc aagtatggcg tgaagcgtcc taaggcttag gttaataaca 900
ggcctgctgg taatcgcagg ccttttattt tttacacctg cgttttagag ctagaaatag 960
caagttaaaa taaggctagt ccgttatcaa cttgaaaaag tggcaccgag tcggtgcttt 1020 ttttttgtt ttttatcgat gcgcgcac 1048

<210> SEQ ID NO 96
<211> LENGTH: 300
<212> TYPE: DNA
<213> ORGANISM: Yarrowia lipolytica

<400> SEQUENCE: 96
attttttttg attttctttt ttgaccccgt cttcaattac acttcccaac tgggaacacc 60
cctctttatc gacccatttt aggtaattta ccctagccca ttgtctccat aaggaatatt 120
accctaaccc acagtccagg gtgcccaggt ccttctttgg ccaaatttta acttcggtcc 180
tatggcacag cggtagcgcg tgagattgca aatcttaagg tcccgagttc gaatctcggt 240
gggacctagt tatttttgat agataatttc gtgatgatta gaaacttaac gcaaaataat 300

<210> SEQ ID NO 97
<211> LENGTH: 544
<212> TYPE: DNA
<213> ORGANISM: Escherichia coli
<220> FEATURE:
<221> NAME/KEY: misc_feature
<222> LOCATION: (1)..(544)
<223> OTHER INFORMATION: rpsL counterselection cassette

<400> SEQUENCE: 97
atggcgggat cgttgtatat ttcttgacac cttttcggca tcgccctaaa ttcggcgtcc 60
tcatattgtg tgaggacgtt ttattacgtg tttacgaagc aaaagctaaa accaggagct 120
atttaatggc aacagttaac cagctggtac gcaaaccacg tgctcgcaaa gttgcgaaaa 180
gcaacgtgcc tgcgctggaa gcatgcccgc aaaaacgtgg cgtatgtact cgtgtatata 240

```
ctaccactcc taaaaaaccg aactccgcgc tgcgtaaagt atgccgtgtt cgtctgacta    300

acggtttcga agtgacttcc tacatcggtg gtgaaggtca caacctgcag gagcactccg    360

tgatcctgat ccgtggcggt cgtgttaaag acctcccggg tgttcgttac cacaccgtac    420

gtggtgcgct tgactgctcc ggcgttaaag accgtaagca ggctcgttcc aagtatggcg    480

tgaagcgtcc taaggcttag gttaataaca ggcctgctgg taatcgcagg cctttttatt    540

ttta                                                                 544
```

<210> SEQ ID NO 98
<211> LENGTH: 11714
<212> TYPE: DNA
<213> ORGANISM: Artificial Sequence
<220> FEATURE:
<223> OTHER INFORMATION: pRF291

<400> SEQUENCE: 98

```
cgataaaaaa caaaaaaaaa agcaccgact cggtgccact ttttcaagtt gataacggac     60

tagccttatt ttaacttgct atttctagct ctaaaacgca ggtgtaaaaa taaaaaggcc    120

tgcgattacc agcaggcctg ttattaacct aagccttagg acgcttcacg ccatacttgg    180

aacgagcctg cttacggtct ttaacgccgg agcagtcaag cgcaccacgt acggtgtggt    240

aacgaacacc cgggaggtct ttaacacgac cgccacggat caggatcacg gagtgctcct    300

gcaggttgtg accttcacca ccgatgtagg aagtcacttc gaaaccgtta gtcagacgaa    360

cacggcatac tttacgcagc gcggagttcg gtttttttagg agtggtagta tatacacgag    420

tacatacgcc acgtttttgc gggcatgctt ccagcgcagg cacgttgctt ttcgcaactt    480

tgcgagcacg tggtttgcgt accagctggt taactgttgc cattaaatag ctcctggttt    540

tagcttttgc ttcgtaaaca cgtaataaaa cgtcctcaca caatatgagg acgccgaatt    600

tagggcgatg ccgaaaaggt gtcaagaaat atacaacgat cccgccatca cctgcgtccc    660

attcgccatg ccgaagcatg ttgcccagcc ggcgccagcg aggaggctgg gaccatgccg    720

gccattattt tgcgttaagt ttctaatcat cacgaaatta tctatcaaaa ataactaggt    780

cccaccgaga ttcgaactcg ggaccttaag atttgcaatc tcacgcgcta ccgctgtgcc    840

ataggaccga agttaaaatt tggccaaaga aggacctggg caccctggac tgtgggttag    900

ggtaatattc cttatggaga caatgggcta gggtaaatta cctaaaatgg gtcgataaag    960

aggggtgttc ccagttggga agtgtaattg aagacggggt caaaaaagaa aatcaaaaaa   1020

aatttaatta agtcatacac aagtcagctt tcttcgagcc tcatataagt ataagtagtt   1080

caacgtatta gcactgtacc cagcatctcc gtatcgagaa acacaacaac atgccccatt   1140

ggacagatca tgcggataca caggttgtgc agtatcatac atactcgatc agacaggtcg   1200

tctgaccatc atacaagctg aacaagcgct ccatacttgc acgctctcta tatacacagt   1260

taaattacat atccatagtc taacctctaa cagttaatct tctggtaagc ctcccagcca   1320

gccttctggt atcgcttggc ctcctcaata ggatctcggt tctggccgta cagacctcgg   1380

ccgacaatta tgatatccgt tccggtagac atgacatcct caacagttcg gtactgctgt   1440

ccgagagcgt ctcccttgtc gtcaagaccc accccggggg tcagaataag ccagtcctca   1500

gagtcgccct taggtcggtt ctgggcaatg aagccaacca caaactcggg gtcggatcgg   1560

gcaagctcaa tggtctgctt ggagtactcg ccagtggcca gagagccctt gcaagacagc   1620

tcggccagca tgagcagacc tctggccagc ttctcgttgg gagaggggac taggaactcc   1680

ttgtactggg agttctcgta gtcagagacg tcctccttct tctgttcaga gacagtttcc   1740
```

```
tcggcaccag ctcgcaggcc agcaatgatt ccggttccgg gtacaccgtg ggcgttggtg   1800
atatcggacc actcggcgat tcggtgacac cggtactggt gcttgacagt gttgccaata   1860
tctgcgaact ttctgtcctc gaacaggaag aaaccgtgct taagagcaag ttccttgagg   1920
gggagcacag tgccggcgta ggtgaagtcg tcaatgatgt cgatatgggt tttgatcatg   1980
cacacataag gtccgacctt atcggcaagc tcaatgagct ccttggtggt ggtaacatcc   2040
agagaagcac acaggttggt tttcttggct gccacgagct tgagcactcg agcggcaaag   2100
gcggacttgt ggacgttagc tcgagcttcg taggagggca ttttggtggt gaagaggaga   2160
ctgaaataaa tttagtctgc agaacttttt atcggaacct tatctggggc agtgaagtat   2220
atgttatggt aatagttacg agttagttga acttatagat agactggact atacggctat   2280
cggtccaaat tagaaagaac gtcaatggct ctctgggcgt cgcctttgcc gacaaaaatg   2340
tgatcatgat gaaagccagc aatgacgttg cagctgatat tgttgtcggc caaccgcgcc   2400
gaaaacgcag ctgtcagacc cacagcctcc aacgaagaat gtatcgtcaa agtgatccaa   2460
gcacactcat agttggagtc gtactccaaa ggcggcaatg acgagtcaga cagatactcg   2520
tcgacgttta aaccatcatc taagggcctc aaaactacct cggaactgct gcgctgatct   2580
ggacaccaca gaggttccga gcactttagg ttgcaccaaa tgtcccacca ggtgcaggca   2640
gaaaacgctg gaacagcgtg tacagtttgt cttaacaaaa agtgagggcg ctgaggtcga   2700
gcagggtggt gtgacttgtt atagccttta gagctgcgaa agcgcgtatg gatttggctc   2760
atcaggccag attgagggtc tgtggacaca tgtcatgtta gtgtacttca atcgccccct   2820
ggatatagcc ccgacaatag gccgtggcct catttttttg ccttccgcac atttccattg   2880
ctcggtaccc acaccttgct tctcctgcac ttgccaacct taatactggt ttacattgac   2940
caacatctta caagcggggg gcttgtctag ggtatatata aacagtggct ctcccaatcg   3000
gttgccagtc tcttttttcc tttctttccc cacagattcg aaatctaaac tacacatcac   3060
accatggaca agaaatactc catcggcctg gacattggaa ccaactctgt cggctgggct   3120
gtcatcaccg acgagtacaa ggtgccctcc aagaaattca aggtcctcgg aaacaccgat   3180
cgacactcca tcaagaaaaa cctcattggt gccctgttgt tcgattctgg cgagactgcc   3240
gaagctacca gactcaagcg aactgctcgg cgacgttaca cccgacggaa gaaccgaatc   3300
tgctacctgc aggagatctt ttccaacgag atggccaagg tggacgattc gttctttcat   3360
cgactggagg aatccttcct cgtcgaggaa gacaagaaac acgagcgtca tcccatcttt   3420
ggcaacattg tggacgaggt tgcttaccac gagaagtatc ctaccatcta ccatctccga   3480
aagaaactcg tcgattccac cgacaaggcg gatctcagac ttatctacct cgctctggca   3540
cacatgatca agtttcgagg tcatttcctc atcgagggcg atctcaatcc cgacaacagc   3600
gatgtggaca agctgttcat tcagctcgtt cagacctaca accagctgtt cgaggaaaac   3660
cccatcaatg cctccggagt cgatgcaaag gccatcttgt ctgctcgact ctcgaagagc   3720
agacgactgg agaacctcat tgcccaactt cctggcgaga aaaagaacgg actgtttggc   3780
aacctcattg ccctttctct tggtctcaca cccaacttca agtccaactt cgatctggcg   3840
gaggacgcca agctccagct gtccaaggac acctacgacg atgacctcga caacctgctt   3900
gcacagattg gcgatcagta cgccgacctg tttctcgctg ccaagaacct ttcggatgct   3960
attctcttgt ctgacattct gcgagtcaac accgagatca caaaggctcc cctttctgcc   4020
tccatgatca agcgatacga cgagcaccat caggatctca cactgctcaa ggctcttgtc   4080
```

-continued cgacagcaac tgcccgagaa gtacaaggag atctttttcg atcagtcgaa gaacggctac 4140
gctggataca tcgacggcgg agcctctcag gaagagttct acaagttcat caagccaatt 4200
ctcgagaaga tggacggaac cgaggaactg cttgtcaagc tcaatcgaga ggatctgctt 4260
cggaagcaac gaaccttcga caacggcagc attcctcatc agatccacct cggtgagctg 4320
cacgccattc ttcgacgtca ggaagacttc taccccttc tcaaggacaa ccgagagaag 4380
atcgagaaga ttcttacctt tcgaatcccc tactatgttg gtcctcttgc cagaggaaac 4440
tctcgatttg cttggatgac tcgaaagtcc gaggaaacca tcactccctg gaacttcgag 4500
gaagtcgtgg acaagggtgc ctctgcacag tccttcatcg agcgaatgac caacttcgac 4560
aagaatctgc ccaacgagaa ggttcttccc aagcattcgc tgctctacga gtactttaca 4620
gtctacaacg aactcaccaa agtcaagtac gttaccgagg gaatgcgaaa gcctgccttc 4680
ttgtctggcg aacagaagaa agccattgtc gatctcctgt tcaagaccaa ccgaaaggtc 4740
actgttaagc agctcaagga ggactacttc aagaaaatcg agtgtttcga cagcgtcgag 4800
atttccggag ttgaggaccg attcaacgcc tctttgggca cctatcacga tctgctcaag 4860
attatcaagg acaaggattt tctcgacaac gaggaaaacg aggacattct ggaggacatc 4920
gtgctcactc ttaccctgtt cgaagatcgg gagatgatcg aggaacgact caagacatac 4980
gctcacctgt tcgacgacaa ggtcatgaaa caactcaagc gacgtagata caccggctgg 5040
ggaagacttt cgcgaaagct catcaacggc atcagagaca agcagtccgg aaagaccatt 5100
ctggactttc tcaagtccga tggctttgcc aaccgaaact tcatgcagct cattcacgac 5160
gattctctta ccttcaagga ggacatccag aaggcacaag tgtccggtca gggcgacagc 5220
ttgcacgaac atattgccaa cctggctggt tcgccagcca tcaagaaagg cattctccag 5280
actgtcaagg ttgtcgacga gctggtgaag gtcatgggac gtcacaagcc cgagaacatt 5340
gtgatcgaga tggccagaga gaaccagaca actcaaaagg gtcagaaaaa ctcgcgagag 5400
cggatgaagc gaatcgagga aggcatcaag gagctgggat cccagattct caaggagcat 5460
cccgtcgaga acactcaact gcagaacgag aagctgtatc tctactatct gcagaatggt 5520
cgagacatgt acgtggatca ggaactggac atcaatcgtc tcagcgacta cgatgtggac 5580
cacattgtcc ctcaatcctt tctcaaggac gattctatcg acaacaaggt ccttacacga 5640
tccgacaaga acagaggcaa gtcggacaac gttcccagcg aagaggtggt caaaaagatg 5700
aagaactact ggcgacagct gctcaacgcc aagctcatta cccagcgaaa gttcgacaat 5760
cttaccaagg ccgagcgagg cggtctgtcc gagctcgaca aggctggctt catcaagcgt 5820
caactcgtcg agaccagaca gatcacaaag cacgtcgcac agattctcga ttctcggatg 5880
aacaccaagt acgacgagaa cgacaagctc atccgagagg tcaaggtgat tactctcaag 5940
tccaaactgg tctccgattt ccgaaaggac tttcagttct acaaggtgcg agagatcaac 6000
aattaccacc atgcccacga tgcttacctc aacgccgtcg ttggcactgc gctcatcaag 6060
aaatacccca agctcgaaag cgagttcgtt tacggcgatt acaaggtcta cgacgttcga 6120
aagatgattg ccaagtccga acaggagatt ggcaaggcta ctgccaagta cttcttttac 6180
tccaacatca tgaacttttt caagaccgag atcaccttgg ccaacggaga gattcgaaag 6240
agaccactta tcgagaccaa cggcgaaact ggagagatcg tgtgggacaa gggtcgagac 6300
tttgcaaccg tgcgaaaggt tctgtcgatg cctcaggtca acatcgtcaa gaaaaccgag 6360
gttcagactg gcggattctc caaggagtcg attctgccca agcgaaactc cgacaagctc 6420
atcgctcgaa agaaagactg ggatcccaag aaatacggtg gcttcgattc tcctaccgtc 6480

-continued

```
gcctattccg tgcttgtcgt tgcgaaggtc gagaagggca agtccaaaaa gctcaagtcc   6540
gtcaaggagc tgctcggaat taccatcatg gagcgatcga gcttcgagaa gaatcccatc   6600
gacttcttgg aagccaaggg ttacaaggag gtcaagaaag acctcattat caagctgccc   6660
aagtactctc tgttcgaact ggagaacggt cgaaagcgta tgctcgcctc cgctggcgag   6720
ctgcagaagg gaaacgagct tgccttgcct tcgaagtacg tcaactttct ctatctggct   6780
tctcactacg agaagctcaa gggttctccc gaggacaacg aacagaagca actcttcgtt   6840
gagcagcaca aacattacct cgacgagatt atcgagcaga tttccgagtt ttcgaagcga   6900
gtcatcctgg ctgatgccaa cttggacaag gtgctctctg cctacaacaa gcatcgggac   6960
aaacccattc gagaacaggc ggagaacatc attcacctgt ttactcttac caacctgggt   7020
gctcctgcag ctttcaagta cttcgatacc actatcgacc gaaagcggta cacatccacc   7080
aaggaggttc tcgatgccac cctgattcac cagtccatca ctggcctgta cgagacccga   7140
atcgacctgt ctcagcttgg tggcgactcc agagccgatc ccaagaaaaa gcgaaaggtc   7200
taagcggccg caagtgtgga tggggaagtg agtgcccggt tctgtgtgca caattggcaa   7260
tccaagatgg atggattcaa cacagggata tagcgagcta cgtggtggtg cgaggatata   7320
gcaacggata tttatgtttg acacttgaga atgtacgata caagcactgt ccaagtacaa   7380
tactaaacat actgtacata ctcatactcg tacccgggca acggtttcac ttgagtgcag   7440
tggctagtgc tcttactcgt acagtgtgca atactgcgta tcatagtctt tgatgtatat   7500
cgtattcatt catgttagtt gcgtacgagc cggaagcata aagtgtaaag cctggggtgc   7560
ctaatgagtg agctaactca cattaattgc gttgcgctca ctgcccgctt tccagtcggg   7620
aaacctgtcg tgccagctgc attaatgaat cggccaacgc gcggggagag gcggtttgcg   7680
tattgggcgc tcttccgctt cctcgctcac tgactcgctg cgctcggtcg ttcggctgcg   7740
gcgagcggta tcagctcact caaaggcggt aatacggtta tccacagaat caggggataa   7800
cgcaggaaag aacatgtgag caaaaggcca gcaaaaggcc aggaaccgta aaaaggccgc   7860
gttgctggcg tttttccata ggctccgccc ccctgacgag catcacaaaa atcgacgctc   7920
aagtcagagg tggcgaaacc cgacaggact ataaagatac caggcgtttc cccctggaag   7980
ctccctcgtg cgctctcctg ttccgaccct gccgcttacc ggatacctgt ccgcctttct   8040
cccttcggga agcgtggcgc tttctcatag ctcacgctgt aggtatctca gttcggtgta   8100
ggtcgttcgc tccaagctgg gctgtgtgca cgaacccccc gttcagcccg accgctgcgc   8160
cttatccggt aactatcgtc ttgagtccaa cccggtaaga cacgacttat cgccactggc   8220
agcagccact ggtaacagga ttagcagagc gaggtatgta ggcggtgcta cagagttctt   8280
gaagtggtgg cctaactacg gctacactag aaggacagta tttggtatct gcgctctgct   8340
gaagccagtt accttcggaa aaagagttgg tagctcttga tccggcaaac aaaccaccgc   8400
tggtagcggt ggtttttttg tttgcaagca gcagattacg cgcagaaaaa aaggatctca   8460
agaagatcct ttgatctttt ctacggggtc tgacgctcag tggaacgaaa actcacgtta   8520
agggattttg gtcatgagat tatcaaaaag gatcttcacc tagatccttt taaattaaaa   8580
atgaagtttt aaatcaatct aaagtatata tgagtaaact tggtctgaca gttaccaatg   8640
cttaatcagt gaggcaccta tctcagcgat ctgtctattt cgttcatcca tagttgcctg   8700
actccccgtc gtgtagataa ctacgatacg ggagggctta ccatctggcc ccagtgctgc   8760
aatgataccg cgagacccac gctcaccggc tccagattta tcagcaataa accagccagc   8820
```

```
cggaagggcc gagcgcagaa gtggtcctgc aactttatcc gcctccatcc agtctattaa   8880
ttgttgccgg gaagctagag taagtagttc gccagttaat agtttgcgca acgttgttgc   8940
cattgctaca ggcatcgtgg tgtcacgctc gtcgtttggt atggcttcat tcagctccgg   9000
ttcccaacga tcaaggcgag ttacatgatc ccccatgttg tgcaaaaaag cggttagctc   9060
cttcggtcct ccgatcgttg tcagaagtaa gttggccgca gtgttatcac tcatggttat   9120
ggcagcactg cataattctc ttactgtcat gccatccgta agatgctttt ctgtgactgg   9180
tgagtactca accaagtcat tctgagaata gtgtatgcgg cgaccgagtt gctcttgccc   9240
ggcgtcaata cgggataata ccgcgccaca tagcagaact ttaaaagtgc tcatcattgg   9300
aaaacgttct tcggggcgaa aactctcaag gatcttaccg ctgttgagat ccagttcgat   9360
gtaacccact cgtgcaccca actgatcttc agcatctttt actttcacca gcgtttctgg   9420
gtgagcaaaa acaggaaggc aaaatgccgc aaaaaaggga ataagggcga cacggaaatg   9480
ttgaatactc atactcttcc tttttcaata ttattgaagc atttatcagg gttattgtct   9540
catgagcgga tacatatttg aatgtattta gaaaaataaa caaatagggg ttccgcgcac   9600
atttccccga aaagtgccac ctgacgcgcc ctgtagcggc gcattaagcg cggcgggtgt   9660
ggtggttacg cgcagcgtga ccgctacact tgccagcgcc ctagcgcccg ctcctttcgc   9720
tttcttccct tcctttctcg ccacgttcgc cggctttccc cgtcaagctc taaatcgggg   9780
gctcccttta gggttccgat ttagtgcttt acggcacctc gaccccaaaa aacttgatta   9840
gggtgatggt tcacgtagtg ggccatcgcc ctgatagacg gtttttcgcc ctttgacgtt   9900
ggagtccacg ttctttaata gtggactctt gttccaaact ggaacaacac tcaaccctat   9960
ctcggtctat tcttttgatt tataagggat tttgccgatt tcggcctatt ggttaaaaaa  10020
tgagctgatt taacaaaaat ttaacgcgaa ttttaacaaa atattaacgc ttacaatttc  10080
cattcgccat tcaggctgcg caactgttgg gaagggcgat cggtgcgggc ctcttcgcta  10140
ttacgccagc tggcgaaagg gggatgtgct gcaaggcgat taagttgggt aacgccaggg  10200
ttttcccagt cacgacgttg taaaacgacg gccagtgaat tgtaatacga ctcactatag  10260
ggcgaattgg gtaccgggcc ccccctcgag gtcgatggtg tcgataagct tgatatcgaa  10320
ttcatgtcac acaaaccgat cttcgcctca aggaaaccta attctacatc cgagagactg  10380
ccgagatcca gtctacactg attaattttc gggccaataa tttaaaaaaa tcgtgttata  10440
taatattata tgtattatat atatacatca tgatgatact gacagtcatg tcccattgct  10500
aaatagacag actccatctg ccgcctccaa ctgatgttct caatatttaa ggggtcatct  10560
cgcattgttt aataataaac agactccatc taccgcctcc aaatgatgtt ctcaaaatat  10620
attgtatgaa cttattttta ttacttagta ttattagaca acttacttgc tttatgaaaa  10680
acacttccta tttaggaaac aatttataat ggcagttcgt tcatttaaca atttatgtag  10740
aataaatgtt ataaatgcgt atgggaaatc ttaaatatgg atagcataaa tgatatctgc  10800
attgcctaat tcgaaatcaa cagcaacgaa aaaaatccct tgtacaacat aaatagtcat  10860
cgagaaatat caactatcaa agaacagcta ttcacacgtt actattgaga ttattattgg  10920
acgagaatca cacactcaac tgtctttctc tcttctagaa atacaggtac aagtatgtac  10980
tattctcatt gttcatactt ctagtcattt catcccacat attccttgga tttctctcca  11040
atgaatgaca ttctatcttg caaattcaac aattataata agatatacca aagtagcggt  11100
atagtggcaa tcaaaaagct tctctggtgt gcttctcgta tttattttta ttctaatgat  11160
ccattaaagg tatatattta tttcttgtta tataatcctt ttgtttatta catgggctgg  11220
```

atacataaag gtattttgat ttaatttttt gcttaaattc aatcccccct cgttcagtgt 11280
caactgtaat ggtaggaaat taccatactt ttgaagaagc aaaaaaaatg aaagaaaaaa 11340
aaaatcgtat ttccaggtta gacgttccgc agaatctaga atgcggtatg cggtacattg 11400
ttcttcgaac gtaaaagttg cgctccctga gatattgtac atttttgctt ttacaagtac 11460
aagtacatcg tacaactatg tactactgtt gatgcatcca caacagtttg ttttgttttt 11520
ttttgttttt tttttttcta atgattcatt accgctatgt atacctactt gtacttgtag 11580
taagccgggt tattggcgtt caattaatca tagacttatg aatctgcacg gtgtgcgctg 11640
cgagttactt ttagcttatg catgctactt gggtgtaata ttgggatctg ttcggaaatc 11700
aacggatgct caat 11714

<210> SEQ ID NO 99
<211> LENGTH: 32
<212> TYPE: DNA
<213> ORGANISM: Artificial sequence
<220> FEATURE:
<223> OTHER INFORMATION: Can1-1F

<400> SEQUENCE: 99
aatgggactc aaacgattac ccaccctcgt tt 32

<210> SEQ ID NO 100
<211> LENGTH: 32
<212> TYPE: DNA
<213> ORGANISM: Artificial sequence
<220> FEATURE:
<223> OTHER INFORMATION: Can1-1R

<400> SEQUENCE: 100
tctaaaacga gggtgggtaa tcgtttgagt cc 32

<210> SEQ ID NO 101
<211> LENGTH: 23
<212> TYPE: DNA
<213> ORGANISM: Yarrowia lipolytica
<220> FEATURE:
<221> NAME/KEY: misc_feature
<222> LOCATION: (1)..(23)
<223> OTHER INFORMATION: Can1-1 target site and PAM

<400> SEQUENCE: 101
tcaaacgatt acccaccctc cgg 23

<210> SEQ ID NO 102
<211> LENGTH: 480
<212> TYPE: DNA
<213> ORGANISM: Artificial sequence
<220> FEATURE:
<223> OTHER INFORMATION: Can1-1 gRNA expression cassette

<400> SEQUENCE: 102 atttttttg attttctttt ttgaccccgt cttcaattac acttcccaac tgggaacacc 60
cctctttatc gacccatttt aggtaattta ccctagccca ttgtctccat aaggaatatt 120
accctaaccc acagtccagg gtgcccaggt ccttctttgg ccaaatttta acttcggtcc 180
tatggcacag cggtagcgcg tgagattgca aatcttaagg tcccgagttc gaatctcggt 240
gggacctagt tatttttgat agataatttc gtgatgatta gaaacttaac gcaaaataat 300
ggccggcatg gtcccagcct cctcgctggc gccggctggg caacatgctt cggcatggcg 360
aatgggactc aaacgattac ccaccctcgt tttagagcta gaaatagcaa ttaaaataag 420
gctagtccgt tatcaacttg aaaaagtggc accgagtcgg tgcttttttt tttgtttttt 480

<210> SEQ ID NO 103
<211> LENGTH: 11176
<212> TYPE: DNA
<213> ORGANISM: Artificial sequence
<220> FEATURE:
<223> OTHER INFORMATION: pRF303

<400> SEQUENCE: 103
tctaaaacga gggtgggtaa tcgtttgagt cccattcgcc atgccgaagc atgttgccca 60
gccggcgcca gcgaggaggc tgggaccatg ccggccatta ttttgcgtta agtttctaat 120
catcacgaaa ttatctatca aaaataacta ggtcccaccg agattcgaac tcgggacctt 180
aagatttgca atctcacgcg ctaccgctgt gccataggac cgaagttaaa atttggccaa 240
agaaggacct gggcaccctg gactgtgggt tagggtaata ttccttatgg agacaatggg 300
ctagggtaaa ttacctaaaa tgggtcgata aagaggggtg ttcccagttg ggaagtgtaa 360
ttgaagacgg ggtcaaaaaa gaaaatcaaa aaaaatttaa ttaagtcata cacaagtcag 420
ctttcttcga gcctcatata agtataagta gttcaacgta ttagcactgt acccagcatc 480
tccgtatcga gaaacacaac aacatgcccc attggacaga tcatgcggat acacaggttg 540
tgcagtatca tacatactcg atcagacagg tcgtctgacc atcatacaag ctgaacaagc 600
gctccatact tgcacgctct ctatatacac agttaaatta catatccata gtctaacctc 660
taacagttaa tcttctggta agcctcccag ccagccttct ggtatcgctt ggcctcctca 720
ataggatctc ggttctggcc gtacagacct cggccgacaa ttatgatatc cgttccggta 780
gacatgacat cctcaacagt tcggtactgc tgtccgagag cgtctccctt gtcgtcaaga 840
cccaccccgg gggtcagaat aagccagtcc tcagagtcgc ccttaggtcg gttctgggca 900
atgaagccaa ccacaaactc ggggtcggat cgggcaagct caatggtctg cttggagtac 960
tcgccagtgg ccagagagcc cttgcaagac agctcggcca gcatgagcag acctctggcc 1020
agcttctcgt tgggagaggg gactaggaac tccttgtact gggagttctc gtagtcagag 1080
acgtcctcct tcttctgttc agagacagtt tcctcggcac cagctcgcag gccagcaatg 1140
attccggttc cgggtacacc gtgggcgttg gtgatatcgg accactcggc gattcggtga 1200
caccggtact ggtgcttgac agtgttgcca atatctgcga actttctgtc ctcgaacagg 1260
aagaaaccgt gcttaagagc aagttccttg agggggagca cagtgccggc gtaggtgaag 1320
tcgtcaatga tgtcgatatg ggttttgatc atgcacacat aaggtccgac cttatcggca 1380
agctcaatga gctccttggt ggtggtaaca tccagagaag cacacaggtt ggttttcttg 1440
gctgccacga gcttgagcac tcgagcggca aaggcggact tgtggacgtt agctcgagct 1500
tcgtaggagg gcattttggt ggtgaagagg agactgaaat aaatttagtc tgcagaactt 1560
tttatcggaa ccttatctgg ggcagtgaag tatatgttat ggtaatagtt acgagttagt 1620
tgaacttata gatagactgg actatacggc tatcggtcca aattagaaag aacgtcaatg 1680
gctctctggg cgtcgccttt gccgacaaaa atgtgatcat gatgaaagcc agcaatgacg 1740
ttgcagctga tattgttgtc ggccaaccgc gccgaaaacg cagctgtcag acccacagcc 1800
tccaacgaag aatgtatcgt caaagtgatc caagcacact catagttgga gtcgtactcc 1860
aaaggcggca atgacgagtc agacagatac tcgtcgacgt ttaaaccatc atctaagggc 1920
ctcaaaacta cctcggaact gctgcgctga tctggacacc acagaggttc cgagcacttt 1980

```
aggttgcacc aaatgtccca ccaggtgcag gcagaaaacg ctggaacagc gtgtacagtt   2040
tgtcttaaca aaaagtgagg gcgctgaggt cgagcagggt ggtgtgactt gttatagcct   2100
ttagagctgc gaaagcgcgt atggatttgg ctcatcaggc cagattgagg gtctgtggac   2160
acatgtcatg ttagtgtact tcaatcgccc cctggatata gccccgacaa taggccgtgg   2220
cctcattttt ttgccttccg cacatttcca ttgctcggta cccacacctt gcttctcctg   2280
cacttgccaa ccttaatact ggtttacatt gaccaacatc ttacaagcgg ggggcttgtc   2340
tagggtatat ataaacagtg gctctcccaa tcggttgcca gtctcttttt tcctttcttt   2400
ccccacagat tcgaaatcta aactacacat cacaccatgg acaagaaata ctccatcggc   2460
ctggacattg gaaccaactc tgtcggctgg gctgtcatca ccgacgagta caaggtgccc   2520
tccaagaaat tcaaggtcct cggaaacacc gatcgacact ccatcaagaa aaacctcatt   2580
ggtgccctgt tgttcgattc tggcgagact gccgaagcta ccagactcaa gcgaactgct   2640
cggcgacgtt acacccgacg gaagaaccga atctgctacc tgcaggagat cttttccaac   2700
gagatggcca aggtggacga ttcgttcttt catcgactgg aggaatcctt cctcgtcgag   2760
gaagacaaga aacacgagcg tcatcccatc tttggcaaca ttgtggacga ggttgcttac   2820
cacgagaagt atcctaccat ctaccatctc cgaaagaaac tcgtcgattc caccgacaag   2880
gcggatctca gacttatcta cctcgctctg gcacacatga tcaagtttcg aggtcatttc   2940
ctcatcgagg gcgatctcaa tcccgacaac agcgatgtgg acaagctgtt cattcagctc   3000
gttcagacct acaaccagct gttcgaggaa aaccccatca atgcctccgg agtcgatgca   3060
aaggccatct tgtctgctcg actctcgaag agcagacgac tggagaacct cattgcccaa   3120
cttcctggcg agaaaaagaa cggactgttt ggcaacctca ttgccctttc tcttggtctc   3180
acacccaact tcaagtccaa cttcgatctg gcggaggacg ccaagctcca gctgtccaag   3240
gacacctacg acgatgacct cgacaacctg cttgcacaga ttggcgatca gtacgccgac   3300
ctgtttctcg ctgccaagaa cctttcggat gctattctct tgtctgacat tctgcgagtc   3360
aacaccgaga tcacaaaggc tccccttct gcctccatga tcaagcgata cgacgagcac   3420
catcaggatc tcacactgct caaggctctt gtccgacagc aactgcccga gaagtacaag   3480
gagatctttt tcgatcagtc gaagaacggc tacgctggat acatcgacgg cggagcctct   3540
caggaagagt tctacaagtt catcaagcca attctcgaga agatggacgg aaccgaggaa   3600
ctgcttgtca agctcaatcg agaggatctg cttcggaagc aacgaacctt cgacaacggc   3660
agcattcctc atcagatcca cctcggtgag ctgcacgcca ttcttcgacg tcaggaagac   3720
ttctacccct ttctcaagga caaccgagag aagatcgaga agattcttac ctttcgaatc   3780
ccctactatg ttggtcctct tgccagagga aactctcgat ttgcttggat gactcgaaag   3840
tccgaggaaa ccatcactcc ctggaacttc gaggaagtcg tggacaaggg tgcctctgca   3900
cagtccttca tcgagcgaat gaccaacttc gacaagaatc tgcccaacga gaaggttctt   3960
cccaagcatt cgctgctcta cgagtacttt acagtctaca acgaactcac caaagtcaag   4020
tacgttaccg agggaatgcg aaagcctgcc ttcttgtctg gcgaacagaa gaaagccatt   4080
gtcgatctcc tgttcaagac caaccgaaag gtcactgtta agcagctcaa ggaggactac   4140
ttcaagaaaa tcgagtgttt cgacagcgtc gagatttccg gagttgagga ccgattcaac   4200
gcctctttgg gcacctatca cgatctgctc aagattatca aggacaagga ttttctcgac   4260
aacgaggaaa acgaggacat tctggaggac atcgtgctca ctcttaccct gttcgaagat   4320
```

-continued

```
cgggagatga tcgaggaacg actcaagaca tacgctcacc tgttcgacga caaggtcatg   4380
aaacaactca agcgacgtag atacaccggc tggggaagac tttcgcgaaa gctcatcaac   4440
ggcatcagag acaagcagtc cggaaagacc attctggact ttctcaagtc cgatggcttt   4500
gccaaccgaa acttcatgca gctcattcac gacgattctc ttaccttcaa ggaggacatc   4560
cagaaggcac aagtgtccgg tcagggcgac agcttgcacg aacatattgc caacctggct   4620
ggttcgccag ccatcaagaa aggcattctc cagactgtca aggttgtcga cgagctggtg   4680
aaggtcatgg gacgtcacaa gcccgagaac attgtgatcg agatggccag agagaaccag   4740
acaactcaaa agggtcagaa aaactcgcga gagcggatga agcgaatcga ggaaggcatc   4800
aaggagctgg gatcccagat tctcaaggag catcccgtcg agaacactca actgcagaac   4860
gagaagctgt atctctacta tctgcagaat ggtcgagaca tgtacgtgga tcaggaactg   4920
gacatcaatc gtctcagcga ctacgatgtg gaccacattg tccctcaatc ctttctcaag   4980
gacgattcta tcgacaacaa ggtccttaca cgatccgaca agaacagagg caagtcggac   5040
aacgttccca gcgaagaggt ggtcaaaaag atgaagaact actggcgaca gctgctcaac   5100
gccaagctca ttacccagcg aaagttcgac aatcttacca aggccgagcg aggcggtctg   5160
tccgagctcg acaaggctgg cttcatcaag cgtcaactcg tcgagaccag acagatcaca   5220
aagcacgtcg cacagattct cgattctcgg atgaacacca agtacgacga gaacgacaag   5280
ctcatccgag aggtcaaggt gattactctc aagtccaaac tggtctccga tttccgaaag   5340
gactttcagt tctacaaggt gcgagagatc aacaattacc accatgccca cgatgcttac   5400
ctcaacgccg tcgttggcac tgcgctcatc aagaaatacc ccaagctcga aagcgagttc   5460
gtttacggcg attacaaggt ctacgacgtt cgaaagatga ttgccaagtc cgaacaggag   5520
attggcaagg ctactgccaa gtacttcttt tactccaaca tcatgaactt tttcaagacc   5580
gagatcacct tggccaacgg agagattcga aagagaccac ttatcgagac caacggcgaa   5640
actggagaga tcgtgtggga caagggtcga gactttgcaa ccgtgcgaaa ggttctgtcg   5700
atgcctcagg tcaacatcgt caagaaaacc gaggttcaga ctggcggatt ctccaaggag   5760
tcgattctgc ccaagcgaaa ctccgacaag ctcatcgctc gaaagaaaga ctgggatccc   5820
aagaaatacg gtggcttcga ttctcctacc gtcgcctatt ccgtgcttgt cgttgcgaag   5880
gtcgagaagg gcaagtccaa aaagctcaag tccgtcaagg agctgctcgg aattaccatc   5940
atggagcgat cgagcttcga gaagaatccc atcgacttct tggaagccaa gggttacaag   6000
gaggtcaaga aagacctcat tatcaagctg cccaagtact ctctgttcga actggagaac   6060
ggtcgaaagc gtatgctcgc ctccgctggc gagctgcaga agggaaacga gcttgccttg   6120
ccttcgaagt acgtcaactt tctctatctg gcttctcact acgagaagct caagggttct   6180
cccgaggaca acgaacagaa gcaactcttc gttgagcagc acaaacatta cctcgacgag   6240
attatcgagc agatttccga gttttcgaag cgagtcatcc tggctgatgc caacttggac   6300
aaggtgctct ctgcctacaa caagcatcgg gacaaaccca ttcgagaaca ggcggagaac   6360
atcattcacc tgtttactct taccaacctg ggtgctcctg cagctttcaa gtacttcgat   6420
accactatcg accgaaagcg gtacacatcc accaaggagg ttctcgatgc caccctgatt   6480
caccagtcca tcactggcct gtacgagacc cgaatcgacc tgtctcagct tggtggcgac   6540
tccagagccg atcccaagaa aaagcgaaag gtctaagcgg ccgcaagtgt ggatggggaa   6600
gtgagtgccc ggttctgtgt gcacaattgg caatccaaga tggatggatt caacacaggg   6660
atatagcgag ctacgtggtg gtgcgaggat atagcaacgg atatttatgt ttgacacttg   6720
```

```
agaatgtacg atacaagcac tgtccaagta caatactaaa catactgtac atactcatac   6780
tcgtacccgg gcaacggttt cacttgagtg cagtggctag tgctcttact cgtacagtgt   6840
gcaatactgc gtatcatagt ctttgatgta tatcgtattc attcatgtta gttgcgtacg   6900
agccggaagc ataaagtgta aagcctgggg tgcctaatga gtgagctaac tcacattaat   6960
tgcgttgcgc tcactgcccg ctttccagtc gggaaacctg tcgtgccagc tgcattaatg   7020
aatcggccaa cgcgcgggga gaggcggttt gcgtattggg cgctcttccg cttcctcgct   7080
cactgactcg ctgcgctcgg tcgttcggct gcggcgagcg gtatcagctc actcaaaggc   7140
ggtaatacgg ttatccacag aatcagggga taacgcagga aagaacatgt gagcaaaagg   7200
ccagcaaaag gccaggaacc gtaaaaaggc cgcgttgctg gcgtttttcc ataggctccg   7260
cccccctgac gagcatcaca aaaatcgacg ctcaagtcag aggtggcgaa acccgacagg   7320
actataaaga taccaggcgt ttccccctgg aagctccctc gtgcgctctc ctgttccgac   7380
cctgccgctt accggatacc tgtccgcctt tctcccttcg ggaagcgtgg cgctttctca   7440
tagctcacgc tgtaggtatc tcagttcggt gtaggtcgtt cgctccaagc tgggctgtgt   7500
gcacgaaccc cccgttcagc ccgaccgctg cgccttatcc ggtaactatc gtcttgagtc   7560
caacccggta agacacgact tatcgccact ggcagcagcc actggtaaca ggattagcag   7620
agcgaggtat gtaggcggtg ctacagagtt cttgaagtgg tggcctaact acggctacac   7680
tagaaggaca gtatttggta tctgcgctct gctgaagcca gttaccttcg gaaaaagagt   7740
tggtagctct tgatccggca aacaaaccac cgctggtagc ggtggttttt ttgtttgcaa   7800
gcagcagatt acgcgcagaa aaaaaggatc tcaagaagat cctttgatct tttctacggg   7860
gtctgacgct cagtggaacg aaaactcacg ttaagggatt ttggtcatga gattatcaaa   7920
aaggatcttc acctagatcc ttttaaatta aaaatgaagt tttaaatcaa tctaaagtat   7980
atatgagtaa acttggtctg acagttacca atgcttaatc agtgaggcac ctatctcagc   8040
gatctgtcta tttcgttcat ccatagttgc ctgactcccc gtcgtgtaga taactacgat   8100
acgggagggc ttaccatctg gccccagtgc tgcaatgata ccgcgagacc cacgctcacc   8160
ggctccagat ttatcagcaa taaaccagcc agccggaagg gccgagcgca gaagtggtcc   8220
tgcaacttta tccgcctcca tccagtctat taattgttgc cgggaagcta gagtaagtag   8280
ttcgccagtt aatagtttgc gcaacgttgt tgccattgct acaggcatcg tggtgtcacg   8340
ctcgtcgttt ggtatggctt cattcagctc cggttcccaa cgatcaaggc gagttacatg   8400
atcccccatg ttgtgcaaaa aagcggttag ctccttcggt cctccgatcg ttgtcagaag   8460
taagttggcc gcagtgttat cactcatggt tatggcagca ctgcataatt ctcttactgt   8520
catgccatcc gtaagatgct tttctgtgac tggtgagtac tcaaccaagt cattctgaga   8580
atagtgtatg cggcgaccga gttgctcttg cccggcgtca atacgggata ataccgcgcc   8640
acatagcaga actttaaaag tgctcatcat tggaaaacgt tcttcggggc gaaaactctc   8700
aaggatctta ccgctgttga gatccagttc gatgtaaccc actcgtgcac ccaactgatc   8760
ttcagcatct tttactttca ccagcgtttc tgggtgagca aaaacaggaa ggcaaaatgc   8820
cgcaaaaaag ggaataaggg cgacacggaa atgttgaata ctcatactct tcctttttca   8880
atattattga agcatttatc agggttattg tctcatgagc ggatacatat ttgaatgtat   8940
ttagaaaaat aaacaaatag gggttccgcg cacatttccc cgaaaagtgc cacctgacgc   9000
gccctgtagc ggcgcattaa gcgcggcggg tgtggtggtt acgcgcagcg tgaccgctac   9060
```

-continued

```
acttgccagc gccctagcgc ccgctccttt cgctttcttc ccttcctttc tcgccacgtt   9120

cgccggcttt ccccgtcaag ctctaaatcg gggctccct ttagggttcc gatttagtgc    9180

tttacggcac ctcgacccca aaaaacttga ttagggtgat ggttcacgta gtgggccatc   9240

gccctgatag acggtttttc gccctttgac gttggagtcc acgttcttta atagtggact   9300

cttgttccaa actggaacaa cactcaaccc tatctcggtc tattcttttg atttataagg   9360

gattttgccg atttcggcct attggttaaa aaatgagctg atttaacaaa aatttaacgc   9420

gaattttaac aaaatattaa cgcttacaat ttccattcgc cattcaggct gcgcaactgt   9480

tgggaagggc gatcggtgcg ggcctcttcg ctattacgcc agctggcgaa agggggatgt   9540

gctgcaaggc gattaagttg ggtaacgcca gggttttccc agtcacgacg ttgtaaaacg   9600

acggccagtg aattgtaata cgactcacta tagggcgaat tgggtaccgg gccccccctc   9660

gaggtcgatg gtgtcgataa gcttgatatc gaattcatgt cacacaaacc gatcttcgcc   9720

tcaaggaaac ctaattctac atccgagaga ctgccgagat ccagtctaca ctgattaatt   9780

ttcgggccaa taatttaaaa aaatcgtgtt atataatatt atatgtatta tatatataca   9840

tcatgatgat actgacagtc atgtcccatt gctaaataga cagactccat ctgccgcctc   9900

caactgatgt tctcaatatt taaggggtca tctcgcattg tttaataata aacagactcc   9960

atctaccgcc tccaaatgat gttctcaaaa tatattgtat gaacttattt ttattactta  10020

gtattattag acaacttact tgctttatga aaaacacttc ctatttagga aacaatttat  10080

aatggcagtt cgttcattta acaatttatg tagaataaat gttataaatg cgtatgggaa  10140

atcttaaata tggatagcat aaatgatatc tgcattgcct aattcgaaat caacagcaac  10200

gaaaaaaatc ccttgtacaa cataaatagt catcgagaaa tatcaactat caaagaacag  10260

ctattcacac gttactattg agattattat tggacgagaa tcacacactc aactgtcttt  10320

ctctcttcta gaaatacagg tacaagtatg tactattctc attgttcata cttctagtca  10380

tttcatccca catattcctt ggatttctct ccaatgaatg acattctatc ttgcaaattc  10440

aacaattata ataagatata ccaaagtagc ggtatagtgg caatcaaaaa gcttctctgg  10500

tgtgcttctc gtatttattt ttattctaat gatccattaa aggtatatat ttatttcttg  10560

ttatataatc cttttgttta ttacatgggc tggatacata aaggtatttt gatttaattt  10620

tttgcttaaa ttcaatcccc cctcgttcag tgtcaactgt aatggtagga aattaccata  10680

cttttgaaga agcaaaaaaa atgaaagaaa aaaaaaatcg tatttccagg ttagacgttc  10740

cgcagaatct agaatgcggt atgcggtaca ttgttcttcg aacgtaaaag ttgcgctccc  10800

tgagatattg tacatttttg cttttacaag tacaagtaca tcgtacaact atgtactact  10860

gttgatgcat ccacaacagt ttgttttgtt ttttttgtt ttttttttt ctaatgattc   10920

attaccgcta tgtataccta cttgtacttg tagtaagccg ggttattggc gttcaattaa  10980

tcatagactt atgaatctgc acggtgtgcg ctgcgagtta cttttagctt atgcatgcta  11040

cttgggtgta atattgggat ctgttcggaa atcaacggat gctcaatcga taaaaaacaa  11100

aaaaaaaagc accgactcgg tgccactttt tcaagttgat aacggactag ccttatttta  11160

acttgctatt tctagc                                                  11176
```

<210> SEQ ID NO 104
<211> LENGTH: 168
<212> TYPE: RNA
<213> ORGANISM: Artificial sequence
<220> FEATURE:
<223> OTHER INFORMATION: ribozyme-guide RNA of Cas1-1

<400> SEQUENCE: 104
ggccggcaug gucccagccu ccucgcuggc gccggcuggg caacaugcuu cggcauggcg 60
aaugggacuc aaacgauuac ccacccucgu uuuagagcua gaaauagcaa guuaaaauaa 120
ggcuaguccg uuaucaacuu gaaaaagugg caccgagucg gugcuuuu 168

<210> SEQ ID NO 105
<211> LENGTH: 1719
<212> TYPE: DNA
<213> ORGANISM: Yarrowia lipolytica
<220> FEATURE:
<221> NAME/KEY: misc_feature
<222> LOCATION: (1)..(1719)
<223> OTHER INFORMATION: Can1 gene

<400> SEQUENCE: 105
atggaaaaga cattttcaaa cgattaccca ccctccggga ctgaggccca catccacatc 60
aaccacacgg cccactcgga tgactcagag gaggtgccct cgcacaagga aaattacaac 120
accagtggcc acgacctgga ggagtccgac ccggataacc atgtcggtga gaccctcgag 180
gtcaagcgag gtctcaagat gcgacacatc tccatgatct cgcttggagg aaccattggt 240
accggtctct tcattggtac cggaggagct ctccagcagg ccggtccctg tggcgccctc 300
gtcgcctacg tgttcatggc caccattgtc tactctgttg ccgagtctct tggagaactg 360
gctacgtaca ttcccatcac cggctccttt gccgtcttta ctacccgata tctgtcacag 420
tcgtttggtg cctccatggg ctggctatac tggttctcgt gggcgatcac cttcgccatc 480
gagctcaaca ccattggtcc cgtgattgag tactggactg acgccgttcc tactgctgcc 540
tggattgcca tcttcttcgt catcctcact accatcaact tcttccccgt gggcttctat 600
ggcgaagtcg agttctgggt ggcctccgtg aaggtcattg ccatcattgg atggctcatc 660
tacgcgctct gcatgacgtg tggagcaggt gtaacaggtc ctgtgggatt cagatactgg 720
aaccaccccg gacccatggg agacggaatc tggaccgacg gcgtgcccat tgtgcgaaac 780
gcgcccggtc gacgattcat gggatggctc aattcgctcg ttaacgccgc cttcacctac 840
cagggctgtg agctggtcgg agtcactgcc ggtgaggccc agaaccccag aaagtccgtc 900
cctcgagcca tcaaccgagt ctttgctcga atttgcatct tctacattgg ctctatcttc 960
ttcatgggca tgctcgtgcc ctttaacgac cccaagctga ccgatgactc ctccgtcatc 1020
gcctcctctc cttttgttat tgccattatc aactctggca ccaaggtgct ccctcacatt 1080
ttcaacgccg tcattctcat caccctgatt tcggcaggaa actccaacgt ctacattggc 1140
tcgcgagtgg tctacgccct ggctgactcc ggaaccgcac caaagttctt caagcgaacc 1200
accaagaagg gagtgccgta cgtggcagtc tgcttcacct cggcgtttgg tctgctggcc 1260
ttcatgtctg tgtccgagtc gtcgtccact gtcttcgact ggttcatcaa catctccgct 1320
gtggccggcc tcatctgttg ggccttcatc tctgcctccc acatccgatt catgcaagtg 1380
cttaagcaca gagggatctc cagagatacg ctgcccttca aggcacgatg gcagccattc 1440
tactcatggt acgcgctcgt ctccatcatc ttcatcactc tcatccaggg cttcacgtcc 1500
ttctggcact ttaccgccgc caagttcatg actgcataca tctccgtcat tgtctgggtc 1560
ggtttgtaca ttatcttcca gtgtctgttc cgatgcaagt tccttatccc tattgaggat 1620
gtggacattg acaccggccg acgagagatt gacgacgatg tgtgggagga gaagatcccc 1680
acaaagtggt acgagaagtt ttggaatatt attgcataa 1719

<210> SEQ ID NO 106
<211> LENGTH: 23
<212> TYPE: DNA
<213> ORGANISM: Yarrowia lipolytica
<220> FEATURE:
<221> NAME/KEY: misc_feature
<222> LOCATION: (1)..(23)
<223> OTHER INFORMATION: Can1-2 target site and PAM

<400> SEQUENCE: 106
ggcccactcg gatgactcag agg 23

<210> SEQ ID NO 107
<211> LENGTH: 27
<212> TYPE: DNA
<213> ORGANISM: Yarrowia lipolytica
<220> FEATURE:
<221> NAME/KEY: misc_feature
<222> LOCATION: (1)..(17)
<223> OTHER INFORMATION: Sou2-1 target site and PAM

<400> SEQUENCE: 107
gtctggacct tccaccctcg ccacggg 27

<210> SEQ ID NO 108
<211> LENGTH: 25
<212> TYPE: DNA
<213> ORGANISM: Yarrowia lipolytica
<220> FEATURE:
<221> NAME/KEY: misc_feature
<222> LOCATION: (1)..(25)
<223> OTHER INFORMATION: Sou2-2 target site and PAM

<400> SEQUENCE: 108
gcagtcccgt ggcgagggtg gaagg 25

<210> SEQ ID NO 109
<211> LENGTH: 20
<212> TYPE: RNA
<213> ORGANISM: Artificial sequence
<220> FEATURE:
<223> OTHER INFORMATION: Variable targeting domain of Can1-2

<400> SEQUENCE: 109
ggcccacucg gaugacucag 20

<210> SEQ ID NO 110
<211> LENGTH: 24
<212> TYPE: RNA
<213> ORGANISM: artificial sequence
<220> FEATURE:
<223> OTHER INFORMATION: Variable targeting domain of Sou2-1

<400> SEQUENCE: 110
gucuggaccu uccacccucg ccac 24

<210> SEQ ID NO 111
<211> LENGTH: 22
<212> TYPE: RNA
<213> ORGANISM: artificial sequence
<220> FEATURE:
<223> OTHER INFORMATION: Variable targeting domain of Sou2-2

<400> SEQUENCE: 111
gcagucccgu ggcgagggug ga 22

<210> SEQ ID NO 112
<211> LENGTH: 23
<212> TYPE: DNA
<213> ORGANISM: Yarrowia lipolytica

<400> SEQUENCE: 112
cagctcgaga cgtcctagaa cgg 23

<210> SEQ ID NO 113
<211> LENGTH: 23
<212> TYPE: DNA
<213> ORGANISM: Yarrowia lipolytica

<400> SEQUENCE: 113
ttcctctgtc acagacgttt cgg 23

<210> SEQ ID NO 114
<211> LENGTH: 23
<212> TYPE: DNA
<213> ORGANISM: Yarrowia lipolytica

<400> SEQUENCE: 114
gaaaagtgcg ttttgattct cgg 23

<210> SEQ ID NO 115
<211> LENGTH: 19
<212> TYPE: RNA
<213> ORGANISM: artificial sequence
<220> FEATURE:
<223> OTHER INFORMATION: Variable targeting domain of ura3-1

<400> SEQUENCE: 115
gccgcucgag ugcucaagc 19

<210> SEQ ID NO 116
<211> LENGTH: 22
<212> TYPE: DNA
<213> ORGANISM: Yarrowia lipolytica
<220> FEATURE:
<221> NAME/KEY: misc_feature
<222> LOCATION: (1)..(22)
<223> OTHER INFORMATION: URa3-1 target site and PAM

<400> SEQUENCE: 116
gccgctcgag tgctcaagct cg 22

<210> SEQ ID NO 117
<211> LENGTH: 1379
<212> TYPE: PRT
<213> ORGANISM: Artificial sequence
<220> FEATURE:
<223> OTHER INFORMATION: Cas9-SV40 NLS D10A H840A

<400> SEQUENCE: 117

Met Asp Lys Lys Tyr Ser Ile Gly Leu Ala Ile Gly Thr Asn Ser Val
1 5 10 15

Gly Trp Ala Val Ile Thr Asp Glu Tyr Lys Val Pro Ser Lys Lys Phe
20 25 30

Lys Val Leu Gly Asn Thr Asp Arg His Ser Ile Lys Lys Asn Leu Ile
35 40 45

Gly Ala Leu Leu Phe Asp Ser Gly Glu Thr Ala Glu Ala Thr Arg Leu
50 55 60

Lys Arg Thr Ala Arg Arg Arg Tyr Thr Arg Arg Lys Asn Arg Ile Cys
65 70 75 80

-continued

```
Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495
```

```
Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
```

```
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                 1015                 1020

Lys Ser  Glu Gln Glu Ile Gly  Lys Ala Thr Ala Lys  Tyr Phe Phe
    1025                 1030                 1035

Tyr Ser  Asn Ile Met Asn Phe  Phe Lys Thr Glu Ile  Thr Leu Ala
    1040                 1045                 1050

Asn Gly  Glu Ile Arg Lys Arg  Pro Leu Ile Glu Thr  Asn Gly Glu
    1055                 1060                 1065

Thr Gly  Glu Ile Val Trp Asp  Lys Gly Arg Asp Phe  Ala Thr Val
    1070                 1075                 1080

Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320
```

```
Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365

Ser Arg  Ala Asp Pro Lys Lys  Lys Arg Lys Val
    1370                 1375
```

<210> SEQ ID NO 118
<211> LENGTH: 41
<212> TYPE: DNA
<213> ORGANISM: Artificial sequence
<220> FEATURE:
<223> OTHER INFORMATION: D10AF

<400> SEQUENCE: 118
gaaatactcc atcggcctgg ccattggaac caactctgtc g 41

<210> SEQ ID NO 119
<211> LENGTH: 41
<212> TYPE: DNA
<213> ORGANISM: Artificial Sequence
<220> FEATURE:
<223> OTHER INFORMATION: D10AR

<400> SEQUENCE: 119
cgacagagtt ggttccaatg gccaggccga tggagtattt c 41

<210> SEQ ID NO 120
<211> LENGTH: 4140
<212> TYPE: DNA
<213> ORGANISM: Artificial Sequence
<220> FEATURE:
<223> OTHER INFORMATION: Yarrowia optimized Cas9 D10A

<400> SEQUENCE: 120
atggacaaga aatactccat cggcctggcc attggaacca actctgtcgg ctgggctgtc 60
atcaccgacg agtacaaggt gccctccaag aaattcaagg tcctcggaaa caccgatcga 120
cactccatca agaaaaacct cattggtgcc ctgttgttcg attctggcga gactgccgaa 180
gctaccagac tcaagcgaac tgctcggcga cgttacaccc gacggaagaa ccgaatctgc 240
tacctgcagg agatcttttc caacgagatg gccaaggtgg acgattcgtt ctttcatcga 300
ctggaggaat ccttcctcgt cgaggaagac aagaaacacg agcgtcatcc catctttggc 360
aacattgtgg acgaggttgc ttaccacgag aagtatccta ccatctacca cctgcgaaag 420
aaactcgtcg attccaccga caaggcggat ctcagactta tctacctcgc tctggcacac 480
atgatcaagt ttcgaggtca tttcctcatc gagggcgatc tcaatcccga caacagcgat 540
gtggacaagc tgttcattca gctcgttcag acctacaacc agctgttcga ggaaaacccc 600
atcaatgcct ccggagtcga tgcaaaggcc atcttgtctg ctcgactctc gaagagcaga 660
cgactggaga acctcattgc ccaacttcct ggcgagaaaa agaacggact gtttggcaac 720
ctcattgccc tttctcttgg tctcacaccc aacttcaagt ccaacttcga tctggcggag 780
gacgccaagc tccagctgtc caaggacacc tacgacgatg acctcgacaa cctgcttgca 840
cagattggcg atcagtacgc cgacctgttt ctcgctgcca agaacctttc ggatgctatt 900
ctcttgtctg acattctgcg agtcaacacc gagatcacaa aggctcccct ttctgcctcc 960

```
atgatcaagc gatacgacga gcaccatcag gatctcacac tgctcaaggc tcttgtccga   1020
cagcaactgc ccgagaagta caaggagatc tttttcgatc agtcgaagaa cggctacgct   1080
ggatacatcg acggcggagc ctctcaggaa gagttctaca agttcatcaa gccaattctc   1140
gagaagatgg acggaaccga ggaactgctt gtcaagctca atcgagagga tctgcttcgg   1200
aagcaacgaa ccttcgacaa cggcagcatt cctcatcaga tccacctcgg tgagctgcac   1260
gccattcttc gacgtcagga agacttctac ccctttctca aggacaaccg agagaagatc   1320
gagaagattc ttacctttcg aatcccctac tatgttggtc ctcttgccag aggaaactct   1380
cgatttgctt ggatgactcg aaagtccgag gaaaccatca ctccctggaa cttcgaggaa   1440
gtcgtggaca agggtgcctc tgcacagtcc ttcatcgagc gaatgaccaa cttcgacaag   1500
aatctgccca acgagaaggt tcttcccaag cattcgctgc tctacgagta ctttacagtc   1560
tacaacgaac tcaccaaagt caagtacgtt accgagggaa tgcgaaagcc tgccttcttg   1620
tctggcgaac agaagaaagc cattgtcgat ctcctgttca agaccaaccg aaaggtcact   1680
gttaagcagc tcaaggagga ctacttcaag aaaatcgagt gtttcgacag cgtcgagatt   1740
tccggagttg aggaccgatt caacgcctct ttgggcacct atcacgatct gctcaagatt   1800
atcaaggaca aggatttttct cgacaacgag gaaaacgagg acattctgga ggacatcgtg   1860
ctcactctta ccctgttcga agatcgggag atgatcgagg aacgactcaa gacatacgct   1920
cacctgttcg acgacaaggt catgaaacaa ctcaagcgac gtagatacac cggctgggga   1980
agactttcgc gaaagctcat caacggcatc agagacaagc agtccggaaa gaccattctg   2040
gactttctca agtccgatgg ctttgccaac cgaaacttca tgcagctcat tcacgacgat   2100
tctcttacct tcaaggagga catccagaag gcacaagtgt ccggtcaggg cgacagcttg   2160
cacgaacata ttgccaacct ggctggttcg ccagccatca agaaaggcat tctccagact   2220
gtcaaggttg tcgacgagct ggtgaaggtc atgggacgtc acaagcccga gaacattgtg   2280
atcgagatgg ccagagagaa ccagacaact caaaagggtc agaaaaactc gcgagagcgg   2340
atgaagcgaa tcgaggaagg catcaaggag ctgggatccc agattctcaa ggagcatccc   2400
gtcgagaaca ctcaactgca gaacgagaag ctgtatctct actatctgca gaatggtcga   2460
gacatgtacg tggatcagga actggacatc aatcgtctca gcgactacga tgtggaccac   2520
attgtccctc aatcctttct caaggacgat tctatcgaca acaaggtcct tacacgatcc   2580
gacaagaaca gaggcaagtc ggacaacgtt cccagcgaag aggtggtcaa aaagatgaag   2640
aactactggc gacagctgct caacgccaag ctcattaccc agcgaaagtt cgacaatctt   2700
accaaggccg agcgaggcgg tctgtccgag ctcgacaagg ctggcttcat caagcgtcaa   2760
ctcgtcgaga ccagacagat cacaaagcac gtcgcacaga ttctcgattc tcggatgaac   2820
accaagtacg acgagaacga caagctcatc cgagaggtca aggtgattac tctcaagtcc   2880
aaactggtct ccgatttccg aaaggacttt cagttctaca aggtgcgaga gatcaacaat   2940
taccaccatg cccacgatgc ttacctcaac gccgtcgttg gcactgcgct catcaagaaa   3000
taccccaagc tcgaaagcga gttcgtttac ggcgattaca aggtctacga cgttcgaaag   3060
atgattgcca agtccgaaca ggagattggc aaggctactg ccaagtactt cttttactcc   3120
aacatcatga actttttcaa gaccgagatc accttggcca acggagagat tcgaaagaga   3180
ccacttatcg agaccaacgg cgaaactgga gagatcgtgt gggacaaggg tcgagacttt   3240
gcaaccgtgc gaaaggttct gtcgatgcct caggtcaaca tcgtcaagaa aaccgaggtt   3300
cagactggcg gattctccaa ggagtcgatt ctgcccaagc gaaactccga caagctcatc   3360
```

gctcgaaaga aagactggga tcccaagaaa tacggtggct tcgattctcc taccgtcgcc 3420
tattccgtgc ttgtcgttgc gaaggtcgag aagggcaagt ccaaaaagct caagtccgtc 3480
aaggagctgc tcggaattac catcatggag cgatcgagct tcgagaagaa tcccatcgac 3540
ttcttggaag ccaagggtta caaggaggtc aagaaagacc tcattatcaa gctgcccaag 3600
tactctctgt tcgaactgga gaacggtcga aagcgtatgc tcgcctccgc tggcgagctg 3660
cagaagggaa acgagcttgc cttgccttcg aagtacgtca actttctcta tctggcttct 3720
cactacgaga agctcaaggg ttctcccgag gacaacgaac agaagcaact cttcgttgag 3780
cagcacaaac attacctcga cgagattatc gagcagattt ccgagttttc gaagcgagtc 3840
atcctggctg atgccaactt ggacaaggtg ctctctgcct acaacaagca tcgggacaaa 3900
cccattcgag aacaggcgga gaacatcatt cacctgttta ctcttaccaa cctgggtgct 3960
cctgcagctt tcaagtactt cgataccact atcgaccgaa agcggtacac atccaccaag 4020
gaggttctcg atgccaccct gattcaccag tccatcactg gcctgtacga gacccgaatc 4080
gacctgtctc agcttggtgg cgactccaga gccgatccca agaaaaagcg aaaggtctaa 4140

<210> SEQ ID NO 121
<211> LENGTH: 10706
<212> TYPE: DNA
<213> ORGANISM: Artificial sequence
<220> FEATURE:
<223> OTHER INFORMATION: pRF111

<400> SEQUENCE: 121
catggacaag aaatactcca tcggcctggc cattggaacc aactctgtcg gctgggctgt 60
catcaccgac gagtacaagg tgccctccaa gaaattcaag gtcctcggaa acaccgatcg 120
acactccatc aagaaaaacc tcattggtgc cctgttgttc gattctggcg agactgccga 180
agctaccaga ctcaagcgaa ctgctcggcg acgttacacc cgacggaaga accgaatctg 240
ctacctgcag gagatctttt ccaacgagat ggccaaggtg gacgattcgt tctttcatcg 300
actggaggaa tccttcctcg tcgaggaaga caagaaacac gagcgtcatc ccatctttgg 360
caacattgtg gacgaggttg cttaccacga gaagtatcct accatctacc acctgcgaaa 420
gaaactcgtc gattccaccg acaaggcgga tctcagactt atctacctcg ctctggcaca 480
catgatcaag tttcgaggtc atttcctcat cgagggcgat ctcaatcccg acaacagcga 540
tgtggacaag ctgttcattc agctcgttca gacctacaac cagctgttcg aggaaaaccc 600
catcaatgcc tccggagtcg atgcaaaggc catcttgtct gctcgactct cgaagagcag 660
acgactggag aacctcattg cccaacttcc tggcgagaaa aagaacggac tgtttggcaa 720
cctcattgcc ctttctcttg gtctcacacc caacttcaag tccaacttcg atctggcgga 780
ggacgccaag ctccagctgt ccaaggacac ctacgacgat gacctcgaca acctgcttgc 840
acagattggc gatcagtacg ccgacctgtt tctcgctgcc aagaaccttt cggatgctat 900
tctcttgtct gacattctgc gagtcaacac cgagatcaca aaggctcccc tttctgcctc 960
catgatcaag cgatacgacg agcaccatca ggatctcaca ctgctcaagg ctcttgtccg 1020
acagcaactg cccgagaagt acaaggagat ctttttcgat cagtcgaaga acggctacgc 1080
tggatacatc gacggcggag cctctcagga agagttctac aagttcatca agccaattct 1140
cgagaagatg gacggaaccg aggaactgct tgtcaagctc aatcgagagg atctgcttcg 1200
gaagcaacga accttcgaca acggcagcat tcctcatcag atccacctcg gtgagctgca 1260

-continued

```
cgccattctt cgacgtcagg aagacttcta cccctttctc aaggacaacc gagagaagat   1320
cgagaagatt cttacctttc gaatccccta ctatgttggt cctcttgcca gaggaaactc   1380
tcgatttgct tggatgactc gaaagtccga ggaaaccatc actccctgga acttcgagga   1440
agtcgtggac aagggtgcct ctgcacagtc cttcatcgag cgaatgacca acttcgacaa   1500
gaatctgccc aacgagaagg ttcttcccaa gcattcgctg ctctacgagt actttacagt   1560
ctacaacgaa ctcaccaaag tcaagtacgt taccgaggga atgcgaaagc ctgccttctt   1620
gtctggcgaa cagaagaaag ccattgtcga tctcctgttc aagaccaacc gaaaggtcac   1680
tgttaagcag ctcaaggagg actacttcaa gaaaatcgag tgtttcgaca gcgtcgagat   1740
ttccggagtt gaggaccgat tcaacgcctc tttgggcacc tatcacgatc tgctcaagat   1800
tatcaaggac aaggattttc tcgacaacga ggaaaacgag gacattctgg aggacatcgt   1860
gctcactctt accctgttcg aagatcggga gatgatcgag gaacgactca agacatacgc   1920
tcacctgttc gacgacaagg tcatgaaaca actcaagcga cgtagataca ccggctgggg   1980
aagactttcg cgaaagctca tcaacggcat cagagacaag cagtccggaa agaccattct   2040
ggactttctc aagtccgatg gctttgccaa ccgaaacttc atgcagctca ttcacgacga   2100
ttctcttacc ttcaaggagg acatccagaa ggcacaagtg tccggtcagg gcgacagctt   2160
gcacgaacat attgccaacc tggctggttc gccagccatc aagaaaggca ttctccagac   2220
tgtcaaggtt gtcgacgagc tggtgaaggt catgggacgt cacaagcccg agaacattgt   2280
gatcgagatg gccagagaga accagacaac tcaaaagggt cagaaaaact cgcgagagcg   2340
gatgaagcga atcgaggaag gcatcaagga gctgggatcc cagattctca aggagcatcc   2400
cgtcgagaac actcaactgc agaacgagaa gctgtatctc tactatctgc agaatggtcg   2460
agacatgtac gtggatcagg aactggacat caatcgtctc agcgactacg atgtggacca   2520
cattgtccct caatcctttc tcaaggacga ttctatcgac aacaaggtcc ttacacgatc   2580
cgacaagaac agaggcaagt cggacaacgt tcccagcgaa gaggtggtca aaaagatgaa   2640
gaactactgg cgacagctgc tcaacgccaa gctcattacc cagcgaaagt tcgacaatct   2700
taccaaggcc gagcgaggcg gtctgtccga gctcgacaag gctggcttca tcaagcgtca   2760
actcgtcgag accagacaga tcacaaagca cgtcgcacag attctcgatt ctcggatgaa   2820
caccaagtac gacgagaacg acaagctcat ccgagaggtc aaggtgatta ctctcaagtc   2880
caaactggtc tccgatttcc gaaaggactt tcagttctac aaggtgcgag agatcaacaa   2940
ttaccaccat gcccacgatg cttacctcaa cgccgtcgtt ggcactgcgc tcatcaagaa   3000
ataccccaag ctcgaaagcg agttcgttta cggcgattac aaggtctacg acgttcgaaa   3060
gatgattgcc aagtccgaac aggagattgg caaggctact gccaagtact tcttttactc   3120
caacatcatg aactttttca agaccgagat caccttggcc aacggagaga ttcgaaagag   3180
accacttatc gagaccaacg gcgaaactgg agagatcgtg tgggacaagg gtcgagactt   3240
tgcaaccgtg cgaaaggttc tgtcgatgcc tcaggtcaac atcgtcaaga aaaccgaggt   3300
tcagactggc ggattctcca aggagtcgat tctgcccaag cgaaactccg acaagctcat   3360
cgctcgaaag aaagactggg atcccaagaa atacggtggc ttcgattctc ctaccgtcgc   3420
ctattccgtg cttgtcgttg cgaaggtcga gaagggcaag tccaaaaagc tcaagtccgt   3480
caaggagctg ctcggaatta ccatcatgga gcgatcgagc ttcgagaaga atcccatcga   3540
cttcttggaa gccaagggtt acaaggaggt caagaaagac ctcattatca agctgcccaa   3600
gtactctctg ttcgaactgg agaacggtcg aaagcgtatg ctcgcctccg ctggcgagct   3660
```

-continued

```
gcagaaggga aacgagcttg ccttgccttc gaagtacgtc aactttctct atctggcttc   3720
tcactacgag aagctcaagg gttctcccga ggacaacgaa cagaagcaac tcttcgttga   3780
gcagcacaaa cattacctcg acgagattat cgagcagatt tccgagtttt cgaagcgagt   3840
catcctggct gatgccaact tggacaaggt gctctctgcc tacaacaagc atcgggacaa   3900
acccattcga gaacaggcgg agaacatcat tcacctgttt actcttacca acctgggtgc   3960
tcctgcagct ttcaagtact tcgataccac tatcgaccga aagcggtaca catccaccaa   4020
ggaggttctc gatgccaccc tgattcacca gtccatcact ggcctgtacg agacccgaat   4080
cgacctgtct cagcttggtg gcgactccag agccgatccc aagaaaaagc gaaaggtcta   4140
agcggccgca agtgtggatg gggaagtgag tgcccggttc tgtgtgcaca attggcaatc   4200
caagatggat ggattcaaca cagggatata gcgagctacg tggtggtgcg aggatatagc   4260
aacggatatt tatgtttgac acttgagaat gtacgataca agcactgtcc aagtacaata   4320
ctaaacatac tgtacatact catactcgta cccgggcaac ggtttcactt gagtgcagtg   4380
gctagtgctc ttactcgtac agtgtgcaat actgcgtatc atagtctttg atgtatatcg   4440
tattcattca tgttagttgc gtacgagccg gaagcataaa gtgtaaagcc tggggtgcct   4500
aatgagtgag ctaactcaca ttaattgcgt tgcgctcact gcccgctttc cagtcgggaa   4560
acctgtcgtg ccagctgcat taatgaatcg gccaacgcgc ggggagaggc ggtttgcgta   4620
ttgggcgctc ttccgcttcc tcgctcactg actcgctgcg ctcggtcgtt cggctgcggc   4680
gagcggtatc agctcactca aaggcggtaa tacggttatc cacagaatca ggggataacg   4740
caggaaagaa catgtgagca aaaggccagc aaaaggccag gaaccgtaaa aaggccgcgt   4800
tgctggcgtt tttccatagg ctccgccccc ctgacgagca tcacaaaaat cgacgctcaa   4860
gtcagaggtg gcgaaacccg acaggactat aaagatacca ggcgtttccc cctggaagct   4920
ccctcgtgcg ctctcctgtt ccgaccctgc cgcttaccgg atacctgtcc gcctttctcc   4980
cttcgggaag cgtggcgctt tctcatagct cacgctgtag gtatctcagt tcggtgtagg   5040
tcgttcgctc caagctgggc tgtgtgcacg aaccccccgt tcagcccgac cgctgcgcct   5100
tatccggtaa ctatcgtctt gagtccaacc cggtaagaca cgacttatcg ccactggcag   5160
cagccactgg taacaggatt agcagagcga ggtatgtagg cggtgctaca gagttcttga   5220
agtggtggcc taactacggc tacactagaa ggacagtatt tggtatctgc gctctgctga   5280
agccagttac cttcggaaaa agagttggta gctcttgatc cggcaaacaa accaccgctg   5340
gtagcggtgg tttttttgtt tgcaagcagc agattacgcg cagaaaaaaa ggatctcaag   5400
aagatccttt gatcttttct acggggtctg acgctcagtg gaacgaaaac tcacgttaag   5460
ggattttggt catgagatta tcaaaaagga tcttcaccta gatcctttta aattaaaaat   5520
gaagttttaa atcaatctaa agtatatatg agtaaacttg gtctgacagt taccaatgct   5580
taatcagtga ggcacctatc tcagcgatct gtctatttcg ttcatccata gttgcctgac   5640
tccccgtcgt gtagataact acgatacggg agggcttacc atctggcccc agtgctgcaa   5700
tgataccgcg agacccacgc tcaccggctc cagatttatc agcaataaac cagccagccg   5760
gaagggccga gcgcagaagt ggtcctgcaa ctttatccgc ctccatccag tctattaatt   5820
gttgccggga agctagagta agtagttcgc cagttaatag tttgcgcaac gttgttgcca   5880
ttgctacagg catcgtggtg tcacgctcgt cgtttggtat ggcttcattc agctccggtt   5940
cccaacgatc aaggcgagtt acatgatccc ccatgttgtg caaaaaagcg gttagctcct   6000
```

-continued

```
tcggtcctcc gatcgttgtc agaagtaagt tggccgcagt gttatcactc atggttatgg   6060
cagcactgca taattctctt actgtcatgc catccgtaag atgcttttct gtgactggtg   6120
agtactcaac caagtcattc tgagaatagt gtatgcggcg accgagttgc tcttgcccgg   6180
cgtcaatacg ggataatacc gcgccacata gcagaacttt aaaagtgctc atcattggaa   6240
aacgttcttc ggggcgaaaa ctctcaagga tcttaccgct gttgagatcc agttcgatgt   6300
aacccactcg tgcacccaac tgatcttcag catcttttac tttcaccagc gtttctgggt   6360
gagcaaaaac aggaaggcaa aatgccgcaa aaaagggaat aagggcgaca cggaaatgtt   6420
gaatactcat actcttcctt tttcaatatt attgaagcat ttatcagggt tattgtctca   6480
tgagcggata catatttgaa tgtatttaga aaaataaaca aataggggtt ccgcgcacat   6540
ttccccgaaa agtgccacct gacgcgccct gtagcggcgc attaagcgcg gcgggtgtgg   6600
tggttacgcg cagcgtgacc gctacacttg ccagcgccct agcgcccgct cctttcgctt   6660
tcttcccttc ctttctcgcc acgttcgccg gctttccccg tcaagctcta aatcgggggc   6720
tccctttagg gttccgattt agtgctttac ggcacctcga ccccaaaaaa cttgattagg   6780
gtgatggttc acgtagtggg ccatcgccct gatagacggt ttttcgccct ttgacgttgg   6840
agtccacgtt ctttaatagt ggactcttgt tccaaactgg aacaacactc aaccctatct   6900
cggtctattc ttttgattta taagggattt tgccgatttc ggcctattgg ttaaaaaatg   6960
agctgattta acaaaaattt aacgcgaatt ttaacaaaat attaacgctt acaatttcca   7020
ttcgccattc aggctgcgca actgttggga agggcgatcg gtgcgggcct cttcgctatt   7080
acgccagctg gcgaaagggg gatgtgctgc aaggcgatta agttgggtaa cgccagggtt   7140
ttcccagtca cgacgttgta aaacgacggc cagtgaattg taatacgact cactataggg   7200
cgaattgggt accgggcccc ccctcgaggt cgatggtgtc gataagcttg atatcgaatt   7260
catgtcacac aaaccgatct tcgcctcaag gaaacctaat tctacatccg agagactgcc   7320
gagatccagt ctacactgat taattttcgg gccaataatt taaaaaaatc gtgttatata   7380
atattatatg tattatatat atacatcatg atgatactga cagtcatgtc ccattgctaa   7440
atagacagac tccatctgcc gcctccaact gatgttctca atatttaagg ggtcatctcg   7500
cattgtttaa taataaacag actccatcta ccgcctccaa atgatgttct caaaatatat   7560
tgtatgaact tatttttatt acttagtatt attagacaac ttacttgctt tatgaaaaac   7620
acttcctatt taggaaacaa tttataatgg cagttcgttc atttaacaat ttatgtagaa   7680
taaatgttat aaatgcgtat gggaaatctt aaatatggat agcataaatg atatctgcat   7740
tgcctaattc gaaatcaaca gcaacgaaaa aaatcccttg tacaacataa atagtcatcg   7800
agaaatatca actatcaaag aacagctatt cacacgttac tattgagatt attattggac   7860
gagaatcaca cactcaactg tctttctctc ttctagaaat acaggtacaa gtatgtacta   7920
ttctcattgt tcatacttct agtcatttca tcccacatat tccttggatt tctctccaat   7980
gaatgacatt ctatcttgca aattcaacaa ttataataag atataccaaa gtagcggtat   8040
agtggcaatc aaaaagcttc tctggtgtgc ttctcgtatt tatttttatt ctaatgatcc   8100
attaaaggta tatatttatt tcttgttata taatcctttt gtttattaca tgggctggat   8160
acataaaggt attttgattt aatttttgc ttaaattcaa tccccccctcg ttcagtgtca   8220
actgtaatgg taggaaatta ccatactttt gaagaagcaa aaaaaatgaa agaaaaaaaa   8280
aatcgtattt ccaggttaga cgttccgcag aatctagaat gcggtatgcg gtacattgtt   8340
cttcgaacgt aaaagttgcg ctccctgaga tattgtacat tttgcttttt acaagtacaa   8400
```

-continued

```
gtacatcgta caactatgta ctactgttga tgcatccaca acagtttgtt ttgttttttt   8460
ttgttttttt tttttctaat gattcattac cgctatgtat acctacttgt acttgtagta   8520
agccgggtta ttggcgttca attaatcata gacttatgaa tctgcacggt gtgcgctgcg   8580
agttactttt agcttatgca tgctacttgg gtgtaatatt gggatctgtt cggaaatcaa   8640
cggatgctca atcgatttcg acagtaatta attaagtcat acacaagtca gctttcttcg   8700
agcctcatat aagtataagt agttcaacgt attagcactg tacccagcat ctccgtatcg   8760
agaaacacaa caacatgccc cattggacag atcatgcgga tacacaggtt gtgcagtatc   8820
atacatactc gatcagacag gtcgtctgac catcatacaa gctgaacaag cgctccatac   8880
ttgcacgctc tctatataca cagttaaatt acatatccat agtctaacct ctaacagtta   8940
atcttctggt aagcctccca gccagccttc tggtatcgct tggcctcctc aataggatct   9000
cggttctggc cgtacagacc tcggccgaca attatgatat ccgttccggt agacatgaca   9060
tcctcaacag ttcggtactg ctgtccgaga gcgtctccct tgtcgtcaag acccaccccg   9120
ggggtcagaa taagccagtc ctcagagtcg cccttaggtc ggttctgggc aatgaagcca   9180
accacaaact cggggtcgga tcgggcaagc tcaatggtct gcttggagta ctcgccagtg   9240
gccagagagc ccttgcaaga cagctcggcc agcatgagca gacctctggc cagcttctcg   9300
ttgggagagg ggactaggaa ctccttgtac tgggagttct cgtagtcaga gacgtcctcc   9360
ttcttctgtt cagagacagt ttcctcggca ccagctcgca ggccagcaat gattccggtt   9420
ccgggtacac cgtgggcgtt ggtgatatcg gaccactcgg cgattcggtg acaccggtac   9480
tggtgcttga cagtgttgcc aatatctgcg aactttctgt cctcgaacag gaagaaaccg   9540
tgcttaagag caagttcctt gagggggagc acagtgccgg cgtaggtgaa gtcgtcaatg   9600
atgtcgatat gggttttgat catgcacaca taaggtccga ccttatcggc aagctcaatg   9660
agctccttgg tggtggtaac atccagagaa gcacacaggt tggttttctt ggctgccacg   9720
agcttgagca ctcgagcggc aaaggcggac ttgtggacgt tagctcgagc ttcgtaggag   9780
ggcattttgg tggtgaagag gagactgaaa taaatttagt ctgcagaact ttttatcgga   9840
accttatctg gggcagtgaa gtatatgtta tggtaatagt tacgagttag ttgaacttat   9900
agatagactg gactatacgg ctatcggtcc aaattagaaa gaacgtcaat ggctctctgg   9960
gcgtcgcctt tgccgacaaa aatgtgatca tgatgaaagc cagcaatgac gttgcagctg  10020
atattgttgt cggccaaccg cgccgaaaac gcagctgtca gacccacagc ctccaacgaa  10080
gaatgtatcg tcaaagtgat ccaagcacac tcatagttgg agtcgtactc caaaggcggc  10140
aatgacgagt cagacagata ctcgtcgacg tttaaaccat catctaaggg cctcaaaact  10200
acctcggaac tgctgcgctg atctggacac cacagaggtt ccgagcactt taggttgcac  10260
caaatgtccc accaggtgca ggcagaaaac gctggaacag cgtgtacagt ttgtcttaac  10320
aaaaagtgag ggcgctgagg tcgagcaggg tggtgtgact tgttatagcc tttagagctg  10380
cgaaagcgcg tatggatttg gctcatcagg ccagattgag ggtctgtgga cacatgtcat  10440
gttagtgtac ttcaatcgcc ccctggatat agccccgaca ataggccgtg gcctcatttt  10500
tttgccttcc gcacatttcc attgctcggt acccacacct tgcttctcct gcacttgcca  10560
accttaatac tggtttacat tgaccaacat cttacaagcg gggggcttgt ctagggtata  10620
tataaacagt ggctctccca atcggttgcc agtctctttt ttcctttctt tccccacaga  10680
ttcgaaatct aaactacaca tcacac                                       10706
```

<210> SEQ ID NO 122
<211> LENGTH: 43
<212> TYPE: DNA
<213> ORGANISM: Artificial sequence
<220> FEATURE:
<223> OTHER INFORMATION: H840A1

<400> SEQUENCE: 122
tcagcgacta cgatgtggac gccattgtcc ctcaatcctt tct 43

<210> SEQ ID NO 123
<211> LENGTH: 43
<212> TYPE: DNA
<213> ORGANISM: Artificial sequence
<220> FEATURE:
<223> OTHER INFORMATION: H840A2

<400> SEQUENCE: 123
agaaaggatt gagggacaat ggcgtccaca tcgtagtcgc tga 43

<210> SEQ ID NO 124
<211> LENGTH: 4140
<212> TYPE: DNA
<213> ORGANISM: Artificial Sequence
<220> FEATURE:
<223> OTHER INFORMATION: YArrowia codon optimized inactivated Cas9

<400> SEQUENCE: 124
atggacaaga aatactccat cggcctggcc attggaacca actctgtcgg ctgggctgtc 60
atcaccgacg agtacaaggt gccctccaag aaattcaagg tcctcggaaa caccgatcga 120
cactccatca agaaaaacct cattggtgcc ctgttgttcg attctggcga gactgccgaa 180
gctaccagac tcaagcgaac tgctcggcga cgttacaccc gacggaagaa ccgaatctgc 240
tacctgcagg agatcttttc caacgagatg gccaaggtgg acgattcgtt ctttcatcga 300
ctggaggaat ccttcctcgt cgaggaagac aagaaacacg agcgtcatcc catctttggc 360
aacattgtgg acgaggttgc ttaccacgag aagtatccta ccatctacca cctgcgaaag 420
aaactcgtcg attccaccga caaggcggat ctcagactta tctacctcgc tctggcacac 480
atgatcaagt ttcgaggtca tttcctcatc gagggcgatc tcaatcccga caacagcgat 540
gtggacaagc tgttcattca gctcgttcag acctacaacc agctgttcga ggaaaacccc 600
atcaatgcct ccggagtcga tgcaaaggcc atcttgtctg ctcgactctc gaagagcaga 660
cgactggaga acctcattgc ccaacttcct ggcgagaaaa agaacggact gtttggcaac 720
ctcattgccc tttctcttgg tctcacaccc aacttcaagt ccaacttcga tctggcggag 780
gacgccaagc tccagctgtc caaggacacc tacgacgatg acctcgacaa cctgcttgca 840
cagattggcg atcagtacgc cgacctgttt ctcgctgcca agaacctttc ggatgctatt 900
ctcttgtctg acattctgcg agtcaacacc gagatcacaa aggctcccct ttctgcctcc 960
atgatcaagc gatacgacga gcaccatcag gatctcacac tgctcaaggc tcttgtccga 1020
cagcaactgc ccgagaagta caaggagatc tttttcgatc agtcgaagaa cggctacgct 1080
ggatacatcg acggcggagc ctctcaggaa gagttctaca agttcatcaa gccaattctc 1140
gagaagatgg acggaaccga ggaactgctt gtcaagctca atcgagagga tctgcttcgg 1200
aagcaacgaa ccttcgacaa cggcagcatt cctcatcaga tccacctcgg tgagctgcac 1260
gccattcttc gacgtcagga agacttctac ccctttctca aggacaaccg agagaagatc 1320
gagaagattc ttacctttcg aatcccctac tatgttggtc ctcttgccag aggaaactct 1380
cgatttgctt ggatgactcg aaagtccgag gaaaccatca ctccctggaa cttcgaggaa 1440
gtcgtggaca agggtgcctc tgcacagtcc ttcatcgagc gaatgaccaa cttcgacaag 1500
aatctgccca acgagaaggt tcttcccaag cattcgctgc tctacgagta ctttacagtc 1560
tacaacgaac tcaccaaagt caagtacgtt accgagggaa tgcgaaagcc tgccttcttg 1620
tctggcgaac agaagaaagc cattgtcgat ctcctgttca agaccaaccg aaaggtcact 1680
gttaagcagc tcaaggagga ctacttcaag aaaatcgagt gtttcgacag cgtcgagatt 1740
tccggagttg aggaccgatt caacgcctct ttgggcacct atcacgatct gctcaagatt 1800
atcaaggaca aggattttct cgacaacgag gaaaacgagg acattctgga ggacatcgtg 1860
ctcactctta ccctgttcga agatcgggag atgatcgagg aacgactcaa gacatacgct 1920
cacctgttcg acgacaaggt catgaaacaa ctcaagcgac gtagatacac cggctgggga 1980
agactttcgc gaaagctcat caacggcatc agagacaagc agtccggaaa gaccattctg 2040
gactttctca agtccgatgg ctttgccaac cgaaacttca tgcagctcat tcacgacgat 2100
tctcttacct tcaaggagga catccagaag gcacaagtgt ccggtcaggg cgacagcttg 2160
cacgaacata ttgccaacct ggctggttcg ccagccatca agaaaggcat tctccagact 2220
gtcaaggttg tcgacgagct ggtgaaggtc atgggacgtc acaagcccga gaacattgtg 2280
atcgagatgg ccagagagaa ccagacaact caaaagggtc agaaaaactc gcgagagcgg 2340
atgaagcgaa tcgaggaagg catcaaggag ctgggatccc agattctcaa ggagcatccc 2400
gtcgagaaca ctcaactgca gaacgagaag ctgtatctct actatctgca gaatggtcga 2460
gacatgtacg tggatcagga actggacatc aatcgtctca gcgactacga tgtggacgcc 2520
attgtccctc aatcctttct caaggacgat tctatcgaca acaaggtcct tacacgatcc 2580
gacaagaaca gaggcaagtc ggacaacgtt cccagcgaag aggtggtcaa aaagatgaag 2640
aactactggc gacagctgct caacgccaag ctcattaccc agcgaaagtt cgacaatctt 2700
accaaggccg agcgaggcgg tctgtccgag ctcgacaagg ctggcttcat caagcgtcaa 2760
ctcgtcgaga ccagacagat cacaaagcac gtcgcacaga ttctcgattc tcggatgaac 2820
accaagtacg acgagaacga caagctcatc cgagaggtca aggtgattac tctcaagtcc 2880
aaactggtct ccgatttccg aaaggacttt cagttctaca aggtgcgaga gatcaacaat 2940
taccaccatg cccacgatgc ttacctcaac gccgtcgttg gcactgcgct catcaagaaa 3000
taccccaagc tcgaaagcga gttcgtttac ggcgattaca aggtctacga cgttcgaaag 3060
atgattgcca agtccgaaca ggagattggc aaggctactg ccaagtactt cttttactcc 3120
aacatcatga actttttcaa gaccgagatc accttggcca acggagagat tcgaaagaga 3180
ccacttatcg agaccaacgg cgaaactgga gagatcgtgt gggacaaggg tcgagacttt 3240
gcaaccgtgc gaaaggttct gtcgatgcct caggtcaaca tcgtcaagaa aaccgaggtt 3300
cagactggcg gattctccaa ggagtcgatt ctgcccaagc gaaactccga caagctcatc 3360
gctcgaaaga aagactggga tcccaagaaa tacggtggct tcgattctcc taccgtcgcc 3420
tattccgtgc ttgtcgttgc gaaggtcgag aagggcaagt ccaaaaagct caagtccgtc 3480
aaggagctgc tcggaattac catcatggag cgatcgagct tcgagaagaa tcccatcgac 3540
ttcttggaag ccaagggtta caaggaggtc aagaaagacc tcattatcaa gctgcccaag 3600
tactctctgt tcgaactgga gaacggtcga aagcgtatgc tcgcctccgc tggcgagctg 3660
cagaagggaa acgagcttgc cttgccttcg aagtacgtca actttctcta tctggcttct 3720
cactacgaga agctcaaggg ttctcccgag gacaacgaac agaagcaact cttcgttgag 3780
cagcacaaac attacctcga cgagattatc gagcagattt ccgagttttc gaagcgagtc 3840
atcctggctg atgccaactt ggacaaggtg ctctctgcct acaacaagca tcgggacaaa 3900
cccattcgag aacaggcgga gaacatcatt cacctgttta ctcttaccaa cctgggtgct 3960
cctgcagctt tcaagtactt cgataccact atcgaccgaa agcggtacac atccaccaag 4020
gaggttctcg atgccaccct gattcaccag tccatcactg gcctgtacga gacccgaatc 4080
gacctgtctc agcttggtgg cgactccaga gccgatccca agaaaaagcg aaaggtctaa 4140

<210> SEQ ID NO 125
<211> LENGTH: 10706
<212> TYPE: DNA
<213> ORGANISM: Artificial sequence
<220> FEATURE:
<223> OTHER INFORMATION: pRF143

<400> SEQUENCE: 125
catggacaag aaatactcca tcggcctggc cattggaacc aactctgtcg gctgggctgt 60
catcaccgac gagtacaagg tgccctccaa gaaattcaag gtcctcggaa acaccgatcg 120
acactccatc aagaaaaacc tcattggtgc cctgttgttc gattctggcg agactgccga 180
agctaccaga ctcaagcgaa ctgctcggcg acgttacacc cgacggaaga accgaatctg 240
ctacctgcag gagatctttt ccaacgagat ggccaaggtg gacgattcgt tctttcatcg 300
actggaggaa tccttcctcg tcgaggaaga caagaaacac gagcgtcatc ccatctttgg 360
caacattgtg gacgaggttg cttaccacga gaagtatcct accatctacc acctgcgaaa 420
gaaactcgtc gattccaccg acaaggcgga tctcagactt atctacctcg ctctggcaca 480
catgatcaag tttcgaggtc atttcctcat cgagggcgat ctcaatcccg acaacagcga 540
tgtggacaag ctgttcattc agctcgttca gacctacaac cagctgttcg aggaaaaccc 600
catcaatgcc tccggagtcg atgcaaaggc catcttgtct gctcgactct cgaagagcag 660
acgactggag aacctcattg cccaacttcc tggcgagaaa aagaacggac tgtttggcaa 720
cctcattgcc ctttctcttg gtctcacacc caacttcaag tccaacttcg atctggcgga 780
ggacgccaag ctccagctgt ccaaggacac ctacgacgat gacctcgaca acctgcttgc 840
acagattggc gatcagtacg ccgacctgtt tctcgctgcc aagaaccttt cggatgctat 900
tctcttgtct gacattctgc gagtcaacac cgagatcaca aaggctcccc tttctgcctc 960
catgatcaag cgatacgacg agcaccatca ggatctcaca ctgctcaagg ctcttgtccg 1020
acagcaactg cccgagaagt acaaggagat ctttttcgat cagtcgaaga acggctacgc 1080
tggatacatc gacggcggag cctctcagga agagttctac aagttcatca agccaattct 1140
cgagaagatg gacggaaccg aggaactgct tgtcaagctc aatcgagagg atctgcttcg 1200
gaagcaacga accttcgaca acggcagcat tcctcatcag atccacctcg gtgagctgca 1260
cgccattctt cgacgtcagg aagacttcta cccctttctc aaggacaacc gagagaagat 1320
cgagaagatt cttacctttc gaatccccta ctatgttggt cctcttgcca gaggaaactc 1380
tcgatttgct tggatgactc gaaagtccga ggaaaccatc actccctgga acttcgagga 1440
agtcgtggac aagggtgcct ctgcacagtc cttcatcgag cgaatgacca acttcgacaa 1500
gaatctgccc aacgagaagg ttcttcccaa gcattcgctg ctctacgagt actttacagt 1560
ctacaacgaa ctcaccaaag tcaagtacgt taccgaggga atgcgaaagc ctgccttctt 1620
gtctggcgaa cagaagaaag ccattgtcga tctcctgttc aagaccaacc gaaaggtcac 1680

-continued tgttaagcag ctcaaggagg actacttcaa gaaaatcgag tgtttcgaca gcgtcgagat 1740
ttccggagtt gaggaccgat tcaacgcctc tttgggcacc tatcacgatc tgctcaagat 1800
tatcaaggac aaggattttc tcgacaacga ggaaaacgag gacattctgg aggacatcgt 1860
gctcactctt accctgttcg aagatcggga gatgatcgag gaacgactca agacatacgc 1920
tcacctgttc gacgacaagg tcatgaaaca actcaagcga cgtagataca ccggctgggg 1980
aagactttcg cgaaagctca tcaacggcat cagagacaag cagtccggaa agaccattct 2040
ggactttctc aagtccgatg gctttgccaa ccgaaacttc atgcagctca ttcacgacga 2100
ttctcttacc ttcaaggagg acatccagaa ggcacaagtg tccggtcagg gcgacagctt 2160
gcacgaacat attgccaacc tggctggttc gccagccatc aagaaaggca ttctccagac 2220
tgtcaaggtt gtcgacgagc tggtgaaggt catgggacgt cacaagcccg agaacattgt 2280
gatcgagatg gccagagaga accagacaac tcaaaagggt cagaaaaact cgcgagagcg 2340
gatgaagcga atcgaggaag gcatcaagga gctgggatcc cagattctca aggagcatcc 2400
cgtcgagaac actcaactgc agaacgagaa gctgtatctc tactatctgc agaatggtcg 2460
agacatgtac gtggatcagg aactggacat caatcgtctc agcgactacg atgtggacgc 2520
cattgtccct caatcctttc tcaaggacga ttctatcgac aacaaggtcc ttacacgatc 2580
cgacaagaac agaggcaagt cggacaacgt tcccagcgaa gaggtggtca aaaagatgaa 2640
gaactactgg cgacagctgc tcaacgccaa gctcattacc cagcgaaagt tcgacaatct 2700
taccaaggcc gagcgaggcg gtctgtccga gctcgacaag gctggcttca tcaagcgtca 2760
actcgtcgag accagacaga tcacaaagca cgtcgcacag attctcgatt ctcggatgaa 2820
caccaagtac gacgagaacg acaagctcat ccgagaggtc aaggtgatta ctctcaagtc 2880
caaactggtc tccgatttcc gaaaggactt tcagttctac aaggtgcgag agatcaacaa 2940
ttaccaccat gcccacgatg cttacctcaa cgccgtcgtt ggcactgcgc tcatcaagaa 3000
ataccccaag ctcgaaagcg agttcgttta cggcgattac aaggtctacg acgttcgaaa 3060
gatgattgcc aagtccgaac aggagattgg caaggctact gccaagtact tcttttactc 3120
caacatcatg aactttttca agaccgagat caccttggcc aacggagaga ttcgaaagag 3180
accacttatc gagaccaacg gcgaaactgg agagatcgtg tgggacaagg gtcgagactt 3240
tgcaaccgtg cgaaaggttc tgtcgatgcc tcaggtcaac atcgtcaaga aaaccgaggt 3300
tcagactggc ggattctcca aggagtcgat tctgcccaag cgaaactccg acaagctcat 3360
cgctcgaaag aaagactggg atcccaagaa atacggtggc ttcgattctc ctaccgtcgc 3420
ctattccgtg cttgtcgttg cgaaggtcga gaagggcaag tccaaaaagc tcaagtccgt 3480
caaggagctg ctcggaatta ccatcatgga gcgatcgagc ttcgagaaga atcccatcga 3540
cttcttggaa gccaagggtt acaaggaggt caagaaagac ctcattatca agctgcccaa 3600
gtactctctg ttcgaactgg agaacggtcg aaagcgtatg ctcgcctccg ctggcgagct 3660
gcagaaggga aacgagcttg ccttgccttc gaagtacgtc aactttctct atctggcttc 3720
tcactacgag aagctcaagg gttctcccga ggacaacgaa cagaagcaac tcttcgttga 3780
gcagcacaaa cattacctcg acgagattat cgagcagatt tccgagtttt cgaagcgagt 3840
catcctggct gatgccaact tggacaaggt gctctctgcc tacaacaagc atcgggacaa 3900
acccattcga gaacaggcgg agaacatcat tcacctgttt actcttacca acctgggtgc 3960
tcctgcagct ttcaagtact tcgataccac tatcgaccga aagcggtaca catccaccaa 4020

-continued

```
ggaggttctc gatgccaccc tgattcacca gtccatcact ggcctgtacg agacccgaat   4080
cgacctgtct cagcttggtg gcgactccag agccgatccc aagaaaaagc gaaaggtcta   4140
agcggccgca agtgtggatg gggaagtgag tgcccggttc tgtgtgcaca attggcaatc   4200
caagatggat ggattcaaca cagggatata gcgagctacg tggtggtgcg aggatatagc   4260
aacggatatt tatgtttgac acttgagaat gtacgataca agcactgtcc aagtacaata   4320
ctaaacatac tgtacatact catactcgta cccgggcaac ggtttcactt gagtgcagtg   4380
gctagtgctc ttactcgtac agtgtgcaat actgcgtatc atagtctttg atgtatatcg   4440
tattcattca tgttagttgc gtacgagccg gaagcataaa gtgtaaagcc tggggtgcct   4500
aatgagtgag ctaactcaca ttaattgcgt tgcgctcact gcccgctttc cagtcgggaa   4560
acctgtcgtg ccagctgcat taatgaatcg gccaacgcgc ggggagaggc ggtttgcgta   4620
ttgggcgctc ttccgcttcc tcgctcactg actcgctgcg ctcggtcgtt cggctgcggc   4680
gagcggtatc agctcactca aaggcggtaa tacggttatc cacagaatca ggggataacg   4740
caggaaagaa catgtgagca aaaggccagc aaaaggccag gaaccgtaaa aaggccgcgt   4800
tgctggcgtt tttccatagg ctccgccccc ctgacgagca tcacaaaaat cgacgctcaa   4860
gtcagaggtg gcgaaacccg acaggactat aaagatacca ggcgtttccc cctggaagct   4920
ccctcgtgcg ctctcctgtt ccgaccctgc cgcttaccgg atacctgtcc gcctttctcc   4980
cttcgggaag cgtggcgctt tctcatagct cacgctgtag gtatctcagt tcggtgtagg   5040
tcgttcgctc caagctgggc tgtgtgcacg aaccccccgt tcagcccgac cgctgcgcct   5100
tatccggtaa ctatcgtctt gagtccaacc cggtaagaca cgacttatcg ccactggcag   5160
cagccactgg taacaggatt agcagagcga ggtatgtagg cggtgctaca gagttcttga   5220
agtggtggcc taactacggc tacactagaa ggacagtatt tggtatctgc gctctgctga   5280
agccagttac cttcggaaaa agagttggta gctcttgatc cggcaaacaa accaccgctg   5340
gtagcggtgg tttttttgtt tgcaagcagc agattacgcg cagaaaaaaa ggatctcaag   5400
aagatccttt gatcttttct acggggtctg acgctcagtg gaacgaaaac tcacgttaag   5460
ggattttggt catgagatta tcaaaaagga tcttcaccta gatcctttta aattaaaaat   5520
gaagttttaa atcaatctaa agtatatatg agtaaacttg gtctgacagt taccaatgct   5580
taatcagtga ggcacctatc tcagcgatct gtctatttcg ttcatccata gttgcctgac   5640
tccccgtcgt gtagataact acgatacggg agggcttacc atctggcccc agtgctgcaa   5700
tgataccgcg agacccacgc tcaccggctc cagatttatc agcaataaac cagccagccg   5760
gaagggccga gcgcagaagt ggtcctgcaa ctttatccgc ctccatccag tctattaatt   5820
gttgccggga agctagagta agtagttcgc cagttaatag tttgcgcaac gttgttgcca   5880
ttgctacagg catcgtggtg tcacgctcgt cgtttggtat ggcttcattc agctccggtt   5940
cccaacgatc aaggcgagtt acatgatccc ccatgttgtg caaaaaagcg gttagctcct   6000
tcggtcctcc gatcgttgtc agaagtaagt tggccgcagt gttatcactc atggttatgg   6060
cagcactgca taattctctt actgtcatgc catccgtaag atgcttttct gtgactggtg   6120
agtactcaac caagtcattc tgagaatagt gtatgcggcg accgagttgc tcttgcccgg   6180
cgtcaatacg ggataatacc gcgccacata gcagaacttt aaaagtgctc atcattggaa   6240
aacgttcttc ggggcgaaaa ctctcaagga tcttaccgct gttgagatcc agttcgatgt   6300
aacccactcg tgcacccaac tgatcttcag catcttttac tttcaccagc gtttctgggt   6360
gagcaaaaac aggaaggcaa aatgccgcaa aaaagggaat aagggcgaca cggaaatgtt   6420
```

gaatactcat actcttcctt tttcaatatt attgaagcat ttatcagggt tattgtctca 6480
tgagcggata catatttgaa tgtatttaga aaaataaaca aataggggtt ccgcgcacat 6540
ttccccgaaa agtgccacct gacgcgccct gtagcggcgc attaagcgcg gcgggtgtgg 6600
tggttacgcg cagcgtgacc gctacacttg ccagcgccct agcgcccgct cctttcgctt 6660
tcttcccttc ctttctcgcc acgttcgccg gctttccccg tcaagctcta aatcgggggc 6720
tccctttagg gttccgattt agtgctttac ggcacctcga ccccaaaaaa cttgattagg 6780
gtgatggttc acgtagtggg ccatcgccct gatagacggt ttttcgccct ttgacgttgg 6840
agtccacgtt ctttaatagt ggactcttgt tccaaactgg aacaacactc aaccctatct 6900
cggtctattc ttttgattta taagggattt tgccgatttc ggcctattgg ttaaaaaatg 6960
agctgattta acaaaaattt aacgcgaatt ttaacaaaat attaacgctt acaatttcca 7020
ttcgccattc aggctgcgca actgttggga agggcgatcg gtgcgggcct cttcgctatt 7080
acgccagctg gcgaaagggg gatgtgctgc aaggcgatta agttgggtaa cgccagggtt 7140
ttcccagtca cgacgttgta aaacgacggc cagtgaattg taatacgact cactataggg 7200
cgaattgggt accgggcccc ccctcgaggt cgatggtgtc gataagcttg atatcgaatt 7260
catgtcacac aaaccgatct tcgcctcaag gaaacctaat tctacatccg agagactgcc 7320
gagatccagt ctacactgat taattttcgg gccaataatt taaaaaaatc gtgttatata 7380
atattatatg tattatatat atacatcatg atgatactga cagtcatgtc ccattgctaa 7440
atagacagac tccatctgcc gcctccaact gatgttctca atatttaagg ggtcatctcg 7500
cattgtttaa taataaacag actccatcta ccgcctccaa atgatgttct caaaatatat 7560
tgtatgaact tatttttatt acttagtatt attagacaac ttacttgctt tatgaaaaac 7620
acttcctatt taggaaacaa tttataatgg cagttcgttc atttaacaat ttatgtagaa 7680
taaatgttat aaatgcgtat gggaaatctt aaatatggat agcataaatg atatctgcat 7740
tgcctaattc gaaatcaaca gcaacgaaaa aaatcccttg tacaacataa atagtcatcg 7800
agaaatatca actatcaaag aacagctatt cacacgttac tattgagatt attattggac 7860
gagaatcaca cactcaactg tctttctctc ttctagaaat acaggtacaa gtatgtacta 7920
ttctcattgt tcatacttct agtcatttca tcccacatat tccttggatt tctctccaat 7980
gaatgacatt ctatcttgca aattcaacaa ttataataag atataccaaa gtagcggtat 8040
agtggcaatc aaaaagcttc tctggtgtgc ttctcgtatt tatttttatt ctaatgatcc 8100
attaaaggta tatatttatt tcttgttata taatcctttt gtttattaca tgggctggat 8160
acataaaggt attttgattt aatttttttgc ttaaattcaa tccccccctcg ttcagtgtca 8220 actgtaatgg taggaaatta ccatactttt gaagaagcaa aaaaaatgaa agaaaaaaaa 8280
aatcgtattt ccaggttaga cgttccgcag aatctagaat gcggtatgcg gtacattgtt 8340
cttcgaacgt aaaagttgcg ctccctgaga tattgtacat ttttgctttt acaagtacaa 8400
gtacatcgta caactatgta ctactgttga tgcatccaca acagtttgtt ttgttttttt 8460
ttgttttttt tttttctaat gattcattac cgctatgtat acctacttgt acttgtagta 8520
agccgggtta ttggcgttca attaatcata gacttatgaa tctgcacggt gtgcgctgcg 8580
agttactttt agcttatgca tgctacttgg gtgtaatatt gggatctgtt cggaaatcaa 8640
cggatgctca atcgatttcg acagtaatta attaagtcat acacaagtca gctttcttcg 8700
agcctcatat aagtataagt agttcaacgt attagcactg tacccagcat ctccgtatcg 8760

-continued

```
agaaacacaa caacatgccc cattggacag atcatgcgga tacacaggtt gtgcagtatc   8820

atacatactc gatcagacag gtcgtctgac catcatacaa gctgaacaag cgctccatac   8880

ttgcacgctc tctatataca cagttaaatt acatatccat agtctaacct ctaacagtta   8940

atcttctggt aagcctccca gccagccttc tggtatcgct tggcctcctc aataggatct   9000

cggttctggc cgtacagacc tcggccgaca attatgatat ccgttccggt agacatgaca   9060

tcctcaacag ttcggtactg ctgtccgaga gcgtctccct tgtcgtcaag acccaccccg   9120

ggggtcagaa taagccagtc ctcagagtcg ccccttaggtc ggttctgggc aatgaagcca   9180

accacaaact cggggtcgga tcgggcaagc tcaatggtct gcttggagta ctcgccagtg   9240

gccagagagc ccttgcaaga cagctcggcc agcatgagca gacctctggc cagcttctcg   9300

ttgggagagg ggactaggaa ctccttgtac tgggagttct cgtagtcaga gacgtcctcc   9360

ttcttctgtt cagagacagt ttcctcggca ccagctcgca ggccagcaat gattccggtt   9420

ccgggtacac cgtgggcgtt ggtgatatcg gaccactcgg cgattcggtg acaccggtac   9480

tggtgcttga cagtgttgcc aatatctgcg aactttctgt cctcgaacag gaagaaaccg   9540

tgcttaagag caagttcctt gagggggagc acagtgccgg cgtaggtgaa gtcgtcaatg   9600

atgtcgatat gggttttgat catgcacaca taaggtccga ccttatcggc aagctcaatg   9660

agctccttgg tggtggtaac atccagagaa gcacacaggt tggttttctt ggctgccacg   9720

agcttgagca ctcgagcggc aaaggcggac ttgtggacgt tagctcgagc ttcgtaggag   9780

ggcattttgg tggtgaagag gagactgaaa taaatttagt ctgcagaact ttttatcgga   9840

accttatctg gggcagtgaa gtatatgtta tggtaatagt tacgagttag ttgaacttat   9900

agatagactg gactatacgg ctatcggtcc aaattagaaa gaacgtcaat ggctctctgg   9960

gcgtcgcctt tgccgacaaa aatgtgatca tgatgaaagc cagcaatgac gttgcagctg  10020

atattgttgt cggccaaccg cgccgaaaac gcagctgtca gacccacagc ctccaacgaa  10080

gaatgtatcg tcaaagtgat ccaagcacac tcatagttgg agtcgtactc caaaggcggc  10140

aatgacgagt cagacagata ctcgtcgacg tttaaaccat catctaaggg cctcaaaact  10200

acctcggaac tgctgcgctg atctggacac cacagaggtt ccgagcactt taggttgcac  10260

caaatgtccc accaggtgca ggcagaaaac gctggaacag cgtgtacagt ttgtcttaac  10320

aaaaagtgag ggcgctgagg tcgagcaggg tggtgtgact tgttatagcc tttagagctg  10380

cgaaagcgcg tatggatttg gctcatcagg ccagattgag ggtctgtgga cacatgtcat  10440

gttagtgtac ttcaatcgcc ccctggatat agccccgaca ataggccgtg gcctcatttt  10500

tttgccttcc gcacatttcc attgctcggt acccacacct tgcttctcct gcacttgcca  10560

accttaatac tggtttacat tgaccaacat cttacaagcg gggggcttgt ctagggtata  10620

tataaacagt ggctctccca atcggttgcc agtctctttt ttcctttctt tccccacaga  10680

ttcgaaatct aaactacaca tcacac                                        10706
```

<210> SEQ ID NO 126
<211> LENGTH: 678
<212> TYPE: DNA
<213> ORGANISM: Artificial sequence
<220> FEATURE:
<223> OTHER INFORMATION: Yarrowia optimized dsREDexpress ORF

<400> SEQUENCE: 126

```
atggcctcct cggaggacgt catcaaggag ttcatgcgat tcaaggtccg aatggaaggc     60

tccgtgaacg gtcacgagtt tgagattgag ggagagggtg aaggccgacc ctacgaaggc    120
```

acccagaccg cgaagctgaa ggtgaccaag ggtggacccc tgcccttcgc ctgggacatt 180
ctgtctcctc agtttcagta cggttctaag gtgtacgtga agcaccctgc tgacattccc 240
gactacaaga aactttcctt tcccgagggc ttcaagtggg agcgagttat gaacttcgag 300
gatggcggtg tcgttaccgt tactcaggac tcctcgctcc aggacggctc gttcatctac 360
aaggttaagt tcatcggtgt caacttccct agcgatggac ccgtcatgca aaagaaaact 420
atgggatggg aagcctctac agagcggctg taccctcgag acggagtgtt gaagggcgag 480
attcacaagg ccctgaagct caaggacggt ggacactatc tcgttgagtt taagtctatc 540
tacatggcaa agaaacccgt gcagcttcca ggctactatt acgtcgattc caagctcgat 600
atcaccagcc ataatgagga ctacactatt gtcgaacagt acgagcgtgc tgagggaaga 660
caccatctgt ttctttaa 678

<210> SEQ ID NO 127
<211> LENGTH: 696
<212> TYPE: DNA
<213> ORGANISM: Artificial sequence
<220> FEATURE:
<223> OTHER INFORMATION: Yarrowia optimized dsREDexpress cloning fragment

<400> SEQUENCE: 127
ggggccatgg cctcctcgga ggacgtcatc aaggagttca tgcgattcaa ggtccgaatg 60
gaaggctccg tgaacggtca cgagtttgag attgagggag agggtgaagg ccgaccctac 120
gaaggcaccc agaccgcgaa gctgaaggtg accaagggtg gacccctgcc cttcgcctgg 180
gacattctgt ctcctcagtt tcagtacggt tctaaggtgt acgtgaagca ccctgctgac 240
attcccgact acaagaaact ttcctttccc gagggcttca agtgggagcg agttatgaac 300
ttcgaggatg gcggtgtcgt taccgttact caggactcct cgctccagga cggctcgttc 360
atctacaagg ttaagttcat cggtgtcaac ttccctagcg atggacccgt catgcaaaag 420
aaaactatgg gatgggaagc ctctacagag cggctgtacc ctcgagacgg agtgttgaag 480
ggcgagattc acaaggccct gaagctcaag gacggtggac actatctcgt tgagtttaag 540
tctatctaca tggcaaagaa acccgtgcag cttccaggct actattacgt cgattccaag 600
ctcgatatca ccagccataa tgaggactac actattgtcg aacagtacga gcgtgctgag 660
ggaagacacc atctgtttct ttaagcggcc gcgggg 696

<210> SEQ ID NO 128
<211> LENGTH: 1212
<212> TYPE: DNA
<213> ORGANISM: Artificial Sequence
<220> FEATURE:
<223> OTHER INFORMATION: FBA1-dsREDexpress expression cassette

<400> SEQUENCE: 128
aaaccatcat ctaagggcct caaaactacc tcggaactgc tgcgctgatc tggacaccac 60
agaggttccg agcactttag gttgcaccaa atgtcccacc aggtgcaggc agaaaacgct 120
ggaacagcgt gtacagtttg tcttaacaaa aagtgagggc gctgaggtcg agcagggtgg 180
tgtgacttgt tatagccttt agagctgcga aagcgcgtat ggatttggct catcaggcca 240
gattgagggt ctgtggacac atgtcatgtt agtgtacttc aatcgccccc tggatatagc 300
cccgacaata ggccgtggcc tcattttttt gccttccgca catttccatt gctcggtacc 360
cacaccttgc ttctcctgca cttgccaacc ttaatactgg tttacattga ccaacatctt 420

```
acaagcgggg ggcttgtcta gggtatatat aaacagtggc tctcccaatc ggttgccagt    480
ctctttttc ctttctttcc ccacagattc gaaatctaaa ctacacatca caccatggcc    540
tcctcggagg acgtcatcaa ggagttcatg cgattcaagg tccgaatgga aggctccgtg    600
aacggtcacg agtttgagat tgagggagag ggtgaaggcc gaccctacga aggcacccag    660
accgcgaagc tgaaggtgac caagggtgga cccctgccct tcgcctggga cattctgtct    720
cctcagtttc agtacggttc taaggtgtac gtgaagcacc ctgctgacat tcccgactac    780
aagaaacttt cctttcccga gggcttcaag tgggagcgag ttatgaactt cgaggatggc    840
ggtgtcgtta ccgttactca ggactcctcg ctccaggacg gctcgttcat ctacaaggtt    900
aagttcatcg gtgtcaactt ccctagcgat ggacccgtca tgcaaaagaa aactatggga    960
tgggaagcct ctacagagcg gctgtaccct cgagacggag tgttgaaggg cgagattcac   1020
aaggccctga agctcaagga cggtggacac tatctcgttg agtttaagtc tatctacatg   1080
gcaaagaaac ccgtgcagct tccaggctac tattacgtcg attccaagct cgatatcacc   1140
agccataatg aggactacac tattgtcgaa cagtacgagc gtgctgaggg aagacaccat   1200
ctgtttcttt aa                                                       1212
```

<210> SEQ ID NO 129
<211> LENGTH: 7244
<212> TYPE: DNA
<213> ORGANISM: Artificial Sequence
<220> FEATURE:
<223> OTHER INFORMATION: pRF165

<400> SEQUENCE: 129

```
ggccgcaagt gtggatgggg aagtgagtgc ccggttctgt gtgcacaatt ggcaatccaa     60
gatggatgga ttcaacacag ggatatagcg agctacgtgg tggtgcgagg atatagcaac    120
ggatatttat gtttgacact tgagaatgta cgatacaagc actgtccaag tacaatacta    180
aacatactgt acatactcat actcgtaccc gggcaacggt ttcacttgag tgcagtggct    240
agtgctctta ctcgtacagt gtgcaatact gcgtatcata gtctttgatg tatatcgtat    300
tcattcatgt tagttgcgta cgagccggaa gcataaagtg taaagcctgg ggtgcctaat    360
gagtgagcta actcacatta attgcgttgc gctcactgcc cgctttccag tcgggaaacc    420
tgtcgtgcca gctgcattaa tgaatcggcc aacgcgcggg gagaggcggt ttgcgtattg    480
ggcgctcttc cgcttcctcg ctcactgact cgctgcgctc ggtcgttcgg ctgcggcgag    540
cggtatcagc tcactcaaag gcggtaatac ggttatccac agaatcaggg gataacgcag    600
gaaagaacat gtgagcaaaa ggccagcaaa aggccaggaa ccgtaaaaag gccgcgttgc    660
tggcgttttt ccataggctc cgcccccctg acgagcatca caaaaatcga cgctcaagtc    720
agaggtggcg aaacccgaca ggactataaa gataccaggc gtttccccct ggaagctccc    780
tcgtgcgctc tcctgttccg accctgccgc ttaccggata cctgtccgcc tttctccctt    840
cgggaagcgt ggcgctttct catagctcac gctgtaggta tctcagttcg gtgtaggtcg    900
ttcgctccaa gctgggctgt gtgcacgaac cccccgttca gcccgaccgc tgcgccttat    960
ccggtaacta tcgtcttgag tccaacccgg taagacacga cttatcgcca ctggcagcag   1020
ccactggtaa caggattagc agagcgaggt atgtaggcgg tgctacagag ttcttgaagt   1080
ggtggcctaa ctacggctac actagaagga cagtatttgg tatctgcgct ctgctgaagc   1140
cagttacctt cggaaaaaga gttggtagct cttgatccgg caaacaaacc accgctggta   1200
```

-continued

```
gcggtggttt ttttgtttgc aagcagcaga ttacgcgcag aaaaaaagga tctcaagaag   1260
atcctttgat cttttctacg gggtctgacg ctcagtggaa cgaaaactca cgttaaggga   1320
ttttggtcat gagattatca aaaaggatct tcacctagat ccttttaaat taaaaatgaa   1380
gttttaaatc aatctaaagt atatatgagt aaacttggtc tgacagttac caatgcttaa   1440
tcagtgaggc acctatctca gcgatctgtc tatttcgttc atccatagtt gcctgactcc   1500
ccgtcgtgta gataactacg atacgggagg gcttaccatc tggccccagt gctgcaatga   1560
taccgcgaga cccacgctca ccggctccag atttatcagc aataaaccag ccagccggaa   1620
gggccgagcg cagaagtggt cctgcaactt tatccgcctc catccagtct attaattgtt   1680
gccgggaagc tagagtaagt agttcgccag ttaatagttt gcgcaacgtt gttgccattg   1740
ctacaggcat cgtggtgtca cgctcgtcgt ttggtatggc ttcattcagc tccggttccc   1800
aacgatcaag gcgagttaca tgatccccca tgttgtgcaa aaaagcggtt agctccttcg   1860
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga gaatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttccttttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgccctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct ttccccgtca agctctaaat cgggggctcc   2580
ctttagggtt ccgatttagt gctttacggc acctcgaccc caaaaaactt gattagggtg   2640
atggttcacg tagtgggcca tcgccctgat agacggtttt tcgccctttg acgttggagt   2700
ccacgttctt taatagtgga ctcttgttcc aaactggaac aacactcaac cctatctcgg   2760
tctattcttt tgatttataa gggattttgc cgatttcggc ctattggtta aaaaatgagc   2820
tgatttaaca aaaatttaac gcgaatttta acaaaatatt aacgcttaca atttccattc   2880
gccattcagg ctgcgcaact gttgggaagg gcgatcggtg cgggcctctt cgctattacg   2940
ccagctggcg aaagggggat gtgctgcaag gcgattaagt tgggtaacgc cagggttttc   3000
ccagtcacga cgttgtaaaa cgacggccag tgaattgtaa tacgactcac tatagggcga   3060
attgggtacc gggccccccc tcgaggtcga tggtgtcgat aagcttgata tcgaattcat   3120
gtcacacaaa ccgatcttcg cctcaaggaa acctaattct acatccgaga gactgccgag   3180
atccagtcta cactgattaa ttttcgggcc aataatttaa aaaaatcgtg ttatataata   3240
ttatatgtat tatatatata catcatgatg atactgacag tcatgtccca ttgctaaata   3300
gacagactcc atctgccgcc tccaactgat gttctcaata tttaaggggt catctcgcat   3360
tgtttaataa taaacagact ccatctaccg cctccaaatg atgttctcaa aatatattgt   3420
atgaacttat ttttattact tagtattatt agacaactta cttgctttat gaaaaacact   3480
tcctatttag gaaacaattt ataatggcag ttcgttcatt taacaattta tgtagaataa   3540
atgttataaa tgcgtatggg aaatcttaaa tatggatagc ataaatgata tctgcattgc   3600
```

ctaattcgaa atcaacagca acgaaaaaaa tcccttgtac aacataaata gtcatcgaga 3660
aatatcaact atcaaagaac agctattcac acgttactat tgagattatt attggacgag 3720
aatcacacac tcaactgtct ttctctcttc tagaaataca ggtacaagta tgtactattc 3780
tcattgttca tacttctagt catttcatcc cacatattcc ttggatttct ctccaatgaa 3840
tgacattcta tcttgcaaat tcaacaatta taataagata taccaaagta gcggtatagt 3900
ggcaatcaaa aagcttctct ggtgtgcttc tcgtatttat ttttattcta atgatccatt 3960
aaaggtatat atttatttct tgttatataa tccttttgtt tattacatgg gctggataca 4020
taaaggtatt ttgatttaat tttttgctta aattcaatcc cccctcgttc agtgtcaact 4080
gtaatggtag gaaattacca tacttttgaa gaagcaaaaa aaatgaaaga aaaaaaaaat 4140
cgtatttcca ggttagacgt tccgcagaat ctagaatgcg gtatgcggta cattgttctt 4200
cgaacgtaaa agttgcgctc cctgagatat tgtacatttt tgcttttaca agtacaagta 4260
catcgtacaa ctatgtacta ctgttgatgc atccacaaca gtttgttttg tttttttttg 4320
tttttttttt ttctaatgat tcattaccgc tatgtatacc tacttgtact tgtagtaagc 4380
cgggttattg gcgttcaatt aatcatagac ttatgaatct gcacggtgtg cgctgcgagt 4440
tacttttagc ttatgcatgc tacttgggtg taatattggg atctgttcgg aaatcaacgg 4500
atgctcaatc gatttcgaca gtaattaatt aagtcataca caagtcagct ttcttcgagc 4560
ctcatataag tataagtagt tcaacgtatt agcactgtac ccagcatctc cgtatcgaga 4620
aacacaacaa catgccccat tggacagatc atgcggatac acaggttgtg cagtatcata 4680
catactcgat cagacaggtc gtctgaccat catacaagct gaacaagcgc tccatacttg 4740
cacgctctct atatacacag ttaaattaca tatccatagt ctaacctcta acagttaatc 4800
ttctggtaag cctcccagcc agccttctgg tatcgcttgg cctcctcaat aggatctcgg 4860
ttctggccgt acagacctcg gccgacaatt atgatatccg ttccggtaga catgacatcc 4920
tcaacagttc ggtactgctg tccgagagcg tctcccttgt cgtcaagacc caccccgggg 4980
gtcagaataa gccagtcctc agagtcgccc ttaggtcggt tctgggcaat gaagccaacc 5040
acaaactcgg ggtcggatcg ggcaagctca atggtctgct tggagtactc gccagtggcc 5100
agagagccct tgcaagacag ctcggccagc atgagcagac ctctggccag cttctcgttg 5160
ggagaggga ctaggaactc cttgtactgg gagttctcgt agtcagagac gtcctccttc 5220
ttctgttcag agacagtttc ctcggcacca gctcgcaggc cagcaatgat tccggttccg 5280
ggtacaccgt gggcgttggt gatatcggac cactcggcga ttcggtgaca ccggtactgg 5340
tgcttgacag tgttgccaat atctgcgaac tttctgtcct cgaacaggaa gaaaccgtgc 5400
ttaagagcaa gttccttgag ggggagcaca gtgccggcgt aggtgaagtc gtcaatgatg 5460
tcgatatggg ttttgatcat gcacacataa ggtccgacct tatcggcaag ctcaatgagc 5520
tccttggtgg tggtaacatc cagagaagca cacaggttgg ttttcttggc tgccacgagc 5580
ttgagcactc gagcggcaaa ggcggacttg tggacgttag ctcgagcttc gtaggagggc 5640
attttggtgg tgaagaggag actgaaataa atttagtctg cagaactttt tatcggaacc 5700
ttatctgggg cagtgaagta tatgttatgg taatagttac gagttagttg aacttataga 5760
tagactggac tatacggcta tcggtccaaa ttagaaagaa cgtcaatggc tctctgggcg 5820
tcgcctttgc cgacaaaaat gtgatcatga tgaaagccag caatgacgtt gcagctgata 5880
ttgttgtcgg ccaaccgcgc cgaaaacgca gctgtcagac ccacagcctc caacgaagaa 5940

```
tgtatcgtca aagtgatcca agcacactca tagttggagt cgtactccaa aggcggcaat   6000

gacgagtcag acagatactc gtcgacgttt aaaccatcat ctaagggcct caaaactacc   6060

tcggaactgc tgcgctgatc tggacaccac agaggttccg agcactttag gttgcaccaa   6120

atgtcccacc aggtgcaggc agaaaacgct ggaacagcgt gtacagtttg tcttaacaaa   6180

aagtgagggc gctgaggtcg agcagggtgg tgtgacttgt tatagccttt agagctgcga   6240

aagcgcgtat ggatttggct catcaggcca gattgagggt ctgtggacac atgtcatgtt   6300

agtgtacttc aatcgccccc tggatatagc cccgacaata ggccgtggcc tcattttttt   6360

gccttccgca catttccatt gctcggtacc cacaccttgc ttctcctgca cttgccaacc   6420

ttaatactgg tttacattga ccaacatctt acaagcgggg ggcttgtcta gggtatatat   6480

aaacagtggc tctcccaatc ggttgccagt ctcttttttc ctttctttcc ccacagattc   6540

gaaatctaaa ctacacatca caccatggcc tcctcggagg acgtcatcaa ggagttcatg   6600

cgattcaagg tccgaatgga aggctccgtg aacggtcacg agtttgagat tgagggagag   6660

ggtgaaggcc gaccctacga aggcacccag accgcgaagc tgaaggtgac caagggtgga   6720

cccctgccct tcgcctggga cattctgtct cctcagtttc agtacggttc taaggtgtac   6780

gtgaagcacc ctgctgacat tcccgactac aagaaacttt cctttcccga gggcttcaag   6840

tgggagcgag ttatgaactt cgaggatggc ggtgtcgtta ccgttactca ggactcctcg   6900

ctccaggacg gctcgttcat ctacaaggtt aagttcatcg gtgtcaactt ccctagcgat   6960

ggacccgtca tgcaaaagaa aactatggga tgggaagcct ctacagagcg gctgtaccct   7020

cgagacggag tgttgaaggg cgagattcac aaggccctga agctcaagga cggtggacac   7080

tatctcgttg agtttaagtc tatctacatg gcaaagaaac ccgtgcagct tccaggctac   7140

tattacgtcg attccaagct cgatatcacc agccataatg aggactacac tattgtcgaa   7200

cagtacgagc gtgctgaggg aagacaccat ctgtttcttt aagc                    7244
```

<210> SEQ ID NO 130
<211> LENGTH: 1214
<212> TYPE: DNA
<213> ORGANISM: Artificial sequence
<220> FEATURE:
<223> OTHER INFORMATION: FBA1 Yarrowia dsREDexpress cassette from pRF165 on PmeI NotI fragment

<400> SEQUENCE: 130

```
aaaccatcat ctaagggcct caaaactacc tcggaactgc tgcgctgatc tggacaccac     60

agaggttccg agcactttag gttgcaccaa atgtcccacc aggtgcaggc agaaaacgct    120

ggaacagcgt gtacagtttg tcttaacaaa aagtgagggc gctgaggtcg agcagggtgg    180

tgtgacttgt tatagccttt agagctgcga aagcgcgtat ggatttggct catcaggcca    240

gattgagggt ctgtggacac atgtcatgtt agtgtacttc aatcgccccc tggatatagc    300

cccgacaata ggccgtggcc tcattttttt gccttccgca catttccatt gctcggtacc    360

cacaccttgc ttctcctgca cttgccaacc ttaatactgg tttacattga ccaacatctt    420

acaagcgggg ggcttgtcta gggtatatat aaacagtggc tctcccaatc ggttgccagt    480

ctcttttttc ctttctttcc ccacagattc gaaatctaaa ctacacatca caccatggcc    540

tcctcggagg acgtcatcaa ggagttcatg cgattcaagg tccgaatgga aggctccgtg    600

aacggtcacg agtttgagat tgagggagag ggtgaaggcc gaccctacga aggcacccag    660

accgcgaagc tgaaggtgac caagggtgga cccctgccct tcgcctggga cattctgtct    720
```

-continued

```
cctcagtttc agtacggttc taaggtgtac gtgaagcacc ctgctgacat tcccgactac     780

aagaaacttt cctttcccga gggcttcaag tgggagcgag ttatgaactt cgaggatggc     840

ggtgtcgtta ccgttactca ggactcctcg ctccaggacg gctcgttcat ctacaaggtt     900

aagttcatcg gtgtcaactt ccctagcgat ggacccgtca tgcaaaagaa aactatggga     960

tgggaagcct ctacagagcg gctgtaccct cgagacggag tgttgaaggg cgagattcac    1020

aaggccctga agctcaagga cggtggacac tatctcgttg agtttaagtc tatctacatg    1080

gcaaagaaac ccgtgcagct tccaggctac tattacgtcg attccaagct cgatatcacc    1140

agccataatg aggactacac tattgtcgaa cagtacgagc gtgctgaggg aagacaccat    1200

ctgtttcttt aagc                                                      1214


<210> SEQ ID NO 131
<211> LENGTH: 11526
<212> TYPE: DNA
<213> ORGANISM: Artificial sequence
<220> FEATURE:
<223> OTHER INFORMATION: p2P069 integration vector

<400> SEQUENCE: 131

ggccgcaagt gtggatgggg aagtgagtgc ccggttctgt gtgcacaatt ggcaatccaa      60

gatggatgga ttcaacacag ggatatagcg agctacgtgg tggtgcgagg atatagcaac     120

ggatatttat gtttgacact tgagaatgta cgatacaagc actgtccaag tacaatacta     180

aacatactgt acatactcat actcgtaccc gggcaacggt ttcacttgag tgcagtggct     240

agtgctctta ctcgtacagt gtgcaatact gcgtatcata gtctttgatg tatatcgtat     300

tcattcatgt tagttgcgta cgggcgtcgt tgcttgtgtg atttttgagg acccatccct     360

ttggtatata agtatactct ggggttaagg ttgcccgtgt agtctaggtt atagttttca     420

tgtgaaatac cgagagccga gggagaataa acgggggtat ttggacttgt ttttttcgcg     480

gaaaagcgtc gaatcaaccc tgcgggcctt gcaccatgtc cacgacgtgt ttctcgcccc     540

aattcgcccc ttgcacgtca aaattaggcc tccatctaga cccctccata acatgtgact     600

gtggggaaaa gtataaggga aaccatgcaa ccatagacga cgtgaaagac ggggaggaac     660

caatggaggc caaagaaatg gggtagcaac agtccaggag acagacaagg agacaaggag     720

agggcgcccg aaagatcgga aaaacaaaca tgtccaattg ggcagtgac ggaaacgaca      780

cggacacttc agtacaatgg accgaccatc tccaagccag ggttattccg gtatcacctt     840

ggccgtaacc tcccgctggt acctgatatt gtacacgttc acattcaata tactttcagc     900

tacaataaga gaggctgttt gtcgggcatg tgtgtccgtc gtatggggtg atgtccgagg     960

gcgaaattcg ctacaagctt aactctggcg cttgtccagt atgaatagac aagtcaagac    1020

cagtggtgcc atgattgaca gggaggtaca agacttcgat actcgagcat tactcggact    1080

tgtggcgatt gaacagacgg gcgatcgctt ctcccccgta ttgccggcgc gccagctgca    1140

ttaatgaatc ggccaacgcg cggggagagg cggtttgcgt attgggcgct cttccgcttc    1200

ctcgctcact gactcgctgc gctcggtcgt tcggctgcgg cgagcggtat cagctcactc    1260

aaaggcggta atacggttat ccacagaatc aggggataac gcaggaaaga acatgtgagc    1320

aaaaggccag caaaaggcca ggaaccgtaa aaaggccgcg ttgctggcgt ttttccatag    1380

gctccgcccc cctgacgagc atcacaaaaa tcgacgctca agtcagaggt ggcgaaaccc    1440

gacaggacta taaagatacc aggcgtttcc ccctggaagc tccctcgtgc gctctcctgt    1500

tccgaccctg ccgcttaccg gatacctgtc cgcctttctc ccttcgggaa gcgtggcgct    1560
```

```
ttctcatagc tcacgctgta ggtatctcag ttcggtgtag gtcgttcgct ccaagctggg   1620
ctgtgtgcac gaaccccccg ttcagcccga ccgctgcgcc ttatccggta actatcgtct   1680
tgagtccaac ccggtaagac acgacttatc gccactggca gcagccactg gtaacaggat   1740
tagcagagcg aggtatgtag gcggtgctac agagttcttg aagtggtggc ctaactacgg   1800
ctacactaga agaacagtat ttggtatctg cgctctgctg aagccagtta ccttcggaaa   1860
aagagttggt agctcttgat ccggcaaaca aaccaccgct ggtagcggtg gtttttttgt   1920
ttgcaagcag cagattacgc gcagaaaaaa aggatctcaa gaagatcctt tgatcttttc   1980
tacggggtct gacgctcagt ggaacgaaaa ctcacgttaa gggattttgg tcatgagatt   2040
atcaaaaagg atcttcacct agatcctttt aaattaaaaa tgaagtttta aatcaatcta   2100
aagtatatat gagtaaactt ggtctgacag ttaccaatgc ttaatcagtg aggcacctat   2160
ctcagcgatc tgtctatttc gttcatccat agttgcctga ctccccgtcg tgtagataac   2220
tacgatacgg gagggcttac catctggccc cagtgctgca atgataccgc gagacccacg   2280
ctcaccggct ccagatttat cagcaataaa ccagccagcc ggaagggccg agcgcagaag   2340
tggtcctgca actttatccg cctccatcca gtctattaat tgttgccggg aagctagagt   2400
aagtagttcg ccagttaata gtttgcgcaa cgttgttgcc attgctacag gcatcgtggt   2460
gtcacgctcg tcgtttggta tggcttcatt cagctccggt tcccaacgat caaggcgagt   2520
tacatgatcc cccatgttgt gcaaaaaagc ggttagctcc ttcggtcctc cgatcgttgt   2580
cagaagtaag ttggccgcag tgttatcact catggttatg gcagcactgc ataattctct   2640
tactgtcatg ccatccgtaa gatgcttttc tgtgactggt gagtactcaa ccaagtcatt   2700
ctgagaatag tgtatgcggc gaccgagttg ctcttgcccg gcgtcaatac gggataatac   2760
cgcgccacat agcagaactt taaaagtgct catcattgga aaacgttctt cggggcgaaa   2820
actctcaagg atcttaccgc tgttgagatc cagttcgatg taacccactc gtgcacccaa   2880
ctgatcttca gcatctttta ctttcaccag cgtttctggg tgagcaaaaa caggaaggca   2940
aaatgccgca aaaaagggaa taagggcgac acggaaatgt tgaatactca tactcttcct   3000
ttttcaatat tattgaagca tttatcaggg ttattgtctc atgagcggat acatatttga   3060
atgtatttag aaaaataaac aaataggggt tccgcgcaca tttccccgaa aagtgccacc   3120
tgatgcggtg tgaaataccg cacagatgcg taaggagaaa ataccgcatc aggaaattgt   3180
aagcgttaat attttgttaa aattcgcgtt aaatttttgt taaatcagct cattttttaa   3240
ccaataggcc gaaatcggca aaatccctta taaatcaaaa gaatagaccg agatagggtt   3300
gagtgttgtt ccagtttgga acaagagtcc actattaaag aacgtggact ccaacgtcaa   3360
agggcgaaaa accgtctatc agggcgatgg cccactacgt gaaccatcac cctaatcaag   3420
ttttttgggg tcgaggtgcc gtaaagcact aaatcggaac cctaaaggga gcccccgatt   3480
tagagcttga cggggaaagc cggcgaacgt ggcgagaaag gaagggaaga aagcgaaagg   3540
agcgggcgct agggcgctgg caagtgtagc ggtcacgctg cgcgtaacca ccacacccgc   3600
cgcgcttaat gcgccgctac agggcgcgtc cattcgccat tcaggctgcg caactgttgg   3660
gaagggcgat cggtgcgggc ctcttcgcta ttacgccagc tggcgaaagg gggatgtgct   3720
gcaaggcgat taagttgggt aacgccaggg ttttcccagt cacgacgttg taaaacgacg   3780
gccagtgaat tgtaatacga ctcactatag ggcgaattgg gcccgacgtc gcatgcgctg   3840
atgacacttt ggtctgaaag agatgcattt tgaatcccaa acttgcagtg cccaagtgac   3900
```

```
atacatctcc gcgttttgga aaatgttcag aaacagttga ttgtgttgga atggggaatg   3960
gggaatggaa aaatgactca agtatcaatt ccaaaaactt ctctggctgg cagtacctac   4020
tgtccatact actgcatttt ctccagtcag gccactctat actcgacgac acagtagtaa   4080
aacccagata atttcgacat aaacaagaaa acagacccaa taatatttat atatagtcag   4140
ccgtttgtcc agttcagact gtaatagccg aaaaaaaatc caaagtttct attctaggaa   4200
aatatattcc aatattttta attcttaatc tcatttattt tattctagcg aaatacattt   4260
cagctacttg agacatgtga tacccacaaa tcggattcgg actcggttgt tcagaagagc   4320
atatggcatt cgtgctcgct tgttcacgta ttcttcctgt tccatctctt ggccgacaat   4380
cacacaaaaa tggggttttt tttttaattc taatgattca ttacagcaaa attgagatat   4440
agcagaccac gtattccata atcaccaagg aagttcttgg gcgtcttaat taagttgcga   4500
cacatgtctt gatagtatct tggcttctct ctcttgagct tttccataac aagttcttct   4560
gcctccagga agtccatggt gaatgattct tatactcaga aggaaatgct taacgatttc   4620
gggtgtgagt tgacaaggag agagagaaaa gaagaggaaa ggtaattcgg ggacggtggt   4680
cttttatacc cttggctaaa gtcccaacca caaagcaaaa aaattttcag tagtctattt   4740
tgcgtccggc atgggttacc cggatggcca gacaaagaaa ctagtacaaa gtctgaacaa   4800
gcgtagattc cagactgcag taccctacgc ccttaacggc aagtgtggga accgggggag   4860
gtttgatatg tggggtgaag gggctctcg ccggggttgg gcccgctact gggtcaattt   4920
ggggtcaatt ggggcaattg gggctgtttt ttgggacaca aatacgccgc caacccggtc   4980
tctcctgaat tctgcagatg ggctgcagga attccgtcgt cgcctgagtc gacatcattt   5040
atttaccagt tggccacaaa cccttgacga tctcgtatgt cccctccgac atactcccgg   5100
ccggctgggg tacgttcgat agcgctatcg gcatcgacaa ggtttgggtc cctagccgat   5160
accgcactac ctgagtcaca atcttcggag gtttagtctt ccacatagca cgggcaaaag   5220
tgcgtatata tacaagagcg tttgccagcc acagattttc actccacaca ccacatcaca   5280
catacaacca cacacatcca caatggaacc cgaaactaag aagaccaaga ctgactccaa   5340
gaagattgtt cttctcggcg gcgacttctg tggccccgag gtgattgccg aggccgtcaa   5400
ggtgctcaag tctgttgctg aggcctccgg caccgagttt gtgtttgagg accgactcat   5460
tggaggagct gccattgaga aggagggcga gcccatcacc gacgctactc tcgacatctg   5520
ccgaaaggct gactctatta tgctcggtgc tgtcggaggc gctgccaaca ccgtatggac   5580
cactcccgac ggacgaaccg acgtgcgacc cgagcagggt ctcctcaagc tgcgaaagga   5640
cctgaacctg tacgccaacc tgcgaccctg ccagctgctg tcgcccaagc tcgccgatct   5700
ctcccccatc cgaaacgttg agggcaccga cttcatcatt gtccgagagc tcgtcggagg   5760
tatctacttt ggagagcgaa aggaggatga cggatctggc gtcgcttccg acaccgagac   5820
ctactccgtt cctgaggttg agcgaattgc ccgaatggcc gccttcctgg cccttcagca   5880
caaccccccct cttcccgtgt ggtctcttga caaggccaac gtgctggcct cctctcgact   5940
ttggcgaaag actgtcactc gagtcctcaa ggacgaattc ccccagctcg agctcaacca   6000
ccagctgatc gactcggccg ccatgatcct catcaagcag ccctccaaga tgaatggtat   6060
catcatcacc accaacatgt ttggcgatat catctccgac gaggcctccg tcatccccgg   6120
ttctctgggt ctgctgccct ccgcctctct ggcttctctg cccgacacca acgaggcgtt   6180
cggtctgtac gagccctgtc acggatctgc ccccgatctc ggcaagcaga aggtcaaccc   6240
cattgccacc attctgtctg ccgccatgat gctcaagttc tctcttaaca tgaagcccgc   6300
```

```
cggtgacgct gttgaggctg ccgtcaagga gtccgtcgag gctggtatca ctaccgccga   6360
tatcggaggc tcttcctcca cctccgaggt cggagacttg ttgccaacaa ggtcaaggag   6420
ctgctcaaga aggagtaagt cgtttctacg acgcattgat ggaaggagca aactgacgcg   6480
cctgcgggtt ggtctaccgg cagggtccgc tagtgtataa gactctataa aaagggccct   6540
gccctgctaa tgaaatgatg atttataatt taccggtgta gcaaccttga ctagaagaag   6600
cagattgggt gtgtttgtag tggaggacag tggtacgttt tggaaacagt cttcttgaaa   6660
gtgtcttgtc tacagtatat tcactcataa cctcaatagc caagggtgta gtcggtttat   6720
taaaggaagg gagttgtggc tgatgtggat agatatcttt aagctggcga ctgcacccaa   6780
cgagtgtggt ggtagcttgt tagatctgta tattcggtaa gatatatttt gtggggtttt   6840
agtggtgttt aaaccatcat ctaagggcct caaaactacc tcggaactgc tgcgctgatc   6900
tggacaccac agaggttccg agcactttag gttgcaccaa atgtcccacc aggtgcaggc   6960
agaaaacgct ggaacagcgt gtacagtttg tcttaacaaa aagtgagggc gctgaggtcg   7020
agcagggtgg tgtgacttgt tatagccttt agagctgcga aagcgcgtat ggatttggct   7080
catcaggcca gattgagggt ctgtggacac atgtcatgtt agtgtacttc aatcgccccc   7140
tggatatagc cccgacaata ggccgtggcc tcattttttt gccttccgca catttccatt   7200
gctcggtacc cacaccttgc ttctcctgca cttgccaacc ttaatactgg tttacattga   7260
ccaacatctt acaagcgggg ggcttgtcta gggtatatat aaacagtggc tctcccaatc   7320
ggttgccagt ctcttttttc ctttctttcc ccacagattc gaaatctaaa ctacacatca   7380
caccatggac aagaaatact ccatcggcct ggacattgga accaactctg tcggctgggc   7440
tgtcatcacc gacgagtaca aggtgccctc caagaaattc aaggtcctcg gaaacaccga   7500
tcgacactcc atcaagaaaa acctcattgg tgccctgttg ttcgattctg gcgagactgc   7560
cgaagctacc agactcaagc gaactgctcg gcgacgttac acccgacgga agaaccgaat   7620
ctgctacctg caggagatct tttccaacga gatggccaag gtggacgatt cgttctttca   7680
tcgactggag gaatccttcc tcgtcgagga agacaagaaa cacgagcgtc atcccatctt   7740
tggcaacatt gtggacgagg ttgcttacca cgagaagtat cctaccatct accacctgcg   7800
aaagaaactc gtcgattcca ccgacaaggc ggatctcaga cttatctacc tcgctctggc   7860
acacatgatc aagtttcgag gtcatttcct catcgagggc gatctcaatc ccgacaacag   7920
cgatgtggac aagctgttca ttcagctcgt tcagacctac aaccagctgt tcgaggaaaa   7980
ccccatcaat gcctccggag tcgatgcaaa ggccatcttg tctgctcgac tctcgaagag   8040
cagacgactg gagaacctca ttgcccaact tcctggcgag aaaaagaacg gactgtttgg   8100
caacctcatt gccctttctc ttggtctcac acccaacttc aagtccaact tcgatctggc   8160
ggaggacgcc aagctccagc tgtccaagga cacctacgac gatgacctcg acaacctgct   8220
tgcacagatt ggcgatcagt acgccgacct gtttctcgct gccaagaacc tttcggatgc   8280
tattctcttg tctgacattc tgcgagtcaa caccgagatc acaaaggctc ccctttctgc   8340
ctccatgatc aagcgatacg acgagcacca tcaggatctc acactgctca aggctcttgt   8400
ccgacagcaa ctgcccgaga agtacaagga gatctttttc gatcagtcga agaacggcta   8460
cgctggatac atcgacggcg gagcctctca ggaagagttc tacaagttca tcaagccaat   8520
tctcgagaag atggacggaa ccgaggaact gcttgtcaag ctcaatcgag aggatctgct   8580
tcggaagcaa cgaaccttcg acaacggcag cattcctcat cagatccacc tcggtgagct   8640
```

-continued

```
gcacgccatt cttcgacgtc aggaagactt ctaccccttt ctcaaggaca accgagagaa   8700
gatcgagaag attcttacct ttcgaatccc ctactatgtt ggtcctcttg ccagaggaaa   8760
ctctcgattt gcttggatga ctcgaaagtc cgaggaaacc atcactccct ggaacttcga   8820
ggaagtcgtg gacaagggtg cctctgcaca gtccttcatc gagcgaatga ccaacttcga   8880
caagaatctg cccaacgaga aggttcttcc caagcattcg ctgctctacg agtactttac   8940
agtctacaac gaactcacca aagtcaagta cgttaccgag ggaatgcgaa agcctgcctt   9000
cttgtctggc gaacagaaga aagccattgt cgatctcctg ttcaagacca accgaaaggt   9060
cactgttaag cagctcaagg aggactactt caagaaaatc gagtgtttcg acagcgtcga   9120
gatttccgga gttgaggacc gattcaacgc ctctttgggc acctatcacg atctgctcaa   9180
gattatcaag gacaaggatt ttctcgacaa cgaggaaaac gaggacattc tggaggacat   9240
cgtgctcact cttaccctgt tcgaagatcg ggagatgatc gaggaacgac tcaagacata   9300
cgctcacctg ttcgacgaca aggtcatgaa acaactcaag cgacgtagat acaccggctg   9360
ggaagactt  tcgcgaaagc tcatcaacgg catcagagac aagcagtccg gaaagaccat   9420
tctggacttt ctcaagtccg atggctttgc caaccgaaac ttcatgcagc tcattcacga   9480
cgattctctt accttcaagg aggacatcca gaaggcacaa gtgtccggtc agggcgacag   9540
cttgcacgaa catattgcca acctggctgg ttcgccagcc atcaagaaag gcattctcca   9600
gactgtcaag gttgtcgacg agctggtgaa ggtcatggga cgtcacaagc ccgagaacat   9660
tgtgatcgag atggccagag agaaccagac aactcaaaag ggtcagaaaa actcgcgaga   9720
gcggatgaag cgaatcgagg aaggcatcaa ggagctggga tcccagattc tcaaggagca   9780
tcccgtcgag aacactcaac tgcagaacga gaagctgtat ctctactatc tgcagaatgg   9840
tcgagacatg tacgtggatc aggaactgga catcaatcgt ctcagcgact acgatgtgga   9900
ccacattgtc cctcaatcct ttctcaagga cgattctatc gacaacaagg tccttacacg   9960
atccgacaag aacagaggca agtcggacaa cgttcccagc gaagaggtgg tcaaaaagat  10020
gaagaactac tggcgacagc tgctcaacgc caagctcatt acccagcgaa agttcgacaa  10080
tcttaccaag gccgagcgag gcggtctgtc cgagctcgac aaggctggct tcatcaagcg  10140
tcaactcgtc gagaccagac agatcacaaa gcacgtcgca cagattctcg attctcggat  10200
gaacaccaag tacgacgaga acgacaagct catccgagag gtcaaggtga ttactctcaa  10260
gtccaaactg gtctccgatt tccgaaagga ctttcagttc tacaaggtgc gagagatcaa  10320
caattaccac catgcccacg atgcttacct caacgccgtc gttggcactg cgctcatcaa  10380
gaaatacccc aagctcgaaa gcgagttcgt ttacggcgat tacaaggtct acgacgttcg  10440
aaagatgatt gccaagtccg aacaggagat tggcaaggct actgccaagt acttctttta  10500
ctccaacatc atgaactttt tcaagaccga gatcaccttg gccaacggag agattcgaaa  10560
gagaccactt atcgagacca acggcgaaac tggagagatc gtgtgggaca agggtcgaga  10620
ctttgcaacc gtgcgaaagg ttctgtcgat gcctcaggtc aacatcgtca agaaaaccga  10680
ggttcagact ggcggattct ccaaggagtc gattctgccc aagcgaaact ccgacaagct  10740
catcgctcga aagaaagact gggatcccaa gaaatacggt ggcttcgatt ctcctaccgt  10800
cgcctattcc gtgcttgtcg ttgcgaaggt cgagaagggc aagtccaaaa agctcaagtc  10860
cgtcaaggag ctgctcggaa ttaccatcat ggagcgatcg agcttcgaga agaatcccat  10920
cgacttcttg gaagccaagg gttacaagga ggtcaagaaa gacctcatta tcaagctgcc  10980
caagtactct ctgttcgaac tggagaacgg tcgaaagcgt atgctcgcct ccgctggcga  11040
```

gctgcagaag ggaaacgagc ttgccttgcc ttcgaagtac gtcaactttc tctatctggc 11100
ttctcactac gagaagctca agggttctcc cgaggacaac gaacagaagc aactcttcgt 11160
tgagcagcac aaacattacc tcgacgagat tatcgagcag atttccgagt tttcgaagcg 11220
agtcatcctg gctgatgcca acttggacaa ggtgctctct gcctacaaca agcatcggga 11280
caaacccatt cgagaacagg cggagaacat cattcacctg tttactctta ccaacctggg 11340
tgctcctgca gctttcaagt acttcgatac cactatcgac cgaaagcggt acacatccac 11400
caaggaggtt ctcgatgcca ccctgattca ccagtccatc actggcctgt acgagacccg 11460
aatcgacctg tctcagcttg gtggcgactc cagagccgat cccaagaaaa agcgaaaggt 11520
ctaagc 11526

<210> SEQ ID NO 132
<211> LENGTH: 8064
<212> TYPE: DNA
<213> ORGANISM: artificial sequence
<220> FEATURE:
<223> OTHER INFORMATION: pRF201

<400> SEQUENCE: 132
aaaccatcat ctaagggcct caaaactacc tcggaactgc tgcgctgatc tggacaccac 60
agaggttccg agcactttag gttgcaccaa atgtcccacc aggtgcaggc agaaaacgct 120
ggaacagcgt gtacagtttg tcttaacaaa aagtgagggc gctgaggtcg agcagggtgg 180
tgtgacttgt tatagccttt agagctgcga aagcgcgtat ggatttggct catcaggcca 240
gattgagggt ctgtggacac atgtcatgtt agtgtacttc aatcgccccc tggatatagc 300
cccgacaata ggccgtggcc tcattttttt gccttccgca catttccatt gctcggtacc 360
cacaccttgc ttctcctgca cttgccaacc ttaatactgg tttacattga ccaacatctt 420
acaagcgggg ggcttgtcta gggtatatat aaacagtggc tctcccaatc ggttgccagt 480 ctctttttc ctttctttcc ccacagattc gaaatctaaa ctacacatca caccatggcc 540
tcctcggagg acgtcatcaa ggagttcatg cgattcaagg tccgaatgga aggctccgtg 600
aacggtcacg agtttgagat tgagggagag ggtgaaggcc gaccctacga aggcacccag 660
accgcgaagc tgaaggtgac caagggtgga cccctgccct tcgcctggga cattctgtct 720
cctcagtttc agtacggttc taaggtgtac gtgaagcacc ctgctgacat tcccgactac 780
aagaaacttt cctttcccga gggcttcaag tgggagcgag ttatgaactt cgaggatggc 840
ggtgtcgtta ccgttactca ggactcctcg ctccaggacg gctcgttcat ctacaaggtt 900
aagttcatcg gtgtcaactt ccctagcgat ggacccgtca tgcaaaagaa aactatggga 960
tgggaagcct ctacagagcg gctgtaccct cgagacggag tgttgaaggg cgagattcac 1020
aaggccctga agctcaagga cggtggacac tatctcgttg agtttaagtc tatctacatg 1080
gcaaagaaac ccgtgcagct tccaggctac tattacgtcg attccaagct cgatatcacc 1140
agccataatg aggactacac tattgtcgaa cagtacgagc gtgctgaggg aagacaccat 1200
ctgtttcttt aagcggccgc aagtgtggat ggggaagtga gtgcccggtt ctgtgtgcac 1260
aattggcaat ccaagatgga tggattcaac acagggatat agcgagctac gtggtggtgc 1320
gaggatatag caacggatat ttatgtttga cacttgagaa tgtacgatac aagcactgtc 1380
caagtacaat actaaacata ctgtacatac tcatactcgt acccgggcaa cggtttcact 1440
tgagtgcagt ggctagtgct cttactcgta cagtgtgcaa tactgcgtat catagtcttt 1500

-continued

```
gatgtatatc gtattcattc atgttagttg cgtacgggcg tcgttgcttg tgtgattttt   1560
gaggacccat ccctttggta tataagtata ctctggggtt aaggttgccc gtgtagtcta   1620
ggttatagtt ttcatgtgaa ataccgagag ccgagggaga ataaacgggg gtatttggac   1680
ttgttttttt cgcggaaaag cgtcgaatca accctgcggg ccttgcacca tgtccacgac   1740
gtgtttctcg ccccaattcg ccccttgcac gtcaaaatta ggcctccatc tagacccctc   1800
cataacatgt gactgtgggg aaaagtataa gggaaaccat gcaaccatag acgacgtgaa   1860
agacggggag gaaccaatgg aggccaaaga aatggggtag caacagtcca ggagacagac   1920
aaggagacaa ggagagggcg cccgaaagat cggaaaaaca aacatgtcca attggggcag   1980
tgacggaaac gacacggaca cttcagtaca atggaccgac catctccaag ccagggttat   2040
tccggtatca ccttggccgt aacctcccgc tggtacctga tattgtacac gttcacattc   2100
aatatacttt cagctacaat aagagaggct gtttgtcggg catgtgtgtc cgtcgtatgg   2160
ggtgatgtcc gagggcgaaa ttcgctacaa gcttaactct ggcgcttgtc cagtatgaat   2220
agacaagtca agaccagtgg tgccatgatt gacagggagg tacaagactt cgatactcga   2280
gcattactcg gacttgtggc gattgaacag acgggcgatc gcttctcccc cgtattgccg   2340
gcgcgccagc tgcattaatg aatcggccaa cgcgcgggga gaggcggttt gcgtattggg   2400
cgctcttccg cttcctcgct cactgactcg ctgcgctcgg tcgttcggct gcggcgagcg   2460
gtatcagctc actcaaaggc ggtaatacgg ttatccacag aatcagggga taacgcagga   2520
aagaacatgt gagcaaaagg ccagcaaaag gccaggaacc gtaaaaaggc cgcgttgctg   2580
gcgtttttcc ataggctccg cccccctgac gagcatcaca aaaatcgacg ctcaagtcag   2640
aggtggcgaa acccgacagg actataaaga taccaggcgt ttccccctgg aagctccctc   2700
gtgcgctctc ctgttccgac cctgccgctt accggatacc tgtccgcctt tctcccttcg   2760
ggaagcgtgg cgctttctca tagctcacgc tgtaggtatc tcagttcggt gtaggtcgtt   2820
cgctccaagc tgggctgtgt gcacgaaccc cccgttcagc ccgaccgctg cgccttatcc   2880
ggtaactatc gtcttgagtc caacccggta agacacgact tatcgccact ggcagcagcc   2940
actggtaaca ggattagcag agcgaggtat gtaggcggtg ctacagagtt cttgaagtgg   3000
tggcctaact acggctacac tagaagaaca gtatttggta tctgcgctct gctgaagcca   3060
gttaccttcg gaaaaagagt tggtagctct tgatccggca aacaaaccac cgctggtagc   3120
ggtggttttt ttgtttgcaa gcagcagatt acgcgcagaa aaaaaggatc tcaagaagat   3180
cctttgatct tttctacggg gtctgacgct cagtggaacg aaaactcacg ttaagggatt   3240
ttggtcatga gattatcaaa aaggatcttc acctagatcc ttttaaatta aaaatgaagt   3300
tttaaatcaa tctaaagtat atatgagtaa acttggtctg acagttacca atgcttaatc   3360
agtgaggcac ctatctcagc gatctgtcta tttcgttcat ccatagttgc ctgactcccc   3420
gtcgtgtaga taactacgat acgggagggc ttaccatctg gccccagtgc tgcaatgata   3480
ccgcgagacc cacgctcacc ggctccagat ttatcagcaa taaaccagcc agccggaagg   3540
gccgagcgca gaagtggtcc tgcaacttta tccgcctcca tccagtctat taattgttgc   3600
cgggaagcta gagtaagtag ttcgccagtt aatagtttgc gcaacgttgt tgccattgct   3660
acaggcatcg tggtgtcacg ctcgtcgttt ggtatggctt cattcagctc cggttcccaa   3720
cgatcaaggc gagttacatg atcccccatg ttgtgcaaaa aagcggttag ctccttcggt   3780
cctccgatcg ttgtcagaag taagttggcc gcagtgttat cactcatggt tatggcagca   3840
ctgcataatt ctcttactgt catgccatcc gtaagatgct tttctgtgac tggtgagtac   3900
```

```
tcaaccaagt cattctgaga atagtgtatg cggcgaccga gttgctcttg cccggcgtca   3960
atacgggata ataccgcgcc acatagcaga actttaaaag tgctcatcat tggaaaacgt   4020
tcttcggggc gaaaactctc aaggatctta ccgctgttga gatccagttc gatgtaaccc   4080
actcgtgcac ccaactgatc ttcagcatct tttactttca ccagcgtttc tgggtgagca   4140
aaaacaggaa ggcaaaatgc cgcaaaaaag ggaataaggg cgacacggaa atgttgaata   4200
ctcatactct tcctttttca atattattga agcatttatc agggttattg tctcatgagc   4260
ggatacatat ttgaatgtat ttagaaaaat aaacaaatag gggttccgcg cacatttccc   4320
cgaaaagtgc cacctgatgc ggtgtgaaat accgcacaga tgcgtaagga gaaaataccg   4380
catcaggaaa ttgtaagcgt taatattttg ttaaaattcg cgttaaattt ttgttaaatc   4440
agctcatttt ttaaccaata ggccgaaatc ggcaaaatcc cttataaatc aaaagaatag   4500
accgagatag ggttgagtgt tgttccagtt tggaacaaga gtccactatt aaagaacgtg   4560
gactccaacg tcaaagggcg aaaaaccgtc tatcagggcg atggcccact acgtgaacca   4620
tcaccctaat caagtttttt ggggtcgagg tgccgtaaag cactaaatcg gaaccctaaa   4680
gggagccccc gatttagagc ttgacgggga aagccggcga acgtggcgag aaaggaaggg   4740
aagaaagcga aaggagcggg cgctagggcg ctggcaagtg tagcggtcac gctgcgcgta   4800
accaccacac ccgccgcgct taatgcgccg ctacagggcg cgtccattcg ccattcaggc   4860
tgcgcaactg ttgggaaggg cgatcggtgc gggcctcttc gctattacgc cagctggcga   4920
aagggggatg tgctgcaagg cgattaagtt gggtaacgcc agggttttcc cagtcacgac   4980
gttgtaaaac gacggccagt gaattgtaat acgactcact atagggcgaa ttgggcccga   5040
cgtcgcatgc gctgatgaca ctttggtctg aaagagatgc attttgaatc ccaaacttgc   5100
agtgcccaag tgacatacat ctccgcgttt tggaaaatgt tcagaaacag ttgattgtgt   5160
tggaatgggg aatggggaat ggaaaaatga ctcaagtatc aattccaaaa acttctctgg   5220
ctggcagtac ctactgtcca tactactgca ttttctccag tcaggccact ctatactcga   5280
cgacacagta gtaaaaccca gataatttcg acataaacaa gaaaacagac ccaataatat   5340
ttatatatag tcagccgttt gtccagttca gactgtaata gccgaaaaaa aatccaaagt   5400
ttctattcta ggaaaatata ttccaatatt tttaattctt aatctcattt attttattct   5460
agcgaaatac atttcagcta cttgagacat gtgataccca caaatcggat tcggactcgg   5520
ttgttcagaa gagcatatgg cattcgtgct cgcttgttca cgtattcttc ctgttccatc   5580
tcttggccga caatcacaca aaaatggggt ttttttttta attctaatga ttcattacag   5640
caaaattgag atatagcaga ccacgtattc cataatcacc aaggaagttc ttgggcgtct   5700
taattaagtt gcgacacatg tcttgatagt atcttggctt ctctctcttg agcttttcca   5760
taacaagttc ttctgcctcc aggaagtcca tggtgaatga ttcttatact cagaaggaaa   5820
tgcttaacga tttcgggtgt gagttgacaa ggagagagag aaaagaagag gaaaggtaat   5880
tcggggacgg tggtctttta tacccttggc taaagtccca accacaaagc aaaaaaattt   5940
tcagtagtct attttgcgtc cggcatgggt tacccggatg gccagacaaa gaaactagta   6000
caaagtctga acaagcgtag attccagact gcagtaccct acgcccttaa cggcaagtgt   6060
gggaaccggg ggaggtttga tatgtggggt gaagggggct ctcgccgggg ttgggcccgc   6120
tactgggtca atttggggtc aattggggca attggggctg tttttggga cacaaatacg   6180
ccgccaaccc ggtctctcct gaattctgca gatgggctgc aggaattccg tcgtcgcctg   6240
```

agtcgacatc atttatttac cagttggcca caaacccttg acgatctcgt atgtcccctc 6300
cgacatactc ccggccggct ggggtacgtt cgatagcgct atcggcatcg acaaggtttg 6360
ggtccctagc cgataccgca ctacctgagt cacaatcttc ggaggtttag tcttccacat 6420
agcacgggca aaagtgcgta tatatacaag agcgtttgcc agccacagat tttcactcca 6480
cacaccacat cacacataca accacacaca tccacaatgg aacccgaaac taagaagacc 6540
aagactgact ccaagaagat tgttcttctc ggcggcgact tctgtggccc cgaggtgatt 6600
gccgaggccg tcaaggtgct caagtctgtt gctgaggcct ccggcaccga gtttgtgttt 6660
gaggaccgac tcattggagg agctgccatt gagaaggagg gcgagcccat caccgacgct 6720
actctcgaca tctgccgaaa ggctgactct attatgctcg gtgctgtcgg aggcgctgcc 6780
aacaccgtat ggaccactcc cgacggacga accgacgtgc gacccgagca gggtctcctc 6840
aagctgcgaa aggacctgaa cctgtacgcc aacctgcgac cctgccagct gctgtcgccc 6900
aagctcgccg atctctcccc catccgaaac gttgagggca ccgacttcat cattgtccga 6960
gagctcgtcg gaggtatcta ctttggagag cgaaaggagg atgacggatc tggcgtcgct 7020
tccgacaccg agacctactc cgttcctgag gttgagcgaa ttgcccgaat ggccgccttc 7080
ctggcccttc agcacaaccc ccctcttccc gtgtggtctc ttgacaaggc caacgtgctg 7140
gcctcctctc gactttggcg aaagactgtc actcgagtcc tcaaggacga attcccccag 7200
ctcgagctca accaccagct gatcgactcg gccgccatga tcctcatcaa gcagccctcc 7260
aagatgaatg gtatcatcat caccaccaac atgtttggcg atatcatctc cgacgaggcc 7320
tccgtcatcc ccggttctct gggtctgctg ccctccgcct ctctggcttc tctgcccgac 7380
accaacgagg cgttcggtct gtacgagccc tgtcacggat ctgcccccga tctcggcaag 7440
cagaaggtca accccattgc caccattctg tctgccgcca tgatgctcaa gttctctctt 7500
aacatgaagc ccgccggtga cgctgttgag gctgccgtca aggagtccgt cgaggctggt 7560
atcactaccg ccgatatcgg aggctcttcc tccacctccg aggtcggaga cttgttgcca 7620
acaaggtcaa ggagctgctc aagaaggagt aagtcgtttc tacgacgcat tgatggaagg 7680
agcaaactga cgcgcctgcg ggttggtcta ccggcagggt ccgctagtgt ataagactct 7740
ataaaaaggg ccctgccctg ctaatgaaat gatgatttat aatttaccgg tgtagcaacc 7800
ttgactagaa gaagcagatt gggtgtgttt gtagtggagg acagtggtac gttttggaaa 7860
cagtcttctt gaaagtgtct tgtctacagt atattcactc ataacctcaa tagccaaggg 7920
tgtagtcggt ttattaaagg aagggagttg tggctgatgt ggatagatat ctttaagctg 7980
gcgactgcac ccaacgagtg tggtggtagc ttgttagatc tgtatattcg gtaagatata 8040
ttttgtgggg ttttagtggt gttt 8064

<210> SEQ ID NO 133
<211> LENGTH: 5356
<212> TYPE: DNA
<213> ORGANISM: Artificial seuqnece
<220> FEATURE:
<223> OTHER INFORMATION: AscI/SphI integration fragment from pRF201

<400> SEQUENCE: 133
cgctgatgac actttggtct gaaagagatg cattttgaat cccaaacttg cagtgcccaa 60
gtgacataca tctccgcgtt ttggaaaatg ttcagaaaca gttgattgtg ttggaatggg 120
gaatggggaa tggaaaaatg actcaagtat caattccaaa aacttctctg gctggcagta 180
cctactgtcc atactactgc attttctcca gtcaggccac tctatactcg acgacacagt 240

```
agtaaaaccc agataatttc gacataaaca agaaaacaga cccaataata tttatatata    300
gtcagccgtt tgtccagttc agactgtaat agccgaaaaa aaatccaaag tttctattct    360
aggaaaatat attccaatat ttttaattct taatctcatt tattttattc tagcgaaata    420
catttcagct acttgagaca tgtgataccc acaaatcgga ttcggactcg gttgttcaga    480
agagcatatg gcattcgtgc tcgcttgttc acgtattctt cctgttccat ctcttggccg    540
acaatcacac aaaaatgggg ttttttttt aattctaatg attcattaca gcaaaattga    600
gatatagcag accacgtatt ccataatcac caaggaagtt cttgggcgtc ttaattaagt    660
tgcgacacat gtcttgatag tatcttggct tctctctctt gagcttttcc ataacaagtt    720
cttctgcctc caggaagtcc atggtgaatg attcttatac tcagaaggaa atgcttaacg    780
atttcgggtg tgagttgaca aggagagaga gaaaagaaga ggaaaggtaa ttcggggacg    840
gtggtctttt atacccttgg ctaaagtccc aaccacaaag caaaaaaatt ttcagtagtc    900
tattttgcgt ccggcatggg ttacccggat ggccagacaa agaaactagt acaaagtctg    960
aacaagcgta gattccagac tgcagtaccc tacgccctta acggcaagtg tgggaaccgg   1020
gggaggtttg atatgtgggg tgaagggggc tctcgccggg gttgggcccg ctactgggtc   1080
aatttggggt caattggggc aattggggct gttttttggg acacaaatac gccgccaacc   1140
cggtctctcc tgaattctgc agatgggctg caggaattcc gtcgtcgcct gagtcgacat   1200
catttattta ccagttggcc acaaaccctt gacgatctcg tatgtcccct ccgacatact   1260
cccggccggc tggggtacgt tcgatagcgc tatcggcatc gacaaggttt gggtccctag   1320
ccgataccgc actacctgag tcacaatctt cggaggttta gtcttccaca tagcacgggc   1380
aaaagtgcgt atatatacaa gagcgtttgc cagccacaga ttttcactcc acacaccaca   1440
tcacacatac aaccacacac atccacaatg gaacccgaaa ctaagaagac caagactgac   1500
tccaagaaga ttgttcttct cggcggcgac ttctgtggcc ccgaggtgat tgccgaggcc   1560
gtcaaggtgc tcaagtctgt tgctgaggcc tccggcaccg agtttgtgtt tgaggaccga   1620
ctcattggag gagctgccat tgagaaggag ggcgagccca tcaccgacgc tactctcgac   1680
atctgccgaa aggctgactc tattatgctc ggtgctgtcg gaggcgctgc caacaccgta   1740
tggaccactc ccgacggacg aaccgacgtg cgacccgagc agggtctcct caagctgcga   1800
aaggacctga acctgtacgc caacctgcga ccctgccagc tgctgtcgcc caagctcgcc   1860
gatctctccc ccatccgaaa cgttgagggc accgacttca tcattgtccg agagctcgtc   1920
ggaggtatct actttggaga gcgaaaggag gatgacggat ctggcgtcgc ttccgacacc   1980
gagacctact ccgttcctga ggttgagcga attgcccgaa tggccgcctt cctggccctt   2040
cagcacaacc cccctcttcc cgtgtggtct cttgacaagg ccaacgtgct ggcctcctct   2100
cgactttggc gaaagactgt cactcgagtc ctcaaggacg aattccccca gctcgagctc   2160
aaccaccagc tgatcgactc ggccgccatg atcctcatca agcagccctc caagatgaat   2220
ggtatcatca tcaccaccaa catgtttggc gatatcatct ccgacgaggc ctccgtcatc   2280
cccggttctc tgggtctgct gccctccgcc tctctggctt ctctgcccga caccaacgag   2340
gcgttcggtc tgtacgagcc ctgtcacgga tctgcccccg atctcggcaa gcagaaggtc   2400
aaccccattg ccaccattct gtctgccgcc atgatgctca agttctctct taacatgaag   2460
cccgccggtg acgctgttga ggctgccgtc aaggagtccg tcgaggctgg tatcactacc   2520
gccgatatcg gaggctcttc ctccacctcc gaggtcggag acttgttgcc aacaaggtca   2580
```

```
aggagctgct caagaaggag taagtcgttt ctacgacgca ttgatggaag gagcaaactg   2640
acgcgcctgc gggttggtct accggcaggg tccgctagtg tataagactc tataaaaagg   2700
gccctgccct gctaatgaaa tgatgattta taatttaccg gtgtagcaac cttgactaga   2760
agaagcagat tgggtgtgtt tgtagtggag gacagtggta cgttttggaa acagtcttct   2820
tgaaagtgtc ttgtctacag tatattcact cataacctca atagccaagg gtgtagtcgg   2880
tttattaaag gaagggagtt gtggctgatg tggatagata tctttaagct ggcgactgca   2940
cccaacgagt gtggtggtag cttgttagat ctgtatattc ggtaagatat attttgtggg   3000
gttttagtgg tgtttaaacc atcatctaag ggcctcaaaa ctacctcgga actgctgcgc   3060
tgatctggac accacagagg ttccgagcac tttaggttgc accaaatgtc ccaccaggtg   3120
caggcagaaa acgctggaac agcgtgtaca gtttgtctta acaaaaagtg agggcgctga   3180
ggtcgagcag ggtggtgtga cttgttatag cctttagagc tgcgaaagcg cgtatggatt   3240
tggctcatca ggccagattg agggtctgtg gacacatgtc atgttagtgt acttcaatcg   3300
ccccctggat atagccccga caataggccg tggcctcatt tttttgcctt ccgcacattt   3360
ccattgctcg gtacccacac cttgcttctc ctgcacttgc caaccttaat actggtttac   3420
attgaccaac atcttacaag cggggggctt gtctagggta tatataaaca gtggctctcc   3480
caatcggttg ccagtctctt ttttcctttc tttccccaca gattcgaaat ctaaactaca   3540
catcacacca tggcctcctc ggaggacgtc atcaaggagt tcatgcgatt caaggtccga   3600
atggaaggct ccgtgaacgg tcacgagttt gagattgagg gagagggtga aggccgaccc   3660
tacgaaggca cccagaccgc gaagctgaag gtgaccaagg gtggacccct gcccttcgcc   3720
tgggacattc tgtctcctca gtttcagtac ggttctaagg tgtacgtgaa gcaccctgct   3780
gacattcccg actacaagaa actttccttt cccgagggct tcaagtggga gcgagttatg   3840
aacttcgagg atggcggtgt cgttaccgtt actcaggact cctcgctcca ggacggctcg   3900
ttcatctaca aggttaagtt catcggtgtc aacttcccta gcgatggacc cgtcatgcaa   3960
aagaaaacta tgggatggga agcctctaca gagcggctgt accctcgaga cggagtgttg   4020
aagggcgaga ttcacaaggc cctgaagctc aaggacggtg gacactatct cgttgagttt   4080
aagtctatct acatggcaaa gaaacccgtg cagcttccag gctactatta cgtcgattcc   4140
aagctcgata tcaccagcca taatgaggac tacactattg tcgaacagta cgagcgtgct   4200
gagggaagac accatctgtt tctttaagcg gccgcaagtg tggatgggga agtgagtgcc   4260
cggttctgtg tgcacaattg gcaatccaag atggatggat tcaacacagg gatatagcga   4320
gctacgtggt ggtgcgagga tatagcaacg gatatttatg tttgacactt gagaatgtac   4380
gatacaagca ctgtccaagt acaatactaa acatactgta catactcata ctcgtacccg   4440
ggcaacggtt tcacttgagt gcagtggcta gtgctcttac tcgtacagtg tgcaatactg   4500
cgtatcatag tctttgatgt atatcgtatt cattcatgtt agttgcgtac gggcgtcgtt   4560
gcttgtgtga tttttgagga cccatccctt tggtatataa gtatactctg gggttaaggt   4620
tgcccgtgta gtctaggtta tagttttcat gtgaaatacc gagagccgag ggagaataaa   4680
cgggggtatt tggacttgtt tttttcgcgg aaaagcgtcg aatcaaccct gcgggccttg   4740
caccatgtcc acgacgtgtt tctcgcccca attcgcccct tgcacgtcaa aattaggcct   4800
ccatctagac ccctccataa catgtgactg tggggaaaag tataagggaa accatgcaac   4860
catagacgac gtgaaagacg gggaggaacc aatggaggcc aaagaaatgg ggtagcaaca   4920
gtccaggaga cagacaagga gacaaggaga gggcgcccga aagatcggaa aaacaaacat   4980
```

```
gtccaattgg ggcagtgacg gaaacgacac ggacacttca gtacaatgga ccgaccatct   5040

ccaagccagg gttattccgg tatcaccttg gccgtaacct cccgctggta cctgatattg   5100

tacacgttca cattcaatat actttcagct acaataagag aggctgtttg tcgggcatgt   5160

gtgtccgtcg tatggggtga tgtccgaggg cgaaattcgc tacaagctta actctggcgc   5220

ttgtccagta tgaatagaca agtcaagacc agtggtgcca tgattgacag ggaggtacaa   5280

gacttcgata ctcgagcatt actcggactt gtggcgattg aacagacggg cgatcgcttc   5340

tcccccgtat tgccgg                                                   5356
```

<210> SEQ ID NO 134
<211> LENGTH: 38
<212> TYPE: DNA
<213> ORGANISM: Artificial Sequence
<220> FEATURE:
<223> OTHER INFORMATION: HY026

<400> SEQUENCE: 134

```
gcgcgtttaa accatcatct aagggcctca aaactacc                             38
```

<210> SEQ ID NO 135
<211> LENGTH: 38
<212> TYPE: DNA
<213> ORGANISM: Artificial Sequence
<220> FEATURE:
<223> OTHER INFORMATION: HY027

<400> SEQUENCE: 135

```
gagagcggcc gcttaaagaa acagatggtg tcttccct                             38
```

<210> SEQ ID NO 136
<211> LENGTH: 11952
<212> TYPE: DNA
<213> ORGANISM: Artificial Sequence
<220> FEATURE:
<223> OTHER INFORMATION: pRF169

<400> SEQUENCE: 136

```
catggacaag aaatactcca tcggcctgga cattggaacc aactctgtcg gctgggctgt     60

catcaccgac gagtacaagg tgccctccaa gaaattcaag gtcctcggaa acaccgatcg    120

acactccatc aagaaaaacc tcattggtgc cctgttgttc gattctggcg agactgccga    180

agctaccaga ctcaagcgaa ctgctcggcg acgttacacc cgacggaaga accgaatctg    240

ctacctgcag gagatctttt ccaacgagat ggccaaggtg gacgattcgt tctttcatcg    300

actggaggaa tccttcctcg tcgaggaaga caagaaacac gagcgtcatc ccatctttgg    360

caacattgtg gacgaggttg cttaccacga gaagtatcct accatctacc atctccgaaa    420

gaaactcgtc gattccaccg acaaggcgga tctcagactt atctacctcg ctctggcaca    480

catgatcaag tttcgaggtc atttcctcat cgagggcgat ctcaatcccg acaacagcga    540

tgtggacaag ctgttcattc agctcgttca gacctacaac cagctgttcg aggaaaaccc    600

catcaatgcc tccggagtcg atgcaaaggc catcttgtct gctcgactct cgaagagcag    660

acgactggag aacctcattg cccaacttcc tggcgagaaa aagaacggac tgtttggcaa    720

cctcattgcc ctttctcttg gtctcacacc caacttcaag tccaacttcg atctggcgga    780

ggacgccaag ctccagctgt ccaaggacac ctacgacgat gacctcgaca acctgcttgc    840

acagattggc gatcagtacg ccgacctgtt tctcgctgcc aagaaccttt cggatgctat    900
```

-continued

```
tctcttgtct gacattctgc gagtcaacac cgagatcaca aaggctcccc tttctgcctc    960
catgatcaag cgatacgacg agcaccatca ggatctcaca ctgctcaagg ctcttgtccg   1020
acagcaactg cccgagaagt acaaggagat ctttttcgat cagtcgaaga acggctacgc   1080
tggatacatc gacggcggag cctctcagga agagttctac aagttcatca agccaattct   1140
cgagaagatg gacggaaccg aggaactgct tgtcaagctc aatcgagagg atctgcttcg   1200
gaagcaacga accttcgaca acggcagcat tcctcatcag atccacctcg gtgagctgca   1260
cgccattctt cgacgtcagg aagacttcta cccctttctc aaggacaacc gagagaagat   1320
cgagaagatt cttacctttc gaatccccta ctatgttggt cctcttgcca gaggaaactc   1380
tcgatttgct tggatgactc gaaagtccga ggaaaccatc actccctgga acttcgagga   1440
agtcgtggac aagggtgcct ctgcacagtc cttcatcgag cgaatgacca acttcgacaa   1500
gaatctgccc aacgagaagg ttcttcccaa gcattcgctg ctctacgagt actttacagt   1560
ctacaacgaa ctcaccaaag tcaagtacgt taccgaggga atgcgaaagc ctgccttctt   1620
gtctggcgaa cagaagaaag ccattgtcga tctcctgttc aagaccaacc gaaaggtcac   1680
tgttaagcag ctcaaggagg actacttcaa gaaaatcgag tgtttcgaca gcgtcgagat   1740
ttccggagtt gaggaccgat tcaacgcctc tttgggcacc tatcacgatc tgctcaagat   1800
tatcaaggac aaggattttc tcgacaacga ggaaaacgag gacattctgg aggacatcgt   1860
gctcactctt accctgttcg aagatcggga gatgatcgag gaacgactca agacatacgc   1920
tcacctgttc gacgacaagg tcatgaaaca actcaagcga cgtagataca ccggctgggg   1980
aagactttcg cgaaagctca tcaacggcat cagagacaag cagtccggaa agaccattct   2040
ggactttctc aagtccgatg gctttgccaa ccgaaacttc atgcagctca ttcacgacga   2100
ttctcttacc ttcaaggagg acatccagaa ggcacaagtg tccggtcagg gcgacagctt   2160
gcacgaacat attgccaacc tggctggttc gccagccatc aagaaaggca ttctccagac   2220
tgtcaaggtt gtcgacgagc tggtgaaggt catgggacgt cacaagcccg agaacattgt   2280
gatcgagatg gccagagaga accagacaac tcaaaagggt cagaaaaact cgcgagagcg   2340
gatgaagcga atcgaggaag gcatcaagga gctgggatcc cagattctca aggagcatcc   2400
cgtcgagaac actcaactgc agaacgagaa gctgtatctc tactatctgc agaatggtcg   2460
agacatgtac gtggatcagg aactggacat caatcgtctc agcgactacg atgtggacca   2520
cattgtccct caatcctttc tcaaggacga ttctatcgac aacaaggtcc ttacacgatc   2580
cgacaagaac agaggcaagt cggacaacgt tcccagcgaa gaggtggtca aaaagatgaa   2640
gaactactgg cgacagctgc tcaacgccaa gctcattacc cagcgaaagt tcgacaatct   2700
taccaaggcc gagcgaggcg gtctgtccga gctcgacaag gctggcttca tcaagcgtca   2760
actcgtcgag accagacaga tcacaaagca cgtcgcacag attctcgatt ctcggatgaa   2820
caccaagtac gacgagaacg acaagctcat ccgagaggtc aaggtgatta ctctcaagtc   2880
caaactggtc tccgatttcc gaaaggactt tcagttctac aaggtgcgag agatcaacaa   2940
ttaccaccat gcccacgatg cttacctcaa cgccgtcgtt ggcactgcgc tcatcaagaa   3000
ataccccaag ctcgaaagcg agttcgttta cggcgattac aaggtctacg acgttcgaaa   3060
gatgattgcc aagtccgaac aggagattgg caaggctact gccaagtact tcttttactc   3120
caacatcatg aactttttca agaccgagat caccttggcc aacggagaga ttcgaaagag   3180
accacttatc gagaccaacg gcgaaactgg agagatcgtg tgggacaagg gtcgagactt   3240
tgcaaccgtg cgaaaggttc tgtcgatgcc tcaggtcaac atcgtcaaga aaaccgaggt   3300
```

```
tcagactggc ggattctcca aggagtcgat tctgcccaag cgaaactccg acaagctcat   3360
cgctcgaaag aaagactggg atcccaagaa atacggtggc ttcgattctc ctaccgtcgc   3420
ctattccgtg cttgtcgttg cgaaggtcga gaagggcaag tccaaaaagc tcaagtccgt   3480
caaggagctg ctcggaatta ccatcatgga gcgatcgagc ttcgagaaga atcccatcga   3540
cttcttggaa gccaagggtt acaaggaggt caagaaagac ctcattatca agctgcccaa   3600
gtactctctg ttcgaactgg agaacggtcg aaagcgtatg ctcgcctccg ctggcgagct   3660
gcagaaggga aacgagcttg ccttgccttc gaagtacgtc aactttctct atctggcttc   3720
tcactacgag aagctcaagg gttctcccga ggacaacgaa cagaagcaac tcttcgttga   3780
gcagcacaaa cattacctcg acgagattat cgagcagatt tccgagtttt cgaagcgagt   3840
catcctggct gatgccaact tggacaaggt gctctctgcc tacaacaagc atcgggacaa   3900
acccattcga gaacaggcgg agaacatcat tcacctgttt actcttacca acctgggtgc   3960
tcctgcagct ttcaagtact tcgataccac tatcgaccga aagcggtaca catccaccaa   4020
ggaggttctc gatgccaccc tgattcacca gtccatcact ggcctgtacg agacccgaat   4080
cgacctgtct cagcttggtg gcgactccag agccgatccc aagaaaaagc gaaaggtcta   4140
agcggccgca agtgtggatg gggaagtgag tgcccggttc tgtgtgcaca attggcaatc   4200
caagatggat ggattcaaca cagggatata gcgagctacg tggtggtgcg aggatatagc   4260
aacggatatt tatgtttgac acttgagaat gtacgataca agcactgtcc aagtacaata   4320
ctaaacatac tgtacatact catactcgta cccgggcaac ggtttcactt gagtgcagtg   4380
gctagtgctc ttactcgtac agtgtgcaat actgcgtatc atagtctttg atgtatatcg   4440
tattcattca tgttagttgc gtacgagccg gaagcataaa gtgtaaagcc tggggtgcct   4500
aatgagtgag ctaactcaca ttaattgcgt tgcgctcact gcccgctttc cagtcgggaa   4560
acctgtcgtg ccagctgcat taatgaatcg gccaacgcgc ggggagaggc ggtttgcgta   4620
ttgggcgctc ttccgcttcc tcgctcactg actcgctgcg ctcggtcgtt cggctgcggc   4680
gagcggtatc agctcactca aaggcggtaa tacggttatc cacagaatca ggggataacg   4740
caggaaagaa catgtgagca aaaggccagc aaaaggccag gaaccgtaaa aaggccgcgt   4800
tgctggcgtt tttccatagg ctccgccccc ctgacgagca tcacaaaaat cgacgctcaa   4860
gtcagaggtg gcgaaacccg acaggactat aaagatacca ggcgtttccc cctggaagct   4920
ccctcgtgcg ctctcctgtt ccgaccctgc cgcttaccgg atacctgtcc gcctttctcc   4980
cttcgggaag cgtggcgctt tctcatagct cacgctgtag gtatctcagt tcggtgtagg   5040
tcgttcgctc caagctgggc tgtgtgcacg aaccccccgt tcagcccgac cgctgcgcct   5100
tatccggtaa ctatcgtctt gagtccaacc cggtaagaca cgacttatcg ccactggcag   5160
cagccactgg taacaggatt agcagagcga ggtatgtagg cggtgctaca gagttcttga   5220
agtggtggcc taactacggc tacactagaa ggacagtatt tggtatctgc gctctgctga   5280
agccagttac cttcggaaaa agagttggta gctcttgatc cggcaaacaa accaccgctg   5340
gtagcggtgg tttttttgtt tgcaagcagc agattacgcg cagaaaaaaa ggatctcaag   5400
aagatccttt gatcttttct acggggtctg acgctcagtg gaacgaaaac tcacgttaag   5460
ggattttggt catgagatta tcaaaaagga tcttcaccta gatcctttta aattaaaaat   5520
gaagttttaa atcaatctaa agtatatatg agtaaacttg gtctgacagt taccaatgct   5580
taatcagtga ggcacctatc tcagcgatct gtctatttcg ttcatccata gttgcctgac   5640
```

-continued

```
tccccgtcgt gtagataact acgatacggg agggcttacc atctggcccc agtgctgcaa   5700
tgataccgcg agacccacgc tcaccggctc cagatttatc agcaataaac cagccagccg   5760
gaagggccga gcgcagaagt ggtcctgcaa ctttatccgc ctccatccag tctattaatt   5820
gttgccggga agctagagta agtagttcgc cagttaatag tttgcgcaac gttgttgcca   5880
ttgctacagg catcgtggtg tcacgctcgt cgtttggtat ggcttcattc agctccggtt   5940
cccaacgatc aaggcgagtt acatgatccc ccatgttgtg caaaaaagcg gttagctcct   6000
tcggtcctcc gatcgttgtc agaagtaagt tggccgcagt gttatcactc atggttatgg   6060
cagcactgca taattctctt actgtcatgc catccgtaag atgcttttct gtgactggtg   6120
agtactcaac caagtcattc tgagaatagt gtatgcggcg accgagttgc tcttgcccgg   6180
cgtcaatacg ggataatacc gcgccacata gcagaacttt aaaagtgctc atcattggaa   6240
aacgttcttc ggggcgaaaa ctctcaagga tcttaccgct gttgagatcc agttcgatgt   6300
aacccactcg tgcacccaac tgatcttcag catcttttac tttcaccagc gtttctgggt   6360
gagcaaaaac aggaaggcaa aatgccgcaa aaaagggaat aagggcgaca cggaaatgtt   6420
gaatactcat actcttcctt tttcaatatt attgaagcat ttatcagggt tattgtctca   6480
tgagcggata catatttgaa tgtatttaga aaaataaaca aataggggtt ccgcgcacat   6540
ttccccgaaa agtgccacct gacgcgccct gtagcggcgc attaagcgcg gcgggtgtgg   6600
tggttacgcg cagcgtgacc gctacacttg ccagcgccct agcgcccgct cctttcgctt   6660
tcttcccttc ctttctcgcc acgttcgccg gctttccccg tcaagctcta aatcgggggc   6720
tccctttagg gttccgattt agtgctttac ggcacctcga ccccaaaaaa cttgattagg   6780
gtgatggttc acgtagtggg ccatcgccct gatagacggt ttttcgccct ttgacgttgg   6840
agtccacgtt ctttaatagt ggactcttgt tccaaactgg aacaacactc aaccctatct   6900
cggtctattc ttttgattta taagggattt tgccgatttc ggcctattgg ttaaaaaatg   6960
agctgattta acaaaaattt aacgcgaatt ttaacaaaat attaacgctt acaatttcca   7020
ttcgccattc aggctgcgca actgttggga agggcgatcg gtgcgggcct cttcgctatt   7080
acgccagctg gcgaaagggg gatgtgctgc aaggcgatta agttgggtaa cgccagggtt   7140
ttcccagtca cgacgttgta aaacgacggc cagtgaattg taatacgact cactataggg   7200
cgaattgggt accgggcccc ccctcgaggt cgatggtgtc gataagcttg atatcgaatt   7260
catgtcacac aaaccgatct tcgcctcaag gaaacctaat tctacatccg agagactgcc   7320
gagatccagt ctacactgat taattttcgg gccaataatt taaaaaaatc gtgttatata   7380
atattatatg tattatatat atacatcatg atgatactga cagtcatgtc ccattgctaa   7440
atagacagac tccatctgcc gcctccaact gatgttctca atatttaagg ggtcatctcg   7500
cattgtttaa taataaacag actccatcta ccgcctccaa atgatgttct caaaatatat   7560
tgtatgaact tatttttatt acttagtatt attagacaac ttacttgctt tatgaaaaac   7620
acttcctatt taggaaacaa tttataatgg cagttcgttc atttaacaat ttatgtagaa   7680
taaatgttat aaatgcgtat gggaaatctt aaatatggat agcataaatg atatctgcat   7740
tgcctaattc gaaatcaaca gcaacgaaaa aaatcccttg tacaacataa atagtcatcg   7800
agaaatatca actatcaaag aacagctatt cacacgttac tattgagatt attattggac   7860
gagaatcaca cactcaactg tctttctctc ttctagaaat acaggtacaa gtatgtacta   7920
ttctcattgt tcatacttct agtcatttca tcccacatat tccttggatt tctctccaat   7980
gaatgacatt ctatcttgca aattcaacaa ttataataag atataccaaa gtagcggtat   8040
```

```
agtggcaatc aaaaagcttc tctggtgtgc ttctcgtatt tatttttatt ctaatgatcc   8100
attaaaggta tatatttatt tcttgttata taatcctttt gtttattaca tgggctggat   8160
acataaaggt attttgattt aatttttttgc ttaaattcaa tccccccctcg ttcagtgtca   8220
actgtaatgg taggaaatta ccatactttt gaagaagcaa aaaaaatgaa agaaaaaaaa   8280
aatcgtattt ccaggttaga cgttccgcag aatctagaat gcggtatgcg gtacattgtt   8340
cttcgaacgt aaaagttgcg ctccctgaga tattgtacat ttttgctttt acaagtacaa   8400
gtacatcgta caactatgta ctactgttga tgcatccaca acagtttgtt ttgttttttt   8460
ttgttttttt tttttctaat gattcattac cgctatgtat acctacttgt acttgtagta   8520
agccgggtta ttggcgttca attaatcata gacttatgaa tctgcacggt gtgcgctgcg   8580
agttactttt agcttatgca tgctacttgg gtgtaatatt gggatctgtt cggaaatcaa   8640
cggatgctca atcgatcgcc agcaacgcgg ccttagacat aaaaaacaaa aaaaaaaagc   8700
accgactcgg tgccactttt tcaagttgat aacggactag ccttatttta acttgctatt   8760
tctagctcta aaacgcaggt gtaaaaataa aaaggcctgc gattaccagc aggcctgtta   8820
ttaacctaag ccttaggacg cttcacgcca tacttggaac gagcctgctt acggtcttta   8880
acgccggagc agtcaagcgc accacgtacg gtgtggtaac gaacacccgg gaggtcttta   8940
acacgaccgc cacggatcag gatcacggag tgctcctgca ggttgtgacc ttcaccaccg   9000
atgtaggaag tcacttcgaa accgttagtc agacgaacac ggcatacttt acgcagcgcg   9060
gagttcggtt ttttaggagt ggtagtatat acacgagtac atacgccacg tttttgcggg   9120
catgcttcca gcgcaggcac gttgcttttc gcaactttgc gagcacgtgg tttgcgtacc   9180
agctggttaa ctgttgccat taaatagctc ctggttttag cttttgcttc gtaaacacgt   9240
aataaaacgt cctcacacaa tatgaggacg ccgaatttag ggcgatgccg aaaaggtgtc   9300
aagaaatata caacgatccc gccatcggcg cgcccacctg ctacgcatgg ttgatgtgtg   9360
tttaattcaa gaatgaatat agagaagaga agaagaaaaa agattcaatt gagccggcga   9420
tgcagaccct tatataaatg ttgccttgga cagacggagc aagcccgccc aaacctacgt   9480
tcggtataat atgttaagct ttttaacaca aaggtttggc ttggggtaac ctgatgtggt   9540
gcaaaagacc gggcgttggc gagccattgc gcgggcgaat ggggtcgtga ctcgtctcaa   9600
attcgagggc gtgcctcaat tcgtgccccc gtggcttttt cccgccgttt ccgccccgtt   9660
tgcaccactg cagccgcttc tttggttcgg acaccttgct gcgagctagg tgccttgtgc   9720
tacttaaaaa gtggcctccc aacaccaaca tgacatgagt gcgtgggcca agacacgttg   9780
gcggggtcgc agtcggctca atggcccgga aaaaacgctg ctggagctgg ttcggacgca   9840
gtccgccgcg gcgtatggat atccgcaagg ttccatagcg ccattgccct ccgtcggcgt   9900
ctatcccgca accttaatta agtcatacac aagtcagctt tcttcgagcc tcatataagt   9960
ataagtagtt caacgtatta gcactgtacc cagcatctcc gtatcgagaa acacaacaac  10020
atgccccatt ggacagatca tgcggataca caggttgtgc agtatcatac atactcgatc  10080
agacaggtcg tctgaccatc atacaagctg aacaagcgct ccatacttgc acgctctcta  10140
tatacacagt taaattacat atccatagtc taacctctaa cagttaatct tctggtaagc  10200
ctcccagcca gccttctggt atcgcttggc ctcctcaata ggatctcggt tctggccgta  10260
cagacctcgg ccgacaatta tgatatccgt tccggtagac atgacatcct caacagttcg  10320
gtactgctgt ccgagagcgt ctcccttgtc gtcaagaccc accccggggg tcagaataag  10380
```

ccagtcctca gagtcgccct taggtcggtt ctgggcaatg aagccaacca caaactcggg 10440
gtcggatcgg gcaagctcaa tggtctgctt ggagtactcg ccagtggcca gagagccctt 10500
gcaagacagc tcggccagca tgagcagacc tctggccagc ttctcgttgg gagaggggac 10560
taggaactcc ttgtactggg agttctcgta gtcagagacg tcctccttct tctgttcaga 10620
gacagtttcc tcggcaccag ctcgcaggcc agcaatgatt ccggttccgg gtacaccgtg 10680
ggcgttggtg atatcggacc actcggcgat tcggtgacac cggtactggt gcttgacagt 10740
gttgccaata tctgcgaact ttctgtcctc gaacaggaag aaaccgtgct taagagcaag 10800
ttccttgagg gggagcacag tgccggcgta ggtgaagtcg tcaatgatgt cgatatgggt 10860
tttgatcatg cacacataag gtccgacctt atcggcaagc tcaatgagct ccttggtggt 10920
ggtaacatcc agagaagcac acaggttggt tttcttggct gccacgagct tgagcactcg 10980
agcggcaaag gcggacttgt ggacgttagc tcgagcttcg taggagggca ttttggtggt 11040
gaagaggaga ctgaaataaa tttagtctgc agaacttttt atcggaacct tatctggggc 11100
agtgaagtat atgttatggt aatagttacg agttagttga acttatagat agactggact 11160
atacggctat cggtccaaat tagaaagaac gtcaatggct ctctgggcgt cgcctttgcc 11220
gacaaaaatg tgatcatgat gaaagccagc aatgacgttg cagctgatat tgttgtcggc 11280
caaccgcgcc gaaaacgcag ctgtcagacc cacagcctcc aacgaagaat gtatcgtcaa 11340
agtgatccaa gcacactcat agttggagtc gtactccaaa ggcggcaatg acgagtcaga 11400
cagatactcg tcgacgttta aaccatcatc taagggcctc aaaactacct cggaactgct 11460
gcgctgatct ggacaccaca gaggttccga gcactttagg ttgcaccaaa tgtcccacca 11520
ggtgcaggca gaaaacgctg gaacagcgtg tacagtttgt cttaacaaaa agtgagggcg 11580
ctgaggtcga gcagggtggt gtgacttgtt atagccttta gagctgcgaa agcgcgtatg 11640
gatttggctc atcaggccag attgagggtc tgtggacaca tgtcatgtta gtgtacttca 11700
atcgccccct ggatatagcc ccgacaatag gccgtggcct catttttttg ccttccgcac 11760
atttccattg ctcggtaccc acaccttgct tctcctgcac ttgccaacct taatactggt 11820
ttacattgac caacatctta caagcggggg gcttgtctag ggtatatata aacagtggct 11880
ctcccaatcg gttgccagtc tctttttcc tttctttccc cacagattcg aaatctaaac 11940
tacacatcac ac 11952

<210> SEQ ID NO 137
<211> LENGTH: 564
<212> TYPE: DNA
<213> ORGANISM: Yarrowia lipolytica
<220> FEATURE:
<221> NAME/KEY: misc_feature
<222> LOCATION: (1)..(564)
<223> OTHER INFORMATION: GPD Promoter

<400> SEQUENCE: 137
ggttgcggga tagacgccga cggagggcaa tggcgctatg gaaccttgcg gatatccata 60
cgccgcggcg gactgcgtcc gaaccagctc cagcagcgtt ttttccgggc cattgagccg 120
actgcgaccc cgccaacgtg tcttggccca cgcactcatg tcatgttggt gttgggaggc 180
cactttttaa gtagcacaag gcacctagct cgcagcaagg tgtccgaacc aaagaagcgg 240
ctgcagtggt gcaaacgggg cggaaacggc gggaaaaagc cacgggggca cgaattgagg 300
cacgccctcg aatttgagac gagtcacgac cccattcgcc cgcgcaatgg ctcgccaacg 360
cccggtcttt tgcaccacat caggttaccc caagccaaac ctttgtgtta aaaagcttaa 420

```
catattatac cgaacgtagg tttgggcggg cttgctccgt ctgtccaagg caacatttat    480

ataagggtct gcatcgccgg ctcaattgaa tcttttttct tcttctcttc tctatattca    540

ttcttgaatt aaacacacat caac                                           564
```

<210> SEQ ID NO 138
<211> LENGTH: 1271
<212> TYPE: DNA
<213> ORGANISM: Artificial sequence
<220> FEATURE:
<223> OTHER INFORMATION: GPD promoter-counterselectable marker-CER-
terminator

<400> SEQUENCE: 138

```
ttaattaagg ttgcgggata gacgccgacg gagggcaatg gcgctatgga accttgcgga     60

tatccatacg ccgcggcgga ctgcgtccga accagctcca gcagcgtttt ttccgggcca    120

ttgagccgac tgcgaccccg ccaacgtgtc ttggcccacg cactcatgtc atgttggtgt    180

tgggaggcca ctttttaagt agcacaaggc acctagctcg cagcaaggtg tccgaaccaa    240

agaagcggct gcagtggtgc aaacggggcg gaaacggcgg gaaaaagcca cgggggcacg    300

aattgaggca cgccctcgaa tttgagacga gtcacgaccc cattcgcccg cgcaatggct    360

cgccaacgcc cggtcttttg caccacatca ggttacccca agccaaacct ttgtgttaaa    420

aagcttaaca tattataccg aacgtaggtt tgggcgggct tgctccgtct gtccaaggca    480

acatttatat aagggtctgc atcgccggct caattgaatc ttttttcttc ttctcttctc    540

tatattcatt cttgaattaa acacacatca accatgcgta gcaggtgggc gcgccgatgg    600

cgggatcgtt gtatatttct tgacaccttt tcggcatcgc cctaaattcg gcgtcctcat    660

attgtgtgag gacgttttat tacgtgttta cgaagcaaaa gctaaaacca ggagctattt    720

aatggcaaca gttaaccagc tggtacgcaa accacgtgct cgcaaagttg cgaaaagcaa    780

cgtgcctgcg ctggaagcat gcccgcaaaa acgtggcgta tgtactcgtg tatatactac    840

cactcctaaa aaaccgaact ccgcgctgcg taaagtatgc cgtgttcgtc tgactaacgg    900

tttcgaagtg acttcctaca tcggtggtga aggtcacaac ctgcaggagc actccgtgat    960

cctgatccgt ggcggtcgtg ttaaagacct cccgggtgtt cgttaccaca ccgtacgtgg   1020

tgcgcttgac tgctccggcg ttaaagaccg taagcaggct cgttccaagt atggcgtgaa   1080

gcgtcctaag gcttaggtta ataacaggcc tgctggtaat cgcaggcctt tttattttta   1140

cacctgcgtt ttagagctag aaatagcaag ttaaaataag gctagtccgt tatcaacttg   1200

aaaaagtggc accgagtcgg tgcttttttt ttttgttttt tatgtctaag gccgcgttgc   1260

tggcgatcga t                                                        1271
```

<210> SEQ ID NO 139
<211> LENGTH: 23
<212> TYPE: DNA
<213> ORGANISM: Artificial sequence
<220> FEATURE:
<223> OTHER INFORMATION: ds-temp-1 target site

<400> SEQUENCE: 139

```
tcagtttcag tacggttcta agg                                             23
```

<210> SEQ ID NO 140
<211> LENGTH: 23
<212> TYPE: DNA
<213> ORGANISM: Artificial sequence
<220> FEATURE:
<223> OTHER INFORMATION: ds-temp-2 target site

<400> SEQUENCE: 140
cggtgtcgtt accgttactc agg 23

<210> SEQ ID NO 141
<211> LENGTH: 23
<212> TYPE: DNA
<213> ORGANISM: Artificial sequence
<220> FEATURE:
<223> OTHER INFORMATION: ds-nontemp-3 target site

<400> SEQUENCE: 141
cttggtcacc ttcagcttcg cgg 23

<210> SEQ ID NO 142
<211> LENGTH: 63
<212> TYPE: DNA
<213> ORGANISM: Artificial sequence
<220> FEATURE:
<223> OTHER INFORMATION: Hammerhead ribozyme-VT fusion
<220> FEATURE:
<221> NAME/KEY: misc_feature
<222> LOCATION: (1)..(6)
<223> OTHER INFORMATION: n is a, c, g, or t
<220> FEATURE:
<221> NAME/KEY: misc_feature
<222> LOCATION: (44)..(63)
<223> OTHER INFORMATION: n is a, c, g, or t

<400> SEQUENCE: 142
nnnnnnctga tgagtccgtg aggacgaaac gagtaagctc gtcnnnnnnn nnnnnnnnnn 60 nnn 63

<210> SEQ ID NO 143
<211> LENGTH: 63
<212> TYPE: RNA
<213> ORGANISM: Artificial sequence
<220> FEATURE:
<223> OTHER INFORMATION: Hammerhead ribozyme-VT fusion
<220> FEATURE:
<221> NAME/KEY: misc_feature
<222> LOCATION: (1)..(6)
<223> OTHER INFORMATION: n is a, c, g, or u
<220> FEATURE:
<221> NAME/KEY: misc_feature
<222> LOCATION: (44)..(63)
<223> OTHER INFORMATION: n is a, c, g, or u

<400> SEQUENCE: 143
nnnnnncuga ugaguccgug aggacgaaac gaguaagcuc gucnnnnnnn nnnnnnnnnn 60 nnn 63

<210> SEQ ID NO 144
<211> LENGTH: 75
<212> TYPE: DNA
<213> ORGANISM: Artificial sequence
<220> FEATURE:
<223> OTHER INFORMATION: ds-temp-1F

<400> SEQUENCE: 144
catgcgtaaa ctgactgatg agtccgtgag gacgaaacga gtaagctcgt ctcagtttca 60
gtacggttct agttt 75

<210> SEQ ID NO 145

<211> LENGTH: 75
<212> TYPE: DNA
<213> ORGANISM: Artificial sequence
<220> FEATURE:
<223> OTHER INFORMATION: 145 ds-temp-1R

<400> SEQUENCE: 145
tctaaaacta gaaccgtact gaaactgaga cgagcttact cgtttcgtcc tcacggactc 60
atcagtcagt ttacg 75

<210> SEQ ID NO 146
<211> LENGTH: 75
<212> TYPE: DNA
<213> ORGANISM: Artificial sequence
<220> FEATURE:
<223> OTHER INFORMATION: 146 ds-temp-2F

<400> SEQUENCE: 146
catgcgtaac accgctgatg agtccgtgag gacgaaacga gtaagctcgt ccggtgtcgt 60
taccgttact cgttt 75

<210> SEQ ID NO 147
<211> LENGTH: 75
<212> TYPE: DNA
<213> ORGANISM: Artificial sequence
<220> FEATURE:
<223> OTHER INFORMATION: ds-temp-2R

<400> SEQUENCE: 147
tctaaaacga gtaacggtaa cgacaccgga cgagcttact cgtttcgtcc tcacggactc 60
atcagcggtg ttacg 75

<210> SEQ ID NO 148
<211> LENGTH: 75
<212> TYPE: DNA
<213> ORGANISM: Artificial sequence
<220> FEATURE:
<223> OTHER INFORMATION: ds-nontemp-1F

<400> SEQUENCE: 148
catgcgtaac caggctgatg agtccgtgag gacgaaacga gtaagctcgt ccttggtcac 60
cttcagcttc ggttt 75

<210> SEQ ID NO 149
<211> LENGTH: 75
<212> TYPE: DNA
<213> ORGANISM: Artificial sequence
<220> FEATURE:
<223> OTHER INFORMATION: ds-nontemp-1R

<400> SEQUENCE: 149
tctaaaaccg aagctgaagg tgaccaagga cgagcttact cgtttcgtcc tcacggactc 60
atcagcctgg ttacg 75

<210> SEQ ID NO 150
<211> LENGTH: 11448
<212> TYPE: DNA
<213> ORGANISM: Artificial sequence
<220> FEATURE:
<223> OTHER INFORMATION: pRF296

<400> SEQUENCE: 150
catggacaag aaatactcca tcggcctgga cattggaacc aactctgtcg gctgggctgt 60

-continued

```
catcaccgac gagtacaagg tgccctccaa gaaattcaag gtcctcggaa acaccgatcg    120
acactccatc aagaaaaacc tcattggtgc cctgttgttc gattctggcg agactgccga    180
agctaccaga ctcaagcgaa ctgctcggcg acgttacacc cgacggaaga accgaatctg    240
ctacctgcag gagatctttt ccaacgagat ggccaaggtg gacgattcgt tctttcatcg    300
actggaggaa tccttcctcg tcgaggaaga caagaaacac gagcgtcatc ccatctttgg    360
caacattgtg gacgaggttg cttaccacga gaagtatcct accatctacc atctccgaaa    420
gaaactcgtc gattccaccg acaaggcgga tctcagactt atctacctcg ctctggcaca    480
catgatcaag tttcgaggtc atttcctcat cgagggcgat ctcaatcccg acaacagcga    540
tgtggacaag ctgttcattc agctcgttca gacctacaac cagctgttcg aggaaaaccc    600
catcaatgcc tccggagtcg atgcaaaggc catcttgtct gctcgactct cgaagagcag    660
acgactggag aacctcattg cccaacttcc tggcgagaaa aagaacggac tgtttggcaa    720
cctcattgcc ctttctcttg gtctcacacc caacttcaag tccaacttcg atctggcgga    780
ggacgccaag ctccagctgt ccaaggacac ctacgacgat gacctcgaca acctgcttgc    840
acagattggc gatcagtacg ccgacctgtt tctcgctgcc aagaaccttt cggatgctat    900
tctcttgtct gacattctgc gagtcaacac cgagatcaca aaggctcccc tttctgcctc    960
catgatcaag cgatacgacg agcaccatca ggatctcaca ctgctcaagg ctcttgtccg   1020
acagcaactg cccgagaagt acaaggagat ctttttcgat cagtcgaaga acggctacgc   1080
tggatacatc gacggcggag cctctcagga agagttctac aagttcatca agccaattct   1140
cgagaagatg gacggaaccg aggaactgct tgtcaagctc aatcgagagg atctgcttcg   1200
gaagcaacga accttcgaca acggcagcat tcctcatcag atccacctcg gtgagctgca   1260
cgccattctt cgacgtcagg aagacttcta cccctttctc aaggacaacc gagagaagat   1320
cgagaagatt cttacctttc gaatccccta ctatgttggt cctcttgcca gaggaaactc   1380
tcgatttgct tggatgactc gaaagtccga ggaaaccatc actccctgga acttcgagga   1440
agtcgtggac aagggtgcct ctgcacagtc cttcatcgag cgaatgacca acttcgacaa   1500
gaatctgccc aacgagaagg ttcttcccaa gcattcgctg ctctacgagt actttacagt   1560
ctacaacgaa ctcaccaaag tcaagtacgt taccgaggga atgcgaaagc ctgccttctt   1620
gtctggcgaa cagaagaaag ccattgtcga tctcctgttc aagaccaacc gaaaggtcac   1680
tgttaagcag ctcaaggagg actacttcaa gaaaatcgag tgtttcgaca gcgtcgagat   1740
ttccggagtt gaggaccgat tcaacgcctc tttgggcacc tatcacgatc tgctcaagat   1800
tatcaaggac aaggattttc tcgacaacga ggaaaacgag gacattctgg aggacatcgt   1860
gctcactctt accctgttcg aagatcggga gatgatcgag gaacgactca agacatacgc   1920
tcacctgttc gacgacaagg tcatgaaaca actcaagcga cgtagataca ccggctgggg   1980
aagactttcg cgaaagctca tcaacggcat cagagacaag cagtccggaa agaccattct   2040
ggactttctc aagtccgatg gctttgccaa ccgaaacttc atgcagctca ttcacgacga   2100
ttctcttacc ttcaaggagg acatccagaa ggcacaagtg tccggtcagg gcgacagctt   2160
gcacgaacat attgccaacc tggctggttc gccagccatc aagaaaggca ttctccagac   2220
tgtcaaggtt gtcgacgagc tggtgaaggt catgggacgt cacaagcccg agaacattgt   2280
gatcgagatg gccagagaga accagacaac tcaaaagggt cagaaaaact cgcgagagcg   2340
gatgaagcga atcgaggaag gcatcaagga gctgggatcc cagattctca aggagcatcc   2400
```

-continued

```
cgtcgagaac actcaactgc agaacgagaa gctgtatctc tactatctgc agaatggtcg   2460
agacatgtac gtggatcagg aactggacat caatcgtctc agcgactacg atgtggacca   2520
cattgtccct caatcctttc tcaaggacga ttctatcgac aacaaggtcc ttacacgatc   2580
cgacaagaac agaggcaagt cggacaacgt tcccagcgaa gaggtggtca aaaagatgaa   2640
gaactactgg cgacagctgc tcaacgccaa gctcattacc cagcgaaagt tcgacaatct   2700
taccaaggcc gagcgaggcg gtctgtccga gctcgacaag gctggcttca tcaagcgtca   2760
actcgtcgag accagacaga tcacaaagca cgtcgcacag attctcgatt ctcggatgaa   2820
caccaagtac gacgagaacg acaagctcat ccgagaggtc aaggtgatta ctctcaagtc   2880
caaactggtc tccgatttcc gaaaggactt tcagttctac aaggtgcgag agatcaacaa   2940
ttaccaccat gcccacgatg cttacctcaa cgccgtcgtt ggcactgcgc tcatcaagaa   3000
ataccccaag ctcgaaagcg agttcgttta cggcgattac aaggtctacg acgttcgaaa   3060
gatgattgcc aagtccgaac aggagattgg caaggctact gccaagtact tcttttactc   3120
caacatcatg aactttttca agaccgagat caccttggcc aacggagaga ttcgaaagag   3180
accacttatc gagaccaacg gcgaaactgg agagatcgtg tgggacaagg gtcgagactt   3240
tgcaaccgtg cgaaaggttc tgtcgatgcc tcaggtcaac atcgtcaaga aaaccgaggt   3300
tcagactggc ggattctcca aggagtcgat tctgcccaag cgaaactccg acaagctcat   3360
cgctcgaaag aaagactggg atcccaagaa atacggtggc ttcgattctc ctaccgtcgc   3420
ctattccgtg cttgtcgttg cgaaggtcga gaagggcaag tccaaaaagc tcaagtccgt   3480
caaggagctg ctcggaatta ccatcatgga gcgatcgagc ttcgagaaga atcccatcga   3540
cttcttggaa gccaagggtt acaaggaggt caagaaagac ctcattatca agctgcccaa   3600
gtactctctg ttcgaactgg agaacggtcg aaagcgtatg ctcgcctccg ctggcgagct   3660
gcagaaggga aacgagcttg ccttgccttc gaagtacgtc aactttctct atctggcttc   3720
tcactacgag aagctcaagg gttctcccga ggacaacgaa cagaagcaac tcttcgttga   3780
gcagcacaaa cattacctcg acgagattat cgagcagatt tccgagtttt cgaagcgagt   3840
catcctggct gatgccaact tggacaaggt gctctctgcc tacaacaagc atcgggacaa   3900
acccattcga gaacaggcgg agaacatcat tcacctgttt actcttacca acctgggtgc   3960
tcctgcagct ttcaagtact tcgataccac tatcgaccga aagcggtaca catccaccaa   4020
ggaggttctc gatgccaccc tgattcacca gtccatcact ggcctgtacg agacccgaat   4080
cgacctgtct cagcttggtg gcgactccag agccgatccc aagaaaaagc gaaaggtcta   4140
agcggccgca agtgtggatg gggaagtgag tgcccggttc tgtgtgcaca attggcaatc   4200
caagatggat ggattcaaca cagggatata gcgagctacg tggtggtgcg aggatatagc   4260
aacggatatt tatgtttgac acttgagaat gtacgataca agcactgtcc aagtacaata   4320
ctaaacatac tgtacatact catactcgta cccgggcaac ggtttcactt gagtgcagtg   4380
gctagtgctc ttactcgtac agtgtgcaat actgcgtatc atagtctttg atgtatatcg   4440
tattcattca tgttagttgc gtacgagccg gaagcataaa gtgtaaagcc tggggtgcct   4500
aatgagtgag ctaactcaca ttaattgcgt tgcgctcact gcccgctttc cagtcgggaa   4560
acctgtcgtg ccagctgcat taatgaatcg gccaacgcgc ggggagaggc ggtttgcgta   4620
ttgggcgctc ttccgcttcc tcgctcactg actcgctgcg ctcggtcgtt cggctgcggc   4680
gagcggtatc agctcactca aaggcggtaa tacggttatc cacagaatca ggggataacg   4740
caggaaagaa catgtgagca aaaggccagc aaaaggccag gaaccgtaaa aaggccgcgt   4800
```

-continued

```
tgctggcgtt tttccatagg ctccgccccc ctgacgagca tcacaaaaat cgacgctcaa   4860
gtcagaggtg gcgaaacccg acaggactat aaagatacca ggcgtttccc cctggaagct   4920
ccctcgtgcg ctctcctgtt ccgaccctgc cgcttaccgg atacctgtcc gcctttctcc   4980
cttcgggaag cgtggcgctt tctcatagct cacgctgtag gtatctcagt tcggtgtagg   5040
tcgttcgctc caagctgggc tgtgtgcacg aaccccccgt tcagcccgac cgctgcgcct   5100
tatccggtaa ctatcgtctt gagtccaacc cggtaagaca cgacttatcg ccactggcag   5160
cagccactgg taacaggatt agcagagcga ggtatgtagg cggtgctaca gagttcttga   5220
agtggtggcc taactacggc tacactagaa ggacagtatt tggtatctgc gctctgctga   5280
agccagttac cttcggaaaa agagttggta gctcttgatc cggcaaacaa accaccgctg   5340
gtagcggtgg tttttttgtt tgcaagcagc agattacgcg cagaaaaaaa ggatctcaag   5400
aagatccttt gatcttttct acggggtctg acgctcagtg gaacgaaaac tcacgttaag   5460
ggattttggt catgagatta tcaaaaagga tcttcaccta gatcctttta aattaaaaat   5520
gaagttttaa atcaatctaa agtatatatg agtaaacttg gtctgacagt taccaatgct   5580
taatcagtga ggcacctatc tcagcgatct gtctatttcg ttcatccata gttgcctgac   5640
tccccgtcgt gtagataact acgatacggg agggcttacc atctggcccc agtgctgcaa   5700
tgataccgcg agacccacgc tcaccggctc cagatttatc agcaataaac cagccagccg   5760
gaagggccga gcgcagaagt ggtcctgcaa ctttatccgc ctccatccag tctattaatt   5820
gttgccggga agctagagta agtagttcgc cagttaatag tttgcgcaac gttgttgcca   5880
ttgctacagg catcgtggtg tcacgctcgt cgtttggtat ggcttcattc agctccggtt   5940
cccaacgatc aaggcgagtt acatgatccc ccatgttgtg caaaaaagcg gttagctcct   6000
tcggtcctcc gatcgttgtc agaagtaagt tggccgcagt gttatcactc atggttatgg   6060
cagcactgca taattctctt actgtcatgc catccgtaag atgcttttct gtgactggtg   6120
agtactcaac caagtcattc tgagaatagt gtatgcggcg accgagttgc tcttgcccgg   6180
cgtcaatacg ggataatacc gcgccacata gcagaacttt aaaagtgctc atcattggaa   6240
aacgttcttc ggggcgaaaa ctctcaagga tcttaccgct gttgagatcc agttcgatgt   6300
aacccactcg tgcacccaac tgatcttcag catcttttac tttcaccagc gtttctgggt   6360
gagcaaaaac aggaaggcaa aatgccgcaa aaaagggaat aagggcgaca cggaaatgtt   6420
gaatactcat actcttcctt tttcaatatt attgaagcat ttatcagggt tattgtctca   6480
tgagcggata catatttgaa tgtatttaga aaaataaaca aataggggtt ccgcgcacat   6540
ttccccgaaa agtgccacct gacgcgccct gtagcggcgc attaagcgcg gcgggtgtgg   6600
tggttacgcg cagcgtgacc gctacacttg ccagcgccct agcgcccgct cctttcgctt   6660
tcttcccttc ctttctcgcc acgttcgccg gctttccccg tcaagctcta aatcgggggc   6720
tccctttagg gttccgattt agtgctttac ggcacctcga ccccaaaaaa cttgattagg   6780
gtgatggttc acgtagtggg ccatcgccct gatagacggt ttttcgccct ttgacgttgg   6840
agtccacgtt ctttaatagt ggactcttgt tccaaactgg aacaacactc aaccctatct   6900
cggtctattc ttttgattta taagggattt tgccgatttc ggcctattgg ttaaaaaatg   6960
agctgattta acaaaaattt aacgcgaatt ttaacaaaat attaacgctt acaatttcca   7020
ttcgccattc aggctgcgca actgttggga agggcgatcg gtgcgggcct cttcgctatt   7080
acgccagctg gcgaaagggg gatgtgctgc aaggcgatta agttgggtaa cgccagggtt   7140
```

```
ttcccagtca cgacgttgta aaacgacggc cagtgaattg taatacgact cactataggg   7200
cgaattgggt accgggcccc ccctcgaggt cgatggtgtc gataagcttg atatcgaatt   7260
catgtcacac aaaccgatct tcgcctcaag gaaacctaat tctacatccg agagactgcc   7320
gagatccagt ctacactgat taattttcgg gccaataatt taaaaaaatc gtgttatata   7380
atattatatg tattatatat atacatcatg atgatactga cagtcatgtc ccattgctaa   7440
atagacagac tccatctgcc gcctccaact gatgttctca atatttaagg ggtcatctcg   7500
cattgtttaa taataaacag actccatcta ccgcctccaa atgatgttct caaaatatat   7560
tgtatgaact tatttttatt acttagtatt attagacaac ttacttgctt tatgaaaaac   7620
acttcctatt taggaaacaa tttataatgg cagttcgttc atttaacaat ttatgtagaa   7680
taaatgttat aaatgcgtat gggaaatctt aaatatggat agcataaatg atatctgcat   7740
tgcctaattc gaaatcaaca gcaacgaaaa aaatcccttg tacaacataa atagtcatcg   7800
agaaatatca actatcaaag aacagctatt cacacgttac tattgagatt attattggac   7860
gagaatcaca cactcaactg tctttctctc ttctagaaat acaggtacaa gtatgtacta   7920
ttctcattgt tcatacttct agtcatttca tcccacatat tccttggatt tctctccaat   7980
gaatgacatt ctatcttgca aattcaacaa ttataataag atataccaaa gtagcggtat   8040
agtggcaatc aaaaagcttc tctggtgtgc ttctcgtatt tatttttatt ctaatgatcc   8100
attaaaggta tatatttatt tcttgttata taatcctttt gtttattaca tgggctggat   8160
acataaaggt attttgattt aattttttgc ttaaattcaa tccccccctcg ttcagtgtca   8220
actgtaatgg taggaaatta ccatactttt gaagaagcaa aaaaaatgaa agaaaaaaaa   8280
aatcgtattt ccaggttaga cgttccgcag aatctagaat gcggtatgcg gtacattgtt   8340
cttcgaacgt aaaagttgcg ctccctgaga tattgtacat ttttgctttt acaagtacaa   8400
gtacatcgta caactatgta ctactgttga tgcatccaca acagtttgtt ttgttttttt   8460
ttgttttttt tttttctaat gattcattac cgctatgtat acctacttgt acttgtagta   8520
agccgggtta ttggcgttca attaatcata gacttatgaa tctgcacggt gtgcgctgcg   8580
agttactttt agcttatgca tgctacttgg gtgtaatatt gggatctgtt cggaaatcaa   8640
cggatgctca atcgatcgcc agcaacgcgg ccttagacat aaaaaacaaa aaaaaaaagc   8700
accgactcgg tgccactttt tcaagttgat aacggactag ccttatttta acttgctatt   8760
tctagctcta aaactagaac cgtactgaaa ctgagacgag cttactcgtt tcgtcctcac   8820
ggactcatca gtcagtttac gcatggttga tgtgtgttta attcaagaat gaatatagag   8880
aagagaagaa gaaaaaagat tcaattgagc cggcgatgca gacccttata taaatgttgc   8940
cttggacaga cggagcaagc ccgcccaaac ctacgttcgg tataatatgt taagcttttt   9000
aacacaaagg tttggcttgg ggtaacctga tgtggtgcaa aagaccgggc gttggcgagc   9060
cattgcgcgg gcgaatgggg tcgtgactcg tctcaaattc gagggcgtgc ctcaattcgt   9120
gcccccgtgg ctttttcccg ccgtttccgc cccgtttgca ccactgcagc cgcttctttg   9180
gttcggacac cttgctgcga gctaggtgcc ttgtgctact taaaaagtgg cctcccaaca   9240
ccaacatgac atgagtgcgt gggccaagac acgttggcgg ggtcgcagtc ggctcaatgg   9300
cccggaaaaa acgctgctgg agctggttcg gacgcagtcc gccgcggcgt atggatatcc   9360
gcaaggttcc atagcgccat tgccctccgt cggcgtctat cccgcaacct taattaagtc   9420
atacacaagt cagctttctt cgagcctcat ataagtataa gtagttcaac gtattagcac   9480
tgtacccagc atctccgtat cgagaaacac aacaacatgc cccattggac agatcatgcg   9540
```

gatacacagg ttgtgcagta tcatacatac tcgatcagac aggtcgtctg accatcatac 9600
aagctgaaca agcgctccat acttgcacgc tctctatata cacagttaaa ttacatatcc 9660
atagtctaac ctctaacagt taatcttctg gtaagcctcc cagccagcct tctggtatcg 9720
cttggcctcc tcaataggat ctcggttctg gccgtacaga cctcggccga caattatgat 9780
atccgttccg gtagacatga catcctcaac agttcggtac tgctgtccga gagcgtctcc 9840
cttgtcgtca agacccaccc cgggggtcag aataagccag tcctcagagt cgccccttagg 9900 tcggttctgg gcaatgaagc caaccacaaa ctcggggtcg gatcgggcaa gctcaatggt 9960
ctgcttggag tactcgccag tggccagaga gcccttgcaa gacagctcgg ccagcatgag 10020
cagacctctg gccagcttct cgttgggaga ggggactagg aactccttgt actgggagtt 10080
ctcgtagtca gagacgtcct ccttcttctg ttcagagaca gtttcctcgg caccagctcg 10140
caggccagca atgattccgg ttccgggtac accgtgggcg ttggtgatat cggaccactc 10200
ggcgattcgg tgacaccggt actggtgctt gacagtgttg ccaatatctg cgaactttct 10260
gtcctcgaac aggaagaaac cgtgcttaag agcaagttcc ttgaggggga gcacagtgcc 10320
ggcgtaggtg aagtcgtcaa tgatgtcgat atgggttttg atcatgcaca cataaggtcc 10380
gaccttatcg gcaagctcaa tgagctcctt ggtggtggta acatccagag aagcacacag 10440
gttggttttc ttggctgcca cgagcttgag cactcgagcg gcaaaggcgg acttgtggac 10500
gttagctcga gcttcgtagg agggcatttt ggtggtgaag aggagactga aataaattta 10560
gtctgcagaa ctttttatcg gaaccttatc tggggcagtg aagtatatgt tatggtaata 10620
gttacgagtt agttgaactt atagatagac tggactatac ggctatcggt ccaaattaga 10680
aagaacgtca atggctctct gggcgtcgcc tttgccgaca aaaatgtgat catgatgaaa 10740
gccagcaatg acgttgcagc tgatattgtt gtcggccaac cgcgccgaaa acgcagctgt 10800
cagacccaca gcctccaacg aagaatgtat cgtcaaagtg atccaagcac actcatagtt 10860
ggagtcgtac tccaaaggcg gcaatgacga gtcagacaga tactcgtcga cgtttaaacc 10920
atcatctaag ggcctcaaaa ctacctcgga actgctgcgc tgatctggac accacagagg 10980
ttccgagcac tttaggttgc accaaatgtc ccaccaggtg caggcagaaa acgctggaac 11040
agcgtgtaca gtttgtctta acaaaaagtg agggcgctga ggtcgagcag ggtggtgtga 11100
cttgttatag cctttagagc tgcgaaagcg cgtatggatt tggctcatca ggccagattg 11160
agggtctgtg gacacatgtc atgttagtgt acttcaatcg ccccctggat atagccccga 11220
caataggccg tggcctcatt tttttgcctt ccgcacattt ccattgctcg gtacccacac 11280
cttgcttctc ctgcacttgc caaccttaat actggtttac attgaccaac atcttacaag 11340
cggggggctt gtctagggta tatataaaca gtggctctcc caatcggttg ccagtctctt 11400
ttttcctttc tttccccaca gattcgaaat ctaaactaca catcacac 11448

<210> SEQ ID NO 151
<211> LENGTH: 11448
<212> TYPE: DNA
<213> ORGANISM: Artificial Sequence
<220> FEATURE:
<223> OTHER INFORMATION: pRF298

<400> SEQUENCE: 151
catggacaag aaatactcca tcggcctgga cattggaacc aactctgtcg gctgggctgt 60
catcaccgac gagtacaagg tgccctccaa gaaattcaag gtcctcggaa acaccgatcg 120

-continued

```
acactccatc aagaaaaacc tcattggtgc cctgttgttc gattctggcg agactgccga    180
agctaccaga ctcaagcgaa ctgctcggcg acgttacacc cgacggaaga accgaatctg    240
ctacctgcag gagatctttt ccaacgagat ggccaaggtg gacgattcgt tctttcatcg    300
actggaggaa tccttcctcg tcgaggaaga caagaaacac gagcgtcatc ccatctttgg    360
caacattgtg gacgaggttg cttaccacga gaagtatcct accatctacc atctccgaaa    420
gaaactcgtc gattccaccg acaaggcgga tctcagactt atctacctcg ctctggcaca    480
catgatcaag tttcgaggtc atttcctcat cgagggcgat ctcaatcccg acaacagcga    540
tgtggacaag ctgttcattc agctcgttca gacctacaac cagctgttcg aggaaaaccc    600
catcaatgcc tccggagtcg atgcaaaggc catcttgtct gctcgactct cgaagagcag    660
acgactggag aacctcattg cccaacttcc tggcgagaaa aagaacggac tgtttggcaa    720
cctcattgcc ctttctcttg gtctcacacc caacttcaag tccaacttcg atctggcgga    780
ggacgccaag ctccagctgt ccaaggacac ctacgacgat gacctcgaca acctgcttgc    840
acagattggc gatcagtacg ccgacctgtt tctcgctgcc aagaaccttt cggatgctat    900
tctcttgtct gacattctgc gagtcaacac cgagatcaca aaggctcccc tttctgcctc    960
catgatcaag cgatacgacg agcaccatca ggatctcaca ctgctcaagg ctcttgtccg   1020
acagcaactg cccgagaagt acaaggagat ctttttcgat cagtcgaaga acggctacgc   1080
tggatacatc gacggcggag cctctcagga agagttctac aagttcatca agccaattct   1140
cgagaagatg gacggaaccg aggaactgct tgtcaagctc aatcgagagg atctgcttcg   1200
gaagcaacga accttcgaca acggcagcat tcctcatcag atccacctcg gtgagctgca   1260
cgccattctt cgacgtcagg aagacttcta cccctttctc aaggacaacc gagagaagat   1320
cgagaagatt cttacctttc gaatccccta ctatgttggt cctcttgcca gaggaaactc   1380
tcgatttgct tggatgactc gaaagtccga ggaaaccatc actccctgga acttcgagga   1440
agtcgtggac aagggtgcct ctgcacagtc cttcatcgag cgaatgacca acttcgacaa   1500
gaatctgccc aacgagaagg ttcttcccaa gcattcgctg ctctacgagt actttacagt   1560
ctacaacgaa ctcaccaaag tcaagtacgt taccgaggga atgcgaaagc ctgccttctt   1620
gtctggcgaa cagaagaaag ccattgtcga tctcctgttc aagaccaacc gaaaggtcac   1680
tgttaagcag ctcaaggagg actacttcaa gaaaatcgag tgtttcgaca gcgtcgagat   1740
ttccggagtt gaggaccgat tcaacgcctc tttgggcacc tatcacgatc tgctcaagat   1800
tatcaaggac aaggattttc tcgacaacga ggaaaacgag gacattctgg aggacatcgt   1860
gctcactctt accctgttcg aagatcggga gatgatcgag gaacgactca agacatacgc   1920
tcacctgttc gacgacaagg tcatgaaaca actcaagcga cgtagataca ccggctgggg   1980
aagactttcg cgaaagctca tcaacggcat cagagacaag cagtccggaa agaccattct   2040
ggactttctc aagtccgatg gctttgccaa ccgaaacttc atgcagctca ttcacgacga   2100
ttctcttacc ttcaaggagg acatccagaa ggcacaagtg tccggtcagg gcgacagctt   2160
gcacgaacat attgccaacc tggctggttc gccagccatc aagaaaggca ttctccagac   2220
tgtcaaggtt gtcgacgagc tggtgaaggt catgggacgt cacaagcccg agaacattgt   2280
gatcgagatg gccagagaga accagacaac tcaaaagggt cagaaaaact cgcgagagcg   2340
gatgaagcga atcgaggaag gcatcaagga gctgggatcc cagattctca aggagcatcc   2400
cgtcgagaac actcaactgc agaacgagaa gctgtatctc tactatctgc agaatggtcg   2460
agacatgtac gtggatcagg aactggacat caatcgtctc agcgactacg atgtggacca   2520
```

```
cattgtccct caatcctttc tcaaggacga ttctatcgac aacaaggtcc ttacacgatc   2580
cgacaagaac agaggcaagt cggacaacgt tcccagcgaa gaggtggtca aaaagatgaa   2640
gaactactgg cgacagctgc tcaacgccaa gctcattacc cagcgaaagt tcgacaatct   2700
taccaaggcc gagcgaggcg gtctgtccga gctcgacaag gctggcttca tcaagcgtca   2760
actcgtcgag accagacaga tcacaaagca cgtcgcacag attctcgatt ctcggatgaa   2820
caccaagtac gacgagaacg acaagctcat ccgagaggtc aaggtgatta ctctcaagtc   2880
caaactggtc tccgatttcc gaaaggactt tcagttctac aaggtgcgag agatcaacaa   2940
ttaccaccat gcccacgatg cttacctcaa cgccgtcgtt ggcactgcgc tcatcaagaa   3000
ataccccaag ctcgaaagcg agttcgttta cggcgattac aaggtctacg acgttcgaaa   3060
gatgattgcc aagtccgaac aggagattgg caaggctact gccaagtact tcttttactc   3120
caacatcatg aactttttca agaccgagat caccttggcc aacggagaga ttcgaaagag   3180
accacttatc gagaccaacg gcgaaactgg agagatcgtg tgggacaagg gtcgagactt   3240
tgcaaccgtg cgaaaggttc tgtcgatgcc tcaggtcaac atcgtcaaga aaaccgaggt   3300
tcagactggc ggattctcca aggagtcgat tctgcccaag cgaaactccg acaagctcat   3360
cgctcgaaag aaagactggg atcccaagaa atacggtggc ttcgattctc ctaccgtcgc   3420
ctattccgtg cttgtcgttg cgaaggtcga gaagggcaag tccaaaaagc tcaagtccgt   3480
caaggagctg ctcggaatta ccatcatgga gcgatcgagc ttcgagaaga atcccatcga   3540
cttcttggaa gccaagggtt acaaggaggt caagaaagac ctcattatca agctgcccaa   3600
gtactctctg ttcgaactgg agaacggtcg aaagcgtatg ctcgcctccg ctggcgagct   3660
gcagaaggga aacgagcttg ccttgccttc gaagtacgtc aactttctct atctggcttc   3720
tcactacgag aagctcaagg gttctcccga ggacaacgaa cagaagcaac tcttcgttga   3780
gcagcacaaa cattacctcg acgagattat cgagcagatt tccgagtttt cgaagcgagt   3840
catcctggct gatgccaact tggacaaggt gctctctgcc tacaacaagc atcgggacaa   3900
acccattcga gaacaggcgg agaacatcat tcacctgttt actcttacca acctgggtgc   3960
tcctgcagct ttcaagtact tcgataccac tatcgaccga aagcggtaca catccaccaa   4020
ggaggttctc gatgccaccc tgattcacca gtccatcact ggcctgtacg agacccgaat   4080
cgacctgtct cagcttggtg gcgactccag agccgatccc aagaaaaagc gaaaggtcta   4140
agcggccgca agtgtggatg gggaagtgag tgcccggttc tgtgtgcaca attggcaatc   4200
caagatggat ggattcaaca cagggatata gcgagctacg tggtggtgcg aggatatagc   4260
aacggatatt tatgtttgac acttgagaat gtacgataca agcactgtcc aagtacaata   4320
ctaaacatac tgtacatact catactcgta cccgggcaac ggtttcactt gagtgcagtg   4380
gctagtgctc ttactcgtac agtgtgcaat actgcgtatc atagtctttg atgtatatcg   4440
tattcattca tgttagttgc gtacgagccg gaagcataaa gtgtaaagcc tggggtgcct   4500
aatgagtgag ctaactcaca ttaattgcgt tgcgctcact gcccgctttc cagtcgggaa   4560
acctgtcgtg ccagctgcat taatgaatcg gccaacgcgc ggggagaggc ggtttgcgta   4620
ttgggcgctc ttccgcttcc tcgctcactg actcgctgcg ctcggtcgtt cggctgcggc   4680
gagcggtatc agctcactca aaggcggtaa tacggttatc cacagaatca ggggataacg   4740
caggaaagaa catgtgagca aaaggccagc aaaaggccag gaaccgtaaa aaggccgcgt   4800
tgctggcgtt tttccatagg ctccgccccc ctgacgagca tcacaaaaat cgacgctcaa   4860
```

-continued

```
gtcagaggtg gcgaaacccg acaggactat aaagatacca ggcgtttccc cctggaagct   4920
ccctcgtgcg ctctcctgtt ccgaccctgc cgcttaccgg atacctgtcc gcctttctcc   4980
cttcgggaag cgtggcgctt tctcatagct cacgctgtag gtatctcagt tcggtgtagg   5040
tcgttcgctc caagctgggc tgtgtgcacg aaccccccgt tcagcccgac cgctgcgcct   5100
tatccggtaa ctatcgtctt gagtccaacc cggtaagaca cgacttatcg ccactggcag   5160
cagccactgg taacaggatt agcagagcga ggtatgtagg cggtgctaca gagttcttga   5220
agtggtggcc taactacggc tacactagaa ggacagtatt tggtatctgc gctctgctga   5280
agccagttac cttcggaaaa agagttggta gctcttgatc cggcaaacaa accaccgctg   5340
gtagcggtgg tttttttgtt tgcaagcagc agattacgcg cagaaaaaaa ggatctcaag   5400
aagatccttt gatcttttct acggggtctg acgctcagtg gaacgaaaac tcacgttaag   5460
ggattttggt catgagatta tcaaaaagga tcttcaccta gatcctttta aattaaaaat   5520
gaagttttaa atcaatctaa agtatatatg agtaaacttg gtctgacagt taccaatgct   5580
taatcagtga ggcacctatc tcagcgatct gtctatttcg ttcatccata gttgcctgac   5640
tccccgtcgt gtagataact acgatacggg agggcttacc atctggcccc agtgctgcaa   5700
tgataccgcg agacccacgc tcaccggctc cagatttatc agcaataaac cagccagccg   5760
gaagggccga gcgcagaagt ggtcctgcaa ctttatccgc ctccatccag tctattaatt   5820
gttgccggga agctagagta agtagttcgc cagttaatag tttgcgcaac gttgttgcca   5880
ttgctacagg catcgtggtg tcacgctcgt cgtttggtat ggcttcattc agctccggtt   5940
cccaacgatc aaggcgagtt acatgatccc ccatgttgtg caaaaaagcg gttagctcct   6000
tcggtcctcc gatcgttgtc agaagtaagt tggccgcagt gttatcactc atggttatgg   6060
cagcactgca taattctctt actgtcatgc catccgtaag atgcttttct gtgactggtg   6120
agtactcaac caagtcattc tgagaatagt gtatgcggcg accgagttgc tcttgcccgg   6180
cgtcaatacg ggataatacc gcgccacata gcagaacttt aaaagtgctc atcattggaa   6240
aacgttcttc ggggcgaaaa ctctcaagga tcttaccgct gttgagatcc agttcgatgt   6300
aacccactcg tgcacccaac tgatcttcag catcttttac tttcaccagc gtttctgggt   6360
gagcaaaaac aggaaggcaa aatgccgcaa aaaagggaat aagggcgaca cggaaatgtt   6420
gaatactcat actcttcctt tttcaatatt attgaagcat ttatcagggt tattgtctca   6480
tgagcggata catatttgaa tgtatttaga aaaataaaca aataggggtt ccgcgcacat   6540
ttccccgaaa agtgccacct gacgcgccct gtagcggcgc attaagcgcg gcgggtgtgg   6600
tggttacgcg cagcgtgacc gctacacttg ccagcgccct agcgcccgct cctttcgctt   6660
tcttcccttc ctttctcgcc acgttcgccg gctttccccg tcaagctcta aatcgggggc   6720
tccctttagg gttccgattt agtgctttac ggcacctcga ccccaaaaaa cttgattagg   6780
gtgatggttc acgtagtggg ccatcgccct gatagacggt ttttcgccct ttgacgttgg   6840
agtccacgtt ctttaatagt ggactcttgt tccaaactgg aacaacactc aaccctatct   6900
cggtctattc ttttgattta taagggattt tgccgatttc ggcctattgg ttaaaaaatg   6960
agctgattta acaaaaattt aacgcgaatt ttaacaaaat attaacgctt acaatttcca   7020
ttcgccattc aggctgcgca actgttggga agggcgatcg gtgcgggcct cttcgctatt   7080
acgccagctg gcgaaagggg gatgtgctgc aaggcgatta agttgggtaa cgccagggtt   7140
ttcccagtca cgacgttgta aaacgacggc cagtgaattg taatacgact cactataggg   7200
cgaattgggt accgggcccc ccctcgaggt cgatggtgtc gataagcttg atatcgaatt   7260
```

```
catgtcacac aaaccgatct tcgcctcaag gaaacctaat tctacatccg agagactgcc   7320
gagatccagt ctacactgat taattttcgg gccaataatt taaaaaaatc gtgttatata   7380
atattatatg tattatatat atacatcatg atgatactga cagtcatgtc ccattgctaa   7440
atagacagac tccatctgcc gcctccaact gatgttctca atatttaagg ggtcatctcg   7500
cattgtttaa taataaacag actccatcta ccgcctccaa atgatgttct caaaatatat   7560
tgtatgaact tatttttatt acttagtatt attagacaac ttacttgctt tatgaaaaac   7620
acttcctatt taggaaacaa tttataatgg cagttcgttc atttaacaat ttatgtagaa   7680
taaatgttat aaatgcgtat gggaaatctt aaatatggat agcataaatg atatctgcat   7740
tgcctaattc gaaatcaaca gcaacgaaaa aaatcccttg tacaacataa atagtcatcg   7800
agaaatatca actatcaaag aacagctatt cacacgttac tattgagatt attattggac   7860
gagaatcaca cactcaactg tctttctctc ttctagaaat acaggtacaa gtatgtacta   7920
ttctcattgt tcatacttct agtcatttca tcccacatat tccttggatt tctctccaat   7980
gaatgacatt ctatcttgca aattcaacaa ttataataag atataccaaa gtagcggtat   8040
agtggcaatc aaaaagcttc tctggtgtgc ttctcgtatt tatttttatt ctaatgatcc   8100
attaaaggta tatatttatt tcttgttata taatcctttt gtttattaca tgggctggat   8160
acataaaggt attttgattt aattttttgc ttaaattcaa tccccccctcg ttcagtgtca   8220
actgtaatgg taggaaatta ccatactttt gaagaagcaa aaaaaatgaa agaaaaaaaa   8280
aatcgtattt ccaggttaga cgttccgcag aatctagaat gcggtatgcg gtacattgtt   8340
cttcgaacgt aaaagttgcg ctccctgaga tattgtacat ttttgctttt acaagtacaa   8400
gtacatcgta caactatgta ctactgttga tgcatccaca acagtttgtt ttgttttttt   8460
ttgttttttt tttttctaat gattcattac cgctatgtat acctacttgt acttgtagta   8520
agccgggtta ttggcgttca attaatcata gacttatgaa tctgcacggt gtgcgctgcg   8580
agttactttt agcttatgca tgctacttgg gtgtaatatt gggatctgtt cggaaatcaa   8640
cggatgctca atcgatcgcc agcaacgcgg ccttagacat aaaaaacaaa aaaaaaaagc   8700
accgactcgg tgccactttt tcaagttgat aacggactag ccttatttta acttgctatt   8760
tctagctcta aaacgagtaa cggtaacgac accggacgag cttactcgtt tcgtcctcac   8820
ggactcatca gcggtgttac gcatggttga tgtgtgttta attcaagaat gaatatagag   8880
aagagaagaa gaaaaaagat tcaattgagc cggcgatgca gacccttata taaatgttgc   8940
cttggacaga cggagcaagc ccgcccaaac ctacgttcgg tataatatgt taagcttttt   9000
aacacaaagg tttggcttgg ggtaacctga tgtggtgcaa aagaccgggc gttggcgagc   9060
cattgcgcgg gcgaatgggg tcgtgactcg tctcaaattc gagggcgtgc ctcaattcgt   9120
gcccccgtgg ctttttcccg ccgtttccgc cccgtttgca ccactgcagc cgcttctttg   9180
gttcggacac cttgctgcga gctaggtgcc ttgtgctact taaaaagtgg cctcccaaca   9240
ccaacatgac atgagtgcgt gggccaagac acgttggcgg ggtcgcagtc ggctcaatgg   9300
cccggaaaaa acgctgctgg agctggttcg gacgcagtcc gccgcggcgt atggatatcc   9360
gcaaggttcc atagcgccat tgccctccgt cggcgtctat cccgcaacct taattaagtc   9420
atacacaagt cagctttctt cgagcctcat ataagtataa gtagttcaac gtattagcac   9480
tgtacccagc atctccgtat cgagaaacac aacaacatgc cccattggac agatcatgcg   9540
gatacacagg ttgtgcagta tcatacatac tcgatcagac aggtcgtctg accatcatac   9600
```

```
aagctgaaca agcgctccat acttgcacgc tctctatata cacagttaaa ttacatatcc   9660
atagtctaac ctctaacagt taatcttctg gtaagcctcc cagccagcct tctggtatcg   9720
cttggcctcc tcaataggat ctcggttctg gccgtacaga cctcggccga caattatgat   9780
atccgttccg gtagacatga catcctcaac agttcggtac tgctgtccga gagcgtctcc   9840
cttgtcgtca agacccaccc cgggggtcag aataagccag tcctcagagt cgcccttagg   9900
tcggttctgg gcaatgaagc caaccacaaa ctcggggtcg gatcgggcaa gctcaatggt   9960
ctgcttggag tactcgccag tggccagaga gcccttgcaa gacagctcgg ccagcatgag  10020
cagacctctg gccagcttct cgttgggaga ggggactagg aactccttgt actgggagtt  10080
ctcgtagtca gagacgtcct ccttcttctg ttcagagaca gtttcctcgg caccagctcg  10140
caggccagca atgattccgg ttccgggtac accgtgggcg ttggtgatat cggaccactc  10200
ggcgattcgg tgacaccggt actggtgctt gacagtgttg ccaatatctg cgaactttct  10260
gtcctcgaac aggaagaaac cgtgcttaag agcaagttcc ttgaggggga gcacagtgcc  10320
ggcgtaggtg aagtcgtcaa tgatgtcgat atgggttttg atcatgcaca cataaggtcc  10380
gaccttatcg gcaagctcaa tgagctcctt ggtggtggta acatccagag aagcacacag  10440
gttggttttc ttggctgcca cgagcttgag cactcgagcg gcaaaggcgg acttgtggac  10500
gttagctcga gcttcgtagg agggcatttt ggtggtgaag aggagactga aataaattta  10560
gtctgcagaa ctttttatcg gaaccttatc tggggcagtg aagtatatgt tatggtaata  10620
gttacgagtt agttgaactt atagatagac tggactatac ggctatcggt ccaaattaga  10680
aagaacgtca atggctctct gggcgtcgcc tttgccgaca aaaatgtgat catgatgaaa  10740
gccagcaatg acgttgcagc tgatattgtt gtcggccaac cgcgccgaaa acgcagctgt  10800
cagacccaca gcctccaacg aagaatgtat cgtcaaagtg atccaagcac actcatagtt  10860
ggagtcgtac tccaaaggcg gcaatgacga gtcagacaga tactcgtcga cgtttaaacc  10920
atcatctaag ggcctcaaaa ctacctcgga actgctgcgc tgatctggac accacagagg  10980
ttccgagcac tttaggttgc accaaatgtc ccaccaggtg caggcagaaa acgctggaac  11040
agcgtgtaca gtttgtctta acaaaaagtg agggcgctga ggtcgagcag ggtggtgtga  11100
cttgttatag cctttagagc tgcgaaagcg cgtatggatt tggctcatca ggccagattg  11160
agggtctgtg gacacatgtc atgttagtgt acttcaatcg ccccctggat atagccccga  11220
caataggccg tggcctcatt tttttgcctt ccgcacattt ccattgctcg gtacccacac  11280
cttgcttctc ctgcacttgc caaccttaat actggtttac attgaccaac atcttacaag  11340
cggggggctt gtctagggta tatataaaca gtggctctcc caatcggttg ccagtctctt  11400
ttttcctttc tttccccaca gattcgaaat ctaaactaca catcacac               11448
```

<210> SEQ ID NO 152
<211> LENGTH: 11448
<212> TYPE: DNA
<213> ORGANISM: Artificial Sequence
<220> FEATURE:
<223> OTHER INFORMATION: pRF300

<400> SEQUENCE: 152

```
catggacaag aaatactcca tcggcctgga cattggaacc aactctgtcg gctgggctgt     60
catcaccgac gagtacaagg tgccctccaa gaaattcaag gtcctcggaa acaccgatcg    120
acactccatc aagaaaaacc tcattggtgc cctgttgttc gattctggcg agactgccga    180
agctaccaga ctcaagcgaa ctgctcggcg acgttacacc cgacggaaga accgaatctg    240
```

-continued

```
ctacctgcag gagatctttt ccaacgagat ggccaaggtg gacgattcgt tctttcatcg    300
actggaggaa tccttcctcg tcgaggaaga caagaaacac gagcgtcatc ccatctttgg    360
caacattgtg gacgaggttg cttaccacga gaagtatcct accatctacc atctccgaaa    420
gaaactcgtc gattccaccg acaaggcgga tctcagactt atctacctcg ctctggcaca    480
catgatcaag tttcgaggtc atttcctcat cgagggcgat ctcaatcccg acaacagcga    540
tgtggacaag ctgttcattc agctcgttca gacctacaac cagctgttcg aggaaaaccc    600
catcaatgcc tccggagtcg atgcaaaggc catcttgtct gctcgactct cgaagagcag    660
acgactggag aacctcattg cccaacttcc tggcgagaaa aagaacggac tgtttggcaa    720
cctcattgcc ctttctcttg gtctcacacc caacttcaag tccaacttcg atctggcgga    780
ggacgccaag ctccagctgt ccaaggacac ctacgacgat gacctcgaca acctgcttgc    840
acagattggc gatcagtacg ccgacctgtt tctcgctgcc aagaaccttt cggatgctat    900
tctcttgtct gacattctgc gagtcaacac cgagatcaca aaggctcccc tttctgcctc    960
catgatcaag cgatacgacg agcaccatca ggatctcaca ctgctcaagg ctcttgtccg   1020
acagcaactg cccgagaagt acaaggagat ctttttcgat cagtcgaaga acggctacgc   1080
tggatacatc gacggcggag cctctcagga agagttctac aagttcatca agccaattct   1140
cgagaagatg gacggaaccg aggaactgct tgtcaagctc aatcgagagg atctgcttcg   1200
gaagcaacga accttcgaca acggcagcat tcctcatcag atccacctcg gtgagctgca   1260
cgccattctt cgacgtcagg aagacttcta cccctttctc aaggacaacc gagagaagat   1320
cgagaagatt cttacctttc gaatccccta ctatgttggt cctcttgcca gaggaaactc   1380
tcgatttgct tggatgactc gaaagtccga ggaaaccatc actccctgga acttcgagga   1440
agtcgtggac aagggtgcct ctgcacagtc cttcatcgag cgaatgacca acttcgacaa   1500
gaatctgccc aacgagaagg ttcttcccaa gcattcgctg ctctacgagt actttacagt   1560
ctacaacgaa ctcaccaaag tcaagtacgt taccgaggga atgcgaaagc ctgccttctt   1620
gtctggcgaa cagaagaaag ccattgtcga tctcctgttc aagaccaacc gaaaggtcac   1680
tgttaagcag ctcaaggagg actacttcaa gaaaatcgag tgtttcgaca gcgtcgagat   1740
ttccggagtt gaggaccgat tcaacgcctc tttgggcacc tatcacgatc tgctcaagat   1800
tatcaaggac aaggattttc tcgacaacga ggaaaacgag gacattctgg aggacatcgt   1860
gctcactctt accctgttcg aagatcggga gatgatcgag gaacgactca agacatacgc   1920
tcacctgttc gacgacaagg tcatgaaaca actcaagcga cgtagataca ccggctgggg   1980
aagactttcg cgaaagctca tcaacggcat cagagacaag cagtccggaa agaccattct   2040
ggactttctc aagtccgatg gctttgccaa ccgaaacttc atgcagctca ttcacgacga   2100
ttctcttacc ttcaaggagg acatccagaa ggcacaagtg tccggtcagg gcgacagctt   2160
gcacgaacat attgccaacc tggctggttc gccagccatc aagaaaggca ttctccagac   2220
tgtcaaggtt gtcgacgagc tggtgaaggt catgggacgt cacaagcccg agaacattgt   2280
gatcgagatg gccagagaga accagacaac tcaaaagggt cagaaaaact cgcgagagcg   2340
gatgaagcga atcgaggaag gcatcaagga gctgggatcc cagattctca aggagcatcc   2400
cgtcgagaac actcaactgc agaacgagaa gctgtatctc tactatctgc agaatggtcg   2460
agacatgtac gtggatcagg aactggacat caatcgtctc agcgactacg atgtggacca   2520
cattgtccct caatcctttc tcaaggacga ttctatcgac aacaaggtcc ttacacgatc   2580
```

-continued

```
cgacaagaac agaggcaagt cggacaacgt tcccagcgaa gaggtggtca aaaagatgaa   2640
gaactactgg cgacagctgc tcaacgccaa gctcattacc cagcgaaagt tcgacaatct   2700
taccaaggcc gagcgaggcg gtctgtccga gctcgacaag gctggcttca tcaagcgtca   2760
actcgtcgag accagacaga tcacaaagca cgtcgcacag attctcgatt ctcggatgaa   2820
caccaagtac gacgagaacg acaagctcat ccgagaggtc aaggtgatta ctctcaagtc   2880
caaactggtc tccgatttcc gaaaggactt tcagttctac aaggtgcgag agatcaacaa   2940
ttaccaccat gcccacgatg cttacctcaa cgccgtcgtt ggcactgcgc tcatcaagaa   3000
ataccccaag ctcgaaagcg agttcgttta cggcgattac aaggtctacg acgttcgaaa   3060
gatgattgcc aagtccgaac aggagattgg caaggctact gccaagtact tcttttactc   3120
caacatcatg aactttttca agaccgagat caccttggcc aacggagaga ttcgaaagag   3180
accacttatc gagaccaacg gcgaaactgg agagatcgtg tgggacaagg gtcgagactt   3240
tgcaaccgtg cgaaaggttc tgtcgatgcc tcaggtcaac atcgtcaaga aaaccgaggt   3300
tcagactggc ggattctcca aggagtcgat tctgcccaag cgaaactccg acaagctcat   3360
cgctcgaaag aaagactggg atcccaagaa atacggtggc ttcgattctc ctaccgtcgc   3420
ctattccgtg cttgtcgttg cgaaggtcga gaagggcaag tccaaaaagc tcaagtccgt   3480
caaggagctg ctcggaatta ccatcatgga gcgatcgagc ttcgagaaga atcccatcga   3540
cttcttggaa gccaagggtt acaaggaggt caagaaagac ctcattatca agctgcccaa   3600
gtactctctg ttcgaactgg agaacggtcg aaagcgtatg ctcgcctccg ctggcgagct   3660
gcagaaggga aacgagcttg ccttgccttc gaagtacgtc aactttctct atctggcttc   3720
tcactacgag aagctcaagg gttctcccga ggacaacgaa cagaagcaac tcttcgttga   3780
gcagcacaaa cattacctcg acgagattat cgagcagatt tccgagtttt cgaagcgagt   3840
catcctggct gatgccaact tggacaaggt gctctctgcc tacaacaagc atcgggacaa   3900
acccattcga gaacaggcgg agaacatcat tcacctgttt actcttacca acctgggtgc   3960
tcctgcagct ttcaagtact tcgataccac tatcgaccga aagcggtaca catccaccaa   4020
ggaggttctc gatgccaccc tgattcacca gtccatcact ggcctgtacg agacccgaat   4080
cgacctgtct cagcttggtg gcgactccag agccgatccc aagaaaaagc gaaaggtcta   4140
agcggccgca agtgtggatg gggaagtgag tgcccggttc tgtgtgcaca attggcaatc   4200
caagatggat ggattcaaca cagggatata gcgagctacg tggtggtgcg aggatatagc   4260
aacggatatt tatgtttgac acttgagaat gtacgataca agcactgtcc aagtacaata   4320
ctaaacatac tgtacatact catactcgta cccgggcaac ggtttcactt gagtgcagtg   4380
gctagtgctc ttactcgtac agtgtgcaat actgcgtatc atagtctttg atgtatatcg   4440
tattcattca tgttagttgc gtacgagccg gaagcataaa gtgtaaagcc tggggtgcct   4500
aatgagtgag ctaactcaca ttaattgcgt tgcgctcact gcccgctttc cagtcgggaa   4560
acctgtcgtg ccagctgcat taatgaatcg gccaacgcgc ggggagaggc ggtttgcgta   4620
ttgggcgctc ttccgcttcc tcgctcactg actcgctgcg ctcggtcgtt cggctgcggc   4680
gagcggtatc agctcactca aaggcggtaa tacggttatc cacagaatca ggggataacg   4740
caggaaagaa catgtgagca aaaggccagc aaaaggccag gaaccgtaaa aaggccgcgt   4800
tgctggcgtt tttccatagg ctccgccccc ctgacgagca tcacaaaaat cgacgctcaa   4860
gtcagaggtg gcgaaacccg acaggactat aaagatacca ggcgtttccc cctggaagct   4920
ccctcgtgcg ctctcctgtt ccgaccctgc cgcttaccgg atacctgtcc gcctttctcc   4980
```

cttcgggaag cgtggcgctt tctcatagct cacgctgtag gtatctcagt tcggtgtagg 5040
tcgttcgctc caagctgggc tgtgtgcacg aaccccccgt tcagcccgac cgctgcgcct 5100
tatccggtaa ctatcgtctt gagtccaacc cggtaagaca cgacttatcg ccactggcag 5160
cagccactgg taacaggatt agcagagcga ggtatgtagg cggtgctaca gagttcttga 5220
agtggtggcc taactacggc tacactagaa ggacagtatt tggtatctgc gctctgctga 5280
agccagttac cttcggaaaa agagttggta gctcttgatc cggcaaacaa accaccgctg 5340
gtagcggtgg tttttttgtt tgcaagcagc agattacgcg cagaaaaaaa ggatctcaag 5400
aagatccttt gatcttttct acggggtctg acgctcagtg gaacgaaaac tcacgttaag 5460
ggattttggt catgagatta tcaaaaagga tcttcaccta gatcctttta aattaaaaat 5520
gaagttttaa atcaatctaa agtatatatg agtaaacttg gtctgacagt taccaatgct 5580
taatcagtga ggcacctatc tcagcgatct gtctatttcg ttcatccata gttgcctgac 5640
tccccgtcgt gtagataact acgatacggg agggcttacc atctggcccc agtgctgcaa 5700
tgataccgcg agacccacgc tcaccggctc cagatttatc agcaataaac cagccagccg 5760
gaagggccga gcgcagaagt ggtcctgcaa ctttatccgc ctccatccag tctattaatt 5820
gttgccggga agctagagta agtagttcgc cagttaatag tttgcgcaac gttgttgcca 5880
ttgctacagg catcgtggtg tcacgctcgt cgtttggtat ggcttcattc agctccggtt 5940
cccaacgatc aaggcgagtt acatgatccc ccatgttgtg caaaaaagcg gttagctcct 6000
tcggtcctcc gatcgttgtc agaagtaagt tggccgcagt gttatcactc atggttatgg 6060
cagcactgca taattctctt actgtcatgc catccgtaag atgcttttct gtgactggtg 6120
agtactcaac caagtcattc tgagaatagt gtatgcggcg accgagttgc tcttgcccgg 6180
cgtcaatacg ggataatacc gcgccacata gcagaacttt aaaagtgctc atcattggaa 6240
aacgttcttc ggggcgaaaa ctctcaagga tcttaccgct gttgagatcc agttcgatgt 6300
aacccactcg tgcacccaac tgatcttcag catcttttac tttcaccagc gtttctgggt 6360
gagcaaaaac aggaaggcaa aatgccgcaa aaaagggaat aagggcgaca cggaaatgtt 6420
gaatactcat actcttcctt tttcaatatt attgaagcat ttatcagggt tattgtctca 6480
tgagcggata catatttgaa tgtatttaga aaaataaaca aataggggtt ccgcgcacat 6540
ttccccgaaa agtgccacct gacgcgccct gtagcggcgc attaagcgcg gcgggtgtgg 6600
tggttacgcg cagcgtgacc gctacacttg ccagcgccct agcgcccgct cctttcgctt 6660
tcttcccttc ctttctcgcc acgttcgccg gctttccccg tcaagctcta aatcgggggc 6720
tccctttagg gttccgattt agtgctttac ggcacctcga ccccaaaaaa cttgattagg 6780
gtgatggttc acgtagtggg ccatcgccct gatagacggt ttttcgccct ttgacgttgg 6840
agtccacgtt ctttaatagt ggactcttgt tccaaactgg aacaacactc aaccctatct 6900
cggtctattc ttttgattta taagggattt tgccgatttc ggcctattgg ttaaaaaatg 6960
agctgattta acaaaaattt aacgcgaatt ttaacaaaat attaacgctt acaatttcca 7020
ttcgccattc aggctgcgca actgttggga agggcgatcg gtgcgggcct cttcgctatt 7080
acgccagctg gcgaaagggg gatgtgctgc aaggcgatta agttgggtaa cgccagggtt 7140
ttcccagtca cgacgttgta aaacgacggc cagtgaattg taatacgact cactataggg 7200
cgaattgggt accgggcccc ccctcgaggt cgatggtgtc gataagcttg atatcgaatt 7260
catgtcacac aaaccgatct tcgcctcaag gaaacctaat tctacatccg agagactgcc 7320

-continued

```
gagatccagt ctacactgat taattttcgg gccaataatt taaaaaaatc gtgttatata   7380
atattatatg tattatatat atacatcatg atgatactga cagtcatgtc ccattgctaa   7440
atagacagac tccatctgcc gcctccaact gatgttctca atatttaagg ggtcatctcg   7500
cattgtttaa taataaacag actccatcta ccgcctccaa atgatgttct caaaatatat   7560
tgtatgaact tatttttatt acttagtatt attagacaac ttacttgctt tatgaaaaac   7620
acttcctatt taggaaacaa tttataatgg cagttcgttc atttaacaat ttatgtagaa   7680
taaatgttat aaatgcgtat gggaaatctt aaatatggat agcataaatg atatctgcat   7740
tgcctaattc gaaatcaaca gcaacgaaaa aaatcccttg tacaacataa atagtcatcg   7800
agaaatatca actatcaaag aacagctatt cacacgttac tattgagatt attattggac   7860
gagaatcaca cactcaactg tctttctctc ttctagaaat acaggtacaa gtatgtacta   7920
ttctcattgt tcatacttct agtcatttca tcccacatat tccttggatt tctctccaat   7980
gaatgacatt ctatcttgca aattcaacaa ttataataag atataccaaa gtagcggtat   8040
agtggcaatc aaaaagcttc tctggtgtgc ttctcgtatt tatttttatt ctaatgatcc   8100
attaaaggta tatatttatt tcttgttata taatcctttt gtttattaca tgggctggat   8160
acataaaggt attttgattt aatttttttgc ttaaattcaa tccccccctcg ttcagtgtca   8220
actgtaatgg taggaaatta ccatactttt gaagaagcaa aaaaaatgaa agaaaaaaaa   8280
aatcgtattt ccaggttaga cgttccgcag aatctagaat gcggtatgcg gtacattgtt   8340
cttcgaacgt aaaagttgcg ctccctgaga tattgtacat ttttgctttt acaagtacaa   8400
gtacatcgta caactatgta ctactgttga tgcatccaca acagtttgtt ttgttttttt   8460
ttgttttttt tttttctaat gattcattac cgctatgtat acctacttgt acttgtagta   8520
agccgggtta ttggcgttca attaatcata gacttatgaa tctgcacggt gtgcgctgcg   8580
agttactttt agcttatgca tgctacttgg gtgtaatatt gggatctgtt cggaaatcaa   8640
cggatgctca atcgatcgcc agcaacgcgg ccttagacat aaaaaaacaaa aaaaaaaagc   8700
accgactcgg tgccactttt tcaagttgat aacggactag ccttatttta acttgctatt   8760
tctagctcta aaaccgaagc tgaaggtgac caaggacgag cttactcgtt tcgtcctcac   8820
ggactcatca gcctggttac gcatggttga tgtgtgttta attcaagaat gaatatagag   8880
aagagaagaa gaaaaaagat tcaattgagc cggcgatgca gacccttata taaatgttgc   8940
cttggacaga cggagcaagc ccgcccaaac ctacgttcgg tataatatgt taagcttttt   9000
aacacaaagg tttggcttgg ggtaacctga tgtggtgcaa aagaccgggc gttggcgagc   9060
cattgcgcgg gcgaatgggg tcgtgactcg tctcaaattc gagggcgtgc ctcaattcgt   9120
gcccccgtgg ctttttcccg ccgtttccgc cccgtttgca ccactgcagc cgcttctttg   9180
gttcggacac cttgctgcga gctaggtgcc ttgtgctact taaaaagtgg cctcccaaca   9240
ccaacatgac atgagtgcgt gggccaagac acgttggcgg ggtcgcagtc ggctcaatgg   9300
cccggaaaaa acgctgctgg agctggttcg gacgcagtcc gccgcggcgt atggatatcc   9360
gcaaggttcc atagcgccat tgccctccgt cggcgtctat cccgcaacct taattaagtc   9420
atacacaagt cagctttctt cgagcctcat ataagtataa gtagttcaac gtattagcac   9480
tgtacccagc atctccgtat cgagaaacac aacaacatgc cccattggac agatcatgcg   9540
gatacacagg ttgtgcagta tcatacatac tcgatcagac aggtcgtctg accatcatac   9600
aagctgaaca agcgctccat acttgcacgc tctctatata cacagttaaa ttacatatcc   9660
atagtctaac ctctaacagt taatcttctg gtaagcctcc cagccagcct tctggtatcg   9720
```

```
cttggcctcc tcaataggat ctcggttctg gccgtacaga cctcggccga caattatgat   9780
atccgttccg gtagacatga catcctcaac agttcggtac tgctgtccga gagcgtctcc   9840
cttgtcgtca agacccaccc cgggggtcag aataagccag tcctcagagt cgcccttagg   9900
tcggttctgg gcaatgaagc caaccacaaa ctcggggtcg gatcgggcaa gctcaatggt   9960
ctgcttggag tactcgccag tggccagaga gcccttgcaa gacagctcgg ccagcatgag  10020
cagacctctg gccagcttct cgttgggaga ggggactagg aactccttgt actgggagtt  10080
ctcgtagtca gagacgtcct ccttcttctg ttcagagaca gtttcctcgg caccagctcg  10140
caggccagca atgattccgg ttccgggtac accgtgggcg ttggtgatat cggaccactc  10200
ggcgattcgg tgacaccggt actggtgctt gacagtgttg ccaatatctg cgaactttct  10260
gtcctcgaac aggaagaaac cgtgcttaag agcaagttcc ttgaggggga gcacagtgcc  10320
ggcgtaggtg aagtcgtcaa tgatgtcgat atgggttttg atcatgcaca cataaggtcc  10380
gaccttatcg gcaagctcaa tgagctcctt ggtggtggta acatccagag aagcacacag  10440
gttggttttc ttggctgcca cgagcttgag cactcgagcg gcaaaggcgg acttgtggac  10500
gttagctcga gcttcgtagg agggcatttt ggtggtgaag aggagactga aataaattta  10560
gtctgcagaa ctttttatcg gaaccttatc tggggcagtg aagtatatgt tatggtaata  10620
gttacgagtt agttgaactt atagatagac tggactatac ggctatcggt ccaaattaga  10680
aagaacgtca atggctctct gggcgtcgcc tttgccgaca aaaatgtgat catgatgaaa  10740
gccagcaatg acgttgcagc tgatattgtt gtcggccaac cgcgccgaaa acgcagctgt  10800
cagacccaca gcctccaacg aagaatgtat cgtcaaagtg atccaagcac actcatagtt  10860
ggagtcgtac tccaaaggcg gcaatgacga gtcagacaga tactcgtcga cgtttaaacc  10920
atcatctaag ggcctcaaaa ctacctcgga actgctgcgc tgatctggac accacagagg  10980
ttccgagcac tttaggttgc accaaatgtc ccaccaggtg caggcagaaa acgctggaac  11040
agcgtgtaca gtttgtctta acaaaaagtg agggcgctga ggtcgagcag ggtggtgtga  11100
cttgttatag cctttagagc tgcgaaagcg cgtatggatt tggctcatca ggccagattg  11160
agggtctgtg gacacatgtc atgttagtgt acttcaatcg ccccctggat atagccccga  11220
caataggccg tggcctcatt tttttgcctt ccgcacattt ccattgctcg gtacccacac  11280
cttgcttctc ctgcacttgc caaccttaat actggtttac attgaccaac atcttacaag  11340
cggggggctt gtctagggta tatataaaca gtggctctcc caatcggttg ccagtctctt  11400
ttttcctttc tttccccaca gattcgaaat ctaaactaca catcacac               11448
```

<210> SEQ ID NO 153
<211> LENGTH: 11448
<212> TYPE: DNA
<213> ORGANISM: Artificial sequence
<220> FEATURE:
<223> OTHER INFORMATION: pRF339

<400> SEQUENCE: 153

```
catggacaag aaatactcca tcggcctggc cattggaacc aactctgtcg gctgggctgt     60
catcaccgac gagtacaagg tgccctccaa gaaattcaag gtcctcggaa acaccgatcg    120
acactccatc aagaaaaacc tcattggtgc cctgttgttc gattctggcg agactgccga    180
agctaccaga ctcaagcgaa ctgctcggcg acgttacacc cgacggaaga accgaatctg    240
ctacctgcag gagatctttt ccaacgagat ggccaaggtg gacgattcgt tctttcatcg    300
```

```
actggaggaa tccttcctcg tcgaggaaga caagaaacac gagcgtcatc ccatctttgg    360
caacattgtg gacgaggttg cttaccacga gaagtatcct accatctacc acctgcgaaa    420
gaaactcgtc gattccaccg acaaggcgga tctcagactt atctacctcg ctctggcaca    480
catgatcaag tttcgaggtc atttcctcat cgagggcgat ctcaatcccg acaacagcga    540
tgtggacaag ctgttcattc agctcgttca gacctacaac cagctgttcg aggaaaaccc    600
catcaatgcc tccggagtcg atgcaaaggc catcttgtct gctcgactct cgaagagcag    660
acgactggag aacctcattg cccaacttcc tggcgagaaa aagaacggac tgtttggcaa    720
cctcattgcc ctttctcttg gtctcacacc caacttcaag tccaacttcg atctggcgga    780
ggacgccaag ctccagctgt ccaaggacac ctacgacgat gacctcgaca acctgcttgc    840
acagattggc gatcagtacg ccgacctgtt tctcgctgcc aagaaccttt cggatgctat    900
tctcttgtct gacattctgc gagtcaacac cgagatcaca aaggctcccc tttctgcctc    960
catgatcaag cgatacgacg agcaccatca ggatctcaca ctgctcaagg ctcttgtccg   1020
acagcaactg cccgagaagt acaaggagat ctttttcgat cagtcgaaga acggctacgc   1080
tggatacatc gacggcggag cctctcagga agagttctac aagttcatca agccaattct   1140
cgagaagatg gacggaaccg aggaactgct tgtcaagctc aatcgagagg atctgcttcg   1200
gaagcaacga accttcgaca acggcagcat tcctcatcag atccacctcg gtgagctgca   1260
cgccattctt cgacgtcagg aagacttcta cccctttctc aaggacaacc gagagaagat   1320
cgagaagatt cttacctttc gaatccccta ctatgttggt cctcttgcca gaggaaactc   1380
tcgatttgct tggatgactc gaaagtccga ggaaaccatc actccctgga acttcgagga   1440
agtcgtggac aagggtgcct ctgcacagtc cttcatcgag cgaatgacca acttcgacaa   1500
gaatctgccc aacgagaagg ttcttcccaa gcattcgctg ctctacgagt actttacagt   1560
ctacaacgaa ctcaccaaag tcaagtacgt taccgaggga atgcgaaagc ctgccttctt   1620
gtctggcgaa cagaagaaag ccattgtcga tctcctgttc aagaccaacc gaaaggtcac   1680
tgttaagcag ctcaaggagg actacttcaa gaaaatcgag tgtttcgaca gcgtcgagat   1740
ttccggagtt gaggaccgat tcaacgcctc tttgggcacc tatcacgatc tgctcaagat   1800
tatcaaggac aaggattttc tcgacaacga ggaaaacgag gacattctgg aggacatcgt   1860
gctcactctt accctgttcg aagatcggga gatgatcgag gaacgactca agacatacgc   1920
tcacctgttc gacgacaagg tcatgaaaca actcaagcga cgtagataca ccggctgggg   1980
aagactttcg cgaaagctca tcaacggcat cagagacaag cagtccggaa agaccattct   2040
ggactttctc aagtccgatg gctttgccaa ccgaaacttc atgcagctca ttcacgacga   2100
ttctcttacc ttcaaggagg acatccagaa ggcacaagtg tccggtcagg gcgacagctt   2160
gcacgaacat attgccaacc tggctggttc gccagccatc aagaaaggca ttctccagac   2220
tgtcaaggtt gtcgacgagc tggtgaaggt catgggacgt cacaagcccg agaacattgt   2280
gatcgagatg gccagagaga accagacaac tcaaaagggt cagaaaaact cgcgagagcg   2340
gatgaagcga atcgaggaag gcatcaagga gctgggatcc cagattctca aggagcatcc   2400
cgtcgagaac actcaactgc agaacgagaa gctgtatctc tactatctgc agaatggtcg   2460
agacatgtac gtggatcagg aactggacat caatcgtctc agcgactacg atgtggacgc   2520
cattgtccct caatcctttc tcaaggacga ttctatcgac aacaaggtcc ttacacgatc   2580
cgacaagaac agaggcaagt cggacaacgt tcccagcgaa gaggtggtca aaaagatgaa   2640
gaactactgg cgacagctgc tcaacgccaa gctcattacc cagcgaaagt tcgacaatct   2700
```

```
taccaaggcc gagcgaggcg gtctgtccga gctcgacaag gctggcttca tcaagcgtca   2760
actcgtcgag accagacaga tcacaaagca cgtcgcacag attctcgatt ctcggatgaa   2820
caccaagtac gacgagaacg acaagctcat ccgagaggtc aaggtgatta ctctcaagtc   2880
caaactggtc tccgatttcc gaaaggactt tcagttctac aaggtgcgag agatcaacaa   2940
ttaccaccat gcccacgatg cttacctcaa cgccgtcgtt ggcactgcgc tcatcaagaa   3000
ataccccaag ctcgaaagcg agttcgttta cggcgattac aaggtctacg acgttcgaaa   3060
gatgattgcc aagtccgaac aggagattgg caaggctact gccaagtact tcttttactc   3120
caacatcatg aactttttca agaccgagat caccttggcc aacggagaga ttcgaaagag   3180
accacttatc gagaccaacg gcgaaactgg agagatcgtg tgggacaagg gtcgagactt   3240
tgcaaccgtg cgaaaggttc tgtcgatgcc tcaggtcaac atcgtcaaga aaaccgaggt   3300
tcagactggc ggattctcca aggagtcgat tctgcccaag cgaaactccg acaagctcat   3360
cgctcgaaag aaagactggg atcccaagaa atacggtggc ttcgattctc ctaccgtcgc   3420
ctattccgtg cttgtcgttg cgaaggtcga gaagggcaag tccaaaaagc tcaagtccgt   3480
caaggagctg ctcggaatta ccatcatgga gcgatcgagc ttcgagaaga atcccatcga   3540
cttcttggaa gccaagggtt acaaggaggt caagaaagac ctcattatca agctgcccaa   3600
gtactctctg ttcgaactgg agaacggtcg aaagcgtatg ctcgcctccg ctggcgagct   3660
gcagaaggga aacgagcttg ccttgccttc gaagtacgtc aactttctct atctggcttc   3720
tcactacgag aagctcaagg gttctcccga ggacaacgaa cagaagcaac tcttcgttga   3780
gcagcacaaa cattacctcg acgagattat cgagcagatt tccgagtttt cgaagcgagt   3840
catcctggct gatgccaact tggacaaggt gctctctgcc tacaacaagc atcgggacaa   3900
acccattcga gaacaggcgg agaacatcat tcacctgttt actcttacca acctgggtgc   3960
tcctgcagct ttcaagtact tcgataccac tatcgaccga aagcggtaca catccaccaa   4020
ggaggttctc gatgccaccc tgattcacca gtccatcact ggcctgtacg agacccgaat   4080
cgacctgtct cagcttggtg gcgactccag agccgatccc aagaaaaagc gaaaggtcta   4140
agcggccgca agtgtggatg gggaagtgag tgcccggttc tgtgtgcaca attggcaatc   4200
caagatggat ggattcaaca cagggatata gcgagctacg tggtggtgcg aggatatagc   4260
aacggatatt tatgtttgac acttgagaat gtacgataca agcactgtcc aagtacaata   4320
ctaaacatac tgtacatact catactcgta cccgggcaac ggtttcactt gagtgcagtg   4380
gctagtgctc ttactcgtac agtgtgcaat actgcgtatc atagtctttg atgtatatcg   4440
tattcattca tgttagttgc gtacgagccg gaagcataaa gtgtaaagcc tggggtgcct   4500
aatgagtgag ctaactcaca ttaattgcgt tgcgctcact gcccgctttc cagtcgggaa   4560
acctgtcgtg ccagctgcat taatgaatcg gccaacgcgc ggggagaggc ggtttgcgta   4620
ttgggcgctc ttccgcttcc tcgctcactg actcgctgcg ctcggtcgtt cggctgcggc   4680
gagcggtatc agctcactca aaggcggtaa tacggttatc cacagaatca ggggataacg   4740
caggaaagaa catgtgagca aaaggccagc aaaaggccag gaaccgtaaa aaggccgcgt   4800
tgctggcgtt tttccatagg ctccgccccc ctgacgagca tcacaaaaat cgacgctcaa   4860
gtcagaggtg gcgaaacccg acaggactat aaagatacca ggcgtttccc cctggaagct   4920
ccctcgtgcg ctctcctgtt ccgaccctgc cgcttaccgg atacctgtcc gcctttctcc   4980
cttcgggaag cgtggcgctt tctcatagct cacgctgtag gtatctcagt tcggtgtagg   5040
```

-continued

```
tcgttcgctc caagctgggc tgtgtgcacg aacccccgt tcagcccgac cgctgcgcct   5100
tatccggtaa ctatcgtctt gagtccaacc cggtaagaca cgacttatcg ccactggcag   5160
cagccactgg taacaggatt agcagagcga ggtatgtagg cggtgctaca gagttcttga   5220
agtggtggcc taactacggc tacactagaa ggacagtatt tggtatctgc gctctgctga   5280
agccagttac cttcggaaaa agagttggta gctcttgatc cggcaaacaa accaccgctg   5340
gtagcggtgg tttttttgtt tgcaagcagc agattacgcg cagaaaaaaa ggatctcaag   5400
aagatccttt gatcttttct acggggtctg acgctcagtg gaacgaaaac tcacgttaag   5460
ggattttggt catgagatta tcaaaaagga tcttcaccta gatcctttta aattaaaaat   5520
gaagttttaa atcaatctaa agtatatatg agtaaacttg gtctgacagt taccaatgct   5580
taatcagtga ggcacctatc tcagcgatct gtctatttcg ttcatccata gttgcctgac   5640
tccccgtcgt gtagataact acgatacggg agggcttacc atctggcccc agtgctgcaa   5700
tgataccgcg agacccacgc tcaccggctc cagatttatc agcaataaac cagccagccg   5760
gaagggccga gcgcagaagt ggtcctgcaa ctttatccgc ctccatccag tctattaatt   5820
gttgccggga agctagagta agtagttcgc cagttaatag tttgcgcaac gttgttgcca   5880
ttgctacagg catcgtggtg tcacgctcgt cgtttggtat ggcttcattc agctccggtt   5940
cccaacgatc aaggcgagtt acatgatccc ccatgttgtg caaaaaagcg gttagctcct   6000
tcggtcctcc gatcgttgtc agaagtaagt tggccgcagt gttatcactc atggttatgg   6060
cagcactgca taattctctt actgtcatgc catccgtaag atgcttttct gtgactggtg   6120
agtactcaac caagtcattc tgagaatagt gtatgcggcg accgagttgc tcttgcccgg   6180
cgtcaatacg ggataatacc gcgccacata gcagaacttt aaaagtgctc atcattggaa   6240
aacgttcttc ggggcgaaaa ctctcaagga tcttaccgct gttgagatcc agttcgatgt   6300
aacccactcg tgcacccaac tgatcttcag catcttttac tttcaccagc gtttctgggt   6360
gagcaaaaac aggaaggcaa aatgccgcaa aaaagggaat aagggcgaca cggaaatgtt   6420
gaatactcat actcttcctt tttcaatatt attgaagcat ttatcagggt tattgtctca   6480
tgagcggata catatttgaa tgtatttaga aaaataaaca aataggggtt ccgcgcacat   6540
ttccccgaaa agtgccacct gacgcgccct gtagcggcgc attaagcgcg gcgggtgtgg   6600
tggttacgcg cagcgtgacc gctacacttg ccagcgccct agcgcccgct cctttcgctt   6660
tcttcccttc ctttctcgcc acgttcgccg gctttccccg tcaagctcta aatcgggggc   6720
tccctttagg gttccgattt agtgctttac ggcacctcga ccccaaaaaa cttgattagg   6780
gtgatggttc acgtagtggg ccatcgccct gatagacggt ttttcgccct ttgacgttgg   6840
agtccacgtt ctttaatagt ggactcttgt tccaaactgg aacaacactc aaccctatct   6900
cggtctattc ttttgattta taagggattt tgccgatttc ggcctattgg ttaaaaaatg   6960
agctgattta acaaaaattt aacgcgaatt ttaacaaaat attaacgctt acaatttcca   7020
ttcgccattc aggctgcgca actgttggga agggcgatcg gtgcgggcct cttcgctatt   7080
acgccagctg gcgaaagggg gatgtgctgc aaggcgatta agttgggtaa cgccagggtt   7140
ttcccagtca cgacgttgta aaacgacggc cagtgaattg taatacgact cactataggg   7200
cgaattgggt accgggcccc ccctcgaggt cgatggtgtc gataagcttg atatcgaatt   7260
catgtcacac aaaccgatct tcgcctcaag gaaacctaat tctacatccg agagactgcc   7320
gagatccagt ctacactgat taattttcgg gccaataatt taaaaaaatc gtgttatata   7380
atattatatg tattatatat atacatcatg atgatactga cagtcatgtc ccattgctaa   7440
```

-continued

```
atagacagac tccatctgcc gcctccaact gatgttctca atatttaagg ggtcatctcg   7500
cattgtttaa taataaacag actccatcta ccgcctccaa atgatgttct caaaatatat   7560
tgtatgaact tatttttatt acttagtatt attagacaac ttacttgctt tatgaaaaac   7620
acttcctatt taggaaacaa tttataatgg cagttcgttc atttaacaat ttatgtagaa   7680
taaatgttat aaatgcgtat gggaaatctt aaatatggat agcataaatg atatctgcat   7740
tgcctaattc gaaatcaaca gcaacgaaaa aaatcccttg tacaacataa atagtcatcg   7800
agaaatatca actatcaaag aacagctatt cacacgttac tattgagatt attattggac   7860
gagaatcaca cactcaactg tctttctctc ttctagaaat acaggtacaa gtatgtacta   7920
ttctcattgt tcatacttct agtcatttca tcccacatat tccttggatt tctctccaat   7980
gaatgacatt ctatcttgca aattcaacaa ttataataag atataccaaa gtagcggtat   8040
agtggcaatc aaaaagcttc tctggtgtgc ttctcgtatt tatttttatt ctaatgatcc   8100
attaaaggta tatatttatt tcttgttata taatcctttt gtttattaca tgggctggat   8160
acataaaggt attttgattt aattttttgc ttaaattcaa tccccccctcg ttcagtgtca   8220
actgtaatgg taggaaatta ccatactttt gaagaagcaa aaaaaatgaa agaaaaaaaa   8280
aatcgtattt ccaggttaga cgttccgcag aatctagaat gcggtatgcg gtacattgtt   8340
cttcgaacgt aaaagttgcg ctccctgaga tattgtacat ttttgctttt acaagtacaa   8400
gtacatcgta caactatgta ctactgttga tgcatccaca acagtttgtt ttgtttttttt   8460
ttgtttttttt tttttctaat gattcattac cgctatgtat acctacttgt acttgtagta   8520
agccgggtta ttggcgttca attaatcata gacttatgaa tctgcacggt gtgcgctgcg   8580
agttactttt agcttatgca tgctacttgg gtgtaatatt gggatctgtt cggaaatcaa   8640
cggatgctca atcgatcgcc agcaacgcgg ccttagacat aaaaaacaaa aaaaaaaagc   8700
accgactcgg tgccactttt tcaagttgat aacggactag ccttatttta acttgctatt   8760
tctagctcta aaactagaac cgtactgaaa ctgagacgag cttactcgtt tcgtcctcac   8820
ggactcatca gtcagtttac gcatggttga tgtgtgttta attcaagaat gaatatagag   8880
aagagaagaa gaaaaaagat tcaattgagc cggcgatgca gacccttata taaatgttgc   8940
cttggacaga cggagcaagc ccgcccaaac ctacgttcgg tataatatgt taagcttttt   9000
aacacaaagg tttggcttgg ggtaacctga tgtggtgcaa aagaccgggc gttggcgagc   9060
cattgcgcgg gcgaatgggg tcgtgactcg tctcaaattc gagggcgtgc ctcaattcgt   9120
gcccccgtgg ctttttcccg ccgtttccgc cccgtttgca ccactgcagc cgcttctttg   9180
gttcggacac cttgctgcga gctaggtgcc ttgtgctact taaaaagtgg cctcccaaca   9240
ccaacatgac atgagtgcgt gggccaagac acgttggcgg ggtcgcagtc ggctcaatgg   9300
cccggaaaaa acgctgctgg agctggttcg gacgcagtcc gccgcggcgt atggatatcc   9360
gcaaggttcc atagcgccat tgccctccgt cggcgtctat cccgcaacct taattaagtc   9420
atacacaagt cagctttctt cgagcctcat ataagtataa gtagttcaac gtattagcac   9480
tgtacccagc atctccgtat cgagaaacac aacaacatgc cccattggac agatcatgcg   9540
gatacacagg ttgtgcagta tcatacatac tcgatcagac aggtcgtctg accatcatac   9600
aagctgaaca agcgctccat acttgcacgc tctctatata cacagttaaa ttacatatcc   9660
atagtctaac ctctaacagt taatcttctg gtaagcctcc cagccagcct tctggtatcg   9720
cttggcctcc tcaataggat ctcggttctg gccgtacaga cctcggccga caattatgat   9780
```

-continued

```
atccgttccg gtagacatga catcctcaac agttcggtac tgctgtccga gagcgtctcc   9840
cttgtcgtca agacccaccc cgggggtcag aataagccag tcctcagagt cgcccttagg   9900
tcggttctgg gcaatgaagc caaccacaaa ctcggggtcg gatcgggcaa gctcaatggt   9960
ctgcttggag tactcgccag tggccagaga gcccttgcaa gacagctcgg ccagcatgag  10020
cagacctctg gccagcttct cgttgggaga ggggactagg aactccttgt actgggagtt  10080
ctcgtagtca gagacgtcct ccttcttctg ttcagagaca gtttcctcgg caccagctcg  10140
caggccagca atgattccgg ttccgggtac accgtgggcg ttggtgatat cggaccactc  10200
ggcgattcgg tgacaccggt actggtgctt gacagtgttg ccaatatctg cgaactttct  10260
gtcctcgaac aggaagaaac cgtgcttaag agcaagttcc ttgaggggga gcacagtgcc  10320
ggcgtaggtg aagtcgtcaa tgatgtcgat atgggttttg atcatgcaca cataaggtcc  10380
gaccttatcg gcaagctcaa tgagctcctt ggtggtggta acatccagag aagcacacag  10440
gttggttttc ttggctgcca cgagcttgag cactcgagcg gcaaaggcgg acttgtggac  10500
gttagctcga gcttcgtagg agggcatttt ggtggtgaag aggagactga aataaattta  10560
gtctgcagaa ctttttatcg gaaccttatc tggggcagtg aagtatatgt tatggtaata  10620
gttacgagtt agttgaactt atagatagac tggactatac ggctatcggt ccaaattaga  10680
aagaacgtca atggctctct gggcgtcgcc tttgccgaca aaaatgtgat catgatgaaa  10740
gccagcaatg acgttgcagc tgatattgtt gtcggccaac cgcgccgaaa acgcagctgt  10800
cagacccaca gcctccaacg aagaatgtat cgtcaaagtg atccaagcac actcatagtt  10860
ggagtcgtac tccaaaggcg gcaatgacga gtcagacaga tactcgtcga cgtttaaacc  10920
atcatctaag ggcctcaaaa ctacctcgga actgctgcgc tgatctggac accacagagg  10980
ttccgagcac tttaggttgc accaaatgtc ccaccaggtg caggcagaaa acgctggaac  11040
agcgtgtaca gtttgtctta acaaaaagtg agggcgctga ggtcgagcag ggtggtgtga  11100
cttgttatag cctttagagc tgcgaaagcg cgtatggatt tggctcatca ggccagattg  11160
agggtctgtg gacacatgtc atgttagtgt acttcaatcg ccccctggat atagccccga  11220
caataggccg tggcctcatt tttttgcctt ccgcacattt ccattgctcg gtacccacac  11280
cttgcttctc ctgcacttgc caaccttaat actggtttac attgaccaac atcttacaag  11340
cggggggctt gtctagggta tatataaaca gtggctctcc caatcggttg ccagtctctt  11400
ttttcctttc tttccccaca gattcgaaat ctaaactaca catcacac              11448
```

<210> SEQ ID NO 154
<211> LENGTH: 11448
<212> TYPE: DNA
<213> ORGANISM: Artificial Sequence
<220> FEATURE:
<223> OTHER INFORMATION: pRF341

<400> SEQUENCE: 154

```
catggacaag aaatactcca tcggcctggc cattggaacc aactctgtcg gctgggctgt     60
catcaccgac gagtacaagg tgccctccaa gaaattcaag gtcctcggaa acaccgatcg    120
acactccatc aagaaaaacc tcattggtgc cctgttgttc gattctggcg agactgccga    180
agctaccaga ctcaagcgaa ctgctcggcg acgttacacc cgacggaaga accgaatctg    240
ctacctgcag gagatctttt ccaacgagat ggccaaggtg gacgattcgt tctttcatcg    300
actggaggaa tccttcctcg tcgaggaaga caagaaacac gagcgtcatc ccatctttgg    360
caacattgtg gacgaggttg cttaccacga gaagtatcct accatctacc acctgcgaaa    420
```

-continued

```
gaaactcgtc gattccaccg acaaggcgga tctcagactt atctacctcg ctctggcaca    480
catgatcaag tttcgaggtc atttcctcat cgagggcgat ctcaatcccg acaacagcga    540
tgtggacaag ctgttcattc agctcgttca gacctacaac cagctgttcg aggaaaaccc    600
catcaatgcc tccggagtcg atgcaaaggc catcttgtct gctcgactct cgaagagcag    660
acgactggag aacctcattg cccaacttcc tggcgagaaa aagaacggac tgtttggcaa    720
cctcattgcc ctttctcttg gtctcacacc caacttcaag tccaacttcg atctggcgga    780
ggacgccaag ctccagctgt ccaaggacac ctacgacgat gacctcgaca acctgcttgc    840
acagattggc gatcagtacg ccgacctgtt tctcgctgcc aagaaccttt cggatgctat    900
tctcttgtct gacattctgc gagtcaacac cgagatcaca aaggctcccc tttctgcctc    960
catgatcaag cgatacgacg agcaccatca ggatctcaca ctgctcaagg ctcttgtccg   1020
acagcaactg cccgagaagt acaaggagat ctttttcgat cagtcgaaga acggctacgc   1080
tggatacatc gacggcggag cctctcagga agagttctac aagttcatca agccaattct   1140
cgagaagatg gacggaaccg aggaactgct tgtcaagctc aatcgagagg atctgcttcg   1200
gaagcaacga accttcgaca acggcagcat tcctcatcag atccacctcg gtgagctgca   1260
cgccattctt cgacgtcagg aagacttcta cccctttctc aaggacaacc gagagaagat   1320
cgagaagatt cttacctttc gaatccccta ctatgttggt cctcttgcca gaggaaactc   1380
tcgatttgct tggatgactc gaaagtccga ggaaaccatc actccctgga acttcgagga   1440
agtcgtggac aagggtgcct ctgcacagtc cttcatcgag cgaatgacca acttcgacaa   1500
gaatctgccc aacgagaagg ttcttcccaa gcattcgctg ctctacgagt actttacagt   1560
ctacaacgaa ctcaccaaag tcaagtacgt taccgaggga atgcgaaagc ctgccttctt   1620
gtctggcgaa cagaagaaag ccattgtcga tctcctgttc aagaccaacc gaaaggtcac   1680
tgttaagcag ctcaaggagg actacttcaa gaaaatcgag tgtttcgaca gcgtcgagat   1740
ttccggagtt gaggaccgat tcaacgcctc tttgggcacc tatcacgatc tgctcaagat   1800
tatcaaggac aaggattttc tcgacaacga ggaaaacgag gacattctgg aggacatcgt   1860
gctcactctt accctgttcg aagatcggga gatgatcgag gaacgactca agacatacgc   1920
tcacctgttc gacgacaagg tcatgaaaca actcaagcga cgtagataca ccggctgggg   1980
aagactttcg cgaaagctca tcaacggcat cagagacaag cagtccggaa agaccattct   2040
ggactttctc aagtccgatg gctttgccaa ccgaaacttc atgcagctca ttcacgacga   2100
ttctcttacc ttcaaggagg acatccagaa ggcacaagtg tccggtcagg gcgacagctt   2160
gcacgaacat attgccaacc tggctggttc gccagccatc aagaaaggca ttctccagac   2220
tgtcaaggtt gtcgacgagc tggtgaaggt catgggacgt cacaagcccg agaacattgt   2280
gatcgagatg gccagagaga accagacaac tcaaaagggt cagaaaaact cgcgagagcg   2340
gatgaagcga atcgaggaag gcatcaagga gctgggatcc cagattctca aggagcatcc   2400
cgtcgagaac actcaactgc agaacgagaa gctgtatctc tactatctgc agaatggtcg   2460
agacatgtac gtggatcagg aactggacat caatcgtctc agcgactacg atgtggacgc   2520
cattgtccct caatcctttc tcaaggacga ttctatcgac aacaaggtcc ttacacgatc   2580
cgacaagaac agaggcaagt cggacaacgt tcccagcgaa gaggtggtca aaaagatgaa   2640
gaactactgg cgacagctgc tcaacgccaa gctcattacc cagcgaaagt tcgacaatct   2700
taccaaggcc gagcgaggcg gtctgtccga gctcgacaag gctggcttca tcaagcgtca   2760
```

-continued

```
actcgtcgag accagacaga tcacaaagca cgtcgcacag attctcgatt ctcggatgaa   2820
caccaagtac gacgagaacg acaagctcat ccgagaggtc aaggtgatta ctctcaagtc   2880
caaactggtc tccgatttcc gaaaggactt tcagttctac aaggtgcgag agatcaacaa   2940
ttaccaccat gcccacgatg cttacctcaa cgccgtcgtt ggcactgcgc tcatcaagaa   3000
ataccccaag ctcgaaagcg agttcgttta cggcgattac aaggtctacg acgttcgaaa   3060
gatgattgcc aagtccgaac aggagattgg caaggctact gccaagtact tcttttactc   3120
caacatcatg aactttttca agaccgagat caccttggcc aacggagaga ttcgaaagag   3180
accacttatc gagaccaacg gcgaaactgg agagatcgtg tgggacaagg gtcgagactt   3240
tgcaaccgtg cgaaaggttc tgtcgatgcc tcaggtcaac atcgtcaaga aaaccgaggt   3300
tcagactggc ggattctcca aggagtcgat tctgcccaag cgaaactccg acaagctcat   3360
cgctcgaaag aaagactggg atcccaagaa atacggtggc ttcgattctc ctaccgtcgc   3420
ctattccgtg cttgtcgttg cgaaggtcga gaagggcaag tccaaaaagc tcaagtccgt   3480
caaggagctg ctcggaatta ccatcatgga gcgatcgagc ttcgagaaga atcccatcga   3540
cttcttggaa gccaagggtt acaaggaggt caagaaagac ctcattatca agctgcccaa   3600
gtactctctg ttcgaactgg agaacggtcg aaagcgtatg ctcgcctccg ctggcgagct   3660
gcagaaggga aacgagcttg ccttgccttc gaagtacgtc aactttctct atctggcttc   3720
tcactacgag aagctcaagg gttctcccga ggacaacgaa cagaagcaac tcttcgttga   3780
gcagcacaaa cattacctcg acgagattat cgagcagatt tccgagtttt cgaagcgagt   3840
catcctggct gatgccaact tggacaaggt gctctctgcc tacaacaagc atcgggacaa   3900
acccattcga gaacaggcgg agaacatcat tcacctgttt actcttacca acctgggtgc   3960
tcctgcagct ttcaagtact tcgataccac tatcgaccga aagcggtaca catccaccaa   4020
ggaggttctc gatgccaccc tgattcacca gtccatcact ggcctgtacg agacccgaat   4080
cgacctgtct cagcttggtg gcgactccag agccgatccc aagaaaaagc gaaaggtcta   4140
agcggccgca agtgtggatg gggaagtgag tgcccggttc tgtgtgcaca attggcaatc   4200
caagatggat ggattcaaca cagggatata gcgagctacg tggtggtgcg aggatatagc   4260
aacggatatt tatgtttgac acttgagaat gtacgataca agcactgtcc aagtacaata   4320
ctaaacatac tgtacatact catactcgta cccgggcaac ggtttcactt gagtgcagtg   4380
gctagtgctc ttactcgtac agtgtgcaat actgcgtatc atagtctttg atgtatatcg   4440
tattcattca tgttagttgc gtacgagccg gaagcataaa gtgtaaagcc tggggtgcct   4500
aatgagtgag ctaactcaca ttaattgcgt tgcgctcact gcccgctttc cagtcgggaa   4560
acctgtcgtg ccagctgcat taatgaatcg gccaacgcgc ggggagaggc ggtttgcgta   4620
ttgggcgctc ttccgcttcc tcgctcactg actcgctgcg ctcggtcgtt cggctgcggc   4680
gagcggtatc agctcactca aaggcggtaa tacggttatc cacagaatca ggggataacg   4740
caggaaagaa catgtgagca aaaggccagc aaaaggccag gaaccgtaaa aaggccgcgt   4800
tgctggcgtt tttccatagg ctccgccccc ctgacgagca tcacaaaaat cgacgctcaa   4860
gtcagaggtg gcgaaacccg acaggactat aaagatacca ggcgtttccc cctggaagct   4920
ccctcgtgcg ctctcctgtt ccgaccctgc cgcttaccgg atacctgtcc gcctttctcc   4980
cttcgggaag cgtggcgctt tctcatagct cacgctgtag gtatctcagt tcggtgtagg   5040
tcgttcgctc caagctgggc tgtgtgcacg aaccccccgt tcagcccgac cgctgcgcct   5100
tatccggtaa ctatcgtctt gagtccaacc cggtaagaca cgacttatcg ccactggcag   5160
```

cagccactgg taacaggatt agcagagcga ggtatgtagg cggtgctaca gagttcttga 5220
agtggtggcc taactacggc tacactagaa ggacagtatt tggtatctgc gctctgctga 5280
agccagttac cttcggaaaa agagttggta gctcttgatc cggcaaacaa accaccgctg 5340
gtagcggtgg tttttttgtt tgcaagcagc agattacgcg cagaaaaaaa ggatctcaag 5400
aagatccttt gatcttttct acggggtctg acgctcagtg gaacgaaaac tcacgttaag 5460
ggattttggt catgagatta tcaaaaagga tcttcaccta gatcctttta aattaaaaat 5520
gaagttttaa atcaatctaa agtatatatg agtaaacttg gtctgacagt taccaatgct 5580
taatcagtga ggcacctatc tcagcgatct gtctatttcg ttcatccata gttgcctgac 5640
tccccgtcgt gtagataact acgatacggg agggcttacc atctggcccc agtgctgcaa 5700
tgataccgcg agacccacgc tcaccggctc cagatttatc agcaataaac cagccagccg 5760
gaagggccga gcgcagaagt ggtcctgcaa ctttatccgc ctccatccag tctattaatt 5820
gttgccggga agctagagta agtagttcgc cagttaatag tttgcgcaac gttgttgcca 5880
ttgctacagg catcgtggtg tcacgctcgt cgtttggtat ggcttcattc agctccggtt 5940
cccaacgatc aaggcgagtt acatgatccc ccatgttgtg caaaaaagcg gttagctcct 6000
tcggtcctcc gatcgttgtc agaagtaagt tggccgcagt gttatcactc atggttatgg 6060
cagcactgca taattctctt actgtcatgc catccgtaag atgcttttct gtgactggtg 6120
agtactcaac caagtcattc tgagaatagt gtatgcggcg accgagttgc tcttgcccgg 6180
cgtcaatacg ggataatacc gcgccacata gcagaacttt aaaagtgctc atcattggaa 6240
aacgttcttc ggggcgaaaa ctctcaagga tcttaccgct gttgagatcc agttcgatgt 6300
aacccactcg tgcacccaac tgatcttcag catcttttac tttcaccagc gtttctgggt 6360
gagcaaaaac aggaaggcaa aatgccgcaa aaaagggaat aagggcgaca cggaaatgtt 6420
gaatactcat actcttcctt tttcaatatt attgaagcat ttatcagggt tattgtctca 6480
tgagcggata catatttgaa tgtatttaga aaaataaaca aataggggtt ccgcgcacat 6540
ttccccgaaa agtgccacct gacgcgccct gtagcggcgc attaagcgcg gcgggtgtgg 6600
tggttacgcg cagcgtgacc gctacacttg ccagcgccct agcgcccgct cctttcgctt 6660
tcttcccttc ctttctcgcc acgttcgccg gctttccccg tcaagctcta aatcgggggc 6720
tccctttagg gttccgattt agtgctttac ggcacctcga ccccaaaaaa cttgattagg 6780
gtgatggttc acgtagtggg ccatcgccct gatagacggt ttttcgccct ttgacgttgg 6840
agtccacgtt ctttaatagt ggactcttgt tccaaactgg aacaacactc aaccctatct 6900
cggtctattc ttttgattta taagggattt tgccgatttc ggcctattgg ttaaaaaatg 6960
agctgattta acaaaaattt aacgcgaatt ttaacaaaat attaacgctt acaatttcca 7020
ttcgccattc aggctgcgca actgttggga agggcgatcg gtgcgggcct cttcgctatt 7080
acgccagctg gcgaaagggg gatgtgctgc aaggcgatta agttgggtaa cgccagggtt 7140
ttcccagtca cgacgttgta aaacgacggc cagtgaattg taatacgact cactataggg 7200
cgaattgggt accgggcccc ccctcgaggt cgatggtgtc gataagcttg atatcgaatt 7260
catgtcacac aaaccgatct tcgcctcaag gaaacctaat tctacatccg agagactgcc 7320
gagatccagt ctacactgat taattttcgg gccaataatt taaaaaaatc gtgttatata 7380
atattatatg tattatatat atacatcatg atgatactga cagtcatgtc ccattgctaa 7440
atagacagac tccatctgcc gcctccaact gatgttctca atatttaagg ggtcatctcg 7500

-continued

```
cattgtttaa taataaacag actccatcta ccgcctccaa atgatgttct caaaatatat   7560
tgtatgaact tatttttatt acttagtatt attagacaac ttacttgctt tatgaaaaac   7620
acttcctatt taggaaacaa tttataatgg cagttcgttc atttaacaat ttatgtagaa   7680
taaatgttat aaatgcgtat gggaaatctt aaatatggat agcataaatg atatctgcat   7740
tgcctaattc gaaatcaaca gcaacgaaaa aaatcccttg tacaacataa atagtcatcg   7800
agaaatatca actatcaaag aacagctatt cacacgttac tattgagatt attattggac   7860
gagaatcaca cactcaactg tctttctctc ttctagaaat acaggtacaa gtatgtacta   7920
ttctcattgt tcatacttct agtcatttca tcccacatat tccttggatt tctctccaat   7980
gaatgacatt ctatcttgca aattcaacaa ttataataag atataccaaa gtagcggtat   8040
agtggcaatc aaaaagcttc tctggtgtgc ttctcgtatt tatttttatt ctaatgatcc   8100
attaaaggta tatatttatt tcttgttata taatcctttt gtttattaca tgggctggat   8160
acataaaggt attttgattt aatttttgc ttaaattcaa tccccccctcg ttcagtgtca   8220
actgtaatgg taggaaatta ccatactttt gaagaagcaa aaaaaatgaa agaaaaaaaa   8280
aatcgtattt ccaggttaga cgttccgcag aatctagaat gcggtatgcg gtacattgtt   8340
cttcgaacgt aaaagttgcg ctccctgaga tattgtacat ttttgctttt acaagtacaa   8400
gtacatcgta caactatgta ctactgttga tgcatccaca acagtttgtt ttgttttttt   8460
ttgttttttt tttttctaat gattcattac cgctatgtat acctacttgt acttgtagta   8520
agccgggtta ttggcgttca attaatcata gacttatgaa tctgcacggt gtgcgctgcg   8580
agttactttt agcttatgca tgctacttgg gtgtaatatt gggatctgtt cggaaatcaa   8640
cggatgctca atcgatcgcc agcaacgcgg ccttagacat aaaaaacaaa aaaaaaaagc   8700
accgactcgg tgccactttt tcaagttgat aacggactag ccttatttta acttgctatt   8760
tctagctcta aaacgagtaa cggtaacgac accggacgag cttactcgtt tcgtcctcac   8820
ggactcatca gcggtgttac gcatggttga tgtgtgttta attcaagaat gaatatagag   8880
aagagaagaa gaaaaaagat tcaattgagc cggcgatgca gacccttata taaatgttgc   8940
cttggacaga cggagcaagc ccgcccaaac ctacgttcgg tataatatgt taagcttttt   9000
aacacaaagg tttggcttgg ggtaacctga tgtggtgcaa aagaccgggc gttggcgagc   9060
cattgcgcgg gcgaatgggg tcgtgactcg tctcaaattc gagggcgtgc ctcaattcgt   9120
gcccccgtgg ctttttcccg ccgtttccgc cccgtttgca ccactgcagc cgcttctttg   9180
gttcggacac cttgctgcga gctaggtgcc ttgtgctact taaaaagtgg cctcccaaca   9240
ccaacatgac atgagtgcgt gggccaagac acgttggcgg ggtcgcagtc ggctcaatgg   9300
cccggaaaaa acgctgctgg agctggttcg gacgcagtcc gccgcggcgt atggatatcc   9360
gcaaggttcc atagcgccat tgccctccgt cggcgtctat cccgcaacct taattaagtc   9420
atacacaagt cagctttctt cgagcctcat ataagtataa gtagttcaac gtattagcac   9480
tgtacccagc atctccgtat cgagaaacac aacaacatgc cccattggac agatcatgcg   9540
gatacacagg ttgtgcagta tcatacatac tcgatcagac aggtcgtctg accatcatac   9600
aagctgaaca agcgctccat acttgcacgc tctctatata cacagttaaa ttacatatcc   9660
atagtctaac ctctaacagt taatcttctg gtaagcctcc cagccagcct tctggtatcg   9720
cttggcctcc tcaataggat ctcggttctg gccgtacaga cctcggccga caattatgat   9780
atccgttccg gtagacatga catcctcaac agttcggtac tgctgtccga gagcgtctcc   9840
cttgtcgtca agacccaccc cgggggtcag aataagccag tcctcagagt cgcccttagg   9900
```

tcggttctgg gcaatgaagc caaccacaaa ctcggggtcg gatcgggcaa gctcaatggt 9960
ctgcttggag tactcgccag tggccagaga gcccttgcaa gacagctcgg ccagcatgag 10020
cagacctctg gccagcttct cgttgggaga ggggactagg aactccttgt actgggagtt 10080
ctcgtagtca gagacgtcct ccttcttctg ttcagagaca gtttcctcgg caccagctcg 10140
caggccagca atgattccgg ttccgggtac accgtgggcg ttggtgatat cggaccactc 10200
ggcgattcgg tgacaccggt actggtgctt gacagtgttg ccaatatctg cgaactttct 10260
gtcctcgaac aggaagaaac cgtgcttaag agcaagttcc ttgaggggga gcacagtgcc 10320
ggcgtaggtg aagtcgtcaa tgatgtcgat atgggttttg atcatgcaca cataaggtcc 10380
gaccttatcg gcaagctcaa tgagctcctt ggtggtggta acatccagag aagcacacag 10440
gttggttttc ttggctgcca cgagcttgag cactcgagcg gcaaaggcgg acttgtggac 10500
gttagctcga gcttcgtagg agggcatttt ggtggtgaag aggagactga aataaattta 10560
gtctgcagaa ctttttatcg gaaccttatc tggggcagtg aagtatatgt tatggtaata 10620
gttacgagtt agttgaactt atagatagac tggactatac ggctatcggt ccaaattaga 10680
aagaacgtca atggctctct gggcgtcgcc tttgccgaca aaaatgtgat catgatgaaa 10740
gccagcaatg acgttgcagc tgatattgtt gtcggccaac cgcgccgaaa acgcagctgt 10800
cagacccaca gcctccaacg aagaatgtat cgtcaaagtg atccaagcac actcatagtt 10860
ggagtcgtac tccaaaggcg gcaatgacga gtcagacaga tactcgtcga cgtttaaacc 10920
atcatctaag ggcctcaaaa ctacctcgga actgctgcgc tgatctggac accacagagg 10980
ttccgagcac tttaggttgc accaaatgtc ccaccaggtg caggcagaaa acgctggaac 11040
agcgtgtaca gtttgtctta acaaaaagtg agggcgctga ggtcgagcag ggtggtgtga 11100
cttgttatag cctttagagc tgcgaaagcg cgtatggatt tggctcatca ggccagattg 11160
agggtctgtg gacacatgtc atgttagtgt acttcaatcg ccccctggat atagccccga 11220
caataggccg tggcctcatt tttttgcctt ccgcacattt ccattgctcg gtacccacac 11280
cttgcttctc ctgcacttgc caaccttaat actggtttac attgaccaac atcttacaag 11340
cggggggctt gtctagggta tatataaaca gtggctctcc caatcggttg ccagtctctt 11400
ttttcctttc tttccccaca gattcgaaat ctaaactaca catcacac 11448

<210> SEQ ID NO 155
<211> LENGTH: 11448
<212> TYPE: DNA
<213> ORGANISM: Artificial sequence
<220> FEATURE:
<223> OTHER INFORMATION: pRF343

<400> SEQUENCE: 155
catggacaag aaatactcca tcggcctggc cattggaacc aactctgtcg gctgggctgt 60
catcaccgac gagtacaagg tgccctccaa gaaattcaag gtcctcggaa acaccgatcg 120
acactccatc aagaaaaacc tcattggtgc cctgttgttc gattctggcg agactgccga 180
agctaccaga ctcaagcgaa ctgctcggcg acgttacacc cgacggaaga accgaatctg 240
ctacctgcag gagatctttt ccaacgagat ggccaaggtg gacgattcgt tctttcatcg 300
actggaggaa tccttcctcg tcgaggaaga caagaaacac gagcgtcatc ccatctttgg 360
caacattgtg gacgaggttg cttaccacga gaagtatcct accatctacc acctgcgaaa 420
gaaactcgtc gattccaccg acaaggcgga tctcagactt atctacctcg ctctggcaca 480

-continued

```
catgatcaag tttcgaggtc atttcctcat cgagggcgat ctcaatcccg acaacagcga    540
tgtggacaag ctgttcattc agctcgttca gacctacaac cagctgttcg aggaaaaccc    600
catcaatgcc tccggagtcg atgcaaaggc catcttgtct gctcgactct cgaagagcag    660
acgactggag aacctcattg cccaacttcc tggcgagaaa aagaacggac tgtttggcaa    720
cctcattgcc ctttctcttg gtctcacacc caacttcaag tccaacttcg atctggcgga    780
ggacgccaag ctccagctgt ccaaggacac ctacgacgat gacctcgaca acctgcttgc    840
acagattggc gatcagtacg ccgacctgtt tctcgctgcc aagaaccttt cggatgctat    900
tctcttgtct gacattctgc gagtcaacac cgagatcaca aaggctcccc tttctgcctc    960
catgatcaag cgatacgacg agcaccatca ggatctcaca ctgctcaagg ctcttgtccg   1020
acagcaactg cccgagaagt acaaggagat cttttttcgat cagtcgaaga acggctacgc   1080
tggatacatc gacggcggag cctctcagga agagttctac aagttcatca agccaattct   1140
cgagaagatg gacggaaccg aggaactgct tgtcaagctc aatcgagagg atctgcttcg   1200
gaagcaacga accttcgaca acggcagcat tcctcatcag atccacctcg gtgagctgca   1260
cgccattctt cgacgtcagg aagacttcta cccctttctc aaggacaacc gagagaagat   1320
cgagaagatt cttacctttc gaatccccta ctatgttggt cctcttgcca gaggaaactc   1380
tcgatttgct tggatgactc gaaagtccga ggaaaccatc actccctgga acttcgagga   1440
agtcgtggac aagggtgcct ctgcacagtc cttcatcgag cgaatgacca acttcgacaa   1500
gaatctgccc aacgagaagg ttcttcccaa gcattcgctg ctctacgagt actttacagt   1560
ctacaacgaa ctcaccaaag tcaagtacgt taccgaggga atgcgaaagc ctgccttctt   1620
gtctggcgaa cagaagaaag ccattgtcga tctcctgttc aagaccaacc gaaaggtcac   1680
tgttaagcag ctcaaggagg actacttcaa gaaaatcgag tgtttcgaca gcgtcgagat   1740
ttccggagtt gaggaccgat tcaacgcctc tttgggcacc tatcacgatc tgctcaagat   1800
tatcaaggac aaggattttc tcgacaacga ggaaaacgag gacattctgg aggacatcgt   1860
gctcactctt accctgttcg aagatcggga gatgatcgag gaacgactca agacatacgc   1920
tcacctgttc gacgacaagg tcatgaaaca actcaagcga cgtagataca ccggctgggg   1980
aagactttcg cgaaagctca tcaacggcat cagagacaag cagtccggaa agaccattct   2040
ggactttctc aagtccgatg gctttgccaa ccgaaacttc atgcagctca ttcacgacga   2100
ttctcttacc ttcaaggagg acatccagaa ggcacaagtg tccggtcagg gcgacagctt   2160
gcacgaacat attgccaacc tggctggttc gccagccatc aagaaaggca ttctccagac   2220
tgtcaaggtt gtcgacgagc tggtgaaggt catgggacgt cacaagcccg agaacattgt   2280
gatcgagatg gccagagaga accagacaac tcaaaagggt cagaaaaact cgcgagagcg   2340
gatgaagcga atcgaggaag gcatcaagga gctgggatcc cagattctca aggagcatcc   2400
cgtcgagaac actcaactgc agaacgagaa gctgtatctc tactatctgc agaatggtcg   2460
agacatgtac gtggatcagg aactggacat caatcgtctc agcgactacg atgtggacgc   2520
cattgtccct caatcctttc tcaaggacga ttctatcgac aacaaggtcc ttacacgatc   2580
cgacaagaac agaggcaagt cggacaacgt tcccagcgaa gaggtggtca aaaagatgaa   2640
gaactactgg cgacagctgc tcaacgccaa gctcattacc cagcgaaagt tcgacaatct   2700
taccaaggcc gagcgaggcg gtctgtccga gctcgacaag gctggcttca tcaagcgtca   2760
actcgtcgag accagacaga tcacaaagca cgtcgcacag attctcgatt ctcggatgaa   2820
caccaagtac gacgagaacg acaagctcat ccgagaggtc aaggtgatta ctctcaagtc   2880
```

```
caaactggtc tccgatttcc gaaaggactt tcagttctac aaggtgcgag agatcaacaa   2940
ttaccaccat gcccacgatg cttacctcaa cgccgtcgtt ggcactgcgc tcatcaagaa   3000
ataccccaag ctcgaaagcg agttcgttta cggcgattac aaggtctacg acgttcgaaa   3060
gatgattgcc aagtccgaac aggagattgg caaggctact gccaagtact tcttttactc   3120
caacatcatg aactttttca agaccgagat caccttggcc aacggagaga ttcgaaagag   3180
accacttatc gagaccaacg gcgaaactgg agagatcgtg tgggacaagg gtcgagactt   3240
tgcaaccgtg cgaaaggttc tgtcgatgcc tcaggtcaac atcgtcaaga aaaccgaggt   3300
tcagactggc ggattctcca aggagtcgat tctgcccaag cgaaactccg acaagctcat   3360
cgctcgaaag aaagactggg atcccaagaa atacggtggc ttcgattctc ctaccgtcgc   3420
ctattccgtg cttgtcgttg cgaaggtcga gaagggcaag tccaaaaagc tcaagtccgt   3480
caaggagctg ctcggaatta ccatcatgga gcgatcgagc ttcgagaaga atcccatcga   3540
cttcttggaa gccaagggtt acaaggaggt caagaaagac ctcattatca agctgcccaa   3600
gtactctctg ttcgaactgg agaacggtcg aaagcgtatg ctcgcctccg ctggcgagct   3660
gcagaaggga aacgagcttg ccttgccttc gaagtacgtc aactttctct atctggcttc   3720
tcactacgag aagctcaagg gttctcccga ggacaacgaa cagaagcaac tcttcgttga   3780
gcagcacaaa cattacctcg acgagattat cgagcagatt tccgagtttt cgaagcgagt   3840
catcctggct gatgccaact tggacaaggt gctctctgcc tacaacaagc atcgggacaa   3900
acccattcga gaacaggcgg agaacatcat tcacctgttt actcttacca acctgggtgc   3960
tcctgcagct ttcaagtact tcgataccac tatcgaccga aagcggtaca catccaccaa   4020
ggaggttctc gatgccaccc tgattcacca gtccatcact ggcctgtacg agacccgaat   4080
cgacctgtct cagcttggtg gcgactccag agccgatccc aagaaaaagc gaaaggtcta   4140
agcggccgca agtgtggatg gggaagtgag tgcccggttc tgtgtgcaca attggcaatc   4200
caagatggat ggattcaaca cagggatata gcgagctacg tggtggtgcg aggatatagc   4260
aacggatatt tatgtttgac acttgagaat gtacgataca agcactgtcc aagtacaata   4320
ctaaacatac tgtacatact catactcgta cccgggcaac ggtttcactt gagtgcagtg   4380
gctagtgctc ttactcgtac agtgtgcaat actgcgtatc atagtctttg atgtatatcg   4440
tattcattca tgttagttgc gtacgagccg gaagcataaa gtgtaaagcc tggggtgcct   4500
aatgagtgag ctaactcaca ttaattgcgt tgcgctcact gcccgctttc cagtcgggaa   4560
acctgtcgtg ccagctgcat taatgaatcg gccaacgcgc ggggagaggc ggtttgcgta   4620
ttgggcgctc ttccgcttcc tcgctcactg actcgctgcg ctcggtcgtt cggctgcggc   4680
gagcggtatc agctcactca aaggcggtaa tacggttatc cacagaatca ggggataacg   4740
caggaaagaa catgtgagca aaaggccagc aaaaggccag gaaccgtaaa aaggccgcgt   4800
tgctggcgtt tttccatagg ctccgccccc ctgacgagca tcacaaaaat cgacgctcaa   4860
gtcagaggtg gcgaaacccg acaggactat aaagatacca ggcgtttccc cctggaagct   4920
ccctcgtgcg ctctcctgtt ccgaccctgc cgcttaccgg atacctgtcc gcctttctcc   4980
cttcgggaag cgtggcgctt tctcatagct cacgctgtag gtatctcagt tcggtgtagg   5040
tcgttcgctc caagctgggc tgtgtgcacg aaccccccgt tcagcccgac cgctgcgcct   5100
tatccggtaa ctatcgtctt gagtccaacc cggtaagaca cgacttatcg ccactggcag   5160
cagccactgg taacaggatt agcagagcga ggtatgtagg cggtgctaca gagttcttga   5220
```

-continued

```
agtggtggcc taactacggc tacactagaa ggacagtatt tggtatctgc gctctgctga   5280
agccagttac cttcggaaaa agagttggta gctcttgatc cggcaaacaa accaccgctg   5340
gtagcggtgg tttttttgtt tgcaagcagc agattacgcg cagaaaaaaa ggatctcaag   5400
aagatccttt gatcttttct acggggtctg acgctcagtg gaacgaaaac tcacgttaag   5460
ggattttggt catgagatta tcaaaaagga tcttcaccta gatcctttta aattaaaaat   5520
gaagttttaa atcaatctaa agtatatatg agtaaacttg gtctgacagt taccaatgct   5580
taatcagtga ggcacctatc tcagcgatct gtctatttcg ttcatccata gttgcctgac   5640
tccccgtcgt gtagataact acgatacggg agggcttacc atctggcccc agtgctgcaa   5700
tgataccgcg agacccacgc tcaccggctc cagatttatc agcaataaac cagccagccg   5760
gaagggccga gcgcagaagt ggtcctgcaa ctttatccgc ctccatccag tctattaatt   5820
gttgccggga agctagagta agtagttcgc cagttaatag tttgcgcaac gttgttgcca   5880
ttgctacagg catcgtggtg tcacgctcgt cgtttggtat ggcttcattc agctccggtt   5940
cccaacgatc aaggcgagtt acatgatccc ccatgttgtg caaaaaagcg gttagctcct   6000
tcggtcctcc gatcgttgtc agaagtaagt tggccgcagt gttatcactc atggttatgg   6060
cagcactgca taattctctt actgtcatgc catccgtaag atgcttttct gtgactggtg   6120
agtactcaac caagtcattc tgagaatagt gtatgcggcg accgagttgc tcttgcccgg   6180
cgtcaatacg ggataatacc gcgccacata gcagaacttt aaaagtgctc atcattggaa   6240
aacgttcttc ggggcgaaaa ctctcaagga tcttaccgct gttgagatcc agttcgatgt   6300
aacccactcg tgcacccaac tgatcttcag catcttttac tttcaccagc gtttctgggt   6360
gagcaaaaac aggaaggcaa aatgccgcaa aaaagggaat aagggcgaca cggaaatgtt   6420
gaatactcat actcttcctt tttcaatatt attgaagcat ttatcagggt tattgtctca   6480
tgagcggata catatttgaa tgtatttaga aaaataaaca aataggggtt ccgcgcacat   6540
ttccccgaaa agtgccacct gacgcgccct gtagcggcgc attaagcgcg gcgggtgtgg   6600
tggttacgcg cagcgtgacc gctacacttg ccagcgccct agcgcccgct cctttcgctt   6660
tcttcccttc ctttctcgcc acgttcgccg gctttccccg tcaagctcta aatcgggggc   6720
tccctttagg gttccgattt agtgctttac ggcacctcga ccccaaaaaa cttgattagg   6780
gtgatggttc acgtagtggg ccatcgccct gatagacggt ttttcgccct ttgacgttgg   6840
agtccacgtt ctttaatagt ggactcttgt tccaaactgg aacaacactc aaccctatct   6900
cggtctattc ttttgattta taagggattt tgccgatttc ggcctattgg ttaaaaaatg   6960
agctgattta acaaaaattt aacgcgaatt ttaacaaaat attaacgctt acaatttcca   7020
ttcgccattc aggctgcgca actgttggga agggcgatcg gtgcgggcct cttcgctatt   7080
acgccagctg gcgaaagggg gatgtgctgc aaggcgatta agttgggtaa cgccagggtt   7140
ttcccagtca cgacgttgta aaacgacggc cagtgaattg taatacgact cactataggg   7200
cgaattgggt accgggcccc ccctcgaggt cgatggtgtc gataagcttg atatcgaatt   7260
catgtcacac aaaccgatct tcgcctcaag gaaacctaat tctacatccg agagactgcc   7320
gagatccagt ctacactgat taattttcgg gccaataatt taaaaaaatc gtgttatata   7380
atattatatg tattatatat atacatcatg atgatactga cagtcatgtc ccattgctaa   7440
atagacagac tccatctgcc gcctccaact gatgttctca atatttaagg ggtcatctcg   7500
cattgtttaa taataaacag actccatcta ccgcctccaa atgatgttct caaaatatat   7560
tgtatgaact tatttttatt acttagtatt attagacaac ttacttgctt tatgaaaaac   7620
```

-continued

```
acttcctatt taggaaacaa tttataatgg cagttcgttc atttaacaat ttatgtagaa   7680
taaatgttat aaatgcgtat gggaaatctt aaatatggat agcataaatg atatctgcat   7740
tgcctaattc gaaatcaaca gcaacgaaaa aaatcccttg tacaacataa atagtcatcg   7800
agaaatatca actatcaaag aacagctatt cacacgttac tattgagatt attattggac   7860
gagaatcaca cactcaactg tctttctctc ttctagaaat acaggtacaa gtatgtacta   7920
ttctcattgt tcatacttct agtcatttca tcccacatat tccttggatt tctctccaat   7980
gaatgacatt ctatcttgca aattcaacaa ttataataag atataccaaa gtagcggtat   8040
agtggcaatc aaaaagcttc tctggtgtgc ttctcgtatt tatttttatt ctaatgatcc   8100
attaaaggta tatatttatt tcttgttata taatcctttt gtttattaca tgggctggat   8160
acataaaggt attttgattt aatttttgc ttaaattcaa tcccccctcg ttcagtgtca   8220
actgtaatgg taggaaatta ccatactttt gaagaagcaa aaaaaatgaa agaaaaaaaa   8280
aatcgtattt ccaggttaga cgttccgcag aatctagaat gcggtatgcg gtacattgtt   8340
cttcgaacgt aaaagttgcg ctccctgaga tattgtacat ttttgctttt acaagtacaa   8400
gtacatcgta caactatgta ctactgttga tgcatccaca acagtttgtt ttgttttttt   8460
ttgttttttt tttttctaat gattcattac cgctatgtat acctacttgt acttgtagta   8520
agccgggtta ttggcgttca attaatcata gacttatgaa tctgcacggt gtgcgctgcg   8580
agttactttt agcttatgca tgctacttgg gtgtaatatt gggatctgtt cggaaatcaa   8640
cggatgctca atcgatcgcc agcaacgcgg ccttagacat aaaaaacaaa aaaaaaaagc   8700
accgactcgg tgccactttt tcaagttgat aacggactag ccttatttta acttgctatt   8760
tctagctcta aaaccgaagc tgaaggtgac caaggacgag cttactcgtt tcgtcctcac   8820
ggactcatca gcctggttac gcatggttga tgtgtgttta attcaagaat gaatatagag   8880
aagagaagaa gaaaaaagat tcaattgagc cggcgatgca gacccttata taaatgttgc   8940
cttggacaga cggagcaagc ccgcccaaac ctacgttcgg tataatatgt taagcttttt   9000
aacacaaagg tttggcttgg ggtaacctga tgtggtgcaa aagaccgggc gttggcgagc   9060
cattgcgcgg gcgaatgggg tcgtgactcg tctcaaattc gagggcgtgc ctcaattcgt   9120
gcccccgtgg ctttttcccg ccgtttccgc cccgtttgca ccactgcagc cgcttctttg   9180
gttcggacac cttgctgcga gctaggtgcc ttgtgctact taaaaagtgg cctcccaaca   9240
ccaacatgac atgagtgcgt gggccaagac acgttggcgg ggtcgcagtc ggctcaatgg   9300
cccggaaaaa acgctgctgg agctggttcg gacgcagtcc gccgcggcgt atggatatcc   9360
gcaaggttcc atagcgccat tgccctccgt cggcgtctat cccgcaacct taattaagtc   9420
atacacaagt cagctttctt cgagcctcat ataagtataa gtagttcaac gtattagcac   9480
tgtacccagc atctccgtat cgagaaacac aacaacatgc cccattggac agatcatgcg   9540
gatacacagg ttgtgcagta tcatacatac tcgatcagac aggtcgtctg accatcatac   9600
aagctgaaca agcgctccat acttgcacgc tctctatata cacagttaaa ttacatatcc   9660
atagtctaac ctctaacagt taatcttctg gtaagcctcc cagccagcct tctggtatcg   9720
cttggcctcc tcaataggat ctcggttctg gccgtacaga cctcggccga caattatgat   9780
atccgttccg gtagacatga catcctcaac agttcggtac tgctgtccga gagcgtctcc   9840
cttgtcgtca agacccaccc cgggggtcag aataagccag tcctcagagt cgcccttagg   9900
tcggttctgg gcaatgaagc caaccacaaa ctcggggtcg gatcgggcaa gctcaatggt   9960
```

```
ctgcttggag tactcgccag tggccagaga gcccttgcaa gacagctcgg ccagcatgag  10020
cagacctctg gccagcttct cgttgggaga ggggactagg aactccttgt actgggagtt  10080
ctcgtagtca gagacgtcct ccttcttctg ttcagagaca gtttcctcgg caccagctcg  10140
caggccagca atgattccgg ttccgggtac accgtgggcg ttggtgatat cggaccactc  10200
ggcgattcgg tgacaccggt actggtgctt gacagtgttg ccaatatctg cgaactttct  10260
gtcctcgaac aggaagaaac cgtgcttaag agcaagttcc ttgagggggga gcacagtgcc  10320
ggcgtaggtg aagtcgtcaa tgatgtcgat atgggttttg atcatgcaca cataaggtcc  10380
gaccttatcg gcaagctcaa tgagctcctt ggtggtggta acatccagag aagcacacag  10440
gttggttttc ttggctgcca cgagcttgag cactcgagcg gcaaaggcgg acttgtggac  10500
gttagctcga gcttcgtagg agggcatttt ggtggtgaag aggagactga aataaattta  10560
gtctgcagaa ctttttatcg gaaccttatc tggggcagtg aagtatatgt tatggtaata  10620
gttacgagtt agttgaactt atagatagac tggactatac ggctatcggt ccaaattaga  10680
aagaacgtca atggctctct gggcgtcgcc tttgccgaca aaaatgtgat catgatgaaa  10740
gccagcaatg acgttgcagc tgatattgtt gtcggccaac cgcgccgaaa acgcagctgt  10800
cagacccaca gcctccaacg aagaatgtat cgtcaaagtg atccaagcac actcatagtt  10860
ggagtcgtac tccaaaggcg gcaatgacga gtcagacaga tactcgtcga cgtttaaacc  10920
atcatctaag ggcctcaaaa ctacctcgga actgctgcgc tgatctggac accacagagg  10980
ttccgagcac tttaggttgc accaaatgtc ccaccaggtg caggcagaaa acgctggaac  11040
agcgtgtaca gtttgtctta acaaaaagtg agggcgctga ggtcgagcag ggtggtgtga  11100
cttgttatag cctttagagc tgcgaaagcg cgtatggatt tggctcatca ggccagattg  11160
agggtctgtg gacacatgtc atgttagtgt acttcaatcg ccccctggat atagccccga  11220
caataggccg tggcctcatt tttttgcctt ccgcacattt ccattgctcg gtacccacac  11280
cttgcttctc ctgcacttgc caaccttaat actggtttac attgaccaac atcttacaag  11340
cggggggctt gtctagggta tatataaaca gtggctctcc caatcggttg ccagtctctt  11400
ttttcctttc tttccccaca gattcgaaat ctaaactaca catcacac              11448
```

<210> SEQ ID NO 156
<211> LENGTH: 3901
<212> TYPE: DNA
<213> ORGANISM: Artificial sequence
<220> FEATURE:
<223> OTHER INFORMATION: pRF80

<400> SEQUENCE: 156

```
agcttgctac gttaggagaa gacgcacggc gatgatacgg gtacccctca tgacatcaat     60
atccgctgcc cctcttgcca gcaaggcgtc agcaggtgct tttttcgcta ttttcaccag    120
accacagcct ttttccttgt gtctcatctt ggattccttc aaaggcaact caccgcacct    180
ccgagtcgtg tgaacaatgt aataataggc tattgacttt tttcccacct gtttagcgcc    240
aaacccaaag cgcttttcgc cccccactgca gcccgatgga aggcacatat ggcaagggaa    300
aagtcttcag gtaatacatg cctgctgcaa ctatatgtac tctgactcat tccctcagac    360
gtgggtcata gacagctgtt ttaaaccggg caaatcaatc tctgtcgcac aggtatttct    420
gcccttcaaa accaggttgc cacatcagat tccatcaaag tttttcagac taacttcaat    480
cttaaacggc atctcacaac aagcgaattg gacggaaaaa aagcgtctat cattaccggc    540
acctatccac actaagacag tactaaagga cgacgctccc cacgaaacga cgtttcgacc    600
```

-continued

```
ttaacgaccc tgccgtctcc atccatccga ccactcccga cgctctctcc tggagcaaac    660
cactcttacc aagcatatag catatataat aacgtattga atttattaac tgattgaatt    720
gagagtaaag ccagtagcgt tgtacggctg tagcttttta gaaaagtggc agatgagcga    780
tggtggatat gaaagtacct ttacggcatg tagcgacaca agatcgcttc caagaactcg    840
acattcaagc ccagctcgta caagaaaatg aactagccaa tcatatgaac tagcacattg    900
aagtcaccgc atcatctctg ttggaaacga cgcgcatgta ctcgtgcgta gtaaatccgt    960
atctgtacac tcgaaagatt acagtatgta gtagtagcat gactaacgat gtaacgtcca   1020
aataacgctc tgtgcctact cctgtagatg cattagacca cctgctaacg tctacacgtt   1080
atgtccgtta gctccaagat tgcacttttc cctcaaagac tctgctgggt tacgtcatgg   1140
tctctttcgg gtctctggtc cgttctctgc ccgcccatat ccgcccaggc tgctacgata   1200
caggataagc tcataagctt gcatgcctgc aggtcgactc tagaggatcc ccgggtaccg   1260
agctcgaatt cgtaatcatg gtcatagctg tttcctgtgt gaaattgtta tccgctcaca   1320
attccacaca acatacgagc cggaagcata aagtgtaaag cctggggtgc ctaatgagtg   1380
agctaactca cattaattgc gttgcgctca ctgcccgctt tccagtcggg aaacctgtcg   1440
tgccagctgc attaatgaat cggccaacgc gcggggagag gcggtttgcg tattgggcgc   1500
tcttccgctt cctcgctcac tgactcgctg cgctcggtcg ttcggctgcg gcgagcggta   1560
tcagctcact caaaggcggt aatacggtta tccacagaat caggggataa cgcaggaaag   1620
aacatgtgag caaaaggcca gcaaaaggcc aggaaccgta aaaaggccgc gttgctggcg   1680
tttttccata ggctccgccc ccctgacgag catcacaaaa atcgacgctc aagtcagagg   1740
tggcgaaacc cgacaggact ataaagatac caggcgtttc cccctggaag ctccctcgtg   1800
cgctctcctg ttccgaccct gccgcttacc ggatacctgt ccgcctttct cccttcggga   1860
agcgtggcgc tttctcatag ctcacgctgt aggtatctca gttcggtgta ggtcgttcgc   1920
tccaagctgg gctgtgtgca cgaacccccc gttcagcccg accgctgcgc cttatccggt   1980
aactatcgtc ttgagtccaa cccggtaaga cacgacttat cgccactggc agcagccact   2040
ggtaacagga ttagcagagc gaggtatgta ggcggtgcta cagagttctt gaagtggtgg   2100
cctaactacg gctacactag aaggacagta tttggtatct gcgctctgct gaagccagtt   2160
accttcggaa aaagagttgg tagctcttga tccggcaaac aaaccaccgc tggtagcggt   2220
ggtttttttg tttgcaagca gcagattacg cgcagaaaaa aaggatctca agaagatcct   2280
ttgatctttt ctacggggtc tgacgctcag tggaacgaaa actcacgtta agggattttg   2340
gtcatgagat tatcaaaaag gatcttcacc tagatccttt taaattaaaa atgaagtttt   2400
aaatcaatct aaagtatata tgagtaaact tggtctgaca gttaccaatg cttaatcagt   2460
gaggcaccta tctcagcgat ctgtctattt cgttcatcca tagttgcctg actccccgtc   2520
gtgtagataa ctacgatacg ggagggctta ccatctggcc ccagtgctgc aatgataccg   2580
cgagacccac gctcaccggc tccagattta tcagcaataa accagccagc cggaagggcc   2640
gagcgcagaa gtggtcctgc aactttatcc gcctccatcc agtctattaa ttgttgccgg   2700
gaagctagag taagtagttc gccagttaat agtttgcgca acgttgttgc cattgctaca   2760
ggcatcgtgg tgtcacgctc gtcgtttggt atggcttcat tcagctccgg ttcccaacga   2820
tcaaggcgag ttacatgatc ccccatgttg tgcaaaaaag cggttagctc cttcggtcct   2880
ccgatcgttg tcagaagtaa gttggccgca gtgttatcac tcatggttat ggcagcactg   2940
```

```
cataattctc ttactgtcat gccatccgta agatgctttt ctgtgactgg tgagtactca   3000

accaagtcat tctgagaata gtgtatgcgg cgaccgagtt gctcttgccc ggcgtcaata   3060

cgggataata ccgcgccaca tagcagaact ttaaaagtgc tcatcattgg aaaacgttct   3120

tcggggcgaa aactctcaag gatcttaccg ctgttgagat ccagttcgat gtaacccact   3180

cgtgcaccca actgatcttc agcatctttt actttcacca gcgtttctgg gtgagcaaaa   3240

acaggaaggc aaaatgccgc aaaaaaggga ataagggcga cacggaaatg ttgaatactc   3300

atactcttcc tttttcaata ttattgaagc atttatcagg gttattgtct catgagcgga   3360

tacatatttg aatgtattta gaaaaataaa caaatagggg ttccgcgcac atttccccga   3420

aaagtgccac ctgacgtcta agaaaccatt attatcatga cattaaccta taaaaatagg   3480

cgtatcacga ggccctttcg tctcgcgcgt ttcggtgatg acggtgaaaa cctctgacac   3540

atgcagctcc cggagacggt cacagcttgt ctgtaagcgg atgccgggag cagacaagcc   3600

cgtcagggcg cgtcagcggg tgttggcggg tgtcggggct ggcttaacta tgcggcatca   3660

gagcagattg tactgagagt gcaccatatg cggtgtgaaa taccgcacag atgcgtaagg   3720

agaaaatacc gcatcaggcg ccattcgcca ttcaggctgc gcaactgttg ggaagggcga   3780

tcggtgcggg cctcttcgct attacgccag ctggcgaaag gggatgtgc tgcaaggcga   3840

ttaagttggg taacgccagg gttttcccag tcacgacgtt gtaaaacgac ggccagtgcc   3900

a                                                                   3901
```

```
<210> SEQ ID NO 157
<211> LENGTH: 1215
<212> TYPE: DNA
<213> ORGANISM: Artificial Sequence
<220> FEATURE:
<223> OTHER INFORMATION: short Can1 deletion editing template

<400> SEQUENCE: 157
```

```
agcttgctac gttaggagaa gacgcacggc gatgatacgg gtacccctca tgacatcaat     60

atccgctgcc cctcttgcca gcaaggcgtc agcaggtgct tttttcgcta ttttcaccag    120

accacagcct ttttccttgt gtctcatctt ggattccttc aaaggcaact caccgcacct    180

ccgagtcgtg tgaacaatgt aataataggc tattgacttt tttcccacct gtttagcgcc    240

aaacccaaag cgcttttcgc ccccactgca gcccgatgga aggcacatat ggcaagggaa    300

aagtcttcag gtaatacatg cctgctgcaa ctatatgtac tctgactcat tccctcagac    360

gtgggtcata gacagctgtt ttaaaccggg caaatcaatc tctgtcgcac aggtatttct    420

gcccttcaaa accaggttgc cacatcagat tccatcaaag tttttcagac taacttcaat    480

cttaaacggc atctcacaac aagcgaattg gacggaaaaa aagcgtctat cattaccggc    540

acctatccac actaagacag tactaaagga cgacgctccc cacgaaacga cgtttcgacc    600

ttaacgaccc tgccgtctcc atccatccga ccactcccga cgctctctcc tggagcaaac    660

cactcttacc aagcatatag catatataat aacgtattga atttattaac tgattgaatt    720

gagagtaaag ccagtagcgt tgtacggctg tagcttttta gaaaagtggc agatgagcga    780

tggtggatat gaaagtacct ttacggcatg tagcgacaca agatcgcttc caagaactcg    840

acattcaagc ccagctcgta caagaaaatg aactagccaa tcatatgaac tagcacattg    900

aagtcaccgc atcatctctg ttggaaacga cgcgcatgta ctcgtgcgta gtaaatccgt    960

atctgtacac tcgaaagatt acagtatgta gtagtagcat gactaacgat gtaacgtcca   1020

aataacgctc tgtgcctact cctgtagatg cattagacca cctgctaacg tctacacgtt   1080
```

atgtccgtta gctccaagat tgcacttttc cctcaaagac tctgctgggt tacgtcatgg 1140
tctctttcgg gtctctggtc cgttctctgc ccgcccatat ccgcccaggc tgctacgata 1200
caggataagc tcata 1215

<210> SEQ ID NO 158
<211> LENGTH: 20
<212> TYPE: DNA
<213> ORGANISM: Artificial sequence
<220> FEATURE:
<223> OTHER INFORMATION: primer 80F

<400> SEQUENCE: 158
agcttgctac gttaggagaa 20

<210> SEQ ID NO 159
<211> LENGTH: 20
<212> TYPE: DNA
<213> ORGANISM: Artificial sequence
<220> FEATURE:
<223> OTHER INFORMATION: primer 80R

<400> SEQUENCE: 159
tatgagctta tcctgtatcg 20

<210> SEQ ID NO 160
<211> LENGTH: 2125
<212> TYPE: DNA
<213> ORGANISM: Yarrowia lipolytica
<220> FEATURE:
<221> NAME/KEY: misc_feature
<222> LOCATION: (1)..(2125)
<223> OTHER INFORMATION: Can1 locus WT (wild type)

<400> SEQUENCE: 160
ggaaggcaca tatggcaagg gaaaagtctt caggtaatac atgcctgctg caactatatg 60
tactctgact cattccctca gacgtgggtc atagacagct gttttaaacc gggcaaatca 120
atctctgtcg cacaggtatt tctgcccttc aaaaccaggt tgccacatca gattccatca 180
aagtttttca gactaacttc aatcttaaac ggcatctcac aacaagcgaa ttggacggaa 240
aaaaagcgtc tatcattacc ggcacctatc cacactaaga cagtactaaa ggacgacgct 300
ccccacgaaa cgacgtttcg accttaacga ccctgccgtc tccatccatc cgaccacaat 360
ggaaaagaca ttttcaaacg attacccacc ctccgggact gaggcccaca tccacatcaa 420
ccacacggcc cactcggatg actcagagga ggtgccctcg cacaaggaaa attacaacac 480
cagtggccac gacctggagg agtccgaccc ggataaccat gtcggtgaga ccctcgaggt 540
caagcgaggt ctcaagatgc gacacatctc catgatctcg cttggaggaa ccattggtac 600
cggtctcttc attggtaccg gaggagctct ccagcaggcc ggtccctgtg gcgccctcgt 660
cgcctacgtg ttcatggcca ccattgtcta ctctgttgcc gagtctcttg gagaactggc 720
tacgtacatt cccatcaccg gctcctttgc cgtctttact acccgatatc tgtcacagtc 780
gtttggtgcc tccatgggct ggctatactg gttctcgtgg gcgatcacct tcgccatcga 840
gctcaacacc attggtcccg tgattgagta ctggactgac gccgttccta ctgctgcctg 900
gattgccatc ttcttcgtca tcctcactac catcaacttc ttccccgtgg gcttctatgg 960
cgaagtcgag ttctgggtgg cctccgtgaa ggtcattgcc atcattggat ggctcatcta 1020
cgcgctctgc atgacgtgtg gagcaggtgt aacaggtcct gtgggattca gatactggaa 1080

-continued

```
ccaccccgga cccatgggag acggaatctg gaccgacggc gtgcccattg tgcgaaacgc   1140

gcccggtcga cgattcatgg gatggctcaa ttcgctcgtt aacgccgcct tcacctacca   1200

gggctgtgag ctggtcggag tcactgccgg tgaggcccag aaccccagaa agtccgtccc   1260

tcgagccatc aaccgagtct ttgctcgaat ttgcatcttc tacattggct ctatcttctt   1320

catgggcatg ctcgtgccct ttaacgaccc caagctgacc gatgactcct ccgtcatcgc   1380

ctcctctcct tttgttattg ccattatcaa ctctggcacc aaggtgctcc ctcacatttt   1440

caacgccgtc attctcatca ccctgatttc ggcaggaaac tccaacgtct acattggctc   1500

gcgagtggtc tacgccctgg ctgactccgg aaccgcacca aagttcttca agcgaaccac   1560

caagaaggga gtgccgtacg tggcagtctg cttcacctcg gcgtttggtc tgctggcctt   1620

catgtctgtg tccgagtcgt cgtccactgt cttcgactgg ttcatcaaca tctccgctgt   1680

ggccggcctc atctgttggg ccttcatctc tgcctcccac atccgattca tgcaagtgct   1740

taagcacaga gggatctcca gagatacgct gcccttcaag gcacgatggc agccattcta   1800

ctcatggtac gcgctcgtct ccatcatctt catcactctc atccagggct tcacgtcctt   1860

ctggcacttt accgccgcca agttcatgac tgcatacatc tccgtcattg tctgggtcgg   1920

tttgtacatt atcttccagt gtctgttccg atgcaagttc cttatcccta ttgaggatgt   1980

ggacattgac accggccgac gagagattga cgacgatgtg tgggaggaga agatccccac   2040

aaagtggtac gagaagtttt ggaatattat tgcataagaa gatcggggat tcccgacgct   2100

ctctcctgga gcaaaccact cttac                                         2125
```

<210> SEQ ID NO 161
<211> LENGTH: 392
<212> TYPE: DNA
<213> ORGANISM: Artificial sequence
<220> FEATURE:
<223> OTHER INFORMATION: Can1 Locus deletion strain

<400> SEQUENCE: 161

```
ggaaggcaca tatggcaagg gaaaagtctt caggtaatac atgcctgctg caactatatg     60

tactctgact cattccctca gacgtgggtc atagacagct gttttaaacc gggcaaatca    120

atctctgtcg cacaggtatt tctgcccttc aaaaccaggt tgccacatca gattccatca    180

aagtttttca gactaacttc aatcttaaac ggcatctcac aacaagcgaa ttggacggaa    240

aaaaagcgtc tatcattacc ggcacctatc cacactaaga cagtactaaa ggacgacgct    300

ccccacgaaa cgacgtttcg accttaacga ccctgccgtc tccatccatc cgaccactcc    360

cgacgctctc tcctggagca aaccactctt ac                                  392
```

<210> SEQ ID NO 162
<211> LENGTH: 73
<212> TYPE: DNA
<213> ORGANISM: Artificial sequence
<220> FEATURE:
<223> OTHER INFORMATION: Forward Oligonucleotide of Figure 13-B

<400> SEQUENCE: 162

```
catgcgtaaa ctgactgatg agtccgtgag gacgaaacga gtaagctcgt cagtttcagt     60

acggttctag ttt                                                        73
```

<210> SEQ ID NO 163
<211> LENGTH: 75
<212> TYPE: DNA
<213> ORGANISM: Artificial sequence -continued
<220> FEATURE:
<223> OTHER INFORMATION: Reverse Oligonucleotide of Figure 13-B

<400> SEQUENCE: 163
tctaaaacta gaaccgtact gaaactgaga cgagcttact cgtttcgtcc tcacggactc 60
atcagtcagt ttacg 75

<210> SEQ ID NO 164
<211> LENGTH: 211
<212> TYPE: RNA
<213> ORGANISM: Artificial Sequence
<220> FEATURE:
<223> OTHER INFORMATION: pre-sgRNA URA3.1 (RGR-URA3.1)

<400> SEQUENCE: 164
gaacagcuga ugaguccgug aggacgaaac gaguaagcuc guccuguuca gagacaguuu 60
ccuguuuuag agcuagaaau agcaaguuaa aauaaggcua guccguuauc aacuugaaaa 120
aguggcaccg agucggugcu uuuggccggc augguccag ccuccucgcu ggcgccggcu 180
gggcaacaug cuucggcaug gcgaauggga c 211

<210> SEQ ID NO 165
<211> LENGTH: 20
<212> TYPE: DNA
<213> ORGANISM: Yarrowia lipolytica

<400> SEQUENCE: 165
ctgttcagag acagtttcct 20

<210> SEQ ID NO 166
<211> LENGTH: 211
<212> TYPE: RNA
<213> ORGANISM: Artificial Sequence
<220> FEATURE:
<223> OTHER INFORMATION: pre-sgRNA URA3.2 (RGR-URA3.2

<400> SEQUENCE: 166
auguuacuga ugaguccgug aggacgaaac gaguaagcuc gucuaacauc cagagaagca 60
cacguuuuag agcuagaaau agcaaguuaa aauaaggcua guccguuauc aacuugaaaa 120
aguggcaccg agucggugcu uuuggccggc augguccag ccuccucgcu ggcgccggcu 180
gggcaacaug cuucggcaug gcgaauggga c 211

<210> SEQ ID NO 167
<211> LENGTH: 20
<212> TYPE: DNA
<213> ORGANISM: Yarrowia lipolytica

<400> SEQUENCE: 167
taacatccag agaagcacac 20

<210> SEQ ID NO 168
<211> LENGTH: 838
<212> TYPE: DNA
<213> ORGANISM: Artificial Sequence
<220> FEATURE:
<223> OTHER INFORMATION: FBA1L promoter

<400> SEQUENCE: 168
gtttaaacag tgtacgcagt actatagagg aacaattgcc ccggagaaga cggccaggcc 60
gcctagatga caaattcaac aactcacagc tgactttctg ccattgccac tagggggggg 120

-continued

```
cctttttata tggccaagcc aagctctcca cgtcggttgg gctgcaccca acaataaatg    180

ggtagggttg caccaacaaa gggatgggat ggggggtaga agatacgagg ataacggggc    240

tcaatggcac aaataagaac gaatactgcc attaagactc gtgatccagc gactgacacc    300

attgcatcat ctaagggcct caaaactacc tcggaactgc tgcgctgatc tggacaccac    360

agaggttccg agcactttag gttgcaccaa atgtcccacc aggtgcaggc agaaaacgct    420

ggaacagcgt gtacagtttg tcttaacaaa aagtgagggc gctgaggtcg agcagggtgg    480

tgtgacttgt tatagccttt agagctgcga aagcgcgtat ggatttggct catcaggcca    540

gattgagggt ctgtggacac atgtcatgtt agtgtacttc aatcgccccc tggatatagc    600

cccgacaata ggccgtggcc tcattttttt gccttccgca catttccatt gctcggtacc    660

cacaccttgc ttctcctgca cttgccaacc ttaatactgg tttacattga ccaacatctt    720

acaagcgggg ggcttgtcta gggtatatat aaacagtggc tctcccaatc ggttgccagt    780

ctctttttc ctttctttcc ccacagattc gaaatctaaa ctacacatca caccatgg      838
```

```
<210> SEQ ID NO 169
<211> LENGTH: 1839
<212> TYPE: DNA
<213> ORGANISM: Artificial Sequence
<220> FEATURE:
<223> OTHER INFORMATION: acetohydroxyacid synthase gene

<400> SEQUENCE: 169

atggacgagt ccttcatcgg aatgtctgga ggagagatct tccacgagat gatgctgcga     60

cacaacgtcg acactgtctt cggttacccc ggtggagcca ttctccccgt ctttgacgcc    120

attcacaact ctgaatactt caactttgtg ctccctcgac acgagcaggg tgccggccac    180

atggccgagg gctacgctcg agcctctggt aagcccggtg tcgttctcgt cacctctggc    240

cccggtgcca ccaacgtcat cacccccatg caggacgctc tttccgatgg taccccctatg    300

gttgtcttca ccggtcaggt cctgacctcc gttatcggca ctgacgcctt ccaggaggcc    360

gatgttgtcg gcatctcccg atcttgcacc aagtggaacg tcatggtcaa gaacgttgct    420

gagctccccc gacgaatcaa cgaggccttt gagattgcta cttccggccg acccggtccc    480

gttctcgtcg atctgcccaa ggatgttact gctgccatcc tgcgagagcc catccccacc    540

aagtccacca ttccctcgca ttctctgacc aacctcacct ctgccgccgc caccgagttc    600

cagaagcagg ctatccagcg agccgccaac ctcatcaacc agtccaagaa gcccgtcctt    660

tacgtcggac agggtatcct tggctccgag gagggtccta agctgcttaa ggagctggct    720

gagaaggccg agattcccgt caccactact ctgcagggtc ttggtgcctt tgacgagcga    780

gaccccaagt ctctgcacat gctcggtatg cacggttccg gctacgccaa catggccatg    840

cagaacgctg actgtatcat tgctctcggc gcccgatttg atgaccgagt taccggctcc    900

atccccaagt ttgcccccga ggctcgagcc gctgcccttg agggtcgagg tggtattgtt    960

cactttgaga tccaggccaa gaacatcaac aaggttgttc aggccaccga agccgttgag   1020

ggagacgtta ccgagtctgt ccgacagctc atccccctca tcaacaaggt ctctgccgct   1080

gagcgagctc cctggactga gactatccag tcctggaagc agcagttccc cttcctcttc   1140

gaggctgaag gtgaggatgg tgttatcaag ccccagtccg tcattgctct gctctctgac   1200

ctgacagaga acaacaagga caagaccatc atcaccaccg gtgttggtca gcatcagatg   1260

tggactgccc agcatttccg atggcgacac cctcgaacca tgatcacttc tggtggtctt   1320

ggaactatgg gttacggcct gcccgccgct atcggcgcca aggttgcccg acctgactgc   1380
```

gacgtcattg acattgatgg tgacgcttct ttcaacatga ctctgaccga gctgtccacc 1440
gccgttcagt tcaacattgg cgtcaaggct attgtcctca acaacgagga acagggtatg 1500
gtcacccagc tgcagtctct cttctacgag aaccgatact gccacactca tcagaagaac 1560
cccgacttca tgaagctggc cgagtcgatg ggcatgaagg gtatccgaat cactcacatt 1620
gaccagctgg aggccggtct caaggagatg ctcgcataca agggccctgt gctcgttgag 1680
gttgttgtcg acaagaagat ccccgttctt cctatggttc ccgctggtaa ggctttgcat 1740
gagttccttg tctacgacgc tgacgccgag gctgcttctc gacccgatcg actgaagaat 1800
gcccccgccc ctcacgtcca ccagaccacc tttgagaac 1839

<210> SEQ ID NO 170
<211> LENGTH: 30
<212> TYPE: DNA
<213> ORGANISM: Artificial Sequence
<220> FEATURE:
<223> OTHER INFORMATION: RHO705

<400> SEQUENCE: 170
gtacagacct cggccgacaa ttatgatatc 30

<210> SEQ ID NO 171
<211> LENGTH: 30
<212> TYPE: DNA
<213> ORGANISM: Artificial Sequence
<220> FEATURE:
<223> OTHER INFORMATION: RHO719

<400> SEQUENCE: 171
gttccgaggt agttttgagg cccttagatg 30

<210> SEQ ID NO 172
<211> LENGTH: 30
<212> TYPE: DNA
<213> ORGANISM: Artificial Sequence
<220> FEATURE:
<223> OTHER INFORMATION: RHO733

<400> SEQUENCE: 172
gttgggagag gggactagga actccttgta 30

<210> SEQ ID NO 173
<211> LENGTH: 30
<212> TYPE: DNA
<213> ORGANISM: Artificial Sequence
<220> FEATURE:
<223> OTHER INFORMATION: RHO734

<400> SEQUENCE: 173
ctacgaagct cgagctaacg tccacaagtc 30

<210> SEQ ID NO 174
<211> LENGTH: 30
<212> TYPE: DNA
<213> ORGANISM: Artificial Sequence
<220> FEATURE:
<223> OTHER INFORMATION: RHO707

<400> SEQUENCE: 174
gtcggtggct acaatacgtg agtcagaagg 30

<210> SEQ ID NO 175

<211> LENGTH: 53
<212> TYPE: DNA
<213> ORGANISM: Yarrowia lipolytica

<400> SEQUENCE: 175
cgtcctcctt cttctgttca gagacagttt cctcggcacc agctcgcagg cca 53

<210> SEQ ID NO 176
<211> LENGTH: 52
<212> TYPE: DNA
<213> ORGANISM: Artificial Sequence
<220> FEATURE:
<223> OTHER INFORMATION: fragment of Plasmid URA3 from colony 1

<400> SEQUENCE: 176
cgtcctcctt cttctgttca gagacagttc ctcggcacca gctcgcaggc ca 52

<210> SEQ ID NO 177
<211> LENGTH: 51
<212> TYPE: DNA
<213> ORGANISM: Artificial Sequence
<220> FEATURE:
<223> OTHER INFORMATION: fragment of Plasmid URA3 from colony 2

<400> SEQUENCE: 177
cgtcctcctt cttctgttca gagacagtcc tcggcaccag ctcgcaggcc a 51

<210> SEQ ID NO 178
<211> LENGTH: 52
<212> TYPE: DNA
<213> ORGANISM: Artificial Sequence
<220> FEATURE:
<223> OTHER INFORMATION: fragment of Plasmid URA3 from colony 3

<400> SEQUENCE: 178
cgtcctcctt cttctgttca gagacagttc ctcggcacca gctcgcaggc ca 52

<210> SEQ ID NO 179
<211> LENGTH: 52
<212> TYPE: DNA
<213> ORGANISM: Artificial Sequence
<220> FEATURE:
<223> OTHER INFORMATION: fragment of Plasmid URA3 from colony 5

<400> SEQUENCE: 179
cgtcctcctt cttctgttca gagacagttc ctcggcacca gctcgcaggc ca 52

<210> SEQ ID NO 180
<211> LENGTH: 52
<212> TYPE: DNA
<213> ORGANISM: Artificial Sequence
<220> FEATURE:
<223> OTHER INFORMATION: fragment of Plasmid URA3 from colony 6

<400> SEQUENCE: 180
cgtcctcctt cttctgttca gagacagttc ctcggcacca gctcgcaggc ca 52

<210> SEQ ID NO 181
<211> LENGTH: 39
<212> TYPE: DNA
<213> ORGANISM: Artificial Sequence
<220> FEATURE:
<223> OTHER INFORMATION: fragment of Genomic URA3 from colony 1
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t

<400> SEQUENCE: 181
cgtcctcctt cttctgttca gagacagtnc cncggcccc 39

<210> SEQ ID NO 182
<211> LENGTH: 54
<212> TYPE: DNA
<213> ORGANISM: Artificial Sequence
<220> FEATURE:
<223> OTHER INFORMATION: fragment of Genomic URA3 from colony 2

<400> SEQUENCE: 182
cgtcctcctt cttctgttca gagacagttt acctcggcac cagctcgcag gcca 54

<210> SEQ ID NO 183
<211> LENGTH: 44
<212> TYPE: DNA
<213> ORGANISM: Artificial Sequence
<220> FEATURE:
<223> OTHER INFORMATION: fragment of Genomic URA3 from colony 3

<400> SEQUENCE: 183
cgtcctcctt cttctgttca gagacagttt cagctcgcag gcca 44

<210> SEQ ID NO 184
<211> LENGTH: 49
<212> TYPE: DNA
<213> ORGANISM: Artificial Sequence
<220> FEATURE:
<223> OTHER INFORMATION: fragment of Genomic URA3 from colony 5
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t

<400> SEQUENCE: 184
cgtcctcctt cttctgttca ganacagttt ggcaccanct cgcaggcca 49

<210> SEQ ID NO 185
<211> LENGTH: 54
<212> TYPE: DNA
<213> ORGANISM: Artificial Sequence
<220> FEATURE:
<223> OTHER INFORMATION: fragment of Genomic URA3 from colony 6

<400> SEQUENCE: 185
cgtcctcctt cttctgttca gagacagttt ccctcggcac cagctcgcag gcca 54

<210> SEQ ID NO 186
<211> LENGTH: 1029
<212> TYPE: DNA
<213> ORGANISM: Artificial Sequence
<220> FEATURE:
<223> OTHER INFORMATION: hygromycin antibiotic resistant selection marker

<400> SEQUENCE: 186
atggccaaaa agcctgaact caccgcgacg tctgtcgaga agtttctgat cgaaaagttc 60
gacagcgtct ccgacctgat gcagctctcg gagggcgaag aatctcgtgc tttcagcttc 120

```
gatgtaggag ggcgtggata tgtcctgcgg gtaaatagct gcgccgatgg tttctacaaa    180

gatcgttatg tttatcggca ctttgcatcg gccgcgctcc cgattccgga agtgcttgac    240

attggggagt tcagcgagag cctgacctat tgcatctccc gccgtgcaca gggtgtcacg    300

ttgcaagacc tgcctgaaac cgaactgccc gctgttctgc agccggtcgc ggaggctatg    360

gatgcgatcg ctgcggccga tcttagccag acgagcgggt tcggcccatt cggaccgcaa    420

ggaatcggtc aatacactac atggcgtgat ttcatatgcg cgattgctga tccccatgtg    480

tatcactggc aaactgtgat ggacgacacc gtcagtgcgt ccgtcgcgca ggctctcgat    540

gagctgatgc tttgggccga ggactgcccc gaagtccggc acctcgtgca cgcggatttc    600

ggctccaaca atgtcctgac ggacaatggc cgcataacag cggtcattga ctggagcgag    660

gcgatgttcg gggattccca atacgaggtc gccaacatct tcttctggag gccgtggttg    720

gcttgtatgg agcagcagac gcgctacttc gagcggaggc atccggagct tgcaggatcg    780

ccgcggctcc gggcgtatat gctccgcatt ggtcttgacc aactctatca gagcttggtt    840

gacggcaatt tcgatgatgc agcttgggcg cagggtcgat gcgacgcaat cgtccgatcc    900

ggagccggga ctgtcgggcg tacacaaatc gcccgcagaa gcgcggccgt ctggaccgat    960

ggctgtgtag aagtactcgc cgatagtgga aaccgacgcc ccagcactcg tccgagggca   1020

aaggaatag                                                            1029

<210> SEQ ID NO 187
<211> LENGTH: 565
<212> TYPE: DNA
<213> ORGANISM: Artificial Sequence
<220> FEATURE:
<223> OTHER INFORMATION: TDH1 or GPD promoter

<400> SEQUENCE: 187

ggttgcggga tagacgccga cggagggcaa tggcgctatg gaaccttgcg gatatccata     60

cgccgcggcg gactgcgtcc gaaccagctc cagcagcgtt ttttccgggc cattgagccg    120

actgcgaccc cgccaacgtg tcttggccca cgcactcatg tcatgttggt gttgggaggc    180

cactttttaa gtagcacaag gcacctagct cgcagcaagg tgtccgaacc aaagaagcgg    240

ctgcagtggt gcaaacgggg cggaaacggc gggaaaaagc cacgggggca cgaattgagg    300

cacgccctcg aatttgagac gagtcacggc cccattcgcc cgcgcaatgg ctcgccaacg    360

cccggtcttt tgcaccacat caggttaccc caagccaaac ctttgtgtta aaaagcttaa    420

catattatac cgaacgtagg tttgggcggg cttgctccgt ctgtccaagg caacatttat    480

ataagggtct gcatcgccgg ctcaattgaa tcttttttct tcttctcttc tctatattca    540

ttcttgaatt aaacacacat caacc                                          565

<210> SEQ ID NO 188
<211> LENGTH: 43
<212> TYPE: DNA
<213> ORGANISM: Artificial Sequence
<220> FEATURE:
<223> OTHER INFORMATION: RHO804

<400> SEQUENCE: 188

gatcaacgta cgagtgtacg cagtactata gaggaacaat tgc                       43

<210> SEQ ID NO 189
<211> LENGTH: 44
<212> TYPE: DNA
```

<213> ORGANISM: Artificial Sequence
<220> FEATURE:
<223> OTHER INFORMATION: RHO805

<400> SEQUENCE: 189
gatcaacgta cgccccaagc ttgtcccatt cgccatgccg aagc 44

<210> SEQ ID NO 190
<211> LENGTH: 746
<212> TYPE: DNA
<213> ORGANISM: Artificial Sequence
<220> FEATURE:
<223> OTHER INFORMATION: TDH1 promoter-RGR-URA3.3 fusion

<400> SEQUENCE: 190
gatcaacgta cgatacgccg cggcggactg cgtccgaacc agctccagca gcgtttttc 60 cgggccattg agccgactgc gaccccgcca acgtgtcttg gcccacgcac tcatgtcatg 120
ttggtgttgg gaggccactt tttaagtagc acaaggcacc tagctcgcag caaggtgtcc 180
gaaccaaaga agcggctgca gtggtgcaaa cggggcggaa acggcgggaa aaagccacgg 240
gggcacgaat tgaggcacgc cctcgaattt gagacgagtc acggccccat tcgcccgcgc 300
aatggctcgc caacgcccgg tcttttgcac cacatcaggt taccccaagc caaacctttg 360
tgttaaaaag cttaacatat tataccgaac gtaggtttgg gcgggcttgc tccgtctgtc 420
caaggcaaca tttatataag ggtctgcatc gccggctcaa ttgaatcttt tttcttcttc 480
tcttctctat attcattctt gaattaaaca cacatcaaca atgacagttc tgatgagtcc 540
gtgaggacga aacgagtaag ctcgtcaact gttagaggtt agactagttt tagagctaga 600
aatagcaagt taaaataagg ctagtccgtt atcaacttga aaaagtggca ccgagtcggt 660
gcttttggcc ggcatggtcc cagcctcctc gctggcgccg gctgggcaac atgcttcggc 720
atggcgaatg ggaccgtacg agtcag 746

<210> SEQ ID NO 191
<211> LENGTH: 211
<212> TYPE: RNA
<213> ORGANISM: Artificial Sequence
<220> FEATURE:
<223> OTHER INFORMATION: pre-sgRNA URA3.3 (RGR-URA3.3)

<400> SEQUENCE: 191
acaguucuga ugaguccgug aggacgaaac gaguaagcuc gucaacuguu agagguuaga 60
cuaguuuuag agcuagaaau agcaaguuaa aauaaggcua guccguuauc aacuugaaaa 120
aguggcaccg agucggugcu uuuggccggc auggucccag ccuccucgcu ggcgccggcu 180
gggcaacaug cuucggcaug gcgaauggga c 211

<210> SEQ ID NO 192
<211> LENGTH: 43
<212> TYPE: DNA
<213> ORGANISM: Artificial Sequence
<220> FEATURE:
<223> OTHER INFORMATION: RHO610

<400> SEQUENCE: 192
ggcggcttaa ttaagttgcg acacatgtct tgatagtatc ttg 43

<210> SEQ ID NO 193
<211> LENGTH: 44
<212> TYPE: DNA
<213> ORGANISM: Artificial Sequence

<220> FEATURE:
<223> OTHER INFORMATION: RHO611

<400> SEQUENCE: 193
ggcggcttaa ttaacgagta tctgtctgac tcgtcattgc cgcc 44

<210> SEQ ID NO 194
<211> LENGTH: 30
<212> TYPE: DNA
<213> ORGANISM: Artificial Sequence
<220> FEATURE:
<223> OTHER INFORMATION: RHO704

<400> SEQUENCE: 194
catatacttc actgccccag ataaggttcc 30

<210> SEQ ID NO 195
<211> LENGTH: 39
<212> TYPE: DNA
<213> ORGANISM: Yarrowia lipolytica

<400> SEQUENCE: 195
aaaccaacct gtgtgcttct ctggatgtta ccaccacca 39

<210> SEQ ID NO 196
<211> LENGTH: 24
<212> TYPE: DNA
<213> ORGANISM: Artificial Sequence
<220> FEATURE:
<223> OTHER INFORMATION: Fragment of URA3 sequence from colony 3
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (19)..(23)
<223> OTHER INFORMATION: n is a, c, g, or t

<400> SEQUENCE: 196
aaaccaacct gtgttgntnn nnng 24

<210> SEQ ID NO 197
<211> LENGTH: 37
<212> TYPE: DNA
<213> ORGANISM: Artificial Sequence
<220> FEATURE:
<223> OTHER INFORMATION: Fragment of URA3 sequence from colony 4
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(29)
<223> OTHER INFORMATION: n is a, c, g, or t

<400> SEQUENCE: 197
aaaccaacct gtgtgtttct nggnntnnnc ccccccc 37

<210> SEQ ID NO 198
<211> LENGTH: 39
<212> TYPE: DNA
<213> ORGANISM: Artificial Sequence
<220> FEATURE:

<223> OTHER INFORMATION: Fragment of URA3 sequence from colony 5
<220> FEATURE:
<221> NAME/KEY: misc_feature
<222> LOCATION: (38)..(39)
<223> OTHER INFORMATION: n is a, c, g, or t

<400> SEQUENCE: 198
aaaccaacct gtgtgtgtct ctggatgtta ccaccacnn 39

<210> SEQ ID NO 199
<211> LENGTH: 28
<212> TYPE: DNA
<213> ORGANISM: Artificial Sequence
<220> FEATURE:
<223> OTHER INFORMATION: Fragment of URA3 sequence from colony 6
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (25)..(27)
<223> OTHER INFORMATION: n is a, c, g, or t

<400> SEQUENCE: 199
aaaccaacct gtgtgttttc nnggnnnt 28

<210> SEQ ID NO 200
<211> LENGTH: 29
<212> TYPE: DNA
<213> ORGANISM: Artificial Sequence
<220> FEATURE:
<223> OTHER INFORMATION: Fragment of URA3 sequence from colony 9

<400> SEQUENCE: 200
aaaccaacct gtgttgcttc tctggatgt 29

<210> SEQ ID NO 201
<211> LENGTH: 39
<212> TYPE: DNA
<213> ORGANISM: Artificial Sequence
<220> FEATURE:
<223> OTHER INFORMATION: Fragment of URA3 sequence from colony 10
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (19)..(22)
<223> OTHER INFORMATION: n is a, c, g, or t
<220> FEATURE:
<221> NAME/KEY: misc_feature
<222> LOCATION: (24)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t

<400> SEQUENCE: 201
aaaccaacct gtgnnttcnn nngnnnntnc cncccccna 39

<210> SEQ ID NO 202
<211> LENGTH: 351
<212> TYPE: DNA
<213> ORGANISM: Yarrowia lipolytica

<400> SEQUENCE: 202
aaaccaacct gtgtgcttct ctggatgtta ccaccaccaa ggagctcatt gagcttgccg 60
ataaggtcgg accttatgtg tgcatgatca agacccatat cgacatcatt gacgacttca 120
cctacgccgg cactgtgctc cccctcaagg agcttgctct taagcacggt ttcttcctgt 180
tcgaggacag aaagttcgca gatattggca acactgtcaa gcaccagtac aagaacggtg 240
tctaccgaat cgccgagtgg tccgatatca ccaacgccca cggtgtaccc ggagccggaa 300
tcattgctgg cctgcgagct ggtgccgagg aaactgtctc tgaacagaag a 351

<210> SEQ ID NO 203
<211> LENGTH: 34
<212> TYPE: DNA
<213> ORGANISM: Artificial Sequence
<220> FEATURE:
<223> OTHER INFORMATION: Fragment of URA3 sequence from colony 23

<400> SEQUENCE: 203
aaaccaacct gtgaaactgt ctctgaacag aaga 34

<210> SEQ ID NO 204
<211> LENGTH: 34
<212> TYPE: DNA
<213> ORGANISM: Artificial Sequence
<220> FEATURE:
<223> OTHER INFORMATION: Fragment of URA3 sequence from colony 24

<400> SEQUENCE: 204
aaaccaacct gtgaaactgt ctctgaacag aaga 34

<210> SEQ ID NO 205
<211> LENGTH: 803
<212> TYPE: DNA
<213> ORGANISM: Yarrowia lypolitica

<400> SEQUENCE: 205
aaaccaacct gtgtgcttct ctggatgtta ccaccaccaa ggagctcatt gagcttgccg 60
ataaggtcgg accttatgtg tgcatgatca agacccatat cgacatcatt gacgacttca 120
cctacgccgg cactgtgctc cccctcaagg agcttgctct taagcacggt ttcttcctgt 180
tcgaggacag aaagttcgca gatattggca acactgtcaa gcaccagtac aagaacggtg 240
tctaccgaat cgccgagtgg tccgatatca ccaacgccca cggtgtaccc ggagccggaa 300
tcattgctgg cctgcgagct ggtgccgagg aaactgtctc tgaacagaag aaggaggacg 360
tctctgacta cgagaactcc cagtacaagg agttcctggt cccctctccc aacgagaagc 420
tggccagagg tctgctcatg ctggccgagc tgtcttgcaa gggctctctg gccactggcg 480
agtactccaa gcagaccatt gagcttgccc gatccgaccc cgagtttgtg gttggcttca 540
ttgcccagaa ccgacctaag ggcgactctg aggactggct tattctgacc cccggggtgg 600
gtcttgacga caagggagac gctctcggac agcagtaccg aactgttgag gatgtcatgt 660
ctaccggaac ggatatcata attgtcggcc gaggtctgta cggccagaac cgagatccta 720
ttgaggaggc caagcgatac cagaaggctg gctgggaggc ttaccagaag attaactgtt 780
agaggttaga ctatggatat gta 803

<210> SEQ ID NO 206
<211> LENGTH: 27
<212> TYPE: DNA
<213> ORGANISM: Artificial Sequence
<220> FEATURE:
<223> OTHER INFORMATION: Fragment of URA3 sequence from colony 27

<400> SEQUENCE: 206
aaaccaacct gtgtctatgg atatgta 27

<210> SEQ ID NO 207
<211> LENGTH: 21
<212> TYPE: DNA
<213> ORGANISM: Artificial Sequence
<220> FEATURE:
<223> OTHER INFORMATION: Fragment of URA3 sequence from colony 36

<400> SEQUENCE: 207
aaaccaacct gtggatatgt a 21

<210> SEQ ID NO 208
<211> LENGTH: 1346
<212> TYPE: DNA
<213> ORGANISM: Artificial Sequence
<220> FEATURE:
<223> OTHER INFORMATION: ARS18 sequence

<400> SEQUENCE: 208
aattcatgtc acacaaaccg atcttcgcct caaggaaacc taattctaca tccgagagac 60
tgccgagatc cagtctacac tgattaattt tcgggccaat aatttaaaaa aatcgtgtta 120
tataatatta tatgtattat atatatacat catgatgata ctgacagtca tgtcccattg 180
ctaaatagac agactccatc tgccgcctcc aactgatgtt ctcaatattt aaggggtcat 240
ctcgcattgt ttaataataa acagactcca tctaccgcct ccaaatgatg ttctcaaaat 300
atattgtatg aacttatttt tattacttag tattattaga caacttactt gctttatgaa 360
aaacacttcc tatttaggaa acaatttata atggcagttc gttcatttaa caatttatgt 420
agaataaatg ttataaatgc gtatgggaaa tcttaaatat ggatagcata aatgatatct 480
gcattgccta attcgaaatc aacagcaacg aaaaaaatcc cttgtacaac ataaatagtc 540
atcgagaaat atcaactatc aaagaacagc tattcacacg ttactattga gattattatt 600
ggacgagaat cacacactca actgtctttc tctcttctag aaatacaggt acaagtatgt 660
actattctca ttgttcatac ttctagtcat ttcatcccac atattccttg gatttctctc 720
caatgaatga cattctatct tgcaaattca acaattataa taagatatac caaagtagcg 780
gtatagtggc aatcaaaaag cttctctggt gtgcttctcg tatttatttt tattctaatg 840
atccattaaa ggtatatatt tatttcttgt tatataatcc ttttgtttat tacatgggct 900
ggatacataa aggtattttg atttaatttt ttgcttaaat tcaatccccc ctcgttcagt 960
gtcaactgta atggtaggaa attaccatac ttttgaagaa gcaaaaaaaa tgaaagaaaa 1020
aaaaaatcgt atttccaggt tagacgttcc gcagaatcta gaatgcggta tgcggtacat 1080
tgttcttcga acgtaaaagt tgcgctccct gagatattgt acatttttgc ttttacaagt 1140
acaagtacat cgtacaacta tgtactactg ttgatgcatc cacaacagtt tgttttgttt 1200 tttttgttt tttttttc taatgattca ttaccgctat gtatacctac ttgtacttgt 1260
agtaagccgg gttattggcg ttcaattaat catagactta tgaatctgca cggtgtgcgc 1320
tgcgagttac ttttagctta tgcatg 1346

<210> SEQ ID NO 209
<211> LENGTH: 564
<212> TYPE: DNA
<213> ORGANISM: Artificial Sequence
<220> FEATURE:
<223> OTHER INFORMATION: Yarrowia codon optimized P. aeruginosa Csy4

<400> SEQUENCE: 209
atggaccact acctggatat cagactccga cccgacccag agttccctcc tgcccagctc 60
atgtccgtct tgtttggcaa gctgcaccaa gctctcgtgg cccagggtgg agaccgaatt 120
ggcgtgtcgt tccccgattt ggacgagtcc cgttctcgac ttggagaaag actccgtatt 180
catgcttctg cagacgatct cagagctctg cttgcccgac cctggctgga gggtctccga 240
gatcatctgc agttcggcga gcctgccgtg gttccccatc ctaccccata ccgacaggtg 300
tctcgggttc aggccaaaag caaccccgag cgactcagac ggcgtcttat gcgaagacac 360
gacctgtccg aggaggaagc ccgaaagcgg atccccgaca ccgttgctcg agcgttggac 420
cttcctttcg tcacactgcg atctcaatcg actggtcagc actttcgact gttcatcaga 480
cacggacccc tgcaggtcac cgcagaggaa ggcggtttta cttgctatgg actgtccaag 540
ggtggctttg tcccctggtt ctaa 564

<210> SEQ ID NO 210
<211> LENGTH: 530
<212> TYPE: DNA
<213> ORGANISM: Artificial Sequence
<220> FEATURE:
<223> OTHER INFORMATION: Yarrowia FBA1 promoter

<400> SEQUENCE: 210
catcatctaa gggcctcaaa actacctcgg aactgctgcg ctgatctgga caccacagag 60
gttccgagca ctttaggttg caccaaatgt cccaccaggt gcaggcagaa aacgctggaa 120
cagcgtgtac agtttgtctt aacaaaaagt gagggcgctg aggtcgagca gggtggtgtg 180
acttgttata gcctttagag ctgcgaaagc gcgtatggat ttggctcatc aggccagatt 240
gagggtctgt ggacacatgt catgttagtg tacttcaatc gccccctgga tatagccccg 300
acaataggcc gtggcctcat ttttttgcct tccgcacatt tccattgctc ggtacccaca 360
ccttgcttct cctgcacttg ccaaccttaa tactggttta cattgaccaa catcttacaa 420
gcggggggct tgtctagggt atatataaac agtggctctc ccaatcggtt gccagtctct 480
tttttccttt ctttccccac agattcgaaa tctaaactac acatcacacc 530

<210> SEQ ID NO 211
<211> LENGTH: 659
<212> TYPE: DNA
<213> ORGANISM: Artificial Sequence
<220> FEATURE:
<223> OTHER INFORMATION: TDH1:28bp-gCAN1-28bp

<400> SEQUENCE: 211
cggcggactg cgtccgaacc agctccagca gcgtttttc cgggccattg agccgactgc 60
gaccccgcca acgtgtcttg gcccacgcac tcatgtcatg ttggtgttgg gaggccactt 120
tttaagtagc acaaggcacc tagctcgcag caaggtgtcc gaaccaaaga agcggctgca 180
gtggtgcaaa cggggcggaa acggcgggaa aaagccacgg gggcacgaat tgaggcacgc 240
cctcgaattt gagacgagtc acggccccat tcgcccgcgc aatggctcgc caacgcccgg 300

-continued

```
tcttttgcac cacatcaggt taccccaagc caaacctttg tgttaaaaag cttaacatat    360

tataccgaac gtaggtttgg gcgggcttgc tccgtctgtc caaggcaaca tttatataag    420

ggtctgcatc gccggctcaa ttgaatcttt tttcttcttc tcttctctat attcattctt    480

gaattaaaca cacatcaaca atggttcact gccgtatagg cagctaagaa atcaaacgat    540

tacccaccct cgttttagag ctagaaatag caagttaaaa taaggctagt ccgttatcaa    600

cttgaaaaag tggcaccgag tcggtgcttt tgttcactgc cgtataggca gctaagaaa     659


<210> SEQ ID NO 212
<211> LENGTH: 28
<212> TYPE: RNA
<213> ORGANISM: P. aeruginosa

<400> SEQUENCE: 212

guucacugcc guauaggcag cuaagaaa                                        28


<210> SEQ ID NO 213
<211> LENGTH: 156
<212> TYPE: RNA
<213> ORGANISM: Artificial Sequence
<220> FEATURE:
<223> OTHER INFORMATION: Csy4 recognition sequence flanked sgRNA

<400> SEQUENCE: 213

guucacugcc guauaggcag cuaagaaauc aaacgauuac ccacccucgu uuuagagcua     60

gaaauagcaa guuaaaauaa ggcuaguccg uuaucaacuu gaaaaagugg caccgagucg    120

gugcuuuugu ucacugccgu auaggcagcu aagaaa                              156


<210> SEQ ID NO 214
<211> LENGTH: 23
<212> TYPE: DNA
<213> ORGANISM: Yarrowia lipolytica

<400> SEQUENCE: 214

tcaaacgatt acccaccctc cgg                                             23


<210> SEQ ID NO 215
<211> LENGTH: 45
<212> TYPE: DNA
<213> ORGANISM: Yarrowia lipolytica

<400> SEQUENCE: 215

gaaaagacat tttcaaacga ttacccaccc tccgggactg aggcc                     45


<210> SEQ ID NO 216
<211> LENGTH: 44
<212> TYPE: DNA
<213> ORGANISM: Artificial Sequence
<220> FEATURE:
<223> OTHER INFORMATION: fragment of CAN1 from colony 14

<400> SEQUENCE: 216

gaaaagacat tttcaaacga ttacccacct ccgggactga ggcc                      44


<210> SEQ ID NO 217
<211> LENGTH: 44
<212> TYPE: DNA
<213> ORGANISM: Artificial Sequence
<220> FEATURE:
<223> OTHER INFORMATION: fragment of CAN1 from colony 16

<400> SEQUENCE: 217
```

gaaaagacat tttcaaacga ttacccacct ccgggactga ggcc 44

<210> SEQ ID NO 218
<211> LENGTH: 44
<212> TYPE: DNA
<213> ORGANISM: Artificial Sequence
<220> FEATURE:
<223> OTHER INFORMATION: fragment of CAN1 from colony 18

<400> SEQUENCE: 218
gaaaagacat tttcaaacga ttacccacct ccgggactga ggcc 44

<210> SEQ ID NO 219
<211> LENGTH: 44
<212> TYPE: DNA
<213> ORGANISM: Artificial Sequence
<220> FEATURE:
<223> OTHER INFORMATION: fragment of CAN1 from colony 19

<400> SEQUENCE: 219
gaaaagacat tttcaaacga ttacccacct ccgggactga ggcc 44

<210> SEQ ID NO 220
<211> LENGTH: 44
<212> TYPE: DNA
<213> ORGANISM: Artificial Sequence
<220> FEATURE:
<223> OTHER INFORMATION: fragment of CAN1 from colony 24

<400> SEQUENCE: 220
gaaaagacat tttcaaacga ttacccacct ccgggactga ggcc 44

<210> SEQ ID NO 221
<211> LENGTH: 44
<212> TYPE: DNA
<213> ORGANISM: Artificial Sequence
<220> FEATURE:
<223> OTHER INFORMATION: fragment of CAN1 from colony 25

<400> SEQUENCE: 221
gaaaagacat tttcaaacga ttacccacct ccgggactga ggcc 44

<210> SEQ ID NO 222
<211> LENGTH: 128
<212> TYPE: RNA
<213> ORGANISM: Artificial Sequence
<220> FEATURE:
<223> OTHER INFORMATION: gRNA processed by Csy4

<400> SEQUENCE: 222
cuaagaaauc aaacgauuac ccacccucgu uuuagagcua gaaauagcaa guuaaaauaa 60
ggcuaguccg uuaucaacuu gaaaaagugg caccgagucg gugcuuuugu ucacugccgu 120
auaggcag 128

<210> SEQ ID NO 223
<211> LENGTH: 8
<212> TYPE: RNA
<213> ORGANISM: Artificial Sequence
<220> FEATURE:
<223> OTHER INFORMATION: 5'-flanking sequence after Csy4 cleavage

<400> SEQUENCE: 223 cuaagaaa 8

-continued

```
<210> SEQ ID NO 224
<211> LENGTH: 20
<212> TYPE: RNA
<213> ORGANISM: Artificial Sequence
<220> FEATURE:
<223> OTHER INFORMATION: 3'-flanking sequence after Csy4 cleavage

<400> SEQUENCE: 224

guucacugcc guauaggcag                                                20
```

GENETIC TARGETING IN NON-CONVENTIONAL YEAST USING AN RNA-GUIDED ENDONUCLEASE

CROSS-REFERENCE TO RELATED APPLICATIONS

This application is the National Stage of International Application No. PCT/US2015/041256, filed Jul. 5, 2015, which claims the benefit of U.S. Provisional Application No. 62/036,652, filed Aug. 13, 2014, which are incorporated herein in their entirety by reference.

FIELD OF INVENTION

The invention is in the field of molecular biology. Specifically, this invention pertains to genetic targeting in non-conventional yeast using an RNA-guided endonuclease (RGEN).

REFERENCE TO SEQUENCE LISTING SUBMITTED ELECTRONICALLY

The official copy of the sequence listing is submitted electronically via EFS-Web as an ASCII formatted sequence listing with a file named 20170208_CL6272-US-PCT_SequenceListing_ST25, created on Feb. 9, 2017 and having a size of 411 kilobytes and is filed concurrently with the specification. The sequence listing contained in this ASCII-formatted document is part of the specification and is herein incorporated by reference in its entirety.

BACKGROUND

A powerful way to understand the function of a gene within an organism is to inhibit its expression. Inhibition of gene expression can be accomplished, for example, by interrupting or deleting the DNA sequence of the gene, resulting in "knock-out" of the gene (Austin et al., *Nat. Genetics* 36:921-924). Gene knock-outs mostly have been carried out through homologous recombination (HR), a technique applicable across a wide array of organisms from bacteria to mammals. Another tool for studying gene function can be through genetic "knock-in", which is also usually performed by HR. HR for purposes of gene targeting (knock-out or knock-in) can use the presence of an exogenously supplied DNA having homology with the target site.

Although gene targeting by HR is a powerful tool, it can be a complex, labor-intensive procedure. Most studies using HR have generally been limited to knock-out of a single gene rather than multiple genes in a pathway, since HR is generally difficult to scale-up in a cost-effective manner. This difficulty is exacerbated in organisms in which HR is not efficient. Such low efficiency typically forces practitioners to rely on selectable phenotypes or exogenous markers to help identify cells in which a desired HR event occurred.

HR for gene targeting has been shown to be enhanced when the targeted DNA site contains a double-strand break (Rudin et al., *Genetics* 122:519-534; Smih et al., *Nucl. Acids Res.* 23:5012-5019). Strategies for introducing double-strand breaks to facilitate HR-mediated DNA targeting have therefore been developed. For example, zinc finger nucleases have been engineered to cleave specific DNA sites leading to enhanced levels of HR at the site when a donor DNA was present (Bibikova et al., *Science* 300:764; Bibikova et al., *Mol. Cell. Biol.* 21:289-297). Similarly, artificial meganucleases (homing endonucleases) and transcription activator-like effector (TALE) nucleases have also been developed for use in HR-mediated DNA targeting (Epinat et al., *Nucleic Acids Res.* 31: 2952-2962; Miller et al., *Nat. Biotech.* 29:143-148).

Loci encoding CRISPR (clustered regularly interspaced short palindromic repeats) DNA cleavage systems have been found exclusively in about 40% of bacterial genomes and most archaeal genomes (Horvath and Barrangou, *Science* 327:167-170; Karginov and Hannon, *Mol. Cell* 37:7-19). In particular, the CRISPR-associated (Cas) RNA-guided endonuclease (RGEN), Cas9, of the type II CRIPSR system has been developed as a means for introducing site-specific DNA strand breaks ((U.S. Patent Application US 2015-0082478A1, published on Mar. 19, 2015 and US 2015-0059010A1, published on Feb. 26, 2015, both are hereby incorporated in its entirety by reference). The sequence of the RNA component of Cas9 can be designed such that Cas9 recognizes and cleaves DNA containing (i) sequence complementary to a portion of the RNA component and (ii) a protospacer adjacent motif (PAM) sequence.

Native Cas9/RNA complexes comprise two RNA sequences, a CRISPR RNA (crRNA) and a trans-activating CRISPR RNA (tracrRNA). A crRNA contains, in the 5'-to-3' direction, a unique sequence complementary to a target DNA site and a portion of a sequence encoded by a repeat region of the CRISPR locus from which the crRNA was derived. A tracrRNA contains, in the 5'-to-3' direction, a sequence that anneals with the repeat region of crRNA and a stem loop-containing portion. Recent work has led to the development of guide RNAs (gRNA), which are chimeric sequences containing, in the 5'-to-3' direction, a crRNA linked to a tracrRNA (WO2015/026883, published Feb. 26, 2015.

A method of expressing RNA components such as gRNA in eukaryotic cells for performing Cas9-mediated DNA targeting has been to use RNA polymerase III (Pol III) promoters, which allow for transcription of RNA with precisely defined, unmodified, 5'- and 3'-ends (DiCarlo et al., *Nucleic Acids Res.* 41: 4336-4343; Ma et al., *Mol. Ther. Nucleic Acids* 3:e161). This strategy has been successfully applied in cells of several different species including maize and soybean (WO2015/026883, published Feb. 26, 2015, as well as humans, mouse, zebrafish, *Trichoderma* and *Sacchromyces cerevisiae.*

Nevertheless, as now disclosed in the instant application, performing Cas9-mediated DNA targeting in non-conventional yeast such as *Yarrowia lipolytica* using Pol III promoter-transcribed gRNA has proven to be difficult. Other means for producing RNA components for Cas9 are therefore of interest for providing Cas9-mediated DNA targeting in non-conventional yeast.

SUMMARY OF INVENTION

In one embodiment, the disclosure concerns a non-conventional yeast comprising at least one RNA-guided endonuclease (RGEN) comprising at least one RNA component that does not have a 5'-cap, wherein the RNA component comprises a sequence complementary to a target site sequence on a chromosome or episome in the yeast, wherein the RGEN can bind to the target site sequence. The RGEN can also bind to and cleave the target site.

In one embodiment, the non-conventional yeast is a member of a genus selected from the group consisting of *Yarrowia, Pichia, Schwanniomyces, Kluyveromyces, Arxula, Trichosporon, Candida, Ustilago, Torulopsis, Zygosaccha-*

*romyces, Trigonopsis, Cryptococcus, Rhodotorula, Phaffia, Sporobolomyces,* and *Pachysolen.*

In one embodiment, the RGEN comprises a CRISPR (clustered regularly interspaced short palindromic repeats)-associated (Cas) protein-9 (Cas9) amino acid sequence. The Cas9 protein can be a Streptococcus Cas9 protein whereas the RNA component can comprise a guide RNA (gRNA) comprising a CRISPR RNA (crRNA) operably linked to a trans-activating CRISPR RNA (tracrRNA). A PAM (protospacer-adjacent motif) sequence can be adjacent to the target site sequence. The RGEN can also bind to and cleave the target site. The RNA transcribed from the nucleotide sequence can autocatalytically remove the ribozyme to yield said RNA component, wherein said RNA component does not have a 5' cap. Such ribozyme can include a hammerhead ribozyme, hepatitis delta virus ribozyme, group I intron ribozyme, RnaseP ribozyme, or hairpin ribozyme. The RNA transcribed from the nucleotide sequence can be an RNA molecule that does not autocatalytically removes the ribozyme to yield a ribozyme-RNA component fusion molecule without a 5' cap.

In one embodiment, the disclosure concerns a non-conventional yeast comprising a Cas endonuclease and a polynucleotide sequence comprising a promoter operably linked to at least one nucleotide sequence, wherein said nucleotide sequence comprises a DNA sequence encoding a ribozyme upstream of a DNA sequence encoding an RNA component, wherein said RNA component comprises a variable targeting domain complementary to a target site sequence on a chromosome or episome in the yeast, wherein the RNA component can form a RNA-guided endonuclease (RGEN) with the Cas endonuclease, wherein said RGEN can bind to the target site sequence.

In one embodiment, the method described herein comprises a method for modifying a target site on a chromosome or episome in a non-conventional yeast, the method comprising providing to a non-conventional yeast a first recombinant DNA construct comprising a DNA sequence encoding a Cas endonuclease, and a second recombinant DNA construct comprising a DNA sequence encoding a ribozyme upstream of an RNA component, wherein the RNA transcribed from the second recombinant DNA construct autocatalytically removes the ribozyme to yield said RNA component, wherein the Cas9 endonuclease introduces a single or double-strand break at said target site.

In one embodiment, the method described herein comprises a method for modifying a target site on a chromosome or episome in a non-conventional yeast, the method comprising providing to a non-conventional yeast a first recombinant DNA construct comprising a DNA sequence encoding a Cas endonuclease, and a second recombinant DNA construct comprising a DNA sequence encoding a ribozyme-RNA component fusion molecule, wherein said ribozyme-RNA component fusion molecule and Cas9 endonuclease can form a RGEN that introduces a single or double-strand break at said target site.

The method can further comprise identifying at least one non-conventional yeast cell that has a modification at said target, wherein the modification includes at least one deletion or substitution of one or more nucleotides in said target site. The method can further comprise providing a donor DNA to said yeast, wherein said donor DNA comprises a polynucleotide of interest.

In one embodiment, the method described herein comprises a method for editing a nucleotide sequence on a chromosome or episome in a non-conventional yeast, the method comprising providing to a non-conventional yeast a polynucleotide modification template DNA, a first recombinant DNA construct comprising a DNA sequence encoding a Cas endonuclease, and a second recombinant DNA construct comprising a DNA sequence encoding a ribozyme upstream of an RNA component, wherein the RNA transcribed from the second recombinant DNA construct autocatalytically removes the ribozyme to yield said RNA component, wherein the Cas9 endonuclease introduces a single or double-strand break at a target site in the chromosome or episome of said yeast, wherein said polynucleotide modification template DNA comprises at least one nucleotide modification of said nucleotide sequence.

In one embodiment, the method described herein comprises a method for silencing a nucleotide sequence on a chromosome or episome in a non-conventional yeast, the method comprising providing to a non-conventional yeast, at least a first recombinant DNA construct comprising a DNA sequence encoding an inactivated Cas9 endonuclease, and at least a second recombinant DNA construct comprising a promoter operably linked to at least one polynucleotide, wherein said at least one polynucleotide encodes a ribozyme-RNA component fusion molecule, wherein said ribozyme-RNA component fusion molecule and the inactivated Cas9 endonuclease can form a RGEN that binds to said nucleotide sequence in the chromosome or episome of said yeast, thereby blocking transcription of said nucleotide sequence.

In one embodiment, the method described herein comprises a high throughput method for the production of multiple guide RNAs for gene modification in non-conventional yeast, the method comprising: a) providing a recombinant DNA construct comprising a promoter operably linked to, in 5' to 3' order, a first DNA sequence encoding a ribozyme, a second DNA sequence encoding a counterselection agent, a third DNA sequence encoding a CER domain of a guide RNA, and a terminator sequence; b) providing at least one oligonucleotide duplex to the recombinant DNA construct of (a), wherein said oligonucleotide duplex is originated from combining a first single stranded oligonucleotide comprising a DNA sequence capable of encoding a variable targeting domain (VT) of a guide RNA target sequence with a second single stranded oligonucleotide comprising the complementary sequence to the DNA sequence encoding the variable targeting domain; c) exchanging the counterselection agent of (a) with the at least one oligoduplex of (b), thereby creating a library of recombinant DNA constructs each comprising a DNA sequence capable of encoding a variable targeting domain of a guide RNA; and, d) transcribing the library of recombinant DNA constructs of (c), thereby creating a library of ribozyme-guideRNA

BRIEF DESCRIPTION OF THE DRAWINGS AND SEQUENCES

FIG. 1: A structural model of a single guide polynucleotide such as a single guide RNA (sgRNA). A variable targeting (VT) domain is shown in gray. A Cas9 endonuclease recognition (CER) domain is shown in black.

Figure 2A:
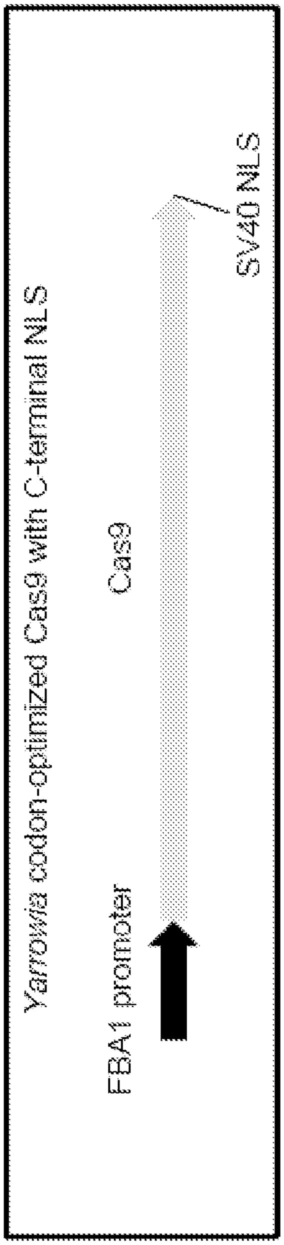

FIG. 2A: *Yarrowia* codon-optimized Cas9 expression cassette. FBA1 promoter is shown in black, and an open reading frame encoding Cas9 with a C-terminal SV40 nuclear localization signal (NLS) is shown in light grey.

Figure 2B:
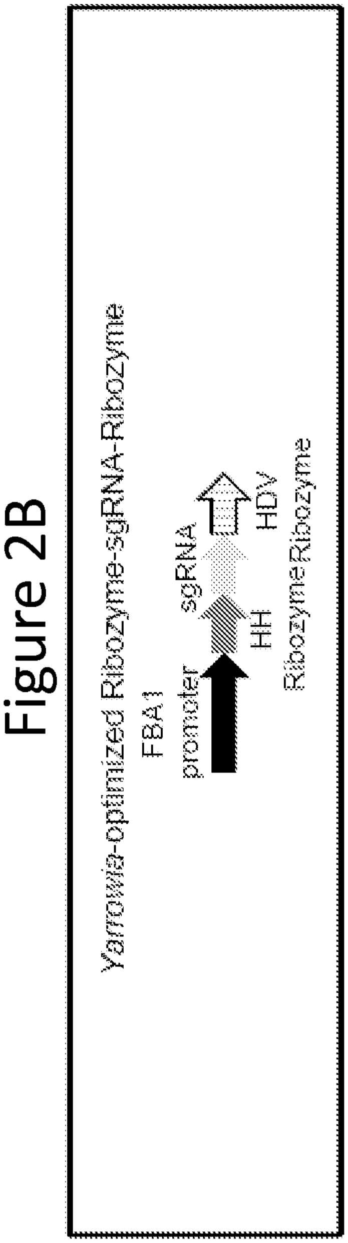

FIG. 2B: *Yarrowia*-optimized pre-sgRNA RGR expression cassette (RGR, ribozyme-sgRNA-ribozyme). FBA1 promoter is shown in black, hammerhead (HH) ribozyme is shown in dark grey, single guide RNA (sgRNA) is shown in light grey, and the HDV ribozyme is shown with vertical stripes.

Figure 2C:
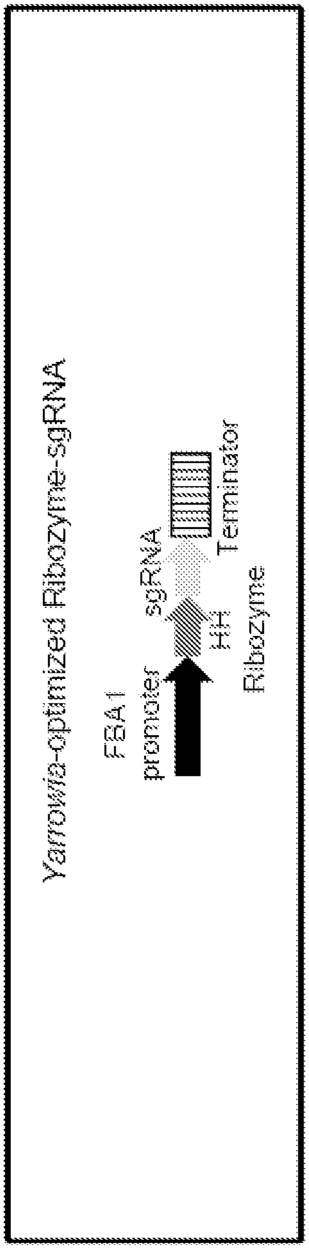

FIG. 2C: *Yarrowia*-optimized pre-sgRNA RG expression cassette (RG, ribozyme-sgRNA). FBA1 promoter is shown in black, hammerhead (HH) ribozyme is shown in dark grey, single guide RNA (sgRNA) is shown in light grey, and the Sup4 terminator is shown with vertical stripes.

Figure 3A:
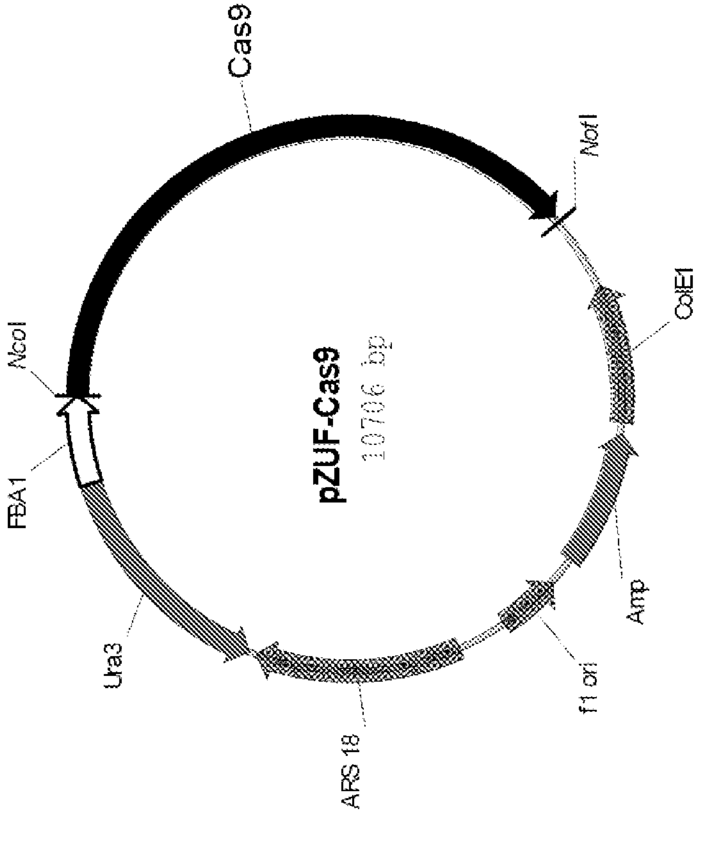

FIG. 3A: pZUFCas9 (SEQ ID NO: 14) plasmid contains the *Yarrowia* codon-optimized Cas9 expression cassette indicated in FIG. 2A. Origins of replication (ARS 18, f1 ori, ColE1) are in cross-hatch, and selectable markers (Ura3, Amp) are in grey.

Figure 3B:
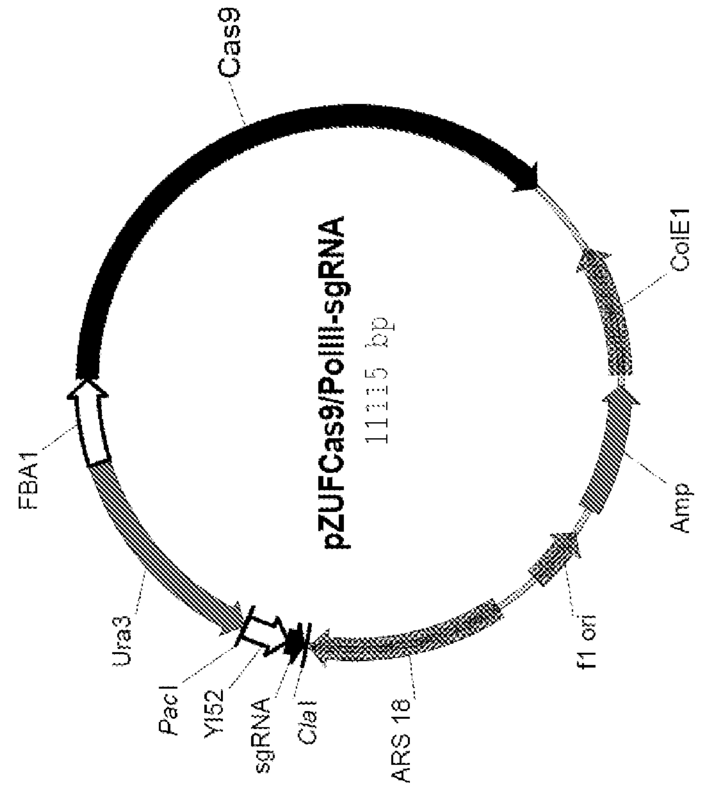

FIG. 3B: pZUFCas9/PolIII-sgRNA plasmid contains the *Yarrowia* codon-optimized Cas9 expression cassette indicated in FIG. 2A, and the Yl Snr52 (Pol III promoter, indicated as "Yl52")-sgRNA expression cassette for targeting Leu2-3 in *Yarrowia*. Though not shown, the sgRNA cassette also contained a *Saccharomyces cerevisiae* Sup4 gene transcription terminator sequence. Origins of replication (ARS 18, f1 ori, ColE1) are in cross-hatch, and selectable markers (Ura3, Amp) are in grey.

Figure 3C:
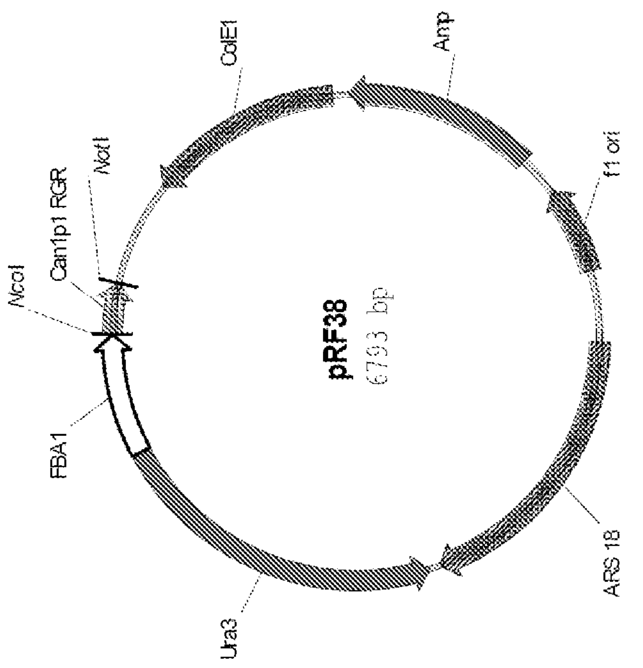

FIG. 3C: pRF38 plasmid (SEQ ID NO:19) contains a *Yarrowia*-optimized pre-sgRNA expression cassette (FBA1 promoter in white, RGR pre-sgRNA in diagonal stripes) of SEQ ID NO:18 for targeting the CAN1 gene in Y. lipolytica. Origins of replication (ARS 18, f1 ori, ColE1) are in cross-hatch, and selectable markers (Ura3, Amp) are in grey.

FIG. 4B: Transient targeting efficiency in *Y. lipolytica* cells transformed with (i) pZUFCas9 (SEQ ID NO:14) alone or (ii) pZUFCas9 and a linear DNA comprising the *Yarrowia*-optimized pre-sgRNA expression cassette of SEQ ID NO:18 (refer to Example 3). The y axis indicates the frequency of cells transformed with pZUFCas9 (i.e., $Ura^+$ cells) that are also canavanine-resistant ($Can^R$). Error bars indicate standard deviation.

FIG. 5: Sequence maps of Cas9/sgRNA cleavage sites in the CAN1 coding region of *Y. lipolytica* cells transformed with pZUFCas9 (SEQ ID NO:14) and a linear DNA comprising the *Yarrowia*-optimized pre-sgRNA expression cassette of SEQ ID NO:18 (refer to Example 3). With reference to the wild type (WT) CAN1 sequence, the Can1-1 target site sequence is shown in bold and the PAM sequence is underlined. The predicted cleavage site is immediately 5' of the third nucleotide upstream of the PAM. Inserted nucleotides are italicized. The number and frequency of each class of mutants (1-18) are represented on the right hand side. The sequences shown in this figure are included in the Sequence Listing as SEQ ID NOs:71-89, as numbered in the figure.

Figure 6:
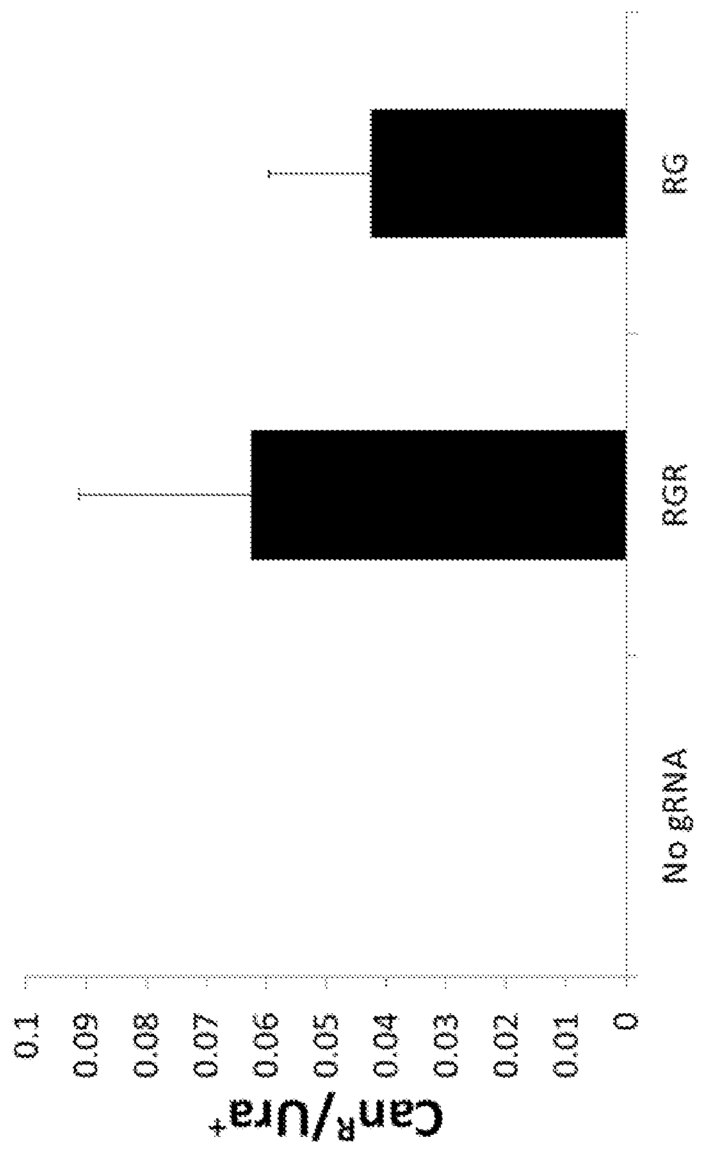

FIG. 6: Transient targeting efficiency in *Y. lipolytica* cells transformed with (i) pZUFCas9 (SEQ ID NO:14) alone, (ii) pZUFCas9 and a linear DNA comprising the *Yarrowia*-optimized pre-sgRNA expression cassette of SEQ ID NO:18 (RGR), or (iii) pZUFCas9 and a linear DNA comprising the *Yarrowia*-optimized pre-sgRNA expression cassette of SEQ ID NO:25 (RG) (refer to Example 4). The y axis indicates the frequency of cells transformed with pZUFCas9 (i.e., $Ura^+$ cells) that are also canavanine-resistant ($Can^R$). Error bars indicate standard deviation.

Figure 7:
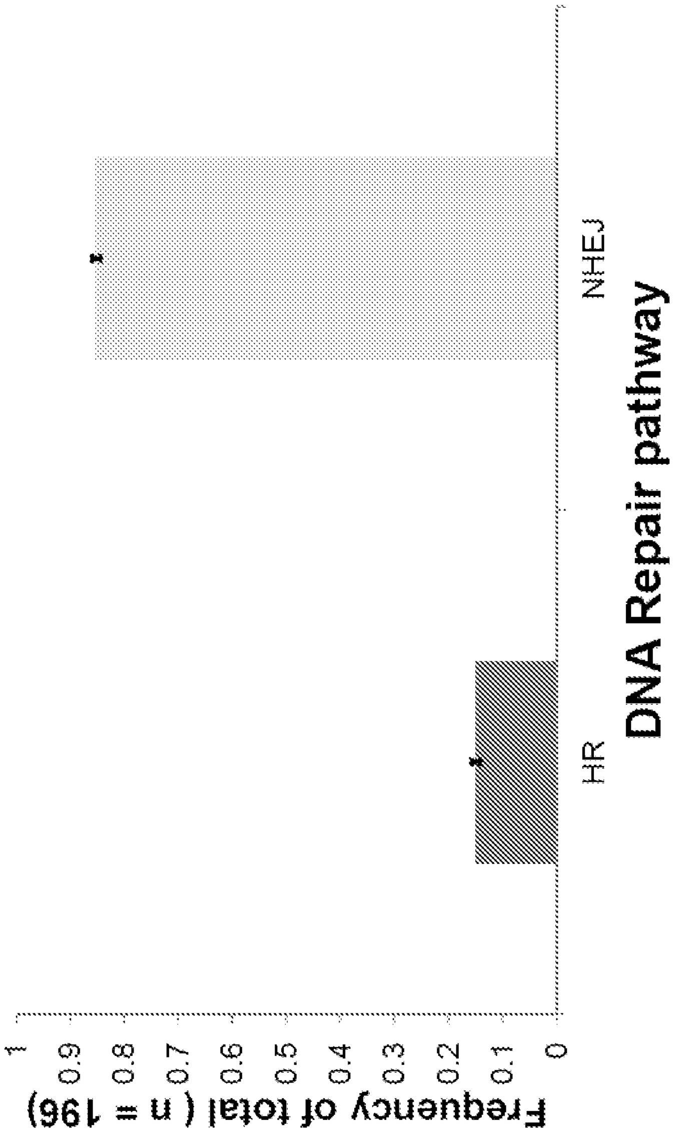

FIG. 7: Comparison of mutation frequency by HR and NHEJ DNA repair pathways. The total frequency of Cas9/sgRNA-mediated DNA double-strand break repair by HR (dark grey) and NHEJ (light grey), when polynucleotide modification template DNA sequences were provided in the transformation, was determined (refer to Example 5). Error bars indicate standard deviation.

Figure 8:
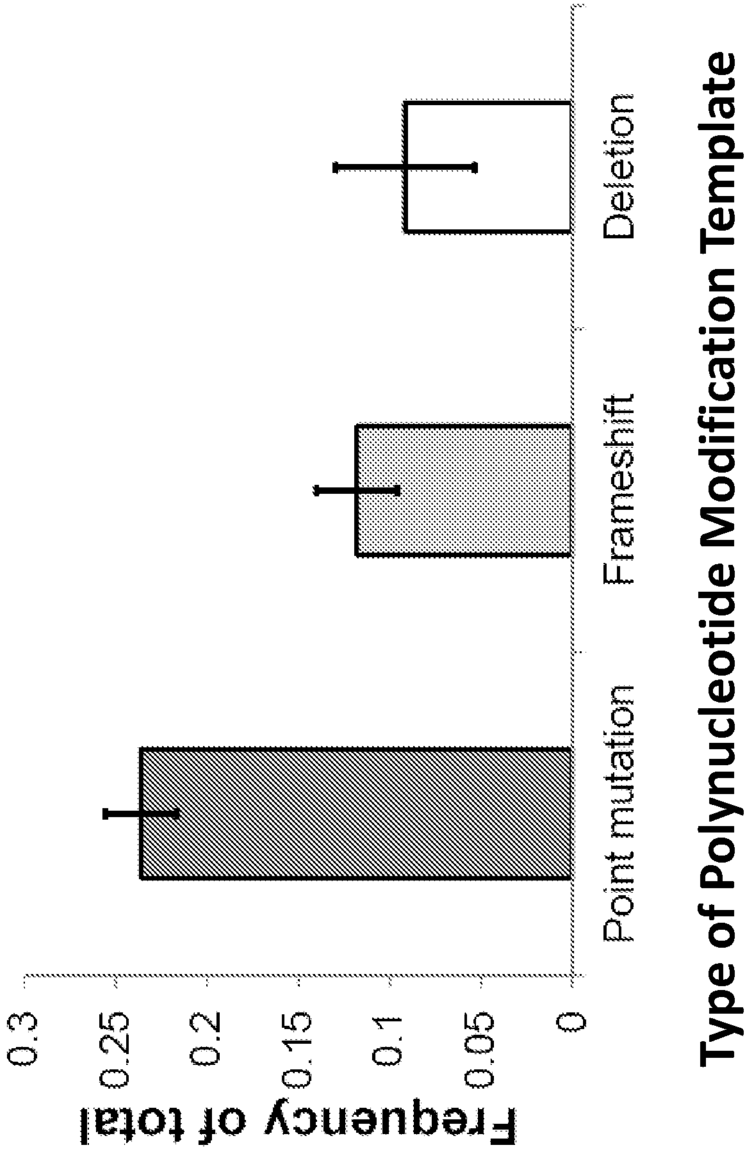

FIG. 8: Frequency of HR at a Cas9/sgRNA-mediated DNA double-strand break site by type of polynucleotide modification template DNA sequence. HR frequency using the point mutation template DNA(dark grey), frameshift template DNA (light grey), and large deletion template DNA (white) are shown (refer to Example 5). Error bars indicate standard deviation.

Figure 9:
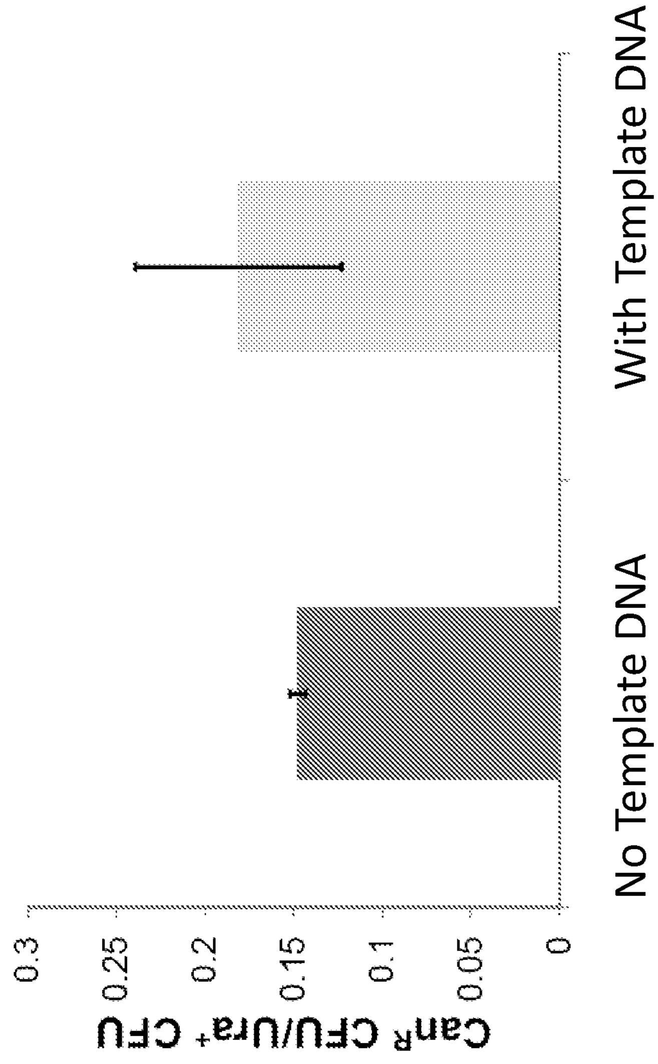

FIG. 9: Mutation frequency at the CAN1 locus in *Yarrowia* (repair at the Can1-1 site cleaved by Cas9/sgRNA) is not affected by the presence of polynucleotide modification template DNA. Canavanine-resistance frequency of cells resulting from transformations not including polynucleotide modification template DNA(dark grey, no template DNA) or including polynucleotide modification template DNA(light grey, with template DNA) (both transformation groups included pZUFCas9 (SEQ ID NO:14) and the RGR expression cassette [SEQ ID NO:18]) (refer to Example 5). The y axis indicates the frequency of cells transformed with pZUFCas9 (i.e., $Ura^+$ cells) that are also canavanine-resistant ($Can^R$). Error bars indicate standard deviation.

Figure 10B:
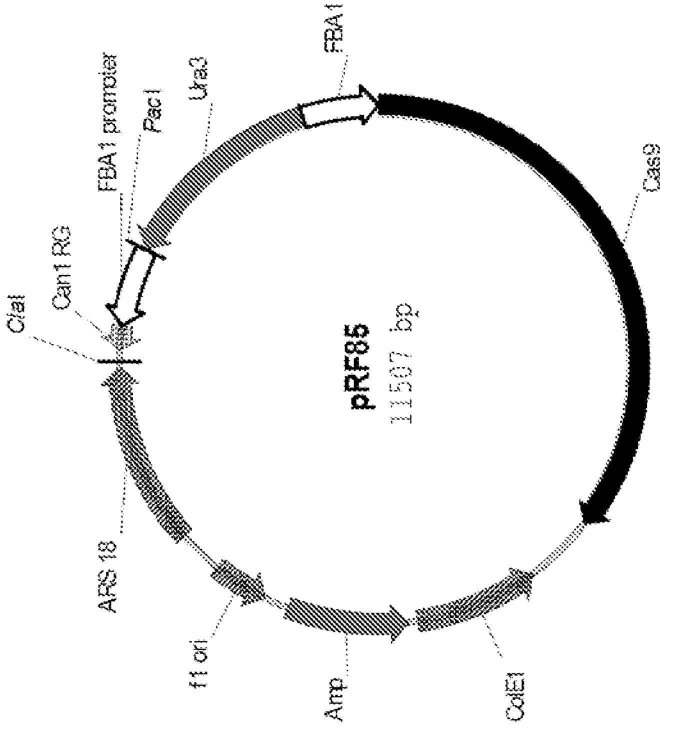
Figure 10A:
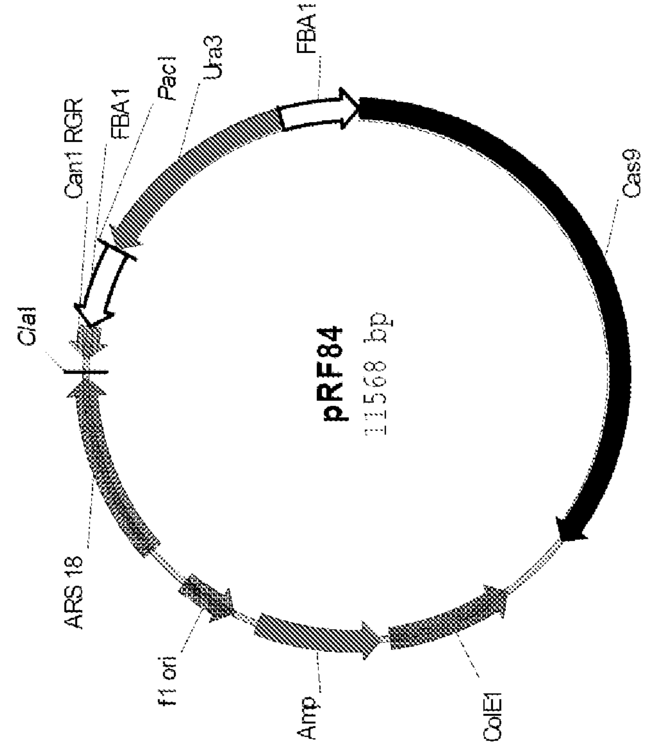

FIG. 10A: pRF84 plasmid (SEQ ID NO:41) contains the *Yarrowia* codon-optimized Cas9 expression cassette indicated in FIG. 2A and the *Yarrowia*-optimized RGR pre-sgRNA cassette of SEQ ID NO:18 (RGR pre-sgRNA coding region ["Can1 RGR"] shown with diagonals lines). Origins of replication (ARS 18, f1 ori, ColE1) are in cross-hatch, and selectable markers (Ura3, Amp) are in grey.

FIG. 10B: pRF85 plasmid (SEQ ID NO:42) contains the *Yarrowia* codon-optimized Cas9 expression cassette indicated in FIG. 2A and the *Yarrowia*-optimized RG pre-sgRNA cassette of SEQ ID NO:25 (RG pre-sgRNA coding region ["Can1 RG"] shown with diagonals lines). Origins of replication (ARS 18, f1 ori, ColE1) are in cross-hatch, and selectable markers (Ura3, Amp) are in grey.

Figure 11:
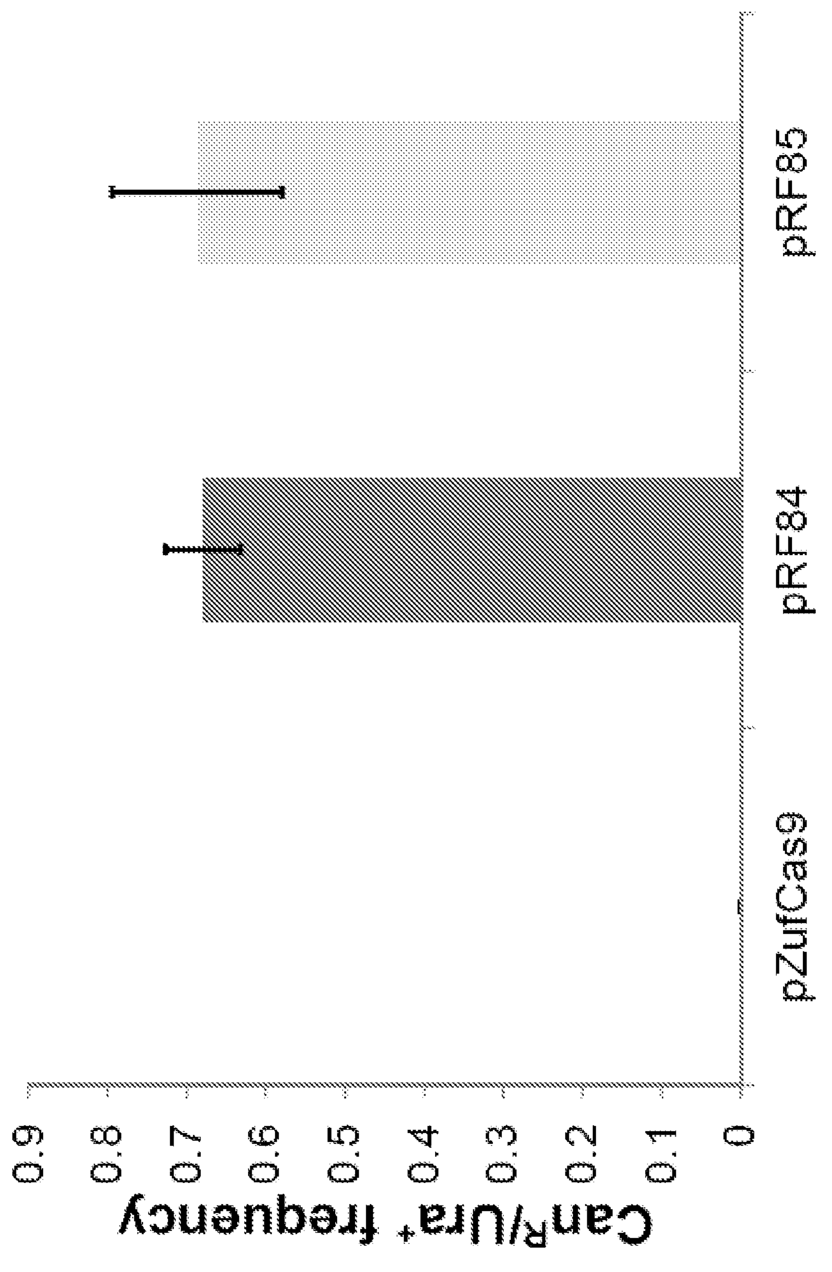

FIG. 11: Mutation frequency at the CAN1 locus in *Yarrowia* by expressing Cas9 alone (pZUFCas9, SEQ ID NO:14), or expressing (i) Cas9 and (ii) RGR pre-sgRNA (pRF84) or RG sgRNA (pRF85) (refer to Example 6). The y axis indicates the frequency of cells transformed with each respective vector (i.e., $Ura^+$ cells) that are also canavanine-resistant ($Can^R$). Error bars indicate standard deviation.

FIG. 12A-12B: Example of a high-throughput cloning cassette to construct HDV-sgRNA fusion expression cassettes. FIG. 12-A illustrates in a black box a promoter sequence, in a gray box a DNA sequence encoding a HDV ribozyme, in the horizontally hatched box is a counterselectable marker for the cloning strain flanked by Type IIs restriction sites, in the black dotted box is the CER domain of the sgRNA for interaction with Cas9, and in the diagonally hatched box is the transcriptional terminator. When a DNA duplex containing a DNA sequence encoding a variable targeting domain and the appropriate overhangs for the TypeIIs restriction sites (vertically hatched box VT) is mixed with a plasmid, DNA Ligase, and the TypeIIs enzyme, the DNA sequence encoding a variable targeting domain (VT) will replace the counterselectable marker, thereby creating the HDV-sgRNA expression cassette (Promoter-HDV-VT-CER-Terminator). When the HDV-sgRNA expression cassette is transcribed, it produces an RNA transcript (HDV-VT-CER transcript) of which the HDV ribozyme cleaves off any 5' sequences. FIG. 12-B shows an example of a duplex DNA molecule (oligoduplex of SEQ ID NO: 99 and SEQ ID NO: 100) containing a DNA sequence encoding the Can1-1 target site and the appropriate overhangs for cloning into plasmid pRF291.

FIG. 13A-13B: Example of a high-throughput cloning cassette to construct HH-sgRNA expression cassettes. FIG.

13-shows in a black box the promoter sequence; in the horizontally hatched box is a counterselectable marker for the cloning strain flanked by Type IIs restriction sites; in the black dotted box is the CER domain of the sgRNA for interaction with Cas9, in the diagonally hatched box is the transcriptional terminator. When a DNA duplex containing the target-site specific hammerhead ribozyme encoding DNA (Vertically hatched box HH, the targeting sequence and the appropriate overhangs for the TypeIIs sites (dotted box TS) is mixed with the plasmid, DNA Ligase and the Type-II enzyme, the HH-target site duplex replaces the counterselectable marker, creating the HH-sgRNA expression cassette. When the expression cassette is transcribed, it produces a transcript and the HH ribozyme cleaves off itself and any 5' sequences. FIG. 13B shows an example of a duplex DNA molecule (of SEQ ID NO: 162 and SEQ ID NO: 163) containing a variable targeting domain for targeting the ds-temp-1 target site (VT) and the sequence specific HH ribozyme encoding DNA (HH), and the appropriate overhangs for cloning into plasmid pRF291.

Figure 14:
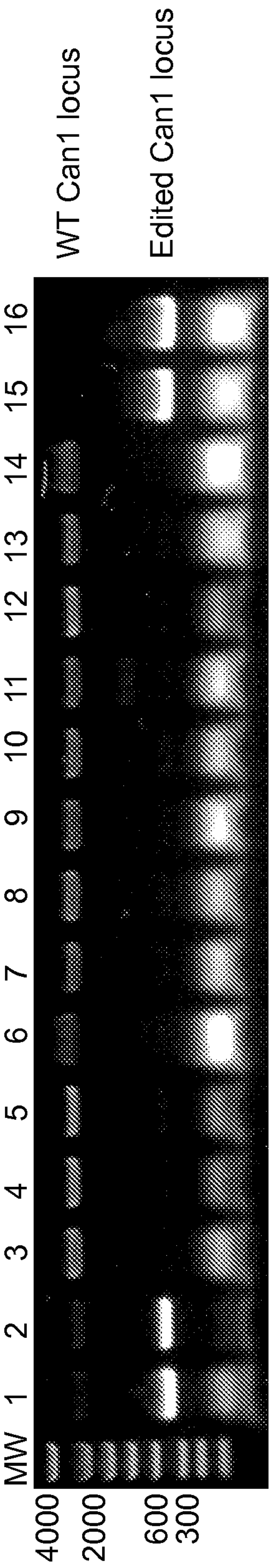

FIG. 14: Example of Gel electrophoresis of Can1 locus from cells transformed with pRF303 (SEQ ID NO: 103) and Can1 short editing template (SEQ ID NO: 157). Lane marked MW is the molecular weight marker. Lanes 1-16 represent individual colonies from streak purified transformants. The higher MW band is the correct size for the WT Can1 locus (SEQ ID NO: 160) or the Can1 locus with small indel mutations. The smaller molecular weight band is the correct size for the Can1 locus edited (SEQ ID NO: 161) with the short Can1 editing template (SEQ ID NO: 157).

FIG. 15 shows a representative sequencing result of the plasmid and genomic URA3 genes from colony PCR and their alignment. Dash and bold indicate deletions and insertions, respectively. PAM sequence is underlined.

FIG. 16-A shows relative positions of the targeting sequences for the RGR-URA3.1, RGR-URA3.2, and RGR-URA3.3 within the *Yarrowia* URA3 gene. FIG. 16-B shows the sequencing result and sequence alignment of the colony PCR of the pYRH222 transformants that were grown on SC medium containing 5-FOA. Bold indicates insertions. PAM sequence is underlined. The "N"s represent mixed sequences. FIG. 16-C shows the sequencing result and sequence alignment of the colony PCR of the pYRH282 transformants that were grown on SC medium containing 5-FOA. Dashed line indicates deletion. PAM sequence is underlined. The "N"s represent mixed sequences. FIG. 16-D shows the sequencing result and sequence alignment of the colony PCR of the pYRH283 transformants that were grown on SC medium containing 5-FOA. Dashed line indicates deletion. PAM sequence is underlined. The "N"s represent mixed sequences.

Figure 17:
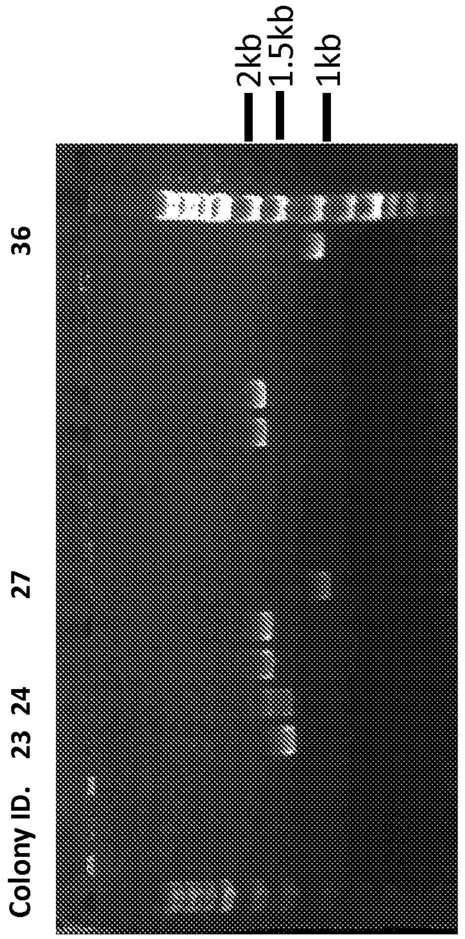

FIG. 17 shows different migration of PCR products from pYRH282 (colony ID. 23 and 24) and pYRH283 (colony ID. 27 and 36) transformants. DNA size from ladder is indicated on the right.

FIG. 18 shows a representative sequencing result of the Can1 target sequences. Dash indicates deletions, respectively. PAM sequence is indicated in bold.

TABLE 1

Summary of Nucleic Acid and Protein SEQ ID Numbers

| Description | Nucleic acid SEQ ID NO. | Protein SEQ ID NO. |
|---|---|---|
| Cas9 endonuclease recognition (CER) domain of a gRNA. | 1 (80 bases) | |
| *Y. lipolytica* Leu2-1 target site, or alternatively, DNA encoding Leu2-1 variable target domain of a gRNA. | 2 (20 bases) | |
| *Y. lipolytica* Leu2-2 target site, or alternatively, DNA encoding Leu2-2 variable target domain of a gRNA. | 3 (20 bases) | |
| *Y. lipolytica* Leu2-3 target site, or DNA encoding Leu2-2 variable target domain of a gRNA. | 4 (20 bases) | |
| *S. cerevisiae* Snr52 promoter. | 5 (300 bases) | |
| *S. cerevisiae* Rprl promoter. | 6 (300 bases) | |
| *Y. lipolytica* Snr52 promoter. | 7 (300 bases) | |
| *S. cerevisiae* Sup4 terminator. | 8 (20 bases) | |
| *Streptococcus pyogenes* Cas9 open reading frame codon-optimized for expression in *Y. lipolytica*. | 9 (4107 bases) | |
| *Streptococcus pyogenes* Cas9 including C-terminal linker and SV40 NLS ("Cas9-NLS"); open reading frame codon-optimized for expression in *Y. lipolytica*. | 10 (4140 bases) | 11 (1379 aa) |
| *Y. lipolytica* FBA1 promoter. | 12 (543 bases) | |
| Cas9-NLS expression cassette (promoter and Cas9-NLS open reading frame). | 13 (4683 bases) | |
| pZUFCas9 plasmid. | 14 (10706 bases) | |
| Hammerhead (HH) ribozyme. | 15 (43 bases) | |
| HDV ribozyme. | 16 (68 bases) | |
| *Y. lipolytica* Can1-1 target site, or alternatively, DNA encodinq Can1-1 variable target domain of a gRNA. | 17 (20 bases) | |
| FBA1 promoter: HH-sgRNA-HDV (RGR) pre-sgRNA expression cassette, or alternatively, "RGR" expression cassette. | 18 (760 bases) | |
| pRF38 plasmid. | 19 (6793 bases) | |
| RGR forward PCR primer. | 20 (19 bases) | |
| RGR reverse PCR primer. | 21 (19 bases) | |
| CAN1 forward PCR primer. | 22 (20 bases) | |
| CAN1 reverse PCR primer. | 23 (21 bases) | |
| CAN1 sequencing primer. | 24 (21 bases) | |
| FBA1 promoter: HH-sgRNA-Sup4 terminator (RG) pre-sgRNA expression cassette, or alternatively, "RG" expression cassette. | 25 (709 bases) | |
| Poly-A. | 26 (10 bases) | |
| Poly-T. | 27 (10 bases) | |
| CAN1 frameshift template DNA. | 28 (100 bases) | |

TABLE 1-continued

| Summary of Nucleic Acid and Protein SEQ ID Numbers | | |
|---|---|---|
| Description | Nucleic acid SEQ ID NO. | Protein SEQ ID NO. |
| CAN1 frameshift template DNA complement. | 29 (100 bases) | |
| CAN1 point mutation template DNA. | 30 (106 bases) | |
| CAN1 point mutation template DNA complement. | 31 (106 bases) | |
| CAN1 upstream template arm. | 32 (655 bases) | |
| Forward PCR primer for amplifying CAN1 upstream template arm. | 33 (29 bases) | |
| Reverse PCR primer for amplifying CAN1 upstream template arm. | 34 (37 bases) | |
| CAN1 downstream template arm. | 35 (658 bases) | |
| Forward PCR primer for amplifying CAN1 downstream teamplate DNA arm. | 36 (37 bases) | |
| Reverse PCR primer for amplifying CAN1 downstream template DNA arm. | 37 (22 bases) | |
| CAN1 large deletion template DNA. | 38 (1276 bases) | |
| RG/RGR forward PCR primer. | 39 (31 bases) | |
| RG/RGR reverse PCR primer. | 40 (29 bases) | |
| pRF84 plasmid. | 41 (11568 bases) | |
| pRF85 plasmid. | 42 (11507 bases) | |
| RNA loop-forming seguence (GAAA). | 43 (4 bases) | |
| RNA loop-forming seguence (CAAA). | 44 (4 bases) | |
| RNA loop-forming seguence (AAAG). | 45 (4 bases) | |
| Example of a Cas9 target site: PAM sequence. | 46 (23 bases) | |
| PAM sequence NGG. | 47 (3 bases) | |
| PAM sequence NNAGAA. | 48 (6 bases) | |
| PAM sequence NNAGAAW. | 49 (7 bases) | |
| PAM sequence NGGNG. | 50 (5 bases) | |
| PAM sequence NNNNGATT. | 51 (8 bases) | |
| PAM sequence NAAAAC. | 52 (6 bases) | |
| PAM sequence NG. | 53 (2 bases) | |
| TracrRNA mate sequence example 1. | 54 (22 bases) | |
| TracrRNA mate sequence example 2. | 55 (15 bases) | |
| TracrRNA mate sequence example 3. | 56 (12 bases) | |
| TracrRNA mate sequence example 4. | 57 (13 bases) | |
| TracrRNA example 1. | 58 (60 bases) | |
| TracrRNA example 2. | 59 (45 bases) | |
| TracrRNA example 3. | 60 (32 bases) | |
| TracrRNA example 4. | 61 (85 bases) | |
| TracrRNA example 5. | 62 (77 bases) | |
| TracrRNA example 6. | 63 (65 bases) | |
| gRNA example 1. | 64 (131 bases) | |
| gRNA example 2. | 65 (117 bases) | |
| gRNA example 3. | 66 (104 bases) | |
| gRNA example 4. | 67 (99 bases) | |
| gRNA example 5. | 68 (81 bases) | |
| gRNA example 6. | 69 (68 bases) | |
| gRNA example 7. | 70 (100 bases) | |
| WT sequence shown in FIG. 5. | 71 | |
| Sequence 1 shown in FIG. 5. | 72 | |
| Sequence 2 shown in FIG. 5. | 73 | |
| Sequence 3 shown in FIG. 5. | 74 | |
| Sequence 4 shown in FIG. 5. | 75 | |
| Sequence 5 shown in FIG. 5. | 76 | |
| Sequence 6 shown in FIG. 5. | 77 | |
| Sequence 7 shown in FIG. 5. | 78 | |
| Sequence 8 shown in FIG. 5. | 79 | |
| Sequence 9 shown in FIG. 5. | 80 | |
| Sequence 10 shown in FIG. 5. | 81 | |
| Sequence 11 shown in FIG. 5. | 82 | |
| Sequence 12 shown in FIG. 5. | 83 | |
| Sequence 13 shown in FIG. 5. | 84 | |
| Sequence 14 shown in FIG. 5. | 85 | |
| Sequence 15 shown in FIG. 5. | 86 | |
| Sequence 16 shown in FIG. 5. | 87 | |
| Sequence 17 shown in FIG. 5. | 88 | |
| Sequence 18 shown in FIG. 5. | 89 | |
| Primer Aarl-removal-1 | 90 | |
| Primer Aarl-removal-2 | 91 | |
| Plasmid pRF109 | 92 | |
| modified Aar1- Cas9 gene | 93 | |
| Plasmid pRF141 | 94 | |
| High throughput cloning cassette | 95 | |
| yI52 promoter | 96 | |
| *Escherichia coli* counterselection cassette rpsL | 97 | |
| Plasmid pRF291 | 98 | |
| Oligonucleotide Can1-1F | 99 | |

TABLE 1-continued

Summary of Nucleic Acid and Protein SEQ ID Numbers

| Description | Nucleic acid SEQ ID NO. | Protein SEQ ID NO. |
|---|---|---|
| Oligonucleotide Can1-1R | 100 | |
| Can1-1 target site and PAM sequence | 101 | |
| Recombinant HDV-sgRNA expression cassette for targeting Can1-1 | 102 | |
| Plasmid pRF303 | 103 | |
| HDV ribozyme-guide RNA | 104 | |
| Can1 gene from *Yarrowia lipolytica* | 105 | |
| Can1-2 target site | 106 | |
| Sou2-1 target site | 107 | |
| Sou2-2 target site | 108 | |
| Variable targeting domain of Can1-2 | 109 | |
| Variable targeting domain of Sou2-1 | 110 | |
| Variable targeting domain of Sou2-2 | 111 | |
| Tgl1-1 target site | 112 | |
| Acos10-1 target site | 113 | |
| Fat1-1 target site | 114 | |
| Variable targeting domain of ura3-1 | 115 | |
| URa3-1 target site | 116 | |
| Cas9-SV40 NLS D10A H840A | | 117 |
| Primer D10AF | 118 | |
| Primer D10AR | 119 | |
| *Yarrowia* optimized Cas9 D10A gene | 120 | |
| Plasmid pRF111 | 121 | |
| Primer H840A1 | 122 | |
| Primer H840A2 | 123 | |
| *Yarrowia* codon optimized inactivated Cas9 gene | 124 | |
| pRF143 | 125 | |
| *Yarrowia* optimized dsREDexpress ORF | 126 | |
| *Yarrowia* optimized dsREDexpress cloning fragment | 127 | |
| FBA1-dsREDexpress expression cassette | 128 | |
| pRF165 | 129 | |
| FBA1 *Yarrowia* dsREDexpress cassette from pRF165 on PmeI NotI fragment | 130 | |
| p2PO69 integration vector | 131 | |
| pRF201 | 132 | |
| AscI/SphI integration fragment from pRF201 | 133 | |
| HY026 | 134 | |
| HY027 | 135 | |
| pRF169 | 136 | |
| GPD Promoter | 137 | |
| GPD promoter-counterselectable marker-CER-terminator | 138 | |
| ds-temp-1 target site | 139 | |
| ds-temp-2 target site | 140 | |
| ds-nontemp-3 target site | 141 | |
| Hammerhead ribozyme-VTD fusion | 142 | |
| Hammerhead ribozyme-VTD fusion | 143 | |
| ds-temp-1F | 144 | |
| ds-temp-1R | 145 | |
| ds-temp-2F | 146 | |
| ds-temp-2R | 147 | |
| ds-nontemp-1F | 148 | |
| ds-nontemp-1R | 149 | |
| pRF296 | 150 | |
| pRF298 | 151 | |
| pRF300 | 152 | |
| pRF339 | 153 | |
| pRF341 | 154 | |
| pRF343 | 155 | |
| pRF80 | 156 | |
| short Can1 deletion editing template | 157 | |
| Primer 80F | 158 | |
| Primer 80R | 159 | |
| Can1 locus WT (wild type) | 160 | |
| Can1 Loci deletion strains | 161 | |
| Forward Oligonucleotide of FIG. 13-B | 162 | |
| Reverse Oligonucleotide of FIG. 13-B | 163 | |
| pre-sgRNA URA3.1 (RGR-URA3.1) | 164 | |
| URA3.1 target sequence | 165 | |
| pre-sgRNA URA3.2 (RGR-URA3.2 | 166 | |
| URA3.2 target sequence | 167 | |
| FBA1L promoter | 168 | |
| acetohydroxyacid synthase gene | 169 | |
| primer RHO705 | 170 | |

TABLE 1-continued

Summary of Nucleic Acid and Protein SEQ ID Numbers

| Description | Nucleic acid SEQ ID NO. | Protein SEQ ID NO. |
|---|---|---|
| primer RHO719 | 171 | |
| primer RHO733 | 172 | |
| primer RHO734 | 173 | |
| primer RHO707 | 174 | |
| fragment of wild type URA3 sequence | 175 | |
| fragment of Plasmid URA3 from colony 1 | 176 | |
| fragment of Plasmid URA3 from colony 2 | 177 | |
| fragment of Plasmid URA3 from colony 3 | 178 | |
| fragment of Plasmid URA3 from colony 5 | 179 | |
| fragment of Plasmid URA3 from colony 6 | 180 | |
| fragment of Genomic URA3 from colony 1 | 181 | |
| fragment of Genomic URA3 from colony 2 | 182 | |
| fragment of Genomic URA3 from colony 3 | 183 | |
| fragment of Genomic URA3 from colony 5 | 184 | |
| fragment of Genomic URA3 from colony 6 | 185 | |
| hygromycin antibiotic resistant selection marker | 186 | |
| TDH1 or GPD promoter | 187 | |
| primer RHO804 | 188 | |
| primer RHO805 | 189 | |
| TDH1 promoter-RGR-URA3.3 fusion | 190 | |
| pre-sgRNA URA3.3 (RGR-URA3.3) | 191 | |
| primer RHO610 | 192 | |
| primer RHO611 | 193 | |
| primer RHO704 | 194 | |
| fragment of Wild type URA3 sequence | 195 | |
| Fragment of URA3 sequence from colony 3 | 196 | |
| Fragment of URA3 sequence from colony 4 | 197 | |
| Fragment of URA3 sequence from colony 5 | 198 | |
| Fragment of URA3 sequence from colony 6 | 199 | |
| Fragment of URA3 sequence from colony 9 | 200 | |
| Fragment of URA3 sequence from colony 10 | 201 | |
| fragment of wild type URA3 sequence | 202 | |
| Fragment of URA3 sequence from colony 23 | 203 | |
| Fragment of URA3 sequence from colony 24 | 204 | |
| fragment of wild type URA3 sequence | 205 | |
| Fragment of URA3 sequence from colony 27 | 206 | |
| Fragment of URA3 sequence from colony 36 | 207 | |
| ARS18 sequence | 208 | |
| *Yarrowia* codon optimized *P. aeruginosa* Csy4 | 209 | |
| *Yarrowia* FBA1 promoter | 210 | |
| TDH1: 28 bp-gCAN1-28 bp | 211 | |
| Csy4 recognition sequence | 212 | |
| Csy4 recognition sequence flanked sgRNA | 213 | |
| CAN1 target sequence | 214 | |
| fragment of wild type CAN1 sequence | 215 | |
| fragment of CAN1 from colony 14 | 216 | |
| fragment of CAN1 from colony 16 | 217 | |
| fragment of CAN1 from colony 18 | 218 | |
| fragment of CAN1 from colony 19 | 219 | |
| fragment of CAN1 from colony 24 | 220 | |
| fragment of CAN1 from colony 25 | 221 | |
| sgRNA processed by Csy4 | 222 | |
| 5'-flanking sequence after Csy4 cleavage | 223 | |
| 3'-flanking sequence after Csy4 cleavage | 224 | |

DETAILED DESCRIPTION OF THE INVENTION

The disclosures of all cited patent and non-patent literature are incorporated herein by reference in their entirety.

As used herein, the term "invention" or "disclosed invention" is not meant to be limiting, but applies generally to any of the inventions defined in the claims or described herein. These terms are used interchangeably herein.

The term "non-conventional yeast" herein refers to any yeast that is not a *Saccharomyces* (e.g., *S. cerevisiae*) or *Schizosaccharomyces* yeast species. Non-conventional yeast are described in Non-Conventional Yeasts in Genetics, Biochemistry and Biotechnology: Practical Protocols (K. Wolf, K. D. Breunig, G. Barth, Eds., Springer-Verlag, Berlin, Germany, 2003), which is incorporated herein by reference. Non-conventional yeast in certain embodiments may additionally (or alternatively) be yeast that favor non-homologous end-joining (NHEJ) DNA repair processes over repair processes mediated by homologous recombination (HR). Definition of a non-conventional yeast along these lines—preference of NHEJ over HR—is further disclosed by Chen et al. (*PLoS ONE* 8:e57952), which is incorporated herein by reference. Preferred non-conventional yeast herein are those of the genus *Yarrowia* (e.g., *Yarrowia lipolytica*). The term "yeast" herein refers to fungal species that predominantly exist in unicellular form. Yeast can alternative be referred to as "yeast cells" herein.

The term "RNA-guided endonuclease" (RGEN) herein refers to a complex comprising at least one CRISPR (clustered regularly interspaced short palindromic repeats)-associated (Cas) protein and at least one RNA component. Briefly, an RNA component of an RGEN contains sequence that is complementary to a DNA sequence in a target site sequence. Based on this complementarity, an RGEN can specifically recognize and cleave a particular DNA target site sequence. An RGEN herein can comprise Cas protein(s) and suitable RNA component(s) of any of the four known CRISPR systems (Horvath and Barrangou, *Science* 327:167-170) such as a type I, II, or III CRISPR system. An RGEN in preferred embodiments comprises a Cas9 endonuclease (CRISPR II system) and at least one RNA component (e.g., a crRNA and tracrRNA, or a gRNA).

The term "CRISPR" (clustered regularly interspaced short palindromic repeats) refers to certain genetic loci encoding factors of class I, II, or III DNA cleavage systems, for example, used by bacterial and archaeal cells to destroy foreign DNA (Horvath and Barrangou, *Science* 327:167-170). Components of CRISPR systems are taken advantage of herein for DNA targeting in non-conventional yeast cells.

The terms "type II CRISPR system" and "type II CRISPR-Cas system" are used interchangeably herein and refer to a DNA cleavage system utilizing a Cas9 endonuclease in complex with at least one RNA component. For example, a Cas9 can be in complex with a CRISPR RNA (crRNA) and a trans-activating CRISPR RNA (tracrRNA). In another example, a Cas9 can be in complex with a guide RNA. Thus, crRNA, tracrRNA, and guide RNA are non-limiting examples of RNA components herein.

The term CRISPR-associated ("Cas") endonuclease herein refers to a Cas protein encoded by a Cas gene. A Cas endonuclease, when in complex with a suitable RNA component, is capable of cleaving all or part of a specific DNA target sequence in certain embodiments. For example, it is can be capable of introducing a single- or double-strand break in a specific DNA target sequence; it can alternatively be characterized as being able to cleave one or both strands of a specific DNA target sequence. A Cas endonuclease unwinds the DNA duplex at the target sequence and cleaves at least one DNA strand, as mediated by recognition of the target sequence by a crRNA or guide RNA that is in complex with the Cas. Such recognition and cutting of a target sequence by a Cas endonuclease typically occurs if the correct protospacer-adjacent motif (PAM) is located at or adjacent to the 3' end of the DNA target sequence. Alternatively, a Cas protein herein may lack DNA cleavage or nicking activity, but can still specifically bind to a DNA target sequence when complexed with a suitable RNA component. A preferred Cas protein herein is Cas9.

"Cas9" (formerly referred to as Cas5, Csn1, or Csx12) herein refers to a Cas endonuclease of a type II CRISPR system that forms a complex with crRNA and tracrRNA, or with a guide RNA, for specifically recognizing and cleaving all or part of a DNA target sequence. Cas9 protein comprises an RuvC nuclease domain and an HNH (H-N-H) nuclease domain, each of which cleaves a single DNA strand at a target sequence (the concerted action of both domains leads to DNA double-strand cleavage, whereas activity of one domain leads to a nick). In general, the RuvC domain comprises subdomains I, II and III, where domain I is located near the N-terminus of Cas9 and subdomains II and Ill are located in the middle of the protein, flanking the HNH domain (Hsu et al, Cell 157:1262-1278). "Apo-Cas9" refers to Cas9 that is not complexed with an RNA component. Apo-Cas9 can bind DNA, but does so in a non-specific manner, and cannot cleave DNA (Sternberg et al., *Nature* 507:62-67).

In some embodiments, the Cas endonuclease can comprises a modified form of the Cas9 polypeptide. The modified form of the Cas9 polypeptide can include an amino acid change (e.g., deletion, insertion, or substitution) that reduces the naturally-occurring nuclease activity of the Cas9 protein. For example, in some instances, the modified form of the Cas9 protein has less than 50%, less than 40%, less than 30%, less than 20%, less than 10%, less than 5%, or less than 1% of the nuclease activity of the corresponding wild-type Cas9 polypeptide (US patent application US20140068797 A1, published on Mar. 6, 2014). In some cases, the modified form of the Cas9 polypeptide has no substantial nuclease activity and is referred to as catalytically "inactivated Cas9" or "deactivated cas9 (dCas9)." Catalytically inactivated Cas9 variants include Cas9 variants that contain mutations in the HNH and RuvC nuclease domains. These catalytically inactivated Cas9 variants are capable of interacting with sgRNA and binding to the target site in vivo but cannot cleave either strand of the target DNA. This mode of action, binding but not breaking the DNA can be used to transiently decrease the expression of specific loci in the chromosome without causing permanent genetic changes.

A catalytically inactive Cas9 can be fused to a heterologous sequence (US patent application US20140068797 A1, published on Mar. 6, 2014). Suitable fusion partners include, but are not limited to, a polypeptide that provides an activity that indirectly increases transcription by acting directly on the target DNA or on a polypeptide (e.g., a histone or other DNA-binding protein) associated with the target DNA. Additional suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity. Further suitable fusion partners include, but are not limited to, a polypeptide that directly provides for increased transcription of the target nucleic acid (e.g., a transcription activator or a fragment thereof, a protein or fragment thereof that recruits a transcription activator, a small molecule/drug-responsive transcription regulator, etc.). A catalytically inactive Cas9 can also be fused to a Fokl nuclease to generate double strand breaks (Guilinger et al. Nature biotechnology, volume 32, number 6, June 2014).

The term "RNA component" herein refers to an RNA component of an RGEN containing a ribonucleic acid sequence that is complementary to a strand of a DNA target sequence. This complementary sequence is referred to herein as a "guide sequence" or "variable targeting domain" sequence. Examples of suitable RNA components herein include crRNA and guide RNA. Also, an RNA component herein does not have a 5'-cap.

The term "CRISPR RNA" (crRNA) herein refers to an RNA sequence that can form a complex with one or more Cas proteins (e.g., Cas9) and provides DNA binding specificity to the complex. A crRNA provides DNA binding specificity since it contains "guide sequence" ("variable targeting domain" [VT]) that is complementary to a strand of a DNA target sequence. A crRNA further comprises a "repeat sequence" ("tracr RNA mate sequence") encoded by a repeat region of the CRISPR locus from which the crRNA was derived. A repeat sequence of a crRNA can anneal to sequence at the 5'-end of a tracrRNA. crRNA in native CRISPR systems is derived from a "pre-crRNA" transcribed from a CRISPR locus. A pre-crRNA comprises spacer regions and repeat regions; spacer regions contain unique sequence complementary to a DNA target site sequence. Pre-crRNA in native systems is processed to multiple different crRNAs, each with a guide sequence along with a portion of repeat sequence. CRISPR systems utilize crRNA, for example, for DNA targeting specificity.

The term "trans-activating CRISPR RNA" (tracrRNA) herein refers to a non-coding RNA used in type II CRISPR systems, and contains, in the 5'-to-3' direction, (i) a sequence that anneals with the repeat region of CRISPR type II crRNA and (ii) a stem loop-containing portion (Deltcheva et al., *Nature* 471:602-607).

The terms "guide RNA" (gRNA) and "single guide RNA" (sgRNA) are used interchangeably herein. A gRNA herein may refer to a chimeric sequence containing a crRNA operably linked to a tracrRNA. Alternatively, a gRNA can refer to a synthetic fusion of a crRNA and a tracrRNA, for example. Jinek et al. (*Science* 337:816-821) disclose some gRNA features. A gRNA can also be characterized in terms of having a guide sequence (variable targeting domain) followed by a Cas endonuclease recognition (CER) domain [WO2015026883, published on 02-26-2015, U.S. Patent Application US 2015-0082478 A1, published on Mar. 19, 2015 and US 2015-0059010 A1, published on Feb. 26, 2015, all are hereby incorporated in its entirety by reference]. A CER domain comprises a tracrRNA mate sequence followed by a tracrRNA sequence.

The terms "target site sequence", "target site", "target sequence", "target DNA", "DNA target sequence", "target locus", "genomic target site", "genomic target sequence", "genomic target locus", and "protospacer" are used interchangeably herein. A target site sequence refers to a polynucleotide sequence on a chromosome, episome, or any other DNA molecule in the genome of a non-conventional yeast to which an RGEN herein can recognize, bind to, and optionally nick or cleave. A target site can be (i) an endogenous/native site in the yeast, (ii) heterologous to the yeast and therefore not be naturally occurring in the genome, or (iii) found in a heterologous genomic location compared to where it natively occurs.

A target site sequence herein is at least 13 nucleotides in length and has a strand with sufficient complementarity to a guide sequence (of a crRNA or gRNA) to be capable of hybridizing with the guide sequence and direct sequence-specific binding of a Cas protein or Cas protein complex to the target sequence (if a suitable PAM is adjacent to the target sequence in certain embodiments). A cleavage/nick site (applicable with a endonucleolytic or nicking Cas) can be within the target sequence (e.g., using a Cas9) or a cleavage/nick site could be outside of the target sequence (e.g., using a Cas9 fused to a heterologous endonuclease domain such as one derived from a FokI enzyme).

An "artificial target site" or "artificial target sequence" herein refers to a target sequence that has been introduced into the genome of a non-conventional yeast. An artificial target sequence in some embodiments can be identical in sequence to a native target sequence in the genome of the yeast, but be located at a different position (a heterologous position) in the genome or it can different from the native target sequence if located at the same position in the genome of the yeast.

An "episome" herein refers to a DNA molecule that can exist in a yeast cell autonomously (can replicate and pass on to daughter cells) apart from the chromosomes of the yeast cell. Episomal DNA can be either native or heterologous to a yeast cell. Examples of native episomes herein include mitochondrial DNA (mtDNA). Examples of heterologous episomes herein include plasmids and yeast artificial chromosomes (YACs).

A "protospacer adjacent motif" (PAM) herein refers to a short sequence that is recognized by an RGEN herein. The sequence and length of a PAM herein can differ depending on the Cas protein or Cas protein complex used, but are typically 2, 3, 4, 5, 6, 7, or 8 nucleotides long, for example.

The terms "5'-cap" and "7-methylguanylate ($m^7G$) cap" are used interchangeably herein. A 7-methylguanylate residue is located on the 5' terminus of messenger RNA (mRNA) in eukaryotes. RNA polymerase II (Pol II) transcribes mRNA in eukaryotes. Messenger RNA capping occurs generally as follows: The most terminal 5' phosphate group of the mRNA transcript is removed by RNA terminal phosphatase, leaving two terminal phosphates. A guanosine monophosphate (GMP) is added to the terminal phosphate of the transcript by a guanylyl transferase, leaving a 5'-5' triphosphate-linked guanine at the transcript terminus. Finally, the 7-nitrogen of this terminal guanine is methylated by a methyl transferase.

The terminology "not having a 5'-cap" herein is used to refer to RNA having, for example, a 5'-hydroxyl group instead of a 5'-cap. Such RNA can be referred to as "uncapped RNA", for example. Uncapped RNA can better accumulate in the nucleus following transcription, since 5'-capped RNA is subject to nuclear export. One or more RNA components herein are uncapped.

The terms "ribozyme" and "ribonucleic acid enzyme" are used interchangeably herein. A ribozyme refers to one or more RNA sequences that form secondary, tertiary, and/or quaternary structure(s) that can cleave RNA at a specific site. A ribozyme includes a "self-cleaving ribozyme" that is capable of cleaving RNA at a cis-site relative to the ribozyme sequence (i.e., auto-catalytic, or self-cleaving). The general nature of ribozyme nucleolytic activity has been described (e.g., Lilley, *Biochem. Soc. Trans.* 39:641-646). A "hammerhead ribozyme" (HHR) herein may comprise a small catalytic RNA motif made up of three base-paired stems and a core of highly conserved, non-complementary nucleotides that are involved in catalysis. Pley et al. (*Nature* 372:68-74) and Hammann et al. (*RNA* 18:871-885), which are incorporated herein by reference, disclose hammerhead ribozyme structure and activity. A hammerhead ribozyme herein may comprise a "minimal hammerhead" sequence as disclosed by Scott et al. (*Cell* 81:991-1002, incorporated herein by reference), for example.

In one embodiment of the disclosure, the method comprises a method of targeting an RNA-guided endonuclease (RGEN) to a target site sequence on a chromosome or episome in a non-conventional yeast, said method comprising providing to said yeast a first recombinant DNA construct comprising a DNA sequence encoding a Cas endonuclease, and at least a second recombinant DNA construct comprising a DNA sequence encoding a ribozyme upstream of an RNA component, wherein the RNA transcribed from the second recombinant DNA construct autocatalytically removes the ribozyme to yield said RNA component , wherein the RNA component and the Cas9 endonuclease can form an RGEN that can bind to all or part of the target site sequence.

In one embodiment of the disclosure the non-conventional yeast comprises a polynucleotide sequence comprising a promoter operably linked to at least one nucleotide sequence, wherein said nucleotide sequence comprises a DNA sequence encoding a ribozyme upstream of a DNA sequence encoding an RNA component, wherein said RNA component comprises a variable targeting domain complementary to a target site sequence on a chromosome or episome in the yeast, wherein the RNA component can form a RNA-guided endonuclease (RGEN), wherein said RGEN can bind to all or part of the target site sequence, wherein the RNA transcribed from the nucleotide sequence autocatalytically removes the ribozyme to yield said RNA component, wherein said RNA component does not have a 5' cap.

A ribozyme also includes a ribozyme that cleaves 5' of its own sequence removing any preceding transcript but leaving the ribozyme sequence intact.

In one embodiment of the disclosure the non-conventional yeast comprises a polynucleotide sequence comprising a promoter operably linked to at least one nucleotide sequence, wherein said nucleotide sequence comprises a DNA sequence encoding a ribozyme upstream of a DNA sequence encoding an RNA component, wherein said RNA component comprises a variable targeting domain complementary to a target site sequence on a chromosome or episome in the yeast, wherein the RNA component can form a RNA-guided endonuclease (RGEN), wherein said RGEN can bind to all or part of the target site sequence, wherein the RNA transcribed from the nucleotide sequence autocatalytically removes the ribozyme to yield said RNA component, wherein the RNA transcribed from the nucleotide sequence does not autocatalytically removes the ribozyme to yield a ribozyme-RNA component fusion molecule without a 5' cap.

The terms "targeting", "gene targeting", "DNA targeting", "editing", "gene editing" and "DNA editing" are used interchangeably herein. DNA targeting herein may be the specific introduction of an indel, knock-out, or knock-in at a particular DNA sequence, such as in a chromosome or episome of a non-conventional yeast. In general, DNA targeting can be performed herein by cleaving one or both strands at a specific DNA sequence in a non-conventional yeast with a Cas protein associated with a suitable RNA component. Such DNA cleavage, if a double-strand break (DSB), can prompt NHEJ processes which can lead to indel formation at the target site. Also, regardless of whether the cleavage is a single-strand break (SSB) or DSB, HR processes can be prompted if a suitable donor DNA polynucleotide is provided at the DNA nick or cleavage site. Such an HR process can be used to introduce a knock-out or knock-in at the target site, depending on the sequence of the donor DNA polynucleotide.

Alternatively, DNA targeting herein can refer to specific association of a Cas/RNA component complex herein to a target DNA sequence, where the Cas protein does or does not cut a DNA strand (depending on the status of the Cas protein's endonucleolytic domains).

The term "indel" herein refers to an insertion or deletion of nucleotide bases in a target DNA sequence in a chromosome or episome. Such an insertion or deletion may be of 1, 2, 3, 4, 5, 6, 7, 8, 9, 10, or more bases, for example. An indel in certain embodiments can be even larger, at least about 20, 30, 40, 50, 60, 70p, 80, 90, or 100 bases If an indel is introduced within an open reading frame (ORF) of a gene, oftentimes the indel disrupts wild type expression of protein encoded by the ORF by creating a frameshift mutation.

The terms "knock-out", "gene knock-out" and "genetic knock-out" are used interchangeably herein. A knock-out represents a DNA sequence of a non-conventional yeast herein that has been rendered partially or completely inoperative by targeting with a Cas protein; such a DNA sequence prior to knock-out could have encoded an amino acid sequence, or could have had a regulatory function (e.g., promoter), for example. A knock-out may be produced by an indel (by NHEJ), or by specific removal of sequence that reduces or completely destroys the function of sequence at or near the targeting site. A knocked out DNA polynucleotide sequence herein can alternatively be characterized as being partially or totally disrupted or downregulated, for example.

In one embodiment, the disclosure concerns a non-conventional yeast comprising a Cas9 endonuclease and a polynucleotide sequence comprising a promoter operably linked to at least one nucleotide sequence, wherein said nucleotide sequence comprises a DNA sequence encoding a ribozyme upstream of a DNA sequence encoding an RNA component, wherein said RNA component comprises a variable targeting domain complementary to a target site sequence on a chromosome or episome in the yeast, wherein the RNA component can form a RNA-guided endonuclease (RGEN) with the Cas endonuclease, wherein said RGEN can bind to the target site sequence. The Cas9 endonuclease can be introduced in the yeast as a protein or can be introduced via a recombinant DNA construct. The Cas9 endonuclease can be expressed in a stable or transient manner by any method known in the art.

The terms "knock-in", "gene knock-in" and "genetic knock-in" are used interchangeably herein. A knock-in represents the replacement or insertion of a DNA sequence at a specific DNA sequence in a non-conventional yeast by targeting with a Cas protein. Examples of knock-ins are a specific insertion of a heterologous amino acid coding sequence in a coding region of a gene, or a specific insertion of a transcriptional regulatory element in a genetic locus.

The terms "donor polynucleotide", "donor DNA", "targeting polynucleotide" and "targeting DNA" are used interchangeably herein. A donor polynucleotide refers to a DNA sequence that comprises at least one sequence that is homologous to a sequence at or near a DNA target site (e.g., a sequence specifically targeted by a Cas protein herein). A donor DNA polynucleotide that includes a polynucleotide that comprises at least one nucleotide modification when compared to the nucleotide sequence to be edited, is also referred to as a "polynucleotide modification template", "polynucleotide modification template DNA" or "template DNA". A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

A "homologous sequence" within a donor polynucleotide herein can comprise or consist of a sequence of at least about 25 nucleotides that have 100% identity with a sequence at or near a target site, or at least about 95%, 96%, 97%, 98%, or 99% identity with a sequence at or near a target site.

In certain embodiments, a donor DNA polynucleotide can have two homologous sequences separated by a sequence that is heterologous to sequence at a target site. These two homologous sequences of such a donor polynucleotide can be referred to as "homology arms", which flank the heterologous sequence. HR between a target site and a donor polynucleotide with two homology arms typically results in the replacement of a sequence at the target site with the heterologous sequence of the donor polynucleotide (target site sequence located between DNA sequences homologous to the homology arms of the donor polynucleotide is replaced by the heterologous sequence of the donor polynucleotide). In a donor polynucleotide with two homology arms, the arms can be separated by 1 or more nucleotides (i.e., the heterologous sequence in the donor polynucleotide can be at least 1 nucleotide in length). Various HR procedures that can be performed in a non-conventional yeast herein are disclosed, for example, in *DNA Recombination: Methods and Protocols:* 1st Edition (H. Tsubouchi, Ed., Springer-Verlag, New York, 2011), which is incorporated herein by reference.

In one embodiment, the donor DNA construct comprises a polynucleotide of Interest to be inserted into the target site of a Cas endonuclease, wherein the donor DNA construct further comprises a first and a second region of homology that flank the polynucleotide of Interest. The first and second regions of homology of the donor DNA share homology to a first and a second genomic region, respectively, present in or flanking the target site of the plant genome.

The terms "percent by volume", "volume percent", "vol %" and "v/v %" are used interchangeably herein. The percent by volume of a solute in a solution can be determined using the formula: [(volume of solute)/(volume of solution)]×100%.

The terms "percent by weight", "weight percentage (wt %)" and "weight-weight percentage (% w/w)" are used interchangeably herein. Percent by weight refers to the percentage of a material on a mass basis as it is comprised in a composition, mixture, or solution.

The terms "polynucleotide", "polynucleotide sequence", and "nucleic acid sequence" are used interchangeably herein. These terms encompass nucleotide sequences and the like. A polynucleotide may be a polymer of DNA or RNA that is single- or double-stranded, that optionally contains synthetic, non-natural or altered nucleotide bases. A polynucleotide may be comprised of one or more segments of cDNA, genomic DNA, synthetic DNA, or mixtures thereof. Nucleotides (ribonucleotides or deoxyribonucleotides) can be referred to by a single letter designation as follows: "A" for adenylate or deoxyadenylate (for RNA or DNA, respectively), "C" for cytidylate or deoxycytidylate (for RNA or DNA, respectively), "G" for guanylate or deoxyguanylate (for RNA or DNA, respectively), "U" for uridylate (for RNA), "T" for deoxythymidylate (for DNA), "R" for purines (A or G), "Y" for pyrimidines (C or T), "K" for G or T, "H" for A or C or T, "I" for inosine, "W" for A or T, and "N" for any nucleotide (e.g., N can be A, C, T, or G, if referring to a DNA sequence; N can be A, C, U, or G, if referring to an RNA sequence). Any RNA sequence (e.g., crRNA, tracrRNA, gRNA) disclosed herein may be encoded by a suitable DNA sequence.

The term "isolated" as used herein refers to a polynucleotide or polypeptide molecule that has been completely or partially purified from its native source. In some instances, the isolated polynucleotide or polypeptide molecule is part of a greater composition, buffer system or reagent mix. For example, the isolated polynucleotide or polypeptide molecule can be comprised within a cell or organism in a heterologous manner.

The term "gene" as used herein refers to a DNA polynucleotide sequence that expresses an RNA (RNA is transcribed from the DNA polynucleotide sequence) from a coding region, which RNA can be a messenger RNA (encoding a protein) or a non-protein-coding RNA (e.g., a crRNA, tracrRNA, or gRNA herein). A gene may refer to the coding region alone, or may include regulatory sequences upstream and/or downstream to the coding region (e.g., promoters, 5'-untranslated regions, 3'-transcription terminator regions). A coding region encoding a protein can alternatively be referred to herein as an "open reading frame" [ORF]. A gene that is "native" or "endogenous" refers to a gene as found in nature with its own regulatory sequences; such a gene is located in its natural location in the genome of a host cell. A "chimeric" gene refers to any gene that is not a native gene, comprising regulatory and coding sequences that are not found together in nature (i.e., the regulatory and coding regions are heterologous with each other). Accordingly, a chimeric gene may comprise regulatory sequences and coding sequences that are derived from different sources, or regulatory sequences and coding sequences derived from the same source, but arranged in a manner different than that found in nature. A "foreign" or "heterologous" gene refers to a gene that is introduced into the host organism by gene transfer. Foreign genes can comprise native genes inserted into a non-native organism, native genes introduced into a new location within the native host, or chimeric genes. The polynucleotide sequences in certain embodiments disclosed herein are heterologous. A "transgene" is a gene that has been introduced into the genome by a transformation procedure. A "codon-optimized" open reading frame has its frequency of codon usage designed to mimic the frequency of preferred codon usage of the host cell.

A native amino acid sequence or polynucleotide sequence is naturally occurring, whereas a non-native amino acid sequence or polynucleotide sequence does not occur in nature.

"Regulatory sequences" as used herein refer to nucleotide sequences located upstream of a gene's transcription start site (e.g., promoter), 5' untranslated regions, and 3' non-coding regions, and which may influence the transcription, processing or stability, or translation of an RNA transcribed from the gene. Regulatory sequences herein may include promoters, enhancers, silencers, 5' untranslated leader sequences, introns, polyadenylation recognition sequences, RNA processing sites, effector binding sites, stem-loop structures, and other elements involved in regulation of gene expression. One or more regulatory elements herein may be heterologous to a coding region herein.

A "promoter" as used herein refers to a DNA sequence capable of controlling the transcription of RNA from a gene. In general, a promoter sequence is upstream of the transcription start site of a gene. Promoters may be derived in their entirety from a native gene, or be composed of different elements derived from different promoters found in nature, or even comprise synthetic DNA segments. Promoters that cause a gene to be expressed in most cell types at most times are commonly referred to as "constitutive promoters". One or more promoters herein may be heterologous to a coding region herein.

A "strong promoter" as used herein refers to a promoter that can direct a relatively large number of productive initiations per unit time, and/or is a promoter driving a higher level of gene transcription than the average transcription level of the genes in the yeast.

The terms "3' non-coding sequence", "transcription terminator" and "terminator" as used herein refer to DNA sequences located downstream of a coding sequence. This includes polyadenylation recognition sequences and other sequences encoding regulatory signals capable of affecting mRNA processing or gene expression.

The term "cassette" as used herein refers to a promoter operably linked to a sequence encoding a protein or non-protein-coding RNA. A cassette may optionally be operably linked to a 3' non-coding sequence.

The terms "upstream" and "downstream" as used herein with respect to polynucleotides refer to "5' of" and "3' of", respectively.

The term "expression" as used herein refers to (i) transcription of RNA (e.g., mRNA or a non-protein coding RNA such as crRNA, tracrRNA or gRNA) from a coding region, or (ii) translation of a polypeptide from mRNA.

When used to describe the expression of a gene or polynucleotide sequence, the terms "down-regulation", "disruption", "inhibition", "inactivation", and "silencing" are used interchangeably herein to refer to instances when the transcription of the polynucleotide sequence is reduced or eliminated. This results in the reduction or elimination of RNA transcripts from the polynucleotide sequence, which results in a reduction or elimination of protein expression derived from the polynucleotide sequence (if the gene comprised an ORF). Alternatively, down-regulation can refer to instances where protein translation from transcripts produced by the polynucleotide sequence is reduced or eliminated. Alternatively still, down-regulation can refer to instances where a protein expressed by the polynucleotide sequence has reduced activity. The reduction in any of the above processes (transcription, translation, protein activity) in a cell can be by about 40%, 50%, 60%, 70%, 80%, 90%, 95%, or 100% relative to the transcription, translation, or protein activity of a suitable control cell. Down-regulation can be the result of a targeting event as disclosed herein (e.g., indel, knock-out), for example.

The terms "control cell" and "suitable control cell" are used interchangeably herein and may be referenced with respect to a cell in which a particular modification (e.g., over-expression of a polynucleotide, down-regulation of a polynucleotide) has been made (i.e., an "experimental cell"). A control cell may be any cell that does not have or does not express the particular modification of the experimental cell. Thus, a control cell may be an untransformed wild type cell or may be genetically transformed but does not express the genetic transformation. For example, a control cell may be a direct parent of the experimental cell, which direct parent cell does not have the particular modification that is in the experimental cell. Alternatively, a control cell may be a parent of the experimental cell that is removed by one or more generations. Alternatively still, a control cell may be a sibling of the experimental cell, which sibling does not comprise the particular modification that is present in the experimental cell.

The term "increased" as used herein may refer to a quantity or activity that is at least 1%, 2%, 3%, 4%, 5%, 6%, 7%, 8%, 9%, 10%, 11%, 12%, 13%, 14%, 15%, 16%, 17%, 18%, 19% or 20% more than the quantity or activity for which the increased quantity or activity is being compared. The terms "increased", "greater than", and "improved" are used interchangeably herein. The term "increased" can be used to characterize the expression of a polynucleotide encoding a protein, for example, where "increased expression" can also mean "over-expression".

The term "operably linked" as used herein refers to the association of two or more nucleic acid sequences such that that the function of one is affected by the other. For example, a promoter is operably linked with a coding sequence when it is capable of affecting the expression of that coding sequence. That is, the coding sequence is under the transcriptional control of the promoter. Coding sequences can be operably linked to regulatory sequences, for example. Also, for example, a crRNA can be operably linked (fused to) a tracrRNA herein such that the tracrRNA mate sequence of the crRNA anneals with 5' sequence of the tracrRNA. Such operable linkage may comprise a suitable loop-forming sequence such as GAAA (SEQ ID NO:43), CAAA (SEQ ID NO:44), or AAAG (SEQ ID NO:45).

The term "recombinant" as used herein refers to an artificial combination of two otherwise separated segments of sequence, e.g., by chemical synthesis or by the manipulation of isolated segments of nucleic acids by genetic engineering techniques. The terms "recombinant", "transgenic", "transformed", "engineered" or "modified for exogenous gene expression" are used interchangeably herein.

Methods for preparing recombinant constructs/vectors herein (e.g., a DNA polynucleotide encoding a ribozyme-RNA component cassette herein, or a DNA polynucleotide encoding a Cas protein herein) can follow standard recombinant DNA and molecular cloning techniques as described by J. Sambrook and D. Russell (*Molecular Cloning: A Laboratory Manual,* 3rd Edition, Cold Spring Harbor Laboratory Press, Cold Spring Harbor, N.Y., 2001); T. J. Silhavy et al. (*Experiments with Gene Fusions*, Cold Spring Harbor Laboratory Press, Cold Spring Harbor, N.Y., 1984); and F. M. Ausubel et al. (*Short Protocols in Molecular Biology,* 5th Ed. Current Protocols, John Wiley and Sons, Inc., NY, 2002).

The term "transformation" as used herein refers to the transfer of a nucleic acid molecule into a host organism or host cell. For example, the nucleic acid molecule may be one that replicates autonomously in a cell, or that integrates into the genome of the host organism/cell, or that exists transiently in a cell without replicating or integrating. Non-limiting examples of nucleic acid molecules suitable for transformation are disclosed herein, such as plasmids and linear DNA molecules. Host organisms/cells (e.g., non-conventional yeast herein) containing the transformed nucleic acid fragments can be referred to as "transgenic", "recombinant", "transformed", or as "transformants".

The terms "sequence identity" or "identity" as used herein with respect to polynucleotide or polypeptide sequences refer to the nucleic acid residues or amino acid residues in two sequences that are the same when aligned for maximum correspondence over a specified comparison window. Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. It would be understood that, when calculating sequence identity between a DNA sequence and an RNA sequence, T residues of the DNA sequence align with, and can be considered "identical" with, U residues of the RNA sequence. For purposes of determining percent complementarity of first and second polynucleotides, one can obtain this by determining (i) the percent identity between the first polynucleotide and the complement sequence of the second polynucleotide (or vice versa), for example, and/or (ii) the percentage of bases between the first and second polynucleotides that would create canonical Watson and Crick base pairs.

The Basic Local Alignment Search Tool (BLAST) algorithm, which is available online at the National Center for Biotechnology Information (NCBI) website, may be used, for example, to measure percent identity between or among two or more of the polynucleotide sequences (BLASTN algorithm) or polypeptide sequences (BLASTP algorithm) disclosed herein. Alternatively, percent identity between sequences may be performed using a Clustal algorithm (e.g., ClustalW or ClustalV). For multiple alignments using a Clustal method of alignment, the default values may correspond to GAP PENALTY=10 and GAP LENGTH PENALTY=10. Default parameters for pairwise alignments and calculation of percent identity of protein sequences using a Clustal method may be KTUPLE=1, GAP PENALTY=3, WINDOW=5 and DIAGONALS SAVED=5. For nucleic acids, these parameters may be KTUPLE=2, GAP PENALTY=5, WINDOW=4 and DIAGONALS SAVED=4. Alternatively still, percent identity between sequences may be performed using an EMBOSS algorithm (e.g., needle) with parameters such as GAP OPEN=10, GAP EXTEND=0.5, END GAP PENALTY=false, END GAP OPEN=10, END GAP EXTEND=0.5 using a BLOSUM matrix (e.g., BLOSUM62).

Herein, a first sequence that is “complementary” to a second sequence can alternatively be referred to as being in the “antisense” orientation with the second sequence.

Various polypeptide amino acid sequences and polynucleotide sequences are disclosed herein as features of certain embodiments of the disclosed invention. Variants of these sequences that are at least about 70-85%, 85-90%, or 90%-95% identical to the sequences disclosed herein can be used. Alternatively, a variant amino acid sequence or polynucleotide sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence has the same function/activity of the disclosed sequence, or at least about 80%, 81%, 82%, 83%, 84%, 85%, 86%, 87%, 88%, 89%, 90%, 91%, 92%, 93%, 94%, 95%, 96%, 97%, 98%, or 99% of the function/activity of the disclosed sequence.

All the amino acid residues disclosed herein at each amino acid position of Cas9 proteins herein are examples. Given that certain amino acids share similar structural and/or charge features with each other (i.e., conserved), the amino acid at each position in a Cas9 can be as provided in the disclosed sequences or substituted with a conserved amino acid residue (“conservative amino acid substitution”) as follows:

1. The following small aliphatic, nonpolar or slightly polar residues can substitute for each other: Ala (A), Ser (S), Thr (T), Pro (P), Gly (G);
2. The following polar, negatively charged residues and their amides can substitute for each other: Asp (D), Asn (N), Glu (E), Gln (Q);
3. The following polar, positively charged residues can substitute for each other: His (H), Arg (R), Lys (K);
4. The following aliphatic, nonpolar residues can substitute for each other: Ala (A), Leu (L), Ile (I), Val (V), Cys (C), Met (M); and
5. The following large aromatic residues can substitute for each other: Phe (F), Tyr (Y), Trp (W).

As shown below in Example 1, performing Cas9-mediated DNA targeting in non-conventional yeast such as *Yarrowia lipolytica* using Pol III promoter-transcribed gRNA has proven to be difficult. Other means for producing RNA components for Cas9 are therefore of interest for providing Cas9-mediated DNA targeting in non-conventional yeast.

Embodiments of the disclosed invention concern a non-conventional yeast comprising at least one RNA-guided endonuclease (RGEN) comprising at least one RNA component that does not have a 5'-cap. This uncapped RNA component comprises a sequence complementary to a target site sequence in a chromosome or episome in the yeast. The RGEN can bind to, and optionally cleave, all or part of a target site sequence.

Significantly, RGEN-mediated DNA targeting occur in these non-conventional yeast, as manifested by indel formation or increased levels of homologous recombination (HR) between the RGEN target site sequence and exogenously supplied donor DNA sequence. Prior to the instant disclosure, non-conventional yeast were generally intractable to gene targeting by HR, typically relying on random, infrequent DNA breaks at a target site to prompt its HR with a donor DNA. This is due to non-conventional yeast having low HR activity and instead favoring non-homologous end-joining (NHEJ) activity. Thus, genetic targeting by HR in non-conventional yeast may now be just as feasible as it has been in conventional yeasts such as S. cerevisiae that favor HR over NHEJ processes. While not wishing to be bound to any theory, it is believed that providing at least one RNA component without a 5'-cap in a non-conventional yeast cell leads to better accumulation of the RNA component in the nucleus, where it can participate in RGEN-mediated DNA targeting.

RNA processing tools, such as a Csy4 (Cas6)-based RNA processing tool have been described (Nissim et al. 2014 .Molecular Cell 54:698-710). Csy4 binds pre-crRNA stem-loop repeats and specifically cleaves its cognate substrate to produce mature crRNA’s that contain a spacer sequence flanked by fragments of the repeat (Sternberg et al. 2012. RNA,18(4):661-72). Disclosed herein (Example 12) is the use of a Csy4 to process a guide RNA such that it results in an RNA component (guide RNA) that does not have a 5'cap, wherein the RNA component can form an RGEN that is can bind to and cleave a target site in the genome of a non-conventional yeast.

A non-conventional yeast herein is not a “conventional” (“model”) yeast such as a *Saccharomyces* (e.g., *S. cerevisiae*, which is also known as budding yeast, baker’s yeast, and/or brewer’s yeast) or *Schizosaccharomyces* (e.g., *S. pombe*, which is also known as fission yeast) species. Conventional yeasts in certain embodiments are yeast that favor HR DNA repair processes over repair processes mediated by NHEJ.

Non-conventional yeast in certain embodiments can be yeast that favor NHEJ DNA repair processes over repair processes mediated by HR. Conventional yeasts such as *Saccharomyces cerevisiae* and *Schizosaccharomyces pombe* typically exhibit specific integration of donor DNA with short flanking homology arms (30-50 bp) with efficiencies routinely over 70%, whereas non-conventional yeasts such as *Pichia pastoris, Hansenula polymorpha, Yarrowia lipolytica, Pichia stipitis* and *Kluyveromyces lactis* usually show specific integration with similarly structured donor DNA at efficiencies of less than 1% (Chen et al., PLoS ONE 8:e57952). Thus, a preference for HR processes can be gauged, for example, by transforming yeast with a suitable donor DNA and determining the degree to which it is specifically recombined with a genomic site predicted to be targeted by the donor DNA. A preference for NHEJ (or low preference for HR), for example, would be manifest if such an assay yielded a high degree of random integration of the donor DNA in the yeast genome. Assays for determining the rate of specific (HR-mediated) and/or random (NHEJ-mediated) integration of DNA in yeast are known in the art (e.g., Ferreira and Cooper, *Genes Dev.* 18:2249-2254; Corrigan et al., PLoS ONE 8:e69628; Weaver et al., *Proc. Natl. Acad. Sci. U.S.A.* 78:6354-6358; Keeney and Boeke, *Genetics* 136:849-856).

Given their low level of HR activity, non-conventional yeast herein can (i) exhibit a rate of specific targeting by a suitable donor DNA having 30-50 bp flanking homology arms of less than about 1%, 2%, 3%, 4%, 5%, 6%, 7%, or 8%, for example, and/or (ii) exhibit a rate of random integration of the foregoing donor DNA of more than about 65%, 66%, 67%, 68%, 69%, 70%, 71%, 72%, 73%, 74%, or 75%, for example. These rates of (i) specific targeting and/or (ii) random integration of a suitable donor DNA can characterize a non-conventional yeast as it exists before being provided an RGEN as disclosed herein. An aim for providing an RGEN to a non-conventional yeast in certain embodiments is to create site-specific DNA single-strand breaks (SSB) or double-strand breaks (DSB) for biasing the yeast toward HR at the specific site. Thus, a non-conventional yeast comprising a suitable RGEN herein typically should exhibit an increased rate of HR with a particular donor DNA. Such an increased rate can be at least about 2-, 3-, 4-, 5-, 6-, 7-, 8-, 9-, or 10-fold higher than the rate of HR in a suitable control (e.g., same non-conventional yeast transformed with the same donor DNA, but lacking a suitable RGEN).

A non-conventional yeast in certain aspects herein can be one that reproduces asexually (anamorphic) or sexually (teleomorphic). While non-conventional yeast herein typically exist in unicellular form, certain types of these yeast may optionally be able to form pseudohyphae (strings of connected budding cells). In still further aspects, a non-conventional yeast may be haploid or diploid, and/or may have the ability to exist in either of these ploidy forms.

A non-conventional yeast herein can be cultivated following any means known in the art, such as described in *Non-Conventional Yeasts in Genetics, Biochemistry and Biotechnology: Practical Protocols* (K. Wolf, K. D. Breunig, G. Barth, Eds., Springer-Verlag, Berlin, Germany, 2003), *Yeasts in Natural and Artificial Habitats* (J. F. T. Spencer, D. M. Spencer, Eds., Springer-Verlag, Berlin, Germany, 1997), and/or *Yeast Biotechnology: Diversity and Applications* (T. Satyanarayana, G. Kunze, Eds., Springer, 2009), all of which are incorporated herein by reference.

Non-limiting examples of non-conventional yeast herein include yeasts of the following genera: *Yarrowia, Pichia, Schwanniomyces, Kluyveromyces, Arxula, Trichosporon, Candida, Ustilago, Torulopsis, Zygosaccharomyces, Trigonopsis, Cryptococcus, Rhodotorula, Phaffia, Sporobolomyces*, and *Pachysolen*. A suitable example of a *Yarrowia* species is *Y. lipolytica*. Suitable examples of Pichia species include *P. pastoris, P. methanolica, P. stipitis, P. anomala* and *P. angusta*. Suitable examples of *Schwanniomyces* species include *S. castellii, S. alluvius, S. hominis, S. occidentalis, S. capriottii, S. etchellsii, S. polymorphus, S. pseudopolymorphus, S. vanrijiae* and *S. yamadae*. Suitable examples of *Kluyveromyces* species include *K. lactis, K. marxianus, K. fragilis, K. drosophilarum, K. thermotolerans, K. phaseolosporus, K. vanudenii, K. waltii, K. africanus* and *K. polysporus*. Suitable examples of *Arxula* species include *A. adeninivorans* and *A. terrestre*. Suitable examples of *Trichosporon* species include *T. cutaneum, T. capitatum, T. inkin* and *T. beemeri*. Suitable examples of *Candida* species include *C. albicans, C. ascalaphidarum, C. amphixiae, C. antarctica, C. argentea, C. atlantica, C. atmosphaerica, C. blattae, C. bromeliacearum, C. carpophila, C. carvajalis, C. cerambycidarum, C. chauliodes, C. corydali, C. dosseyi, C. dubliniensis, C. ergatensis, C. fructus, C. glabrata, C. fermentati, C. guiffiermondii, C. haemulonii, C. insectamens, C. insectorum, C. intermedia, C. jeffresii, C. kefyr, C. keroseneae, C. krusei, C. lusitaniae, C. lyxosophila, C. maltosa, C. marina, C. membranifaciens, C. milleri, C. mogii, C. oleophila, C. oregonensis, C. parapsilosis, C. quercitrusa, C. rugosa, C. sake, C. shehatea, C. temnochilae, C. tenuis, C. theae, C. tolerans, C. tropicalis, C. tsuchiyae, C. sinolaborantium, C. sojae, C. subhashii, C. viswanathii, C. utilis, C. ubatubensis* and *C. zemplinina*. Suitable examples of *Ustilago* species include *U. avenae, U. esculenta, U. hordei, U. maydis, U. nuda* and *U. tritici*. Suitable examples of *Torulopsis* species include *T. geochares, T. azyma, T. glabrata and T. candida*. Suitable examples of *Zygosaccharomyces* species include *Z. bailii, Z. bisporus, Z. cidri, Z. fermentati, Z. florentinus, Z. kombuchaensis, Z. lentus, Z. mellis, Z. microellipsoides, Z. mrakii, Z. pseudorouxii* and *Z. rouxii*. Suitable examples of *Trigonopsis* species include *T. variabilis*. Suitable examples of *Cryptococcus* species include *C. laurentii, C. albidus, C. neoformans, C. gattii, C. uniguttulatus, C. adeliensis, C. aerius, C. albidosimilis, C. antarcticus, C. aquaticus, C. ater, C. bhutanensis, C. consortionis, C. curvatus, C. phenolicus, C. skinneri, C. terreus* and *C. vishniacci*. Suitable examples of *Rhodotorula* species include *R. acheniorum, R. tula, R. acuta, R. americana, R. araucariae, R. arctica, R. armeniaca, R. aurantiaca, R. auriculariae, R. bacarum, R. benthica, R. biourgei, R. bogoriensis, R. bronchialis, R. buffonii, R. calyptogenae, R. chungnamensis, R. cladiensis, R. coraffina, R. cresolica, R. crocea, R. cycloclastica, R. dairenensis, R. diffluens, R. evergladiensis, R. ferulica, R. foliorum, R. fragaria, R. fujisanensis, R. futronensis, R. gelatinosa, R. glacialis, R. glutinis, R. gracilis, R. graminis, R. grinbergsii, R. himalayensis, R. hinnulea, R. histolytica, R. hylophila, R. incarnata, R. ingeniosa, R. javanica, R. koishikawensis, R. lactosa, R. lameffibrachiae, R. laryngis, R. lignophila, R. lini, R. longissima, R. ludwigii, R. lysinophila, R. marina, R. martyniae-fragantis, R. matritensis, R. meli, R. minuta, R. mucilaginosa, R. nitens, R. nothofagi, R. oryzae, R. pacifica, R. pallida, R. peneaus, R. philyla, R. phylloplana, R. pilatii, R. pilimanae, R. pinicola, R. plicata, R. polymorpha, R. psychrophenolica, R. psychrophila, R. pustula, R. retinophila, R. rosacea, R. rosulata, R. rubefaciens, R. rubella, R. rubescens, R. rubra, R. rubrorugosa, R. rufula, R. rutila, R. sanguines, R. sanniei, R. sartoryi, R. silvestris, R. simplex, R. sinensis, R. slooffiae, R. sonckii, R. straminea, R. subericola, R. suganii, R. taiwanensis, R. taiwaniana, R. terpenoidalis, R. terrea, R. texensis, R. tokyoensis, R. ulzamae, R. vanillica, R. vuilleminii, R. yarrowii, R. yunnanensis* and *R. zsoltii*. Suitable examples of Phaffia species include P. rhodozyma. Suitable examples of *Sporobolomyces* species include *S. alborubescens, S. bannaensis, S. beijingensis, S. bischofiae, S. clavatus, S. coprosmae, S. coprosmicola, S. corallinus, S. dimmenae, S. dracophylli, S. elongatus, S. gracilis, S. inositophilus, S. johnsonii, S. koalae, S. magnisporus, S. novozealandicus, S. odorus, S. patagonicus, S. productus, S. roseus, S. sasicola, S. shibatanus, S. singularis, S. subbrunneus, S. symmetricus, S. syzygii, S. taupoensis, S. tsugae, S. xanthus* and *S. yunnanensis*. Suitable examples of *Pachysolen* species include *P. tannophilus*.

*Yarrowia lipolytica* is preferred in certain embodiments disclosed herein. Examples of suitable *Y. lipolytica* include the following isolates available from the American Type Culture Collection (ATCC, Manassas, Va.): strain designations ATCC #20362, #8862, #8661, #8662, #9773, #15586, #16617, #16618, #18942, #18943, #18944, #18945, #20114, #20177, #20182, #20225, #20226, #20228, #20327, #20255,

#20287, #20297, #20315, #20320, #20324, #20336, #20341, #20346, #20348, #20363, #20364, #20372, #20373, #20383, #20390, #20400, #20460, #20461, #20462, #20496, #20510, #20628, #20688, #20774, #20775, #20776, #20777, #20778, #20779, #20780, #20781, #20794, #20795, #20875, #20241, #20422, #20423, #32338, #32339, #32340, #32341, #34342, #32343, #32935, #34017, #34018, #34088, #34922, #34922, #38295, #42281, #44601, #46025, #46026, #46027, #46028, #46067, #46068, #46069, #46070, #46330, #46482, #46483, #46484, #46436, #60594, #62385, #64042, #74234, #76598, #76861, #76862, #76982, #90716, #90811, #90812, #90813, #90814, #90903, #90904, #90905, #96028, #201241, #201242, #201243, #201244, #201245, #201246, #201247, #201249, and/or #201847.

A *Y. lipolytica*, as well as any other non-conventional yeast herein, may be oleaginous (e.g., produce at least 25% of its dry cell weight as oil) and/or produce one or more polyunsaturated fatty acids (e.g., omega-6 or omega-3). Such oleaginy may be a result of the yeast being genetically engineered to produce an elevated amount of lipids compared to its wild type form. Examples of oleaginous *Y. lipolytica* strains are disclosed in U.S. Pat. Appl. Publ. Nos. 2009/0093543, 2010/0317072, 2012/0052537 and 2014/0186906, which are herein incorporated by reference.

Embodiments disclosed herein for non-conventional yeast can also be applied to other microorgansims such as fungi. Fungi in certain embodiments can be fungi that favor NHEJ DNA repair processes over repair processes mediated by HR. A fungus herein can be a *Basidiomycetes, Zygomycetes, Chytridiomycetes*, or *Ascomycetes* fungus. Examples of filamentous fungi herein include those of the genera *Trichoderma, Chrysosporium, Thielavia, Neurospora* (e.g., *N. crassa, N. sitophila*), *Cryphonectria* (e.g., *C. parasitica*), *Aureobasidium* (e.g., *A. pullulans*), *Filibasidium, Piromyces, Cryplococcus, Acremonium, Tolypocladium, Scytalidium, Schizophyllum, Sporotrichum, Penicillium* (e.g., *P. bilaiae, P. camemberti, P. candidum, P. chrysogenum, P. expansum, P. funiculosum, P. glaucum, P. mameffei, P. roqueforti, P. verrucosum, P. viridicatum*), *Gibberella* (e.g., *G. acuminata, G. avenacea, G. baccata, G. circinata, G. cyanogena, G. fujikuroi, G. intricans, G. pulicaris, G. stilboides, G. tricincta, G. zeae*), *Myceliophthora, Mucor* (e.g., *M. rouxii, M. circinelloides*), *Aspergillus* (e.g., *A. niger, A. oryzae, A. nidulans, A. flavus, A. lentulus, A. terreus, A. clavatus, A. fumigatus*), *Fusarium* (e.g., *F. graminearum, F. oxysporum, F. bubigenum, F. solani, F. oxysporum, F. verticillioides, F. proliferatum, F. venenatum*), and *Humicola*, and anamorphs and teleomorphs thereof. The genus and species of fungi herein can be defined, if desired, by morphology as disclosed in Barnett and Hunter (*Illustrated Genera of Imperfect Fungi*, 3rd Edition, Burgess Publishing Company, 1972). A fungus can optionally be characterized as a pest/pathogen, such as a pest/pathogen of an animal (e.g., human).

*Trichoderma* species in certain aspects herein include *T. aggressivum, T. amazonicum, T. asperellum, T. atroviride, T. aureoviride, T. austrokoningii, T. brevicompactum, T. candidum, T. caribbaeum, T. catoptron, T. cremeum, T. ceramicum, T. cerinum, T. chlorosporum, T. chromospermum, T. cinnamomeum, T. citrinoviride, T. crassum, T. cremeum, T. dingleyeae, T. dorotheae, T. effusum, T. erinaceum, T. estonicum, T. fertile, T. gelatinosus, T. ghanense, T. hamatum, T. harzianurn, T. helicum, T. intricatum, T. konilangbra, T. koningii, T. koningiopsis, T. longibrachiatum, T. longipile, T. minutisporum, T. oblongisporum, T. ovalisporum, T. petersenii, T. phyllostahydis, T. piluliferum, T. pleuroticola, T. pleurotum, T. polysporum, T. pseudokoningii, T. pubescens, T. reesei, T. rogersonii, T. rossicum, T. satumisporum, T. sinensis, T. sinuosum, T. spirale, T. stramineum, T. strigosum, T. stromaticum, T. surrotundum, T. taiwanense, T. thailandicum, T. thelephoricolum, T. theobromicola, T. tomentosum, T. velutinum, T. virens, T. viride* and *T. viridescens*. A *Trichoderma* species herein can be cultivated and/or manipulated as described in *Trichoderma: Biology and Applications* (P.K. Mukherjee et al., Eds., CABI, Oxfordshire, UK, 2013), for example, which is incorporated herein by reference.

A microbial cell in certain embodiments is an algal cell. For example, an algal cell can be from any of the following: Chlorophyta (green algae), Rhodophyta (red algae), Phaeophyceae (brown algae), Bacillariophycaeae (diatoms), and Dinoflagellata (dinoflagellates). An algal cell can be of a microalgae (e.g., phytoplankton, microphytes, or planktonic algae) or macroalgae (kelp, seaweed) in other aspects. As further examples, an algal cell herein can be a *Porphyra* (purple laver), *Palmaria* species such as *P. palmata* (dulse), *Arthrospira* species such as *A. platensis* (*spirulina*), *Chlorella* (e.g., *C. protothecoides*), a *Chondrus* species such as *C. crispus* (Irish moss), *Aphanizomenon, Sargassum, Cochayuyo, Botryococcus* (e.g., *B. braunii*), *Dunaliella* (e.g., *D. tertiolecta*), *Gracilaria, Pleurochrysis* (e.g., *P. carterae*), *Ankistrodesmus, Cyclotella, Hantzschia, Nannochloris, Nannochloropsis, Nitzschia, Phaeodactylum* (e.g., *P. tricornutum*), *Scenedesmus, Stichococcus, Tetraselmis* (e.g., *T. suecica*), *Thalassiosira* (e.g., *T. pseudonana*), *Crypthecodinium* (e.g., *C. cohnii*), *Neochloris* (e.g., *N. oleoabundans*), or *Schiochytrium*. An algal species herein can be cultivated and/or manipulated as described in Thompson (*Algal Cell Culture. Encyclopedia of Life Support System* (EOLSS), Biotechnology Vol 1, available at eolss.net/sample-chapters internet site), for example, which is incorporated herein by reference.

A non-conventional yeast herein comprising at least one RGEN comprising at least one RNA component that does not have a 5'-cap does not occur in nature. Without wishing to be held to any particular theory, it is believed that such yeast do not occur naturally since RGENs herein have only been found to occur in prokaryotes, for example. Also, it is believed that certain embodiments of yeast do not naturally occur by virtue of comprising an RGEN with an RNA component comprising a gRNA, which represents a heterologous linkage of a crRNA with a tracrRNA.

An RGEN herein refers to a complex comprising at least one Cas protein and at least one RNA component. Examples of suitable Cas proteins include one or more Cas endonucleases of type I, II, or III CRISPR systems (Bhaya et al., *Annu. Rev. Genet.* 45:273-297, incorporated herein by reference). A type I CRISPR Cas protein can be a Cas3 or Cas4 protein, for example. A type II CRISPR Cas protein can be a Cas9 protein, for example. A type III CRISPR Cas protein can be a Cas10 protein, for example. A Cas9 protein is used in preferred embodiments. A Cas protein in certain embodiments may be a bacterial or archaeal protein. Type I-III CRISPR Cas proteins herein are typically prokaryotic in origin; type I and III Cas proteins can be derived from bacterial or archaeal species, whereas type II Cas proteins (i.e., a Cas9) can be derived from bacterial species, for example. In other embodiments, suitable Cas proteins include one or more of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof.

In other aspects of the disclosed invention, a Cas protein herein can be from any of the following genera: *Aeropyrum, Pyrobaculum, Sulfolobus, Archaeoglobus, Haloarcula, Methanobacteriumn, Methanococcus, Methanosarcina, Methanopyrus, Pyrococcus, Picrophilus, Thernioplasnia, Corynebacterium, Mycobacterium, Streptomyces, Aquifrx, Porphvromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myrococcus, Campylobacter, Wolinella, Acinetobacter, Erwinia, Escherichia, Legionella, Methylococcus, Pasteurella, Photobacterium, Salmonella, Xanthomonas, Yersinia, Streptococcus, Treponema, Francisella*, or *Thermotoga*. Alternatively, a Cas protein herein can be encoded, for example, by any of SEQ ID NOs:462-465, 467-472, 474-477, 479-487, 489-492, 494-497, 499-503, 505-508, 510-516, or 517-521 as disclosed in U.S. Appl. Publ. No. 2010/0093617, which is incorporated herein by reference.

An RGEN in certain embodiments comprises a Cas9 amino acid sequence. The amino acid sequence of a Cas9 protein herein, as well as certain other Cas proteins herein, may be derived from a *Streptococcus* (e.g., *S. pyogenes, S. pneumoniae, S. thermophilus, S. agalactiae, S. parasanguinis, S. oralis, S. salivarius, S. macacae, S. dysgalactiae, S. anginosus, S. constellatus, S. pseudoporcinus, S. mutans*), *Listeria* (e.g., *L. innocua*), *Spiroplasma* (e.g., *S. apis, S. syrphidicola*), *Peptostreptococcaceae, Atopobium, Porphyromonas* (e.g., *P. catoniae*), *Prevotella* (e.g., *P. intermedia*), *Veillonella, Treponema* (e.g., *T. socranskii, T. denticola*), *Capnocytophaga, Finegoldia* (e.g., *F. magna*), *Coriobacteriaceae* (e.g., *C. bacterium*), *Olsenella* (e.g., *O. profusa*), *Haemophilus* (e.g., *H. sputorum, H. pittmaniae*), *Pasteurella* (e.g., *P. bettyae*), *Olivibacter* (e.g., *O. sitiensis*), *Epilithonimonas* (e.g., *E. tenax*), *Mesonia* (e.g., *M. mobilis*), *Lactobacillus* (e.g., *L. plantarum*), *Bacillus* (e.g., *B. cereus*), *Aquimarina* (e.g., *A. muelleri*), *Chryseobacterium* (e.g., *C. palustre*), *Bacteroides* (e.g., *B. graminisolvens*), *Neisseria* (e.g., *N. meningitidis*), *Francisella* (e.g., *F. novicida*), or *Flavobacterium* (e.g., *F. frigidarium, F. soli*) species, for example. An *S. pyogenes* Cas9 is preferred in certain aspects herein. As another example, a Cas9 protein can be any of the Cas9 proteins disclosed in Chylinski et al. (*RNA Biology* 10:726-737), which is incorporated herein by reference.

Accordingly, the sequence of a Cas9 protein herein can comprise, for example, any of the Cas9 amino acid sequences disclosed in GenBank Accession Nos. G3ECR1 (*S. thermophilus*), WP_026709422, WP_027202655, WP_027318179, WP_027347504, WP_027376815, WP_027414302, WP_027821588, WP_027886314, WP_027963583, WP_028123848, WP_028298935, Q03JI6 (*S. thermophilus*), EGP66723, EGS38969, EGV05092, EHI65578 (*S. pseudoporcinus*), EIC75614 (*S. oralis*), EID22027 (*S. constellatus*), EIJ69711, EJP22331 (*S. oralis*), EJP26004 (*S. anginosus*), EJP30321, EPZ44001 (*S. pyogenes*), EPZ46028 (*S. pyogenes*), EQL78043 (*S. pyogenes*), EQL78548 (*S. pyogenes*), ERL10511, ERL12345, ERL19088 (*S. pyogenes*), ESA57807 (*S. pyogenes*), ESA59254 (*S. pyogenes*), ESU85303 (*S. pyogenes*), ETS96804, UC75522, EGR87316 (*S. dysgalactiae*), EGS33732, EGV01468 (*S. oralis*), EHJ52063 (*S. macacae*), EID26207 (*S. oralis*), EID33364, EIG27013 (*S. parasanguinis*), EJF37476, EJ019166 (*Streptococcus* sp. BS35b), EJU16049, EJU32481, YP_006298249, ERF61304, ERK04546, ETJ95568 (*S. agalactiae*), TS89875, ETS90967 (*Streptococcus* sp. SR4), ETS92439, EUB27844 (*Streptococcus* sp. BS21), AFJ08616, EUC82735 (*Streptococcus* sp. CM6), EWC92088, EWC94390, EJP25691, YP_008027038, YP_008868573, AGM26527, AHK22391, AHB36273, Q927P4, G3ECR1, or Q99ZW2 (*S. pyogenes*), which are incorporated by reference. A variant of any of these Cas9 protein sequences may be used, but should have specific binding activity, and optionally endonucleolytic activity, toward DNA when associated with an RNA component herein. Such a variant may comprise an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of the reference Cas9.

Alternatively, a Cas9 protein herein can be encoded by any of SEQ ID NOs:462 (*S. thermophilus*), 474 (*S. thermophilus*), 489 (*S. agalactiae*), 494 (*S. agalactiae*), 499 (*S. mutans*), 505 (*S. pyogenes*), or 518 (*S. pyogenes*) as disclosed in U.S. Appl. Publ. No. 2010/0093617 (incorporated herein by reference), for example. Alternatively still, a Cas9 protein herein can comprise the amino acid sequence of SEQ ID NO:11, or residues 1-1368 of SEQ ID NO:11, for example. Alternatively still, a Cas9 protein may comprise an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to any of the foregoing amino acid sequences, for example. Such a variant Cas9 protein should have specific binding activity, and optionally cleavage or nicking activity, toward DNA when associated with an RNA component herein.

The origin of a Cas protein used herein (e.g., Cas9) may be from the same species from which the RNA component(s) is derived, or it can be from a different species. For example, an RGEN comprising a Cas9 protein derived from a *Streptococcus* species (e.g., *S. pyogenes* or *S. thermophilus*) may be complexed with at least one RNA component having a sequence (e.g., crRNA repeat sequence, tracrRNA sequence) derived from the same *Streptococcus* species. Alternatively, the origin of a Cas protein used herein (e.g., Cas9) may be from a different species from which the RNA component(s) is derived (the Cas protein and RNA component(s) may be heterologous to each other); such heterologous Cas/RNA component RGENs should have DNA targeting activity.

Determining binding activity and/or endonucleolytic activity of a Cas protein herein toward a specific target DNA sequence may be assessed by any suitable assay known in the art, such as disclosed in U.S. Pat. No. 8,697,359, which is disclosed herein by reference. A determination can be made, for example, by expressing a Cas protein and suitable RNA component in a non-conventional yeast, and then examining the predicted DNA target site for the presence of an indel (a Cas protein in this particular assay would have complete endonucleolytic activity [double-strand cleaving activity]). Examining for the presence of an indel at the predicted target site could be done via a DNA sequencing method or by inferring indel formation by assaying for loss of function of the target sequence, for example. In another example, Cas protein activity can be determined by expressing a Cas protein and suitable RNA component in a non-conventional yeast that has been provided a donor DNA comprising a sequence homologous to a sequence in at or near the target site. The presence of donor DNA sequence at the target site (such as would be predicted by successful HR between the donor and target sequences) would indicate that targeting occurred.

A Cas protein herein such as a Cas9 typically further comprises a heterologous nuclear localization sequence (NLS). A heterologous NIL amino acid sequence herein may be of sufficient strength to drive accumulation of a Cas protein in a detectable amount in the nucleus of a yeast cell herein, for example. An NIL may comprise one (monopartite) or more (e.g., bipartite) short sequences (e.g., 2 to 20 residues) of basic, positively charged residues (e.g., lysine and/or arginine), and can be located anywhere in a Cas amino acid sequence but such that it is exposed on the protein surface. An NIL may be operably linked to the N-terminus or C-terminus of a Cas protein herein, for example. Two or more NIL sequences can be linked to a Cas protein, for example, such as on both the N- and C-termini of a Cas protein. Non-limiting examples of suitable NIL sequences herein include those disclosed in U.S. Pat. Nos. 6,660,830 and 7,309,576 (e.g., Table 1 therein), which are both incorporated herein by reference. Another example of an NIL useful herein includes amino acid residues 1373-1379 of SEQ ID NO:11.

In certain embodiments, a Cas protein and its respective RNA component (e.g., crRNA) that directs DNA-specific targeting by the Cas protein are heterologous to the disclosed non-conventional yeast. The heterologous nature of these RGEN components is due to the fact that Cas proteins and their respective RNA components are only known to exist in prokaryotes (bacteria and archaea).

A Cas protein herein can optionally be expressed in a non-conventional yeast cell using an open reading frame (ORF) that is codon-optimized for expression in the yeast cell. A "codon-optimized" sequence herein is an ORF having its frequency of codon usage designed to mimic the frequency of preferred codon usage of the host cell. In aspects in which *Y. lipolytica* is the non-conventional yeast cell, codon optimization of an ORF can be performed following the Y. lipolytica codon usage profile as provided in U.S. Pat. No. 7,125,672, which is incorporated herein by reference.

In some embodiments, a Cas protein is part of a fusion protein comprising one or more heterologous protein domains (e.g., 1, 2, 3, or more domains in addition to the Cas protein). Such a fusion protein may comprise any additional protein sequence, and optionally a linker sequence between any two domains, such as between Cas and a first heterologous domain. Examples of protein domains that may be fused to a Cas protein herein include, without limitation, epitope tags (e.g., histidine [His], V5, FLAG, influenza hemagglutinin [HA], myc, VSV-G, thioredoxin [Trx]), reporters (e.g., glutathione-5-transferase [GST], horseradish peroxidase [HRP], chloramphenicol acetyltransferase [CAT], beta-galactosidase, beta-glucuronidase [GUS], luciferase, green fluorescent protein [GFP], HcRed, DsRed, cyan fluorescent protein [CFP], yellow fluorescent protein [YFP], blue fluorescent protein [BFP]), and domains having one or more of the following activities: methylase activity, demethylase activity, transcription activation activity (e.g., VP16 or VP64), transcription repression activity, transcription release factor activity, histone modification activity, RNA cleavage activity and nucleic acid binding activity. A Cas protein in other embodiments may be in fusion with a protein that binds DNA molecules or other molecules, such as maltose binding protein (MBP), S-tag, Lex A DNA binding domain (DBD), GAL4A DNA binding domain, and herpes simplex virus (HSV) VP16. Additional domains that may be part of a fusion protein comprising a Cas protein herein are disclosed in U.S. Patent Appl. Publ. No. 2011/0059502, which is incorporated herein by reference. In certain embodiments in which a Cas protein is fused to a heterologous protein (e.g., a transcription factor), the Cas protein has DNA recognition and binding activity (when in complex with a suitable RNA component herein), but no DNA nicking or cleavage activity.

An RGEN herein can bind to, and optionally cleave, a DNA strand at a DNA target sequence. In certain embodiments, an RGEN can cleave one or both strands of a DNA target sequence. An RGEN can cleave both strands of a DNA target sequence, for example.

An RGEN herein that can cleave both strands of a DNA target sequence typically comprises a Cas protein that has all of its endonuclease domains in a functional state (e.g., wild type endonuclease domains or variants thereof retaining some or all activity in each endonuclease domain). Thus, a wild type Cas protein (e.g., a Cas9 protein disclosed herein), or a variant thereof retaining some or all activity in each endonuclease domain of the Cas protein, is a suitable example of an RGEN that can cleave both strands of a DNA target sequence. A Cas9 protein comprising functional RuvC and HNH nuclease domains is an example of a Cas protein that can cleave both strands of a DNA target sequence. An RGEN herein that can cleave both strands of a DNA target sequence typically cuts both strands at the same position such that blunt-ends (i.e., no nucleotide overhangs) are formed at the cut site.

An RGEN herein that can cleave one strand of a DNA target sequence can be characterized herein as having nickase activity (e.g., partial cleaving capability). A Cas nickase (e.g., Cas9 nickase) herein typically comprises one functional endonuclease domain that allows the Cas to cleave only one strand (i.e., make a nick) of a DNA target sequence. For example, a Cas9 nickase may comprise (i) a mutant, dysfunctional RuvC domain and (ii) a functional HNH domain (e.g., wild type HNH domain). As another example, a Cas9 nickase may comprise (i) a functional RuvC domain (e.g., wild type RuvC domain) and (ii) a mutant, dysfunctional HNH domain.

Non-limiting examples of Cas9 nickases suitable for use herein are disclosed by Gasiunas et al. (*Proc. Natl. Acad. Sci. U.S.A.* 109:E2579-E2586), Jinek et al. (*Science* 337: 816-821), Sapranauskas et al. (*Nucleic Acids Res.* 39:9275-9282) and in U.S. Patent Appl. Publ. No. 2014/0189896, which are incorporated herein by reference. For example, a Cas9 nickase herein can comprise an *S. thermophilus* Cas9 having an Asp-31 substitution (e.g., Asp-31-Ala) (an example of a mutant RuvC domain), or a His-865 substitution (e.g., His-865-Ala), Asn-882 substitution (e.g., Asn-882-Ala), or Asn-891 substitution (e.g., Asn-891-Ala) (examples of mutant HNH domains). Also for example, a Cas9 nickase herein can comprise an S. pyogenes Cas9 having an Asp-10 substitution (e.g., Asp-10-Ala), Glu-762 substitution (e.g., Glu-762-Ala), or Asp-986 substitution (e.g., Asp-986-Ala) (examples of mutant RuvC domains), or a His-840 substitution (e.g., His-840-Ala), Asn-854 substitution (e.g., Asn-854-Ala), or Asn-863 substitution (e.g., Asn-863-Ala) (examples of mutant HNH domains). Regarding *S. pyogenes* Cas9, the three RuvC subdomains are generally located at amino acid residues 1-59, 718-769 and 909-1098, respectively, and the HNH domain is located at amino acid residues 775-908 (Nishimasu et al., *Cell* 156:935-949).

A Cas9 nickase herein can be used for various purposes in non-conventional yeast of the disclosed invention. For example, a Cas9 nickase can be used to stimulate HR at or near a DNA target site sequence with a suitable donor polynucleotide. Since nicked DNA is not a substrate for NHEJ processes, but is recognized by HR processes, nicking DNA at a specific target site should render the site more receptive to HR with a suitable donor polynucleotide.

As another example, a pair of Cas9 nickases can be used to increase the specificity of DNA targeting. In general, this can be done by providing two Cas9 nickases that, by virtue of being associated with RNA components with different guide sequences, target and nick nearby DNA sequences on opposite strands in the region for desired targeting. Such nearby cleavage of each DNA strand creates a DSB (i.e., a DSB with single-stranded overhangs), which is then recognized as a substrate for NHEJ (leading to indel formation) or HR (leading to recombination with a suitable donor polynucleotide, if provided). Each nick in these embodiments can be at least about 5, 10, 15, 20, 30, 40, 50, 60, 70, 80, 90, or 100 (or any integer between 5 and 100) bases apart from each other, for example. One or two Cas9 nickase proteins herein can be used in a Cas9 nickase pair as described above. For example, a Cas9 nickase with a mutant RuvC domain, but functioning HNH domain (i.e., Cas9 $HNH^+/RuvC^-$), could be used (e.g., *S. pyogenes* Cas9 $HNH^+/RuvC^-$). Each Cas9 nickase (e.g., Cas9 $HNH^+/RuvC^-$) would be directed to specific DNA sites nearby each other (up to 100 base pairs apart) by using suitable RNA components herein with guide RNA sequences targeting each nickase to each specific DNA site.

An RGEN in certain embodiments can bind to a DNA target site sequence, but does not cleave any strand at the target site sequence. Such an RGEN may comprise a Cas protein in which all of its nuclease domains are mutant, dysfunctional. For example, a Cas9 protein herein that can bind to a DNA target site sequence, but does not cleave any strand at the target site sequence, may comprise both a mutant, dysfunctional RuvC domain and a mutant, dysfunctional HNH domain. Non-limiting examples of such a Cas9 protein comprise any of the RuvC and HNH nuclease domain mutations disclosed above (e.g., an *S. pyogenes Cas*9 with an Asp-10 substitution such as Asp-10-Ala and a His-840 substitution such as His-840-Ala). A Cas protein herein that binds, but does not cleave, a target DNA sequence can be used to modulate gene expression, for example, in which case the Cas protein could be fused with a transcription factor (or portion thereof) (e.g., a repressor or activator, such as any of those disclosed herein). For example, a Cas9 comprising an *S. pyogenes* Cas9 with an Asp-10 substitution (e.g., Asp-10-Ala) and a His-840 substitution (e.g., His-840-Ala) can be fused to a VP16 or VP64 transcriptional activator domain. The guide sequence used in the RNA component of such an RGEN would be complementary to a DNA sequence in a gene promoter or other regulatory element (e.g., intron), for example.

A yeast in certain aspects may comprise (i) an RGEN that can cleave one or both DNA strands of a DNA target sequence and (ii) a donor polynucleotide comprising at least one sequence homologous to a sequence at or near a DNA target site sequence (a sequence specifically targeted by a Cas protein herein). A suitable donor polynucleotide is able to undergo HR with a sequence at or near a DNA target site if the target site contains a SSB or DSB (such as can be introduced using a Cas protein herein). A "homologous sequence" within a donor polynucleotide herein can comprise or consist of a sequence of at least about 25, 50, 75, 100, 150, 200, 300, 400, 500, 600, 700, 800, 900, 1000, 2000, 3000, 4000, 5000, 6000, 7000, 8000, 9000 or 10000 nucleotides, or about 50-500, 50-550, 50-600, 50-650, or 50-700 nucleotides, that have 100% identity with a sequence at or near the target site sequence, or at least about 95%, 96%, 97%, 98%, or 99% identity with a sequence at or near the target site sequence, for example.

A donor polynucleotide herein can have two homologous sequences (homology arms), for example, separated by a sequence that is heterologous to sequence at or near a target site sequence. HR between such a donor polynucleotide and a target site sequence typically results in the replacement of a sequence at the target site with the heterologous sequence of the donor polynucleotide (target site sequence located between target site sequences homologous to the homology arms of the donor polynucleotide is replaced by the heterologous sequence of the donor polynucleotide). In a donor polynucleotide with two homology arms, the arms can be separated by at least about 1, 2, 3, 4, 5, 10, 20, 30, 40, 50, 75, 100, 250, 500, 1000, 2500, 5000, 10000, 15000, 20000, 25000, or 30000 nucleotides (i.e., the heterologous sequence in the donor polynucleotide is at least about 1, 2, 3, 4, 5, 10, 20, 30, 40, 50, 75, 100, 250, 500, 1000, 2500, 5000, 10000, 15000, 20000, 25000, or 30000 nucleotides in length), for example. The length (e.g., any of the lengths disclosed above for a homologous sequence) of each homology arm may be the same or different. The percent identity (e.g., any of the % identities disclosed above for a homologous sequence) of each arm with respective homologous sequences at or near the target site can be the same or different.

A DNA sequence at or near (alternatively, in the locality or proximity of) the target site sequence that is homologous to a corresponding homologous sequence in a donor polynucleotide can be within about 1, 2, 3, 4, 5, 6, 7, 8, 9, 10, 15, 20, 25, 30, 35, 40, 45, 50, 60, 70, 80, 90, 100, 150, 200, 250, 300, 450, 500, 750, 1000, 2000, 3000, 4000, 5000, 6000, 7000, 8000, 9000, 10000, 20000, 30000, 40000, 50000, or 60000 (or any integer between 1 and 60000) nucleotides (e.g., about 1-1000, 100-1000, 500-1000, 1-500, or 100-500 nucleotides), for example, from the predicted Cas protein cut site (DSB or nick) in the target sequence. These nucleotide distances can be marked from the cut site to the first nucleotide of the homologous sequence, going either in the upstream or downstream direction from the cut site. For example, a sequence near a target sequence that is homologous to a corresponding sequence in a donor polynucleotide can start at 500 nucleotide base pairs downstream the predicted Cas protein cut site in a target sequence. In embodiments herein employing a donor polynucleotide with two homology arms (e.g., first and second homology arms separated by a heterologous sequence), a homologous sequence (corresponding in homology with the first homology arm of a donor) can be upstream the predicted Cas cut site, and a homologous sequence (corresponding in homology with the second homology arm of a donor) can be downstream the predicted Cas cut site, for example. The nucleotide distances of each of these upstream and downstream homologous sequences from the predicted cut site can be the same or different, and can be any of the nucleotide distances disclosed above, for example. For instance, the 3' end of a homologous sequence (corresponding in homology with the first homology arm of a donor) may be located 600 nucleotide base pairs upstream a predicted Cas cut site, and the 5' end of a homologous sequence (corresponding in homology with the second homology arm of a donor) may be located 400 nucleotide base pairs downstream the predicted Cas cut site.

An RGEN herein can bind to, and optionally cleave a DNA strand at a target site sequence in a chromosome, episome, or any other DNA molecule in the genome of a non-conventional yeast. This recognition and binding of a target sequence is specific, given that an RNA component of the RGEN comprises a sequence (guide sequence) that is complementary to a strand of the target sequence. A target site in certain embodiments can be unique (i.e., there is a single occurrence of the target site sequence in the subject genome).

The length of a target sequence herein can be at least 13, 14, 15, 16, 17, 18, 19, 20, 21, 22, 23, 24, 25, 26, 27, 28, 29, or 30 nucleotides; between 13-30 nucleotides; between 17-25 nucleotides; or between 17-20 nucleotides, for example. This length can include or exclude a PAM sequence. Also, a strand of a target sequence herein has sufficient complementarity with a guide sequence (of a crRNA or gRNA) to hybridize with the guide sequence and direct sequence-specific binding of a Cas protein or Cas protein complex to the target sequence (if a suitable PAM is adjacent to the target sequence, see below). The degree of complementarity between a guide sequence and a strand of its corresponding DNA target sequence is at least about 90%, 91%, 92%, 93%, 94%, 95%, 96%, 97%, 98%, 99%, or 100%, for example. A target site herein may be located in a sequence encoding a gene product (e.g., a protein or an RNA) or a non-coding sequence (e.g., a regulatory sequence or a "junk" sequence), for example.

A PAM (protospacer-adjacent motif) sequence may be adjacent to the target site sequence. A PAM sequence is a short DNA sequence recognized by an RGEN herein. The associated PAM and first 11 nucleotides of a DNA target sequence are likely important to Cas9/gRNA targeting and cleavage (Jiang et al., Nat. Biotech. 31:233-239). The length of a PAM sequence herein can vary depending on the Cas protein or Cas protein complex used, but is typically 2, 3, 4, 5, 6, 7, or 8 nucleotides long, for example. A PAM sequence is immediately downstream from, or within 2, or 3 nucleotides downstream of, a target site sequence that is complementary to the strand in the target site that is in turn complementary to an RNA component guide sequence, for example. In embodiments herein in which the RGEN is an endonucleolytically active Cas9 protein complexed with an RNA component, the Cas9 binds to the target sequence as directed by the RNA component and cleaves both strands immediately 5' of the third nucleotide position upstream of the PAM sequence. Consider the following example of a target site:PAM sequence:

5'-NNNNNNNNNNNNNNNNN<u>N</u>NN<u>XGG</u>-3' (SEQ ID NO:46).

N can be A, C, T, or G, and X can be A, C, T, or G in this example sequence (X can also be referred to as $N_{PAM}$). The PAM sequence in this example is XGG (underlined). A suitable Cas9/RNA component complex would cleave this target immediately 5' of the double-underlined N. The string of N's in SEQ ID NO:46 represents target sequence that is at least about 90%, 91%, 92%, 93%, 94%, 95%, 96%, 97%, 98%, 99%, or 100% identical, for example, with a guide sequence in an RNA component herein (where any T's of the DNA target sequence would align with any U's of the RNA guide sequence). A guide sequence of an RNA component of a Cas9 complex, in recognizing and binding at this target sequence (which is representative of target sites herein), would anneal with the complement sequence of the string of N's; the percent complementarity between a guide sequence and the target site complement is at least about 90%, 91%, 92%, 93%, 94%, 95%, 96%, 97%, 98%, 99%, or 100%, for example. If a Cas9 nickase is used to target SEQ ID NO:46 in a genome, the nickase would nick immediately 5' of the double-underlined N or at the same position of the complementary strand, depending on which endonuclease domain in the nickase is dysfunctional. If a Cas9 having no nucleolytic activity (both RuvC and HNH domains dysfuntional) is used to target SEQ ID NO:46 in a genome, it would recognize and bind the target sequence, but not make any cuts to the sequence.

A PAM herein is typically selected in view of the type of RGEN being employed. A PAM sequence herein may be one recognized by an RGEN comprising a Cas, such as Cas9, derived from any of the species disclosed herein from which a Cas can be derived, for example. In certain embodiments, the PAM sequence may be one recognized by an RGEN comprising a Cas9 derived from *S. pyogenes, S. thermophilus, S. agalactiae, N. meningitidis, T. denticola,* or *F. novicida*. For example, a suitable Cas9 derived from S. pyogenes could be used to target genomic sequences having a PAM sequence of NGG (SEQ ID NO:47; N can be A, C, T, or G). As other examples, a suitable Cas9 could be derived from any of the following species when targeting DNA sequences having the following PAM sequences: *S. thermophilus* (NNAGAA [SEQ ID NO:48]), *S. agalactiae* (NGG [SEQ ID NO:47]), NNAGAAW [SEQ ID NO:49, W is A or T], NGGNG [SEQ ID NO:50]), *N. meningitidis* (NNNNGATT [SEQ ID NO:51]), T. denticola (NAAAAC [SEQ ID NO:52]), or *F. novicida* (NG [SEQ ID NO:53]) (where N's in all these particular PAM sequences are A, C, T, or G). Other examples of Cas9/PAMs useful herein include those disclosed in Shah et al. (*RNA Biology* 10:891-899) and Esvelt et al. (*Nature Methods* 10:1116-1121), which are incorporated herein by reference. Examples of target sequences herein follow SEQ ID NO:46, but with the 'XGG' PAM replaced by any one of the foregoing PAMs.

At least one RNA component that does not have a 5'-cap is comprised in an RGEN in embodiments herein. This uncapped RNA component comprises a sequence complementary to a target site sequence in a chromosome or episome in a non-conventional yeast. An RGEN specifically binds to, and optionally cleaves, a DNA strand at the target site based on this sequence complementary. Thus, the complementary sequence of an RNA component in embodiments of the disclosed invention can also be referred to as a guide sequence or variable targeting domain.

The guide sequence of an RNA component (e.g., crRNA or gRNA) herein can be at least 13, 14, 15, 16, 17, 18, 19, 20, 21, 22, 23, 24, 25, 26, 27, 28, 29, or 30 ribonucleotides in length; between 13-30 ribonucleotides in length; between 17-25 ribonucleotides in length; or between 17-20 ribonucleotides in length, for example. In general, a guide sequence herein has sufficient complementarity with a strand of a target DNA sequence to hybridize with the target sequence and direct sequence-specific binding of a Cas protein or Cas protein complex to the target sequence (if a suitable PAM is adjacent to the target sequence). The degree of complementarity between a guide sequence and its corresponding DNA target sequence is at least about 90%, 91%, 92%, 93%, 94%, 95%, 96%, 97%, 98%, 99%, or 100%, for example. The guide sequence can be engineered accordingly to target an RGEN to a DNA target sequence in a yeast cell.

An RNA component herein can comprise a crRNA, for example, which comprises a guide sequence and a repeat (tracrRNA mate) sequence. The guide sequence is typically located at or near (within 1, 2, 3, 4, 5, 6, 7, 8, 9, 10 or more bases) the 5' end of the crRNA. Downstream the guide sequence of a crRNA is a "repeat" or "tracrRNA mate" sequence that is complementary to, and can hybridize with, sequence at the 5' end of a tracrRNA. Guide and tracrRNA mate sequences can be immediately adjacent, or separated by 1, 2, 3, 4 or more bases, for example. A tracrRNA mate sequence has, for example, at least 50%, 60%, 70%, 80%, 90%, 95%, 96%, 97%, 98%, or 99% sequence complementarity to the 5' end of a tracrRNA. In general, degree of complementarity can be with reference to the optimal alignment of the tracrRNA mate sequence and tracrRNA sequence, along the length of the shorter of the two sequences. The length of a tracrRNA mate sequence herein can be at least 8, 9, 10, 11, 12, 13, 14, 15, 16, 17, or 18 ribonucleotides in length, for example, and hybridizes with sequence of the same or similar length (e.g., plus or minus 1, 2, 3, 4, or 5 bases) at the 5' end of a tracrRNA. Suitable examples of tracrRNA mate sequences herein comprise SEQ ID NO:54 (guuuuuguacucucaagauuua), SEQ ID NO:55 (guuuuuguacucuca), SEQ ID NO:56 (guuuuagagcua, see Examples), or SEQ ID NO:57 (guuuuagagcuag), or variants thereof that (i) have at least about 90%, 91%, 92%, 93%, 94%, 95%, 96%, 97%, 98%, or 99% sequence identity and (ii) can anneal with the 5'-end sequence of a tracrRNA. The length of a crRNA herein can be at least about 18, 20, 22, 24, 26, 28, 30, 32, 34, 36, 38, 40, 42, 44, 46, or 48 ribonucleotides; or about 18-48 ribonucleotides; or about 25-50 ribonucleotides, for example.

A tracrRNA should be included along with a crRNA in embodiments in which a Cas9 protein of a type II CRISPR system is comprised in the RGEN. A tracrRNA herein comprises in 5'-to-3' direction (i) a sequence that anneals with the repeat region (tracrRNA mate sequence) of crRNA and (ii) a stem loop-containing portion. The length of a sequence of (i) can be the same as, or similar with (e.g., plus or minus 1, 2, 3, 4, or 5 bases), any of the tracrRNA mate sequence lengths disclosed above, for example. The total length of a tracrRNA herein (i.e., sequence components [i] and [ii]) can be at least about 30, 35, 40, 45, 50, 55, 60, 65, 70, 75, 80, 85, or 90 (or any integer between 30 and 90) ribonucleotides, for example. A tracrRNA may further include 1, 2, 3, 4, 5, or more uracil residues at the 3'-end, which may be present by virtue of expressing the tracrRNA with a transcription terminator sequence.

A tracrRNA herein can be derived from any of the bacterial species listed above from which a Cas9 sequence can be derived, for example. Examples of suitable tracrRNA sequences include those disclosed in U.S. Pat. No. 8,697,359 and Chylinski et al. (*RNA Biology* 10:726-737), which are incorporated herein by reference. A preferred tracrRNA herein can be derived from a *Streptococcus* species tracrRNA (e.g., *S. pyogenes*, *S. thermophilus*).

Other suitable examples of tracrRNAs herein may comprise:
SEQ ID NO: 58:
uagcaaguuaaaauaaggcuaguccguuaucaacuugaaaaaguggcacc gagucggugc (see Examples), SEQ ID NO: 59:
uagcaaguuaaaauaaggcuaguccguuaucaacuugaaaaagug,
or SEQ ID NO: 60:
uagcaaguuaaaauaaggcuaguccguuauca, which are derived from *S. pyogenes* tracrRNA.

Other suitable examples of tracrRNAs herein may comprise:
SEQ ID NO: 61:
uaaaucuugcagaagcuacaaagauaaggcuucaugccgaaaucaacacc cugucauuuauggcaggguguuuucguuauuaa, SEQ ID NO: 62:
ugcagaagcuacaaagauaaggcuucaugccgaaaucaacacccugucau uuuauggcaggguguuuucguuauuua,
or SEQ ID NO: 63:
ugcagaagcuacaaagauaaggcuucaugccgaaaucaacacccugucau uuuauggcagggugu, which are derived from *S. thermophilus* tracrRNA.

Still other examples of tracrRNAs herein are variants of these tracrRNA SEQ ID NOs that (i) have at least about 80%, 85%, 90, 91, 92, 93, 94, 95, 96, 97, 98, or 99% sequence identity therewith and (ii) can function as a tracrRNA (e.g., 5'-end sequence can anneal to tracrRNA mate sequence of a crRNA, sequence downstream from the 5'-end sequence can form one or more hairpins, variant tracrRNA can form complex with a Cas9 protein).

An RNA component of an RGEN disclosed herein can comprise, for example, a guide RNA (gRNA) comprising a crRNA operably linked to, or fused to, a tracrRNA. The crRNA component of a gRNA in certain preferred embodiments is upstream of the tracrRNA component (i.e., such a gRNA comprises, in 5'-to-3' direction, a crRNA operably linked to a tracrRNA). Any crRNA and/or tracrRNA (and/or portion thereof, such as a crRNA repeat sequence, tracrRNA mate sequence, or tracrRNA 5'-end sequence) as disclosed herein (e.g., above embodiments) can be comprised in a gRNA, for example.

The tracrRNA mate sequence of the crRNA component of a gRNA herein should be able to anneal with the 5'-end of the tracrRNA component, thereby forming a hairpin structure. Any of the above disclosures regarding lengths of, and percent complementarity between, tracrRNA mate sequences (of crRNA component) and 5'-end sequences (of tracrRNA component) can characterize the crRNA and tracrRNA components of a gRNA, for example. To facilitate this annealing, the operable linkage or fusion of the crRNA and tracrRNA components preferably comprises a suitable loop-forming ribonucleotide sequence (i.e., a loop-forming sequence may link the crRNA and tracrRNA components together, forming the gRNA). Suitable examples of RNA loop-forming sequences include GAAA (SEQ ID NO:43, see Examples), CAAA (SEQ ID NO:44) and AAAG (SEQ ID NO:45). However, longer or shorter loop sequences may be used, as may alternative loop sequences. A loop sequence preferably comprises a ribonucleotide triplet (e.g., AAA) and an additional ribonucleotide (e.g., C or G) at either end of the triplet.

A gRNA herein forms a hairpin ("first hairpin") with annealing of its tracrRNA mate sequence (of the crRNA component) and tracrRNA 5'-end sequence portions. One or more (e.g., 1, 2, 3, or 4) additional hairpin structures can form downstream from this first hairpin, depending on the sequence of the tracrRNA component of the gRNA. A gRNA may therefore have up to five hairpin structures, for example. A gRNA may further include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more residues following the end of the gRNA sequence, which may be present by virtue of expressing the gRNA with a transcription terminator sequence, for example. These additional residues can be all U residues, or at least 90%, 91%, 92%, 93%, 94%, 95%, 96%, 97%, 98%, or 99% U residues, for example, depending on the choice of terminator sequence.

Non-limiting examples of suitable gRNAs useful in the disclosed invention may comprise:

SEQ ID NO: 64:
NNNNNNNNNNNNNNNNNNNNguuuuuguacucucaagauuuaGAAAuaaa
ucuugcagaagcuacaaagauaaggcuucaugccgaaaucaacacccugu
cauuuuauggcaggguguuuucguuauuuaa, SEQ ID NO: 65:
NNNNNNNNNNNNNNNNNNNNguuuuuguacucucaGAAAugcagaagcua
caaagauaaggcuucaugccgaaaucaacacccugucauuuuauggcagg
guguuuucguuauuuaa, SEQ ID NO: 66:
NNNNNNNNNNNNNNNNNNNNguuuuuguacucucaGAAAugcagaagcua
caaagauaaggcuucaugccgaaaucaacacccugucauuuuauggcagg
gugu, SEQ ID NO: 67:
NNNNNNNNNNNNNNNNNNNNguuuuuguacucucaGAAAuagcaaguuaa
aauaaggcuaguccguuaucaacuugaaaaaguggcaccgagucggugc, SEQ ID NO: 68:
NNNNNNNNNNNNNNNNNNNNguuuuagagcuaGAAAuagcaaguuaaaau
aaggcuaguccguuaucaacuugaaaaagug, SEQ ID NO: 69:
NNNNNNNNNNNNNNNNNNNNguuuuagagcuaGAAAuagcaaguuaaaau
aaggcuaguccguuauca,
or SEQ ID NO: 70:
NNNNNNNNNNNNNNNNNNNNguuuuagagcuaGAAAuagcaaguuaaaau
aaggcuaguccguuaucaacuugaaaaaguggcaccgagucggugcuuuu
(see Examples).

In each of SEQ ID NOs:64-70, the single-underlined sequence represents a crRNA portion of the gRNA. Each "N" represents a ribonucleotide base (A, U, G, or C) of a suitable guide sequence. The first block of lower case letters represents tracrRNA mate sequence. The second block of lower case letters represents a tracrRNA portion of the gRNA. The double-underlined sequence approximates that portion of tracrRNA sequence that anneals with the tracrRNA mate sequence to form a first hairpin. A loop sequence (GAAA, SEQ ID NO:43) is shown in capital letters, which operably links the crRNA and tracrRNA portions of each gRNA. Other examples of gRNAs herein include variants of the foregoing gRNAs that (i) have at least about 80%, 85%, 90, 91, 92, 93, 94, 95, 96, 97, 98, or 99% sequence identity (excluding guide sequence in this calculation) with these sequences, and (ii) can function as a gRNA that specifically targets a Cas9 protein to bind with, and optionally nick or cleave, a target DNA sequence.

A gRNA herein can also be characterized in terms of having a guide sequence (VT domain) followed by a Cas endonuclease recognition (CER) domain. A CER domain comprises a tracrRNA mate sequence followed by a tracrRNA sequence. Examples of CER domains useful herein include those comprised in SEQ ID NOs:64-70 above (the CER domain in each is the sequence following the N's of the VT domain). Another suitable example of a CER domain is SEQ ID NO:1 (see Examples), which comprises in 5'-to-3' direction the tracrRNA mate sequence of SEQ ID NO:56, the loop-forming sequence of SEQ ID NO:43 (GAAA), and the tracrRNA sequence of SEQ ID NO:58.

An RNA component of an RGEN of the disclosed invention does not have a 5'-cap (7-methylguanylate [$m^7G$] cap). Thus, an RNA component herein does not have a 7-methylguanylate ($m^7G$) cap at its 5'-terminus. An RNA component herein can have, for example, a 5'-hydroxyl group instead of a 5'-cap. Alternatively, an RNA component herein can have, for example, a 5' phosphate instead of a 5'-cap. It is believed that the RNA component can better accumulate in the nucleus following transcription, since 5'-capped RNA (i.e., RNA having 5' $m^7G$ cap) is subject to nuclear export. Preferred examples of uncapped RNA components herein include suitable gRNAs, crRNAs, and/or tracrRNAs. In certain embodiments, an RNA component herein lacks a 5'-cap, and optionally has a 5'-hydroxyl group instead, by virtue of RNA autoprocessing by a ribozyme sequence at the 5'-end of a precursor of the RNA component (i.e., a precursor RNA comprising a ribozyme sequence upstream of an RNA component such as a gRNA undergoes ribozyme-mediated autoprocessing to remove the ribozyme sequence, thereby leaving the downstream RNA component without a 5'-cap). In certain other embodiments, an RNA component herein is not produced by transcription from an RNA polymerase III (Pol III) promoter.

A yeast in certain embodiments further comprises a DNA polynucleotide sequence comprising (i) a promoter operably linked to (ii) a nucleotide sequence encoding an RNA component. This polynucleotide sequence is used by the yeast to express an RNA component that complexes with an Cas protein to form an RGEN. Such a polynucleotide sequence can be in the form of a plasmid, yeast artificial chromosome (YAC), cosmid, phagemid, bacterial artificial chromosome (BAC), virus, or linear DNA (e.g., linear PCR product), for example, or any other type of vector or construct useful for transferring a polynucleotide sequence into a non-conventional yeast cell. This polynucleotide sequence can exist transiently (i.e., not integrated into the genome) or stably (i.e., integrated into the genome) in a yeast cell herein. Also, this polynucleotide sequence can comprise, or lack, one or more suitable marker sequences (e.g., selection or phenotype marker).

A suitable promoter comprised in a polynucleotide sequence for expressing an RNA component herein is operable in a non-conventional yeast cell, and can be constitutive or inducible, for example. A promoter in certain aspects can comprise a strong promoter, which is a promoter that can direct a relatively large number of productive initiations per unit time, and/or is a promoter driving a higher transcription level than the average transcription level of the genes in the yeast comprising the yeast.

Examples of strong promoters useful herein include those disclosed in U.S. Patent Appl. Publ. Nos. 2012/0252079 (DGAT2), 2012/0252093 (EL1), 2013/0089910 (ALK2), 2013/0089911 (SPS19), 2006/0019297 (GPD and GPM), 2011/0059496 (GPD and GPM), 2005/0130280 (FBA, FBAIN, FBAINm), 2006/0057690 (GPAT) and 2010/0068789 (YAT1), which are incorporated herein by reference. Other examples of suitable strong promoters include those listed in Table 2.

TABLE 2

Strong Promoters

| Promoter Name | Native Gene | Reference[a] |
|---|---|---|
| XPR2 | alkaline extracellular protease | U.S. Pat. No. 4,937,189; EP220864 |
| TEF | translation elongation factor EF1-α (tef) | U.S. Pat. No. 6,265,185 |
| GPD, GPM | glyceraldehyde-3-phosphate-dehydrogenase (gpd), phosphoglycerate mutase (gpm) | U.S. Pat. Nos. 7,259,255 and 7,459,546 |
| GPDIN | glyceraldehyde-3-phosphate-dehydrogenase (gpd) | U.S. Pat. No. 7,459,546 |
| GPM/FBAIN | chimeric phosphoglycerate mutase (gpm)/fructose-bisphosphate aldolase (fba1) | U.S. Pat. No. 7,202,356 |
| FBA, FBAIN, FBAINm | fructose-bisphosphate aldolase (fba1) | U.S. Pat. No. 7,202,356 |
| GPAT | glycerol-3-phosphate O-acyltransferase (gpat) | U.S. Pat. No. 7,264,949 |
| YAT1 | ammonium transporter enzyme (yat1) | U.S. Pat. Appl. Publ. No. 2006/0094102 |
| EXP1 | export protein | U.S. Pat. No. 7,932,077 |

[a]Each reference in this table is incorporated herein by reference.

Though the above-listed strong promoters are from *Yarrowia lipolytica*, it is believed that corresponding promoters (e.g., homologs) thereof from any of the non-conventional yeast disclosed herein, for example, could serve as a strong promoter. Thus, a strong promoter may comprise an XPR2, TEF, GPD, GPM, GPDIN, FBA, FBAIN, FBAINm, GPAT, YAT1, EXP1, DGAT2, EL1, ALK2, or SPS19 promoter, for example. Alternatively, a strong promoter such as any corresponding to any of the foregoing can be from other types of yeast (e.g., *S. cerevisiae, S. pombe*) (e.g., any of the strong promoters disclosed in U.S. Patent Appl. Publ. No. 2010/0150871, which is incorporated herein by reference). Other examples of strong promoters useful herein include PGK1, ADH1, TDH3, TEF1, PHO5, LEU2, and GAL1 promoters, as well as strong yeast promoters disclosed in Velculescu et al. (*Cell* 88:243-251), which is incorporated herein by reference. Still another example of a strong promoter useful herein can comprise SEQ ID NO:12 (a *Yarrowia* FBA1 promoter sequence).

A promoter herein can comprise an RNA polymerase II (Pol II) promoter in certain embodiments. It is believed that all the above-listed strong promoters are examples of suitable Pol II promoters. Transcription from a Pol II promoter may involve formation of an RNA polymerase II complex of at least about 12 proteins (e.g., RPB1-RPN12 proteins), for example. RNA transcribed from a Pol II promoter herein typically is 5'-capped (e.g., contains an $m^7G$ group at the 5'-end). Since an RNA component herein does not have a 5'-cap, a means for removing the 5'-cap from an RNA component should be employed if it is expressed from a Pol II promoter herein. Suitable means for effectively removing a 5'-cap from a Pol II-transcribed RNA component herein include appropriate use of one or more ribozymes (see below), group 1 self-splicing introns, and group 2 self-splicing introns, for example.

A nucleotide sequence herein encoding an RNA component may further encode a ribozyme that is upstream of the sequence encoding the RNA component, for example. Thus, a yeast in certain embodiments further comprises a DNA polynucleotide sequence comprising (i) a promoter operably linked to (ii) a nucleotide sequence encoding, in 5'-to-3' direction, a ribozyme and an RNA component. Transcripts expressed from such a polynucleotide sequence autocatalytically remove the ribozyme sequence to yield an RNA that does not have a 5'-cap but which comprises the RNA component sequence. This "autoprocessed" RNA can comprise a crRNA or gRNA, for example, and can complex with a Cas protein such as a Cas9, thereby forming an RGEN.

A ribozyme herein can be a hammerhead (HH) ribozyme, hepatitis delta virus (HDV) ribozyme, group I intron ribozyme, RnaseP ribozyme, or hairpin ribozyme, for example. Other non-limiting examples of ribozymes herein include Varkud satellite (VS) ribozymes, glucosamine-6-phosphate activated ribozymes (glmS), and CPEB3 ribozymes. Lilley (*Biochem. Soc. Trans.* 39:641-646) discloses information pertaining to ribozyme structure and activity. Examples of ribozymes that should be suitable for use herein include ribozymes disclosed in EP0707638 and U.S. Pat. Nos. 6,063,566, 5,580,967, 5,616,459, and 5,688,670, which are incorporated herein by reference.

A hammerhead ribozyme is used in certain preferred embodiments. This type of ribozyme may be a type I, type II, or type III hammerhead ribozyme, for example, as disclosed in Hammann et al. (*RNA* 18:871-885), which is incorporated herein by reference. Multiple means for identifying DNA encoding a hammerhead ribozyme are disclosed in Hammann et al., which can be utilized accordingly herein. A hammerhead ribozyme herein may be derived from a virus, viroid, plant virus satellite RNA, prokaryote (e.g., Archaea, cyanobacteria, acidobacteria), or eukaryote such as a plant (e.g., *Arabidopsis thaliana*, carnation), protist (e.g., amoeba, euglenoid), fungus (e.g., *Aspergillus, Y. lipolytica*), amphibian (e.g., newt, frog), schistosome, insect (e.g., cricket), mollusc, mammal (e.g., mouse, human), or nematode, for example.

A hammerhead ribozyme herein typically comprises three base-paired helices, each respectively referred to as helix I, II and III, separated by short linkers of conserved sequences. The three types of hammerhead ribozymes (I-III) are generally based on which helix the 5' and 3' ends of the ribozyme are comprised in. For example, if the 5' and 3' ends of a hammerhead ribozyme sequence contribute to stem I, then it can be referred to as a type I hammerhead ribozyme. Of the three possible topological types, type I can be found in the genomes of prokaryotes, eukaryotes and RNA plant pathogens, whereas type II hammerhead ribozymes have only been described in prokaryotes, and type III hammerhead ribozymes are mostly found in plants, plant pathogens and prokaryotes. A hammerhead ribozyme in certain embodiments is a type I hammerhead ribozyme.

In certain embodiments, the sequence encoding a hammerhead ribozyme can comprise at least about 40, 50, 60, 70, 80, 90, 100, 110, 120, 130, 140, or 150 (or any integer between 40 and 150) nucleotides, 40-100 nucleotides, or 40-60 nucleotides.

The sequence encoding a hammerhead ribozyme is upstream of the sequence encoding an RNA component. The sequence encoding a hammerhead ribozyme herein may be, for example, immediately 5' of, or at least 2, 3, 4, 5, 6, 7, 8, 9, or 10 nucleotides 5' of, sequence encoding a guide sequence of an RNA component (e.g., the guide sequence may be that of a crRNA or gRNA). The first 5, 6, 7, 8, 9, 10, 11, 12, 13, 14, or 15 ribonucleotides of the hammerhead ribozyme typically should be complementary to the first same number, respectively, of ribonucleotides of the sequence immediately downstream the hammerhead ribozyme sequence. For example, if a polynucleotide sequence herein encodes an RNA comprising a hammerhead ribozyme sequence that is immediately upstream of the guide sequence of an RNA component, the first 6 ribonucleotides, for instance, of the ribozyme could be complementary to the first 6 ribonucleotides of the guide sequence. In this example, the hammerhead ribozyme would cleave the RNA transcript immediately upstream of the first position of the guide sequence (or stated another way, the hammerhead ribozyme would cleave the RNA transcript immediately downstream the ribozyme sequence). This logic similarly applies to the other foregoing example embodiments. For example, if a polynucleotide sequence herein encodes an RNA comprising a hammerhead ribozyme sequence that is 8 residues upstream of the guide sequence of an RNA component (e.g., there is an 8-residue spacer sequence), the first 6 ribonucleotides, for instance, of the ribozyme could be complementary to the 6 ribonucleotides immediately 3' of the ribozyme sequence. In this example, the hammerhead ribozyme would cleave the RNA transcript immediately downstream the ribozyme sequence. As yet another example, if a polynucleotide sequence herein encodes an RNA comprising a hammerhead ribozyme sequence that is immediately upstream of the guide sequence of an RNA component, the first 10 ribonucleotides, for instance, of the ribozyme could be complementary to the first 10 ribonucleotides of the guide sequence. In this example, the hammerhead ribozyme would cleave the RNA transcript immediately upstream of the first position of the guide sequence (or stated another way, the hammerhead ribozyme would cleave the RNA transcript immediately downstream the ribozyme sequence).

An example of a hammerhead ribozyme sequence can be presented as follows:

NNNNNNcugaugaguccgugaggacgaaacgaguaagcucguc (SEQ ID NO:15, N can be A, U, C, or G; see Examples). The first 6 residues of SEQ ID NO:15 can be designed to complement (anneal to) the first 6 residues (e.g., of a guide sequence of a crRNA or gRNA disclosed herein) immediately following SEQ ID NO:15 in an RNA transcript expressed from a DNA polynucleotide herein. The ribozyme would cleave the transcript immediately following SEQ ID NO:15. Although SEQ ID NO:15 is shown with 6 residues ("N") for annealing with sequence residues immediately following SEQ ID NO:15, there can be 5 to 15 "N" residues at the beginning of this ribozyme for this purpose. It is noted that, with an RNA transcript comprising SEQ ID NO:15, (i) helix I of the hammerhead ribozyme would be formed by the annealing of the N residues with the first 6 residues immediately following SEQ ID NO:15 in a transcript, (ii) helix II would be formed by the annealing of the complementary sequences indicated with single-underlining, and (iii) helix III would be formed by the annealing of the complementary sequences indicated with double-underlining. Thus, a hammerhead ribozyme in certain embodiments can be a variant of SEQ ID NO:15 having (i) at least about 80%, 85%, 90, 91, 92, 93, 94, 95, 96, 97, 98, or 99% sequence identity (excluding "N" sequence in this calculation) with SEQ ID NO:15, and (ii) regions aligning with the single-underlined and double-underlined regions of SEQ ID NO:15 that anneal to each other to form helices II and III (helix I is formed be appropriate selection of the "N" residues).

Examples of sequences that can be linked to SEQ ID NO:15 and various embodiments thereof (above) include gRNAs comprising one of SEQ ID NOs:64-70.

A DNA polynucleotide herein encoding an RNA sequence comprising a 5' hammerhead ribozyme linked to an RNA component (a "ribozyme-RNA component cassette" herein) may be designed to drive transcription of a transcript with a 5'-end beginning immediately with the hammerhead ribozyme sequence (i.e., ribozyme sequence starts at transcription start site). Alternatively, a DNA polynucleotide may be designed to drive transcription of a transcript having non-ribozyme sequence upstream from the ribozyme-RNA component cassette. Such 5' non-ribozyme transcript sequence can be as short as a few nucleotides (1-10) long, up to as long as 5000-20000 nucleotides, for example (this sequence 5' of the ribozyme is removed from the RNA component when the ribozyme cleaves itself from the RNA component).

In certain embodiments, a DNA polynucleotide comprising a ribozyme-RNA component cassette could comprise a suitable transcription termination sequence downstream of the RNA component sequence. Examples of transcription termination sequences useful herein are disclosed in U.S. Pat. Appl. Publ. No. 2014/0186906, which is herein incorporated by reference. For example, an *S. cerevisiae* Sup4 gene transcription terminator sequence (e.g., SEQ ID NO:8) can be used. Such embodiments typically do not comprise a ribozyme sequence located downstream from a ribozyme-RNA component cassette. Also, such embodiments typically comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more residues following the end of the RNA component sequence, depending on the choice of terminator sequence. These additional residues can be all U residues, or at least 90%, 91%, 92%, 93%, 94%, 95%, 96%, 97%, 98%, or 99% U residues, for example, depending on the choice of terminator sequence. Alternatively, a ribozyme sequence (e.g., hammerhead or HDV ribozyme) can be 3' of (e.g., 1, 2, 3, 4, 5, 6, 7, 8, 9, 10 or more nucleotides) the RNA component sequence; the RNA component sequence in such embodiments is flanked by upstream and downstream ribozymes. A 3' ribozyme sequence can be positioned accordingly such that it cleaves itself from the RNA component sequence; such cleavage would render a transcript ending exactly at the end of the RNA component sequence, or with 1, 2, 3, 4, 5, 6, 7, 8, 9, 10, 11, 12, 13, 14, 15, or more residues following the end of the RNA component sequence, for example.

In certain embodiments, a DNA polynucleotide can comprise (i) a promoter operably linked to (ii) a sequence comprising more than one ribozyme-RNA component cassettes (i.e., tandem cassettes). A transcript expressed from such a DNA polynucleotide can have, for example, 2, 3, 4, 5, 6, 7, 8, 9, 10, or more ribozyme-RNA component cassettes. A 3' ribozyme sequence can optionally be included (e.g., as above) following each RNA component sequence to allow cleavage and separation of the RNA component from downstream transcript sequence. Each RNA component in such embodiments typically is designed to guide an RGEN herein to a unique DNA target site. Thus, such a DNA polynucleotide can be used in a non-conventional yeast accordingly to target multiple different target sites at the same time, for example; such use can optionally be characterized as a multiplexing method. A 5' hammerhead ribozyme that is linked to an RNA component that is linked to a 3' ribozyme can be referred to as a "ribozyme-RNA component-ribozyme cassette" herein. A DNA polynucleotide herein for expressing a transcript comprising tandem ribozyme-RNA component-ribozyme cassettes can be designed such that there are about 10, 20, 30, 40, 50, 60, 70, 80, 90, 100, or more nucleotides between each cassette (e.g., non-coding spacer sequence). The distances between each cassette may be the same or different.

Though certain of the above embodiments have been described in terms of hammerhead ribozyme sequences, such embodiments can also be characterized in terms of any other ribozyme sequence herein (e.g., HDV ribozyme), accordingly, instead of a hammerhead ribozyme sequence. One of ordinary skill in the art would understand how to position such other ribozyme sequence to cleave at a particular site.

A yeast in certain embodiments further comprises a DNA polynucleotide sequence comprising (i) a promoter operably linked to (ii) a nucleotide sequence encoding a Cas protein (e.g., Cas9). This polynucleotide sequence is used by the yeast to express a Cas protein that complexes with an RNA component to form an RGEN. Such a polynucleotide sequence can be in the form of a plasmid, YAC, cosmid, phagemid, BAC, virus, or linear DNA (e.g., linear PCR product), for example, or any other type of vector or construct useful for transferring a polynucleotide sequence into a non-conventional yeast cell. Any Pol II promoter disclosed herein may be used, for example. Any of the features disclosed above regarding a DNA polynucleotide sequence for expressing an RNA component may be applied, accordingly, to a DNA polynucleotide sequence for expressing a Cas protein. This polynucleotide sequence can exist transiently (i.e., not integrated into the genome) or stably (i.e., integrated into the genome) in a yeast cell herein. A yeast in other aspects can have, in addition to a DNA polynucleotide for expressing a Cas protein, a DNA polynucleotide for expressing an RNA component (e.g., as described above). Both these DNA polynucleotides may be stable or transient to the yeast; alternatively, a DNA polynucleotide for expressing a Cas protein can be stable and the DNA polynucleotide for expressing an RNA component can be transient (or vice versa).

A DNA polynucleotide sequence can alternatively be one for expressing both a Cas protein and a suitable RNA component for providing an RGEN in a yeast cell. Such a DNA polynucleotide can comprise, for example, (i) a promoter operably linked to a nucleotide sequence encoding an RNA component (of an RGEN) (an RNA component cassette), and (ii) a promoter operably linked to a nucleotide sequence encoding a Cas protein (e.g., Cas9) (a Cas cassette). Any of the above-described features regarding DNA polynucleotides for expressing a Cas protein or an RNA component can be applied, for example, to a DNA polynucleotide sequence for expressing both a Cas protein and a suitable RNA component in a non-conventional yeast cell. Also, any of the Cas proteins and RNA components (e.g., crRNA or gRNA) disclosed herein may be expressed from this DNA polynucleotide sequence. One or more RNA components and/or Cas cassettes may be comprised within a DNA polynucleotide sequence in certain embodiments. In other aspects, one or more RNA components may be expressed in tandem as described above. Promoters used in a Cas cassette and an RNA cassette may be the same or different. It is contemplated that such a DNA polynucleotide sequence would be useful for expressing an RGEN in both non-conventional yeast and conventional yeast.

The disclosed invention also concerns a method of targeting an RNA-guided endonuclease (RGEN) to a target site sequence in a chromosome or episome in a non-conventional yeast. This method comprises providing to the nucleus of the yeast an RGEN comprising at least one RNA component that does not have a 5'-cap, wherein the RNA component comprises a sequence complementary to the target site sequence, and wherein the RGEN binds to, and optionally cleaves, all or part of the target site sequence.

This targeting method can be practiced using any of the above-disclosed embodiments or below Examples regarding each of the method features (e.g., yeast type, RGEN, RNA component, etc.), for example. Thus, any of the features disclosed above or in the Examples, or any combination of these features, can be used appropriately to characterize embodiments of a targeting method herein. The following targeting method features are examples.

A non-conventional yeast in certain embodiments of a targeting method herein can be a member of any of the following genera: *Yarrowia, Pichia, Schwanniomyces, Kluyveromyces, Arxula, Trichosporon, Candida, Ustilago, Torulopsis, Zygosaccharomyces, Trigonopsis, Cryptococcus, Rhodotorula, Phaffia, Sporobolomyces*, and *Pachysolen. Y. lipolytica* is a suitable *Yarrowia* yeast herein. Other non-limiting examples of non-conventional yeast useful in a targeting method are disclosed herein.

An RGEN suitable for use in a targeting method herein can comprise a Cas protein of a type I, II, or III CRISPR system. A Cas9 protein can be used in certain embodiments, such as a *Streptococcus* Cas9. Examples of *Streptococcus* Cas9 proteins suitable for use in a targeting method include Cas9 proteins comprising amino acid sequences derived from an *S. pyogenes, S. thermophilus, S. pneumoniae, S. agalactiae, S. parasanguinis, S. oralis, S. salivarius, S. macacae, S. dysgalactiae, S. anginosus, S. constellatus, S. pseudoporcinus*, or *S. mutans* Cas9 protein. Other non-limiting examples of RGENs and Cas9 proteins useful in a targeting method herein are disclosed herein. For example, an RGEN that can cleave one or both strands at a DNA target sequence may be used.

An RNA component of an RGEN for use in a targeting method herein can comprise, for example, a gRNA comprising a crRNA operably linked to, or fused to, a tracrRNA. Any crRNA and/or tracrRNA (and/or portion thereof, such as a tracrRNA mate sequence, or tracrRNA 5'-end sequence) as disclosed herein can be comprised in a gRNA, for example. Also, any gRNA disclosed herein can be used in the targeting method, for example.

A PAM (protospacer-adjacent motif) sequence may be adjacent to the target site sequence, for example. In certain embodiments of a targeting method herein, a PAM sequence is immediately downstream from, or within 2, or 3 nucleotides downstream of, a target site sequence that is complementary to the strand in the target site that is in turn complementary to an RNA component guide sequence. In embodiments herein in which the RGEN is an endonucleolytically active Cas9 protein complexed with an RNA component, the Cas9 binds to the target sequence as directed by the RNA component and cleaves both strands immediately 5' of the third nucleotide position upstream of the PAM sequence. Examples of suitable PAM sequences include *S. pyogenes* (NGG [SEQ ID NO:47]) and *S. thermophilus* (NNAGAA [SEQ ID NO:48]) PAM sequences, which can be used for targeting with Cas9 proteins derived from each species, respectively. Also, any PAM sequence as disclosed herein can be used in the targeting method, for example.

A yeast in certain embodiments of a targeting method herein further comprises a DNA polynucleotide sequence comprising (i) a promoter operably linked to (ii) a nucleotide sequence encoding an RNA component. It is with such a DNA polynucleotide that an RNA component of an RGEN can be provided to the nucleus of a yeast, since the RNA component is transcribed from the DNA polynucleotide. Examples of suitable DNA polynucleotide sequences for expressing an RNA component (of an RGEN) in a yeast nucleus are disclosed herein. Any of the promoters as disclosed herein can be used in such a DNA polynucleotide sequence, for example, such as a strong promoter and/or one that comprises a Pol II promoter sequence. In certain embodiments, a DNA polynucleotide encoding an RNA component can be used to provide an RNA component in a yeast that has already been engineered to express a Cas protein (e.g., stable Cas expression).

A nucleotide sequence herein encoding an RNA component may further encode a ribozyme that is upstream of the sequence encoding the RNA component, for example. Thus, a yeast in certain embodiments of a targeting method herein may comprise a DNA polynucleotide sequence comprising (i) a promoter operably linked to (ii) a nucleotide sequence encoding, in 5'-to-3' direction, a ribozyme and an RNA component. It is with such a DNA polynucleotide that an RNA component of an RGEN can be provided to the nucleus of a yeast, since the RNA component is transcribed from the DNA polynucleotide. A ribozyme herein can be a hammerhead ribozyme, hepatitis delta virus (HDV) ribozyme, group I intron ribozyme, RnaseP ribozyme, or hairpin ribozyme, for example. Any ribozyme as disclosed herein, as well as any polynucleotide sequence as disclosed herein encoding a ribozyme linked to an RNA component, can be used in the targeting method, for example.

A yeast in certain embodiments of a targeting method herein may further comprise a DNA polynucleotide sequence comprising (i) a promoter operably linked to (ii) a nucleotide sequence encoding a Cas protein (e.g., Cas9). It is with such a DNA polynucleotide that a Cas protein component of an RGEN can be provided in the yeast. Examples of suitable DNA polynucleotide sequences for expressing a Cas protein component (of an RGEN) in a yeast are disclosed herein. Any of the promoters as disclosed herein can be used in such a DNA polynucleotide sequence, for example, such as a strong promoter.

A donor polynucleotide comprising at least one sequence homologous to a sequence at or near a DNA target site sequence can also be provided to the yeast in certain embodiments of a targeting method (along with providing an RGEN that nicks or cuts at the target site sequence). Suitable examples include donor polynucleotides with homology arms. Any donor polynucleotide as disclosed herein can be used in a targeting method, for example. Such embodiments of this method typically involve HR between the donor polynucleotide and the target sequence (after RGEN-mediated nicking or cleavage of the target sequence); thus, these this method can optionally also be referred to as a method of performing HR in a non-conventional yeast. Examples of HR strategies that can be performed by this method are disclosed herein. A suitable amount of a donor DNA polynucleotide for targeting in a yeast cell can be at least about 300, 400, 500, 600, 700, or 800 molecules of the donor DNA per yeast cell.

Any constructs or vectors comprising a DNA polynucleotide described herein for expressing RGEN components may be introduced into a non-conventional yeast cell by any standard technique. These techniques include transformation (e.g., lithium acetate transformation (*Methods in Enzymology,* 194:186-187), biolistic impact, electroporation, and microinjection, for example. As examples, U.S. Pat. Nos. 4,880,741 and 5,071,764, and Chen et al. (*Appl. Microbiol. Biotechnol.* 48:232-235), which are incorporated herein by reference, describe DNA transfer techniques for *Y. lipolytica.*

A targeting method herein can be performed for the purpose of creating an indel in a non-conventional yeast. Such a method can be performed as disclosed above, but without further providing a donor DNA polynucleotide that could undergo HR at or near the target DNA site (i.e., NHEJ is induced in this method). Examples of indels that can be created are disclosed herein. The size of an indel may be 1, 2, 3, 4, 5, 6, 7, 8, 9, 10, or more bases, for example. An indel in certain embodiments can be even larger such as at least about 20, 30, 40, 50, 60, 70, 80, 90, 100, 110, 120, 130, 140, or 150 bases. In still other embodiments, insertions or deletions can be at least about 500, 750, 1000, or 1500 bases. When attempting to create an indel in certain embodiments, a single base substitution may instead be formed in a target site sequence. Thus, a targeting method herein can be performed for the purpose of creating single base substitution, for example.

In certain embodiments of a targeting method herein aimed at indel formation, the frequency of indel formation in a non-conventional yeast (e.g., *Y. lipolytica*) is significantly higher than what would be observed using the same or similar targeting strategy in a conventional yeast such as *S. cerevisiae*. For example, while the frequency of indel formation in a conventional yeast may be about 0.0001 to 0.001 (DiCarlo et al., *Nucleic Acids Res.* 41:4336-4343), the frequency in a non-conventional yeast herein may be at least about 0.05, 0.10, 0.15, 0.20, 0.25, 0.30, 0.35, 0.40, 0.45, 0.50, 0.55, 0.60, 0.65, 0.70, 0.75, or 0.80. Thus, the frequency of indel formation in a non-conventional yeast herein may be at least about 50, 100, 250, 500, 750, 1000, 2000, 4000, or 8000 times higher, for example, than what would be observed using the same or similar Cas-mediated targeting strategy in a conventional yeast. Certain aspects of these embodiments can be with regard to a targeting method that does not include a donor DNA, and/or in which RGEN components (a Cas and a suitable RNA component) are expressed from the same vector/construct.

A targeting method herein can be performed in such a way that 2 or more DNA target sites are targeted in the method, for example. Such a method can comprise providing to a yeast a DNA polynucleotide that expresses a transcript comprising tandem ribozyme-RNA component cassettes (e.g., tandem ribozyme-RNA component-ribozyme cassettes) as disclosed herein. This method can target DNA sites very close to the same sequence (e.g., a promoter or open reading frame, and/or sites that are distant from each other (e.g., in different genes and/or chromosomes). Such a method can be performed with (for HR) or without (for NHEJ leading to indel and/or base substitution) suitable donor DNA polynucleotides, depending on the desired outcome of the targeting.

A targeting method in certain embodiments can be performed to disrupt one or more DNA polynucleotide sequences encoding a protein or a non-coding RNA. An example of such a sequence that can be targeted for disruption is one encoding a marker (i.e., a marker gene). Non-limiting examples of markers herein include screenable markers and selectable markers. A screenable marker herein can be one that renders a yeast visually different under appropriate conditions. Examples of screenable markers include polynucleotides encoding beta-glucuronidase (GUS), beta-galactosidase (lacZ), and fluorescent proteins (e.g., GFP, RFP, YFP, BFP). A selectable marker herein can be one that renders a yeast resistant to a selective agent or selective environment. Examples of selectable markers are auxotrophic markers such as HIS3, LEU2, TRP1, MET15, or URA3, which allow a yeast to survive in the absence of exogenously provided histidine, leucine, tryptophan, methionine, or uracil, respectively. Other examples of selectable markers are antibiotic (antifungal)-resistance markers such as those rendering a yeast resistance to hygromycin B, nourseothricin, phleomycin, puromycin, or neomycin (e.g., G418).

At least one purpose for disrupting a marker in certain embodiments can be for marker recycling. Marker recycling is a process, for example, comprising (i) transforming a yeast with a marker and heterologous DNA sequence, (ii) selecting a transformed yeast comprising the marker and the heterologous DNA sequence (where marker-selectable yeast typically have a higher chance of containing the heterologous DNA sequence), (iii) disrupting the marker, and then repeating steps (i)-(iii) as many times as necessary (using the same marker, but each cycle using a different heterologous DNA sequence) to transform the yeast with multiple heterologous DNA sequences. One or more heterologous sequences in this process may comprise the marker itself in the form of a donor polynucleotide(e.g., marker flanked by homology arms for targeting a particular locus). Examples of marker recycling processes herein include those using URA3 as a marker in non-conventional yeast such as *Y. lipolytica*.

Non-limiting examples of compositions and methods disclosed herein are as follows:

1. A non-conventional yeast comprising at least one RNA-guided endonuclease (RGEN) comprising at least one RNA component that does not have a 5'-cap, wherein the RNA component comprises a sequence complementary to a target site sequence on a chromosome or episome in the yeast, wherein the RGEN can bind to all or part of the target site sequence.
2. The non-conventional yeast of embodiment 1, wherein the RGEN can bind to and cleave all or part of the target site sequence.
3. The yeast of embodiment 1, wherein said yeast is a member of a genus selected from the group consisting of *Yarrowia, Pichia, Schwanniomyces, Kluyveromyces, Arxula, Trichosporon, Candida, Ustilago, Torulopsis, Zygosaccharomyces, Trigonopsis, Cryptococcus, Rhodotorula, Phaffia, Sporobolomyces*, and *Pachysolen*.
4. The yeast of embodiment 1, wherein the RGEN comprises a CRISPR (clustered regularly interspaced short palindromic repeats)-associated (Cas) protein-9 (Cas9) amino acid sequence.
5. The yeast of embodiment 4, wherein the Cas9 protein is a *Streptococcus* Cas9 protein.
6. The yeast of embodiment 4, wherein the RNA component comprises a guide RNA (gRNA) comprising a CRISPR RNA (crRNA) operably linked to a trans-activating CRISPR RNA (tracrRNA).
7. The yeast of embodiment 4, wherein a PAM (protospacer-adjacent motif) sequence is adjacent to the target site sequence.
8. A non-conventional yeast comprising a polynucleotide sequence comprising a promoter operably linked to at least one nucleotide sequence, wherein said nucleotide sequence comprises a DNA sequence encoding a ribozyme upstream of a DNA sequence encoding an RNA component, wherein said RNA component comprises a variable targeting domain complementary to a target site sequence on a chromosome or episome in the yeast, wherein the RNA component can form a RNA-guided endonuclease (RGEN), wherein said RGEN can bind to all or part of the target site sequence.
9. The non-conventional yeast of embodiment 8, wherein the RGEN can bind to and cleave all or part of the target site sequence.

10. The non-conventional yeast of embodiment 8, wherein the RNA transcribed from the nucleotide sequence autocatalytically removes the ribozyme to yield said RNA component, wherein said RNA component does not have a 5' cap.
11. The non-conventional yeast of embodiment 10, wherein the ribozyme is a hammerhead ribozyme, hepatitis delta virus ribozyme, group I intron ribozyme, RnaseP ribozyme, or hairpin ribozyme.
12. The non-conventional yeast of embodiment 8, wherein the RNA transcribed from the nucleotide sequence does not autocatalytically removes the ribozyme to yield a ribozyme-RNA component fusion molecule without a 5' cap.
13. The non-conventional yeast of embodiment 12, wherein the ribozyme is a HDV ribozyme.
14. The non-conventional yeast of embodiment 8, wherein the promoter is a strong promoter.
15. The non-conventional yeast of embodiment 8, wherein the promoter comprises a Pol II promoter sequence.
16. A method of targeting an RNA-guided endonuclease (RGEN) to a target site sequence on a chromosome or episome in a non-conventional yeast, said method comprising providing to said yeast an RGEN comprising at least one RNA component that does not have a 5'-cap, wherein the RNA component comprises a sequence complementary to the target site sequence, wherein the RGEN binds to all or part of the target site sequence.
17. The method of embodiment 16, wherein the RGEN can bind to and cleave all or part of the target site sequence.
18. A method of targeting an RNA-guided endonuclease (RGEN) to a target site sequence on a chromosome or episome in a non-conventional yeast, said method comprising providing to said yeast an RGEN comprising at least one ribozyme-RNA component fusion molecule, wherein the RNA component comprises a sequence complementary to the target site sequence, wherein the RGEN binds to all or part of the target site sequence.
19. The method of embodiment 18, wherein the RGEN can bind to and cleave all or part of the target site sequence.
20. A method of targeting an RNA-guided endonuclease (RGEN) to a target site sequence on a chromosome or episome in a non-conventional yeast, said method comprising providing to said yeast a first recombinant DNA construct comprising a DNA sequence encoding a Cas endonuclease, and at least a second recombinant DNA construct comprising a DNA sequence encoding a ribozyme upstream of an RNA component, wherein the RNA transcribed from the second recombinant DNA construct autocatalytically removes the ribozyme to yield said RNA component , wherein the RNA component and the Cas9 endonuclease can form an RGEN that can bind to all or part of the target site sequence.
21. The method of embodiment 20, wherein the RGEN can bind to and cleave all or part of the target site sequence.
22. A method of targeting an RNA-guided endonuclease (RGEN) to a target site sequence on a chromosome or episome in a non-conventional yeast, said method comprising providing to said yeast a first recombinant DNA construct comprising a DNA sequence encoding a Cas endonuclease, and at least a second recombinant DNA construct comprising a DNA sequence encoding a ribozyme-RNA component fusion molecule, wherein said ribozyme-RNA component fusion molecule and the Cas9 endonuclease can form an RGEN that can bind to, and optionally cleave, all or part of the target site sequence.

23. The method of embodiment 22, wherein the RGEN can bind to and cleave all or part of the target site sequence.
24. A method for modifying a target site on a chromosome or episome in a non-conventional yeast, the method comprising providing to a non-conventional yeast a first recombinant DNA construct comprising a DNA sequence encoding a Cas endonuclease, and a second recombinant DNA construct comprising a DNA sequence encoding a ribozyme upstream of an RNA component, wherein the RNA transcribed from the second recombinant DNA construct autocatalytically removes the ribozyme to yield said RNA component that does not have a 5' cap, wherein the Cas9 endonuclease introduces a single or double-strand break at said target site.
25. A method for modifying a target site on a chromosome or episome in a non-conventional yeast, the method comprising providing to a non-conventional yeast a first recombinant DNA construct comprising a DNA sequence encoding a Cas endonuclease, and a second recombinant DNA construct comprising a DNA sequence encoding a ribozyme-RNA component fusion molecule that does not have a 5'cap, wherein said ribozyme-RNA component fusion molecule and the Cas9 endonuclease can form a RGEN that introduces a single or double-strand break at said target site.
26. A method for modifying multiple target sites on a chromosome or episome in a non-conventional yeast, the method comprising providing to a non-conventional yeast at least a first recombinant DNA construct comprising a DNA sequence encoding a Cas endonuclease, and at least a second recombinant DNA construct comprising a promoter operably linked to at least one polynucleotide, wherein said at least one polynucleotide encodes an RNA molecule comprising a ribozyme upstream of an RNA component, wherein said RNA molecule autocatalytically removes the ribozyme to yield said RNA component , wherein the Cas9 endonuclease introduces a single or double-strand break at said target site.
27. A method for modifying multiple target sites on a chromosome or episome in a non-conventional yeast, the method comprising providing to a non-conventional yeast at least a first recombinant DNA construct comprising a DNA sequence encoding a Cas endonuclease, and at least a second recombinant DNA construct comprising a promoter operably linked to at least one polynucleotide, wherein said at least one polynucleotide encodes a ribozyme-RNA component fusion molecule, wherein said ribozyme-RNA component fusion molecule and the Cas9 endonuclease can form a RGEN that introduces a single or double-strand break at said target site.
28. The method of any of embodiments 22-25, further comprising identifying at least one non-conventional yeast cell that has a modification at said target, wherein the modification includes at least one deletion, addition or substitution of one or more nucleotides in said target site.
29. The method of any of embodiments 24-28, further comprising providing a donor DNA to said yeast, wherein said donor DNA comprises a polynucleotide of interest.
30. The method of embodiment 29, further comprising identifying at least one yeast cell comprising in its chromosome or episome the polynucleotide of interest integrated at said target site.
31. A method for editing a nucleotide sequence on a chromosome or episome in a non-conventional yeast, the method comprising providing to a non-conventional yeast a polynucleotide modification template DNA, a first recombinant DNA construct comprising a DNA sequence encoding a Cas endonuclease, and a second recombinant DNA construct comprising a DNA sequence encoding a ribozyme upstream of an RNA component, wherein the RNA transcribed from the second recombinant DNA construct autocatalytically removes the ribozyme to yield said RNA component that does not have a 5'cap, wherein the Cas9 endonuclease introduces a single or double-strand break at a target site in the chromosome or episome of said yeast, wherein said a polynucleotide modification template DNA comprises at least one nucleotide modification of said nucleotide sequence.
32. A method for editing a nucleotide sequence on a chromosome or episome in a non-conventional yeast, the method comprising providing to a non-conventional yeast a polynucleotide modification template DNA, a first recombinant DNA construct comprising a DNA sequence encoding a Cas endonuclease, and a second recombinant DNA construct comprising a DNA sequence encoding a ribozyme-RNA component fusion molecule that does not have a 5'cap, wherein said ribozyme-RNA component fusion molecule and the Cas9 endonuclease can form a RGEN that introduces a single or double-strand break at a target site in the chromosome or episome of said yeast, wherein said a polynucleotide modification template DNA comprises at least one nucleotide modification of said nucleotide sequence.
33. A method for editing a nucleotide sequences on a chromosome or episome in a non-conventional yeast, the method comprising providing to a non-conventional yeast at least one a polynucleotide modification template DNA, at least a first recombinant DNA construct comprising a DNA sequence encoding a Cas endonuclease, and at least a second recombinant DNA construct comprising a promoter operably linked to at least one polynucleotide, wherein said at least one polynucleotide encodes an RNA molecule comprising a ribozyme upstream of an RNA component, wherein said RNA molecule autocatalytically removes the ribozyme to yield said RNA component that does not have a 5'cap , wherein the Cas9 endonuclease introduces a single or double-strand break at a target site in the chromosome or episome of said yeast, wherein said polynucleotide modification template DNA comprises at least one nucleotide modification of said nucleotide sequence.
34. A method for editing a nucleotide sequence on a chromosome or episome in a non-conventional yeast, the method comprising providing to a non-conventional yeast at least one a polynucleotide modification template DNA, at least a first recombinant DNA construct comprising a DNA sequence encoding a Cas endonuclease, and at least a second recombinant DNA construct comprising a promoter operably linked to at least one polynucleotide, wherein said at least one polynucleotide encodes a ribozyme-RNA component fusion molecule that does not have a 5'cap, wherein said ribozyme-RNA component fusion molecule and the Cas9 endonuclease can form a RGEN that introduces a single or double-strand break at a target site in the chromosome or episome of said yeast, wherein said a polynucleotide modification template DNA comprises at least one nucleotide modification of said nucleotide sequence.
35. The method of any of embodiments 24-34 wherein the first recombinant DNA and the second recombinant DNA are located on the same plasmid.
36. The method of any of embodiments 24-34 wherein the first recombinant DNA and the second recombinant DNA are located on separate plasmid.

37. A method for silencing a nucleotide sequence on a chromosome or episome in a non-conventional yeast, the method comprising providing to a non-conventional yeast, at least a first recombinant DNA construct comprising a DNA sequence encoding an inactivated Cas9 endonuclease, and at least a second recombinant DNA construct comprising a promoter operably linked to at least one polynucleotide, wherein said at least one polynucleotide encodes a ribozyme-RNA component fusion molecule that does not have 5'cap, wherein said ribozyme-RNA component fusion molecule and the inactivated Cas9 endonuclease can form a RGEN that binds to said nucleotide sequence in the chromosome or episome of said yeast, thereby blocking transcription of said nucleotide sequence.

38. A high throughput method for the production of multiple guide RNAs for gene modification in non-conventional yeast, the method comprising:

a) providing a recombinant DNA construct comprising a promoter operably linked to, in 5' to 3' order, a first DNA sequence encoding a ribozyme, a second DNA sequence encoding a counterselection agent, a third DNA sequence encoding a CER domain of a guide RNA, and a terminator sequence;

b) providing at least one oligonucleotide duplex to the recombinant DNA construct of (a), wherein said oligonucleotide duplex is originated from combining a first single stranded oligonucleotide comprising a DNA sequence capable of encoding a variable targeting domain (VT) of a guide RNA target sequence with a second single stranded oligonucleotide comprising the complementary sequence to the DNA sequence encoding the variable targeting domain;

c) exchanging the counterselection agent of (a) with the at least one oligoduplex of (b), thereby creating a library of recombinant DNA constructs each comprising a DNA sequence capable of encoding a variable targeting domain of a guide RNA; and, d) transcribing the library of recombinant DNA constructs of (c), thereby creating a library of ribozyme-guideRNA molecules.

39. The method of embodiment 38, further comprising inducing the library of ribozyme-guide RNA molecules such that said molecules autocatalitically remove the ribozyme and aany RNA sequence upstream of the ribozyme to yield a library of guide RNA molecules that do not contain 5' cap.

40. The method of embodiment 38, further comprising inducing the library of ribozyme-guide RNA molecules such that said molecules cleaves any RNA sequence upstream of the ribozyme TO yield a ribozyme-gRNA fusion molecules that do not contain 5' cap.

41. A recombinant DNA sequence comprising (i) a polymerase-II promoter operably linked to (ii) a nucleotide sequence encoding a ribozyme and a guide RNA, wherein said ribozyme is upstream of said guide RNA, wherein RNA transcribed from the nucleotide sequence of (ii) autocatalically removes the ribozyme to yield said guide RNA, and wherein said guide RNA can form a RGEN that can recognize, bind to, and optionally cleave a target site in the genome of a non-conventional yeast.

42. A recombinant RNA sequence comprising a ribozyme and a guide RNA, wherein said ribozyme is upstream of said guide RNA, wherein said ribozyme can be autocatalically removed to yield said guide RNA, and wherein said guide RNA can form a RGEN that can recognize, bind to, and optionally cleave a target site in the genome of a non-conventional yeast.

43. A recombinant DNA sequence comprising (i) a polymerase-II promoter operably linked to (ii) a nucleotide sequence encoding a ribozyme and a guide RNA, wherein said ribozyme is upstream of said guide RNA, wherein RNA transcribed from the nucleotide sequence of (ii) yields a ribozyme-guide RNA fusion molecule, and wherein said ribozyme-guide fusion molecule can form a RGEN that can recognize, bind to, and optionally cleave a target site in the genome of a non-conventional yeast.

44. A recombinant RNA sequence comprising a ribozyme -guide RNA fusion molecule, wherein said ribozyme-guide RNA fusion molecule can form a RGEN that can recognize, bind to, and optionally cleave a target site in the genome of a non-conventional yeast.

EXAMPLES

The disclosed invention is further defined in the following Examples. It should be understood that these Examples, while indicating certain preferred aspects of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Example 1 sgRNA Expressed from a Pol III Promoter in *Yarrowia* Does Not Guide Cas9 to Target Sites and Mediate DNA Cleavage This example discloses vectors and cassettes designed to express sgRNAs and Cas9 protein in *Yarrowia lipolytica* targeting the Leu2 locus. If sgRNAs and Cas9 produced in this yeast can interact, find and cleave target sites, mutations should be generated via error-prone non-homologous end-joining (NHEJ) at the target sites.

FIG. 1 illustrates a sgRNA molecule, which is a single RNA molecule containing two regions, a variable targeting domain (VT) (guide sequence) and Cas endonuclease recognition domain (CER). The VT region can be a 20 mer of RNA polynucleotide that has identity to a targeted nucleic acid molecule. The VT domain specifies a target site for cleavage in the target site that lies 5' of a PAM motif (e.g., NGG, SEQ ID NO:47). The CER domain interacts with Cas9 protein and allows the VT domain to interact and direct the Cas9 protein cleavage (Jinek et al., *Science* 337:816-821). Both VT and CER domains are required for the function of an sgRNA.

DNA sequences encoding VT domains that target Cas9 to three individual target sites (Leu2-1, Leu2-2, Leu2-3) in the coding region of the LEU2 locus of *Yarrowia* are listed in Table 3. Table 3 also lists a DNA sequence encoding a VT domain targeting the coding region of the *Yarrowia* CAN1 locus.

TABLE 3

DNA Sequences Encoding sgRNA VT domains for Targeting the LEU2 or CAN1 Locus in *Yarrowia* with Cas9

| | |
|---|---|
| Leu2-1[a] (SEQ ID NO: 2) | TCCAAGAAGATTGTTCTTCT |
| Leu2-2[a] (SEQ ID NO: 3) | CTCCGTCATCCCCGGTTCTC |

TABLE 3-continued

DNA Sequences Encoding sgRNA VT domains for Targeting the LEU2 or CAN1 Locus in *Yarrowia* with Cas9

| | |
|---|---|
| Leu2-3[a] (SEQ ID NO: 4) | CGGCGACTTCTGTGGCCCCG |
| Can1-1[b] (SEQ ID NO: 17) | TCAAACGATTACCCACCCTC |

[a]The LEU2 gene sites targeted by Leu2-1, Leu2-2, and Leu2-3 have a CGG, TGG, or AGG, respectively, as a PAM site.
[b]The CAN1 gene site targeted by Can1-1 has a CGG as a PAM site.

Each of the LEU2-targeting DNA sequences in Table 3 was individually fused to a DNA sequence encoding a CER domain (SEQ ID NO:1) that interacts with *Streptococcus pyogenes* Cas9 protein, thereby creating DNA sequences encoding complete sgRNAs having both a CER domain and VT domain (note that SEQ ID NO:1 comprises in the 5'-to-3' direction the tracrRNA mate sequence of SEQ ID NO:56, the loop-forming sequence of SEQ ID NO:43 (GAAA), and the tracrRNA sequence of SEQ ID NO:58. In order to express these sgRNAs in the nucleus of the cell and evade nuclear export and 5' modification systems, DNA sequences encoding the sgRNAs were put under control of RNA Pol III promoters from *Saccharomyces cerevisiae* (Snr52 [SEQ ID NO:5] or Rpr1 [SEQ ID NO:6]) or *Yarrowia lipolytica* (Snr52 [SEQ ID NO:7]). Specifically, Sc Snr52 was fused to Leu2-1, Sc Rpr1 was fused to Leu2-2, and Yl Snr52 was fused to Leu2-3. The 3' end of the DNA sequence encoding each sgRNA was fused to a strong terminator from the Sup4 gene of *Saccharomyces cerevisiae* (SEQ ID NO:8). Thus, three different Pol III-driven sgRNA cassettes were prepared.

The open reading frame of the Cas9 gene from *Streptococcus pyogenes* M1 GAS (SF370) was codon-optimized for expression in *Yarrowia* per standard techniques, yielding SEQ ID NO:9. DNA sequence encoding a simian virus 40 (SV40) monopartite nuclear localization signal (NIL) plus a short linker (4 amino acids) was incorporated after the last sense codon of SEQ ID NO:9 to render SEQ ID NO:10. SEQ ID NO:10 encodes the amino acid sequence shown in SEQ ID NO:11. The last seven amino acids of SEQ ID NO:11 encode the added NIL, whereas residues at positions 1369-1372 of SEQ ID NO:11 encode the added linker. The *Yarrowia* codon-optimized Cas9-NIL sequence (SEQ ID NO:10) was fused to a *Yarrowia* constitutive promoter, FBA1 (SEQ ID NO:12), by standard molecular biology techniques. An example of a *Yarrowia* codon-optimized Cas9 expression cassette (SEQ ID NO:13) is illustrated in FIG. 2A containing the constitutive FBA1 promoter, *Yarrowia* codon-optimized Cas9, and the SV40 NIL. This Cas9 expression cassette (SEQ ID NO:13) was cloned into the plasmid pZUF rendering construct pZUFCas9 (FIG. 3A, SEQ ID NO:14).

Each of the sgRNA expression cassettes (above) were individually cloned into the PacI/ClaI site of pZUFCas9 (SEQ ID NO:14) to render a pZUFCas9/sgRNA construct that could be used to co-transform yeast cells with the *Yarrowia* codon-optimized Cas9 expression cassette and a Pol III-driven sgRNA expression cassette. An example of such a construct is pZUFCas9/PolIII-sgRNA (FIG. 3B), which contains the Yl Snr52 -sgRNA expression cassette for targeting Leu2-3 in *Yarrowia.*

Uracil auxotrophic *Y. lipolytica* cells were transformed with 200 ng of plasmids pZUFCas9 (SEQ ID NO:14) or a particular pZUFCas9/sgRNA (e.g., pZUFCas9/PolIII-sgRNA, FIG. 3B) and selected for uracil prototrophy on complete minimal plates lacking uracil (CM-ura). Colonies arising on the CM-ura plates were screened for leucine auxotrophy on complete minimal plates lacking leucine (CM-leu). None of the uracil prototroph transformants displayed leucine auxotrophy. These results suggest that the *Yarrowia* codon-optimized Cas9 and Pol III promoter-driven sgRNA were not expressed, were not produced, did not interact, did not target DNA, and/or did not cleave DNA. If this experiment had produced leucine auxotrophs, such results would likely have indicated that a Cas9/sgRNA complex targeted and cleaved the Leu2 coding region leading to error-prone NHEJ and consequent indel formation, creating frameshift mutations.

Thus, it appears that Pol III-driven expression of sgRNA might not be useful for providing a functional Cas9-sgRNA complex in *Yarrowia.*

Example 2

*Yarrowia*-Optimized sgRNA Expression Cassettes Comprising 5'- and 3'-Ribozymes Driven by DNA Polymerase II Promoters This example discloses sgRNAs optimized for expression and Cas9-mediated targeting in *Yarrowia*. Each cassette used for such expression comprised a Pol II promoter for driving transcription of an sgRNA fused to a 5'-ribozyme and 3'-ribozyme (ribozyme-sgRNA-ribozyme, or RGR). The 5' and 3' ribozymes were provided to remove Pol II promoter-related transcript modifications from the sgRNA such as 5' cap structures, leaving just the sgRNA sequence. These expression cassettes allow a broader promoter choice for sgRNA expression. Also, sgRNAs transcribed from these cassettes are not subject to nuclear export since they lack a 5'-cap structure. These features allow robust expression of sgRNA in *Yarrowia* cells so they might guide Cas9 endonuclease to targeted regions of the genome in vivo.

The addition of 5' HammerHead (HH) and 3' Hepatitis Delta Virus (HDV) ribozymes to a sgRNA sequence allows expression of the sgRNA from any promoter without consideration for post-transcriptional modifications that occur at promoters transcribed by some RNA polymerases (e.g. Pol II) and circumvents the current limited selection of promoters for sgRNA expression. When such sgRNA is expressed, the ribozymes present in the pre-sgRNA transcript auto-cleave, thereby separating from the transcript leaving an unmodified sgRNA.

For each sgRNA tested, DNA sequence encoding the sgRNA was fused (i) at its 5'-end to a sequence encoding a 5' HH ribozyme (SEQ ID NO:15) and (ii) at its 3'-end to a sequence encoding a 3' HDV ribozyme (SEQ ID NO:16). The 5'-linkage of the HH ribozyme was such that the first 6 nucleotides of the HH ribozyme were the reverse compliment of the first 6 nucleotides of the VT region (guide sequence) of the sgRNA. Each ribozyme-flanked pre-sgRNA (RGR) was fused to the FBA1 promoter (SEQ ID NO:12) using standard molecular biology techniques to yield a *Yarrowia*-optimized sgRNA expression cassette (final cassette depicted in FIG. 2B). An example sequence of such a cassette is shown in SEQ ID NO:18, which comprises an FBA1 promoter (SEQ ID NO:12) operably linked to a sequence encoding an RGR (HH-sgRNA-HDV) in which the sgRNA comprises a VT domain encoded by SEQ ID NO:17 (Can1-1) and SEQ ID NO:1 as its CER domain (note that each of the CER domain-coding regions of SEQ ID NO:18, pRF38 (SEQ ID NO:19) and pRF84 (SEQ ID NO:41) have an added 'TGG', where such 'TGG' is between residue positions corresponding to positions 73-74 of SEQ ID NO:1 (CER domain)). This VT domain targets a site in the coding region of the *Yarrowia* CAN1 gene open reading frame (GenBank Accession No. NC_006068, YALIOB19338g, ~bp 2557513-2559231 of chromosome B). The first 6 residues of the encoded HH ribozyme are complementary to the first 6 residues of the sgRNA (i.e., first 6 residues of the VT domain). Note that there are three residues (ATG) immediately following SEQ ID NO:12 (FBA1 promoter) in SEQ ID NO:18 which are not believed to affect expression and ribozyme-mediated autocatalysis of the pre-sgRNA. SEQ ID NO:18 was cloned into a construct termed pRF38 (FIG. 3C, SEQ ID NO:19).

Thus, DNA cassettes for expressing sgRNA without 5' and 3' pol II promoter-related transcript modifications were prepared. These type of cassettes were used in Example 3 for Cas9 gene targeting in *Yarrowia.*

EXAMPLE 3

*Yarrowia*-Optimized sgRNA Can be Used in an sgRNA/Cas9 Endonuclease System to Cleave Chromosomal DNA This example discloses using *Yarrowia*-optimized sgRNA expression cassettes as described in Example 2 to express sgRNA that can function with Cas9 to recognize and cleave chromosomal DNA in *Yarrowia*. Such cleavage was manifested by the occurrence of mutations in the region of the predicted DNA cleavage site due to error-prone NHEJ DNA repair at the cleavage site.

The CAN1 gene of *Y. lipolytica* was targeted for cleavage. Successful targeting of CAN1 in *Yarrowia* transformants was examined by phenotype (canavanine resistance) and sequencing for mutation frequency and spectra, respectively.

$Ura^-$ *Y. lipolytica* cells (strain Y2224, a uracil auxotroph derived directly from strain ATCC 20362, is disclosed in U.S. Patent Appl. Publ. No. 2010/0062502, which is incorporated herein by reference) were co-transformed by lithium ion-mediated transformation (Ito et al., *J. Bacteriology* 153: 163-168) with pZUFCas9 (FIG. 3A, SEQ ID NO:14) and a linear PCR product amplified from pRF38 (FIG. 3C, SEQ ID NO:19) containing the Yarrowia-optimized RGR pre-sgRNA cassette (comprised in SEQ ID NO:18) for targeting the CAN1 locus. The primers used for this PCR amplification were SEQ ID NO:20 (Forward) and SEQ ID NO:21 (Reverse). $Ura^-$ *Y. lipolytica* cells (Y2224) cells transformed with pZUFCas9 (SEQ ID NO:14) alone served as a negative control. Cells transformed with pZUFCas9 (SEQ ID NO:14) and the RGR pre-sgRNA expression cassettes were selected on CM-ura medium as uracil prototrophs. Cells containing loss-of-function mutations in the CAN1 gene were screened by replica-plating the CM-ura plates onto complete minimal medium lacking uracil, lacking arginine, and supplemented with 60 μg/ml of the toxic arginine analog, canavanine (CM+can). Cells with a functional CAN1 gene can transport canavanine into the cells causing cell death. Cells with a loss-of-function allele in the CAN1 gene do not transport canavanine and are able to grow on the CM+can plates.

Figure 4:
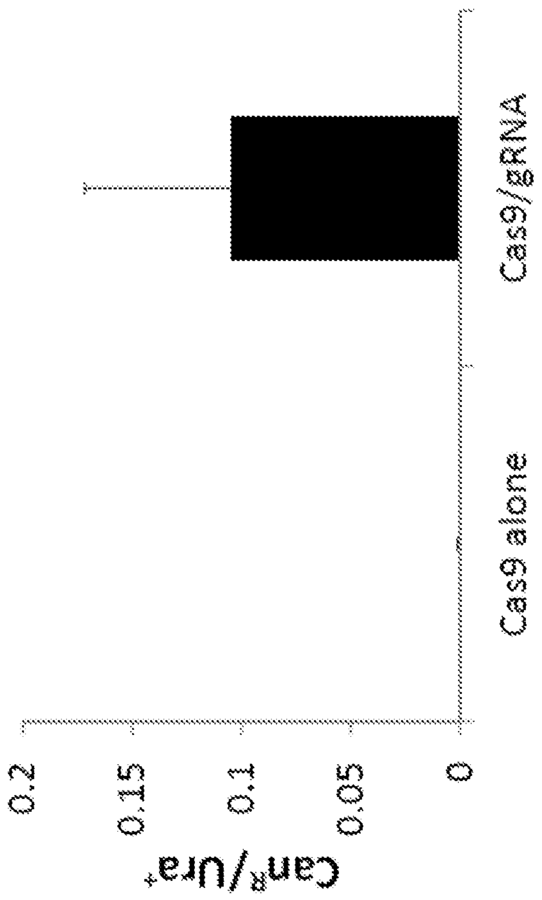

The frequency of loss-of-function mutants recovered by the phenotypic screen of canavanine resistance was zero for cells transformed with Cas9 alone (FIG. 4). However, when Cas9 was co-transformed with the RGR pre-sgRNA expression cassette, the frequency of canavanine-resistant transformants was increased to ten percent (FIG. 4).

The CAN1 locus of canavanine-resistant colonies was amplified using forward (SEQ ID NO:22) and reverse (SEQ ID NO:23) PCR primers. PCR products were purified using Zymoclean™ and concentrator columns (Zymo Research, Irvine, Calif.). The PCR products were sequenced (Sanger method) using sequencing primer SEQ ID NO:24. Sequences were aligned with wild-type (WT) *Yarrowia* CAN1 coding sequence containing the target site (FIG. 5). The primary loss-of-function mutation (73% of sequenced isolates) at the CAN1 locus in cells expressing both Cas9 and the sgRNA was a -1 frameshift mutation at the Cas9 cleavage site (FIG. 5). A smaller number of other deletions and insertions made up the remainder of the mutations at the CAN1 locus. In all, 90% of the mutations were small deletions or insertions (FIG. 5). Rarely, other events occurred such as the insertion of small amounts of sequence from another chromosome (4%), insertion of the *Yarrowia*-optimized sgRNA expression cassette at the cleavage site (1.5%), or larger deletions (1%). 3.5% of the canavanine-resistant colonies screened had complex rearrangements at the CAN1 locus which were not determined by sequencing. Altogether, the mutations observed at the CAN1 target site indicate that error-prone NHEJ was used in the cells to repair the cleavage made by the Cas9/sgRNA complex.

Both (i) the increased frequency of canavanine-resistant colonies in cells transformed to express a CAN1-specific Cas9 endonuclease, and (ii) the sequencing data indicating that the canavanine-resistance mutations were due to error-prone NHEJ events at the predicted Cas9 cleavage site, confirm that the *Yarrowia*-optimized Cas9 and RGR pre-sgRNA expression cassettes described in Example 2 cleave *Yarrowia* chromosomal DNA and generate mutations.

Thus, expressing an RNA component (e.g., sgRNA) of an RGEN (e.g., Cas9) not having a 5'-cap, where the 5' cap of the RNA component is autocatalytically removed by a ribozyme, allows RGEN-mediated targeting of DNA sequences in a non-conventional yeast.

Example 4

*Yarrowia*-Optimized sgRNA Expressed with a 5'-Ribozyme, But without a 3' Ribozyme), Is Useful in an sgRNA/Cas9 Endonuclease System for Cleaving Chromosomal DNA In this example, the functionality of sgRNA produced from a *Yarrowia*-optimized cassette containing only a 5' HH ribozyme, but no 3' ribozyme, was evaluated to determine if the sgRNA could interact with Cas9, recognize a DNA target sequence, induce DNA cleavage by Cas9, and lead to mutation by error-prone NHEJ.

RNAs transcribed from Pol II promoters are heavily processed and modified at both their 5' and 3' ends, suggesting that, to produce a functional sgRNA from a Pol II promoter, the 5' and 3' ends must be cleaved off. It has previously been shown that sgRNAs produced in vitro with flanking regions are (i) non-functional if a 5'-flanking region exists, and (ii) significantly functionally impaired if a 3' flanking region exists (Gao et al., *J. Integr. Plant Biol.* 56:343-349). If pre-sgRNA containing a 5' ribozyme and also a 3' flanking region was expressed *Saccharomyces cerevisiae* along with Cas9, the sgRNA did not function to direct Cas9 to a target site for cleavage (Gao et al., ibid).

To test if a 5' ribozyme-flanked sgRNA (lacking a 3'-located ribozyme) could function in non-conventional yeast, a *Yarrowia*-optimized sgRNA expression cassette (SEQ ID NO:25) was constructed containing, in a 5'-to-3' direction, an FBA1 promoter (SEQ ID NO:12) fused to a HH ribozyme (SEQ ID NO:15) fused to a sequence encoding an sgRNA (an example of SEQ ID NO:70) targeting the Can1-1 target site (SEQ ID NO:17) fused to a strong transcriptional terminator from the *S. cerevisiae* Sup4 gene (SEQ ID NO:8) (this cassette can be characterized as expressing an RG [ribozyme-sgRNA] RNA). The sgRNA encoded in the RG expression cassette comprises a VT domain corresponding to SEQ ID NO:17, linked to a CER domain (SEQ ID NO:1). The first 6 residues of the encoded HH ribozyme are complementary to the first 6 residues of the sgRNA (i.e., first 6 residues of the VT domain). Note that there are three residues (ATG) immediately following SEQ ID NO:12 (FBA1 promoter) in SEQ ID NO:25 which are not believed to affect expression and ribozyme-mediated autocatalysis of the pre-sgRNA. This *Yarrowia*-optimized RG expression cassette (SEQ ID NO:25) is illustrated in FIG. 2C.

To test the ability of the *Yarrowia*-optimized RG cassette to express an sgRNA that can interact with Cas9, direct Cas9 to a DNA target sequence for cleavage by Cas9, PCR product containing either the RG construct (SEQ ID NO:25) or the RGR construct (SEQ ID NO:18, Example 2) was co-transformed with pZUFCas9 (SEQ ID NO:14) into $Ura^-$ *Y. lipolytica* cells (Y2224) by lithium ion-mediated transformation (Ito et al., ibid). $Ura^+$ transformants were replica-plated onto CM+can plates to screen for canavanine-resistant cells (as in Example 3) in which the sgRNA produced from the RG or RGR pre-sgRNA functioned in guiding Cas9 to cleave the CAN1 target sequence resulting in error-prone repair via NHEJ. The frequencies at which the *Yarrowia*-optimized RG or RGR cassettes directed Cas9 mediated cleavage to the target site were the same (FIG. 6), indicating that contrary to results of Gao et al. (*J. Integr. Plant Biol.* 56:343-349) using *S. cerevisiae*, a 3' ribozyme was not necessary for efficient Cas9/sgRNA target cleavage and mutation in *Yarrowia*.

This example demonstrates that, in non-conventional yeast such as *Yarrowia*, only a 5'-flanking ribozyme appears to be necessary to produce a functional sgRNA from Pol II promoters when using a ribozyme strategy. This result contrasts with what has been observed in *S. cerevisiae*, a conventional yeast, in which both 5' and 3' ribozymes were required for efficient cleavage and mutation of a target sequence by Cas9 (Gao et al., ibid).

Thus, this example further demonstrates that expressing an RNA component (e.g., sgRNA) of an RGEN (e.g., Cas9) not having a 5'-cap, where the 5' cap of the RNA component is autocatalytically removed by a ribozyme, allows RGEN-mediated targeting of DNA sequences in a non-conventional yeast.

Example 5

Use of Linear Polynucleotide Modification Templates to Facilitate Homologous Recombination (HR) Repair of Cas9/sqRNA-induced DNA Double-Strand Breaks This example discloses testing for the ability of the HR machinery in *Yarrowia* to use linear polynucleotide modification template DNA sequences to repair double-strand breaks (DSBs) generated by expressing *Yarrowia*-optimized Cas9 and pre-sgRNA expression cassettes. Three different linear template sequences were produced, each having 5'- and 3'-arm sequences that were homologous to regions outside a Cas9/sgRNA targeting site in chromosomal DNA.

The first two types of polynucleotide modification template sequences were generated from synthesized oligonucleotides that were complimentary. The complimentary oligonucleotides were annealed and then purified by ethanol precipitation.

The first polynucleotide modification template was generated using complementary oligonucleotides (SEQ ID NOs:28 and 29) and was designed to delete the 20-nucleotide Can1-1 target site (SEQ ID NO:17), the 3-nucleotide PAM domain and the two nucleotides immediately upstream of the Can1-1 target site, thereby deleting 8 codons and 1 base pair resulting in a -1 by frameshift in the CAN1 gene. The first polynucleotide modification template was assembled by annealing SEQ ID NO:28 and its reverse compliment, SEQ ID NO:29. The homology arms (each about 50-bp) of the first donor DNA are directly next to each other; there is no heterologous sequence between them.

The second polynucleotide modification template generated using complementary oligonucleotides (SEQ ID NOs: 30 and 31) and was designed to generate two in-frame translational stop codons (i.e., nonsense mutations) in the CAN1 open reading frame. It was also designed to disrupt the PAM sequence downstream the Can1-1 target site (replacing CGG with ATG) and the first nucleotide of the seed sequence (i.e., last residue of the Can1-1 target sequence of SEQ ID NO:17) (replacing C with G). This polynucleotide modification template was created by annealing SEQ ID NO:30 and its reverse compliment, SEQ ID NO:31. As can be gleaned from above, the homology arms (each about 50-bp) of the second donor DNA are separated by a few base pairs of heterologous sequence.

A third polynucleotide modification template was generated in part by producing two PCR products. In one of the PCR products (SEQ ID NO:32, amplified from *Y. lipolytica* ATCC 20362 genomic DNA using primers SEQ ID NO:33 [forward] and SEQ ID NO:34 [reverse]), position 638 of SEQ ID NO:32 corresponds to the nucleotide 3 bp upstream of the CAN1 open reading frame start codon. The reverse primer (SEQ ID NO:34) adds 17 nucleotides complementary to sequence lying 37 bp downstream the CAN1 open reading frame. The second PCR product (SEQ ID NO:35, amplified from *Y. lipolytica* ATCC 20362 genomic DNA using primers SEQ ID NO:36 [forward] and SEQ ID NO:37 [reverse]), comprises 637 base pairs starting 14 base pairs downstream the stop codon of the CAN1 open reading frame. The forward primer (SEQ ID NO:36) adds 20 nucleotides complementary to the region ending 2 base pairs upstream the CAN1 open reading frame. Both the upstream (SEQ ID NO:32) and downstream PCR products (SEQ ID NO:35) were purified using Zymoclean™ and concentrator columns. These PCR products (10 ng each) were mixed in a new PCR reaction. The 3'-most 37 nucleotides of the upstream product are identical to the 5'-most 37 nucleotides of the downstream product. The upstream and downstream fragments were used to prime each other creating a single product (SEQ ID NO:38) by synthesis from overlapping ends containing both the upstream and downstream sequences (technique described by Horton et al., *Biotechniques* 54:129-133). The homology arms (each over 600-bp) of the SEQ ID NO:38 donor DNA are directly next to each other; there is no heterologous sequence between them. This polynucleotide modification template can enable a large deletion encompassing the entire CAN1 open reading frame in the region of a Cas9/sgRNA-mediated double-strand break in the Can1-1 target site.

$Ura^-$ *Y. lipolytica* cells (Y2224) were transformed using the above lithium ion transformation method with (i) pZUF-Cas9 (SEQ ID NO:14), (ii) 1 μg of the *Yarrowia*-optimized RGR pre-sgRNA expression cassette (SEQ ID NO:18), and (iii) 1 nmol of the “frameshift template” DNA (SEQ ID NO:28), 1 nmol of the “point mutation template” DNA (SEQ ID NO:30), or 1 μg of the “large deletion template” DNA (SEQ ID NO:38). Transformed cells were recovered as prototrophs for uracil on CM-ura plates. The prototrophic colonies were screened by replica-plating to CM+can to identify canavanine-resistant cells, which have CAN1 mutations. The CAN1 locus of $Can^R$ colonies from each transformation were screened via PCR amplification using forward (SEQ ID NO:22) and reverse primers (SEQ ID NO:23). Each PCR product was purified using ExoSAP-IT® (Affymetrix, Santa Clara, Calif.) and sequenced (Sanger method) using sequencing primer SEQ ID NO:24. The frequency of colonies exhibiting the predicted homologous recombination event out (in view of which particular template DNA was used in the transformation) of the total number of $Can^R$ colonies was about 15% (FIG. 7).

The three different polynucleotide modification template DNA sequences had slightly different efficiencies of HR repair (FIG. 8). Specifically, HR frequencies with each of these templates was roughly between 11% (large deletion and frameshift donors) and 22% (point mutation template) (FIG. 8), indicating that some of the Cas9/sgRNA-generated cleavage events at the Can1-1 target site were repaired using the HR pathway in a high-fidelity manner when polynucleotide modification template DNA was provided.

Use of the two major pathways of DNA repair, NHEJ or HR, demonstrates a clear bias for NHEJ in *Yarrowia* (FIG. 7), which is different from what has been observed in studies of repair at Cas9/sgRNA-mediated cleavage events in conventional yeast. For example, DiCarlo et al. (*Nucleic Acids Res.* 41:4336-4343) showed that almost all *S. cerevisiae* mutants obtained when a donor DNA was provided for repair of a Cas9/sgRNA-mediated DNA cleavage were generated via HR, while the frequency fell by 4 to 5 orders of magnitude when donor DNA was not provided, indicating a clear bias toward HR. In contrast, the total mutation frequency in *Yarrowia* at a Cas9/sgRNA (sgRNA expressed from the RGR cassette) cleavage site did not vary between transformants that received or did not receive polynucleotide modification template DNA (FIG. 9, showing ~15% mutation rates for both types of transformants), and HR only accounts for about 15 percent of the mutant transformants generated when donor DNA is provided (FIG. 7). Thus, the frequency of HR with a polynucleotide modification template DNA sequence in *Yarrowia* as observed above was only about 2.25%, which is in stark contrast to the near 100% HR-mediated mutation rate observed with donor DNA in a conventional yeast (DiCarlo et al., ibid).

Thus, this example further demonstrates that expressing an RNA component (e.g., sgRNA) of an RGEN (e.g., Cas9) not having a 5'-cap, where the 5' cap of the RNA component is autocatalytically removed by a ribozyme, allows RGEN-mediated targeting of DNA sequences in a non-conventional yeast. This example also demonstrates that RGEN-mediated cleavages in a non-conventional yeast can be repaired by HR at a certain rate if a suitable donor DNA (polynucleotide modification template) is provided.

Example 6

Expression of Cas9 and *Yarrowia*-Optimized RGR or RG Pre-sgRNA from a Single Stable Vector Provides Cas9/sgRNA-Mediated Target DNA Cleavage In this example, *Yarrowia*-optimized RGR or RG pre-sgRNA expression cassettes were each individually moved into the same stable expression plasmid as a *Yarrowia*-optimized Cas9 expression cassette. Specifically, SEQ ID NO:18 (for RGR expression) or SEQ ID NO:25 (for RG expression) were each individually cloned into pZUFCas9 (FIG. 3A, SEQ ID NO:14). This allowed for single-component transformation to express both Cas9 endonuclease and the RG or RGR pre-sgRNA in cells, thereby providing Cas9/sgRNA-mediated target site cleavage followed by error prone NHEJ repair.

*Yarrowia*-optimized RGR (SEQ ID NO:18) or RG (SEQ ID NO:25) sgRNA expression cassettes were amplified by PCR using forward (SEQ ID NO:39) and reverse (SEQ ID NO:40) primers. Each product was individually cloned into plasmid pZUFCas9 (SEQ ID NO:14) at PacI/ClaI restriction sites to generate two new plasmids each carrying respective cassettes for Cas9 expression and expression of either the optimized RGR pre-sgRNA (pRF84, SEQ ID NO:41, FIG. 10A) or the optimized RG pre-sgRNA (pRF85, SEQ ID NO:42, FIG. 10B).

To test the ability of the pRF84 (SEQ ID NO:41) and pRF85 (SEQ ID NO:42) plasmid constructs to each effectively express Cas9 and sgRNA to provide Cas9/sgRNA-mediated target site (Can1-1) cleavage, $Ura^-$ *Y. lipolytica* cells (Y2224) were transformed using the above lithium ion transformation method with 200 ng of pRF84 (SEQ ID NO:41), pRF85 (SEQ ID NO:42), or pZUFCas9 (SEQ ID NO:14). Cells transformed with each plasmid were selected as uracil prototrophs on CM-ura medium. Uracil prototrophs from each transformation were screened for CAN1 mutants by replica-plating on CM+can. The number of colonies that grew on the CM+can plates were used to generate a CAN1 mutation frequency (FIG. 11) for the cells transformed with pZUFCas9 (expressing Cas9 alone), pRF84 (expressing Cas9 and RGR pre-sgRNA), or pRF85 (expressing Cas9 and RG pre-sgRNA). *Yarrowia* cells transformed with pZUFCas9 (SEQ ID NO:14) had a 0 frequency of Cas9/sgRNA-mediated mutation at the CAN1 locus, whereas cells expressing (i) Cas9 and (ii) RGR pre-sgRNA (pRF84) or RG sgRNA (pRF85) had similar CAN1 mutation frequencies (~69%) as indicated by canavanine-resistance (FIG. 11).

These results indicate that expressing Cas9 and pre-sgRNA from the same vector lead to significantly higher rates of Cas9/sgRNA-mediated cleavage and consequently NHEJ-mediated mutation at the predicted cleavage site. While *Yarrowia* cells transformed with separate sequences encoding Cas9 and pre-sgRNA (RGR or RG pre-sgRNA) exhibited a targeted mutation frequency of about 5% (Example 4, FIG. 6), placing both Cas9 and sgRNA coding sequences on the same vector used for transformation resulted in a targeted mutation frequency of about 69% (FIG. 11).

Thus, expressing a Cas protein and its corresponding RNA component from the same construct used to transform a non-conventional yeast results in a higher rate of Cas-mediated DNA targeting in the yeast compared to using separate constructs to express the RGEN protein and RNA components.

Example 7

High-efficiency Gene Targeting Using a HDV Ribozyme-sgRNA Fusion in *Yarrowia Lipolytica*

This example discusses the use of single guide RNAs (sgRNAs that are flanked on the 5' end by a HDV ribozyme (Ribozyme-single guide RNA fusion). When expressed, the HDV ribozyme cleaves 5' of its own sequence removing any preceding transcript but leaving the HDV sequence fused to the 5' end of the sgRNA.

Plasmid pZuf-Cas9 (SEQ ID NO: 14) was mutagenized using Agilent QuickChange and the following primers AarI-removal-1 (AGAAGTATCCTACCATCTACcatctc-cGAAAGAAACTCGTCGATTCC, SEQ ID NO: 90) and AarI-removal-2 (GGAATCGACGAGTTTCTTTCggagatg-GTAGATGGTAGGATACTTCT, SEQ ID NO:91) to remove the endogenous AarI site present in the Cas9 gene (SEQ ID NO: 10) on pZuf-Cas9 (SEQ ID NO: 14) and generate pRF109 (SEQ ID NO: 92). The modified AarI-Cas9 gene (SEQ ID NO: 93) was cloned as a NcoI/NotI fragment from pRF109 into the NcoI/NotI site of pZufCas9 replacing the existing Cas9 gene (SEQ ID NO: 10) with the AarI-Cas9 gene to generate pRF141 (SEQ ID NO: 94).

The high throughput cloning cassette (FIG. 12A, SEQ ID NO: 95) is composed of the yl52 promoter (SEQ ID NO: 96), the HDV ribozyme (SEQ ID NO: 16), the *Escherichia coli* counterselection cassette rpsL (SEQ ID NO: 97), the DNA encoding the guide RNA CER domain (SEQ ID NO: 1) and the *S. cerevisiae* Sup4 terminator (SEQ ID NO: 8). Flanking the ends of the high-throughput cloning cassette (SEQ ID NO: 95) are PacI and ClaI restriction enzyme recognition sites. The high-throughput cloning cassette was cloned into the PacI/ClaI sites of pRF141 (SEQ ID NO: 94) to generate pRF291 (SEQ ID NO: 98). The rpsL counterselection cassette (SEQ ID NO: 97) contains a WT copy of the *E. coli* gene rpsL encoding the S12 ribosomal protein subunit (*Escherichia coli* and *Salmonella typhimurium*: Cellular and Molecular Biology, 1987, First ed. American Society of Microbiology, Washington, D.C.). Some mutations in the S12 subunit cause resistance to the antibiotic streptomycin (Ozaki M, Mizushima S, Nomura M. 1969. Identification and functional characterization of the protein controlled by the streptomycin-resistant locus in *E. coli*. Nature 222:333-339) in a recessive manner (Lederberg J. 1951. Streptomycin resistance; a genetically recessive mutation. Journal of bacteriology 61:549-550) such that if a wild-type copy of the rpsL gene is present the strain is phenotypically sensitive to streptomycin . Common cloning strains such as Top10 (Life technologies) have a mutated copy of rpsL on their chromosome such that the cells are resistant to streptomycin.

Cloning a DNA fragment encoding a variable targeting domain of a guide RNA into a plasmid (such as pRF291) requires two partially complimentary oligonucleotides that when annealed they contain the DNA fragment encoding the variable targeting domain, as well as the correct overhangs for cloning into the two AarI sites present in the high-throughput cloning cassette. Two oligonucleotides Can1-1F (AATGGGACtcaaacgattacccaccctcGTTT, SEQ ID NO: 99) and Can1-1R (TCTAAAACgagggtgggtaatcgtttgaGTCC , SEQ ID NO: 100) were resuspended in duplex buffer (30mM HEPES pH 7.5, 100mM Sodium Acetate) at 100pM. Can1-1F (SEQ ID NO: 99) and Can1-1R (SEQ ID NO: 100) were mixed at a final concentration of 50 μM each in a single tube, heated to 95° C. for 5 minutes and cooled to 25° C. at 0.1° C./min to anneal the two oligonucleotides to form a small duplex DNA molecule (FIG. 12B) containing the DNA fragment encoding the variable targeting domain of a guide RNA capable of targeting the Can1-1 target site (shown as SEQ ID NO: 101 which include the PAM sequence CGG) . A single tube digestion/ligation reaction was created containing 50 ng of pRF291, 2.5 μM of the small duplex DNA composed of Can1-1F and Can1-1R 1×T4 ligase buffer (50mM Tris-HCl, 10 mM $MgCl_2$, 1 mM ATP, 10 mM DTT pH 7.5), 0.5 μM AarI oligonucleotide, 2 units AarI, 40 units T4 DNA ligase in a 20 μl final volume. A second control reaction lacking the duplexed Can1-1F and Can1-1R duplex was also assembled. The reactions were incubated at 37° C. for 30 minutes. 10 μl of each reaction was transformed into Top10 *E. coli* cells as previously described (Green MR, Sambrook J. 2012. Molecular Cloning: A Laboratory Manual, Fourth Edition ed. Cold Spring Harbor Laboratory Press, Cold Spring Harbor, N.Y.). In order to select for the presence of pRF291 where the duplex of Can1-1F and Can1-1R had replaced the rpsL counterselection marker flanked by AarI restriction sites (FIG. 12A) cells were plated on lysogeny Broth solidified with 1.5% (w/v) Bacto agar containing 100 μg/ml Ampicillin and 50 μg/ml Streptomycin. The presence of pRF291 containing the high-throughput cloning cassette yielded colonies phenotypically resistant to the antibiotic ampicillin but sensitive to the antibiotic streptomycin due to the presence of the counterselection cassette on the plasmid. However, in cases where the counterselection cassette was removed via the AarI enzyme and the Can1-1 duplex DNA was ligated into the site (removing the recognition sequences for AarI) the cells transformed with the plasmid had an ampicillin resistant, streptomycin resistant phenotype (FIG. 12A). pRF291 containing the DNA fragment encoding the Can1-1 variable targeting domain targeting (replacing the counterselection cassette) created a recombinant HDV-sgRNA expression cassette (SEQ ID NO: 102) containing the yl52 promoter fused to the DNA encoding the HDV ribozyme (SEQ ID NO: 16) fused to the DNA encoding the Can1-1 variable targeting domain (SEQ ID NO: 17) fused to the DNA encoding the guide CER domain (SEQ ID NO: 1) fused to the sup4 terminator (SEQ ID NO: 8). The plasmid containing this construct, pRF303 (SEQ ID NO: 103) was used to encode a HDV ribozyme-guide RNA (SEQ ID NO: 104) that was capable (when in complex with a Cas9 endonuclease) to target the Can1 gene (SEQ ID NO: 21) of *Yarrowia lipolytica* for mutagenesis.

*Yarrowia lipolytica* was transformed (as described in Richard M, Quijano RR, Bezzate S, Bordon-Pallier F, Gaillardin C. 2001. Journal of bacteriology 183:3098-3107) with either no plasmid or 100 ng of plasmid carrying no sgRNA expression cassette (pRF291, SEQ ID NO: 98), pRF84 plasmid carrying an RGR expression cassette (SEQ ID NO: 41), pRF85 plasmid carrying the RG cassette where the 5' ribozyme removed itself from the sgRNA (SEQ ID NO: 42), or pRF303 (SEQ ID NO: 103) carrying the HDV-sgRNA fusion expression cassette (SEQ ID NO: 102) targeting the Can1-1 target site in *Yarrowia*. Transformants were selected for uracil prototrophy and scored for mutations in the Can1 gene by phenotypic resistance to the arginine analog canavanine. The plasmid expressing the HDV-sgRNA fusion caused loss of function mutations in the Can1 gene at the same frequency of the plasmid that expressed either of the sgRNAs that were liberated from the ribozyme suggesting that a 5' fusion of the HDV ribozyme to the sgRNA targeting Can1-1 did not affect sgRNA function (Table 4).

TABLE 4

Mutation frequency of Can1-1 target sequence via different sgRNA variants.

| Plasmid | sgRNA variant | $Can^R$ Frequency ± SD |
|---|---|---|
| pRF291 | No sgRNA | 0 ± 0 |
| pRF84 | RGR that yields sgRNA | 0.70 ± 0.04 |
| pRF85 | RG that yields sgRNA | 0.73 ± 0.11 |
| pRF303 | FIDV-sgRNA fusion | 0.81 ± 0.15 |

A number of additional DNA fragments encoding variable targeting domains targeting a number of additional target sites (Table 5) were cloned into the pRF291 (SEQ ID NO: 98) plasmid using the same strategy as described above and illustrated in FIG. 12A. Including a DNA fragment encoding a variable targeting domain targeting a second target site targeting within the Can1 gene (SEQ ID NO: 105), the can1-2 target site (SEQ ID NO: 106) and other target sites such as sou2-1 (SEQ ID NO: 107), Sou2-2 (SEQ ID NO: 108), Tgl1-1 (SEQ ID NO: 112), Acos10-1 (SEQ ID NO: 113), Fat1-1 (SEQ ID NO: 114) and Ura3-1 (SEQ ID NO: 116).

TABLE 5

DNA Sequences Encoding sgRNA VT domains for Targeting different Loci in *Yarrowia* with Cas9

| | DNA encoding Variable Targeting domain of sgRNA | *Yarrowia* target sites + PAM sequence (bold) |
|---|---|---|
| Can1-2 | Base 1-20 of SEQ ID NO: 106 | GGCCCACTCGGATGACTCAG**AGG** (SEQ ID NO: 106) |
| Sou2-1 | Base 1-24 of SEQ ID NO: 107 | GTCTGGACCTTCCACCCTCGCCA**CGGG** (SEQ ID NO: 107) |
| Sou2-2 | Base 1-22 of SEQ ID NO: 108 | GCAGTCCCGTGGCGAGGGTGGA**AGG** (SEQ ID NO: 108) |
| TGL1-1 | Base 1-20 of SEQ ID NO: 112 | CAGCTCGAGACGTCCTAGAA**CGG** (SEQ ID NO: 112) |
| Acos10-1 | Base 1-20 of SEQ ID NO: 113 | TTCCTCTGTCACAGACGTTT**CGG** (SEQ ID NO: 113) |
| Fat1-1 | Base 1-20 of SEQ ID NO: 114 | GAAAAGTGCGTTTTGATTCT**CGG** (SEQ ID NO: 114) |
| ura3-1 | Base 1-20 of SEQ ID NO: 116 | GCCGCTCGAGTGCTCAAGC**TCG** (SEQ ID NO: 116) |

The mutation frequency of the target sites indicated that all HDV-sgRNA fusions were capable of making a complex with the Cas9 endonuclease which in turn generated cleavage at the respective target site that led to mutations via NHEJ (Table 6).

TABLE 6

Mutation frequency at various target sites in *Yarrowia lipolytica* using HDV-sgRNA fusions.

| Target site | Mutation frequency ± SD |
|---|---|
| Can1-2 | 0.76 ± 0.15 |
| Sou2-1 | 0.19 |
| Sou2-2 | 0.30 |
| TGL1-1 | 0.88 |
| Acos10-1 | 0.36 |
| Fat1-1 | 0.50 |
| ura3-1 | 0.92 |

Example 8

Gene Silencing Using Inactivated-Cas9 and HDV-sgRNA Fusions.

Catalytically inactivated Cas9 variants containing mutations in the HNH and RuvC nuclease domains (SEQ ID NO: 117) are capable of interacting with sgRNA and binding to the target site in vivo but cannot cleave either strand of the target DNA. This mode of action, binding but not breaking the DNA can be used to transiently decrease the expression of specific loci in the chromosome without causing permanent genetic changes.

In order to generate catalytically inactivated Cas9 expression cassettes for *Yarrowia lipolytica* the D10A mutation was introduced to the plasmid pZufCas9 (SEQ ID NO: 14) using quickchange site-directed mutagenesis (Stratagene) as described with the primers D10AF (GAAATACTCCATCGGCCTGGCCATTGGAACCAACTCTGTCG, SEQ ID NO: 118) and D10AR (CGACAGAGTTGGTTCCAATGGCCAGGCCGATGGAGTATTTC, SEQ ID NO: 119). This generated a *Yarrowia* codon optimized Cas9 gene with the D10A mutation inactivating the RuvC nuclease (SEQ ID NO: 120) and the corresponding plasmid containing the construct, pRF111 (SEQ ID NO: 121). In order to inactivate the second nuclease domain (HNH) an additional round of quickchange mutagenesis (Stratagene) was performed using primer H840A1 (TCAGCGACTACGATGTGGACGCCATTGTCCCTCAATCCTTTCT, SEQ ID NO: 122) and H840A2 (AGAAAGGATTGAGGGACAATGGCGTCCACATCGTAGTCGCTGA, SEQ ID NO: 123) introducing the H840A mutation into the *Yarrowia* codon optimized D10A gene creating a *Yarrowia* codon optimized Cas9 inactivated gene (SEQ ID NO: 124) and the plasmid carrying the gene for expression in *Yarrowia*, pRF143 (SEQ ID NO: 125).

In order to assess gene silencing in *Yarrowia lipolytica* a Yarrowia codon optimized dsREDexpress open reading frame (SEQ ID NO: 126) was generated as a cloning fragment with a 5' NcoI restriction site and a 3' NotI restriction site (SEQ ID NO: 127). The cloning fragment (SEQ ID NO: 127) was cloned into the NcoI/NotI sites of pZufCas9 to create an FBA1 promoter (SEQ ID NO: 12) fused to a *Yarrowia* optimized dsREDexpress cloning fragment (SEQ ID NO: 127) creating a FAB1-dsRED fusion cassette (SEQ ID NO: 128) which was contained on plasmid pRF165 (SEQ ID NO: 129). In order to integrate the FBA1-dsREDexpress cassette (SEQ ID NO: 128) into the chromosome, the PmeI-NotI fragment containing the cassette (SEQ ID NO: 130) was ligated into the PmeI/NotI sites of integration plasmid p2P069 (SEQ ID NO: 131) to generate an integration vector carrying the FBA1-dsREDexpressexpression cassette, pRF201 (SEQ ID NO: 132). A SphI/AscI fragment of pRF201 carrying the FBA1-dsREDexpress fusion and a copy of the Leu2 gene (SEQ ID NO: 133) was integrated into the chromosome of *Yarrowia* by selecting for Leucine prototrophy using standard techniques (Richard M, Quijano RR, Bezzate S, Bordon-Pallier F, Gaillardin C. 2001. Tagging morphogenetic genes by insertional mutagenesis in the yeast *Yarrowia lipolytica*. Journal of bacteriology 183:3098-3107). The presence of the FBA1-dsREDexpress expression cassette was confirmed in the *Yarrowia* genome using standard PCR techniques and primers HY026 (GCGCGTTTAAACCATCATCTAAGGGCCTCAAAACTACC, SEQ ID NO: 134) and HY027 (GAGAGCGGCCGCTTAAAGAAACAGATGGTGTCTTCCCT, SEQ ID NO: 135). Two independent strains containing the FBA1-dsREDexpress cassette (SEQ ID NO: 128) were chosen for further use, YRF41 and YRF42.

To create sgRNAs for targeting the *Yarrowia* optimized dsREDexpress expression cassette (SEQ ID NO: 128) a strategy similar to Example 12 was used. A plasmid construct, pRF169 (SEQ ID NO: 136) contained the GPD promoter from *Yarrowia* (SEQ ID NO: 137) counterselectable marker , the DNA encoding the guide RNA CER domain (SEQ ID NO: 1) and a Sup4 terminator (SEQ ID NO: 8) cassette (SEQ ID NO: 138), as illustrated in FIG. 13A. DNA encoding the variable targeting domain of a sgRNA, targeting target sites in *Yarrowia*, linked to a DNA fragment encoding the HH ribozyme were cloned into pRF169 (SEQ ID NO: 136) as described in Example 12 except that the DNA fragments encoding the HH ribozyme were such that the first 6 nucleotides of the hammerhead ribozyme were the reverse compliment of the first 6 nucleotides of the variable targeting domain, as shown in FIG. 13B. When the duplexed oligonucleotides with the correct overhangs replace the counterselection cassettes between the AarI sites a ribozyme-guideRNA (RG) expression cassette was created (FIG. 13-A). When transcribed, the HH ribozyme removes the 5' transcript and itself from the ribozyme-guide RNA molecule, leaving an intact sgRNA in the cell. Three guide RNA's targeting the dsREDexpress open reading frame (SEQ ID NO: 126) were generated; two targeting the template strand, ds-temp-1 (SEQ ID NO: 139), ds-temp-2 (SEQ ID NO: 140), and one targeting the non-template strand ds-nontemp-1 (SEQ ID NO: 141).

For each target site two oligonucleotides were designed containing the DNA sequence encoding the target specific hammerhead ribozyme, the variable targeting domain (VTD) and the correct overlapping ends for cloning into the AarI sites of pRF169. The oligonucleotides for each site; ds-temp-1F (SEQ ID NO: 144) ds-temp-1R (SEQ ID NO: 145), ds-temp-2F (SEQ ID NO: 146), ds-temp-2R (SEQ ID NO: 147), ds-nontemp-1F (SEQ ID NO: 148), and ds-nontemp-1R (SEQ ID NO: 149) were duplexed to form double stranded DNA molecules with the correct overhangs for cloning into the AarI overhangs left in the high throughput cassette (FIG. 13A and 13B) of pRF169 and was performed as described in Example 12 for cloning into pRF291. Insertion of the DNA fragment encoding the variable targeting domain of the sgRNA, replacing the counterselection cassette, generated a new plasmid for each target site carrying a GPD promoter fused to the hammerhead ribozyme-target site duplex DNA fused to DNA encoding the guide RNA CER domain fused to the Sup4 terminator FIG. 13A. The plasmids containing these duplexes are pRF296 (ds-temp-1, SEQ ID NO: 150), pRF298 (ds-temp-2, SEQ ID NO: 151), pRF300 (ds-nontemp-1, SEQ ID NO: 152).

In order to create constructs for gene silencing, the inactivated Cas9 from pRF143 (SEQ ID NO: 125) was cloned into pRF296, pRF298 and pRF300 as a NcoI/NotI fragment using standard techniques and replacing the functional Cas9 (SEQ ID NO: 93) that resided in the NcoI/NotI sites of those plasmids to create plasmids pRF339 (SEQ ID NO: 153), pRF341 (SEQ ID NO: 154), and pRF342 (SEQ ID NO: 155) respectively.

Strains YRF41 and YRF42 were transformed with pRF339, pRF341, and pRF343 using standard techniques to uracil prototrophy (Richard M, Quijano RR, Bezzate S, Bordon-Pallier F, Gaillardin C. 2001. Tagging morphogenetic genes by insertional mutagenesis in the yeast *Yarrowia lipolytica*. Journal of bacteriology 183:3098-3107)). For each transformation 12 transformants were streak purified on plates lacking uracil to maintain the plasmid. Each isolate was used to inoculate 2 ml of CM-ura broth (Teknova) and was grown at 30° C., 250 RPM overnight. 2-5 μl of each overnight was diluted into 200 μl of $ddH_2O$ and analyzed in the dsREDexpress channel of an Accuri flow cytometer to assess the amount of dsREDexpress protein within each cell. Between 7,151 and 10,000 cells were analyzed from each culture. The mean fluorescence of Yarrowia cells without a dsREDexpress expression cassette were subtracted from the mean fluorescence of each of the cultures analyzed to obtain a corrected mean fluorescence within each strain/plasmid combination these were averaged and the standard deviation was determined (Table 7). Inactivated Cas9 combined with a ribozyme-sgRBA (RG) expressed via an expression vector, targeting a gene of interest, silenced the expression of the gene between 2 and 10 fold. The fold silencing varied depended on the location and strandedness of the target site and/or the ability of a ribozyme flanked sgRNA to be expressed from a DNA polymerase promoter in a functional form in a *Yarrowia* cell (Table 7).

TABLE 7

Gene silencing by three target sites in two FBA-dsREDexpress integrated strains.

| Strain | Plasmid | Target Site | Mean fluorescence ± SD | Fold of No Target |
|---|---|---|---|---|
| YRF41 | None | None | 540.6 ± 2.9 | 1 |
| YRF41 | pRF339 (SEQ ID NO: 69) | ds-temp-1 | 299.2 ± 138.7 | 0.55 ± 0.26 |
| YRF41 | pRF341 (SEQ ID NO: 70) | ds-temp-2 | 257.9 ± 139.3 | 0.48 ± 0.26 |
| YRF41 | pRF343 (SEQ ID NO: 71) | ds-nontemp-1 | 169.4 ± 45.3 | 0.31 ± 0.08 |
| YRF42 | None | None | 871.2 ± 36.9 | 1 |
| YRF42 | pRF339 (SEQ ID NO: 69) | ds-temp-1 | 194.3 ± 121.1 | 0.22 ± 0.14 |
| YRF42 | pRF341 (SEQ ID NO: 70) | ds-temp-2 | 168.7 ± 191.6 | 0.19 ± 0.22 |
| YRF42 | pRF343 (SEQ ID NO: 71) | ds-nontemp-1 | 94.9 ± 109.6 | 0.11 ± 0.13 |

Example 9

Precise Gene Editing Using Cas9 and a HDV Ribozyme-sgRNA Fusion (RG) Expressed from a Single Plasmid.

In this example we demonstrate that the stable expression of Cas9 and an HDV-sgRNA fusion expressed from the same stable vector can create DNA double-strand breaks in target sites of *Yarrowia* that can be substrate for precise gene editing via homologous recombination.

The Can1 deletion polynucleotide modification template DNA described in Example 4 (SEQ ID NO: 38) was digested with HinDIII and cloned into the HinDIII site of pUC18 using standard techniques to create pRF80 (SEQ ID NO: 156). A shorter Can1 deletion editing template (SEQ ID NO: 157) was amplified from pRF80 using standard PCR techniques and primers 80F (AGCTTGCTACGTTAGGAGAA, SEQ ID NO: 158) and 80R (TATGAGCTTATCCTGTATCG, SEQ ID NO: 159) to create large quantities of the editing template.

Ura auxotrophic *Yarrowia* cells were transformed using standard techniques (Richard M, Quijano R R, Bezzate S, Bordon-Pallier F, Gaillardin C. 2001. Tagging morphogenetic genes by insertional mutagenesis in the yeast *Yarrowia lipolytica*. Journal of bacteriology 183:3098-3107) with 100ng of plasmid pRF291 carrying a copy of the Cas9 gene but no sgRNA and pRF303 carrying a copy of the Cas9 gene and the Can1-1 target site HDV-sgRNA expression cassette along with either no editing template DNA or 1000 ng of the short Can1 deletion editing template (SEQ ID NO: 157). Transformants were selected on CM-ura medium (Teknova). For each transformation 20 individual colonies were streak purified on CM-ura medium (Teknova). From each of the streak purified colonies 4 individual colonies (80 total per transformation) were patched onto CM-arg plates containing 60 µg/ml of L-canavanine to screen for colonies containing a loss of function allele in the Can1 gene. Patches that demonstrated resistance to Canavanine were scored and frequencies of gene inactivation were scored (Table 8). In order to determine which colonies had lost Can1 function due to homologous recombination and which had lost Can1 function due to NHEJ the Can1 locus (SEQ ID NO: 160) was amplified using Can1-PCRF (GGAAGGCACATATGGCAAGG, SEQ ID NO: 22) and Can1-PCRR (GTAAGAGTGGTTTGCTCCAGG, SEQ ID NO: 23). In cells with small indels as described in previous examples the PCR product should be very similar to the WT Can1 loci (SEQ ID NO: 160) in size (2125 bp) in the strains containing a deletion by homologous recombination with the Can1 deletion editing template the PCR fragment (SEQ ID NO: 161) with Can1-PCRF (SEQ ID NO: 22) and Can1-PCRR (SEQ ID NO: 23) will be smaller (392 bp). 2 µl of the PCR product were resolved via electrophoresis and imaged using standard techniques (FIG. 14). The percentage of the original 20 streaked colonies that yielded 1 or more colonies upon streak purification that had the short band corresponding to recombination with the editing template (SEQ ID NO: 161) were used to determine the frequency of HR (Table 8). In cells that received pRF303 (SEQ ID NO: 103) the frequency of Canavanine resistant colonies was similar whether the cells received an editing template (Table 8). In cells receiving both pRF303 (SEQ ID NO: 103) and Can1 short editing template (SEQ ID NO: 157) in the total population of transformed cells about 1/10$^{th}$ contained precise editing (Table 8) of the Can1 locus from the editing template (SEQ ID NO: 157).

TABLE 8

Canavanine resistance frequency and frequency of precise editing.

| Plasmid | sgRNA | Editing Template | Can$^R$ Frequency ± SD | HR Frequency ± SD |
|---|---|---|---|---|
| pRF291 (SEQ ID NO: 98) | None | None | 0 ± 0 | Not Determined |
| pRF291 (SEQ ID NO: 98) | None | Can1 short (SEQ ID NO: 157) | 0 ± 0 | Not Determined |
| pRF303 (SEQ ID NO: 103) | HDV-Can1-1 sgRNA | None | 0.80 ± 0.10 | Not Determined |
| pRF303 (SEQ ID NO: 103) | HDV-Can1-1 sgRNA | Can1 short (SEQ ID NO: 157) | 0.72 ± 0.12 | 0.09 ± 0.05 |

Example 10

URA3 Gene Inactivation in *Yarrowia*

The present Example describes the construction and use of the plasmids expressing single guide RNA (sgRNA) and Cas9 endonuclease separately or together for URA3 gene inactivation in *Yarrowia*. pYRH235 and pYRH236 expressed a ribozyme flanked pre-sgRNA (RGR-URA3.1; SEQ ID NO: 164) targeting the URA3.1 target sequence (5'-ctgttcagagacagtttcct-3; SEQ ID NO:165) and a ribozyme flanked pre-sgRNA (RGR-URA3.2; SEQ ID NO: 166) targeting the URA3.2 target sequence (5'-taacatccagagaagcacac-3'; SEQ ID NO:167) respectively. A NcoI-NotI restriction digest fragment of the DNA fragment encoding the RGR-URA3.1 and a BspHI-NotI restriction digest fragment encoding the RGR-URA3.2 were fused to the FBA1L promoter (SEQ ID NO: 168) to yield pYRH235 and pYRH236, respectively. The pYRH235 and pYRH236 plasmids contained a marker gene of a native acetohydroxyacid synthase (AHAS or acetolactate synthase; E. C. 4.1.3.18; SEQ ID NO:169) that had a single amino acid change (W497L) that confers sulfonyl urea resistance.

A Ura-minus derivative (Y2224) of *Yarrowia* strain ATCC20362 was first transformed with linearized pZufCas9 (SEQ ID NO: 14) by SphI-BsiWI restriction digest, and transformants were selected on complete minimal (CM) plates lacking uracil. The linearized Cas9 expression cassette was randomly integrated into *Yarrowia* genome, and therefore the transformants contained at least two copies of URA3 gene. Subsequently, pYRH235 or pYRH236 expressing sgRNA was transformed into the Cas9 expressing *Yarrowia* strains, and the transformants were selected on CM plates containing 600 mg/L sulfonylurea. 50 transformants were patched on CM-ura plates and SC plates with 5-FOA to find the frequency of URA3 gene inactivation by Cas9 and sgRNA for URA3. 94% and 100% of the pYRH235 and pYRH236 transformants, respectively, became uracil auxotrophs.

Sequencing confirmation of mutation at target sites URA3.1 or URA3.2 was performed. 20 transformants of pZufCas9 and pYRH235 were randomly chosen for sequencing analysis, and each colony was analyzed for mutation of the URA3 gene of plasmid pZufCas9 and from native genomic URA3. To sequence the URA3 gene from plasmid pZufCas9, primers RHO705 (SEQ ID NO: 170) for URA3 and RHO719 (SEQ ID NO: 171) for FBA1 promoter sequences were used for PCR amplification of the region, and primers RHO733 (SEQ ID NO: 172) or RHO734 (SEQ ID NO: 173) were used for sequencing with the PCR amplification product as template. To sequence the URA3 gene of native genomic origin, primers RH0705 (SEQ ID NO: 170) and RHO707 (SEQ ID NO: 174) were used for PCR amplification, and primers RHO733 (SEQ ID NO: 172) and RHO734 (SEQ ID NO: 173) were used for sequencing with the PCR amplification product as template. All 20 colonies contained mutation at both plasmid and genomic originated URA3 genes (FIG. 15). A fragment alignment of the sequencing results for both plasmid and genomic originated URA3 genes of 5 representative colonies (Colony 1, 2, 3, 5 and 6; SEQ ID NOs: 176, 177, 178, 179 and 180 and SEQ ID NOs: 181, 182, 183,184 and 185, respectively) and wild type URA3.1 (SEQ ID NO: 175) are shown in FIG. 15. These results show that multiple copies of a gene in the same cell were targeted and mutated by sgRNA/Cas9 endonuclease systems in *Yarrowia*.

Example 11

URA3 Gene Mutation or Deletion in *Yarrowia.*

The present Example describes the construction and use of the plasmids expressing two sgRNAs and Cas9 endonuclease on the same vector system for URA3 gene mutation or deletion in Yarrowia for use in marker recycling.

pYRH222 expresses a Cas9 endonuclease (SEQ ID NO: 10) under a FBA1 promoter (SEQ ID NO: 12) and a FBA1L promoter driven DNA fragment encoding the ribozyme flanked pre-sgRNA (RGR-URA3.2; SEQ ID NO: 166) targeting the URA3.2 target sequence (SEQ ID NO:167), illustrated in FIG. 16A. The pYRH222 vector contained a hygromycin antibiotic resistant selection marker (SEQ ID NO:186) expressed under TDH1 (also referred as GPD) promoter (SEQ ID NO:187), as well as autonomously replicating sequence (ARS18; SEQ ID NO:208) which accomodates extrachromosomal replication of a plasmid (PNAS, Fournier, P. et al., 1993, 90:4912-4916). The presence of ARS18 rendered cells to lose plasmid when there was no selection pressure.

pYRH282 was derived from pYRH222. The FBA1L promoter (SEQ ID NO: 168) fused to a DNA fragment encoding the RGR-URA3.1 (SEQ ID NO: 164) from pYRH235 was PCR amplified using primers RH0804 (SEQ ID NO: 188) and RHO805 (SEQ ID NO: 189). The PCR product was then digested with BsiWI and cloned into pYRH222. Orientation and sequence identity of the cloned gene was confirmed by sequencing, and the construct was named pYRH282.

pYRH283 was derived from pYRH222. A synthetic DNA fragment flanked by BsiWI sites (SEQ ID NO: 190) composed of the TDH1 promoter (SEQ ID NO: 187) fusion to the DNA encoding the RGR-URA3.3 (SEQ ID NO: 191) was synthesized by IDT (Coralville, Iowa) and cloned into pYRH222 at BsiWI site. Orientation and sequence identity of the cloned gene was confirmed by sequencing, and the construct was named pYRH283.

A progeny of *Yarrowia* strain ATCC20362 was transformed with pYRH222, pYRH282, and pYRH283, and the transformants were selected on YPD plates containing 300 mg/L hygromycin. Relatively high background growth was observed on no DNA control plate (Table 9). 30 transformants of each construct were randomly selected, and streaked onto SC plates with 5-FOA to counter-select for uracil auxotriophs. No growth was observed with colonies from no DNA control plate. 4 to 11 patches showed growth with pYRH222, pYRH282, and pYRH283 transformants. Colony PCR was performed with primers RHO610 (SEQ ID NO: 192) and RHO611 (SEQ ID NO: 193) to amplify the DNA region containing the sgRNA targeting sites, and PCR amplified products showed different migration on a agarose gel (FIG. 17). Sequencing was performed with the PCR products as template and a sequencing primer RHO704 (SEQ ID NO: 194).

In case of pYRH222 transformants, 6 out of 11 sequencing worked successfully and all of them were mutated at the URA3.2 target site (FIG. 16B; SEQ ID NOs: 195-201). In case of pYRH282, all of the successfully sequencing showed mutations at target site(s), and 2 out of them showed deletion between the two target sites (FIG. 16C; SEQ ID NOs: 202-204). For pYRH283, 7 out of 8 successful sequencing showed mutations at target site(s), and 2 out of them showed deletion between the two target sites (FIG. 16D; SEQ ID NOs: 205-207), creating almost complete deletion of the URA3 gene.

This example shows that two guide RNAs were expressed on the same plasmids to make a targeted deletion between two target sites using a sgRNA/Cas9 endonuclease system in *Yarrowia*, wherein the identification was performed by running a gel or by sequencing. The presence of ARS18 (SEQ ID NO:208) on these plasmids rendered cells to lose plasmid when there was no selection pressure, so that the plasmids could be used repeatedly for URA3 marker recycling.

TABLE 9

Analysis of pYRH222, pYRH282, and pYRH283 transformants. Number of transformants was recorded for each transformation plate including no DNA control.

| | Colonies on Hyg plate | Patched on 5-FOA | Growth on 5-FOA | Targeted mutation/ sequenced |
|---|---|---|---|---|
| No DNA control | 131 | 30 | 0 | — |
| pYRH222 (URA3.2) | 352 | 30 | 11 | 6/6 |
| pYRH282 (URA3.2 + URA3.1) | 244 | 30 | 4 | 4/4 (2 deletions) |
| pYRH283 (URA3.2 + 3.3) | 178 | 30 | 10 | 7/8 (2 deletions) |

Example 12

Use of Csy4 (Cas6) in *Yarrowia* for Gene Inactivation

The present Example describes the use of Csy4 (also referred to as Cas6) to create a guide RNA with no 5' cap that is capable of forming a RGEN complex that can target DNA sequences (such as, but not limiting to, CAN1) in non-conventional yeast.

The gene encoding Csy4 (also known as Cas6) was introduced on a Cas9 expression plasmid together with DNA encoding the CAN1 targeting sgRNA flanked by 28 bp Csy4 recognition sites, for CAN1 gene inactivation in *Yarrowia.* pYRH290 expressed a Cas9 endonuclease (SEQ ID NO: 10) under a FBA1 promoter (SEQ ID NO: 12) and a *Yarrowia lipolytica* codon-optimized gene for Csy4 expression (SEQ ID NO: 209) under FBA1 promoter (SEQ ID NO: 210). pYRH290 also contained a DNA fragment (TDH1:28 bp-gCAN1-28bp; SEQ ID NO: 211) encoding the 28 bp Csy4 endonuclease recognition sequences (SEQ ID:212) flanked pre-sgRNA (SEQ ID NO:213) targeting a CAN1 target sequence (SEQ ID NO:214). After processing by Csy4, the resulting sgRNA (SEQ ID NO: 222) contained an 8-nucleotide 5'-flanking sequence (SEQ ID NO: 223) and a 20-nucleotide 3'-flanking sequence (SEQ ID NO: 224).

A Ura-minus derivative (Y2224) of *Yarrowia* strain ATCC20362 was transformed with pYRH290, and transformants were selected on CM plates lacking uracil. 86 transformants were replica-plated to CM plates containing canavanine to select for cant mutants. 40 out of 86 transformants conferred growth on CM plates containing canavanine. 16 out of 40 canavanine resistant colonies were sequenced to confirm mutations at CAN1 target sites (SEQ ID NO: 214), and 14 colonies were confirmed to have mutations at CAN1 target site. FIG. 18 shows an alignment of a fragment of the wild type CAN1 gene comprising the CAN1 target site (SEQ ID NO: 215) and mutations at the CAN1 target sequence in colonies 14, 16, 18, 19, 24 and 25 , SEQ IDS NOs: 216-221, respectively).

What is claimed is:

1. A non-conventional yeast comprising a Cas endonuclease and a polynucleotide sequence, wherein said polynucleotide sequence comprises an RNA polymerase (II) promoter operably linked to a first DNA sequence encoding a ribozyme and a second DNA sequence encoding an RNA component, wherein said first DNA sequence is located 5' (upstream) of said second DNA sequence, and wherein said polynucleotide sequence does not comprise a third DNA sequence encoding a ribozyme located 3' (downstream) from the second DNA sequence, wherein said RNA component comprises a variable targeting domain complementary to a target site sequence on a chromosome or episome in the yeast, and wherein the RNA component and the Cas endonuclease can form a RNA-guided endonuclease (RGEN), wherein said RGEN can bind to the target site sequence.

2. The non-conventional yeast of claim 1, wherein the RGEN can bind to and cleave the target site sequence.

3. The non-conventional yeast of claim 1, wherein said yeast is a member of a genus selected from the group consisting of *Yarrowia, Pichia, Schwanniomyces, Kluyveromyces, Arxula, Trichosporon, Candida, Ustilago, Torulopsis, Zygosaccharomyces, Trigonopsis, Cryptococcus, Rhodotorula, Phaffia, Sporobolomyces*, and *Pachysolen*.

4. The non-conventional yeast of any one of claims 1 to 3, wherein the RGEN comprises a CRISPR (clustered regularly interspaced short palindromic repeats)-associated (Cas) protein-9 (Cas9) amino acid sequence.

5. The non-conventional yeast of any one of claims 1 to 3, wherein the RNA transcribed from the nucleotide sequence autocatalytically removes the ribozyme to yield said RNA component, wherein said RNA component does not have a 5' cap.

6. The non-conventional yeast of claim 5, wherein the ribozyme is a hammerhead ribozyme, hepatitis delta virus ribozyme, group I intron ribozyme, RnaseP ribozyme, or hairpin ribozyme.

7. The non-conventional yeast of any one of claims 1 to 3, wherein the RNA transcribed from the nucleotide sequence does not autocatalytically remove the ribozyme, wherein said ribozyme cleaves any RNA sequence 5' of itself and yields a ribozyme-RNA component fusion molecule without a 5' cap.

8. A method for modifying a target site on a chromosome or episome in a non-conventional yeast, the method comprising providing to a non-conventional yeast a first recombinant DNA construct comprising a DNA sequence encoding a Cas endonuclease, and a second recombinant DNA construct comprising an RNA polymerase (II) promoter operably linked to a DNA sequence encoding a ribozyme upstream of an RNA component, wherein the second recombinant DNA construct does not comprise a ribozyme sequence located downstream from the ribozyme-RNA component, wherein the RNA transcribed from the second recombinant DNA construct autocatalytically removes the ribozyme to yield said RNA component, wherein the Cas endonuclease introduces a single or double-strand break at said target site.

9. The method of claim 8, further comprising identifying at least one non-conventional yeast cell that has a modification at said target, wherein the modification includes at least one deletion, addition or substitution of one or more nucleotides in said target site.

10. The method of claim 8, further comprising providing a donor DNA to said yeast, wherein said donor DNA comprises a polynucleotide of interest.

11. The method of claim 9, further comprising identifying at least one yeast cell comprising in its chromosome or episome the polynucleotide of interest integrated at said target site.

* * * * *